United States Patent
Huang et al.

(10) Patent No.: US 11,236,055 B2
(45) Date of Patent: Feb. 1, 2022

(54) NON-SYSTEMIC TGR5 AGONISTS

(71) Applicant: Venenum Biodesign, LLC, Lawrence Township, NJ (US)

(72) Inventors: Chia-Yu Huang, Princeton Junction, NJ (US); Brian F. McGuinness, Plainsboro, NJ (US); Dongchuan Shi, Collegeville, PA (US); Steven G. Kultgen, Hamilton, NJ (US); Jeffrey J. Letourneau, East Windsor, NJ (US); James R. Beasley, Doylestown, PA (US); Philip D. Stein, Pennington, NJ (US); Andrew G. Cole, Cranbury, NJ (US)

(73) Assignee: VENENUM BIODESIGN, LLC, Hamilton, NJ (US)

(*) Notice: Subject to any disclaimer, the term of this patent is extended or adjusted under 35 U.S.C. 154(b) by 335 days.

(21) Appl. No.: 16/311,723

(22) PCT Filed: Jun. 29, 2017

(86) PCT No.: PCT/US2017/040010
§ 371 (c)(1),
(2) Date: Dec. 20, 2018

(87) PCT Pub. No.: WO2018/005801
PCT Pub. Date: Jan. 4, 2018

(65) Prior Publication Data
US 2020/0308122 A1    Oct. 1, 2020

Related U.S. Application Data

(60) Provisional application No. 62/357,433, filed on Jul. 1, 2016.

(51) Int. Cl.
| | | |
|---|---|---|
| *C07D 261/08* | (2006.01) | |
| *A61P 5/48* | (2006.01) | |
| *A61P 3/04* | (2006.01) | |
| *C07D 209/44* | (2006.01) | |
| *C07D 213/02* | (2006.01) | |

(Continued)

(52) U.S. Cl.
CPC .............. *C07D 261/08* (2013.01); *A61P 3/04* (2018.01); *A61P 5/48* (2018.01); *A61P 35/00* (2018.01); *C07D 209/44* (2013.01); *C07D 213/02* (2013.01); *C07D 213/26* (2013.01); *C07D 213/65* (2013.01); *C07D 213/73* (2013.01); *C07D 235/14* (2013.01); *C07D 237/08* (2013.01); *C07D 239/26* (2013.01); *C07D 241/08* (2013.01); *C07D 275/02* (2013.01); *C07D 401/12* (2013.01); *C07D 405/10* (2013.01); *C07D 471/04* (2013.01); *C07D 487/04* (2013.01)

(58) Field of Classification Search
CPC .. C07D 261/08; C07D 213/40; C07D 237/08; C07D 239/26; C07D 401/04; C07D 471/04; C07D 487/04; C07D 235/08; C07D 401/10; C07D 241/18; C07D 275/02

See application file for complete search history.

(56) References Cited

U.S. PATENT DOCUMENTS

| | | |
|---|---|---|
| 7,960,365 B2 | 7/2011 | Hamilton et al. |
| 8,785,488 B2 | 7/2014 | Bollou et al. |
| 2103/0102609 | 4/2013 | McGuinness et al. |

FOREIGN PATENT DOCUMENTS

| | | | |
|---|---|---|---|
| WO | WO 9636595 | * | 11/1996 |
| WO | WO 2011103055 | * | 8/2011 |

OTHER PUBLICATIONS

Perino, Trends in Pharmacological Sciences, 2015, 36(12), 847-857 (Year: 2015).*
McMurry, Organic Chemistry, 2000, pp. 95-96 (Year: 2000).*

* cited by examiner

*Primary Examiner* — Noble E Jarrell
(74) *Attorney, Agent, or Firm* — Heslin Rothenberg Farley & Mesiti P.C.

(57) ABSTRACT

The present invention relates to sulfonamide compounds of formula (I) and formula (II), or a pharmaceutically acceptable salt thereof. The present sulfonamide compounds are useful non-systemic TGR5 agonists that can be used to treat diabetic diseases in human. The present invention provides a pharmaceutical composition containing sulfonamide compounds of formula (I) and formula (II) and a method of making as well as a method of using same in treating patients inflicted with metabolic disorders by administering same. The compounds of the present invention may be used in combination with additional anti-diabetic drugs.

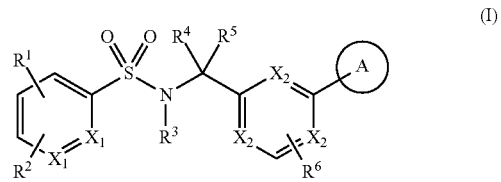

(I)

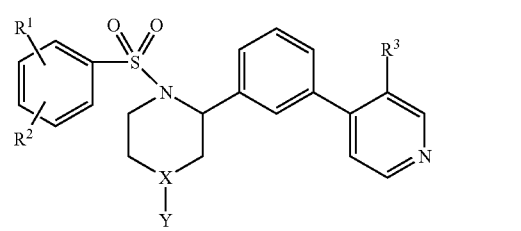

(II)

23 Claims, 9 Drawing Sheets

(51) Int. Cl.
*C07D 213/26* (2006.01)
*C07D 213/65* (2006.01)
*C07D 213/73* (2006.01)
*C07D 235/14* (2006.01)
*C07D 237/08* (2006.01)
*C07D 239/26* (2006.01)
*C07D 241/08* (2006.01)
*C07D 275/02* (2006.01)
*C07D 401/12* (2006.01)
*C07D 405/10* (2006.01)
*C07D 471/04* (2006.01)
*C07D 487/04* (2006.01)
*A61P 35/00* (2006.01)

NON-SYSTEMIC TGR5 AGONISTS

This application claims the benefit of International Application No. PCT/US2017/040010, filed Jun. 29, 2017, which claims the benefit of U.S. Provisional Application Ser. No. 62/357,433, filed on Jul. 1, 2016. The entire teachings of the referenced applications are herein incorporated by reference in their entirety.

FIELD OF THE INVENTION

The present invention relates to novel compounds and pharmaceutically acceptable salts thereof that are useful as non-systemic TGR5 agonists. The present invention also relates to compositions containing such compounds, process of preparing and methods of use thereof.

BACKGROUND OF THE INVENTION

TGR5 (also known as G protein-coupled bile acid receptor 1 (GPBAR1), M-BAR, or BG-371) is a receptor present on L-cells within the gastrointestinal compartment in humans. Upon binding of bile acids, TGR5 causes the release of glucagon-like peptide-1 (GLP-1) which in turn stimulates insulin secretion and suppresses glucagon secretion (Katsuma et al., *Biochem. Biophys. Res. Commun.*, 2005, 329 (1), 386-390). Therapeutic attempts have been made to elevate GLP-1 in the blood to alleviate glycemic controls. One approach involves the use of dipeptidyl peptidase-4 (DPP-4) inhibitors to slow down GLP-1 degradation. Another approach employs GLP-1 analogs that mimic the natural GLP-1. Yet another approach utilizes TGR5 agonists to stimulate the TGR5 receptor and trigger its signal cascades within the L-cells for glucose control.

Multiple TGR5 modulators with diverse structural features have been reported. U.S. Pat. No. 8,114,862 discloses a series of 23-substituted bile acids that mimic natural bile acids as TGR5 modulators. WO2013/164838 discloses TGR5 agonists containing 1, 2, 4-triazole with a linker containing sulfur and their use in treating diabetes, obesity and related disorders. WO2009/026241 discloses TGR5 modulators having a structure of pyrimidin-4-one that is fused with a 5 or 6-membered heterocyclic or heteroaryl group. WO2012/082947 discloses pyrazolyl based TGR5 agonists. WO2011/071565 discloses TGR5 agonists that are imidazole derivatives. WO2012/149236 discloses bicyclic heteroaryl compounds that are TGR5 agonists. WO2013/134527 discloses polycyclic alkaloids as TGR5 agonists. WO2004/067008 discloses TGR5 agonists containing benzodiazepine-2-one. WO2013/096771 discloses TGR5 agonists containing tetrahydroquinoxaline and their use in treating type 2 diabetes mellitus. WO2013/096771 further discloses some TGR5 compounds that are substantially non-bioavailable in the blood stream.

There has been a concern for an increased risk of pancreatitis in type 2 diabetes patients treated with GLP-1-based therapies (Singh et al., *JAMA Intern. Med.*, 2013, 173 (7), 534-539). Subsequent clinical studies, however, do not seem to support this contention (Butler et al., *Diabetes*, 2013, 62 (7), 2595-2604). It remains to be determined if systemic delivery of a TGR5 agonist may attribute to the pancreatitis.

Phillips et al. disclosed trifluoromethyl(pyrimidin-2-yl) azetidine-2-carboxamides as potent, orally bioavailable TGR5 agonists (*J. Med. Chem.*, 2014, 57(8), 3263-3282). The lead Compound (45h) represents a potent and selective TGR5 agonist that has excellent plasma exposure. The authors reported glycemic effect of Compound 45h was lost upon chronic dosing. Phillips et al. questioned toxicological and therapeutic issues that may limit the utility of these systemic TGR5 agonists for treatment of metabolic disease.

There is a continuing need in developing a non-systemic TGR5 agonist, one that is restricted in the gastrointestinal compartment and has clinical safety and efficacy profiles suitable for oral administration in treating metabolic disorders.

SUMMARY OF THE INVENTION

The present invention provides novel compounds represented by formula (I):

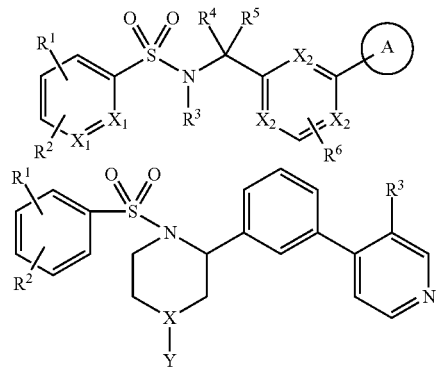

and formula (II):
and pharmaceutically acceptable salts thereof.

The present sulfonamide compounds are useful non-systemic TGR5 agonists to treat metabolic disorders including diabetes and obesity. The present invention provides a pharmaceutical composition containing such compounds as well as a process of making them and a method of administering same to treat patients suffering from metabolic disorders. The present compounds may be used in combination with other anti-diabetic drugs.

DETAILED DESCRIPTION OF THE INVENTION

Definitions

Figure 1:
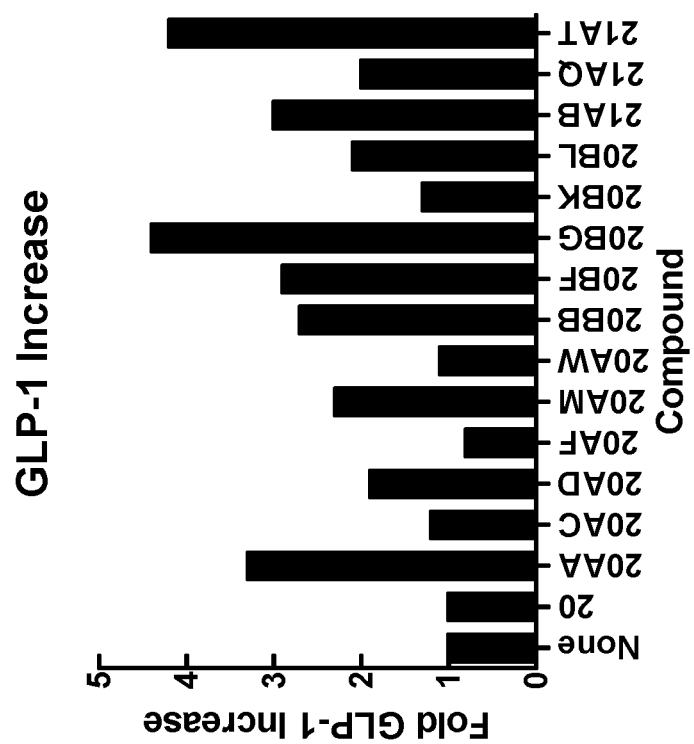
FIG. 1 depicts the fold increase of GLP-1 levels in C57BL/6NTac mice four (4) hours after a single 10 mg/kg oral administration of compounds 20, 20AA, 20AC, 20AD, 20AF, 20AM, 20AW, 20BB, 20BF, 20BG, 20BK, 20BL, 21AB, 21AQ, or 21AT. The mice were dosed with 3 mg/kg sitagliptin exactly 1 hour before oral administration of the compounds.

As used herein, number ranges where provided (e.g., 1-6) refer to each and every number in that range as a discrete embodiment.

As used herein, the term "alkyl" refers to a saturated carbon chain that may be linear, branched or a combination thereof. Exemplary alkyl includes methyl, ethyl, n-propyl, isopropyl, n-butyl, sec- and tert-butyl, pentyl, hexyl and the like. $C_{1-6}$alkyl refers a saturated carbon chain that may be linear, branched or a combination thereof which contains one to six carbon atoms.

As used herein, the term "alkoxy" refers to an alkyl with terminal oxygen. Alkoxy may be linear, branched or a combination thereof. Exemplary alkoxy includes methoxy, ethoxy, propoxy, isopropxy, butoxy and the like.

As used herein, the term "aryl" refers to an aromatic or partially aromatic monocyclic or polycyclic hydrocarbon ring, or an aromatic or partially aromatic hydrocarbon ring that is fused to a cycloalkyl or a heterocycloalkyl group wherein the point of attachment is on the aromatic portion. Exemplary aryl includes phenyl, naphthyl, indanyl, benzocyclobutanyl and the like.

As used herein, the term "cycloalkyl" refers to a saturated monocyclic or polycyclic hydrocarbon ring, or a saturated hydrocarbon ring that is fused to an aryl or heteroaryl group wherein the point of attachment is on the non-aromatic portion. Exemplary cycloalkyl include cyclopropyl, cyclobutyl, cyclopentyl, cyclohexyl, cycloheptyl, tetrahydronaphthyl, decahydronaphthyl and the like.

As used herein, the term "heteroaryl" refers to an aromatic or partially aromatic monocyclic or polycyclic ring in which one or more atoms in the ring, the heteroatom(s), is an element other than carbon and wherein the point of attachment is on the aromatic portion. Heteroatoms are typically oxygen ("O"), sulfur ("S") or nitrogen ("N") atoms. Exemplary heteroaryl include: pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, oxo-dihydroqunoline, indolyl, oxindole, isoquinolyl, dibenzofuranyl and the like.

As used herein, the term "heterocycloalkyl" refers to a saturated monocyclic or polycyclic hydrocarbon ring in which one or more atoms in the ring, the heteroatom(s), is an element other than carbon. Heteroatoms are typically oxygen ("O"), sulfur ("S") or nitrogen ("N") atoms. "Heterocycle" may include a saturated heterocyclic ring that is fused to an aryl or heteroaryl group wherein the point of attachment is on the non-aromatic portion. Exemplary heterocycle includes aziridinyl, azetidinyl, 1,3-benzodioxolyl, dihydroisoindolyl, dihydrobenzodioxinyl, dihydroindolyl, 1,3-dioxanyl, 1,4-dioxanyl, 1,3-dioxolanyl, isoindolinyl, morpholinyl, piperazinyl, pyrrolidinyl, piperidinyl, thiomorpholinyl and the like.

As used herein, the term "halogen" refers to fluorine, chlorine, bromine and iodine.

As used herein, the term "floating bond", when used in connection with a substituent depicted in a structural formula (e.g., ($R^1$)), refers to that substituent (e.g., R') permitted on any available carbon atom in the ring to which the substituent is attached, unless expressly depicted.

As used herein, the term certain group "is optionally substituted" refers to any group having that particular component thereof can be further substituted. For example, "alkyl group is optionally further substituted with" refers any group possessing an alkyl component can be further substituted thereof. The term includes "mono-", "di-" or "tri-" substitutions.

As used herein, the term "meta," "ortho" and "para" (abbreviated as "m-," "o-" and "p-") refers to designate the position of two identical or different substituents relative to each other in a benzene ring. For example, substituents in meta compounds are located in the 1, 3 positions, those in ortho compounds are in the 1,2 positions, and those in para compounds are in the 1, 4 positions.

As used herein, the term "pharmaceutically acceptable" refers to compositions, polymers, solvates, and dosage forms which are, within the scope of sound medical judgment, suitable for use in contact with the tissues of human beings and animals without excessive toxicity, irritation, allergic response, or other problem or complication, commensurate with a reasonable benefit and risk ratio.

As used herein, the term "pharmaceutically acceptable salt" refers to a derivative of the compound of the present invention wherein the parent compound is modified by making acid or base salts thereof. It includes mineral or organic acid salts of basic residues such as amines; and alkali or organic basic salts of acidic residues such as carboxylic acids. Exemplary pharmaceutically acceptable salts include acetate, bicarbonate, bisulfate, formate, hydrochloride, sulfate, trifluoroacetic acid and the like.

As used herein, the term "pharmaceutical composition" refers to a composition comprising a compound of the present invention together with a pharmaceutical acceptable carrier.

As used herein, the term "pharmaceutically acceptable carrier" refers to a pharmaceutically acceptable excipient that is not injurious to a patient. Exemplary pharmaceutically acceptable carrier includes starch, cellulose, gelatin, talc, glycol, polyol, ester, agar, buffering agents, alginic acid and the like that are employed in pharmaceutical formulations.

As used herein, the term "administering" or "administration" refers to providing a compound, a pharmaceutically acceptable salt, solvate or prodrug thereof to a human subject in need of treatment such as oral administration.

As used herein, the term "mammal" refers to animal species that has the distinguished features by the presence of sweat glands, including those that are specialized to produce milk to nourish the young. Exemplary mammals include human, mouse, rat, dog and the like.

As used herein, the term "treating" or "treatment" refers to reducing, ameliorating or preventing the regression of the disease state or condition.

As used herein, the term "therapeutically effective amount" refers to an amount of the compound of the present invention which, as compared to a corresponding human subject who has not received such an amount, results in improved treatment, prevention, or amelioration of a metabolic disease or disorder. The amount will depend on the particular disorder, co-administrated compounds, if any, and the characteristics of the human subject, such as general health, other diseases, age, sex, genotype, body weight and tolerance to drugs. Those skilled in the art will be able to determine appropriate dosages depending on these and other factors.

As used herein, the term "combination" refers to a compound of the present invention and an additional therapeutic agent. Exemplary therapeutic agents include insulin, GLP-1 mimics, DPP-4 inhibitors and the like. DPP-4 inhibitors include, but not limited to alogliptin, linagliptin, saxagliptin, sitagliptin, anagliptin, teneligliptin, trelagliptin, vildagliptin, gemigliptin, omarigliptin, evogliptin, dutogliptin, and the like.

As used herein, the term "metabolic disorder" refers to a disorder that disrupts the normal process of converting food to energy on a cellular level (i.e., metabolism that involves the processing or transport of proteins (amino acids), carbohydrates (sugars and starches), or lipids (fatty acids). Such disruption is usually due to a hormone or enzyme deficiency.

As used herein, the term "TGR5-related metabolic disorder" refers to a metabolic disorder that is resulted from a deficiency in TGR5 signaling. Exemplary TGR5-related metabolic disorders include, but not limited to pre-diabetes, type-2 diabetes, obesity, fibrosing cholangitis, inflammatory diseases such as colitis, digestive diseases such as pancreatitis, and cancer. Such metabolic disorders are understood to be treatable with a TGR5 agonist.

As used herein, the term "diabetic" or "diabetes" or "diabetes mellitus" are used interchangeably in this application to refer to a group of metabolic disorders characterized by hyperglycemia resulting from defects in insulin secretion, insulin action, or both. The term "type-2 diabetes (formerly adult-onset diabetes)" refers to a human clinically diagnosed with any of the three tests: (i) having a fasting plasma blood glucose level of 126 mg/dL or greater on two separate occasions; (ii) an oral glucose tolerance of 200 mg/dL or greater; or (iii) an A1C (hemoglobin A1c test) of 6.5% or greater.

As used herein, the term "pre-diabetic" or "pre-diabetes" refers to a condition in which blood glucose levels are higher than normal, but not high enough to be classified as diabetes. Pre-diabetes in humans is clinically diagnosed with any of the three tests: (i) having a fasting plasma blood glucose level between 100 and 125 mg/dL ("impaired fasting glucose"); (ii) an oral glucose tolerance between 140 and 199 mg/dL ("impaired glucose tolerance"); or (iii) an A1C of 5.7-6.4 percent.

As used herein, the term "non-systemic" refers to minimized systemic exposure of a compound after ingestion. For purposes of this application, "non-systemic" and "low plasma exposure" are used interchangeably and refer to a $C_{max}$ of <200 ng/mL.

As used herein, the term "non-absorbed" refers to a compound that is restricted to the gut compartment and acts within the intestinal lumen without reaching the systemic circulation.

As used herein, the term "bioavailability" or "systemic availability" refers to the extent to which a compound that is taken up by a specific tissue or organ after administration; the proportion of the dose of a drug that reaches the systemic circulation intact after administration by a route other than intravenous. Bioavailability is distinct from its chemical potency.

As used herein, the term "$EC_{50}$" refers to the concentration of a compound which induces a response halfway between the baseline and maximum after a specified exposure time and is used as a measure of compound potency. It represents the concentration of a compound where 50% of its maximal effect is observed.

As used herein, the term "obesity" refers to an adult human who has a body mass index ("BMI") of 30 or higher.

As used herein, the term "pharmacokinetics" (PK) refers to how the body affects a specific drug after administration through the mechanisms of absorption and distribution, as well as the chemical changes of the substance, and the effects and routes of excretion of the metabolites of the drug. Measured PK metrics include: $C_{max}$ (peak plasma concentration of a drug after administration), $t_{max}$ (time to reach $C_{max}$), area under the curve ("AUC" the integral of the concentration-time curve), bioavailability and the like.

The present invention relates to novel sulfonamide compounds and pharmaceutically acceptable salts thereof that are useful in the treatment of a TGR5 related metabolic disease such as type-2 diabetes. The sulfonamide compounds are non-systemic TGR5 agonists. The present invention also relates to pharmaceutical compositions containing the novel sulfonamide compounds, process of making and methods of using same in treating metabolic disorders.

In one aspect, the present invention relates to a compound of formula (I):

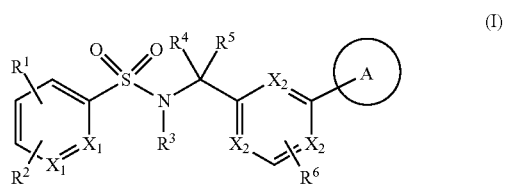

or a pharmaceutically acceptable salt thereof, wherein:
each $X_1$ is independently CH or N;
$R^1$ and $R^2$ are each independently H, halogen, $C_{1-6}$alkyl, $C_{1-6}$alkoxy, CN, $NO_2$ or $NH_2$, wherein alkyl is optionally substituted with 1-4 halogen;
each optionally mono-, di-, or tri-substituted with substituents independently selected from halogen and $C_{1-3}$alkyl, wherein alkyl is optionally substituted with 1-4 halogen;

$R^3$ is H,

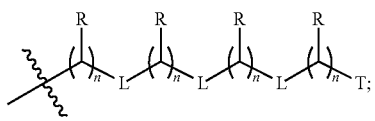

$R^4$ and $R^5$ are each independently H, $C_{1-6}$alkyl, $C_{1-6}$cycloalkyl, phenyl, $C_{1-6}$alkyl-OH, $C_{1-6}$alkyl-CN, $C_{1-6}$alkyl-NH$_2$, $C_{0-6}$alkylC(O)OC$_{1-6}$alkyl, $C_{0-6}$alkylC(O)OH, $C_{0-6}$alkylC(O)NHC$_{1-6}$alkyl, $C_{0-6}$alkylC(O)N(C$_{1-6}$alkyl)(C$_{1-6}$alkyl), $C_{0-6}$alkylC(O)NHC$_{1-6}$alkylS(O)$_2$OH or $C_{0-6}$alkylNHC(O)NHC$_{1-6}$alkylS(O)$_2$OH, or $R^4$ and $R^5$ together with the C to which they are attached form $C_{1-6}$cycloalkyl or oxetanyl;

each $X_2$ is independently CH or N, and no more than one $X_2$ can be N;

$R^6$ is halogen, $C_{1-6}$alkyl, $C_{1-6}$alkoxy, OH or OC$_{1-6}$alkyl-C(O)OH;

A is

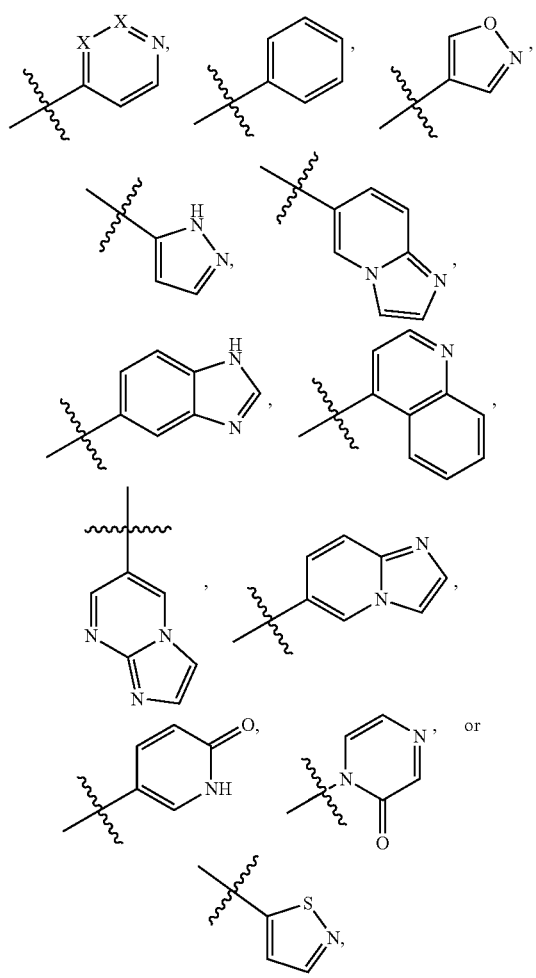

each optionally mono-, di-, or tri-substituted with substituents independently selected from halogen, $C_{1-3}$alkyl, $C_{1-3}$alkoxy, OC$_{1-3}$alkylOC$_{1-3}$alkyl, $C_{1-3}$alkylOH, OH, NH$_2$, N(C$_{1-3}$alkyl)(C$_{1-3}$alkyl), C(O)N(C$_{1-3}$alkyl)(C$_{1-3}$alkyl), NC(O)C$_{1-3}$alkyl, C(O)OC$_{1-3}$alkyl and $C_{1-3}$alkylC(O)NHC$_{1-3}$alkylS(O)$_2$OH, wherein alkyl is optionally substituted with 1-4 halogen;

each L is independently absent,

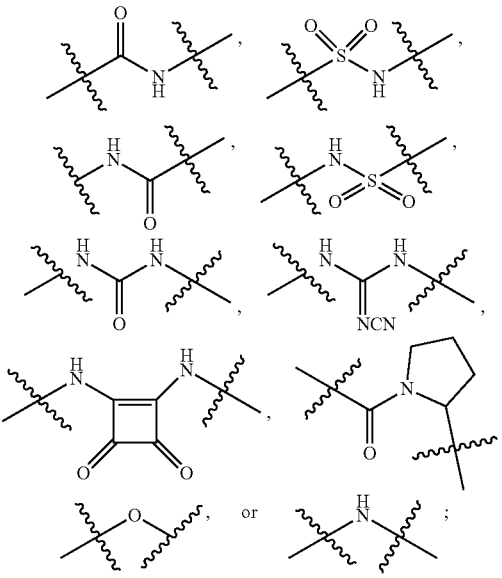

T is NH$_2$, NH(C$_{1-6}$alkyl), NH(C$_{1-6}$alkyl)(C$_{1-6}$alkyl),

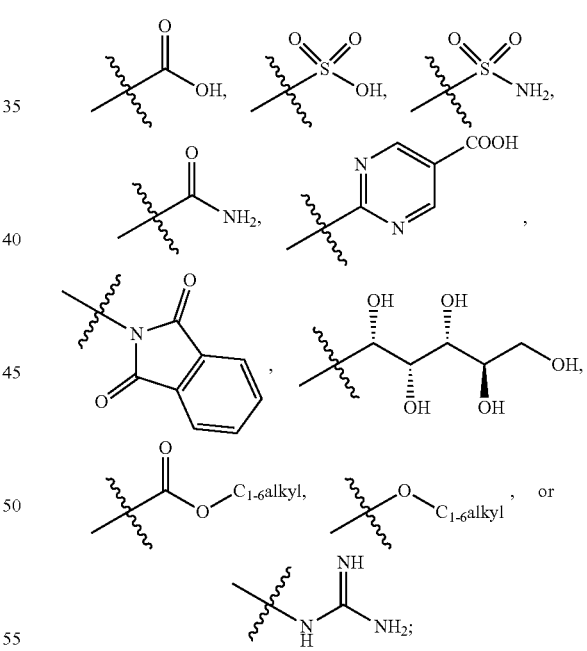

each n is independently 0, 1, 2, 3, 4 or 5, and at least one n is not 0;

each R is $C_{1-3}$alkyl, $C_{1-3}$alkyl-OH or $C_{0-3}$alkyl-C(O)OH; and each X is independently CH or N, and no more than two X can be N.

In one embodiment, $X_1$ is CH; and $X_2$ is CH.

In another embodiment, $R^1$ and $R^2$ are each independently H, halogen, $C_{1-3}$alkyl, CN, NO$_2$ or NH$_2$. Optionally, alkyl is substituted with 1-4 halogen.

In another embodiment, $R^1$ and $R^2$ are each independently H, F, Br, Cl, $CH_3$, $CF_3$ or $NO_2$.

In another embodiment, $R^3$ is hydrogen.

In another embodiment, $R^3$ is

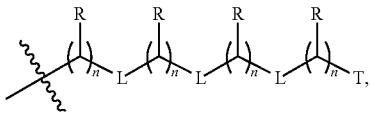

each n is independently 0, 1, 2, 3 or 4, and at least one n is not 0.

Preferably, each R is C(O)OH, $CH_2$C(O)OH or $CH_2$OH.

In another embodiment, $R^4$ and $R^5$ are each independently H, $C_{1-3}$alkyl, $C_{1-3}$cycloalkyl, $C_{1-3}$alkyl-CN, $C_{1-3}$alkylC(O)OC$_{1-3}$alkyl, $C_{1-3}$alkylC(O)NHC$_{1-3}$alkyl, $C_{1-3}$alkylC(O)N(C$_{1-3}$alkyl)($C_{1-3}$alkyl) or $C_{1-3}$alkylC(O)NHC$_{1-3}$alkylS(O)$_2$OH, or $R^4$ and $R^5$ together with the C to which they are attached form $C_{1-3}$cycloalkyl.

In another embodiment, $R^4$ and $R^5$ are each independently H, $CH_3$, $CH_2CH_3$, cyclopropyl, $CH_2CH_2$CN, $CH_2CH_2CH_2$CN, $CH_2$C(O)OCH$_2$CH$_3$, $CH_2$C(O)NHCH$_3$, $CH_2$C(O)NH(CH$_3$)$_2$ or $CH_2CH_2CH_2$C(O)NHCH$_2$S(O)$_2$OH, or $R^4$ and $R^5$ together with the C to which they are attached form cyclopropyl.

Preferably, the C to which $R^4$ and $R^5$ are attached form S configuration.

In another embodiment, $R^6$ is halogen, $C_{1-3}$alkyl, $C_{1-3}$alkoxy, OH or OC$_{1-3}$alkyl-C(O)OH.

In another embodiment, $R^6$ is F, $CH_3$, $OCH_3$ or OH.

In another embodiment, A is

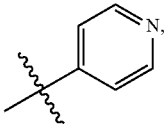 [SMILES: *c1ccncc1]

optionally mono-, di-, or tri-substituted with substituents independently selected from halogen, $C_{1-3}$alkyl, $C_{1-3}$alkoxy, $C_{1-3}$alkylOH, OH, $NH_2$ and C(O)OC$_{1-3}$alkyl, wherein alkyl is optionally substituted with 1-4 halogen.

In another embodiment, A is

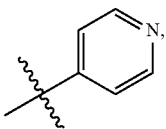 [SMILES: *c1ccncc1]

optionally mono- or di-substituted with substituents independently selected from F, Cl, $CH_3$, $CH_2CH_3$, $OCH_3$, $OCH_2CH_3$, OCH(CH$_3$)$_2$, $CH_2$OH, OH, $NH_2$ and C(O)OCH$_3$.

In one embodiment, the present invention provides a compound of:

1) N-(3-(3,5-dimethylisoxazol-4-yl)benzyl)-3-(trifluoromethyl)benzenesulfonamide;
2) N-(3-(3,5-dimethylisoxazol-4-yl)benzyl)-4-(trifluoromethyl)benzenesulfonamide;
3) 4-chloro-N-(3-(3,5-dimethylisoxazol-4-yl)benzyl)benzenesulfonamide;
4) N-(2-(3-(3,5-dimethylisoxazol-4-yl)phenyl)propan-2-yl)-3-(trifluoromethyl)benzenesulfonamide;
5) N-(2-(3-(pyridin-4-yl)phenyl)propan-2-yl)-3-(trifluoromethyl)benzenesulfonamide;
6) N-(2-(3-(3-fluoropyridin-4-yl)phenyl)propan-2-yl)-3-(trifluoromethyl)benzenesulfonamide;
7) N-(2-(3-(3-chloropyridin-4-yl)phenyl)propan-2-yl)-3-(trifluoromethyl)benzenesulfonamide;
8) N-(2-(3-(2-chloropyridin-4-yl)phenyl)propan-2-yl)-3-(trifluoromethyl)benzenesulfonamide;
9) 3-(trifluoromethyl)-N-(2-(3-(2-(trifluoromethyl)pyridin-4-yl)phenyl)propan-2-yl)benzenesulfonamide;
10) N-(2-(3-(3-methoxypyridin-4-yl)phenyl)propan-2-yl)-3-(trifluoromethyl)benzenesulfonamide;
11) N-(2-(3-(quinolin-4-yl)phenyl)propan-2-yl)-3-(trifluoromethyl)benzenesulfonamide;
12) N-(2-(3-(2-methylpyridin-4-yl)phenyl)propan-2-yl)-3-(trifluoromethyl)benzenesulfonamide;
13) N-(2-(3-(2-aminopyridin-4-yl)phenyl)propan-2-yl)-3-(trifluoromethyl)benzenesulfonamide;
14) N-(2-(3-(3-aminopyridin-4-yl)phenyl)propan-2-yl)-3-(trifluoromethyl)benzenesulfonamide;
15) N-(2-(3-(3-hydroxypyridin-4-yl)phenyl)propan-2-yl)-3-(trifluoromethyl)benzenesulfonamide;
16) N-(2-(3-(3-fluoro-5-methylpyridin-4-yl)phenyl)propan-2-yl)-3-(trifluoromethyl)benzenesulfonamide;
17) N-(3-(3-fluoropyridin-4-yl)benzyl)-3-(trifluoromethyl)benzenesulfonamide;
18) N-(3-(3-chloropyridin-4-yl)benzyl)-3-(trifluoromethyl)benzenesulfonamide;
19) N-(3-(pyridin-4-yl)benzyl)-3-(trifluoromethyl)benzenesulfonamide;
20) N-(4-fluoro-3-(pyridin-4-yl)benzyl)-3-(trifluoromethyl)benzenesulfonamide;
21) N-(3-(3-chloropyridin-4-yl)-4-fluorobenzyl)-3-(trifluoromethyl)benzenesulfonamide;
22) N-(2-fluoro-5-(pyridin-4-yl)benzyl)-3-(trifluoromethyl)benzenesulfonamide;
23) N-(5-(3-chloropyridin-4-yl)-2-fluorobenzyl)-3-(trifluoromethyl)benzenesulfonamide;
24) (S)—N-(1-(3-(pyridin-4-yl)phenyl)ethyl)-3-(trifluoromethyl)benzenesulfonamide;
25) (S)—N-(1-(3-(3-chloropyridin-4-yl)phenyl)ethyl)-3-(trifluoromethyl)benzenesulfonamide;
26) (S)—N-(1-(3-(3-fluoropyridin-4-yl)phenyl)ethyl)-3-(trifluoromethyl)benzene sulfonamide;
27) (S)—N-(1-(3-(3-methoxypyridin-4-yl)phenyl)ethyl)-3-(trifluoromethyl)benzenesulfonamide;
28) (R)—N-(1-(3-(pyridin-4-yl)phenyl)ethyl)-3-(trifluoromethyl)benzenesulfonamide;
29) (R)—N-(1-(3-(3-chloropyridin-4-yl)phenyl)ethyl)-3-(trifluoromethyl)benzenesulfonamide;
30) (R)—N-(1-(3-(3-fluoropyridin-4-yl)phenyl)ethyl)-3-(trifluoromethyl)benzenesulfonamide;
31) (R)—N-(1-(3-(3-methoxypyridin-4-yl)phenyl)ethyl)-3-(trifluoromethyl)benzenesulfonamide;
32) N-(3-(3-methylpyridin-4-yl)benzyl)-3-(trifluoromethyl)benzenesulfonamide;
33) N-(3-(3-aminopyridin-4-yl)benzyl)-3-(trifluoromethyl)benzenesulfonamide;
34) 3-(trifluoromethyl)-N-(3-(3-(trifluoromethyl)pyridin-4-yl)benzyl)benzenesulfonamide;
35) N-(3-(6-methylpyrimidin-4-yl)benzyl)-3-(trifluoromethyl)benzenesulfonamide;

36) 3-(trifluoromethyl)-N-(3-(6-(trifluoromethyl)pyrimidin-4-yl)benzyl)benzenesulfonamide;
37) N-(3-(pyrimidin-4-yl)benzyl)-3-(trifluoromethyl)benzenesulfonamide;
38) N-(2-(3-(pyridazin-4-yl)phenyl)propan-2-yl)-2-(trifluoromethyl)benzenesulfonamide;
39) N-(2-(3-(3-hydroxypyridin-4-yl)phenyl)propan-2-yl)-2-(trifluoromethyl)benzenesulfonamide;
40) N-(1-(3-(3-methoxypyridin-4-yl)phenyl)cyclopropyl)-3-(trifluoromethyl)benzenesulfonamide;
41) (S)-3-chloro-2-methyl-N-(1-(3-(pyridazin-4-yl)phenyl)ethyl)benzenesulfonamide;
42) N-((3'-methoxy-[2,4'-bipyridin]-6-yl)methyl)-3-(trifluoromethyl)benzenesulfonamide;
43) N-((3'-methoxy-[4,4'-bipyridin]-2-yl)methyl)-3-(trifluoromethyl)benzenesulfonamide;
44) N-((3'-methoxy-[2,4'-bipyridin]-4-yl)methyl)-3-(trifluoromethyl)benzenesulfonamide;
45) N-((3'-methoxy-[4,4'-bipyridin]-2-yl)methyl)-2-(trifluoromethyl)benzenesulfonamide;
46) N-(4-chloro-3-(pyridin-4-yl)benzyl)-3-(trifluoromethyl)benzenesulfonamide;
47) N-(3-chloro-5-(pyridin-4-yl)benzyl)-3-(trifluoromethyl)benzenesulfonamide;
48) N-(2-(4-methyl-3-(pyridin-4-yl)phenyl)propan-2-yl)-3-(trifluoromethyl)benzenesulfonamide;
49) (+/−) N-(1-(3-(pyridin-4-yl)phenyl)propyl)-3-(trifluoromethyl)benzenesulfonamide;
50) (+/−) N-((3-(3-methoxypyridin-4-yl)phenyl)(phenyl)methyl)-2-(trifluoromethyl)benzenesulfonamide;
51) (S)—N-(1-(3-(3-methoxypyridin-4-yl)phenyl)propyl)-2-(trifluoromethyl)benzenesulfonamide;
52) methyl 2-(3-(3-methoxypyridin-4-yl)phenyl)-2-(3-(trifluoromethyl)phenyl sulfonamido)acetate;
53) N-(3-(3-methoxypyridin-4-yl)phenethyl)-2-(trifluoromethyl)benzenesulfonamide;
54) N-(3-(3,5-dimethylisoxazol-4-yl)benzyl)-3-methylbenzenesulfonamide;
55) 3-chloro-N-(3-(3,5-dimethylisoxazol-4-yl)benzyl)benzenesulfonamide;
56) N-(3-(3,5-dimethylisoxazol-4-yl)benzyl)-3-methoxybenzenesulfonamide;
57) N-(3-(3,5-dimethylisoxazol-4-yl)benzyl)-2-(trifluoromethyl)-benzene sulfonamide;
58) 4-chloro-N-(3-(3,5-dimethylisoxazol-4-yl)benzyl)-3-(trifluoromethyl)benzenesulfonamide;
59) N-(3-(3,5-dimethylisoxazol-4-yl)benzyl)-4-fluoro-3-(trifluoromethyl)benzenesulfonamide;
60) N-(3-(3,5-dimethylisoxazol-4-yl)benzyl)-2-fluoro-5-(trifluoromethyl)benzenesulfonamide;
61) N-(3-(3,5-dimethylisoxazol-4-yl)benzyl)-3-fluoro-5-(trifluoromethyl)-benzenesulfonamide;
62) N-(3-(3,5-dimethylisoxazol-4-yl)benzyl)-3,5-bis(trifluoromethyl)-benzenesulfonamide
63) 3-methyl-N-(3-(pyridin-4-yl)benzyl)benzenesulfonamide;
64) 3-chloro-N-(3-(pyridin-4-yl)benzyl)benzenesulfonamide;
65) 3-fluoro-N-(3-(pyridin-4-yl)benzyl)benzenesulfonamide;
66) 3-methoxy-N-(3-(pyridin-4-yl)benzyl)benzenesulfonamide;
67) N-(3-(pyridin-4-yl)benzyl)-2-(trifluoromethyl)benzenesulfonamide;
68) 3-nitro-N-(3-(pyridin-4-yl)benzyl)benzenesulfonamide;
69) 2-nitro-N-(3-(pyridin-4-yl)benzyl)benzenesulfonamide;
70) 2-methyl-N-(3-(pyridin-4-yl)benzyl)benzenesulfonamide;
71) 3-bromo-N-(3-(pyridin-4-yl)benzyl)benzenesulfonamide;
72) 2-chloro-N-(3-(pyridin-4-yl)benzyl)benzenesulfonamide;
73) 2-fluoro-N-(3-(pyridin-4-yl)benzyl)benzenesulfonamide;
74) 3-bromo-N-(2-(3-(3-methoxypyridin-4-yl)-phenyl)propan-2-yl)-benzenesulfonamide;
75) N-(2-(3-(3-methoxypyridin-4-yl)phenyl)propan-2-yl)-2-nitrobenzenesulfonamide;
76) N-(3-(pyridin-4-yl)benzyl)-2-(trifluoromethyl)benzenesulfonamide;
77) 2-methoxy-N-(2-(3-(3-methoxypyridin-4-yl)-phenyl)propan-2-yl)-5-(trifluoromethyl)benzenesulfonamide;
78) 2-chloro-N-(2-(3-(3-methoxypyridin-4-yl)phenyl)propan-2-yl)benzene sulfonamide;
79) 3-chloro-N-(2-(3-(3-methoxypyridin-4-yl)phenyl)propan-2-yl)benzene sulfonamide;
80) N-(2-(3-(3-methoxypyridin-4-yl)phenyl)propan-2-yl)-3-methylbenzene sulfonamide;
81) 3-bromo-N-(2-(3-(3-methoxypyridin-4-yl)phenyl)propan-2-yl)-5-(trifluoromethyl)benzenesulfonamide;
82) 2,3-dichloro-N-(2-(3-(3-methoxypyridin-4-yl)phenyl)propan-2-yl)benzenesulfonamide;
83) 4-fluoro-N-(2-(3-(3-methoxypyridin-4-yl)-phenyl)propan-2-yl)-2-(trifluoromethyl)benzenesulfonamide;
84) 2,5-dichloro-N-(2-(3-(3-methoxypyridin-4-yl)phenyl)propan-2-yl)benzenesulfonamide;
85) 4-chloro-N-(2-(3-(3-methoxypyridin-4-yl)phenyl)propan-2-yl)-2-(trifluoromethyl)benzenesulfonamide;
86) 2,4-dichloro-N-(2-(3-(3-methoxypyridin-4-yl)phenyl)propan-2-yl)benzenesulfonamide;
87) 5-chloro-N-(2-(3-(3-methoxypyridin-4-yl)phenyl)propan-2-yl)-2-nitrobenzenesulfonamide;
88) 2,4-dichloro-N-(2-(3-(3-methoxypyridin-4-yl)phenyl)propan-2-yl)benzenesulfonamide;
89) N-(2-(3-(3-methoxypyridin-4-yl)phenyl)propan-2-yl)-2-nitro-4-(trifluoromethyl)benzenesulfonamide;
90) N-(2-(3-(3-methoxypyridin-4-yl)phenyl)propan-2-yl)-2,5-bis(trifluoromethyl)benzenesulfonamide;
91) 3-chloro-N-(2-(3-(3-methoxypyridin-4-yl)phenyl)propan-2-yl)-2-methyl benzenesulfonamide;
92) N-(2-(3-(3-methoxypyridin-4-yl)phenyl)propan-2-yl)-2-methyl-3-(trifluoromethyl)benzenesulfonamide;
93) 2-chloro-4-cyano-N-(2-(3-(3-methoxypyridin-4-yl)phenyl)propan-2-yl)benzenesulfonamide;
94) (S)-3-bromo-N-(1-(3-(3-methoxypyridin-4-yl)-phenyl)ethyl)benzenesulfonamide;
95) (S)—N-(1-(3-(3-methoxypyridin-4-yl)phenyl)ethyl)-2-nitrobenzenesulfonamide
96) (S)—N-(1-(3-(3-methoxypyridin-4-yl)phenyl)ethyl)-2-(trifluoromethyl)benzenesulfonamide;
97) (S)-3-bromo-N-(1-(3-(3-chloropyridin-4-yl)-phenyl)ethyl)benzenesulfonamide;
98) (S)—N-(1-(3-(3-chloropyridin-4-yl)phenyl)ethyl)-2-nitrobenzenesulfonamide;
99) (S)—N-(1-(3-(3-chloropyridin-4-yl)phenyl)ethyl)-2-(trifluoromethyl)benzenesulfonamide;
100) 3-chloro-2-methyl-N-(2-(3-(3-methylpyridin-4-yl)phenyl)-propan-2-yl)benzenesulfonamide;
101) 2,3-dichloro-N-(2-(3-(3-methylpyridin-4-yl)phenyl)propan-2-yl)benzenesulfonamide;
102) 5-bromo-2-methyl-N-(2-(3-(3-methylpyridin-4-yl)phenyl)-propan-2-yl)benzenesulfonamide;

103) 2-methyl-N-(2-(3-(3-methylpyridin-4-yl)phenyl)-propan-2-yl)benzenesulfonamide;
104) 3-chloro-N-(2-(3-(3-ethylpyridin-4-yl)phenyl)propan-2-yl)-2-methylbenzenesulfonamide;
105) (S)-3-chloro-N-(4-cyano-1-(3-(3-methylpyridin-4-yl)phenyl)butyl)-2-methylbenzenesulfonamide;
106) N-(2-(3-(3-ethylpyridin-4-yl)-5-methoxyphenyl)-propan-2-yl)-2-(trifluoromethyl)benzenesulfonamide;
107) N-(2-(3-(6-oxo-1,6-dihydropyridin-3-yl)phenyl)propan-2-yl)-2-(trifluoromethyl)benzenesulfonamide;
108) (S)-3-Chloro-2-methyl-N-(1-(3-(1-methyl-1H-pyrazol-5-yl)phenyl)ethyl)benzenesulfonamide;
109) N-(2-(3-(3-ethylpyridin-4-yl)phenyl)propan-2-yl)-2-(trifluoromethyl)benzenesulfonamide;
110) N-(2-(3-(3-methylpyridin-4-yl)phenyl)propan-2-yl)-3-(trifluoromethyl)benzenesulfonamide;
111) N-(2-(3-(3-ethylpyridin-4-yl)phenyl)propan-2-yl)-3-(trifluoromethyl)benzenesulfonamide;
112) N-(2-(3-(2,3-dimethylpyridin-4-yl)phenyl)propan-2-yl)-3-(trifluoromethyl)benzenesulfonamide;
113) N-(2-(3-(3,5-dimethylpyridin-4-yl)phenyl)propan-2-yl)-3-(trifluoromethyl)benzenesulfonamide;
114) N-(2-(3-(3-(hydroxymethyl)-pyridin-4-yl)phenyl)propan-2-yl)-3-(trifluoromethyl)benzenesulfonamide;
115) N-(2-(3-(imidazo[1,2-a]pyridin-6-yl)phenyl)propan-2-yl)-3-(trifluoromethyl)benzenesulfonamide;
116) (S)—N-(1-(3-(3-methylpyridin-4-yl)phenyl)ethyl)-3-(trifluoromethyl)-benzenesulfonamide;
117) (R)—N-(1-(3-(3-methylpyridin-4-yl)phenyl)ethyl)-3-(trifluoromethyl)-benzenesulfonamide;
118) N-(2-(3-(3-methylpyridin-4-yl)phenyl)propan-2-yl)-2-(trifluoromethyl)benzenesulfonamide;
119) N-(2-(3-(imidazo[1,2-a]pyridin-6-yl)phenyl)propan-2-yl)-2-(trifluoromethyl)benzenesulfonamide;
120) N-(2-(3-(7-methylimidazo[1,2-a]pyridin-6-yl)phenyl)propan-2-yl)-2-(trifluoromethyl)benzenesulfonamide;
121) N-(2-(3-(1H-benzo[d]imidazol-5-yl)phenyl)propan-2-yl)-2-(trifluoromethyl)benzenesulfonamide;
122) N-(2-(3-(imidazo[1,2-a]pyrimidin-6-yl)phenyl)propan-2-yl)-2-(trifluoromethyl)-benzenesulfonamide;
123) N-(2-(3-(3-(hydroxymethyl)pyridin-4-yl)phenyl)propan-2-yl)-2-(trifluoromethyl)benzenesulfonamide;
124) N-(2-(3-(3-ethylpyridin-4-yl)phenyl)propan-2-yl)-2-nitrobenzenesulfonamide;
125) N-(2-(3-(3-methylpyridin-4-yl)phenyl)propan-2-yl)-2-nitrobenzenesulfonamide;
126) (S)—N-(1-(3-(3-ethylpyridin-4-yl)phenyl)ethyl)-2-(trifluoromethyl)benzenesulfonamide;
127) (S)—N-(1-(3-(3-methylpyridin-4-yl)phenyl)ethyl)-2-(trifluoromethyl)benzenesulfonamide;
128) (R)—N-(1-(3-(3-ethylpyridin-4-yl)phenyl)ethyl)-2-(trifluoromethyl)benzenesulfonamide;
129) (R)—N-(1-(3-(3-methylpyridin-4-yl)phenyl)ethyl)-2-(trifluoromethyl)benzenesulfonamide;
130) (+/−) N-(1-(3-(3-methylpyridin-4-yl)phenyl)propyl)-3-(trifluoromethyl)benzenesulfonamide;
131) (+/−) N-(cyclopropyl(3-(3-methylpyridin-4-yl)phenyl)-methyl)-2-(trifluoromethyl)benzenesulfonamide;
132) (S)—N-(1-(3-(3-methylpyridin-4-yl)phenyl)propyl)-2-(trifluoromethyl)benzenesulfonamide;
133) (S)—N-(1-(3-(imidazo[1,2-a]pyridin-6-yl)phenyl)propyl)-2-(trifluoromethyl)benzenesulfonamide;
134) (S)—N-(1-(3-(3-methylpyridin-4-yl)phenyl)propyl)-3-(trifluoromethyl)benzenesulfonamide;
135) (S)—N-methyl-3-(3-(3-methylpyridin-4-yl)phenyl)-3-(2-trifluoromethyl)phenylsulfonamido)propanamide;
136) (S)—N,N-dimethyl-3-(3-(3-methylpyridin-4-yl)phenyl)-3-(2-(trifluoromethyl)phenylsulfonamido)propanamide;
137) (S)—N-(4-cyano-1-(3-(3-methylpyridin-4-yl)phenyl)-butyl)-2-(trifluoromethyl)-benzenesulfonamide;
138) N-(3-(3-methylpyridin-4-yl)phenethyl)-2-(trifluoromethyl)benzenesulfonamide;
139) Methyl 4-(3-(2-(2-(trifluoromethyl)phenylsulfonamido)propan-2-yl)phenyl) nicotinate;
140) N-(2-(3-(5-methylpyrimidin-4-yl)phenyl)propan-2-yl)-2-(trifluoromethyl)benzenesulfonamide;
141) N-(2-(3-(2-(dimethylamino)-pyridin-4-yl)phenyl)propan-2-yl)-2-(trifluoromethyl)benzenesulfonamide;
142) (S)—N-(4-cyano-1-(3-(3-ethylpyridin-4-yl)phenyl)butyl)-2-(trifluoromethyl)benzenesulfonamide;
143) N-(3-cyano-1-(3-(3-methylpyridin-4-yl)phenyl)-propyl)-2-(trifluoromethyl)benzenesulfonamide;
144) (S)-3-Chloro-2-methyl-N-(1-(3-(3-methylpyridin-4-yl)phenyl)ethyl)benzenesulfonamide;
145) (S)-3-chloro-2-methyl-N-(1-(3-(4-methylisothiazol-5-yl)-phenyl)ethyl)benzenesulfonamide;
146) (S)-3-chloro-N-(1-(3-(2,3-dimethylpyridin-4-yl)phenyl)ethyl)-2-methylbenzenesulfonamide;
147) 3-chloro-2-methyl-N-(3-(3-(3-methylpyridin-4-yl)phenyl)oxetan-3-yl)benzenesulfonamide;
148) N-(2-(3-(3-(2-methoxyethoxy)pyridin-4-yl)phenyl)propan-2-yl)-3-(trifluoromethyl)benzenesulfonamide;
149) N-(2-(3-(3-isopropoxypyridin-4-yl)phenyl)propan-2-yl)-3-(trifluoromethyl)benzenesulfonamide;
150) N-(2-(3-(3-ethoxypyridin-4-yl)phenyl)propan-2-yl)-3-(trifluoromethyl)benzenesulfonamide;
151) N-(2-(3-(3-ethoxypyridin-4-yl)phenyl)propan-2-yl)-2-(trifluoromethyl)benzenesulfonamide;
152) N-(4-(3-(2-(2-(trifluoromethyl)phenylsulfonamido) propan-2-yl)phenyl)pyridin-2-yl)acetamide;
153) 2-amino-N-(2-(3-(3-methoxypyridin-4-yl)phenyl)propan-2-yl)benzenesulfonamide;
154) (S)-2-amino-N-(1-(3-(3-methylpyridin-4-yl)phenyl)-ethyl)benzenesulfonamide
155) N,N-dimethyl-4-(3-(2-(2-(trifluoromethyl)phenylsulfonamido)propan-2-yl)phenyl)nicotinamide;
156) (S)-3-chloro-2-methyl-N-(1-(3-(2-oxopyrazin-1(2H)-yl)phenyl)ethyl)benzenesulfonamide;
157) Methyl 2-(N-(2-(3-(3-methylpyridin-4-yl)phenyl)propan-2-yl)-2-(trifluoromethyl)phenylsulfonamido)acetate;
158) N-(2-methoxyethyl)-N-(2-(3-(3-methylpyridin-4-yl)phenyl)propan-2-yl)-2-(trifluoromethyl)benzenesulfonamide;
159) 4-(N-(2-(3-(3-methylpyridin-4-yl)phenyl)propan-2-yl)-2-(trifluoromethyl)phenylsulfonamido)butanoic acid;
160) Ethyl 4-(N-(2-(3-(3-methylpyridin-4-yl)phenyl)propan-2-yl)-2-(trifluoromethyl)phenylsulfonamido)butanoate;
161) (S)-4-(3-chloro-2-methyl-N-(1-(3-(pyridin-4-yl)phenyl)ethyl)phenylsulfonamido) butanoic acid;
162) (S)-4-(3-chloro-N-(1-(3-(2,3-dimethylpyridin-4-yl)phenyl)ethyl)-2-methylphenylsulfonamido)butanoic acid;
163) (S)-4-(N-(1-(3-(3-methylpyridin-4-yl)phenyl)ethyl)-2-(trifluoromethyl)phenylsulfonamido)butanoic acid;
164) (S)-4-(N-(1-(3-(3-ethylpyridin-4-yl)phenyl)ethyl)-2-(trifluoromethyl)phenylsulfonamido)butanoic acid;
165) (S)-tert-butyl 4-(3-chloro-N-(4-cyano-1-(3-(3-methylpyridin-4-yl)phenyl)butyl)-2-methylphenylsulfonamido)butanoate;
166) (S)-4-(3-chloro-N-(4-cyano-1-(3-(3-methylpyridin-4-yl)phenyl)butyl)-2-methylphenylsulfonamido)butanoic acid;

167) (S)-4-(3-Chloro-2-methyl-N-(1-(3-(3-methylpyridin-4-yl)phenyl)ethylphenyl sulfonamido)butanoic acid;
168) (R)-4-(3-chloro-2-methyl-N-(1-(3-(3-methylpyridin-4-yl)-phenyl)ethyl)phenyl-sulfonamido)butanoic acid;
169) (S)-4-(3-chloro-N-(1-(3-(3-ethylpyridin-4-yl)phenyl)-ethyl)-2-methylphenyl-sulfonamido)butanoic acid;
170) 4-(3-chloro-N-(2-(3-(3-(hydroxymethyl)pyridin-4-yl)-phenyl)propan-2-yl)-2-methylphenylsulfonamido)butanoic acid;
171) (S)-4-(2-methyl-N-(1-(3-(3-methylpyridin-4-yl)phenyl)-ethyl)phenylsulfonamido)butanoic acid;
172) (S)-5-(3-chloro-2-methyl-N-(1-(3-(3-methylpyridin-4-yl)phenyl)ethyl)phenylsulfonamido)pentanoic acid;
173) (S)-5-(3-chloro-N-(1-(3-(3-ethylpyridin-4-yl)phenyl)-ethyl)-2-methylphenyl-sulfonamido)pentanoic acid;
174) (S)-4-(3-chloro-2-methyl-N-(1-(3-(4-methylisothiazol-5-yl)phenyl)ethyl)phenyl-sulfonamido)butanoic acid;
175) (S)-3-(3-chloro-2-methyl-N-(1-(3-(3-methylpyridin-4-yl)phenyl)ethyl)phenylsulfonamido)propanoic acid;
176) 4-(3-chloro-2-methyl-N-(3-(3-(3-methylpyridin-4-yl)phenyl)-oxetan-3-yl)phenyl-sulfonamido)butanoic acid;
177) (S)-2-(2-(3-chloro-2-methyl-N-(1-(3-(3-methylpyridin-4-yl)phenyl)ethyl)phenylsulfonamido)ethoxy)acetic acid;
178) (+/−) N-(2-hydroxy-1-(3-(3-methoxypyridin-4-yl)phenyl)ethyl)-3-(trifluoromethyl)benzenesulfonamide;
179) (S)-3-(3-(3-methylpyridin-4-yl)phenyl)-3-(2-(trifluoromethyl)phenyl sulfonamido)propanoic acid;
180) (S)-ethyl 3-(3-(3-methylpyridin-4-yl)phenyl)-3-(2-(trifluoromethyl)phenylsulfonamido)propanoate;
181) 4-(3-(3-methylpyridin-4-yl)phenyl)-4-(2-(trifluoromethyl)phenylsulfonamido) butanoic acid;
182) (S)-5-(3-(3-methylpyridin-4-yl)phenyl)-5-(2-(trifluoromethyl)phenylsulfonamido) pentanoic acid;
183) 2-(4-(N-(2-(3-(3-ethylpyridin-4-yl)phenyl)propan-2-yl)-2-(trifluoromethyl)-phenylsulfonamido)butanamido)ethanesulfonic acid;
184) 2-(4-(N-(2-(3-(3-methylpyridin-4-yl)phenyl)propan-2-yl)-2-(trifluoromethyl)phenylsulfonamido)butanamido)ethanesulfonic acid;
185) (4-(N-(2-(3-(3-methylpyridin-4-yl)phenyl)propan-2-yl)-2-(trifluoromethyl)phenylsulfonamido)butanamido) methanesulfonic acid trifluoromethyl)benzene sulfonamide;
186) 2-(4-(3-chloro-N-(2-(3-(3-ethylpyridin-4-yl)phenyl) propan-2-yl)-2-methylphenylsulfonamido)butanamido) ethanesulfonic acid;
187) 3-(4-(3-chloro-2-methyl-N-(2-(3-(3-methylpyridin-4-yl)phenyl)propan-2-yl)phenylsulfonamido)butanamido) propane-1-sulfonic acid;
188) 4-(3-chloro-2-methyl-N-(2-(3-(3-methylpyridin-4-yl) phenyl)propan-2-yl)phenylsulfonamido)-N-(2-sulfamoylethyl)butanamide;
189) 4-(3-chloro-2-methyl-N-(2-(3-(3-methylpyridin-4-yl) phenyl)propan-2-yl)phenylsulfonamido)-N-((2R,3S,4S, 5S)-2,3,4,5,6-pentahydroxyhexyl) butanamide;
190) 2-(4-(3-chloro-2-methyl-N-(2-(3-(3-methylpyridin-4-yl)phenyl)propan-2-yl)phenylsulfonamido)butanamido) ethanesulfonic acid;
191) (S)-2-(5-(3-chloro-2-methyl-N-(1-(3-(3-methylpyridin-4-yl)phenyl)ethyl)phenylsulfonamido)pentanamido) ethanesulfonic acid;
192) 5-(3-chloro-2-methyl-N—((S)-1-(3-(3-methylpyridin-4-yl)phenyl)ethyl)phenylsulfonamido)-N-((2R,3S,4S,5 S)-2,3,4,5,6-pentahydroxyhexyl) pentanamide;
193) (S)-4-(3-chloro-2-methyl-N-(1-(3-(3-methylpyridin-4-yl)phenyl)ethyl)phenylsulfonamido)-N-(2-sulfamoylethyl)butanamide;
194) 4-(3-chloro-2-methyl-N—((S)-1-(3-(3-methylpyridin-4-yl)phenyl)ethyl)phenylsulfonamido)-N-((2R,3S,4S, 5S)-2,3,4,5,6-pentahydroxyhexyl)butanamide;
195) (S)-3-(4-(3-chloro-2-methyl-N-(1-(3-(3-methylpyridin-4-yl)phenyl)ethyl)phenylsulfonamido)butanamido) propane-1-sulfonic acid;
196) (S)-3-(4-(3-chloro-N-(1-(3-(3-ethylpyridin-4-yl)phenyl)ethyl)-2-methylphenylsulfonamido)butanamido)propane-1-sulfonic acid;
197) 4-(3-chloro-N—((S)-1-(3-(3-ethylpyridin-4-yl)phenyl) ethyl)-2-methylphenyl sulfonamido)-N-((2R,3S,4S,5S)-2,3,4,5,6-pentahydroxyhexyl)butanamide;
198) 2-(4-(3-chloro-N-(2-(3-(3-(hydroxymethyl)pyridin-4-yl)phenyl)propan-2-yl)-2-methylphenylsulfonamido)butanamido)ethanesulfonic acid;
199) (S)-2-(4-(3-chloro-N-(1-(3-(3-(hydroxymethyl)pyridin-4-yl)phenyl)ethyl)-2-methylphenylsulfonamido)butanamido)ethanesulfonic acid;
200) (S)-2-(4-(2-methyl-N-(1-(3-(3-methylpyridin-4-yl) phenyl)ethyl)phenyl sulfonamido)butanamido)ethanesulfonic acid;
201) (S)-2-(4-(N-(1-(3-(3-ethylpyridin-4-yl)phenyl)ethyl)-2-methylphenyl sulfonamido)butanamido)ethanesulfonic acid;
202) (S)-2-(5-(3-chloro-N-(1-(3-(3-ethylpyridin-4-yl)phenyl)ethyl)-2-methylphenylsulfonamido)pentanamido)ethanesulfonic acid;
203) (S)—N-(2-(2-aminoethoxy)ethyl)-5-(3-chloro-2-methyl-N-(1-(3-(3-methylpyridin-4-yl)phenyl)ethyl)phenylsulfonamido)pentanamide;
204) (S)-3-((3-chloro-2-methylphenyl)sulfonyl)-2-(3-(3-methylpyridin-4-yl)phenyl)-7-oxo-11,14,17-trioxa-3,8-diazaicosan-20-oic acid;
205) tert-butyl (2-(4-(3-chloro-2-methyl-N-(2-(3-(3-methylpyridin-4-yl)phenyl) propan-2-yl)phenylsulfonamido) butanamido)ethyl)carbamate;
206) (4-(3-chloro-2-methyl-N-(2-(3-(3-methylpyridin-4-yl) phenyl)propan-2-yl)phenylsulfonamido)-N-butanamidoethylsulfonamido)acetic acid;
207) (S)-2-(4-(2-methyl-N-(1-(3-(3-methylpyridin-4-yl) phenyl)ethyl)phenyl sulfonamido)butanamidoethylsulfonamido)acetate;
208) (S)-4-(3-Chloro-2-methyl-N-(1-(3-(3-methylpyridin-4-yl)phenyl)ethyl)phenylsulfonamido)butanamide;
209) (S) 2-(3-(4-(3-chloro-2-methyl-N-(1-(3-(3-ethylpyridin-4-yl)phenyl)ethyl)phenylsulfonamido)butanamido) ethylsulfonamido)propanoic acid;
210) N-(2-(hydroxythio)ethyl)-4-(N-(1-(3-(3-methylpyridin-4-yl)phenyl)ethyl)-2-(trifluoromethyl)phenylsulfonamido)butanamide;
211) N-(2-(hydroxythio)ethyl)-4-(N-(1-(3-(3-methylpyridin-4-yl)phenyl)ethyl)-3-(trifluoromethyl)phenylsulfonamido)butanamide;
212) (S)-(4-(N-(1-(3-(3-ethylpyridin-4-yl)phenyl)ethyl)-2-(trifluoromethyl)phenylsulfonamido)butanamido)methanesulfonic acid;
213) (S)-2-(4-(N-(1-(3-(3-ethylpyridin-4-yl)phenyl)ethyl)-2-(trifluoromethyl)phenylsulfonamido)butanamido)ethanesulfonic acid;
214) (S) 2-(4-(N-(1-(3-(3-ethylpyridin-4-yl)phenyl)ethyl)-2-(trifluoromethyl)phenylsulfonamido)butanamido)ethylsulfonamido)acetic acid;

215) (S)-2-(4-(N-(1-(3-(3-methylpyridin-4-yl)phenyl)ethyl)-2-(trifluoromethyl)phenylsulfonamido)butanamido)ethanesulfonic acid;
216) (S) 2-(4-(N-(1-(3-(3-methylpyridin-4-yl)phenyl)ethyl)-2-(trifluoromethyl)phenylsulfonamido)butanamido)ethylsulfonamido)propan oic acid;
217) (S) 2-(4-(N-(1-(3-(3-methylpyridin-4-yl)phenyl)ethyl)-2-(trifluoromethyl)phenylsulfonamido)butanamido)ethylsulfonamido)acetic acid;
218) (S) 2-(4-(N-(1-(3-(3-methylpyridin-4-yl)phenyl)ethyl)-2-(trifluoromethyl)phenylsulfonamido)butanamido)ethylsulfonamido)butanoic acid;
219) (S) 2-(4-(N-(1-(3-(3-methylpyridin-4-yl)phenyl)ethyl)-2-(trifluoromethyl)phenylsulfonamidopentanamidoethylsulfonamido)acetic acid;
220) (S) 2-(4-(N-(1-(3-(3-methylpyridin-4-yl)phenyl)ethyl)-2-(trifluoromethyl)phenylsulfonamidopentanamido)ethylsulfonamido)propan oic acid;
221) 2-(4-(3-chloro-2-methyl-N-(3-(3-methylpyridin-4-yl)phenyl)oxetan-3-yl)phenylsulfonamido)butanamido)ethanesulfonic acid;
222) (S)-2-(4-(3-chloro-2-methyl-N-(1-(3-(pyridazin-4-yl)phenyl)ethyl)phenyl sulfonamido)butanamido)ethanesulfonic acid;
223) (S)-2-(4-(3-chloro-2-methyl-N-(1-(3-(4-methylisothiazol-5-yl)phenyl)ethyl)phenylsulfonamido)butanamido)ethanesulfonic acid;
224) (S)-(5-(3-(3-methylpyridin-4-yl)phenyl)-5-(2-(trifluoromethyl)phenyl sulfonamido)pentanamido)methanesulfonic acid;
225) (S)-2-(4-(3-chloro-N-(1-(3-(3-(hydroxymethyl)pyridin-4-yl)phenyl)ethyl)-2-methylphenylsulfonamido)butanamido)ethanesulfonamido acetic acid;
226) 2-(4-(3-chloro-2-methyl-N-(3-(3-methylpyridin-4-yl)phenethyl)phenylsulfonamido)butanamido)ethanesulfonic acid;
227) (S)-2-(4-(2-methyl-N-(1-(3-(3-ethylpyridin-4-yl)phenyl)ethyl)phenyl sulfonamido)butanamidoethylsulfonamido)acetate;
228) (S)-2-(3-(3-chloro-2-methyl-N-(1-(3-(3-methylpyridin-4-yl)phenyl)ethyl)phenylsulfonamido)propanamido)ethanesulfonic acid;
229) (S)-3-(N-(4-(3-chloro-2-methyl-N-(1-(3-(3-methylpyridin-4-yl)phenyl)ethyl)phenylsulfonamido)butanoyl)sulfamoyl)propanoic acid;
230) ((S)—N-(2-aminoethyl)-4-(N-(1-(3-(3-methylpyridin-4-yl)phenyl)ethyl)-2-(trifluoromethyl)phenylsulfonamido)butanamide;
231) N-(2-Aminoethyl)-4-(3-chloro-2-methyl-N-(2-(3-(3-methylpyridin-4-yl)phenyl)propan-2-yl)-phenylsulfonamido)butanamide;
232) (R)-2-(4-(3-chloro-2-methyl-N-(2-(3-(3-methylpyridin-4-yl)phenyl)propan-2-yl)phenylsulfonamido)butanamido)-3-sulfopropanoic acid;
233) 2-(4-(3-chloro-2-methyl-N-(2-(3-(3-methylpyridin-4-yl)phenyl)propan-2-yl)phenylsulfonamido)butanamido)acetic acid;
234) N-(2-amino-2-oxoethyl)-4-(3-chloro-2-methyl-N-(2-(3-(3-methylpyridin-4-yl)phenyl)propan-2-yl)phenylsulfonamido)butanamide;
235) 4-(3-chloro-2-methyl-N-(2-(3-(3-methylpyridin-4-yl)phenyl)propan-2-yl)phenylsulfonamido)-N-(2-(dimethylamino)ethyl)butanamide;
236) (R)-2-(4-(3-chloro-2-methyl-N-(2-(3-(3-methylpyridin-4-yl)phenyl)propan-2-yl)phenylsulfonamido)butanamido)propanoic acid;
237) (S)-2-(4-(3-chloro-2-methyl-N-(2-(3-(3-methylpyridin-4-yl)phenyl)propan-2-yl)phenylsulfonamido)butanamido)propanoic acid;
238) (S)-2-(4-(3-chloro-2-methyl-N-(1-(3-(3-methylpyridin-4-yl)phenyl)ethyl)phenylsulfonamido)butanamido)ethanesulfonic acid;
239) (S)-3-(4-(3-chloro-2-methyl-N-(1-(3-(3-methylpyridin-4-yl)phenyl)ethyl)phenylsulfonamido)butanamido)propanoic acid;
240) (S)-2-(4-(3-chloro-2-methyl-N—((S)-1-(3-(3-methylpyridin-4-yl)phenyl)ethyl)phenylsulfonamido)butanamido)-3-hydroxypropanoic acid;
241) (S)-1-(4-(3-chloro-2-methyl-N—((S)-1-(3-(3-methylpyridin-4-yl)phenyl)ethyl)phenylsulfonamido)butanoyl)pyrrolidine-2-carboxylic acid;
242) (S)-2,2'-((4-(3-chloro-2-methyl-N-(1-(3-(3-methylpyridin-4-yl)phenyl)ethyl)phenylsulfonamido)butanoyl)azanediyl)diacetic acid;
243) (S) 2-(3-(4-(3-chloro-2-methyl-N-(1-(3-(3-methylpyridin-4-yl)phenyl)ethyl)phenylsulfonamido)butanamido)ethylsulfonamido) propanoic acid;
244) (S)-2-(3-(4-(3-chloro-2-methyl-N-(1-(3-(3-methylpyridin-4-yl)phenyl)ethyl)phenylsulfonamido)butanamido)propanamido)acetic acid;
245) (S) 2-(3-(4-(3-chloro-2-methyl-N-(1-(3-(3-methylpyridin-4-yl)phenyl)ethyl)phenylsulfonamido)butanamido)ethylsulfonamido)acetic acid;
246) (S)-2-(2-(2-(3-Chloro-2-methyl-N-(1-(3-(3-methylpyridin-4-yl)phenyl)ethyl)phenylsulfonamido)ethoxy)acetamido)ethanesulfonic acid;
247) (R)-2-(4-(3-Chloro-2-methyl-N-(1-(3-(3-methylpyridin-4-yl)phenyl)ethyl)phenylsulfonamido)butanamido)ethanesulfonic acid;
248) (S)-2-(4-(3-chloro-N-(1-(3-(3-ethylpyridin-4-yl)phenyl)ethyl)-2-methylphenylsulfonamido)butanamido)ethanesulfonic acid;
249) (S)-(4-(3-chloro-N-(1-(3-(3-ethylpyridin-4-yl)phenyl)ethyl)-2-methylphenylsulfonamido)butanamido)methanesulfonic acid;
250) (S)—N-(2-aminoethyl)-4-(3-chloro-N-(1-(3-(3-ethylpyridin-4-yl)phenyl)ethyl)-2-methylphenylsulfonamido)butanamide;
251) (S) 2-(3-(4-(3-chloro-2-methyl-N-(1-(3-(3-ethylpyridin-4-yl)phenyl)ethyl)phenylsulfonamido)butanamidoethylsulfonamido)acetic acid;
252) N-(2-(3-(3-Ethylpyridin-4-yl)-5-hydroxyphenyl)propan-2-yl)-2-(trifluoromethyl)benzenesulfonamide;
253) (S)-2-(4-(N-(1-(3-(3-hydroxypyridin-4-yl)phenyl)ethyl)-2-methylphenyl sulfonamido)butanamido)ethanesulfonic acid;
254) N-(3-aminopropyl)-3-chloro-2-methyl-N-(2-(3-(3-methylpyridin-4-yl)phenyl)propan-2-yl)benzenesulfonamide;
255) (S)—N-(4-aminobutyl)-N-(1-(3-(3-methylpyridin-4-yl)phenyl)ethyl)-2-(trifluoromethyl)benzenesulfonamide;
256) N-(5-amino-1-(3-(3-methylpyridin-4-yl)phenyl)pentyl)-2-(trifluoromethyl)benzenesulfonamide;
257) (S)—N-(4-aminobutyl)-3-chloro-N-(1-(3-(3-ethylpyridin-4-yl)phenyl)ethyl)-2-methylbenzenesulfonamide;
258) (E)-3-(3-(3-((3-chloro-2-methyl-N-(2-(3-(3-methylpyridin-4-yl)phenyl)propan-2-yl)phenyl)sulfonamido)propyl)-2-cyanoguanidino)propanoic acid;
259) Ethyl (E)-3-(3-(3-((3-chloro-2-methyl-N-(2-(3-(3-methylpyridin-4-yl)phenyl)propan-2-yl)phenyl)sulfonamido)propyl)-2-cyanoguanidino)propanoate;

260) N-(3-((2-aminoethyl)sulfonamido)propyl)-3-chloro-2-methyl-N-(2-(3-(3-methylpyridin-4-yl)phenyl)propan-2-yl)benzenesulfonamide;
261) 3-Chloro-N-(3-((2-(1,3-dioxoisoindolin-2-yl)ethyl)sulfonamido)propyl)-2-methyl-N-(2-(3-(3-methylpyridin-4-yl)phenyl)propan-2-yl)benzenesulfonamide;
262) (S)-4-(3-chloro-2-methyl-N-(1-(3-(3-methylpyridin-4-yl)phenyl)ethyl)phenylsulfonamido)butanamido-2-(N-ethylsulfamoyl)acetic acid;
263) (S)-4-(3-chloro-2-methyl-N-(1-(3-(3-methylpyridin-4-yl)phenyl)ethyl)phenylsulfonamido)butanamido-2-(N-ethylsulfamoyl)propanoic acid;
264) (S)-Methyl-4-(3-chloro-2-methyl-N-(1-(3-(3-methylpyridin-4-yl)phenyl)ethyl)phenylsulfonamido) butanamido-2-(N-(2-(2-aminoethoxy)ethylsulfamoyl)acetate;
265) (S)-4-(3-chloro-2-methyl-N-(1-(3-(3-methylpyridin-4-yl)phenyl)ethyl)phenylsulfonamido) butanamido-2-(N-(2-(2-aminoethoxy)ethylsulfamoyl)acetic acid;
266) (S)-3-(N-(4-(3-chloro-N-(1-(3-(3-ethylpyridin-4-yl)phenyl)ethyl)-2-methylphenylsulfonamido)butyl) sulfamoyl)propanoic acid;
267) 2-((3-((3-chloro-2-methyl-N-(2-(3-(3-methylpyridin-4-yl)phenyl)propan-2-yl)phenyl)sulfonamido)propyl)amino)pyrimidine-5-carboxylic acid;
268) 2-((2-(4-(3-chloro-2-methyl-N-(2-(3-(3-methylpyridin-4-yl)phenyl) propan-2-yl)phenylsulfonamido) butanamido)ethyl)amino)pyrimidine-5-carboxylic acid;
269) 4-(3-chloro-2-methyl-N-(2-(3-(3-methylpyridin-4-yl)phenyl)propan-2-yl)phenylsulfonamido)-N-(2-guanidinoethyl)butanamide;
270) 3-chloro-N-(3-((2-guanidinoethyl)sulfonamido)propyl)-2-methyl-N-(2-(3-(3-methylpyridin-4-yl)phenyl)propan-2-yl)benzenesulfonamide;
271) 2-(4-(3-chloro-2-methyl-N-(2-(3-(3-methylpyridin-4-yl)phenyl)propan-2-yl)phenylsulfonamido) butanamido)-N,N,N-trimethylethanaminium;
272) (S)-2-(4-(3-chloro-N-(1-(3-(3-ethylpyridin-4-yl)phenyl)ethyl)-2-methylphenylsulfonamido)butanamido)-N,N,N-trimethylethanaminium;
273) (S)-2-(3-(4-(N-(1-(3-(3-methylpyridin-4-yl)phenyl)ethyl)-2-(trifluoromethyl)phenylsulfonamido)butyl)ureido)ethanesulfonamidopropanoic acid;
274) (S)-2-(3-(4-(N-(1-(3-(3-methylpyridin-4-yl)phenyl)ethyl)-2-(trifluoromethyl)phenylsulfonamido)butyl)ureido)ethanesulfonamido acetic acid;
275) (S)-2-(3-(4-(N-(1-(3-(3-methylpyridin-4-yl)phenyl)ethyl)-2-(trifluoromethyl)phenylsulfonamido)butyl)ureido)ethanesulfonic acid;
276) (S)-(3-(4-(N-(1-(3-(3-methylpyridin-4-yl)phenyl)ethyl)-2-(trifluoromethyl)phenylsulfonamido)butyl)ureido)methanesulfonic acid;
277) 2-(3-(2-(N-(3-((3-chloro-2-methyl-N-(2-(3-(3-methylpyridin-4-yl)phenyl)propan-2-yl)phenyl) sulfonamido)propyl)sulfamoyl)ethyl) ureido)ethane-1-sulfonic acid;
278) 3-(3-(2-(N-(3-((3-chloro-2-methyl-N-(2-(3-(3-methylpyridin-4-yl)phenyl)-propan-2-yl)phenyl)sulfonamido)-propyl)sulfamoyl)ethyl)ureido) propane-1-sulfonic acid;
279) (S)-17-((3-chloro-2-methylphenyl)sulfonyl)-18-(3-(3-methylpyridin-4-yl)phenyl)-4,12-dioxo-8-oxa-3,5,11,17-tetraazanonadecane-1-sulfonic acid;
280) 2-(3-(5-(3-(3-methylpyridin-4-yl)phenyl)-5-(2-(trifluoromethyl)phenyl sulfonamido)pentyl)ureido)ethanesulfonic acid;
281) (S)-(3-(4-(N-(1-(3-(3-ethylpyridin-4-yl)phenyl)ethyl)-2-(trifluoromethyl)phenylsulfonamido)butyl)ureido)methanesulfonic acid;
282) (3-(3-(3-chloro-2-methyl-N-(3-(3-methylpyridin-4-yl)benzyl)phenylsulfonamido)propyl)ureido)methanesulfonic acid;
283) (3-(3-((3-Chloro-2-methyl-N-(2-(3-(3-methylpyridin-4-yl)phenyl) propan-2-yl) phenyl) sulfonamide) propyl) ureido) methanesulfonic acid;
284) 2-(3-(3-((3-Chloro-2-methyl-N-(2-(3-(3-methylpyridin-4-yl) phenyl) propan-2-yl) phenyl) sulfonamide) propyl) ureido)ethane-1-sulfonic acid;
285) 3-Chloro-2-methyl-N-(2-(3-(3-methylpyridin-4-yl) phenyl) propan-2-yl)-N-(3-(3-(2-sulfamoylethyl) ureido) propyl) benzenesulfonamide;
286) 3-(3-(3-((3-Chloro-2-methyl-N-(2-(3-(3-methylpyridin-4-yl) phenyl) sulfonamide) propyl) ureido) propane-1-sulfonic acid;
287) (3-(3-(3-chloro-2-methyl-N-(3-(3-methylpyridin-4-yl)phenethyl) phenylsulfonamido)propyl)ureido)methanesulfonic acid;
288) (S)-3-((3-Chloro-2-methylphenyl)sulfonyl)-2-(3-(3-methylpyridin-4-yl)phenyl)-7,12-dioxo-3,8,11,13-tetraazahexadecane-16-oic acid;
289) (S)-15-((3-chloro-2-methylphenyl)sulfonyl)-16-(3-(3-methylpyridin-4-yl)phenyl)-2,10-dioxo-6-oxa-3,9,15-triazaheptadecane-1-sulfonic acid;
290) (S)-2-((4-(N-(1-(3-(3-methylpyridin-4-yl)phenyl)ethyl)-2-(trifluoromethyl)phenylsulfonamido)butyl)amino)-2-oxoethanesulfonic acid;
291) 2-((3-(3-chloro-2-methyl-N-(2-(3-(3-methylpyridin-4-yl)phenyl)propan-2-yl)phenylsulfonamido)propyl)amino)-2-oxoethanesulfonic acid;
292) (R)-2-amino-3-((4-(N—((S)-1-(3-(3-methylpyridin-4-yl)phenyl)ethyl)-2-(trifluoromethyl)phenylsulfonamido) butyl)amino)-3-oxopropane-1-sulfonic acid;
293) (R)-2-amino-3-((4-(3-chloro-N—((S)-1-(3-(3-ethylpyridin-4-yl)phenyl)ethyl)-2-methylphenylsulfonamido)butyl) amino)-3-oxopropane-1-sulfonic acid;
294) (S)-2-((2-(4-(N-(1-(3-(3-methylpyridin-4-yl)phenyl)ethyl)-2-(trifluoromethyl)phenylsulfonamido)butanamido)ethyl)amino)-2-oxoethanesulfonic acid;
295) (R)-2-amino-3-((2-(4-(N—((S)-1-(3-(3-methylpyridin-4-yl)phenyl)ethyl)-2-(trifluoromethyl)phenylsulfonamido)butanamido)ethyl)amino)-3-oxopropane-1-sulfonic acid;
296) 2-((2-((2-(3-chloro-2-methyl-N-(1-(3-(3-methylpyridin-4-yl)phenyl)ethyl)phenylsulfonamido)ethyl)amino)-3,4-dioxocyclobut-1-en-1-yl)amino)methanesulfonic acid;
297) ((2-((3-(3-chloro-2-methyl-N-(1-(3-(3-methylpyridin-4-yl)phenyl) ethyl)phenylsulfonamido)propyl) amino)-3,4-dioxocyclobut-1-en-1-yl)amino)methanesulfonic acid;
298) 3-((2-((2-(3-chloro-2-methyl-N-(1-(3-(3-methylpyridin-4-yl)phenyl)ethyl)phenylsulfonamido)ethyl)amino)-3,4-dioxocyclobut-1-en-1-yl)amino)propanoic acid;
299) ((2-((3-(3-chloro-2-methyl-N-(1-(3-(3-methylpyridin-4-yl)phenyl)ethyl)phenylsulfonamido)propyl)amino)-3,4-dioxocyclobut-1-en-1-yl)amino)methanesulfonic acid;
300) (S)-3-((4-(3-chloro-2-methyl-N-(1-(3-(3-methylpyridin-4-yl)phenyl)ethyl)phenylsulfonamido)butyl)amino) propanoic acid;
301) (S)-3-(N-(4-(3-chloro-2-methyl-N-(1-(3-(3-methylpyridin-4-yl)phenyl)ethyl)phenylsulfonamido)butyl)acetamido)propanoic acid
302) 3-chloro-N-(5-cyano-1-(3-(3-methylpyridin-4-yl)phenyl)pentyl)-2-methyl benzenesulfonamide;
303) N-(5-cyano-1-(3-(3-methylpyridin-4-yl)phenyl)pentyl)-5-methylpyridine-2-sulfonamide;

304) (S)-2-(4-(4-fluoro-N-(1-(3-(3-methylpyridin-4-yl)phenyl)ethyl)-2-(trifluoromethyl)phenylsulfonamido)butanamido)ethanesulfonamido acetic acid;
305) (S)-2-(4-(3-chloro-N-(1-(3-(3-methylpyridin-4-yl)phenyl)ethyl)-2-chloro-phenylsulfonamido) butanamido)ethanesulfonamido acetic acid;
306) (S)-4-(3-chloro-2-methyl-N-(1-(3-(3-methylpyridin-4-yl)phenyl)ethyl)phenylsulfonamido)-N-(2-(sulfamoylamino)ethyl)butanamide;
307) (S)—N-(2-((N-(tert-butoxy)sulfamoyl)amino)ethyl)-4-(3-chloro-2-methyl-N-(1-(3-(3-methyl pyri din-4-yl)phenyl)ethyl)phenylsulfonamido)butanamide;
308) (S)-4-(3-chloro-N-(1-(3-(3-ethylpyridin-4-yl)phenyl)ethyl)-2-methylphenylsulfonamido)-N-(2-(sulfamoylamino)ethyl)butanamide;
309) (S)-2-((N-(2-(4-(3-chloro-2-methyl-N-(1-(3-(3-methylpyridin-4-yl)phenyl)ethyl)phenylsulfonamido)butanamido)ethyl)sulfamoyl)amino)acetic acid;
310) (S)-2-((N-(2-(4-(3-chloro-N-(1-(3-(3-ethylpyridin-4-yl)phenyl)ethyl)-2-methylphenylsulfonamido) butanamido)ethyl)sulfamoyl)amino)acetic acid;
311) (S)-3-chloro-N-(4-hydroxybutyl)-2-methyl-N-(1-(3-(3-methyl pyri din-4-yl)phenyl)ethyl) benzenesulfonamide;
or a pharmaceutically acceptable salt thereof.
Preferably, the present invention provides a compound of:
1) (S)-3-chloro-N-(4-cyano-1-(3-(3-methylpyridin-4-yl)phenyl)butyl)-2-methylbenzenesulfonamide;
2) (S)—N-(4-cyano-1-(3-(3-methylpyridin-4-yl)phenyl)-butyl)-2-(trifluoromethyl)-benzenesulfonamide;
3) (S)—N-(4-cyano-1-(3-(3-ethylpyridin-4-yl)phenyl)butyl)-2-(trifluoromethyl)-benzenesulfonamide;
4) N-(3-cyano-1-(3-(3-methylpyridin-4-yl)phenyl)-propyl)-2-(trifluoromethyl)-benzenesulfonamide;
5) Methyl 2-(N-(2-(3-(3-methylpyridin-4-yl)phenyl)propan-2-yl)-2-(trifluoromethyl)phenylsulfonamido)acetate;
6) N-(2-methoxyethyl)-N-(2-(3-(3-methylpyridin-4-yl)phenyl)propan-2-yl)-2-(trifluoromethyl)benzenesulfonamide;
7) 4-(N-(2-(3-(3-methylpyridin-4-yl)phenyl)propan-2-yl)-2-(trifluoromethyl)phenylsulfonamido)butanoic acid;
8) Ethyl 4-(N-(2-(3-(3-methylpyridin-4-yl)phenyl)propan-2-yl)-2-(trifluoromethyl) phenylsulfonamido)butanoate;
9) (S)-4-(N-(1-(3-(3-methylpyridin-4-yl)phenyl)ethyl)-2-(trifluoromethyl)phenylsulfonamido)-butanoic acid;
10) (S)-4-(N-(1-(3-(3-ethylpyridin-4-yl)phenyl)ethyl)-2-(trifluoromethyl)phenylsulfonamido)butanoic acid;
11) (S)-5-(3-chloro-2-methyl-N-(1-(3-(3-methylpyridin-4-yl)phenyl)ethyl)phenylsulfonamido)pentanoic acid;
12) (S)-5-(3-chloro-N-(1-(3-(3-ethylpyridin-4-yl)phenyl)-ethyl)-2-methylphenyl-sulfonamido)pentanoic acid;
13) (S)-ethyl 3-(3-(3-methylpyridin-4-yl)phenyl)-3-(2-(trifluoromethyl)phenylsulfonamido)-propanoate;
14) 2-(4-(N-(2-(3-(3-ethylpyridin-4-yl)phenyl)propan-2-yl)-2-(trifluoromethyl)phenylsulfonamido)butanamido) ethanesulfonic acid;
15) 2-(4-(N-(2-(3-(3-methylpyridin-4-yl)phenyl)propan-2-yl)-2-(trifluoromethyl)phenylsulfonamido)butanamido) ethanesulfonic acid;
16) (4-(N-(2-(3-(3-methylpyridin-4-yl)phenyl)propan-2-yl)-2-(trifluoromethyl)phenylsulfonamido)butanamido) methanesulfonic acidtrifluoromethyl)benzenesulfonamide;
17) 2-(4-(3-chloro-N-(2-(3-(3-ethylpyridin-4-yl)phenyl) propan-2-yl)-2-methylphenylsulfonamido)butanamido) ethanesulfonic acid;
18) 3-(4-(3-chloro-2-methyl-N-(2-(3-(3-methylpyridin-4-yl)phenyl)propan-2-yl)phenylsulfonamido)butanamido) propane-1-sulfonic acid;
19) 4-(3-chloro-2-methyl-N-(2-(3-(3-methylpyridin-4-yl) phenyl)propan-2-yl)phenylsulfonamido)-N-(2-sulfamoylethyl)butanamide;
20) 4-(3-chloro-2-methyl-N-(2-(3-(3-methylpyridin-4-yl) phenyl)propan-2-yl)phenylsulfonamido)-N-((2R,3S,4S, 5S)-2,3,4,5,6-pentahydroxyhexyl)butanamide;
21) 2-(4-(3-chloro-2-methyl-N-(2-(3-(3-methylpyridin-4-yl)phenyl)propan-2-yl)phenylsulfonamido)butanamido) ethanesulfonic acid;
22) (S)-2-(5-(3-chloro-2-methyl-N-(1-(3-(3-methylpyridin-4-yl)phenyl)ethyl)phenylsulfonamido)pentanamido)ethanesulfonic acid;
23) 5-(3-chloro-2-methyl-N—((S)-1-(3-(3-methylpyridin-4-yl)phenyl)ethyl)phenylsulfonamido)-N-((2R,3S,4S,5S)-2,3,4,5,6-pentahydroxyhexyl)pentanamide;
24) (S)-4-(3-chloro-2-methyl-N-(1-(3-(3-methylpyridin-4-yl)phenyl)ethyl)phenylsulfonamido)-N-(2-sulfamoylethyl)butanamide;
25) 4-(3-chloro-2-methyl-N—((S)-1-(3-(3-methylpyridin-4-yl)phenyl)ethyl)phenylsulfonamido)-N-((2R,3S,4S,5S)-2,3,4,5,6-pentahydroxyhexyl)butanamide;
26) (S)-3-(4-(3-chloro-2-methyl-N-(1-(3-(3-methylpyridin-4-yl)phenyl)ethyl)phenylsulfonamido)butanamido)propane-1-sulfonic acid;
27) (S)-3-(4-(3-chloro-N-(1-(3-(3-ethylpyridin-4-yl)phenyl) ethyl)-2-methylphenylsulfonamido)butanamido)propane-1-sulfonic acid;
28) 4-(3-chloro-N—((S)-1-(3-(3-ethylpyridin-4-yl)phenyl) ethyl)-2-methylphenyl sulfonamido)-N-((2R,3S,4S,5S)-2,3,4,5,6-pentahydroxyhexyl)butanamide;
29) 2-(4-(3-chloro-N-(2-(3-(3-(hydroxymethyl)pyridin-4-yl)phenyl)propan-2-yl)-2-methylphenylsulfonamido)butanamido)ethanesulfonic acid;
30) (S)-2-(4-(2-methyl-N-(1-(3-(3-methylpyridin-4-yl)phenyl)ethyl)phenylsulfonamido)butanamido)ethanesulfonic acid;
31) (S)-2-(4-(N-(1-(3-(3-ethylpyridin-4-yl)phenyl)ethyl)-2-methylphenyl-sulfonamido)butanamido)ethane sulfonic acid;
32) (S)-2-(5-(3-chloro-N-(1-(3-(3-ethylpyridin-4-yl)phenyl) ethyl)-2-methylphenylsulfonamido)pentanamido)ethanesulfonic acid;
33) (S)—N-(2-(2-aminoethoxy)ethyl)-5-(3-chloro-2-methyl-N-(1-(3-(3-methylpyridin-4-yl)phenyl)ethyl)phenylsulfonamido)pentanamide;
34) tert-butyl (2-(4-(3-chloro-2-methyl-N-(2-(3-(3-methylpyridin-4-yl)phenyl)propan-2-yl)phenylsulfonamido) butanamido)ethyl)carbamate;
35) (4-(3-chloro-2-methyl-N-(2-(3-(3-methylpyridin-4-yl) phenyl)propan-2-yl)phenylsulfonamido)-N-butanamidoethylsulfonamido)acetic acid;
36) (S)-2-(4-(2-methyl-N-(1-(3-(3-methylpyridin-4-yl)phenyl)ethyl)phenylsulfonamido)butanamidoethylsulfonamido)acetate;
37) (S)-4-(3-Chloro-2-methyl-N-(1-(3-(3-methylpyridin-4-yl)phenyl) ethyl)phenylsulfonamido)butanamide;
38) (S) 2-(3-(4-(3-chloro-2-methyl-N-(1-(3-(3-ethylpyridin-4-yl)phenyl) ethyl)phenylsulfonamido)butanamido)ethylsulfonamido) propanoic acid;
39) N-(2-(hydroxythio)ethyl)-4-(N-(1-(3-(3-methylpyridin-4-yl)phenyl)ethyl)-2-(trifluoromethyl)phenylsulfonamido)butanamide;

40) (S)-(4-(N-(1-(3-(3-ethylpyridin-4-yl)phenyl)ethyl)-2-(trifluoromethyl)phenylsulfonamido)butanamido)methanesulfonic acid;
41) (S)-2-(4-(N-(1-(3-(3-ethylpyridin-4-yl)phenyl)ethyl)-2-(trifluoromethyl)phenylsulfonamido)butanamido)ethanesulfonic acid;
42) (S) 2-(4-(N-(1-(3-(3-ethylpyridin-4-yl)phenyl)ethyl)-2-(trifluoromethyl)phenylsulfonamido)butanamido)ethylsulfonamido)acetic acid;
43) (S)-2-(4-(N-(1-(3-(3-methylpyridin-4-yl)phenyl)ethyl)-2-(trifluoromethyl)phenylsulfonamido)butanamido)ethanesulfonic acid;
44) (S) 2-(4-(N-(1-(3-(3-methylpyridin-4-yl)phenyl)ethyl)-2-(trifluoromethyl)phenyl sulfonamido)butanamido)ethylsulfonamido)propanoic acid;
45) (S) 2-(4-(N-(1-(3-(3-methylpyridin-4-yl)phenyl)ethyl)-2-(trifluoromethyl)phenylsulfonamido)butanamido)ethylsulfonamido)acetic acid;
46) (S) 2-(4-(N-(1-(3-(3-methylpyridin-4-yl)phenyl)ethyl)-2-(trifluoromethyl)phenylsulfonamido)butanamido)ethylsulfonamido)butanoic acid;
47) (S) 2-(4-(N-(1-(3-(3-methylpyridin-4-yl)phenyl)ethyl)-2-(trifluoromethyl)phenylsulfonamidopentanamido)ethylsulfonamido)acetic acid;
48) (S) 2-(4-(N-(1-(3-(3-methylpyridin-4-yl)phenyl)ethyl)-2-(trifluoromethyl)phenylsulfonamidopentanamido)ethylsulfonamido)propanoic acid;
49) 2-(4-(3-chloro-2-methyl-N-(3-(3-(3-methylpyridin-4-yl)phenyl)oxetan-3-yl)phenylsulfonamido)butanamido)ethanesulfonic acid;
50) (S)-2-(4-(2-methyl-N-(1-(3-(3-ethylpyridin-4-yl)phenyl)ethyl)phenylsulfonamido)butanamidoethylsulfonamido)acetate;
51) ((S)—N-(2-aminoethyl)-4-(N-(1-(3-(3-methylpyridin-4-yl)phenyl)ethyl)-2-(trifluoromethyl)phenylsulfonamido)butanamide;
52) N-(2-Aminoethyl)-4-(3-chloro-2-methyl-N-(2-(3-(3-methylpyridin-4-yl)phenyl)propan-2-yl)-phenylsulfonamido)butanamide;
53) 2-(4-(3-chloro-2-methyl-N-(2-(3-(3-methylpyridin-4-yl)phenyl)propan-2-yl)phenylsulfonamido)butanamido)acetic acid;
54) N-(2-amino-2-oxoethyl)-4-(3-chloro-2-methyl-N-(2-(3-(3-methylpyridin-4-yl)phenyl)propan-2-yl)phenylsulfonamido)butanamide;
55) 4-(3-chloro-2-methyl-N-(2-(3-(3-methylpyridin-4-yl)phenyl)propan-2-yl)phenylsulfonamido)-N-(2-(dimethylamino)ethyl)butanamide;
56) (R)-2-(4-(3-chloro-2-methyl-N-(2-(3-(3-methylpyridin-4-yl)phenyl)propan-2-yl)phenylsulfonamido)butanamido)propanoic acid;
57) (S)-2-(4-(3-chloro-2-methyl-N-(2-(3-(3-methylpyridin-4-yl)phenyl)propan-2-yl)phenylsulfonamido)butanamido)propanoic acid;
58) (S)-2-(4-(3-chloro-2-methyl-N-(1-(3-(3-methylpyridin-4-yl)phenyl)ethyl)phenylsulfonamido)butanamido)ethanesulfonic acid
59) (S)-3-(4-(3-chloro-2-methyl-N-(1-(3-(3-methylpyridin-4-yl)phenyl)ethyl)phenylsulfonamido)butanamido)propanoic acid;
60) (S)-2-(4-(3-chloro-2-methyl-N—((S)-1-(3-(3-methylpyridin-4-yl)phenyl)ethyl)phenylsulfonamido)butanamido)-3-hydroxypropanoic acid;
61) (S)-1-(4-(3-chloro-2-methyl-N—((S)-1-(3-(3-methylpyridin-4-yl)phenyl)ethyl)phenylsulfonamido)butanoyl)pyrrolidine-2-carboxylic acid;
62) (S) 2-(3-(4-(3-chloro-2-methyl-N-(1-(3-(3-methylpyridin-4-yl)phenyl)ethyl)phenylsulfonamido)butanamido)ethylsulfonamido)propanoic acid;
63) (S)-2-(3-(4-(3-chloro-2-methyl-N-(1-(3-(3-methylpyridin-4-yl)phenyl)ethyl)phenylsulfonamido)butanamido)propanamido)acetic acid;
64) (S) 2-(3-(4-(3-chloro-2-methyl-N-(1-(3-(3-methylpyridin-4-yl)phenyl)ethyl)phenylsulfonamido)butanamido)ethylsulfonamido)acetic acid;
65) (R)-2-(4-(3-chloro-2-methyl-N-(1-(3-(3-methylpyridin-4-yl)phenyl)ethyl)phenylsulfonamido)butanamido)ethanesulfonic acid;
66) (S)-2-(4-(3-chloro-N-(1-(3-(3-ethylpyridin-4-yl)phenyl)ethyl)-2-methylphenylsulfonamido)butanamido)ethanesulfonic acid;
67) (S)-(4-(3-chloro-N-(1-(3-(3-ethylpyridin-4-yl)phenyl)ethyl)-2-methylphenylsulfonamido)butanamido)methanesulfonic acid;
68) (S)—N-(2-aminoethyl)-4-(3-chloro-N-(1-(3-(3-ethylpyridin-4-yl)phenyl)ethyl)-2-methylphenylsulfonamido)butanamide;
69) (S) 2-(3-(4-(3-chloro-2-methyl-N-(1-(3-(3-ethylpyridin-4-yl)phenyl)ethyl)phenylsulfonamido)butanamido)ethylsulfonamido)acetic acid;
70) N-(2-(3-(3-Ethylpyridin-4-yl)-5-hydroxyphenyl)propan-2-yl)-2-(trifluoromethyl)benzenesulfonamide;
71) N-(3-aminopropyl)-3-chloro-2-methyl-N-(2-(3-(3-methylpyridin-4-yl)phenyl)propan-2-yl)benzenesulfonamide;
72) (S)—N-(4-aminobutyl)-N-(1-(3-(3-methylpyridin-4-yl)phenyl)ethyl)-2-(trifluoromethyl)Benzenesulfonamide;
73) (E)-3-(3-(3-((3-chloro-2-methyl-N-(2-(3-(3-methylpyridin-4-yl)phenyl)propan-2-yl)phenyl)sulfonamido)propyl)-2-cyanoguanidino)propanoic acid;
74) N-(3-((2-aminoethyl)sulfonamido)propyl)-3-chloro-2-methyl-N-(2-(3-(3-methylpyridin-4-yl)phenyl)propan-2-yl)benzenesulfonamide;
75) 3-chloro-N-(3-((2-(1,3-dioxoisoindolin-2-yl)ethyl)sulfonamido)propyl)-2-methyl-N-(2-(3-(3-methylpyridin-4-yl)phenyl)propan-2-yl)benzenesulfonamide;
76) (S)-4-(3-chloro-2-methyl-N-(1-(3-(3-methylpyridin-4-yl)phenyl)ethyl)phenylsulfonamido)butanamido-2-(N-ethylsulfamoyl)acetic acid;
77) (S)-4-(3-chloro-2-methyl-N-(1-(3-(3-methylpyridin-4-yl)phenyl)ethyl)phenylsulfonamido)butanamido-2-(N-ethylsulfamoyl)propanoic acid;
78) (S)-4-(3-chloro-2-methyl-N-(1-(3-(3-methylpyridin-4-yl)phenyl) ethyl)phenylsulfonamido)butanamido-2-(N-(2-(2-aminoethoxy)ethylsulfamoyl)acetic acid;
79) (S)-3-(N-(4-(3-chloro-N-(1-(3-(3-ethylpyridin-4-yl)phenyl)ethyl)-2-methylphenylsulfonamido)butyl)sulfamoyl)propanoic acid;
80) 2-((3-((3-chloro-2-methyl-N-(2-(3-(3-methylpyridin-4-yl)phenyl)propan-2-yl)phenyl)sulfonamido)propyl)amino)pyrimidine-5-carboxylic acid;
81) 2-((2-(4-(3-chloro-2-methyl-N-(2-(3-(3-methylpyridin-4-yl)Phenyl)propan-2-yl)phenylsulfonamido)butanamido)ethyl)amino)pyrimidine-5-carboxylic acid;
82) 4-(3-chloro-2-methyl-N-(2-(3-(3-methylpyridin-4-yl)phenyl)propan-2-yl)phenylsulfonamido)-N-(2-guanidinoethyl)butanamide;

83) 3-chloro-N-(3-((2-guanidinoethyl)sulfonamido)propyl)-2-methyl-N-(2-(3-(3-methylpyridin-4-yl)phenyl)propan-2-yl)benzenesulfonamide;

84) 2-(4-(3-chloro-2-methyl-N-(2-(3-(3-methylpyridin-4-yl)phenyl)propan-2-yl)phenylsulfonamido)butanamido)-N,N,N-trimethylethanaminium;

85) (S)-2-(4-(3-chloro-N-(1-(3-(3-ethylpyridin-4-yl)phenyl)ethyl)-2-methylphenylsulfonamido)butanamido)-N,N,N-trimethylethanaminium;

86) (S)-2-(3-(4-(N-(1-(3-(3-methylpyridin-4-yl)phenyl)ethyl)-2-(trifluoromethyl) phenylsulfonamido)butyl)ureido)ethanesulfonamidopropanoic acid;

87) (S)-2-(3-(4-(N-(1-(3-(3-methylpyridin-4-yl)phenyl)ethyl)-2-(trifluoromethyl) phenylsulfonamido)butyl)ureido)ethanesulfonamido acetic acid;

88) (S)-2-(3-(4-(N-(1-(3-(3-methylpyridin-4-yl)phenyl)ethyl)-2-(trifluoromethyl) phenylsulfonamido)butyl)ureido)ethanesulfonic acid;

89) (S)-(3-(4-(N-(1-(3-(3-methylpyridin-4-yl)phenyl)ethyl)-2-(trifluoromethyl)phenylsulfonamido)butyl)ureido) methanesulfonic acid;

90) 2-(3-(2-(N-(3-((3-chloro-2-methyl-N-(2-(3-(3-methylpyridin-4-yl)phenyl)propan-2-yl)phenyl)sulfonamido)propyl)sulfamoyl)ethyl)ureido)ethane-1-sulfonic acid;

91) 3-(3-(2-(N-(3-((3-chloro-2-methyl-N-(2-(3-(3-methylpyridin-4-yl)phenyl)-propan-2-yl)phenyl)sulfonamido)-propyl)sulfamoyl)ethyl)ureido)propane-1-sulfonic acid;

92) (S)-17-((3-chloro-2-methylphenyl)sulfonyl)-18-(3-(3-methylpyridin-4-yl)phenyl)-4,12-dioxo-8-oxa-3,5,11,17-tetraazanonadecane-1-sulfonic acid;

93) (S)-(3-(4-(N-(1-(3-(3-ethylpyridin-4-yl)phenyl)ethyl)-2-(trifluoromethyl)phenylsulfonamido)butyl)ureido) methanesulfonic acid;

94) (3-(3-((3-chloro-2-methyl-N-(2-(3-(3-methylpyridin-4-yl) phenyl) propan-2-yl) phenyl) sulfonamide) propyl) ureido) methanesulfonic acid;

95) 2-(3-(3-((3-chloro-2-methyl-N-(2-(3-(3-methylpyridin-4-yl) phenyl) propan-2-yl) phenyl) sulfonamide) propyl) ureido)ethane-1-sulfonic acid;

96) 3-chloro-2-methyl-N-(2-(3-methylpyridin-4-yl) phenyl) propan-2-yl)-N-(3-(3-(2-sulfamoylethyl) ureido) propyl) benzenesulfonamide;

97) 3-(3-(3-((3-chloro-2-methyl-N-(2-(3-(3-methylpyridin-4-yl) phenyl) sulfonamide)propyl) ureido) propane-1-sulfonic acid;

98) (S)-15-((3-chloro-2-methylphenyl)sulfonyl)-16-(3-(3-methylpyridin-4-yl)phenyl)-2,10-dioxo-6-oxa-3,9,15-triazaheptadecane-1-sulfonic acid;

99) (S)-2-((4-(N-(1-(3-(3-methylpyridin-4-yl)phenyl)ethyl)-2-(trifluoromethyl)phenylsulfonamido)butyl)amino)-2-oxoethanesulfonic acid;

100) 2-((3-(3-chloro-2-methyl-N-(2-(3-(3-methylpyridin-4-yl)phenyl)propan-2-yl)phenylsulfonamido)propyl)amino)-2-oxoethanesulfonic acid;

101) (R)-2-amino-3-((4-(N—((S)-1-(3-(3-methylpyridin-4-yl)phenyl)ethyl)-2-(trifluoromethyl)phenylsulfonamido)butyl)amino)-3-oxopropane-1-sulfonic acid;

102) (R)-2-amino-3-((4-(3-chloro-N—((S)-1-(3-(3-ethylpyridin-4-yl)phenyl)ethyl)-2-methylphenylsulfonamido)butyl)amino)-3-oxopropane-1-sulfonic acid;

103) (S)-2-((2-(4-(N-(1-(3-(3-methylpyridin-4-yl)phenyl)ethyl)-2-(trifluoromethyl)phenylsulfonamido)butanamido)ethyl)amino)-2-oxoethanesulfonic acid;

104) (R)-2-amino-3-((2-(4-(N—((S)-1-(3-(3-methylpyridin-4-yl)phenyl)ethyl)-2-(trifluoromethyl)phenylsulfonamido)butanamido)ethyl)amino)-3-oxopropane-1-sulfonic acid;

105) ((2-((3-(3-chloro-2-methyl-N-(1-(3-(3-methylpyridin-4-yl)phenyl)ethyl)phenylsulfonamido)propyl)amino)-3,4-dioxocyclobut-1-en-1-yl)amino)methanesulfonic acid;

106) (S)-2-(4-(4-fluoro-N-(1-(3-(3-methylpyridin-4-yl)phenyl)ethyl)-2-(trifluoromethyl)phenylsulfonamido)butanamido)ethanesulfonamido acetic acid;

107) (S)-2-(4-(3-chloro-N-(1-(3-(3-methylpyridin-4-yl)phenyl)ethyl)-2-chloro-phenylsulfonamido)butanamido)ethanesulfonamido acetic acid;

108) (S)-4-(3-chloro-2-methyl-N-(1-(3-(3-methylpyridin-4-yl)phenyl)ethyl)phenylsulfonamido)-N-(2-(sulfamoylamino)ethyl)butanamide;

109) (S)—N-(2-((N-(tert-butoxy)sulfamoyl)amino)ethyl)-4-(3-chloro-2-methyl-N-(1-(3-(3-methylpyridin-4-yl)phenyl)ethyl)phenylsulfonamido)butanamide;

110) (S)-4-(3-chloro-N-(1-(3-(3-ethylpyridin-4-yl)phenyl)ethyl)-2-methylphenylsulfonamido)-N-(2-(sulfamoylamino)ethyl)butanamide;

111) S)-2-((N-(2-(4-(3-chloro-2-methyl-N-(1-(3-(3-methylpyridin-4-yl)phenyl)ethyl)phenylsulfonamido)butanamido)ethyl)sulfamoyl)amino)acetic acid;

112) (S)-2-((N-(2-(4-(3-chloro-N-(1-(3-(3-ethylpyridin-4-yl)phenyl)ethyl)-2-methylphenylsulfonamido)butanamido)ethyl)sulfamoyl)amino)acetic acid; and 113) (S)-3-chloro-N-(4-hydroxybutyl)-2-methyl-N-(1-(3-(3-methylpyridin-4-yl)phenyl)ethyl)benzenesulfonamide;
or a pharmaceutically acceptable salt thereof.

More preferably, the present invention provides a compound of:

1) 2-(4-(N-(2-(3-(3-ethylpyridin-4-yl)phenyl)propan-2-yl)-2-(trifluoromethyl)phenylsulfonamido)butanamido)ethanesulfonic acid;

2) (4-(N-(2-(3-(3-methylpyridin-4-yl)phenyl)propan-2-yl)-2-(trifluoromethyl)phenylsulfonamido)butanamido) methanesulfonic acidtrifluoromethyl)benzenesulfonamide;

3) 3-(4-(3-chloro-2-methyl-N-(2-(3-(3-methylpyridin-4-yl)phenyl)propan-2-yl)phenylsulfonamido)butanamido)propane-1-sulfonic acid;

4) 2-(4-(3-chloro-2-methyl-N-(2-(3-(3-methylpyridin-4-yl)phenyl)propan-2-yl)phenylsulfonamido)butanamido)ethanesulfonic acid;

5) (S)-2-(5-(3-chloro-2-methyl-N-(1-(3-(3-methylpyridin-4-yl)phenyl)ethyl)phenylsulfonamido)pentanamido)ethanesulfonic acid;

6) (S)-3-(4-(3-chloro-N-(1-(3-(3-ethylpyridin-4-yl)phenyl)ethyl)-2-methylphenylsulfonamido)butanamido)propane-1-sulfonic acid;

7) 4-(3-chloro-N—((S)-1-(3-(3-ethylpyridin-4-yl)phenyl)ethyl)-2-methyl phenylsulfonamido)-N-((2R,3S,4S,5S)-2,3,4,5,6-pentahydroxyhexyl)butanamide;

8) (S)-2-(4-(N-(1-(3-(3-ethylpyridin-4-yl)phenyl)ethyl)-2-methylphenyl-sulfonamido)butanamido)ethane sulfonic acid;

9) (S)-2-(5-(3-chloro-N-(1-(3-(3-ethylpyridin-4-yl)phenyl)ethyl)-2-methyl phenylsulfonamido)pentanamido)ethanesulfonic acid;

10) (4-(3-chloro-2-methyl-N-(2-(3-(3-methylpyridin-4-yl)phenyl)propan-2-yl)phenylsulfonamido)-N-butanamido-ethyl)sulfonamido)acetic acid;

11) (S) 2-(3-(4-(3-chloro-2-methyl-N-(1-(3-(3-ethylpyridin-4-yl)phenyl)ethyl)phenylsulfonamido)butanamido)ethylsulfonamido)propanoic acid;

12) (S)-2-(4-(N-(1-(3-(3-ethylpyridin-4-yl)phenyl)ethyl)-2-(trifluoromethyl)phenylsulfonamido)butanamido)ethanesulfonic acid;
13) (S) 2-(4-(N-(1-(3-(3-ethylpyridin-4-yl)phenyl)ethyl)-2-(trifluoromethyl)phenylsulfonamido)butanamido)ethylsulfonamido)acetic acid;
14) (S) 2-(4-(N-(1-(3-(3-methylpyridin-4-yl)phenyl)ethyl)-2-(trifluoromethyl)phenylsulfonamido)butanamido)ethylsulfonamido)butanoic acid;
15) (S) 2-(4-(N-(1-(3-(3-methylpyridin-4-yl)phenyl)ethyl)-2-(trifluoromethyl)phenylsulfonamidopentanamido)ethylsulfonamido)acetic acid;
16) (S) 2-(4-(N-(1-(3-(3-methylpyridin-4-yl)phenyl)ethyl)-2-(trifluoromethyl)phenylsulfonamidopentanamido)ethylsulfonamido)propanoic acid;
17) (S)-2-(4-(2-methyl-N-(1-(3-(3-ethylpyridin-4-yl)phenyl)ethyl)phenylsulfonamido) butanamidoethylsulfonamido)acetate;
18) (S) 2-(3-(4-(3-chloro-2-methyl-N-(1-(3-(3-methylpyridin-4-yl)phenyl)ethyl)phenylsulfonamido)butanamido)ethylsulfonamido)acetic acid;
19) (S)-2-(4-(3-chloro-N-(1-(3-(3-ethylpyridin-4-yl)phenyl)ethyl)-2-methyl phenylsulfonamido)butanamido)ethanesulfonic acid;
20) (S) 2-(3-(4-(3-chloro-2-methyl-N-(1-(3-(3-ethylpyridin-4-yl)phenyl)ethyl)phenylsulfonamido)butanamido)ethylsulfonamido)acetic acid;
21) (E)-3-(3-(3-((3-chloro-2-methyl-N-(2-(3-(3-methylpyridin-4-yl)phenyl)propan-2-yl)phenyl)sulfonamido)propyl)-2-cyanoguanidino)propanoic acid;
22) (S)-4-(3-chloro-2-methyl-N-(1-(3-(3-methylpyridin-4-yl)phenyl)ethyl)phenylsulfonamido)butanamido-2-(N-ethylsulfamoyl)acetic acid;
23) (S)-4-(3-chloro-2-methyl-N-(1-(3-(3-methylpyridin-4-yl)phenyl)ethyl)phenylsulfonamido)butanamido-2-(N-ethylsulfamoyl)propanoic acid;
24) (S)-2-(3-(4-(N-(1-(3-(3-methylpyridin-4-yl)phenyl)ethyl)-2-(trifluoromethyl)phenylsulfonamido)butyl)ureido)ethanesulfonamidopropanoic acid;
25) (S)-2-(3-(4-(N-(1-(3-(3-methylpyridin-4-yl)phenyl)ethyl)-2-(trifluoromethyl) phenylsulfonamido)butyl)ureido)ethanesulfonamido acetic acid;
26) (S)-(3-(4-(N-(1-(3-(3-methylpyridin-4-yl)phenyl)ethyl)-2-(trifluoromethyl)phenylsulfonamido)butyl)ureido) methanesulfonic acid;
27) (S)-(3-(4-(N-(1-(3-(3-ethylpyridin-4-yl)phenyl)ethyl)-2-(trifluoromethyl)phenylsulfonamido)butyl)ureido) methanesulfonic acid;
28) (3-(3-((3-Chloro-2-methyl-N-(2-(3-(3-methylpyridin-4-yl) phenyl) propan-2-yl) phenyl) sulfonamide)propyl) ureido) methanesulfonic acid;
29) 2-(3-(3-((3-Chloro-2-methyl-N-(2-(3-(3-methylpyridin-4-yl) phenyl) propan-2-yl) phenyl) sulfonamide)propyl) ureido)ethane-1-sulfonic acid;
30) (S)-2-((4-(N-(1-(3-(3-methylpyridin-4-yl)phenyl)ethyl)-2-(trifluoromethyl)phenylsulfonamido)butyl)amino)-2-oxoethanesulfonic acid;
31) (R)-2-amino-3-((4-(N—((S)-1-(3-(3-methylpyridin-4-yl)phenyl)ethyl)-2-(trifluoromethyl)phenylsulfonamido) butyl)amino)-3-oxopropane-1-sulfonic acid; and
32) (S)-2-((N-(2-(4-(3-chloro-2-methyl-N-(1-(3-(3-methylpyridin-4-yl)phenyl)ethyl)phenylsulfonamido)butanamido)ethyl)sulfamoyl)amino)acetic acid;
or a pharmaceutically acceptable salt thereof.

In another embodiment, the present invention relates to a pharmaceutical composition comprising the compound of formula (I), or a pharmaceutically acceptable salt thereof, and a pharmaceutically acceptable carrier.

In one aspect, the present invention provides a method of treating a human inflicted with a metabolic disorder. Exemplary metabolic disorder includes, but not limited to type-2 diabetes, pre-diabetes, obesity, fibrosing cholangitis, colitis, pancreatitis, and cancer. The treatment comprises administering to humans a therapeutically effective amount of the compound of formula I.

In another aspect, the present invention provides a method of treating a human inflicted with a metabolic disorder comprising administering to a human a therapeutically effective amount of the compound of formula (I), and a therapeutically effective amount of at least one other compound that is useful for treating the metabolic disorder. Preferably, the other compound includes, but not limited to, metformin, glicliazide, glimepiride, glipizide, nateglinide, repalinide, linaglition, saxagliptin, sitagliptin, vildaliptin, glitazones, pioglitazone, acarbose, pralintide, insulin, exenatide, liraglutide, dapagliflozin, canagliflozin and the like.

Preferably, the metabolic disorder is a TGR5-related metabolic disorder. More preferably, the metabolic disorder is type-2 diabetes. More preferably, the metabolic disorder is obesity.

In yet another aspect, the present invention provides a compound of formula (II):

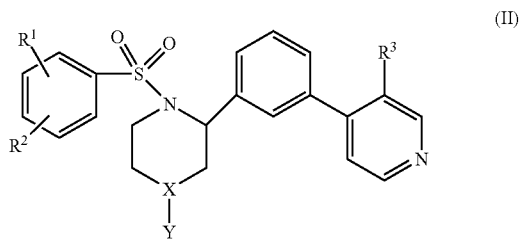

or a pharmaceutically acceptable salt thereof, wherein:
each $R^3$ is independently H, Cl, $CF_3$, alkyl, or methoxy;
each $R^2$ is independently H, $CF_3$, halogen, or methoxy;
X is CH, $CH_2$, N, or X is a bond with the proviso that Y is null when X is a bond or $CH_2$;
Y is H, COMe, COOH,

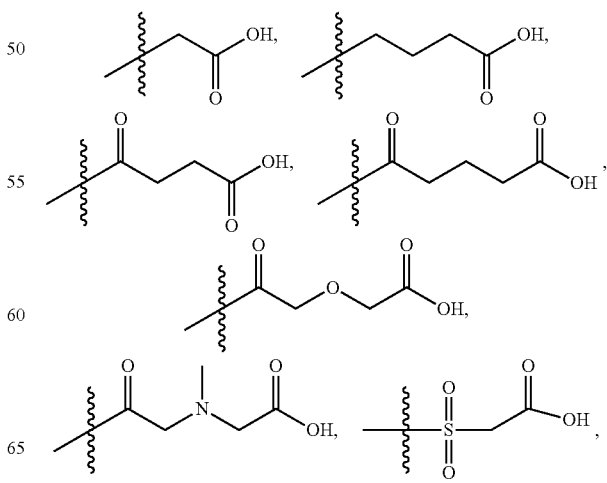

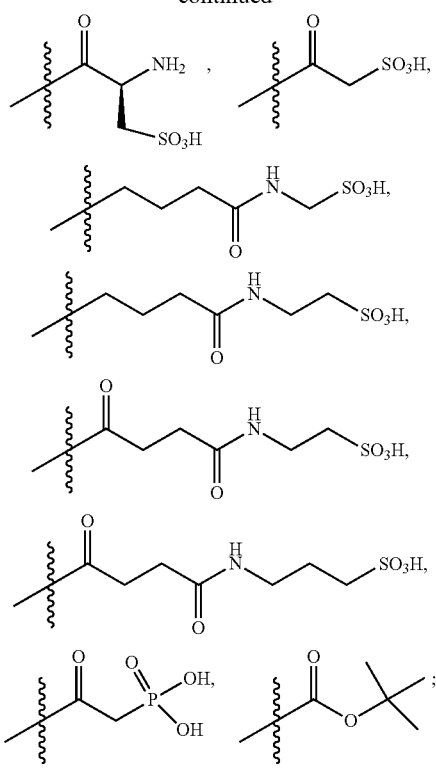

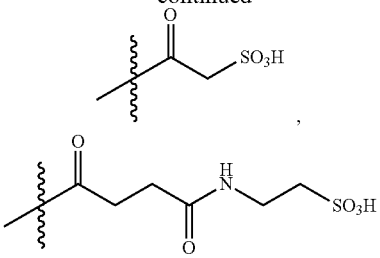

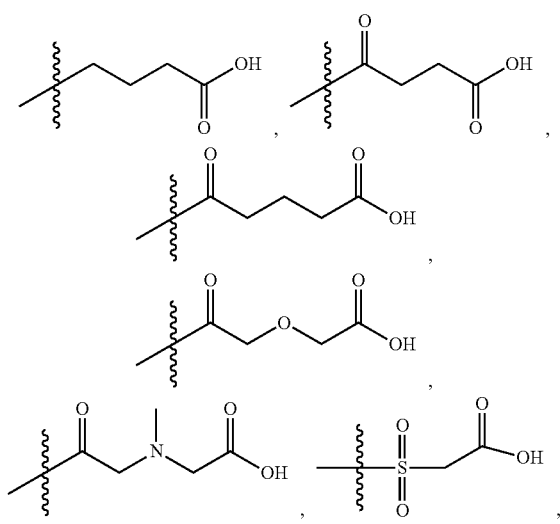

R[3] is H, halogen, alkyl, alkoxy, or ethyl.

In one embodiment, R[3] is Cl, CF$_3$, or methoxy; and R$_2$ is H or Cl.

Preferably, R[3] is CF$_3$ and R[2] is H, R[3] is alkyl and R[2] is Cl; or R[3] is Cl and R[2] is Cl.

In another embodiment, R[3] is alkyl, methoxy, or ethyl. Preferably, R[3] is ethyl.

In another embodiment, X is CH$_2$ or N. Preferably, X is N.

In another embodiment, Y is selected from the group consisting of:

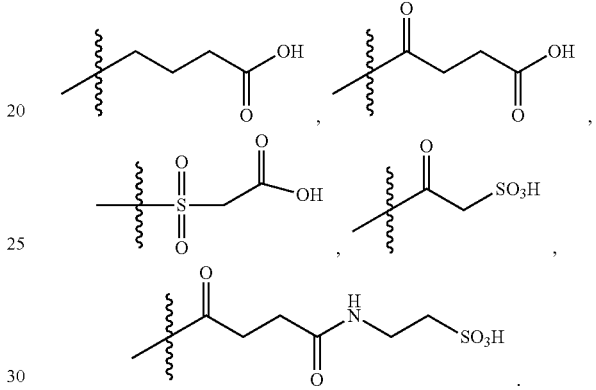

Preferably, Y is selected from the group consisting of:

In another aspect, the present invention provides a compound of:

1) 3-methoxy-4-(3-(1-((3-(trifluoromethyl)phenyl)sulfonyl) pyrrolidin-2-yl)phenyl)pyridine;
2) 3-methoxy-4-(3-(1-((2-(trifluoromethyl)phenyl)sulfonyl) pyrrolidin-2-yl)phenyl)pyridine
3) (+/−) 3-Methyl-4-(3-(1-((2-(trifluoromethyl)phenyl) sulfonyl)pyrrolidin-2-yl)phenyl)pyridine;
4) (+/−) tert-butyl 3-(3-(3-methylpyridin-4-yl)phenyl)-4-((2-(trifluoromethyl)phenyl)sulfonyl)-piperazine-1-carboxylate;
5) (+/−) 1-((3-chloro-2-methylphenyl)sulfonyl)-2-(3-(3-ethylpyridin-4-yl)phenyl)piperazine hydrochloride;
6) 1-((3-chloro-2-methylphenyl)sulfonyl)-2-(3-(3-methylpyridin-4-yl)phenyl)piperazine;
7) (+/−) 2-(3-(3-methylpyridin-4-yl)phenyl)-1-((2-(trifluoromethyl)phenyl)sulfonyl)piperazine;
8) 1-(3-(3-(3-methylpyridin-4-yl)phenyl)-4-((2-(trifluoromethyl)phenyl)sulfonyl)piperazin-1-yl)ethanone;
9) (+/−) 4-(4-((3-Chloro-2-methylphenyl)sulfonyl)-3-(3-(3-ethylpyridin-4-yl)phenyl)piperazin-1-yl)-4-oxobutanoic acid;
10) 5-(4-((3-chloro-2-methylphenyl)sulfonyl)-3-(3-(3-ethylpyridin-4-yl)phenyl)piperazin-1-yl)-5-oxopentanoic acid;
11) 2-(2-(4-((3-chloro-2-methylphenyl)sulfonyl)-3-(3-(3-ethylpyridin-4-yl)phenyl)piperazin-1-yl)-2-oxoethoxy) acetic acid;
12) 2-((2-(4-((3-chloro-2-methylphenyl)sulfonyl)-3-(3-(3-ethylpyridin-4-yl)phenyl)piperazin-1-yl)-2-oxoethyl) (methyl)amino)acetic acid;
13) 4-(4-((3-chloro-2-methylphenyl)sulfonyl)-3-(3-(3-methylpyridin-4-yl)phenyl)piperazin-1-yl)-4-oxobutanoic acid;

14) 5-(4-((3-chloro-2-methylphenyl)sulfonyl)-3-(3-(3-methylpyridin-4-yl)phenyl)piperazin-1-yl)-5-oxopentanoic acid;
15) 4-(4-((3-chloro-2-methylphenyl)sulfonyl)-3-(3-(pyridin-4-yl)phenyl)piperazin-1-yl)-4-oxobutanoic acid;
16) 4-(4-((3-chloro-2-methylphenyl)sulfonyl)-3-(3-(3-chloropyridin-4-yl)phenyl)piperazin-1-yl)-4-oxobutanoic acid;
17) 4-(4-((3-chloro-2-methylphenyl)sulfonyl)-3-(3-(3-methoxypyridin-4-yl)phenyl)piperazin-1-yl)-4-oxobutanoic acid;
18) 4-(3-(3-(3-methylpyridin-4-yl)phenyl)-4-(o-tolylsulfonyl)piperazin-1-yl)-4-oxobutanoic acid;
19) 4-(4-((3-methoxyphenyl)sulfonyl)-3-(3-(3-methylpyridin-4-yl)phenyl)piperazin-1-yl)-4-oxobutanoic acid;
20) 4-(4-((2,3-dichlorophenyl)sulfonyl)-3-(3-(3-methylpyridin-4-yl)phenyl)piperazin-1-yl)-4-oxobutanoic acid;
21) 4-(4-((4-fluoro-2-(trifluoromethyl)phenyl)sulfonyl)-3-(3-(3-methylpyridin-4-yl)phenyl)piperazin-1-yl)-4-oxobutanoic acid;
22) 2-((4-((3-Chloro-2-methylphenyl)sulfonyl)-3-(3-(3-ethylpyridin-4-yl)phenyl)piperazin-1-yl)sulfonyl)acetic acid;
23) (2R)-2-amino-3-(4-((3-chloro-2-methylphenyl)sulfonyl)-3-(3-(3-ethylpyridin-4-yl)phenyl)piperazin-1-yl)-3-oxopropane-1-sulfonic acid hydrochloride;
24) 2-(4-((3-Chloro-2-methylphenyl)sulfonyl)-3-(3-(3-ethylpyridin-4-yl)phenyl)piperazin-1-yl)-2-oxoethanesulfonic acid;
25) 2-(3-(3-(3-methylpyridin-4-yl)phenyl)-4-(o-tolylsulfonyl)piperazin-1-yl)-2-oxoethanesulfonic acid;
26) 2-(4-((3-methoxyphenyl)sulfonyl)-3-(3-(3-methylpyridin-4-yl)phenyl)piperazin-1-yl)-2-oxoethanesulfonic acid;
27) 2-(4-((2,3-dichlorophenyl)sulfonyl)-3-(3-(3-methylpyridin-4-yl)phenyl)piperazin-1-yl)-2-oxoethanesulfonic acid;
28) 2-(4-((3-chloro-2-methylphenyl)sulfonyl)-3-(3-(pyridin-4-yl)phenyl)piperazin-1-yl)-2-oxoethanesulfonic acid;
29) 2-(4-((3-chloro-2-methylphenyl)sulfonyl)-3-(3-(3-chloropyridin-4-yl)phenyl)piperazin-1-yl)-2-oxoethanesulfonic acid;
30) 2-(4-((3-chloro-2-methylphenyl)sulfonyl)-3-(3-(3-methoxypyridin-4-yl)phenyl)piperazin-1-yl)-2-oxoethanesulfonic acid;
31) 2-(3-(3-(3-methylpyridin-4-yl)phenyl)-4-((2-(trifluoromethyl)phenyl)sulfonyl)piperazin-1-yl)-2-oxoethanesulfonic acid;
32) 2-(4-((3-chloro-2-methylphenyl)sulfonyl)-3-(3-(3-ethylpyridin-4-yl)phenyl)piperazin-1-yl)-2-oxoethanesulfonic acid;
33) 2-(4-((3-Chloro-2-methylphenyl)sulfonyl)-3-(3-(3-ethylpyridin-4-yl)phenyl)piperazin-1-yl)acetic acid;
34) 4-(4-((3-chloro-2-methylphenyl)sulfonyl)-3-(3-(3-methylpyridin-4-yl)phenyl)piperazin-1-yl)butanoic acid;
35) 4-(4-((3-chloro-2-methylphenyl)sulfonyl)-3-(3-(3-ethylpyridin-4-yl)phenyl)piperazin-1-yl)butanoic acid;
36) (4-(4-((3-Chloro-2-methylphenyl)sulfonyl)-3-(3-(3-methylpyridin-4-yl)phenyl)piperazin-1-yl)butanamido)methanesulfonic acid;
37) 2-(4-(4-((3-chloro-2-methylphenyl)sulfonyl)-3-(3-(3-methylpyridin-4-yl)phenyl)piperazin-1-yl)butanamido)ethanesulfonic acid;
38) 2-(4-(4-((3-chloro-2-methylphenyl)sulfonyl)-3-(3-(3-ethylpyridin-4-yl)phenyl)piperazin-1-yl)-4-oxobutanamido)ethanesulfonic acid;
39) 3-(4-(4-((3-chloro-2-methylphenyl)sulfonyl)-3-(3-(3-ethylpyridin-4-yl)phenyl)piperazin-1-yl)-4-oxobutanamido)propane-1-sulfonic acid;
40) 3-methyl-4-(3-(1-((2-(trifluoromethyl)phenyl)sulfonyl)piperidin-2-yl)phenyl)pyridine;
41) cis-2-(3-(3-Methylpyridin-4-yl)phenyl)-1-((2-(trifluoromethyl)phenyl)sulfonyl)piperidine-4-carboxylic acid;
or a pharmaceutically acceptable salt thereof.

In a preferred embodiment, the present invention provides a compound of:
1) 3-methoxy-4-(3-(1-((3-(trifluoromethyl)phenyl)sulfonyl)pyrrolidin-2-yl)phenyl)pyridine;
2) 3-methoxy-4-(3-(1-((2-(trifluoromethyl)phenyl)sulfonyl)pyrrolidin-2-yl)phenyl)pyridine;
3) (+/−) 3-methyl-4-(3-(1-((2-(trifluoromethyl)phenyl)sulfonyl)pyrrolidin-2yl)phenyl)pyridine;
4) (+/−) 1-((3-chloro-2-methylphenyl)sulfonyl)-2-(3-(3-ethylpyridin-4-yl)phenyl)piperazine hydrochloride;
5) 1-((3-chloro-2-methylphenyl)sulfonyl)-2-(3-(3-methylpyridin-4-yl)phenyl)piperazine;
6) (+/−) 2-(3-(3-methylpyridin-4-yl)phenyl)-1-((2-(trifluoromethyl)phenyl)sulfonyl)piperazine;
7) (+/−) 4-(4-((3-Chloro-2-methylphenyl)sulfonyl)-3-(3-(3-ethylpyridin-4-yl)phenyl)piperazin-1-yl)-4-oxobutanoic acid;
8) 5-(4-((3-chloro-2-methylphenyl)sulfonyl)-3-(3-(3-ethylpyridin-4-yl)phenyl)piperazin-1-yl)-5-oxopentanoic acid;
9) 2-(2-(4-((3-chloro-2-methylphenyl)sulfonyl)-3-(3-(3-ethylpyridin-4-yl)phenyl)piperazin-1-yl)-2-oxoethoxy)acetic acid;
10) 2-((2-(4-((3-chloro-2-methylphenyl)sulfonyl)-3-(3-(3-ethylpyridin-4-yl)phenyl)piperazin-1-yl)-2-oxoethyl)(methyl)amino)acetic acid;
11) 4-(4-((3-chloro-2-methylphenyl)sulfonyl)-3-(3-(3-methylpyridin-4-yl)phenyl)piperazin-1-yl)-4-oxobutanoic acid;
12) 5-(4-((3-chloro-2-methylphenyl)sulfonyl)-3-(3-(3-methylpyridin-4-yl)phenyl)piperazin-1-yl)-5-oxopentanoic acid;
13) 4-(4-((2,3-dichlorophenyl)sulfonyl)-3-(3-(3-methylpyridin-4-yl)phenyl)piperazin-1-yl)-4-oxobutanoic acid;
14) 4-(4-((4-fluoro-2-(trifluoromethyl)phenyl)sulfonyl)-3-(3-(3-methylpyridin-4yl)phenyl)piperazin-1-yl)-4-oxobutanoic acid;
15) 2-((4-((3-Chloro-2-methylphenyl)sulfonyl)-3-(3-(3-ethylpyridin-4-yl)phenyl)piperazin-1-yl)sulfonyl)acetic acid;
16) 2-(4-((3-Chloro-2-methylphenyl)sulfonyl)-3-(3-(3-ethylpyridin-4-yl)phenyl)piperazin-1-yl)-2-oxoethanesulfonic acid;
17) 2-(4-((2,3-dichlorophenyl)sulfonyl)-3-(3-(3-methylpyridin-4-yl)phenyl)piperazin-1-yl)-2-oxoethanesulfonic acid;
18) 2-(4-((3-chloro-2-methylphenyl)sulfonyl)-3-(3-(3-chloropyridin-4-yl)phenyl)piperazin-1-yl)-2-oxoethanesulfonic acid;
19) 2-(4-((3-chloro-2-methylphenyl)sulfonyl)-3-(3-(3-methoxypyridin-4-yl)phenyl)piperazin-1-yl)-2-oxoethanesulfonic acid;
20) 2-(3-(3-(3-methylpyridin-4-yl)phenyl)-4-((2-(trifluoromethyl)phenyl) sulfonyl)piperazin-1-yl)-2-oxoethanesulfonic acid;
21) 2-(4-((3-chloro-2-methylphenyl)sulfonyl)-3-(3-(3-ethylpyridin-4-yl)phenyl) piperazin-1-yl)-2-oxoethanesulfonic acid;

22) 4-(4-((3-chloro-2-methylphenyl)sulfonyl)-3-(3-ethylpyridin-4-yl)phenyl) piperazin-1-yl)butanoic acid;
23) 2-(4-(4-((3-chloro-2-methylphenyl)sulfonyl)-3-(3-ethylpyridin-4-yl)phenyl)piperazin-1-yl)-4-oxobutanamido)ethanesulfonic acid; and
24) 3-methyl-4-(3-(1-((2-(trifluoromethyl)phenyl)sulfonyl)piperidin-2-yl)phenyl)pyridine;
or a pharmaceutically acceptable salt thereof.

In a more preferred embodiment, the present invention provides a compound of:
1) 3-methoxy-4-(3-(1-((2-(trifluoromethyl)phenyl)sulfonyl)pyrrolidin-2-yl)phenyl)pyridine;
2) (+/−) 3-Methyl-4-(3-(1-((2-(trifluoromethyl)phenyl)sulfonyl)pyrrolidin-2-yl)phenyl)pyridine;
3) (+/−) 1-((3-chloro-2-methylphenyl)sulfonyl)-2-(3-(3-ethylpyridin-4-yl)phenyl)piperazine hydrochloride;
4) (+/−) 4-(4-((3-Chloro-2-methylphenyl)sulfonyl)-3-(3-ethylpyridin-4-yl)phenyl)piperazin-1-yl)-4-oxobutanoic acid;
5) 5-(4-((3-chloro-2-methylphenyl)sulfonyl)-3-(3-ethylpyridin-4-yl)phenyl) piperazin-1-yl)-5-oxopentanoic acid;
6) 2-(2-(4-((3-chloro-2-methylphenyl)sulfonyl)-3-(3-ethylpyridin-4-yl)phenyl)piperazin-1-yl)-2-oxoethoxy)acetic acid;
7) 2-((2-(4-((3-chloro-2-methylphenyl)sulfonyl)-3-(3-ethylpyridin-4-yl)phenyl)piperazin-1-yl)-2-oxoethyl)(methyl)amino)acetic acid;
8) 5-(4-((3-chloro-2-methylphenyl)sulfonyl)-3-(3-methylpyridin-4-yl)phenyl)piperazin-1-yl)-5-oxopentanoic acid;
9) 2-((4-((3-Chloro-2-methylphenyl)sulfonyl)-3-(3-ethylpyridin-4-yl)phenyl)piperazin-1-yl)sulfonyl)acetic acid;
10) 2-(4-((3-Chloro-2-methylphenyl)sulfonyl)-3-(3-ethylpyridin-4-yl)phenyl)piperazin-1-yl)-2-oxoethanesulfonic acid;
11) 2-(4-((2,3-dichlorophenyl)sulfonyl)-3-(3-methylpyridin-4-yl)phenyl)piperazin-1-yl)-2-oxoethanesulfonic acid;
12) 2-(4-((3-chloro-2-methylphenyl)sulfonyl)-3-(3-methoxypyridin-4-yl)phenyl)piperazin-1-yl)-2-oxoethanesulfonic acid;
13) 4-(4-((3-chloro-2-methylphenyl)sulfonyl)-3-(3-ethylpyridin-4-yl)phenyl)piperazin-1-yl)butanoic acid; and
14) 3-methyl-4-(3-(1-((2-(trifluoromethyl)phenyl)sulfonyl)piperidin-2-yl)phenyl)pyridine;
or a pharmaceutically acceptable salt thereof.

In one aspect, the present invention provides a pharmaceutical composition comprising the compounds of formula (II) or a pharmaceutically acceptable salt thereof, and a pharmaceutically acceptable carrier.

In another aspect, the present invention provides a method of treating a human inflicted with a metabolic disorder, comprising administering to a human a therapeutically effective amount of the compound of formula (II). Exemplary metabolic disorders include, but limited to type-2 diabetes, pre-diabetes, obesity, fibrosing cholangitis, colitis, pancreatitis, and cancer.

In yet another aspect, the present invention provides a method of treating a human inflicted with a metabolic disorder, comprising administering to said human a therapeutically effective amount of the compound of formula (II), and a therapeutically effective amount of at least one other compound useful for treating the metabolic disorder.

Preferably, the other compounds useful for treating the metabolic disorder include, but not limited to metformin, glicliazide, glimepiride, glipizide, nateglinide, repalinide, linaglition, saxagliptin, sitagliptin, vildaliptin, glitazones, pioglitazone, acarbose, pralintide, insulin, exenatide, liraglutide, dapagliflozin and canagliflozin.

Preferably, the compounds are useful in treating a human inflicted with a TGR5-related metabolic disorder such as type-2 diabetes, pre-diabetes, obesity, fibrosing cholangitis, colitis, pancreatitis, and cancer. Preferably, the metabolic disorder is type-2 diabetes and obesity. The treatment involves the steps of: (a) administering a pharmaceutically effective amount of the compound of formula (II); and (b) administering an agent selected from the group consisting of metformin, gliclazide, glimepiride, glipizide, nateglinide and repaglinide, linagliptin, saxagliptin, sitagliptin and vildagliptin, glitazones, pioglitazone, acarbose, pramlintide, insulin, exenatide, liraglutide, dapagliflozin, and canagliflozin to a human in need thereof.

The compounds of the present invention may contain an asymmetric center and may thus exist as enantiomers. Where the compounds according to the invention possess two or more asymmetric centers, they may additionally exist as diastereomers. When bonds to the chiral carbon are depicted as straight lines in the formulas of the invention, it is understood that both the (R) and (S) configurations of the chiral carbon, and hence both enantiomers and mixtures thereof, are embraced. The present invention includes all such possible stereoisomers as substantially pure resolved enantiomers, racemic mixtures, as well as mixtures of diastereomers thereof. Except where otherwise specified, the formulae encompassing compounds of the present invention are shown without a definitive stereochemistry at certain positions. The present invention therefore may be understood to include all stereoisomers of compounds and pharmaceutically acceptable salts thereof. It is generally preferable to administer compounds of the present invention as enantiomerically pure formulations.

Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the present invention may be obtained by stereospecific synthesis using optically pure starting materials or reagents of known configuration.

The compounds of the present invention include tautomers of such compounds. Tautomers are defined as compounds that undergo rapid proton shifts from one atom of the compound to another atom of the compound. Some of the compounds described herein may exist as tautomers with different points of attachment of hydrogen. Exemplary tautomer includes a ketone and its enol form known as keto-enol tautomers.

Accordingly, the compounds within the generic structural formulas, embodiments and specific compounds described and claimed herein are intended to encompass salts, all possible stereoisomers and tautomers.

The compounds of the present invention include all suitable isotopic variations of such compounds. An isotopic variation of a compound is defined as one in which at least one atom is replaced by an atom having the same atomic number but an atomic mass different from the atomic mass usually found in nature. Exemplary isotopes include isotopes of hydrogen, carbon, nitrogen and oxygen such as $^2$H, $^3$H, $^{11}$C, $^{13}$C, $^{14}$C, $^{15}$N, $^{17}$O, $^{18}$O, $^{35}$S, $^{18}$F, $^{36}$Cl, $^{123}$I and the like. Certain isotopic variations of the compounds are useful in drug or substrate tissue distribution studies. Others may afford certain therapeutic advantages resulting from greater metabolic stability, such as increased or decreased in vivo half-life or reduced dosage requirements. Isotopic variations of the compounds of the present invention provided herein are prepared by conventional procedures using appropriate isotopic variations of suitable reagents.

In one aspect, the present invention provides a pharmaceutical composition containing a TGR5 compound described herein, method of preparation and use of same in treating metabolic diseases such as diabetic mellitus type-2 in a mammal, preferably a human.

In one embodiment, the present invention provides a pharmaceutical composition containing a compound of formula (I) for use in therapy in humans in need thereof for treatment of diabetic diseases. In another embodiment, the present invention provides a pharmaceutical composition containing a compound of formula (II) for use in therapy for diabetic diseases.

The present composition encompasses a TGR5 compound in the form of a vehicle such as a pharmaceutically acceptable carrier. The pharmaceutical acceptable carrier comprises agents that aid optimization of solubility, absorption, flavor or texture of the composition. Pharmaceutically acceptable carriers are commonly known to a skilled artisan and include a variety of organic or inorganic carriers including starch, cellulose, gelatin, talc, glycol, polyol, ester, agar, buffering agents, alginic acid and the like that are employed in pharmaceutical formulations. Such carriers include, for solid preparations, diluents, lubricants, binders, and disintegrants, and for liquid preparations, solvents, solubilizing agents, suspending agents, isotonic agents, buffer agents, soothing agents, and the like.

Suitable exemplary diluents include lactose, sucrose, D-mannitol, starch, crystalline cellulose, light silica anhydrate, and the like. Suitable exemplary lubricants include magnesium stearate, calcium stearate, talc, colloidal silica, and the like. Suitable exemplary binders include crystalline cellulose, sucrose, D-mannitol, dextrin, hydroxypropylcellulose, hydroxypropylmethylcellulose, polyvinylpyrrolidone, and the like. Suitable exemplary disintegrants include starch, carboxymethylcellulose, calcium carboxymethylcellulose, sodium croscarmellose, sodium carboxymethylstarch, and the like. Suitable exemplary solvents include injectable water, alcohol, propylene glycol, macrogol, sesame oil, corn oil, etc. Suitable exemplary solubilizing agents include polyethylene glycol, propylene glycol, D-mannitol, benzylbenzoate, ethanol, trisaminomethane, cholesterol, triethanolamine, sodium carbonate, sodium citrate, and the like. Suitable exemplary suspending agents include surfactants such as stearyltriethanolamine, sodium laurylsulfate, laurylaminopropionic acid, lecithin, benzalkonium chloride, benzethonium chloride, glycerin monostearate, and the like; and hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose, and the like. Suitable exemplary isotonic agents include sodium chloride, glycerin, D-mannose, and the like. Suitable exemplary buffer agents include buffer solutions of salts, such as phosphate, acetates, carbonates, and citrates. Suitable exemplary soothing agents include benzyl alcohol, and the like. Suitable exemplary antiseptic substances include para-oxybenzoic acid esters, chlorobutanol, benzyl alcohol, phenethyl alcohol, dehydroacetic acid, sorbic acid, and the like. Suitable exemplary antioxidants include sulfite salts, ascorbic acid, and the like. Suitable exemplary sealers include, but are not limited to HPMC (or hypromellose), HPC, PEG and combinations thereof. In some embodiments, disintegrants are added to the formulation to help all or part of the dosage form to disintegrate after consumption, thereby releasing at least a portion of the active ingredients. Some common disintegrants include several modified cellulose derivatives, such as croscarmellose sodium and other modified starch derivatives such as sodium starch glycolate. It will also be understood by one of ordinary skill in the art that a pharmaceutical composition may contain other suitable ingredients, binders and lubricants that provide optimal dissolution profiles of dosage forms.

When the dosage form of pharmaceutical composition is a capsule, it may contain a liquid carrier. Other materials may be present as coatings or to otherwise modify the physical form of the dosage form. For instance, tablets, pills, or capsules may be coated with shellac, sugar or both. A syrup or elixir may contain sucrose as a sweetening agent and methyl and propylparabens as preservatives, a dye and flavoring, such as cherry or orange flavor. Of course, materials used in preparing any dosage form should be pharmaceutically pure and substantially non-toxic in the amounts employed. Pharmaceutical additives such as antiseptic substances, antioxidants, coloring agents, and sweeteners may also be added if necessary.

The present invention, in various embodiments, provides an oral composition suitable for human administration. The present oral composition encompasses various dosage forms. For example, the oral composition can be a tablet, coated tablet, capsule, caplet, cachet, lozenges, gel capsule, hard gelatin capsule, soft gelatin capsule, troche, dragee, dispersion, powder, granule, pill, liquid, an aqueous or non-aqueous liquid suspension, an oil-in-liquid or oil-in-water emulsion, including sustained release formulations that are known in the art. (See, e.g., Introduction to Pharmaceutical Dosage Forms, 1985, Ansel, H. C., Lea and Febiger, Philadelphia, Pa.; *Remington's Pharmaceutical Sciences*, 1995, Mack Publ. Co., Easton, Pa.)

These dosage forms can be prepared using standard procedures that are known to the art, including but not limited to encapsulating procedures. In one embodiment, the dosage form provides a low blood concentration of TGR5 agonists (TGR5 compounds) after ingestion but continues to release TGR5 compounds in the gut compartment over time to permit low pharmaceutical exposure (i.e., TGR5 compounds are restricted to the gut compartment). Preferably, the oral compositions (after ingestion) provide a plasma level of TGR5 compounds at <20 ng/mL. More preferably, the present compounds of the invention have <5 ng/mL.

In one embodiment, the present compositions are formulated into a dosage form releasing TGR5 compounds for a period of 1 to 12, typically 3 to 12 hours, more typically 6-12 hours after ingestion. Preferably, the oral pharmaceutical compositions of the present invention may be administered in single or divided doses, from one to four times a day. The oral dosage forms may be conveniently presented in unit dosage forms and prepared by any methods well known in the art of pharmacy. In another embodiment, the present composition contains a predetermined amount of a therapeutic amount of TGR5 compound effective in treating diabetic diseases.

The present formulations can be prepared by any suitable method of pharmacy which includes the step of bringing into association the therapeutic TGR5 compound compositions and a suitable carrier (which can contain one or more accessory ingredients as noted above). In general, the pharmaceutical compositions according to embodiments of the present invention are prepared by uniformly and intimately admixing the TGR5 compounds with a liquid or finely divided solid carrier, or both, and then, if necessary, shaping the resulting mixture. For example, tablets may be prepared by compressing or molding powders or granules containing the therapeutic TGR5 compounds, optionally with one or more accessory ingredients. Compressed tablets can be prepared by compressing, in a suitable machine, the therapeutic TGR5 compounds in a free-flowing form, including a powder or granules optionally mixed with a binder, lubricant, inert diluent, and/or surface active or dispersing agent(s). Molded tablets can be made by molding, in a suitable machine, the powdered compound moistened with an inert liquid binder. The tablets can optionally be coated or scored and can be formulated so as to provide slow or controlled release of the active ingredient TGR5 compounds therein.

When the pharmaceutical compositions are applied to humans, they are desirably administered via the oral route. The therapeutic effective dose of each TGR5 active compounds depends on the age or symptom of the patient to be treated. Generally, the pharmaceutical preparations may contain about 50 mg, 100 mg, 250 mg, 500 mg or 1,000 mg of the TGR5 compounds per unit dosage form and may be administered to humans or animals at a daily dose of 0.1-100 mg per kilogram of body weight. The optimal dose suitable for a particular patient can be conveniently determined (by a physician) without undue experimentation.

The pharmaceutical compositions generally are administered in a therapeutic effective amount for treatment or prophylaxis of diabetic conditions. Initial dosing in humans can be accompanied by clinical monitoring of symptoms for the selected condition (e.g., blood sugar (glucose) level or HbA1c test). For administration particularly to mammals, and particularly humans, it is expected that the daily dosage level of the TGR5 compounds may be determined to maintain an optimal blood sugar level or HbA1c level.

It will be appreciated that the optimum dosage will be determined by standard methods for each treatment modality and indication, taking into account the indication, its severity, route of administration, complicating conditions and the like. The physician in any event will determine the actual dosage that will be most suitable for an individual and will vary with the age, weight and response of the particular individual. The effectiveness of a selected actual dose can readily be determined, for example, by measuring clinical symptoms or standard diabetic indicia after administration of the selected dose. The above dosages are exemplary of the average case. There can, of course, be individual instances where higher or lower dosage ranges are merited, and such are within the scope of this invention. For conditions or disease states as are treated by the present invention, maintaining consistent daily levels in a subject over an extended period of time, e.g., in a maintenance regime, can be particularly beneficial.

For purposes of the present invention, "treating" or "treatment" in the present context includes alleviating symptoms, enhancing glycemic control or insulin sensitivity, arresting, slowing, retarding or stabilizing progression of a condition or a physiological or morphological marker thereof, or improving clinical outcome, for example as measured by quality of life, incidence or severity of adverse cardiac events, time to end-stage renal disease or survival time.

Without wishing to be bound by a theory, it is discovered that the present sulfonamide compounds are good TGR5 agonists and have a low plasma exposure profile (i.e., low $C_{max}$ or AUC values). Low plasma exposure refers to maintaining a plasma level of TGR5 compounds (i.e., $C_{max}$<200 ng/mL) after administration of the compounds. Preferably, the compounds of the present invention have a $C_{max}$<20 ng/mL. More preferably, the compounds of the present invention have a $C_{max}$<5 ng/mL.

The present inventors discovered that when administered via an oral route, the present compounds are restricted to the gut compartment and thus have low bioavailability in the blood stream (i.e., the compounds do not leak into the circulation and the resulting low plasma level). Not wishing to be bound to a theory, it is speculated that one functional group on the parent molecule may have affected the gut permeability and renders the compounds to be restricted in the gut compartment. It is possible that the functional group acts in concert with other functional groups on the parent molecules to exert this unique effect.

In one aspect, the present invention provides a combination therapy using the compounds as described herein and one or more of an additional therapeutic agent(s). The additional therapeutic agents preferably include medications commonly prescribed for diabetic treatments. Exemplary additional therapeutic agents include, but are not limited to metformin, sulfonylurea (such as gliclazide, glimepiride, and glipizide), nateglinide and repaglinide, dipeptidyl peptidase 4 (DPP-4) inhibitors (such as linagliptin, saxagliptin, sitagliptin and vildagliptin), thiazolidinediones (such as glitazones or pioglitazone), acarbose, pramlintide, insulin, exenatide, liraglutide, dapagliflozin, canagliflozin and the like.

The combination therapy provides the beneficial effect from the co-action of these therapeutic agents, due to synergistic or additive effects. Therapeutic agents are preferably administered simultaneously, or carried out over a defined time interval (e.g., minutes or hours depending upon the combination selected). In one embodiment, co-administration can be accomplished, for example, by administering to the subject a single dosage form (e.g., capsule) having a fixed ratio of each therapeutic agent. In another embodiment, while the TGR5 compound of the present invention is administered by oral route, the second therapeutic agent can be administered by the same route or by different routes (e.g., orally, intravenous injection, intramuscular or nasally). In one embodiment, the combined therapy composition includes an oral TGR5 compound and an injectable insulin. In another embodiment, the combined therapy composition includes an oral TGR5 compound and sitagliptin.

In one aspect, the present invention provides a composition comprising a compound of the present invention or a pharmaceutically acceptable salt, solvate, or prodrug thereof.

In one aspect, the present invention relates to a method of treating diseases in a subject by administering a therapeutically effective amount of a compound of the present invention or a pharmaceutically acceptable salt, solvate, or prodrug thereof.

The present inventors designed the compounds of the present invention to have favorable PK profile characteristics (e.g., low $C_{max}$). Without wishing to be bound by a theory, it is further discovered that the compounds of the present invention, when orally ingested, are not leaking into the blood stream (i.e., low $C_{max}$). The low $C_{max}$, is believed to render the present compounds superior properties of reducing side-effects (such as bile retention in gall-bladder). The compounds of the present invention are therefore superior and suitable for treating TGR5-related metabolic disease, such as pre-diabetes, type-2 diabetes, and obesity. For purposes of this application, TGR5 related metabolic disease may also include type-2 diabetes/glucose homeostasis, obesity, fibrosing cholangitis, colitis, pancreatitis, cancer, and the like.

In one embodiment, the subject in need of treatment is a human. The present compounds are suitable for treating a TGR5 related metabolic disease in a human. In one embodiment, the human disorder is pre-diabetes. In a preferred embodiment, the human metabolic disorder is type-2 diabetes. In another preferred embodiment, the human metabolic disorder is obesity. In further embodiments, the TGR5-related metabolic disorder may include diabetes, insulin resistance, and pre-diabetic insulin resistance. In another embodiment, the human metabolic disorder is fibrosing cholangitis. In another embodiment, the human metabolic disorder is an inflammatory disease, preferably colitis. In another embodiment, the human metabolic disorder is a digestive disease, preferably pancreatitis. In another embodiment, the human metabolic disorder is cancer.

Without wishing to be bound by a theory, it is discovered that one functional group attributes to the non-systemic property of the compounds. The functional group is speculated to render the compound with a low plasma exposure while being surprisingly effective in exerting the glycemic control in diabetic conditions. In accordance with this unexpected finding, the present compounds have practical clinical utility and application in the treatment of TGR5-related metabolic disorders including pre-diabetes, type-2 diabetes, obesity, fibrosing cholangitis, colitis, pancreatitis, cancer, and the like While the invention has been described in conjunction with the detailed description thereof, the foregoing description is intended to illustrate and not limit the scope of the invention, which is defined by the scope of the appended claims. Other embodiments, advantages, and modifications are within the scope of the following claims. It will be understood by those skilled in the art that various changes in form and details may be made therein without departing from the scope of the invention encompassed by the appended claims.

EXAMPLES

General Synthetic Methods:

Compounds of the invention can be prepared using the methods described below. In the general schemes, many of the transformations such as alkylations, reductions, oxidations, displacements, amide bond formations and the like are common synthetic steps known to those skilled in the art.

It will be clear to those skilled in the art that various protecting groups may need to be employed and subsequently removed to generate compounds of the invention. Numerous protecting groups and conditions for their addition and removal are described in Greene's *Protecting Groups in Organic Synthesis* P. G. M. Nuts, T. W. Greene, Fourth Edition, Wiley, New York, 2006.

For example, some of the routes below describe the deprotection of an amine. Those skilled in the art will recognize that the amine protecting group could be a tert-butoxy carbamate, a carboxybenzyl group, a 9-fluorenylmethyl carbamate, a phthalimide group or others. Deprotection conditions of the amine protecting groups are known to those skilled in the art. For example, if the amine is protected as a tert-butoxy carbamate, suitable acidic conditions such as a solution of TFA in DCM or a solution of HCl in dioxane can be used to remove the protecting group. Alternately, if the protecting group is a 9-fluorenylmethyl carbamate, suitable basic conditions such as a solution of piperidine in DMF or a solution of diethylamine in DMF can be used to remove the protecting group. Alternatively, if the amine is protected as a carboxybenzyl group, catalytic hydrogenation can be employed for its deprotection. Furthermore, if the protecting group is a phthalimide, treatment with a nucleophilic amine such as hydrazine or methylamine in a solvent such as ethanol can remove the protecting group.

Other routes require the removal of a carboxylic acid protecting group. Those skilled in the art will recognize that the carboxylic acid protecting group could be a tert-butyl, benzyl, ethyl, or methyl ester, or the like. Removal of a tert-butyl ester can be completed under acid conditions such as treatment with a solution of TFA in DCM. Alternatively, the removal of a benzyl ester can be completed via hydrogenolysis using, for example, palladium on carbon under a hydrogen atmosphere. In further examples, ethyl and methyl esters can be hydrolyzed to the carboxylic acid under hydrolytic conditions such as LiOH in aqueous THF.

In the general schemes below, the synthesis of compounds sometimes requires the formation of an amide bond. Coupling agents such as EDC, DIC, DSC, or HATU can be used to form the amide bond generally in a solvent such as DCM or DMF with a suitable base present such as DIEA or triethylamine as required. An additive such as HOBt, HOAt, or DMAP can also be employed during the reaction.

Specific synthetic transformations not covered in the general schemes below are described in detail in the experimental section. In addition, it will be apparent to those skilled in the art that the order of steps might be adjusted throughout depending on the compound to be produced.

Chemical Syntheses for Formula (I)

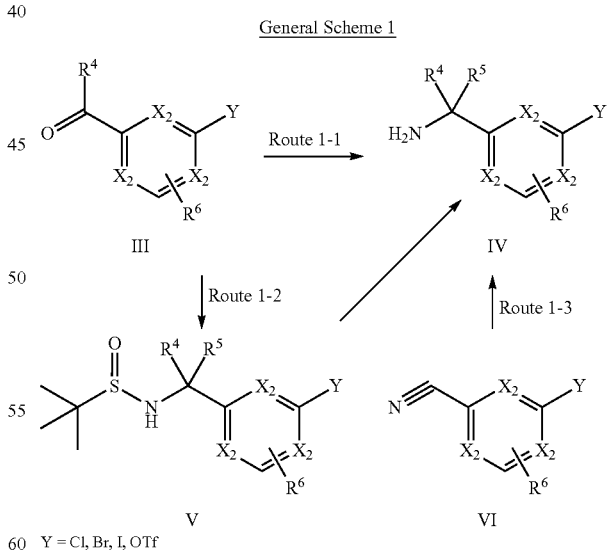

General Scheme 1

Y = Cl, Br, I, OTf

Compounds of formula IV are intermediates in the synthesis of compounds of the invention. Many compounds with the structure IV are commercially available. Compounds of structure IV that are not commercially available can be synthesized via various synthetic routes known to those skilled in the art. As shown in General Scheme 1, Route 1-1, a suitable ketone derivative III can be reductively aminated with a suitable reagent such as ammonium acetate to generate compounds of formula IV. Reducing agents such as sodium cyanoborohydride or sodium triacetoxyborohydride can be employed in solvents such as methanol, ethanol, dimethylformamide, or dichloroethane.

Alternatively, as depicted in Route 1-2, the initial ketone can be reductively aminated with 2-methylpropane-2-sufinamide to generate intermediate V. The reaction is generally carried out with sodium borohydride in a solvent such as THF in the presence of a Lewis acid such as titanium (IV) ethoxide. Intermediate V is then treated with an acid such as hydrochloric acid to generate intermediate IV. R4 and R5 alkyl-substituted versions of intermediate IV can be synthesized by treating intermediate V with a suitable organometallic reagent such as an alkylzinc derivative in the presence of a Lewis acid such as copper (II) triflate in a solvent such as DCM.

Alternatively, a suitable cyano derivative VI can be reacted in various ways to generate intermediate IV. Simple reduction in the presence of a reducing agent such as borane in a solvent such as THF or ether will generate aminomethyl versions of intermediate IV. The reaction of a suitable organometallic reagent such as an alkyl grignard reagent can generate R4 and R5 alkyl-substituted versions of intermediate IV. Usually a Lewis acid such as titanium isopropoxide is employed in the reaction in a solvent such as ether or THF. An alkyllithium can also be employed to convert intermediate VI to intermediate IV in the presence of cerium(III) chloride. Again, solvents such as THF or ether are usually employed.

General Scheme 2

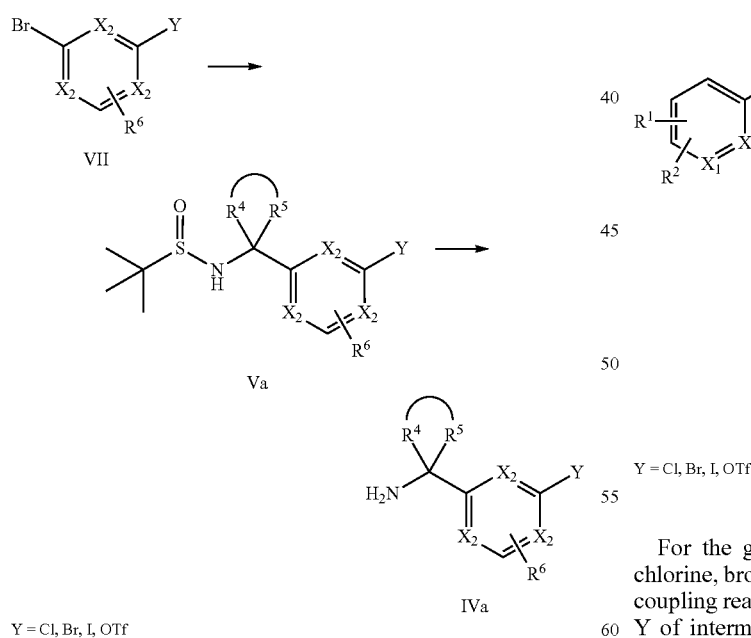

Y = Cl, Br, I, OTf

A subset of intermediates where R4 and R5 are connected to generate a cyclic structure (intermediate IVa) can be synthesized by the route depicted in General Scheme 2.

The brominated intermediate VII can be lithiated with an alkyl lithium reagent such as n-butyllithium in THF and reacted with a cyclic imine such as 2-methyl-N-(3-oxetanylidene)propane-2-sulfinamide to generate intermediate Va. Acidic treatment of intermediate Va using a solution such as hydrogen chloride in dioxane yields the desired intermediate IVa.

General Scheme 3

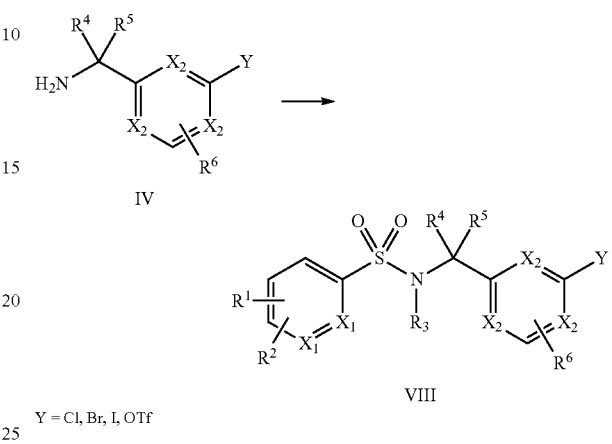

Y = Cl, Br, I, OTf

Those skilled in the art will recognize that intermediate IV can be converted to Intermediate VIII by reaction with a sulfonyl chloride in a suitable solvent such as DMF, DCM, pyridine, or the like. Usually a suitable base such as triethylamine, N,N-diisopropylethylamine, pyridine, or 2,6-lutidine is employed in the reaction. A catalyst such as DMAP can also be employed.

General Scheme 4

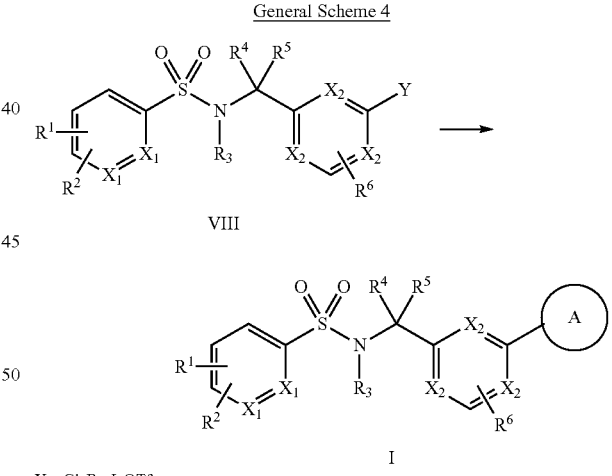

Y = Cl, Br, I, OTf

For the general schemes, Y indicates a group such as chlorine, bromine, iodine, or triflate that can undergo a cross coupling reaction. As shown in General Scheme 4, the group Y of intermediate VIII can be reacted to form an aryl or heteroaryl bearing compound of formula I by conditions known to those skilled in the art. For example, heating of VIII with an aryl or heteroaryl boronic acid or boronic ester in the presence of both a palladium catalyst such as Tetrakis (triphenylphosphine)palladium(0), tris(dibenzylideneacetone)dipalladium(0), [1,1'-Bis(diphenylphosphino)ferrocene]dichloropalladium(II), or the like and a suitable base such as aqueous sodium carbonate or potassium carbonate in a solvent such as dioxane or DMF (Suzuki coupling conditions) will generate compounds of the invention I. Alternatively, reactions of VIII with aryl or heteroaryl tin derivatives using Stille conditions could also generate compounds I. As another example, reactions of VIII with aryl or heteroaryl zinc derivatives using Negishi conditions could also be used generate compounds I.

Those skilled in the art will recognize there are variations to these coupling reactions that can be employed to convert intermediates VIII to compounds of the invention I. For instance, the Molander version of the Suzuki coupling reaction could be utilized. In this variation, an aryl or heteroaryl reagent bearing a bromine or chlorine is first converted to a boronic acid in situ prior to reaction with intermediate VIII. Tetrahydroxydiborane is employed in a suitable solvent such as ethanol or THF. A catalyst and ligand such as XPhos-Pd-G2 and Xphos are utilized to generate the boronic acid in the presence of a suitable base such as potassium acetate. Once generated, the boronic acid can be coupled to intermediate VIII in the same pot with the addition of an aqueous base such as potassium carbonate to yield compounds of the invention I. In general, the reactions in this sequence are heated between 80° C. and 120° C.

In an alternate version of this reaction, Y of intermediate VIII can be converted to a boronic acid prior to coupling with an aryl or heteroaryl partner containing a bromine or chlorine. Again, Molander conditions are employed wherein tetrahydroxydiborane is reacted with intermediate VIII in the presence of a catalyst and ligand such as XPhos-Pd-G2 and Xphos in the presence of a suitable base such as potassium acetate. Heating between 80° C. and 120° C. is employed.

General Scheme 5

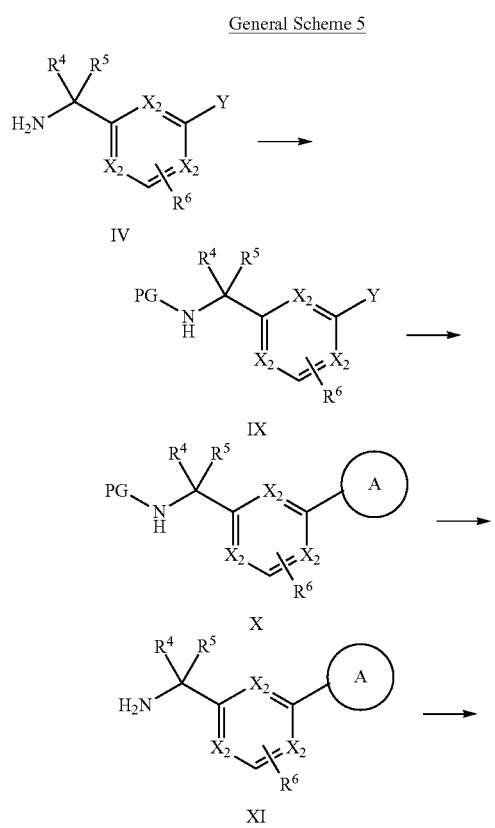

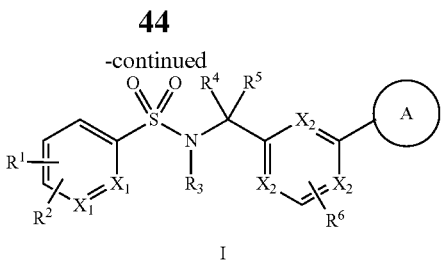

(PG = Protecting Group)
Y = Cl, Br, I, OTf

Those skilled in the art will realize that the order of reactions in General Schemes 1-4 can be varied as necessary to synthesize compounds of the invention I. For instance, in General Scheme 5, the amine of intermediate IV can be protected by the addition of a suitable amine protecting group. Many such groups are known to those skilled in the art. Examples include a tert-butoxy carbamate, a carboxybenzyl group, a 9-fluorenylmethyl carbamate, a phthalimide, and others. The protected material IX can undergo a cross coupling reaction using any of the methods described above in General Scheme 4 to yield X. Deprotection of this intermediate by a suitable method as outlined above generates amine derivative XI. This amine can be reacted with a sulfonyl chloride under conditions as described for General Scheme 3 to produce compounds of the invention I.

General Scheme 6

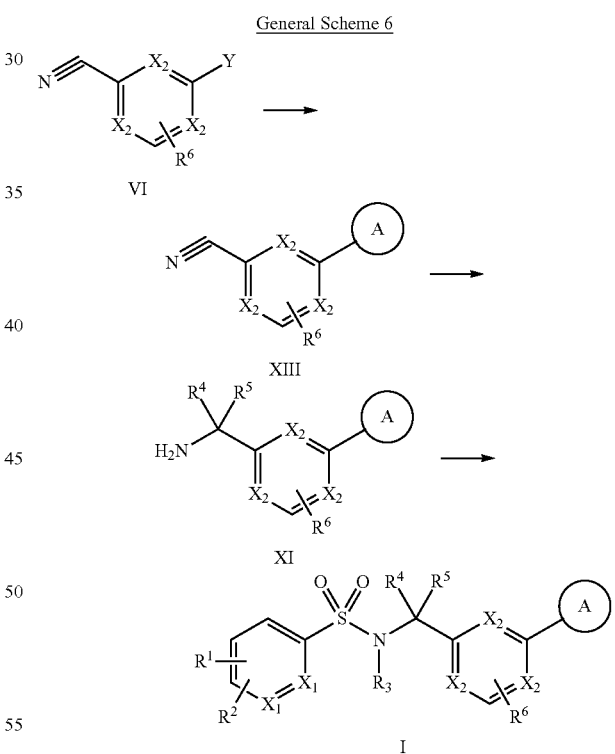

General Scheme 6 outlines another example by which the order of reactions to produce compounds of the invention I can be varied. In this example, intermediate VI first undergoes a cross coupling reaction to generate intermediate XII. Any suitable cross coupling method can be employed as described under General Scheme 4. Reaction of the cyano group of XII under the variety of conditions described under General Scheme 1 produces intermediate XI. Reaction with a suitable sulfonyl chloride under conditions as described for General Scheme 3 produces compounds of the invention I.

General Scheme 7

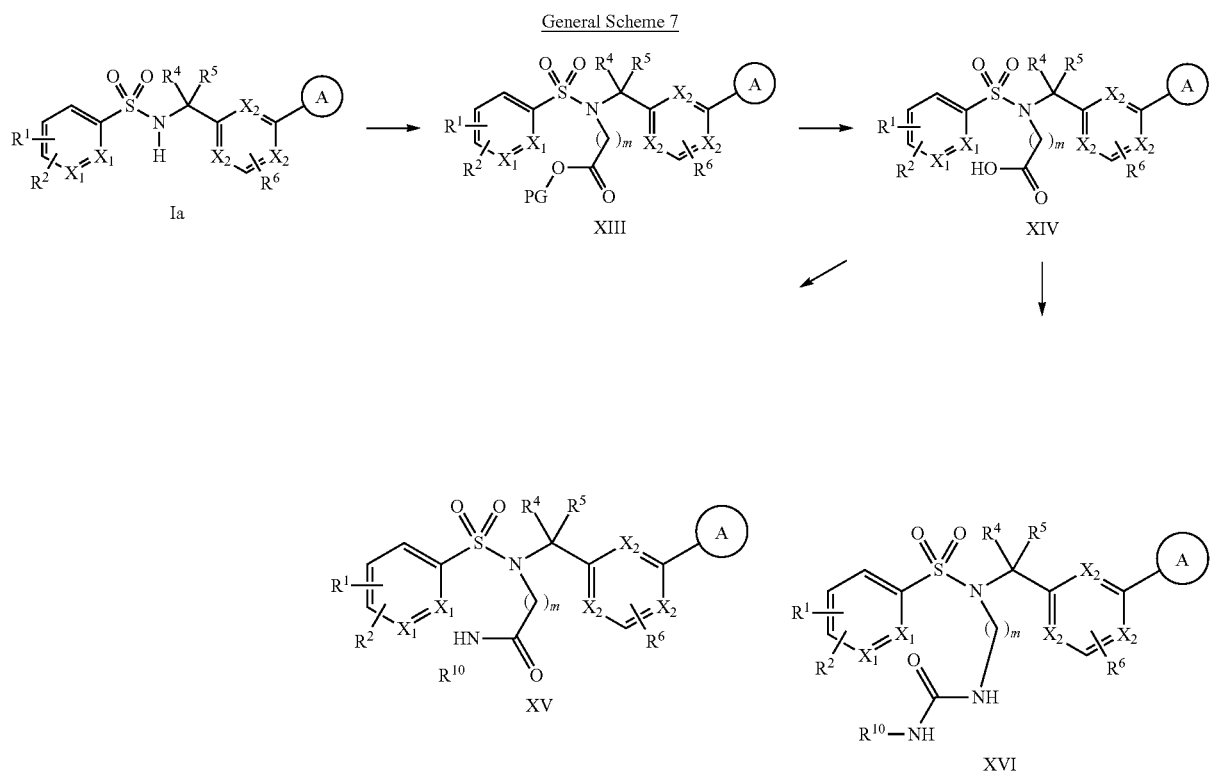

In a certain subset of compounds of the invention I, $R^3$ is hydrogen. These compounds are depicted in General Scheme 7 as Ia. Alkylation of the sulfonamide of Ia can be accomplished to produce further compounds of the invention XIII. In general, these compounds are synthesized by reacting Ia with a protected haloalkylcarboxylic acid such as methyl 2-bromoacetate, ethyl 4-bromobutanoate, tert-butyl 4-bromobutanoate, or the like in a polar aprotic solvent such as DMF. The reaction is usually carried out in the presence of a base such as cesium carbonate, sodium hydride, or the like.

Deprotection of the carboxylic acid of XIII is carried out by conditions known to those skilled in the art as outlined above. The liberated carboxylic acid derivatives XIV are free to be coupled with an amine to yield amide-bearing compounds of the invention XV. Coupling agents such as EDC, DIC, DSC, or HATU can be used to form the amide bond generally in a solvent such as DCM or DMF with a suitable base present such as DIEA or triethylamine as required. An additive such as HOBt, HOAt, or DMAP can also be employed during the reaction.

Alternatively, reaction of compounds XIV under Curtius conditions generates urea-bearing compounds of the invention XVI. This reaction is carried out by treating the deprotected derivative XIV with diphenyl phosphoryl azide in the presence of a base such as triethylamine in a solvent such as toluene. The reaction is generally heated between 60-100° C. to generate an isocyanate intermediate which is directly reacted with an amine to yield compounds of the invention XVI.

General Scheme 8

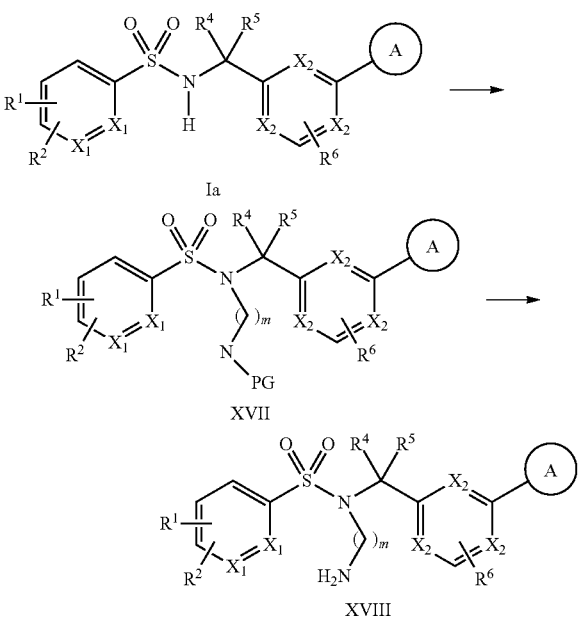

Further compounds of the invention XVII can be synthesized from Ia by treatment with a suitably protected aminoalkylhalide such as 3-bromo-N,N'-bis(trimethylsilyl)propan-1-amine, 2-(4-bromobutyl)isoindoline-1,3-dione, or the like. The reaction is usually carried out in the presence of a suitable base such as cesium carbonate in a polar aprotic solvent such as DMF. Deprotection of the amine under conditions known to those skilled in the art and outlined above generates the amine-bearing compounds of the invention XVIII.

General Scheme 9

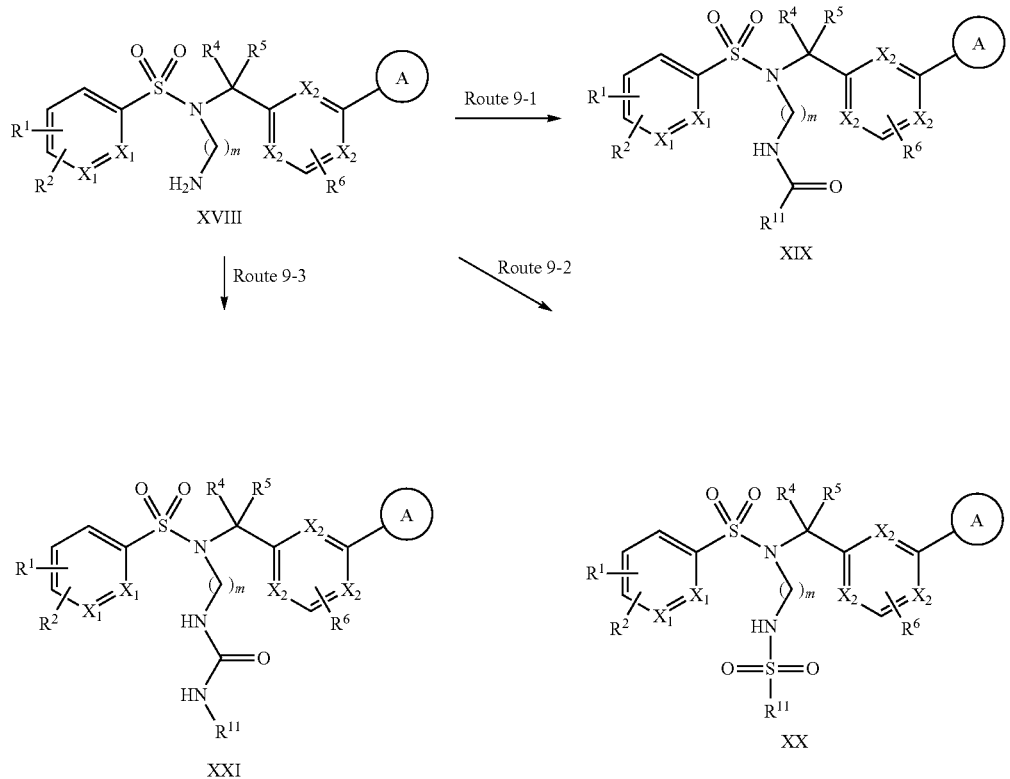

Various reactions of the amine group in XVIII are used to generate further compounds of the invention as shown in General Scheme 9. For instance, as depicted in Route 9-1, amine-bearing derivative XVIII can be coupled with a carboxylic acid to generate amide derivative XIX. Coupling agents as described above are employed. Alternatively, amide compounds of the invention XIX can be synthesized by reaction of an acid chloride with amine XVIII in the presence of a suitable base such as DIEA, triethylamine, or pyridine in a solvent such as DCM.

Further compounds of the invention can be synthesized by converting amine-bearing derivative XVIII to a sulfonamide XX by treatment with a sulfonyl chloride in the presence of a base such as triethylamine, DIEA, or pyridine in a solvent such as DCM (Route 9-2).

As shown via Route 9-3, the amine derivative XVIII can also be transformed into a urea-bearing compound of the invention XXI by conditions known to those skilled in the art. For example, treatment of XVIII with an isocyanate in a suitable solvent such as DCM or DMF will create a urea. Alternatively, treatment of compound XVIII with 1,1'-carbonyldiimidazole in the presence of a suitable base such as DIEA or triethylamine in a solvent such as DCM or DMF followed by heating in the presence of an amine will produce a urea XXI.

General Scheme 10

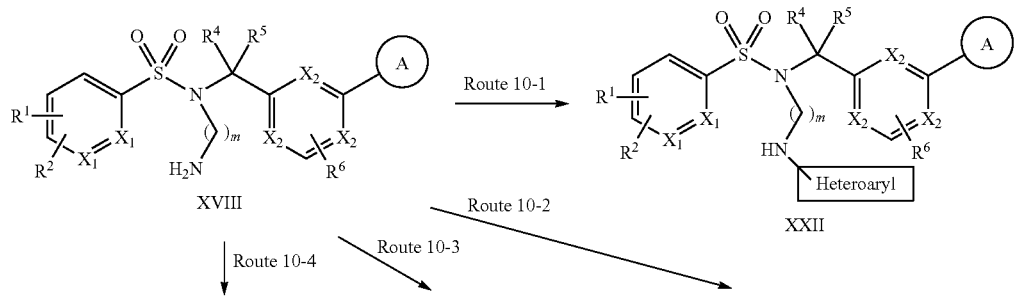

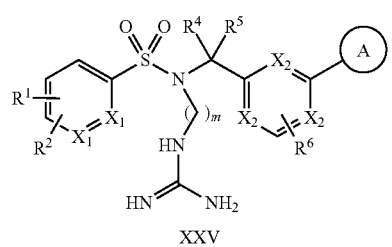

XXV

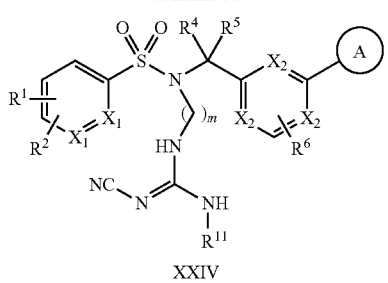

XXIV

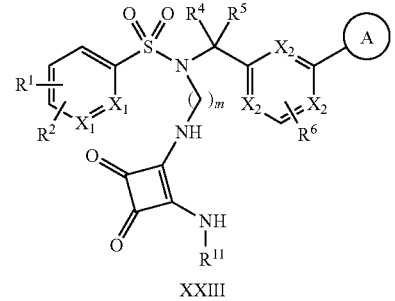

XXIII

Furthermore, the amine-bearing derivative XVIII can be transformed into a heterocyclic-bearing compound of the invention XXII as depicted in Route 10-1. Heterocycles containing a halogen adjacent to a ring nitrogen are activated to undergo displacement with amines. Therefore, heating such a heterocycle with amine XVIII in the presence of a suitable base such as DIEA or triethylamine in a solvent such as acetonitrile, DMSO, DMF, or n-butanol generates heteroaryl-bearing compounds of the invention XXII. Heating from 80° C. to 120° C. is generally employed.

Further compounds of the invention can be synthesized as depicted in Route 10-2. Treatment with a cyclobutenedione derivative such as 4-diethoxycyclobut-3-ene-1,2-dione with an amine in the presence of a base such as triethylamine or DIEA followed by the addition of compound XVIII generates compounds of the invention XXIII.

Further compounds of the invention harboring a cyanoguanidine moiety XXIV can be synthesized from the amine-bearing derivative XVIII. Diphenyl N-cyanocarbodimidate is employed in the presence of an amine and a suitable base such as DIEA or triethylamine (Route 10-3).

As shown in Route 10-4, the amine-bearing derivative XVIII can be transformed into a guanidine derivative XXV by treatment with 1H-pyrazole-1-carboxamidine hydrochloride in the presence of a suitable base such as DIEA or triethylamine in a solvent such as DMF with heating generally in the range of 80° C. to 120° C.

General Scheme 11

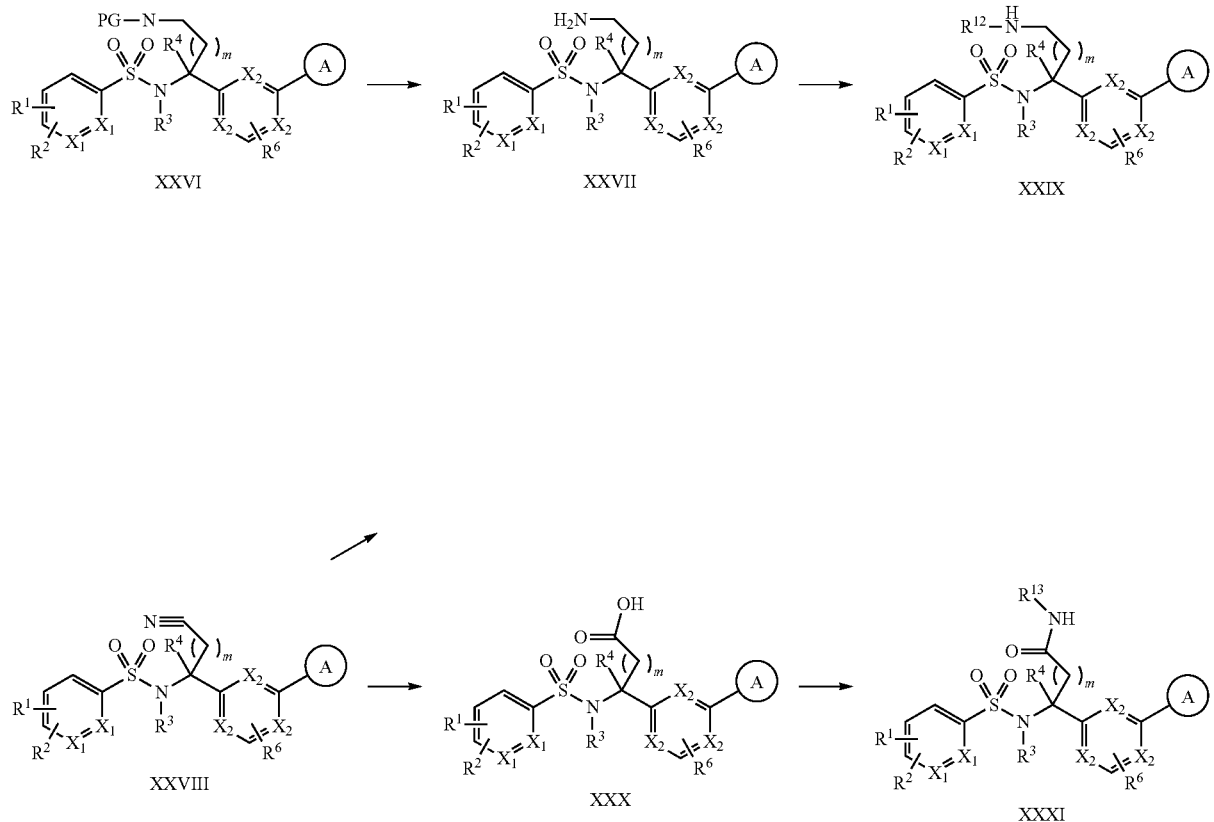

Further compounds of the invention can be synthesized by functional group transformations known to those skilled in the art. Such transformations are employed on side chain functional groups. For instance, intermediate XXVI can be converted to an amine-bearing compound of the invention XXVII by standard amine deprotection conditions outlined previously. Alternatively, cyano-bearing compounds of the invention XXVIII can be converted to amino compounds of the invention XXVII via treatment with a suitable reducing agent such as diborane in a solvent such as THF. Derivatization of compounds XXVII by the reactions outlined in General Schemes 9 and 10 yield compounds of the invention XXIX.

Alternatively, cyano-bearing compounds of the invention XXVIII can be hydrolyzed under acidic conditions such as heating in the presence of aqueous hydrochloric acid to yield carboxylic acid-containing compounds of the invention XXX. These compounds can be further derivatized by the reactions outlined in General Scheme 7 to yield compounds of the invention XXXI.

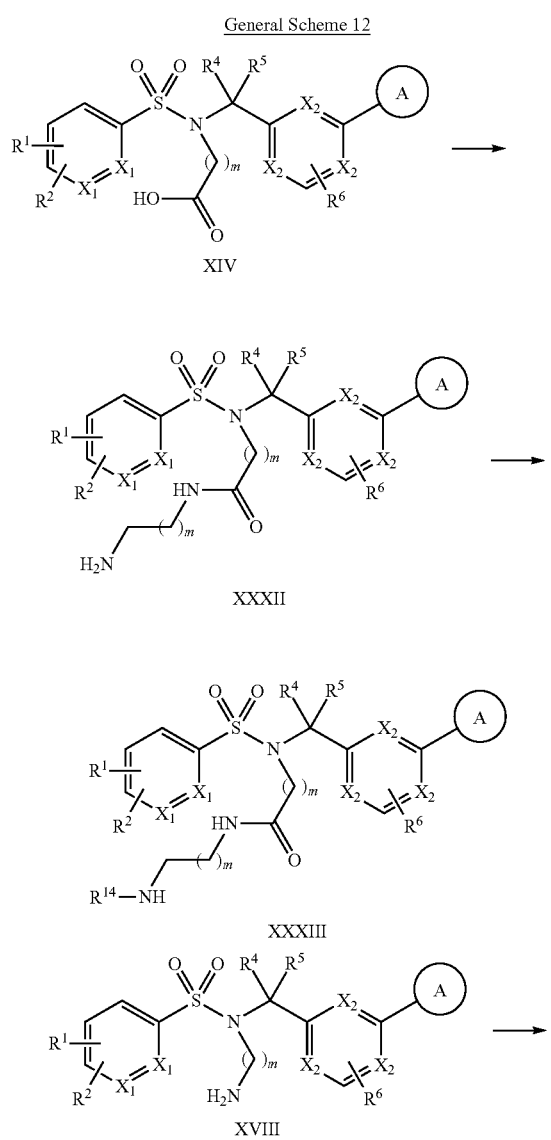

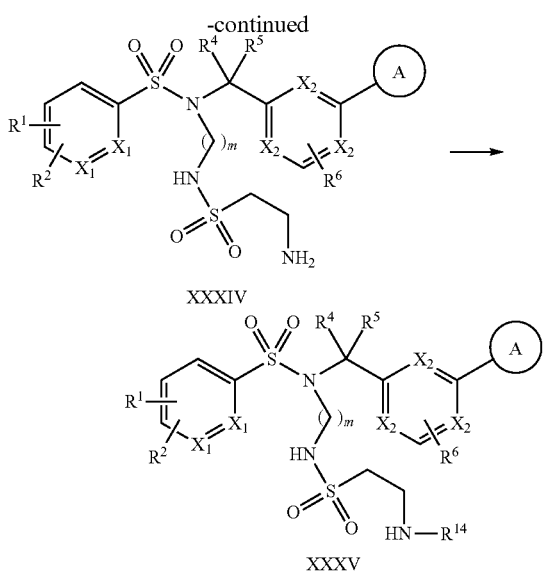

Further compounds of the invention can be synthesized by derivatization of compounds such as XIV and XVIII with bifunctional reagents followed by further reaction. For example, compound XIV can be reacted with a suitably protected diamine using conditions to form an amide bond as outlined previously. Deprotection of the amine as outlined previously yields compounds of the invention XXXII. These compounds can be further derivatized as described in General Schemes 9 and 10 to generate compounds of the invention XXXIII.

In an additional example, compound XVIII can be reacted with a suitably protected aminoalkylsulfonyl chloride in the presence of a base such as triethylamine, DIEA, or pyridine in a solvent such as DCM. Deprotection of the amino group under conditions outlined previously generates compounds of the invention XXXIV. These compounds can be further derivatized as outlined in general schemes 9 and 10 to yield compounds of the invention XXXV.

Chemical Syntheses for Formula (II)

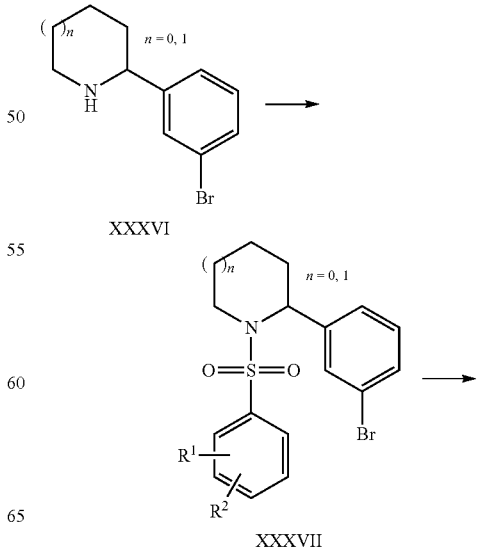

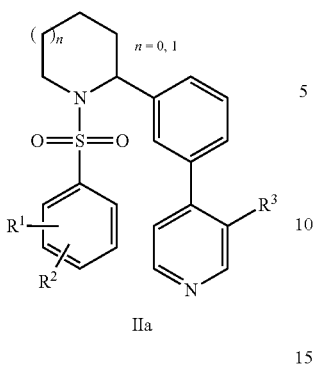

IIa

Compounds of formula IIa can be synthesized as outlined in General Scheme 13. 2-(3-bromophenyl)piperidine or 2-(3-bromophenyl)pyrrolidine derivatives (XXXVI) can be reacted with a sulfonyl chloride in the presence of a base such as triethylamine, DIEA, or pyridine in a solvent such as DCM to produce intermediate XXXVII. The aryl bromide of compound XXXVII can be further reacted to form an aryl or heteroaryl compound of formula IIa by conditions known to those skilled in the art. For example, heating of XXXVII with a aryl or heteroaryl boronic acid or boronic ester in the presence of both a palladium catalyst such as tetrakis(triphenylphosphine)palladium(0), tris(dibenzylideneacetone)dipalladium(0), [1,1'-bis(diphenylphosphino)ferrocene]dichloropalladium(II), or the like and a suitable base such as aqueous sodium carbonate or potassium carbonate in a solvent such as dioxane or DMF (Suzuki coupling conditions) will generate compounds of the invention IIa. Alternatively, reactions of XXXVII with aryl or heteroaryl tin derivatives using Stille conditions could also generate compounds IIa. As another example, reactions of XXXVII with aryl or heteroaryl zinc derivatives using Negishi conditions could also be used to generate compounds IIa.

Alternatively, the Molander version of the Suzuki coupling reaction could be utilized. In this variation, an aryl or heteroaryl reagent bearing a bromine or chlorine is first converted to a boronic acid in situ prior to reaction with intermediate XXXVII. Tetrahydroxydiborane is employed in a suitable solvent such as ethanol or THF. A catalyst and ligand such as XPhos-Pd-G2 and Xphos are utilized to generate the boronic acid in the presence of a suitable base such as potassium acetate. Once generated, the boronic acid can be coupled to intermediate XXXVII in the same pot with the addition of an aqueous base such as potassium carbonate to yield compounds IIa. In general, the reactions in this sequence are heated between 80° C. and 120° C.

General Scheme 14

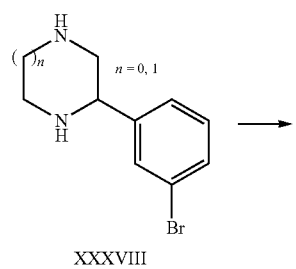

XXXVIII

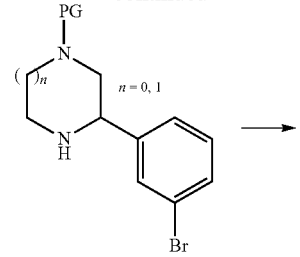

(PG = Protecting Group)
XXXIX

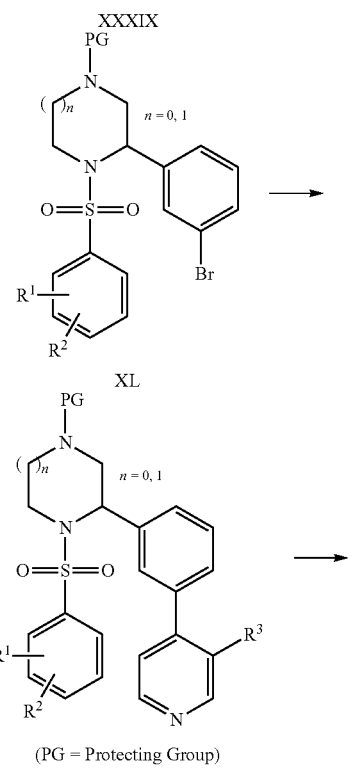

(PG = Protecting Group)
XLI

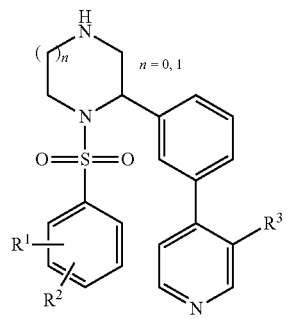

IIb

Compounds of the invention that contain a piperazine central ring can be synthesized via the method outlined in General Scheme 14. A protecting group is added to the least-hindered 4-position of the piperazine ring of XXXVIII. Various protecting groups can be used as outlined previously. A tert-butoxy carbamate is one example that can be added by the reaction of di-tert-butyl dicarbonate in the presence of a base such as triethylamine or diisopropylethylamine in a solvent such as DCM. The intermediate produced, XXXIX, can be reacted with a sulfonyl chloride in the presence of a base such as triethylamine, DIEA, or pyridine in a solvent such as DCM to produce intermediate XL.

The aryl bromide of compound XL can be further reacted to form an aryl or heteroaryl compound of formula XLI by conditions known to those skilled in the art. For example, heating of XL with an aryl or heteroaryl boronic acid or boronic ester in the presence of both a palladium catalyst such as tetrakis(triphenylphosphine)palladium(0), tris(dibenzylideneacetone)dipalladium(0), [1,1'-bis(diphenylphosphino)ferrocene]dichloropalladium(II), or the like and a suitable base such as aqueous sodium carbonate or potassium carbonate in a solvent such as dioxane or DMF (Suzuki coupling conditions) will generate compounds of formula XLI.

Alternatively, reactions of XL with aryl or heteroaryl tin derivatives using Stille conditions could also generate compounds XLI. As another example, reactions of XL with aryl or heteroaryl zinc derivatives using Negishi conditions could also be used generate compounds XLI.

Alternatively, the Molander version of the Suzuki coupling reaction could be utilized. In this variation, an aryl or heteroaryl reagent bearing a bromine or chlorine is first converted to a boronic acid in situ prior to reaction with intermediate XL. Tetrahydroxydiborane is employed in a suitable solvent such as ethanol or THF. A catalyst and ligand such as XPhos-Pd-G2 and Xphos are utilized to generate the boronic acid in the presence of a suitable base such as potassium acetate. Once generated, the boronic acid can be coupled to intermediate XL in the same pot with the addition of an aqueous base such as potassium carbonate to yield compounds XLI. In general, the reactions in this sequence are heated between 80° C. and 120° C.

Removal of the protecting group of XLI generates compounds of the invention IIb. Conditions for protecting group removal will depend on the protecting group employed and are outlined above.

General Scheme 15

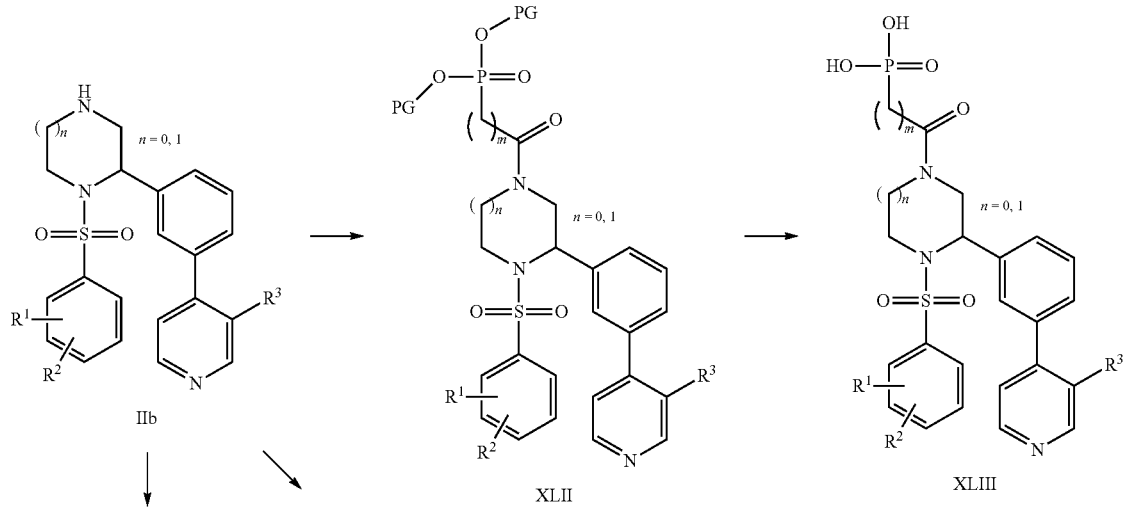

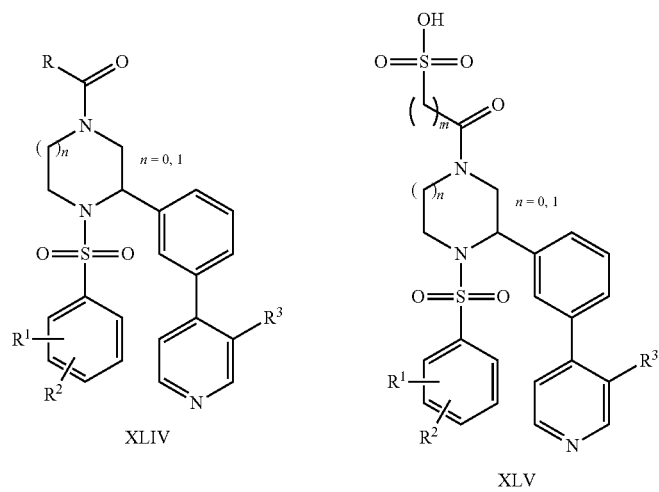

Further compounds of the invention can be synthesized as outlined in General Scheme 15. For example, coupling of compound IIb with a protected phosphoryl organic acid, such as 2-(diethoxyphosphoryl)acetic acid, generates intermediate XLII. Numerous amide bond formation conditions can be employed for the reaction. In one example, treatment of the carboxylic acid with N-(3-dimethylaminopropyl)-N'-ethylcarbodiimide hydrochloride, 1-hydroxybenzotriazole, and DIEA in the presence of the amine IIb will generate XLII. Compound XLIII can be generated by removal of the protecting groups on XLII. Various protection/deprotection schemes can be employed. For example, if intermediate XLII contains a diethylphosphonate, the ethyl protecting groups can be removed via treatment with iodotrimethylsilane in a solvent such as acetonitrile to generate compound of the invention XLIII.

Compounds of the invention XLIV can be synthesized from compound IIb via amide bond formation using the appropriate carboxylic acid and coupling agent familiar to those skilled in the art. General conditions to form an amide bond are outlined above. Treatment of IIb with a preformed anhydride in the presence of a base such as triethylamine in a solvent such as DCM will also synthesize compounds XLIV.

Compounds XLV can also be synthesized from compound IIb via amide bond formation conditions. For example, treatment of amine IIb with a preformed solution of a sulfonic acid-bearing carboxylic acid derivative, N-(3-dimethylaminopropyl)-N'-ethylcarbodiimide hydrochloride, 1-hydroxybenzotriazole, and DIEA in a solvent such as DCM or DMF will complete the transformation to generate XLV.

General Scheme 16

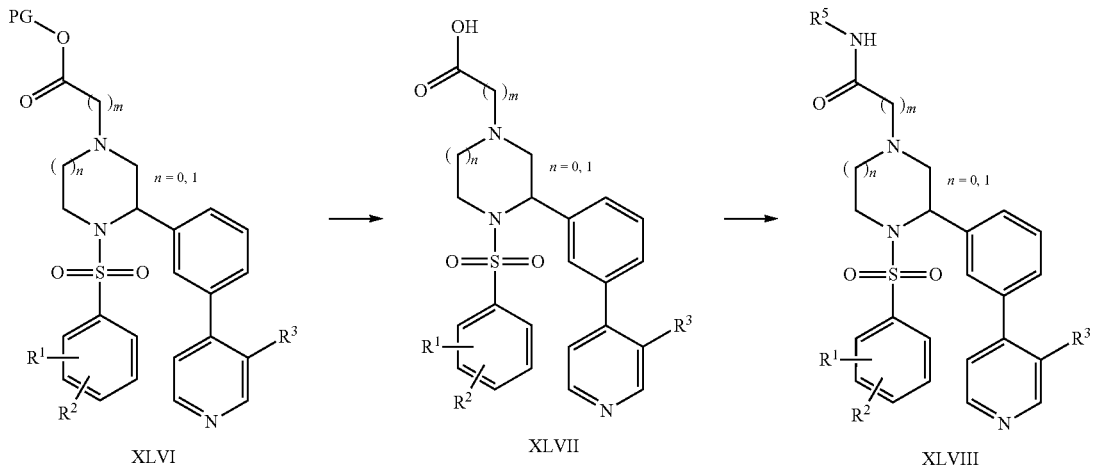

XLVI → XLVII → XLVIII

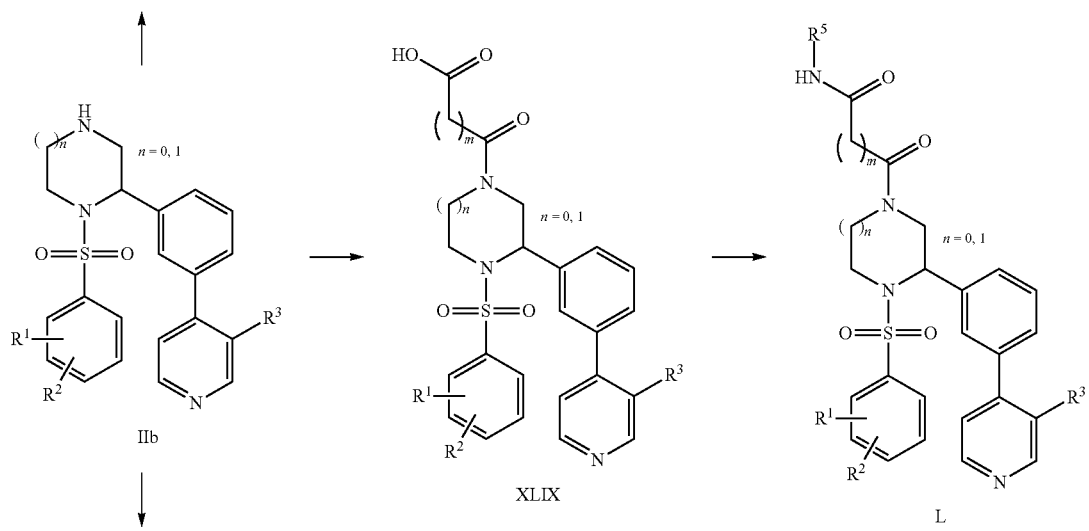

IIb → XLIX → L

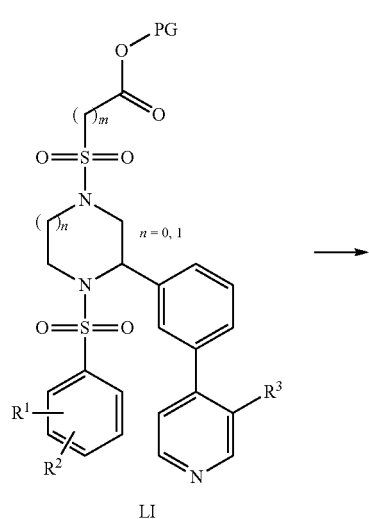
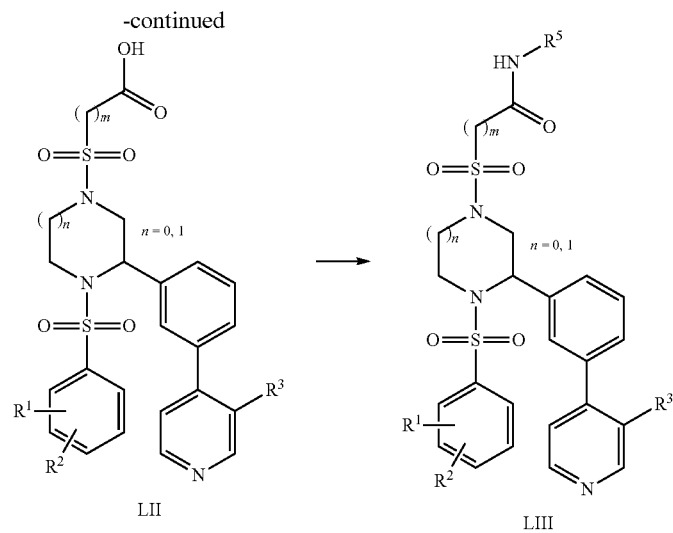

Further compounds of the invention can be synthesized as outlined in General Scheme 16. Alkylation the secondary amine of compound IIb can be accomplished by treatment with a protected haloalkylcarboxylate compound (such as tert-butyl 2-bromoacetate or the like) and a base such as DIEA in a solvent such as DMF. In general, the reaction is heated to 60-70° C. to generate protected intermediate XLVI. Removal of the protecting group provides compound of the invention XLVII. As an example, if the protecting group is a tert-butyl ester, removal can be accomplished by treatment with formic acid either at room temperature or with heating to 50° C. Compound XLVII can be further derivatized by coupling with an amine to generate amide compound XLVIII. Conditions for amide bond formation have been outlined previously.

Heating of compound IIb with a cyclic anhydride in a solvent such as DMF in the presence of an amine such as DIEA produces compounds of the invention XLIX. Reactions are usually heated to 65° C. to affect the transformation. Compound XLIX can be further derivatized by coupling with an amine to generate amide compound L. Conditions for amide bond formation have been outlined previously.

Further compounds of the invention can be synthesized by treatment of compound IIb with a sulfonyl chloride derivative harboring a protected carboxylic acid. The reaction is generally carried out at room temperature in a solvent such as DCM in the presence of a base such as DIEA. The intermediate LI is produced. Removal of the protecting group generates the free carboxylic acid containing compound of the invention LII. A person skilled in the art will realize various protecting groups and deprotection strategies can be employed. For example, if the carboxylic acid is protected as a methyl ester, treatment with a base such as lithium hydroxide in an aqueous solvent mixture such as a THF and water mixture will cause the deprotection. Compound LII can be further derivatized by coupling with an amine to generate amide compound LIII. Conditions for amide bond formation have been outlined previously.

EXAMPLES

The compounds of the present invention were prepared using the experimental procedures described herein. They can be made by alternate methods which are apparent to a chemist skilled in the art.

The following abbreviations are used:

Abbreviations $Ac_2O$=acetic anhydride
ACN=acetonitrile
BnCl=benzyl chloride
Boc=t-butoxy-carbonyl
$(Boc)_2O$=di-t-butyl dicarbonate
n-BuLi=n-butyl lithium
t-BuXPhos=2-Di-tert-butylphosphino-2',4',6'-triisopropyl-biphenyl
CDI=1,1'-carbonyl diimidazole
DCC=N,N'-dicyclohexylcarbodiimide
DCE=dichloroethane
DCM=Dichloromethane
DIAD=diisopropl azodicarboxylate
DIEA=N,N-diisopropylethylamine
DMAP=4-(dimethylamino)pyridine
DME=dimethoxyethane
DMF=dimethylformamide
DMSO=dimethylsulfoxide
DPPA=Diphenylphosphoryl azide
dppe=1,2-Bis(diphenylphosphino)ethane
EDC=1-ethyl-3-(3-dimethylaminopropyl) carbodiimide
EA=EtOAc=ethyl acetate
EtOH=ethanol
$Et_2O$=diethyl ether
HATU=1-[Bis(dimethylamino)methylene]-1H-1,2,3-triazolo[4,5-b]pyridinium 3-oxide hexafluorophosphate
h=hours
HCl=hydrochloric acid
HOBt=N-hydroxybenzotriazole
HPLC=high performance liquid chromatography
Karstedt's catalyst=Pt(0)-1,3-divinyl-1,1,3,3-tetramethyldisiloxane complex
KOAc=potassium acetate
LAH=lithium aluminum hydride
LCMS=Liquid chromatography mass spectrometry
min=minutes
MeMgBr=methyl magnesium bromide
MeMgCl=methyl magnesium chloride
$MeNH_2$=methylamine MeOH=methanol
MS-HPLC=mass-directed reverse phase semi-preparative chromatography
NaOtBu=sodium t-butoxide
NH$_4$OAc=ammonium acetate
PE=petroleum ether
PDA=photo diode array
Pd(dppf)Cl$_2$=[1,1'-Bis(diphenylphosphino)ferrocene]dichloropalladium(II)
Pd$_2$(dba)$_3$=Tris(dibenzylideneacetone)dipalladium(0)
PS-DIEA=polystyrene bound N,N-diisopropylethylamine
PS-HOBt=polystyrene bound N-hydroxybenzotriazole
PS-trisamine=Tris-(2-aminoethyl)aminomethyl polystyrene
Quant.=quantitative
RT=room temperature
Sat.=saturated
TEA=triethylamine
TFA=trifluoroacetic acid
THF=tetrahydrofuran
Ti(OEt)$_4$=titanium (IV) ethoxide
Ti(OiPr)$_4$=titanium isopropoxide
TMS=trimethylsilyl
TMSCl=trimethylsilyl chloride
TMSI=Iodotrimethyl silane
XPhos=2-Dicyclohexylphosphino-2',4',6'-triisopropylbiphenyl
XPhos G-2=Chloro(2-dicyclohexylphosphino-2',4',6'-triisopropyl-1,1'-biphenyl)[2-(2'-amino-1,1'-biphenyl)]palladium(II)

LC/MS Analysis Methods:

Method A—Compounds were analyzed on an Aquity Ultra Performance Liquid Chromatograph employing an Acquity UPLC BEH C18, 1.7 um, 2.1×50 mm column. Detection was via an Aquity PDA detector and a Waters SQD single quadrupole mass spectrometer. The aqueous acetonitrile based solvent gradient was: 0-0.1 min—Isocratic—10% of acetonitrile (0.01% TFA); 0.1-1.3 min—Linear gradient—10%-90% acetonitrile (0.01% TFA); 1.3-1.8 min—Isocratic—90% acetonitrile (0.01% TFA); 1.8-1.9 min—Linear gradient—90%-10% acetonitrile (0.01% TFA); 1.9-2.0 min—Isocratic—10% acetonitrile (0.01% TFA). Flow rate: 0.6 mL/min.

Method B—Compounds were analyzed on an Aquity Ultra Performance Liquid Chromatograph employing an Acquity UPLC BEH C18, 1.7 um, 2.1×50 mm column. Detection was via an Aquity PDA detector and a Waters SQD single quadrupole mass spectrometer. The aqueous acetonitrile based solvent gradient was: 0-0.1 min—Isocratic—2% of acetonitrile (0.01% TFA); 0.1-1.3 min—Linear gradient—2%-80% acetonitrile (0.01% TFA); 1.3-1.8 min—Isocratic—80% acetonitrile (0.01% TFA); 1.8-1.9 min—Linear gradient—80%-2% acetonitrile (0.01% TFA); 1.9-2.0 min—Isocratic—2% acetonitrile (0.01% TFA). Flow rate: 0.6 mL/min.

Method C—Compounds were analyzed on Agilent 1200 Liquid Chromatograph Mass Spectrometer employing an Phenomenex Luna 5u C18 100A, 50×2.00 mm×5 mic column. The aqueous acetonitrile based solvent gradient was: 0-0.4 min—Isocratic—10% of acetonitrile (0.188% TFA) and 90% of water (0.375% TFA); 0.4-3 min—Linear gradient—10%-100% acetonitrile (0.188% TFA), 90% to 0% water (0.375% TFA); 3-3.45 min—Isocratic—100% acetonitrile (0.188% TFA); 3.45-3.46 min—Linear gradient—100%-10% acetonitrile (0.188% TFA), 0 to 90% water (0.375% TFA); 3.46-4.1 min—Isocratic—10% acetonitrile (0.188% TFA) and 90% water (0.375% TFA). Flow rate: 0.8 mL/min.

NMR Spectroscopy:

$^1$H NMR Spectroscopy was conducted on a Bruker 400 MHz Avance II FTNMR Spectrometer.

Experimentals for Formula (I)

Intermediate 1

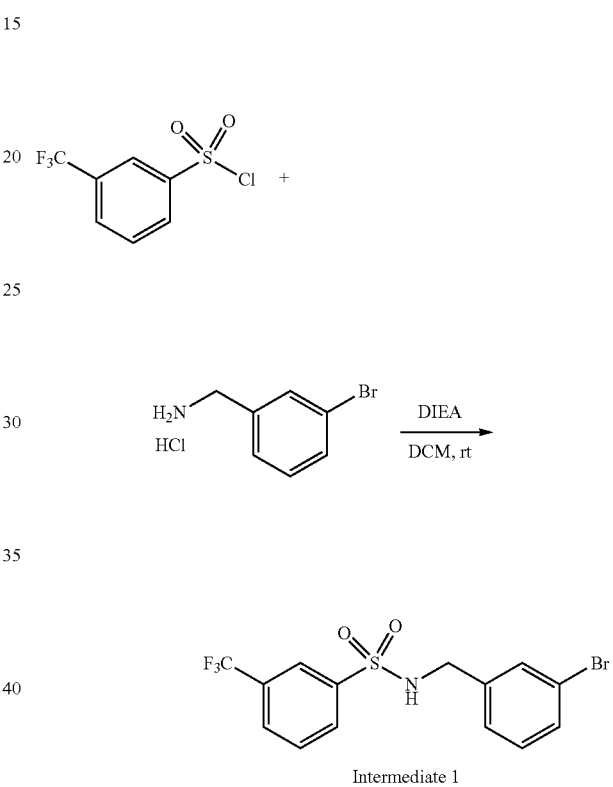

N-(3-bromobenzyl)-3-(trifluoromethyl)benzenesulfonamide (Intermediate 1)

3-(trifluoromethyl)benzene-1-sulfonyl chloride (0.66 mL, 4.1 mmol) was added into a mixture of (3-bromophenyl)methanamine hydrochloride (1.0 g, 4.5 mmol) and DIEA (1.6 mL, 9.0 mmol) in DCM (20 mL). The reaction was stirred at room temperature for approximately 3 hours and washed with 1N HCl (1X) and brine (2X). The organic layer was dried over sodium sulfate, filtered, and concentrated in vacuo. The residue was purified by silica gel chromatography (0-30% EtOAc/Hexanes) to afford the title compound (1.5 g, 96%). $^1$H NMR (CDCl$_3$) δ 8.05 (s, 1H), 8.00 (d, 1H), 7.82 (d, 1H), 7.63 (t, 1H), 7.35 (m, 1H), 7.27 (s, 1H), 7.12 (d, 2H), 5.25 (t, 1H), 4.18 (d, 2H). Using the method outlined above to synthesize Intermediate 1, the following intermediates were made using the appropriate acids and amines as indicated in Intermediate Table 1.

INTERMEDIATE TABLE 1

| Intermediate | Structure | Sulfonyl chloride | Amine | MS (M + H)+ |
|---|---|---|---|---|
| 1B | N-(3-bromobenzyl)-4-(trifluoromethyl)benzenesulfonamide | 4-(trifluoromethyl)benzenesulfonyl chloride | 3-bromobenzylamine | No MS (See NMR below) |
| 1C | N-(3-bromobenzyl)-4-chlorobenzenesulfonamide | 4-chlorobenzenesulfonyl chloride | 3-bromobenzylamine | No MS (See NMR below) |
| 1D | N-(2-(3-bromophenyl)-propan-2-yl)-3-(trifluoromethyl)benzenesulfonamide | 3-(trifluoromethyl)benzenesulfonyl chloride | 2-(3-bromophenyl)propan-2-amine | No MS (See NMR below) |
| 1E | N-(3-bromo-4-fluorobenzyl)-3-(trifluoromethyl)benzenesulfonamide | 3-(trifluoromethyl)benzenesulfonyl chloride | 3-bromo-4-fluorobenzylamine | No MS (See NMR below) |
| 1F | N-(5-bromo-2-fluorobenzyl)-3-(trifluoromethyl)benzenesulfonamide | 3-(trifluoromethyl)benzenesulfonyl chloride | 5-bromo-2-fluorobenzylamine | No MS (See NMR below) |
| 1G | (S)-N-(1-(3-bromophenyl)ethyl)-3-(trifluoromethyl)benzenesulfonamide | 3-(trifluoromethyl)benzenesulfonyl chloride | (S)-1-(3-bromophenyl)ethylamine | No MS (See NMR below) |
| 1H | (R)-N-(1-(3-bromophenyl)ethyl)-3-(trifluoromethyl)benzenesulfonamide | 3-(trifluoromethyl)benzenesulfonyl chloride | (R)-1-(3-bromophenyl)ethylamine | No MS (See NMR below) |
| 1I | N-(3-(4,4,5,5-tetramethyl-1,3,2-dioxaborolan-2-yl)benzyl)-3-(trifluoromethyl)benzenesulfonamide | 3-(trifluoromethyl)benzenesulfonyl chloride | 3-(4,4,5,5-tetramethyl-1,3,2-dioxaborolan-2-yl)benzylamine | No MS (See NMR below) |

INTERMEDIATE TABLE 1-continued

| Intermediate | Structure | Sulfonyl chloride | Amine | MS (M + H)+ |
|---|---|---|---|---|
| 1J | N-(2-(3-bromophenyl)-propan-2-yl)-2-(trifluoromethyl)benzenesulfonamide | | | No MS (See NMR below) |
| 1K | N-(1-(3-bromophenyl)-cyclopropyl)-3-(trifluoromethyl)benzenesulfonamide | | | 420.1/422.1 (method A) |
| 1L | N-(2-(3-bromophenyl)-propan-2-yl)-2-nitrobenzenesulfonamide | | | No MS (See NMR below) |
| 1M | (S)-N-(1-(3-bromophenyl)ethyl)-2-(trifluoromethyl)benzenesulfonamide | | | No MS (See NMR below) |
| 1N | (R)-N-(1-(3-bromophenyl)ethyl)-2-(trifluoromethyl)benzenesulfonamide | | | No MS (See NMR below) |
| 1O | (S)-N-(1-(3-bromophenyl)ethyl)-3-chloro-2-methylbenzenesulfonamide | | | No MS (See NMR below) |
| 1P | (S)-N-(1-(3-bromophenyl)ethyl)-2-methylbenzenesulfonamide | | | No MS (See NMR below) |
| 1Q | N-(2-(3-bromophenyl)-propan-2-yl)-3-chloro-2-methylbenzenesulfonamide | | | No MS (See NMR below) |

INTERMEDIATE TABLE 1-continued

| Intermediate | Structure | Sulfonyl chloride | Amine | MS (M + H)+ |
|---|---|---|---|---|
| 1R | (R)-N-(1-(3-bromophenyl)ethyl)-3-chloro-2-methylbenzenesulfonamide | | | No MS (See NMR below) |
| 1S | (S)-N-(1-(3-bromophenyl)ethyl)-2-nitrobenzenesulfonamide | | | No MS (See NMR below) |
| 1T | N-(3-bromophenethyl)-2-(trifluoromethyl)benzene sulfonamide | | | No MS (See NMR below) |
| 1U | N-(3-bromophenethyl)-3-chloro-2-methylbenzenesulfonamide | | | No MS (See NMR below) |

Intermediate 1B $^1$H NMR (CDCl$_3$) δ 7.94 (d, 2H), 7.75 (d, 2H), 7.37 (m, 1H), 7.28 (s, 1H), 7.12 (m, 2H), 5.03 (t, 1H), 4.18 (d, 2H).

Intermediate 1C $^1$H NMR (CDCl$_3$) δ 7.76 (d, 2H), 7.47 (d, 2H), 7.38 (m, 1H), 7.29 (s, 1H), 7.14 (m, 2H), 4.91 (t, 1H), 4.13 (d, 2H).

Intermediate 1D $^1$H NMR (CDCl$_3$) δ 7.77 (d, 2H), 7.70 (d, 1H), 7.50 (t, 1H), 7.24 (t, 1H), 7.21 (d, 1H), 7.19 (d, 1H), 6.98 (t, 1H), 5.91 (s, 1H), 1.68 (s, 6H).

Intermediate 1E $^1$H NMR (CDCl$_3$) δ 8.05 (s, 1H), 8.00 (d, 1H), 7.83 (d, 1H), 7.65 (t, 1H), 7.34 (dd, 1H), 7.13 (m, 1H), 7.01 (m, 1H), 5.10 (t, 1H), 4.17 (d, 2H).

Intermediate 1F $^1$H NMR (CDCl$_3$) δ 8.01 (s, 1H), 7.97 (d, 1H), 7.78 (d, 1H), 7.61 (t, 1H), 7.29 (m, 2H), 6.80 (t, 1H), 5.05 (t, 1H), 4.27 (d, 2H).

Intermediate 1G $^1$H NMR (CDCl$_3$) δ 7.84 (s, 1H), 7.82 (d, 1H), 7.71 (d, 1H), 7.51 (t, 1H), 7.25 (m, 1H), 7.09 (s, 1H), 7.00 (m, 2H), 4.95 (t, 1H), 4.56 (m, 1H), 1.45 (d, 3H).

Intermediate 1H $^1$H NMR (CDCl$_3$) δ 7.84 (s, 1H), 7.82 (d, 1H), 7.71 (d, 1H), 7.51 (t, 1H), 7.25 (m, 1H), 7.09 (s, 1H), 7.01 (m, 2H), 4.96 (br, 1H), 4.56 (m, 1H), 1.45 (d, 3H).

Intermediate 1I $^1$H NMR (CDCl$_3$) δ 8.07 (s, 1H), 8.01 (d, 1H), 7.80 (d, 1H), 7.68 (m, 1H), 7.62 (t, 1H), 7.56 (s, 1H), 7.27 (m, 2H), 4.80 (t, 1H), 4.21 (d, 2H), 1.33 (s, 12H).

Intermediate 1J $^1$H NMR (CDCl$_3$) δ 7.80 (d, 1H), 7.61 (d, 1H), 7.57 (t, 1H), 7.40 (t, 1H), 7.27 (t, 1H), 7.21 (m, 2H), 7.00 (t, 1H), 5.18 (s, 1H), 1.67 (s, 6H).

Intermediate 1L $^1$H NMR (CDCl$_3$) δ 7.78 (dd, 1H), 7.57 (m, 1H), 7.38-7.32 (m, 3H), 7.28 (m, 1H), 7.18 (m, 1H), 6.98 (t, 1H), 5.82 (s, 1H), 1.76 (s, 6H).

Intermediate 1M $^1$H NMR (CDCl$_3$) δ 7.89 (d, 1H), 7.78 (d, 1H), 7.59 (t, 1H), 7.48 (t, 1H), 7.22 (m, 1H), 7.10 (s, 1H), 7.01 (d, 2H), 4.97 (d, 1H), 4.55 (m, 1H), 1.42 (d, 3H).

Intermediate 1N $^1$H NMR (CDCl$_3$) δ 7.90 (d, 1H), 7.78 (d, 1H), 7.59 (t, 1H), 7.48 (t, 1H), 7.22 (m, 1H), 7.10 (s, 1H), 7.01 (d, 2H), 4.97 (d, 1H), 4.55 (m, 1H), 1.42 (d, 3H).

Intermediate 1O $^1$H NMR (CDCl$_3$) δ 7.72 (dd, 1H), 7.48 (dd, 1H), 7.26 (m, 1H), 7.13-6.96 (m, 4H), 4.85 (d, 1H), 4.44 (m, 1H), 2.57 (s, 3H), 1.45 (d, 3H).

Intermediate 1P $^1$H NMR (CDCl$_3$) δ 7.89 (dd, 1H), 7.38 (td, 1H), 7.27-7.17 (m, 3H), 7.11 (t, 1H), 7.05-6.99 (m, 2H), 4.81 (s, 1H), 4.43 (t, 1H), 2.55 (s, 3H), 1.43 (d, 3H).

Intermediate 1Q $^1$H NMR (CDCl$_3$) δ 7.50 (q, 2H), 7.28 (t, 1H), 7.22 (q, 2H), 7.06-7.01 (m, 2H), 4.90 (s, 1H), 2.67 (s, 3H), 1.65 (s, 6H).

Intermediate 1R $^1$H NMR (CDCl$_3$): δ 7.72 (dd, 1H), 7.48 (dd, 1H), 7.25 (dt, 1H), 7.11 (t, 1H), 7.09-7.07 (m, 1H), 7.03 (t, 1H), 6.98 (dt, 1H), 4.97 (d, 1H), 4.43 (quint, 1H), 2.57 (s, 3H), 1.46 (d, 3H)

Intermediate 1S $^1$H NMR (CDCl$_3$): δ 7.77 (dd, 1H), 7.66 (dd, 1H), 7.59 (m, 1H), 7.45 (m, 1H), 7.23-7.17 (m, 2H), 7.11-7.06 (m, 1H), 7.02-6.96 (m, 1H), 5.75 (d, 1H), 4.66 (m, 1H), 1.52 (d, 3H).

Intermediate 1T $^1$H NMR (CDCl$_3$): δ 8.17 (m, 1H), 7.85 (m, 1H), 7.70 (m, 2H), 7.31 (m, 1H), 7.15 (m, 1H), 7.10 (t, 1H), 7.00 (d, 1H), 4.87 (t, 1H), 3.26 (q, 2H), 2.74 (t, 2H)

Intermediate 1U $^1$H NMR (CDCl$_3$) δ 7.92 (m, 2H), 7.59 (m, 1H), 7.37 (m, 1H), 7.2 (m, 1H), 7.1 (d, 1H), 7 (d, 1H), 4.46 (s, 1H), 3.26 (m, 2H), 2.75 (m, 2H), 2.52 (s, 3H).

Alternatively, the following intermediates were made using similar procedure as described above but with 3,5-lutidine as the base.

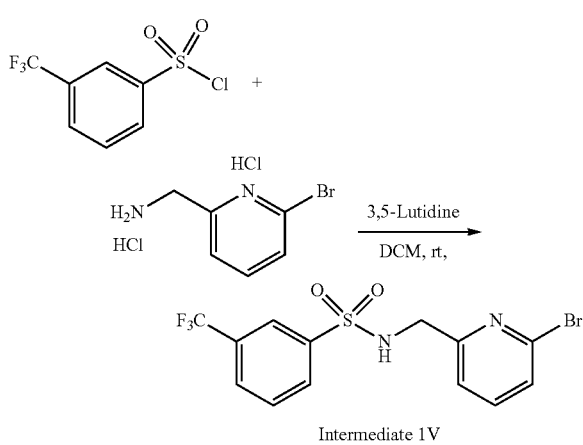

N-((6-bromopyridin-2-yl)methyl)-3-(trifluoromethyl)benzenesulfonamide (Intermediate 1R 3-(Trifluoromethyl)benzene-1-sulfonyl chloride (37 μL, 0.23 mmol) was added into a mixture of (6-bromopyridin-2-yl)methanamine dihydrochloride (60 mg, 0.23 mmol) and 3,5-lutidine (92 μL, 0.81 mmol) in DCM (0.5 mL). The reaction was stirred at room temperature overnight. DCM was added into the reaction and it was washed with HCl (1N,1X) and brine (2X). The organic layer was dried over sodium sulfate, filtered, and concentrated in vacuo to give a crude product which was purified by silica gel chromatography (0-100% EtOAc/Hexanes) to afford the title compound (73 mg, 80%). LCMS (method A): m/z 395.2/397.2 (M+H)$^+$. Using the method outlined above to synthesize Intermediate 1V, the following intermediates were made using the appropriate sulfonyl chloride and amine as indicated in Intermediate Table 2.

INTERMEDIATE TABLE 2

| Intermediate | Structure | Sulfonyl chloride | Amine | MS (M + H)$^+$ |
|---|---|---|---|---|
| 1W | N-((4-bromopyridin-2-yl)methyl)-3-(trifluoromethyl)benzenesulfonamide | | | 395.1/397.2 (method A) |
| 1X | 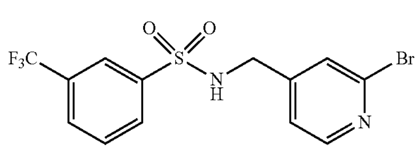 [SMILES: O=S(=O)(NCc1ccnc(Br)c1)c1cccc(C(F)(F)F)c1] | | | 395.3/397.3 (method A) |

INTERMEDIATE TABLE 2-continued

| Intermediate | Structure | Sulfonyl chloride | Amine | MS (M + H)+ |
|---|---|---|---|---|
| 1Y | N-((2-bromopyridin-4-yl)methyl)-3-(trifluoromethyl)benzenesulfonamide <br> 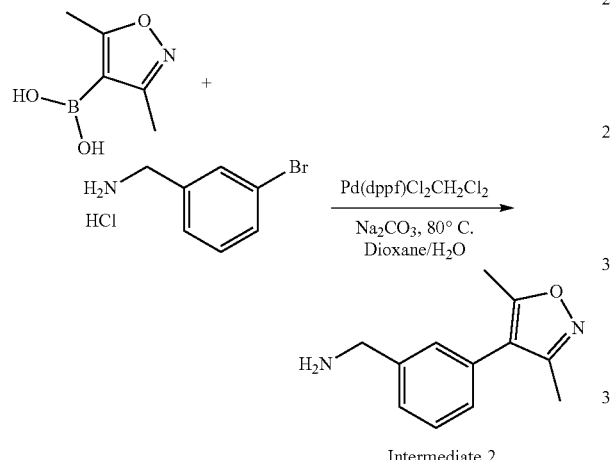 <br> N-((4-bromopyridin-2-yl)methyl)-2-(trifluoromethyl)benzenesulfonamide | | | 395.2/397.2 (method A) |

Intermediate 2

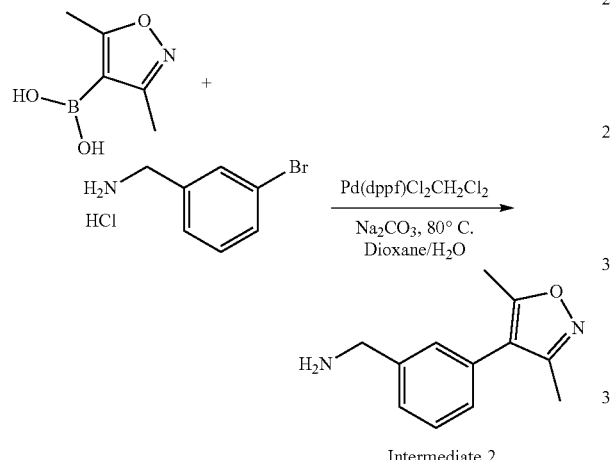

(3-(3,5-dimethylisoxazol-4-yl)phenyl)methanamine (Intermediate 2)

Pd(dppf)Cl₂CH₂Cl₂ (0.19 g, 0.23 mmol) was added into a mixture of (3-bromophenyl)methanamine hydrochloride (0.50 g, 2.3 mmol), (3,5-dimethylisoxazol-4-yl)boronic acid (640 mg, 4.5 mmol), and Na₂CO₃ (960 mg, 9.0 mmol) in dioxane/H₂O (8 mL/2 mL). The reaction was degassed with N₂ and stirred at 80° C. overnight. After cooling to room temperature, DCM was added and the mixture was washed with brine (1X) and water (2X). The organic layer was dried over sodium sulfate, filtered and concentrated in vacuo to give a crude product. Purification by silica gel chromatography (0-10% MeOH/DCM) afforded the title compound (0.34 g, 74%). LCMS (method A): m/z 203.2 (M+H)⁺.

Intermediate 3

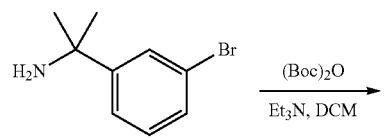

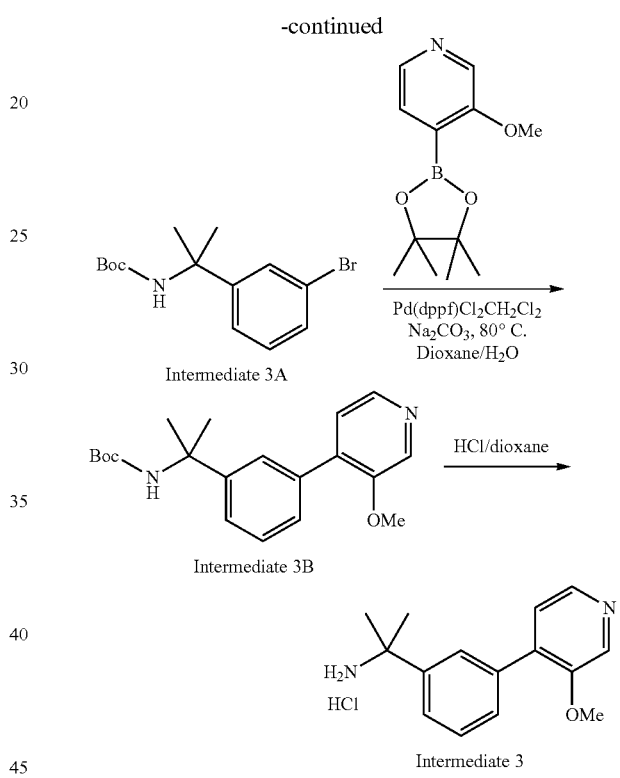

tert-butyl (2-(3-bromophenyl)propan-2-yl)carbamate (Intermediate 3A)

(Boc)₂O (1.1 g, 4.9 mmol) was added into a mixture of 2-(3-bromophenyl)propan-2-amine (1.0 g, 4.7 mmol) and Et₃N (650 µL, 4.7 mmol) in DCM (10 mL). The reaction was stirred at room temperature overnight. The reaction was concentrated in vacuo. The residue was purified by silica gel chromatography (0-30% EtOAc/Hexanes) to afford the title compound (0.99 g, 67%). ¹H NMR (CDCl₃) δ 7.53 (q, 1H), 7.33 (t, 2H), 7.18 (q, 1H), 4.94 (br, 1H), 1.40-1.02 (br, 9H).

tert-butyl (2-(3-(3-methoxypyridin-4-yl)phenyl)propan-2-yl)carbamate (Intermediate 3B)

Using the procedure as described in the preparation of Intermediate 2, Intermediate 3A (0.60 g, 1.9 mmol) was converted to Intermediate 3B (0.52 g, 80%). LCMS (method A): m/z 343.4 (M+H)⁺. ¹H NMR (CDCl₃) δ 8.38 (s, 1H), 8.32 (br, 1H), 7.58 (s, 1H), 7.58-7.39 (m, 3H), 7.24 (d, 1H), 4.95 (br, 1H), 3.90 (s, 3H), 1.26 (br, 6H).

2-(3-(3-methoxypyridin-4-yl)phenyl)propan-2-amine (Intermediate 3)

Intermediate 3B (0.52 g, 1.5 mmol) was dissolved in DCM (5 mL) and HCl (4M in dioxane, 3.8 mL) was added. The reaction was stirred at room temperature overnight. Solvent was removed in vacuo. The residue was dried in vacuo overnight to afford intermediate 3 (quantitative yield). LCMS (method A): m/z 243.2 (M+H)$^+$. Using the method outlined above for Intermediate 3 and substituting the appropriate reagents, the following intermediates were prepared.

INTERMEDIATE TABLE 3

| Intermediate | Structure | Amine | Boronic acid | MS (M + H)$^+$ |
|---|---|---|---|---|
| 3C | (3-(pyridin-4yl)phenyl)methanamine hydrochloride | H$_2$N–CH$_2$–(3-Br-phenyl) | pyridin-4-yl Bpin | 185.2 (method A) |
| 3D | (S)-1-(3-(3-methoxypyridin-4-yl)phenyl)ethanamine hydrochloride | (S)-1-(3-bromophenyl)ethanamine | 3-OMe-pyridin-4-yl Bpin | 229.2 (method A) |
| 3E | (S)-1-(3-(3-chloropyridin-4-yl)phenyl)ethanamine hydrochloride | (S)-1-(3-bromophenyl)ethanamine | 3-Cl-pyridin-4-yl Bpin | 233.2/235.2 (method A) |

Intermediate 4

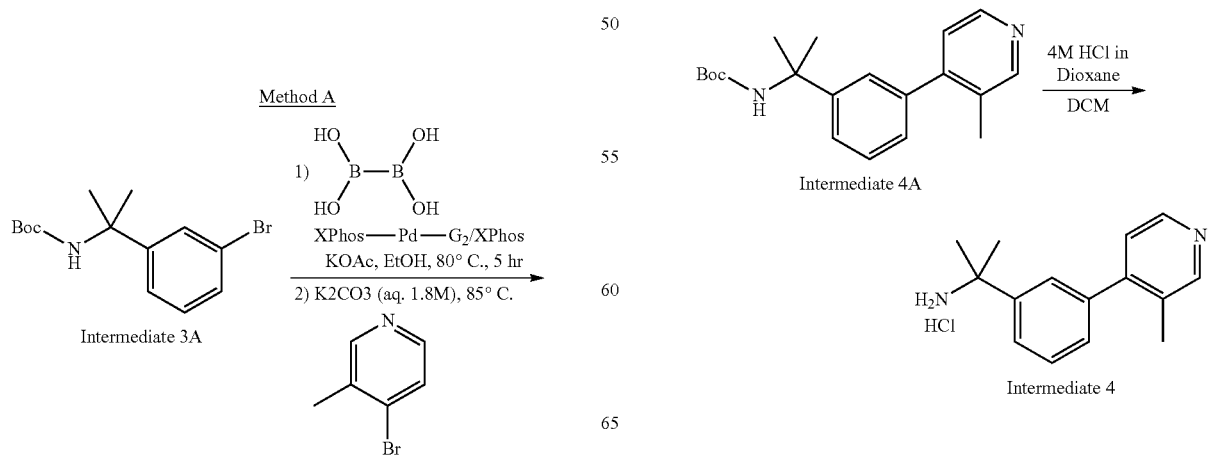

Method A: 1) HO-B(OH)-B(OH)-OH, XPhos—Pd—G$_2$/XPhos, KOAc, EtOH, 80° C., 5 hr; 2) K$_2$CO$_3$ (aq. 1.8M), 85° C., 4-bromo-3-methylpyridine. Then 4M HCl in Dioxane, DCM to give Intermediate 4 from Intermediate 4A.

tert-butyl (2-(3-(3-methylpyridin-4-yl)phenyl)propan-2-yl)carbamate (Intermediate 4A)

EtOH (1 mL) was added into a mixture of Intermediate 3A (50 mg, 0.16 mmol), $B_2(OH)_4$ (43 mg, 0.48 mmol), XPhos-Pd-$G_2$ (13 mg, 0.016 mmol), XPhos (15 mg, 0.032 mmol), and KOAc (47 mg, 0.48 mmol). The reaction was degassed with $N_2$ and stirred at 80° C. for approximately 5 hours. After cooling to room temperature, 4-bromo-3-methylpyridine (43 mg, 0.21 mmol) and $K_2CO_3$ (1.8 M, 0.27 mL, 0.48 mmol) were added to the reaction. The reaction was degassed with $N_2$ again and stirred at 85° C. for 4 hours. The reaction was cooled to room temperature, filtered through celite, and washed with EtOAc (3X). The organic layers were dried over sodium sulfate, filtered and concentrated in vacuo. The residue was purified by silica gel chromatography (0-65% EtOAc/Hexanes) to afford the title compound (41 mg, 79%). LCMS (method A): m/z 327.5 $(M+H)^+$.

2-(3-(3-methylpyridin-4-yl)phenyl)propan-2-amine hydrochloride (Intermediate 4)

To a solution of Intermediate 4A (41 mg, 0.13 mmol) in DCM (5 mL) was added HCl (4M, 1.5 mL). The reaction was stirred at room temperature overnight and concentrated in vacuo to give the title compound. LCMS (method A): m/z 227.3 $(M+H)^+$.

Alternatively, intermediate 4 can be prepared using Method B:

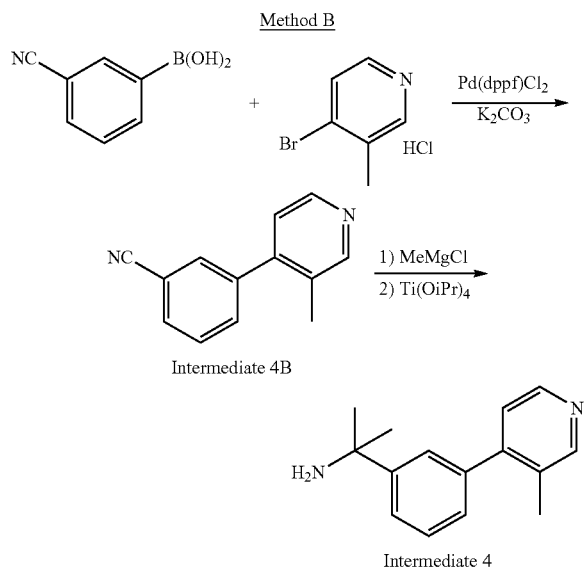

3-(3-methylpyridin-4-yl)benzonitrile (Intermediate 4B)

To a pressure tube was added 3-cyanophenyl boronic acid (1.9 g, 13 mmol), 4-bromo-3-methylpyridine (2.5 g, 12 mmol), potassium carbonate (5.0 g, 36 mmol), dichloro[1,1'-bis(diphenylphosphino)ferrocene]palladium(II) DCM adduct (490 mg, 0.60 mmol), ethylene glycol dimethyl ether (45 mL), and water (15 mL). After being degassed with nitrogen for approximately 2 minutes, the tube was sealed with a septum and heated to 80° C. for 1 hour. The mixture was cooled to room temperature, poured into water, and extracted three times with EtOAc. The combined extracts were washed with brine, dried with sodium sulfate, filtered, and evaporated to dryness. Purification by silica gel chromatography (0-75% EtOAc/hexanes) yielded Intermediate 4B (1.7 g, 73%). LCMS (method A): m/z 195.2 $(M+H)^+$. $^1H$ NMR $(CDCl_3)$ δ 8.56 (s, 1H), 8.52 (d, 1H), 7.73 (m, 1H), 7.65-7.56 (m, 3H), 7.13 (d, 1H), 2.27 (s, 3H).

2-(3-(3-methylpyridin-4-yl)phenyl)propan-2-amine (Intermediate 4)

To Intermediate 4B (0.50 g, 2.6 mmol) in a pressure tube was added dry tetrahydrofuran (10 mL) and the mixture sealed with a septum then degassed with nitrogen for approximately 2 minutes. Methyl magnesium chloride (3 mL of a 3M solution in diethyl ether, 9.0 mmol) was added and the mixture heated to 100° C. for 10 minutes using a microwave reactor. The mixture had turned dark orange and a precipitate had formed. Titanium isopropoxide (0.73 g, 2.6 mmol) was added dropwise at room temperature then heated to 50° C. for 90 minutes using an aluminum heating block. The reaction mixture was cooled to room temperature, quenched with saturated aqueous sodium chloride, and extracted three times with EtOAc. The combined extracts were washed with brine, dried with sodium sulfate, filtered and evaporated to dryness. Purification by silica gel chromatography (100% DCM to 75% 95:5 DCM/7M $NH_3$ in MeOH, 25% DCM) yielded Intermediate 4 (420 mg, 74%). LCMS (method A): m/z 227.3 $(M+H)^+$. $^1H$ NMR $(CDCl_3)$ δ 8.51 (s, 1H), 8.46 (d, 1H), 7.58-7.54 (m, 1H), 7.48 (t, 1H), 7.42 (t, 1H), 7.21-7.15 (m, 2H), 2.29 (s, 3H), 1.53 (s, 6H). Using the methods described above for Intermediate 4 and substituting the appropriate reagents, the following Intermediate was prepared.

INTERMEDIATE TABLE 4

| Intermediate | Structure | Bromide | Amine | MS $(M + H)^+$ |
|---|---|---|---|---|
| 4C | 2-(3-(3-ethylpyridin-4-yl)phenyl)propan-2-amine | | Method A | 241.2 (method A) |

INTERMEDIATE TABLE 4-continued

| Intermediate | Structure | Bromide | Amine | MS (M + H)+ |
|---|---|---|---|---|
| 4D | (3-(3-methylpyridin-4-yl)phenyl)methanamine | 4-bromo-3-methylpyridine | Boc-NH-CH2-C6H4-B(OH)2 Method B | 199.2 (method A) |

Intermediate 5

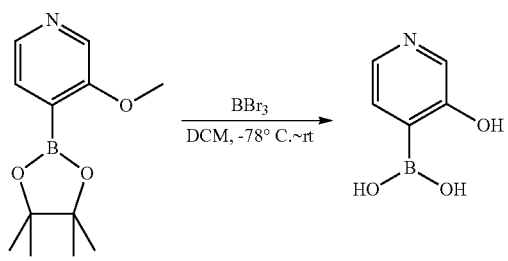

(3-hydroxypyridin-4-yl)boronic acid (Intermediate 5)

BBr₃ (1 M in DCM) (10 mL, 10 mmol) was added into a solution of 3-methoxy-4-(4,4,5,5-tetramethyl-1,3,2-dioxaborolan-2-yl)pyridine (0.40 g, 1.7 mmol) in DCM (8 mL) cooled at −78° C. The reaction was stirred at −78° C. for about 4 hours, allowed to warm up to room temperature, and stirred overnight. Ice was added to quench the reaction, followed by addition of EtOAc (10 mL). The aqueous layer was concentrated in vacuo to give the title compound which was used directly without further purification. LCMS (method A): m/z 140.1 (M+H)+.

Intermediate 6

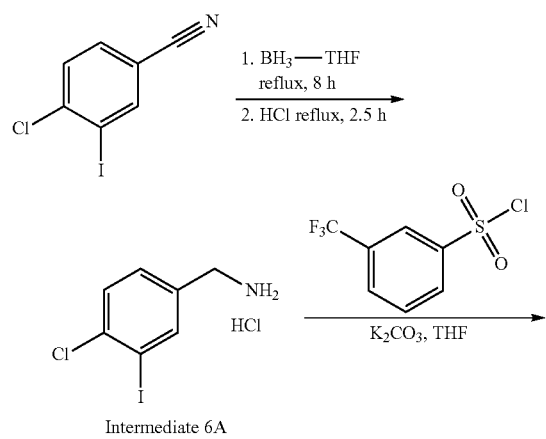

Intermediate 6A

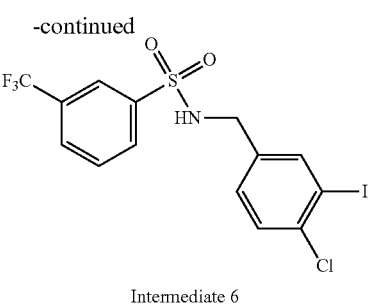

Intermediate 6

(4-chloro-3-iodophenyl)methanamine (Intermediate 6A)

To a solution of 4-chloro-3-iodobenzonitrile (0.80 g, 3.0 mmol) in THF (16 mL) under nitrogen was added BH₃-THF (1M in THF, 4.8 mL, 4.8 mmol). After stirring for 30 minutes at room temperature, the reaction mixture was heated to reflux for 8 hours. The reaction mixture was cooled to 0° C., and a 2M aqueous HCl solution (4.5 mL) was added slowly. The reaction mixture was allowed to warm to room temperature, and heated to reflux for 2.5 hours. After cooling to room temperature, the mixture was concentrated in vacuo to yield crude Intermediate 6A which was used without purification. ¹H NMR (CD₃OD) δ 8.07 (d, 1H), 7.58 (d, 1H), 7.48 (m, 1H), 4.10 (s, 2H).

N-(4-chloro-3-iodobenzyl)-3-(trifluoromethyl)benzenesulfonamide (Intermediate 6)

Crude Intermediate 6A (approximately 3.0 mmol) from the previous step was stirred with potassium carbonate (1.2 g, 9.0 mmol) in THF (12 mL) for 5 minutes. A solution of 3-(trifluoromethyl)benzene-1-sulfonyl chloride (0.48 mL, 3.0 mmol) in THF (2 mL) was added, and the reaction mixture stirred overnight at room temperature. Additional portions of potassium carbonate (0.50 g, 3.6 mmol) and 3-(trifluoromethyl)benzene-1-sulfonyl chloride (0.19 mL, 1.2 mmol) were added. After 1 hour, the reaction mixture was diluted with EtOAc (40 mL), and washed with water (40 mL), aqueous HCl (0.1N solution, 40 mL), and saturated aqueous sodium bicarbonate solution (40 mL). The organics were dried over sodium sulfate, filtered, and concentrated in vacuo. Purification by silica gel chromatography (5-40% EtOAc/hexanes) yielded Intermediate 6 (0.72 g, 50% yield over 2 steps). ¹H NMR (CDCl₃) δ 8.07 (s, 1H), 8.01 (d, 1H), 7.85 (d, 1H), 7.67 (t, 1H), 7.63 (d, 1H), 7.34 (d, 1H), 7.15 (m, 1H), 4.93 (m, 1H), 4.16 (m, 2H). Using the procedure as described above for Intermediate 6 and substituting the appropriate starting material, and using DIEA instead of K₂CO₃ as the base in step 2, the following intermediate was prepared.

INTERMEDIATE TABLE 5

| Intermediate | Structure | Starting material | MS (M + H)+ |
|---|---|---|---|
| 6B | ![N-(3-bromo-5-chloro-benzyl)-3-(trifluoromethyl)benzenesulfonamide] N-(3-bromo-5-chloro-benzyl)-3-(trifluoromethyl)benzenesulfonamide | 3-chloro-5-bromobenzonitrile | No MS (See NMR below) |

Intermediate 6B

¹H NMR (CDCl₃) δ 8.07 (s, 1H), 8.02 (d, 1H), 7.85 (d, 1H), 7.68 (t, 1H), 7.39 (m, 1H), 7.21 (m, 1H), 7.11 (m, 1H), 5.01 (m, 1H), 4.19 (m, 2H).

Intermediate 7

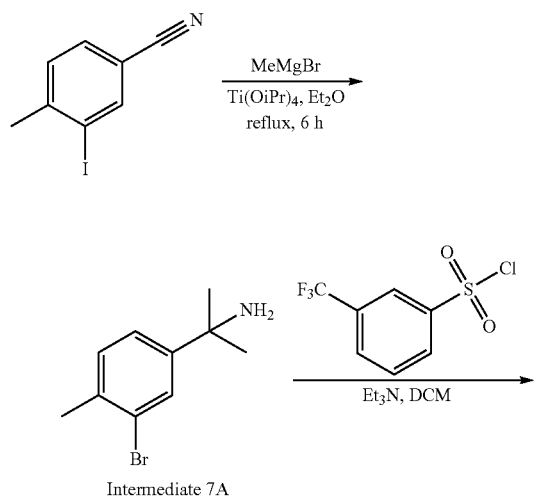

2-(3-bromo-4-methylphenyl)propan-2-amine (Intermediate 7A

A solution was made of 3-bromo-4-methylbenzonitrile (2.0 g, 10.0 mmol) in anhydrous diethyl ether (51 mL) under a nitrogen atmosphere. A solution of methyl magnesium bromide (3.0M in Et₂O, 8.5 mL, 25 mmol) was added to the reaction mixture. The reaction was stirred at room temperature for 90 minutes. After the addition of titanium(IV) isopropoxide, the reaction mixture was heated to reflux for 6 hours. The reaction mixture was cooled to 0° C., and quenched by the slow addition of a sodium hydroxide solution (10% aqueous, 100 mL). The reaction mixture was stirred for 30 minutes at room temperature, and diluted with a 5% aqueous sodium carbonate solution (50 mL). The mixture was extracted 3 times with diethyl ether (50 mL). The combined organics were washed with brine (75 mL), dried over sodium sulfate, and filtered. The mixture was evaporated to dryness to provide crude Intermediate 7A (2.9 g). ¹H NMR (CDCl₃) δ 7.68 (d, 1H), 7.34 (m, 1H), 7.19 (d, 1H), 2.38 (s, 3H), 1.48 (s, 6H).

N-(2-(3-bromo-4-methylphenyl)propan-2-yl)-3-(trifluoromethyl)benzenesulfonamide (Intermediate 7)

Intermediate 7A was reacted with 3-(trifluoromethyl)benzene-1-sulfonyl chloride in a manner similar to the preparation of Intermediate 1 but using Et₃N as the base. Purification by silica gel chromatography (0-40% EtOAc/hexanes) yielded Intermediate 7. ¹H NMR (CDCl₃) δ 7.74 (d, 1H), 7.70 (m, 2H), 7.50 (m, 1H), 7.22 (d, 1H), 7.09 (m, 1H), 6.98 (d, 1H), 4.99 (s, 1H), 2.27 (s, 3H), 1.69 (s, 6H).

Intermediate 8

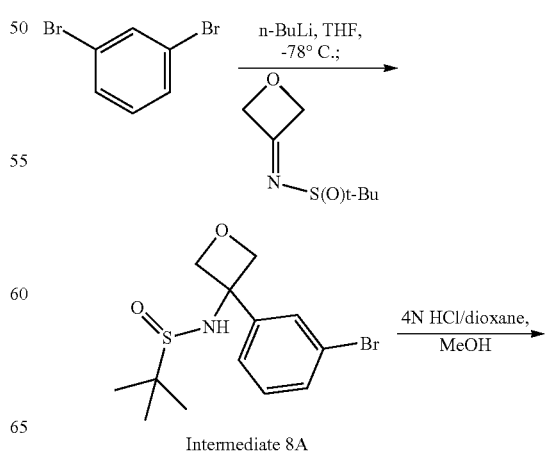

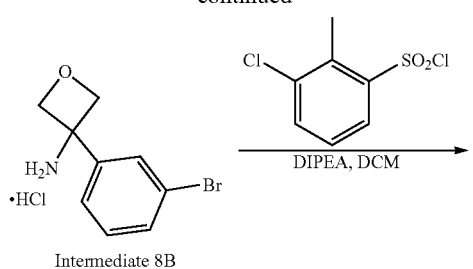

Intermediate 8B

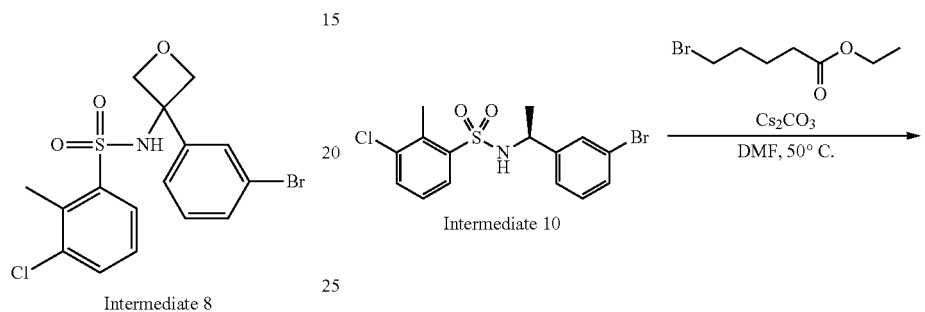

Intermediate 8

N-(3-(3-bromophenyl)oxetan-3-yl)-3-chloro-2-methylbenzenesulfonamide (Intermediate 8)

Using the procedure as described in Intermediate 1 but without purification, Intermediate 8B (0.33 g, 1.24 mmol) was converted to Intermediate 8 (0.51 g, 98%). LCMS (Method A): m/z 416.1/418.1/420.1 (M+H)$^+$. $^1$H NMR (d$_6$-DMSO) δ 9.17 (s, 1H), 7.52 (d, 1H), 7.29-7.23 (m, 4H), 7.11-7.06 (m, 2H), 4.95 (d, 2H), 4.78 (d, 2H).

Intermediate 9

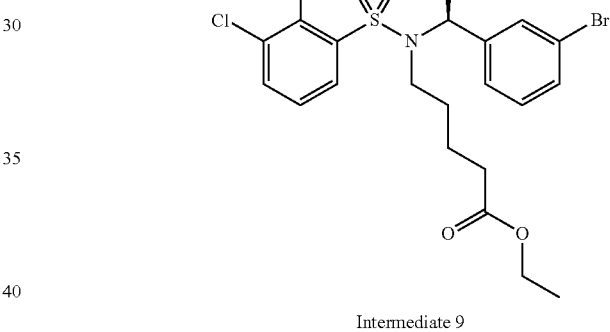

Intermediate 9

N-(3-(3-bromophenyl)oxetan-3-yl)-2-methylpropane-2-sulfinamide (Intermediate 8A To a solution of 1,3-dibromobenzene (0.52 mL, 4.3 mmol) in THF (20 mL) at −78° C. was added n-BuLi (2.5 M in hexanes, 1.6 mL, 4.0 mmol) and the resultant mixture was stirred at −78° C. for 1 hour. 2-methyl-N-(3-oxetanylidene)propane-2-sulfinamide (0.50 g, 2.9 mmol) was added via cannula as a solution in THF (2 mL) and the reaction mixture was stirred at −78° C. for an additional 1 hour. The reaction was quenched with saturated NH$_4$Cl (aq) (20 mL) and extracted with EtOAc (3×30 mL). The combined organic extracts were washed with brine (1×40 mL), filtered, and concentrated in vacuo. The crude residue was purified by silica gel chromatography (25 g, 0-100% EtOAc/hexanes) to give 0.63 g (44%) of Intermediate 8A. LCMS (Method A): m/z 332.2/334.2 (M+H)$^+$. $^1$H NMR (CDCl$_3$) δ 7.53 (m, 1H), 7.49 (m, 1H), 7.36-7.28 (m, 2H), 5.11 (ABq, 2H), 4.98 (ABq, 2H), 4.04 (br s, 1H), 1.23 (s, 9H).

3-(3-bromophenyl)oxetan-3-amine hydrochloride (Intermediate 8B

To a solution of Intermediate 8A (620 mg, 1.9 mmol) in MeOH (3.5 mL) at 0° C. was added 4 N HCl/dioxane (0.70 mL, 2.8 mmol) and the reaction mixture was stirred for 60 seconds and quickly concentrated in vacuo to provide a white solid. This was triturated with ethyl ether and the mother liquor carefully removed with a pipette and discarded. The resulting white solid was further washed with ethyl ether (2X) and then dried in vacuo to give 430 mg (87%) of Intermediate 8B. LCMS (Method A): m/z 228.2/230.2 (M+H)$^+$.

(S)-Ethyl 5-(N-(1-(3-bromophenyl)ethyl)-3-chloro-2-methylphenylsulfonamido)pentanoate (Intermediate 9)

Cs$_2$CO$_3$ (3.4 g, 10 mmol) was added into a mixture of Intermediate 1O (1.0 g, 2.6 mmol) in DMF (6 mL). The reaction was stirred at 50° C. for 10 minutes and ethyl 5-bromopentanoate (0.82 mL, 5.2 mmol) was added. The reaction was heated at 50° C. overnight, filtered and concentrated in vacuo. The residue was purified by silica gel chromatography (0-30% EtOAc/Hexanes) to afford Intermediate 9 (1.3 g, 99%). $^1$H NMR (CDCl$_3$) δ 7.95 (d, 1H), 7.60 (d, 1H), 7.40 (dt, 1H), 7.29~7.24 (m, 2H), 7.22~7.16 (m, 2H), 4.98 (q, 1H), 4.09 (q, 2H), 3.20~3.04 (m, 2H), 2.63 (s, 3H), 2.14 (t, 2H), 1.52 (d, 3H), 1.48~1.38 (m, 3H), 1.28~1.22 (m, 4H). Using the method described above for Intermediate 9 and substituting the appropriate starting materials and reagents, the following intermediates were prepared as indicated in Intermediate Table 6 unless a special reagent/condition was specified.

INTERMEDIATE TABLE 6

| Intermediate | Structure | Starting material | Reagent | MS (M + H)+ |
|---|---|---|---|---|
| 9A | (S)-ethyl 4-(N-(1-(3-bromophenyl)ethyl)-3-chloro-2-methylphenylsulfonamido)butanoate | 1O | ethyl 4-bromobutanoate | No MS (See NMR below) |
| 9B | ethyl 4-(N-(2-(3-bromophenyl)propan-2-yl)-3-chloro-2-methylphenylsulfonamido)butanoate | 1Q | ethyl 4-bromobutanoate | No MS (See NMR below) |
| 9C | (R)-ethyl 4-(N-(1-(3-bromophenyl)ethyl)-3-chloro-2-methylphenylsulfonamido)butanoate | 1R | ethyl 4-bromobutanoate | No MS (See NMR below) |
| 9D | (S)-ethyl 4-(N-(1-(3-bromophenyl)ethyl)-2-methylphenylsulfonamido)butanoate | 1P | ethyl 4-bromobutanoate | No MS (See NMR below) |

INTERMEDIATE TABLE 6-continued

| Intermediate | Structure | Starting material | Reagent | MS (M + H)+ |
|---|---|---|---|---|
| 9E | (S)-ethyl 3-(N-(1-(3-bromophenyl)ethyl)-3-chloro-2-methylphenylsulfonamido)propanoate | 10 | K₂CO₃ Acetone 60° C. | No MS (See NMR below) |
| 9F | (S)-methyl 2-(N-(1-(3-bromophenyl)ethyl)-3-chloro-2-methylphenylsulfonamido)acetate | 10 | K₂CO₃ Acetone 60° C. | No MS (See NMR below) |
| 9G | ethyl 4-(N-(3-(3-bromophenyl)oxetan-3-yl)-3-chloro-2-methylphenylsulfonamido)butanoate | 8 | K₂CO₃ Acetone 60° C. | 530.2/532.3/534.2 (method A) |
| 9H | (S)-N-(1-(3-bromophenyl)ethyl)-3-chloro-N-(4-(1,3-dioxoisoindolin-2-yl)butyl)-2-methylbenzenesulfonamide | 10 | | No MS (See NMR below) |

Intermediate 9A

¹H NMR (CDCl₃) δ 7.95 (d, 1H), 7.60 (d, 1H), 7.40 (dt, 1H), 7.27 (t, 1H), 7.22~7.15 (m, 3H), 4.97 (q, 1H), 4.09 (q, 2H), 3.29~3.11 (m, 2H), 2.61 (s, 3H), 2.25~2.08 (m, 2H), 1.78~1.72 (m, 1H), 1.65~1.57 (m, 1H), 1.57 (d, 3H), 1.23 (t, 3H).

Intermediate 9B

¹H NMR (CDCl₃) δ 7.75 (d, 1H), 7.53 (d, 1H), 7.40 (t, 1H), 7.33 (d, 1H), 7.31 (d, 1H), 7.18 (t, 1H), 7.13 (t, 1H), 4.08 (q, 2H), 3.33 (m, 2H), 2.68 (s, 3H), 2.21 (t, 2H), 2.01~1.97 (m, 2H), 1.72 (s, 6H), 1.23 (t, 3H).

Intermediate 9C

¹H NMR (CD₃OD): δ 7.98 (dd, 1H), 7.70 (dd, 1H), 7.42 (dt, 1H), 7.38 (t, 1H), 7.30-7.26 (m, 2H), 7.25-7.20 (m, 1H), 4.98 (q, 1H), 4.07 (q, 2H), 3.29~3.19 (m, 2H), 2.59 (s, 3H), 2.24-2.08 (m, 2H), 1.74-1.61 (m, 1H), 1.53 (d, 3H), 1.52-1.47 (m, 1H), 1.21 (t, 3H)

Intermediate 9D

¹H NMR (CDCl₃) δ 8.01 (dd, 1H), 7.48 (td, 1H), 7.40~7.32 (m, 3H), 7.21~7.14 (m, 3H), 4.97 (q, 1H), 4.08 (q, 2H), 3.27~3.10 (m, 2H), 2.57 (s, 3H), 2.24~2.05 (m, 2H), 1.76~1.71 (m, 1H), 1.63~1.56 (m, 1H), 1.54 (d, 3H), 1.23 (t, 3H).

Intermediate 9E

¹H NMR (CD₃OD): δ 7.98 (d, 1H), 7.71 (d, 1H), 7.48-7.22 (br m, 4H), 5.01 (q, 1H), 4.03 (q, 2H), 3.55-3.48 (m, 2H), 2.61 (s, 3H), 2.51-2.41 (m, 1H), 2.20-2.10 (m, 1H), 1.50 (d, 3H), 1.19 (t, 3H)

Intermediate 9F

¹H NMR (CD₃OD): δ 8.02 (dd, 1H), 7.69 (dd, 1H), 7.41-7.35 (m, 2H), 7.23-7.16 (m, 3H), 5.03 (q, 1H), 3.95 (s, 1H), 3.75 (s, 1H), 3.54 (s, 3H), 2.56 (s, 3H), 1.49 (d, 3H)

Intermediate 9H

¹H NMR (CDCl₃) δ 7.93 (dd, 1H), 7.87~7.82 (m, 2H), 7.76~7.71 (m, 2H), 7.54 (dd, 1H), 7.26~7.22 (m, 4H), 7.12 (t, 1H), 5.00 (q, 1H), 3.50 (t, 2H), 3.17 (t, 2H), 2.64 (s, 3H), 1.50 (d, 2H), 1.49~1.35 (m, 4H), 1.17~1.10 (m, 1H).

Intermediate 10

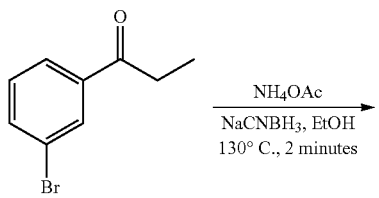

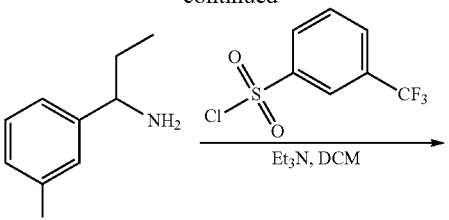

Intermediate 10A

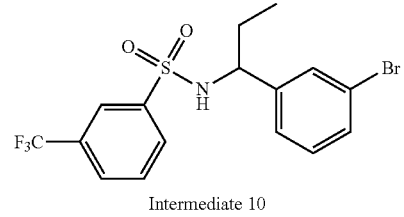

Intermediate 10

(+)-1-(3-bromophenyl)propan-1-amine (Intermediate 10A)

Ammonium acetate (0.94 g, 12 mmol) and sodium cyanoborohydride (61 mg, 0.97 mmol) were added to a mixture of 1-(3-bromophenyl)propan-1-one (0.17 g, 0.80 mmol) in absolute ethanol (1.8 mL) in a Biotage microwave vessel. The vessel was capped and irradiated to 130° C. for 2 minutes. The volatiles were removed in vacuo, and the residue was basified to pH~10 with a 1N NaOH solution. The aqueous mixture was extracted twice with diethyl ether (3 mL). The combined organics were concentrated in vacuo to afford crude Intermediate 10A (140 mg). ¹H NMR (CD₃Cl) δ 7.48 (m, 1H), 7.39 (m, 1H), 7.24 (m, 2H), 3.81 (t, 1H), 1.70 (m, 2H) 0.88 (t, 3H).

(+/−) N-(1-(3-bromophenyl)propyl)-3-(trifluoromethyl)benzenesulfonamide (Intermediate 10)

The crude Intermediate 10A (approximately 0.80 mmol) from the previous step was stirred with triethylamine (0.23 mL, 1.60 mmol) in DCM (8 mL) at 0° C. A solution of 3-(trifluoromethyl)benzene-1-sulfonyl chloride (0.14 mL, 0.84 mmol) in 1 mL DCM was added, and the reaction mixture stirred overnight at room temperature. The reaction mixture was diluted with DCM (15 mL), and washed with aqueous HCl (1 N solution, 10 mL) and saturated aqueous sodium bicarbonate solution (10 mL). The organics were dried over sodium sulfate, filtered, and concentrated in vacuo. The residue was purified by silica gel chromatography (0-40% EtOAc/hexanes) to yield Intermediate 10 (0.21 g, 62% yield over 2 steps). ¹H NMR (CDCl₃) δ 7.78 (m, 2H), 7.68 (d, 1H), 7.48 (t, 1H), 7.24 (m, 1H), 7.02 (m, 2H), 6.95 (m, 1H), 4.90 (d, 1H), 4.28 (q, 1H), 1.80 (m, 1H), 1.73 (m, 1H), 0.87 (t, 3H). Using the method described above for Intermediate 10 and substituting the appropriate starting materials and reagents, the following intermediates were prepared as indicated in Intermediate Table 7.

INTERMEDIATE TABLE 7

| Intermediate | Structure | Starting material | Reagent | MS (M + H)+ |
|---|---|---|---|---|
| 10B | (+/−)N-((3-bromophenyl)(phenyl)methyl)-2-(trifluoromethyl)benzenesulfonamide | | | No MS (See NMR below) |
| 10C | (+/−)N-((3-bromophenyl)(cyclopropyl)methyl)-2-(trifluoromethyl)benzenesulfonamide | | | No MS (See NMR below) |

Intermediate 10B $^1$H NMR (CDCl$_3$) δ 7.93 (d, 1H), 7.76 (d, 1H), 7.60 (t, 1H), 7.49 (t, 1H), 7.31 (m, 1H), 7.24-7.19 (m, 4H), 7.10-7.04 (m, 4H), 5.65 (d, 1H), 5.31 (d, 1H).

Intermediate 10C $^1$H NMR (CDCl$_3$) δ 7.80 (m, 2H), 7.59 (t, 1H), 7.45 (m, 1H), 7.24 (m, 1H), 7.12 (m, 1H), 7.04 (m, 2H), 5.22 (d, 1H), 3.71 (m, 1H), 1.08 (m, 1H), 0.55 (m, 2H), 0.26 (m, 2H).

Intermediate 11

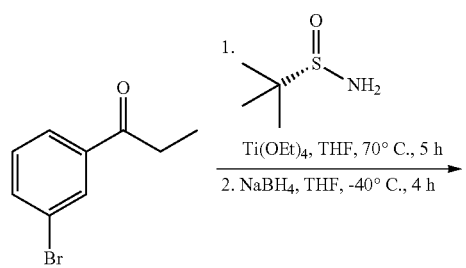

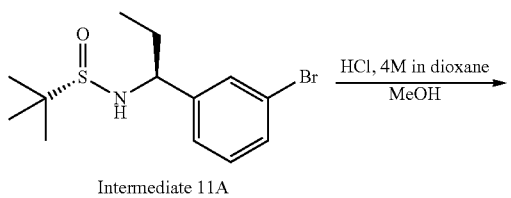

Intermediate 11A

-continued

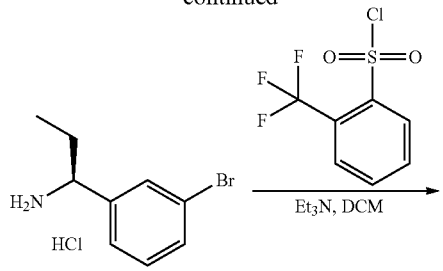

Intermediate 11B

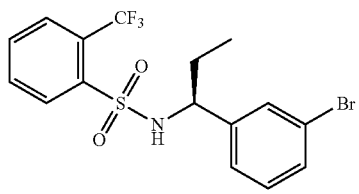 [SMILES: COC(=O)C[C@H](NS(=O)(=O)c1ccccc1C(F)(F)F)c1cccc(Br)c1]

Intermediate 11

(S)—N—((S)-1-(3-bromophenyl)propyl)-2-methylpropane-2-sulfinamide (Intermediate 11A A solution was made of 1-(3-bromophenyl)propan-1-one (3.0 g, 14 mmol) in anhydrous THF (23 mL). Titanium (IV) ethoxide (4.9 mL, 23 mmol) was added to the solution, followed by (S)-2-methylpropane-2-sulfinamide (1.4 g, 12 mmol). The reaction mixture was heated to 70° C. for 5 hours, then 50° C. for 16 hours. The reaction mixture was allowed to cool to room temperature, cooled to −40° C., and cannulated dropwise into a −40° C. suspension of sodium borohydride (1.8 g, 47 mmol) in anhydrous THF (14 mL). After the addition of the imine was complete, the reaction mixture was stirred for 4 hours at −40° C. Anhydrous methanol (12 mL) was added dropwise over 35 minutes. The reaction mixture was stirred at −40° C. for 1 hour, then allowed to warm to room temperature and stirred for 64 hours. Brine (50 mL) was added, and the mixture was filtered through Celite. The Celite cake was washed with EtOAc (60 mL). The layers were separated, and the aqueous layer was extracted with EtOAc (3×30 mL). The combined organics were washed with brine (60 mL), dried over sodium sulfate, filtered, and concentrated in vacuo. Purification by silica gel chromatography (15-70% EtOAc/hexanes) yielded Intermediate 11A (1.8 g, 40%). $^1$H NMR (CDCl$_3$) δ 7.46-7.42 (m, 2H), 7.26-7.21 (m, 2H), 4.25 (m, 1H), 3.37 (d, 1H), 2.05 (m, 1H), 1.77 (m, 1H), 1.24 (s, 9H), 0.81 (t, 3H).

(S)-1-(3-bromophenyl)propan-1-amine (Intermediate 11B

A solution was made of Intermediate 11A (0.66 g, 2.1 mmol) in methanol (1 mL). HCl in dioxane solution (4 M, 1.0 mL, 4.1 mmol) was added slowly to the above stirred solution. A white precipitate formed over 30 minutes. Diethyl ether (15 mL) was added to the reaction mixture, and the white solid was collected by vacuum filtration. The white solid was washed with hexanes, and dried in vacuo to give Intermediate 11B (0.46 g, 88%). $^1$H NMR (DMSO-d6) δ 8.42 (br m, 3H), 7.74 (m, 1H), 7.60 (m, 1H), 7.48 (m, 1H), 7.42 (m, 1H), 4.17 (m, 1H), 1.94 (m, 1H), 1.79 (m, 1H), 0.76 (t, 3H).

(S)—N-(1-(3-bromophenyl)propyl)-2-(trifluoromethyl)benzenesulfonamide (Intermediate 11)

Using similar procedure as described in Intermediate 10, step 2, Intermediate 11B was converted to Intermediate 11. $^1$H NMR (CDCl$_3$) δ 7.85 (d, 1H), 7.74 (d, 1H), 7.56 (t, 1H), 7.45 (t, 1H), 7.19 (m, 1H), 7.01-6.93 (m, 3H), 4.98 (d, 1H), 4.26 (q, 1H), 1.80 (m, 1H), 1.70 (m, 1H), 0.85 (t, 3H). Using similar procedure as described above for Intermediate 11 and substituting the appropriate starting materials and reagents, the following intermediates were prepared as indicated in Intermediate Table 8.

INTERMEDIATE TABLE 8

| Intermediate | Structure | material | Starting Reagent | MS (M + H)$^+$ |
| --- | --- | --- | --- | --- |
| 11C | (S)-N-(1-(3-bromophenyl)propyl)-3-(trifluoromethyl)benzenesulfonamide | 1-(3-bromophenyl)propan-1-one | 3-(trifluoromethyl)benzenesulfonyl chloride | No MS (See NMR below) |
| 11D | N-((S)-1-(3-bromophenyl)-4-cyanobutyl)-2-methylpropane-2-sulfinamide | 4-(3-bromophenyl)-4-oxobutanenitrile | Only step 1 of intermediate 11 | No MS (See NMR below) |
| 11E | (S)-N-(1-(3-bromophenyl)-4-cyanobutyl)-2-(trifluoromethyl)benzenesulfonamide | 11D | Only step 2 &3 of intermediate 11 | No MS (See NMR below) |

INTERMEDIATE TABLE 8-continued

| Intermediate | Structure | Starting material | Reagent | MS (M + H)+ |
|---|---|---|---|---|
| 11F | N-(1-(3-bromophenyl)-3-cyanopropyl)-2-(trifluoromethyl)benzenesulfonamide | 3-bromophenyl 3-oxopropanenitrile ketone | 2-(trifluoromethyl)benzenesulfonyl chloride | No MS (See NMR below) |

Intermediate 11C

¹H NMR (CDCl₃) δ 7.78 (m, 2H), 7.68 (d, 1H), 7.48 (t, 1H), 7.23 (m, 1H), 7.01 (m, 2H), 6.94 (m, 1H), 5.00 (d, 1H), 4.27 (q, 1H), 1.81 (m, 1H), 1.73 (m, 1H), 0.87 (t, 3H).

Intermediate 11D

¹H NMR (CDCl₃) δ 7.47 (s, 2H), 7.26 (m, 2H), 4.35 (m, 1H), 3.41 (d, 1H), 2.34 (t, 2H), 2.16 (m, 1H), 1.91 (m, 1H), 1.60 (m, 1H), 1.51 (m, 1H), 1.25 (s, 9H).

Intermediate 11E

¹H NMR (CDCl₃) δ 7.91 (d, 1H), 7.72 (d, 1H), 7.58 (t, 1H), 7.50 (t, 1H), 7.22 (m, 1H), 7.00 (t, 1H), 6.94 (m, 2H), 5.07 (d, 1H), 4.36 (m, 1H), 2.41 (t, 2H), 1.96-1.82 (m, 3H), 1.69 (m, 1H).

Intermediate 11F

¹H NMR (CDCl₃) δ 8.08 (m, 1H), 7.73 (m, 1H), 7.60 (m, 2H), 7.25 (m, 1H), 7.05 (t, 1H), 6.94 (m, 2H), 5.12 (d, 1H), 4.39 (q, 1H), 2.45 (m, 2H), 2.20 (m, 1H), 2.17 (m, 1H).

Intermediate 12

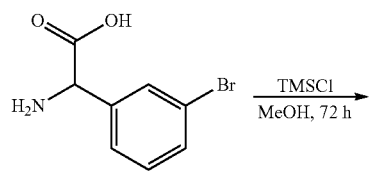

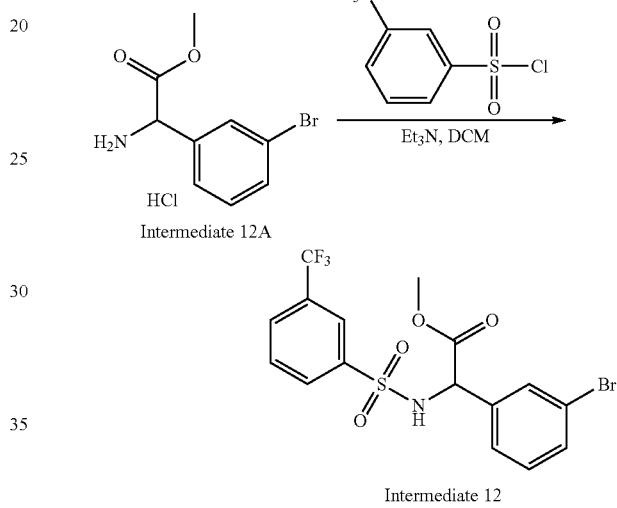

(+/−)Methyl 2-amino-2-(3-bromophenyl)acetate (Intermediate 12A

Trimethylsilyl chloride (1.4 mL, 11 mmol) was added in one portion to a suspension of (+/−) 2-amino-2-(3-bromophenyl)acetic acid (0.50 g, 0.17 mmol) in anhydrous methanol (13 mL). After 72 hours, the volatiles were removed in vacuo to give Intermediate 12A (0.61 g, quantitative yield). LCMS (method B): m/z 244.2/246.2 (M+H)⁺.
¹H NMR (CDCl₃) δ 7.69 (m, 2H), 7.46 (m, 2H), 5.25 (s, 1H), 3.83 (s, 3H).

(+/−) methyl 2-(3-bromophenyl)-2-(3-(trifluoromethyl)phenylsulfonamido)acetate (Intermediate 12)

Using similar procedure as described in Intermediate 10, step 2, Intermediate 12A was converted to Intermediate 12.
¹H NMR (CDCl₃) δ 7.85 (m, 2H), 7.74 (d, 1H), 7.55 (t, 1H), 7.35 (m, 1H), 7.23 (m, 1H), 7.13 (m, 2H), 5.92 (d, 1H), 5.13 (d, 1H), 3.67 (s, 3H).

Using the method described above for Intermediate 12 and substituting the appropriate starting material and reagent, the following intermediate was prepared as indicated in Intermediate Table 9.

INTERMEDIATE TABLE 9

| Intermediate | Structure | Starting material | Reagent | MS (M + H)+ |
|---|---|---|---|---|
| 12B | (S)-methyl 3-(3-bromophenyl)-3(2-(trifluoromethyl)phenylsulfonamido)propanoate | | | No MS (See NMR below) |

Intermediate 12B

¹H NMR (CDCl₃) δ 7.88 (d, 1H), 7.80 (d, 1H), 7.60 (t, 1H), 7.47 (t, 1H), 7.24 (m, 1H), 7.12 (m, 1H), 7.03 (m, 2H), 6.11 (d, 1H), 4.83 (m, 1H), 3.61 (s, 3H), 2.81 (m, 2H).

Intermediate 13

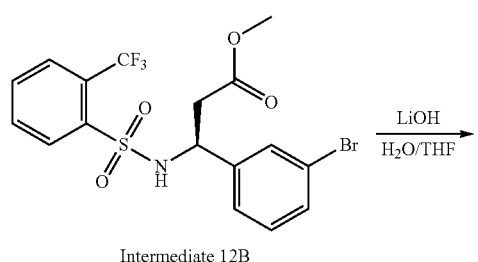

Intermediate 12B

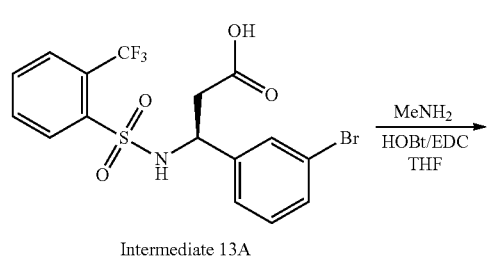

Intermediate 13A

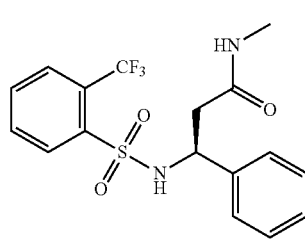

Intermediate 13

(S)-3-(3-Bromophenyl)-3-(2-(trifluoromethyl)phenylsulfonamido)propanoic acid (Intermediate 13A A solution of lithium hydroxide (18 mg, 0.75 mmol) in water (2 mL) was added to a stirred solution of Intermediate 12B (0.34 g, 0.73 mmol) in THF (2.5 mL). After 2 hours, an additional portion of lithium hydroxide solution was added (18 mg, 0.75 mmol in 1 mL water). The reaction mixture was stirred overnight at room temperature. The reaction mixture was acidified to pH-1 with 1N HCl, and extracted with EtOAc (3×6 mL). The combined organic extracts were washed with brine (5 mL), dried over sodium sulfate, filtered, and evaporated to dryness to yield Intermediate 13A (0.31 g, 94%). ¹H NMR (CDCl₃) δ 7.91 (d, 1H), 7.79 (d, 1H), 7.60 (t, 1H), 7.50 (t, 1H), 7.25 (m, 1H), 7.15 (m, 1H), 7.05 (m, 2H), 6.03 (d, 1H), 4.84 (m, 1H), 2.86 (d, 2H).

(S)-3-(3-Bromophenyl)-N-methyl-3-(2-(trifluoromethyl)phenylsulfonamido)propanamide (Intermediate 13)

A mixture of Intermediate 13A (0.12 g, 0.25 mmol), methylamine (2M solution in THF, 0.25 mL, 0.50 mmol), and HOBt (34 mg, 0.25 mmol) in THF (2 mL) was cooled to 0° C. After the addition of N-(3-dimethylaminopropyl)-N'-ethylcarbodiimide hydrochloride (57 mg, 0.30 mmol), the reaction was stirred overnight at room temperature. The reaction mixture was diluted with EtOAc (10 mL), and washed with 0.5 N HCl (5 mL) and a saturated sodium bicarbonate solution. The organic layer was dried over sodium sulfate, filtered, and evaporated to dryness. Purification by silica gel chromatography (5-75% EtOAc/hexanes) yielded Intermediate 13 (85 mg, 73%). ¹H NMR (CDCl₃) δ 7.79 (m, 2H), 7.55 (t, 1H), 7.40 (m, 1H), 7.20 (m, 2H), 7.15 (m, 1H), 7.03 (m, 1H), 6.97 (t, 1H), 5.39 (m, 1H), 4.82 (m, 1H), 2.76 (m, 1H), 2.70 (d, 1H), 2.47 (m, 1H).

Starting with Intermediate 13A and substituting the appropriate amine, the following intermediate was prepared as indicated in Intermediate Table 10.

INTERMEDIATE TABLE 10

| Intermediate | Structure | Reagent | MS (M + H)+ |
|---|---|---|---|
| 13B | 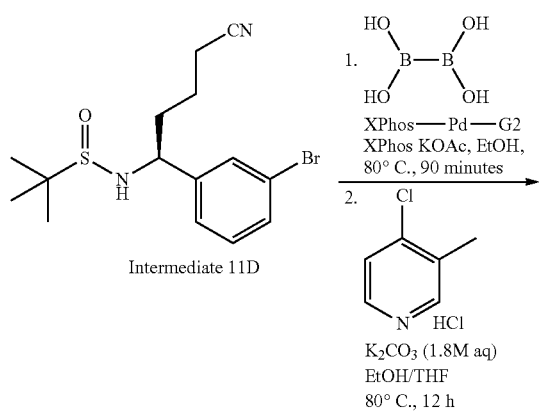  (S)-3-(3-bromophenyl)-N,N-dimethyl-3-(2-(trifluoromethyl)phenylsulfonamido)propanamide | >N—N—H | No MS (See NMR below) |

Intermediate 13B $^1$H NMR (CDCl$_3$) δ 7.80 (m, 2H), 7.55 (t, 1H), 7.41 (t, 1H), 7.25-7.18 (m, 3H), 7.08 (m, 1H), 6.97 (m, 1H), 4.85 (m, 1H), 2.82 (m, 8H).

Intermediate 14

N—((S)-4-cyano-1-(3-(3-methylpyridin-4-yl)phenyl)butyl)-2-methylpropane-2-sulfinamide (Intermediate 14A Following similar procedure as Intermediate 4, method A, step 1, Intermediate 11D was converted to Intermediate 14A.
$^1$H NMR (CDCl$_3$) δ 8.50 (m, 2H), 7.48 (t, 1H), 7.37 (m, 1H), 7.31 (m, 2H), 7.16 (m, 1H), 4.44 (m, 1H), 3.48 (d, 1H), 2.35 (t, 2H), 2.29 (s, 3H), 2.18 (m, 1H), 1.97 (m, 1H), 1.70 (m, 1H), 1.57 (m, 1H), 1.26 (s, 9H).

(S)-5-amino-5-(3-(3-methylpyridin-4-yl)phenyl)pentanenitrile hydrochloride (Intermediate 14)

Following similar procedure as Intermediate 4, method A, step 2, Intermediate 14A was converted to Intermediate 14.
$^1$H NMR (DMSO-d6) δ 8.93 (s, 1H), 8.84 (m, 3H), 7.91 (d, 1H), 7.83 (s, 1H), 7.71 (m, 1H), 7.66 (t, 1H), 7.60 (m, 1H), 4.40 (m, 1H), 2.54 (t, 2H), 2.47 (s, 1H), 2.10 (m, 1H), 2.00 (m, 1H), 1.56 (m, 1H), 1.37 (m, 1H).

Intermediate 15

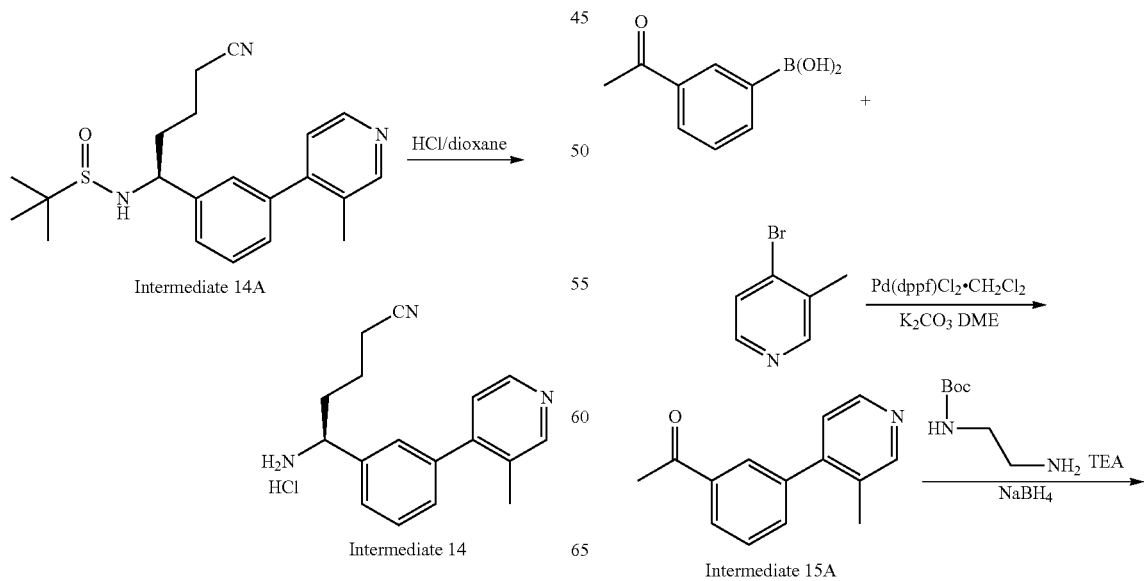

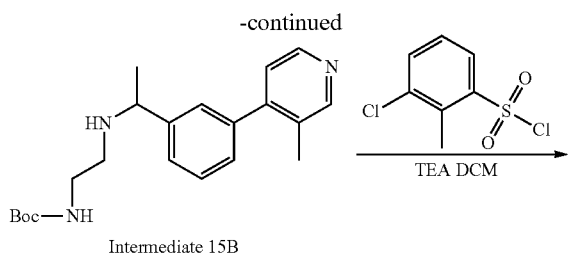

purified by silica gel chromatography (0-80% EtOAc/hexanes) to afford the desired product as an off white solid (1.6 g, 76%). LCMS (method A): m/z 212.2 (M+H)$^+$.

tert-butyl (2-((1-(3-(3-methylpyridin-4-yl)phenyl)ethyl)amino)ethyl)carbamate (Intermediate 15B To a solution of tert-butyl (2-aminoethyl)carbamate (0.66 mL, 2.1 mmol) in THF (5 mL) was added TEA (0.64 mL, 2.5 mmol) followed by Intermediate 15A (0.21 g, 1 mmol) and sodium sulfate (250 mg, 1.8 mmol). The reaction mixture was heated at 70° C. overnight, and cooled to room temperature. The solids were filtered off and the filter cake was washed with MeOH. To the filtrate was added NaBH$_4$ (120 mg, 3 mmol), and the mixture was stirred at room temperature for 30 minutes. Acetone (10 mL) was added and the mixture stirred for another 30 minutes. The solvent was removed in vacuo, and the residue was partitioned between EtOAc and aqueous sodium carbonate. The organic layer was washed with brine, dried over Na$_2$SO$_4$, and concentrated to a residue which was purified by silica gel chromatography (0-5% MeOH/DCM) to afford the desired product (0.26 g, 73%). LCMS (method A): m/z 356.4 (M+H)$^+$ tert-butyl (2-(3-chloro-2-methyl-N-(1-(3-(3-methylpyridin-4-yl)phenyl)ethyl)phenylsulfonamido)ethyl)carbamate (Intermediate 15C Following similar procedure as Intermediate 7, step 2, Intermediate 15B (0.26 g, 0.73 mmol) was converted to Intermediate 15C (0.24 g, 60%). LCMS (method A): m/z 544.4/546.4 (M+H)$^+$.

N-(2-aminoethyl)-3-chloro-2-methyl-N-(1-(3-(3-methylpyridin-4-yl)phenyl)ethyl)-benzenesulfonamide (Intermediate 15)

To a solution of Intermediate 15C (0.24 g, 0.44 mmol) in DCM (5 mL) was added TFA (2 mL) and the mixture was stirred at room temperature for 90 minutes. Volatiles were removed in vacuo. The residue was used in the next step without further purification. LCMS (method A): m/z 444.4/446.4 (M+H)$^+$.

Starting with Intermediate 15A, and following the method described above for Intermediate 15, steps 2-4, and substituting the appropriate reagent, the following intermediate was prepared as indicated in Intermediate Table 11.

INTERMEDIATE TABLE 11

| Intermediate | Structure | Reagent | Reagent | MS (M + H)$^+$ |
|---|---|---|---|---|
| 15D | ![structure] N-(3-aminopropyl)-3-chloro-2-methyl-N-(1-(3-(3-methylpyridin-4-yl)phenyl)-ethyl)benzenesulfonamide | ![reagent Boc-NH-propyl-NH2] | ![reagent sulfonyl chloride] | 458.4/460.4 (method A) |

Intermediate 16

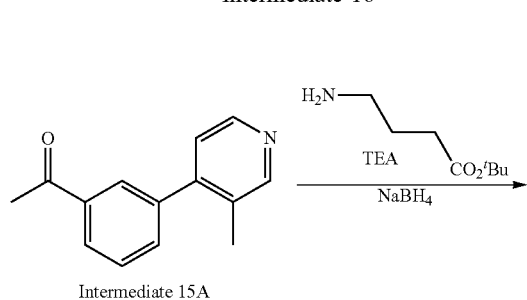

Intermediate 15A

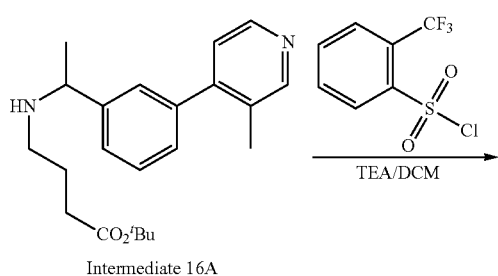

Intermediate 16A

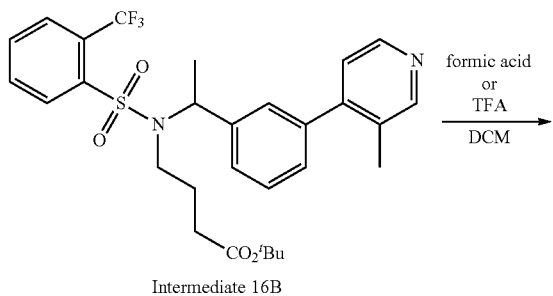

Intermediate 16B

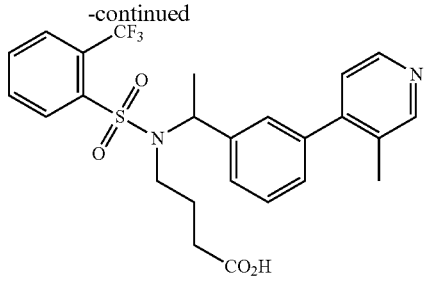

Intermediate 16 tert-butyl 4-((1-(3-(3-methylpyridin-4-yl)phenyl)ethyl)amino)butanoate (Intermediate 16A Following a similar procedure as described in Intermediate 15, step 2, Intermediate 15A (0.42 g, 2 mmole) was converted to Intermediate 16A (0.55 g, 78%). LCMS (method A): m/z 355.4 (M+H)$^+$.

tert-butyl 4-(N-(1-(3-(3-methylpyridin-4-yl)phenyl)ethyl)-2-(trifluoromethyl)-phenylsulfonamido)butanoate (Intermediate 16B Following a similar procedure as described in Intermediate 15, step 3, Intermediate 16A (0.27 g, 0.78 mmole) was converted to Intermediate 16B (0.24 g, 57%). LCMS (method A): m/z 563.5 (M+H)$^+$.

4-(N-(1-(3-(3-methylpyridin-4-yl)phenyl)ethyl)-2-(trifluoromethyl)phenylsulfonamido)-butanoic acid (Intermediate 16)

Intermediate 16B (240 mg, 0.43 mmol) in formic acid (5 mL) was stirred at room temperature overnight. Volatiles were removed in vacuo to afford Intermediate 16 in quantitative yield. Formic acid salt was converted to HCl salt using HCl (4 N in diaoxane). LCMS (method A): m/z 507.4 (M+H)$^+$. Alternatively, TFA can be used instead of formic acid.

Starting with Intermediate 16A, and following the method described above for Intermediate 16, steps 2-3, substituting the appropriate reagent, the following intermediate was prepared as indicated in Intermediate Table 12.

INTERMEDIATE TABLE 12

| Intermediate | Structure | Reagent | MS (M + H)$^+$ |
|---|---|---|---|
| 16C | 4-(N-(1-(3-(3-methylpyridin-4-yl)phenyl)ethyl)-3-(trifluoromethyl)phenylsulfonamido)butanoic acid | | 507.4 (method A) |

Intermediate 17

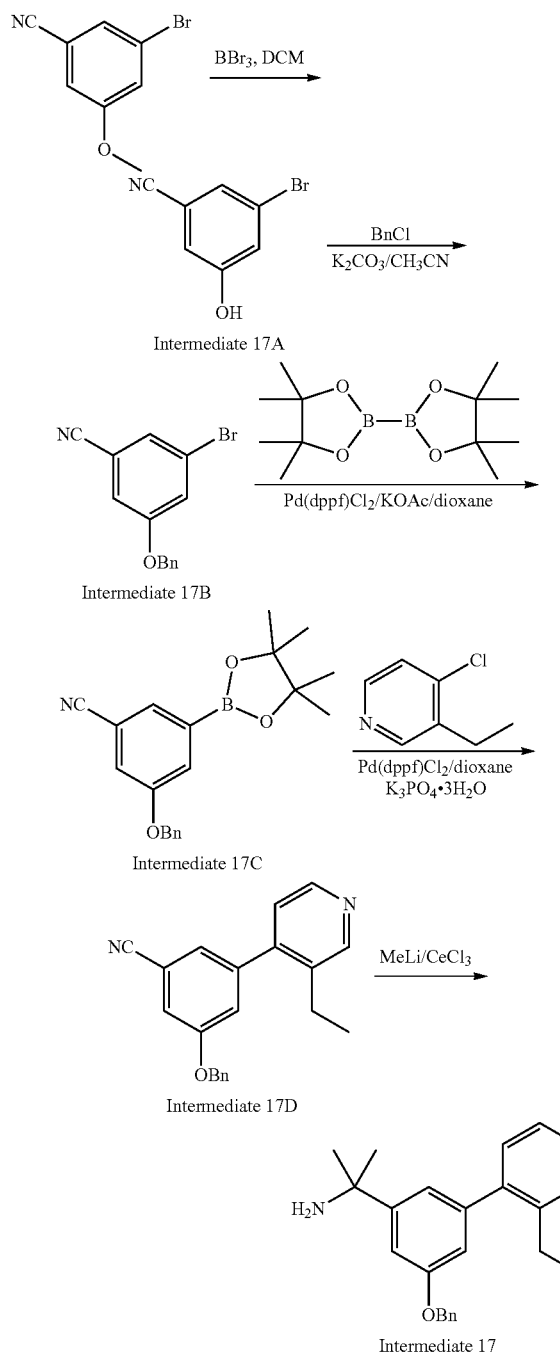

Intermediate 17

3-Bromo-5-hydroxybenzonitrile (Intermediate 17A

To a solution of 3-bromo-5-methoxybenzonitrile (10 g, 4.7 mmol) in DCM (300 mL) was added BBr$_3$ (35 g, 14 mmol) dropwise at 0° C. After stirring for 1.5 hours, the ice-bath was removed and the mixture was stirred at 25° C. overnight. After TLC showed the starting material was consumed completely, the mixture was quenched with MeOH and concentrated to afford the crude Intermediate 17A, which was used in the next step directly (7.0 g, 75%). $^1$H NMR (CD$_3$OD) δ7.32 (s, 1H), 7.24 (s, 1H), 7.05 (s, 1H).

3-(Benzyloxy)-5-bromobenzonitrile (Intermediate 17B

To a solution of Intermediate 17A (7.0 g, 36 mmol) in CH$_3$CN (100 mL) was added K$_2$CO$_3$ (9.8 g, 71 mmol) and BnCl (5.4 g, 43 mmol) and the mixture was stirred at reflux overnight. After LCMS showed the starting material was consumed completely, the reaction mixture was filtered and the filtrate was concentrated to give the crude product, which was purified by silica gel chromatography (2-10% EtOAc/Petroleum Ether) to give Intermediate 17B (10 g, 98%). $^1$H NMR (CDCl$_3$) δ 7.29-7.36 (m, 7H), 7.08 (s, 1H), 5.00 (s, 2H).

3-(benzyloxy)-5-(4,4,5,5-tetramethyl-1,3,2-dioxaborolan-2-yl)benzonitrile (Intermediate 17C To a solution of Intermediate 17B (10 g, 35 mmol) in dry dioxane (300 mL) was added KOAc (6.9 g, 70 mmol), bis(pinacolato)diboron (11 g, 42 mmol) and Pd(dppf)Cl$_2$ (2.0 g). The mixture was stirred at reflux overnight under N$_2$. After LCMS showed the starting material was consumed completely, the reaction mixture was filtered and concentrated to give the crude product, which was purified by column chromatography on silica gel to give Intermediate 17C (10 g, 86%). $^1$H NMR (CDCl$_3$): δ 7.56-7.61 (m, 2H), 7.18-7.34 (m, 6H), 5.02 (s, 2H), 1.27 (s, 12H).

3-(Benzyloxy)-5-(3-ethylpyridin-4-yl)benzonitrile (Intermediate 17D

To a solution of Intermediate 17C (10 g, 30 mmol) in dry dioxane (300 mL) was added 4-chloro-3-ethylpyridine (5.0 g, 36 mmol), K$_3$PO$_4$.3H$_2$O (16 g, 60 mmol) and Pd(dppf)Cl$_2$ (2.0 g), and the mixture was stirred at reflux for 12 hours under N$_2$. After LCMS showed the starting material was consumed completely, the reaction mixture was filtered and concentrated to give the crude product, which was purified by column chromatography on silica gel and preparative HPLC to give Intermediate 17D (800 mg, 8.5%). $^1$H NMR (CD$_3$OD): δ 8.72-8.82 (m, 2H), 7.86 (d, 1H), 7.58 (s, 1H), 7.33-7.46 (m, 6H), 5.23 (s, 2H), 2.72-2.78 (m, 2H), 1.10-1.14 (m, 3H).

2-(3-(Benzyloxy)-5-(3-ethylpyridin-4-yl)phenyl)propan-2-amine (Intermediate 17)

After solid CeCl$_3$ (3.4 g, 15 mmol) was dried with vacuum pump at 120° C. for 8 hours, a solution of Intermediate 17D (800 mg, 2.5 mmol) in dry THF (20 mL) was added and the mixture was stirred for 30 minutes at 25° C. After cooling to −78° C., methyl lithium (15 mL, 15 mmol) was added and the mixture was stirred overnight at 25° C. After LCMS showed the starting material was consumed completely, the mixture was quenched with aqueous NH$_4$Cl and extracted with EtOAc (3×50 mL). The combined organic layers were concentrated to give 1.0 g of crude Intermediate 17, which was used for the next step directly.

Following the method described above for Intermediate 17, skipping step 1 & 2, and starting with 3-bromo-5-methoxybenzonitrile, the following intermediate was prepared as indicated in Intermediate Table 13.

INTERMEDIATE TABLE 13

| Intermediate | Structure | Reagent | MS (M + H)+ |
|---|---|---|---|
| 17E | 4-(N-(1-(3-(3-methylpyridin-4-yl)phenyl)ethyl)-3-(trifluoromethyl)phenyl-sulfonamido)butanoic acid [structure: H$_2$N-C(CH$_3$)$_2$ attached to phenyl bearing OMe and 3-ethylpyridin-4-yl] | [structure: NC-phenyl-Br with OMe substituent] | Used directly to make compound 2CD without purification |

Intermediate Table 18

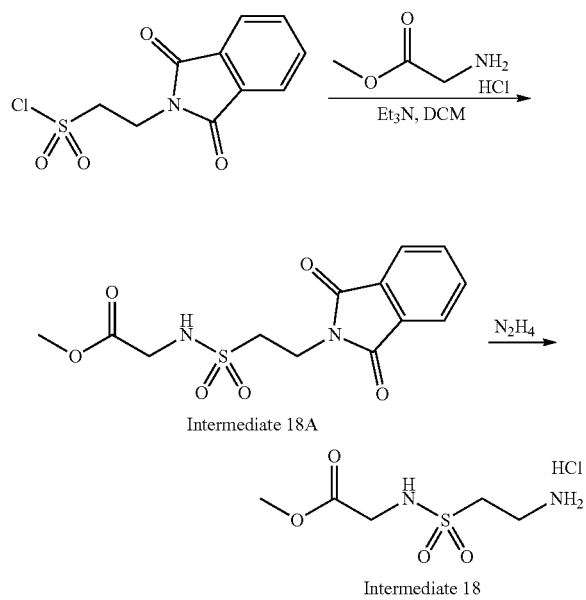

Methyl 2-(2-(1,3-dioxoisoindolin-2-yl)ethylsulfonamido)acetate (Intermediate 18A)

To a solution of methyl 2-aminoacetate hydrochloride (0.25 g, 0.20 mmol) and Et$_3$N (0.69 mL, 0.49 mmol) in DCM (1 mL) was added 2-(1,3-dioxoisoindolin-2-yl)ethanesulfonyl chloride (0.45 g, 0.16 mmol). The reaction mixture was stirred at room temperature for three hours. The reaction mixture was concentrated in vacuo and purified by silica gel chromatography (0-10% MeOH/DCM) to afford Intermediate 18A (0.37 g, 70%). LCMS (method A): m/z 327.2 (M+H)+. $^1$H NMR (CDCl$_3$): δ 7.87-7.84 (m, 2H), 7.76-7.72 (m, 2H), 5.56 (t, 1H), 4.33 (t, 2H), 4.04 (d, 2H), 3.77 (s, 3H), 3.45 (t, 2H).

Methyl 2-(2-aminoethylsulfonamido)acetate hydrochloride (Intermediate 18)

To a solution of Intermediate 18A (0.70 g, 2.2 mmol) in MeOH (4 mL) was added hydrazine monohydrate (0.10 mL, 2.2 mmol). The reaction mixture was stirred at room temperature overnight. Concentrated hydrochloric acid (1.5 mL) was added and the white solid was removed by filtration. The filtrate was evaporated to afford Intermediate 18 (0.72 g). LCMS (method A): m/z 197.1 (M+H)+. This compound was used directly in the next step without further purification.

Starting with 2-(1,3-dioxoisoindolin-2-yl)ethanesulfonyl chloride, and following a similar method as described above for Intermediate 18, the following Intermediates were prepared as indicated in Intermediate Table 14.

INTERMEDIATE TABLE 14

| Intermediate | Structure | Starting material | Reagent | MS (M + H)+ |
|---|---|---|---|---|
| 18B | tert-butyl 2-(2-amino ethylsulfonamido)acetate | [2-(1,3-dioxoisoindolin-2-yl)ethanesulfonyl chloride structure] | [tert-butyl 2-aminoacetate structure] | 239.3 (method A) |

INTERMEDIATE TABLE 14-continued

| Intermediate | Structure | Starting material | Reagent | MS (M + H)+ |
|---|---|---|---|---|
| 18C | tert-butyl 3-(2-amino ethylsulfonamido)propanoate | | | 253.3 (method A) |
| 18D | tert-butyl 4-(2-amino ethylsulfonamido)butanoate | | | 267.3 (method A) |
| 18E | methyl 3-sulfamoylpropanoate | | NH₃ No other base used | No MS (see NMR below) |

Intermediate 18E

¹H NMR (CDCl₃): δ 4.85 (br s, 2H), 3.75 (s, 3H), 3.48 (t, 2H), 2.90 (t, 2H).

Intermediate 19

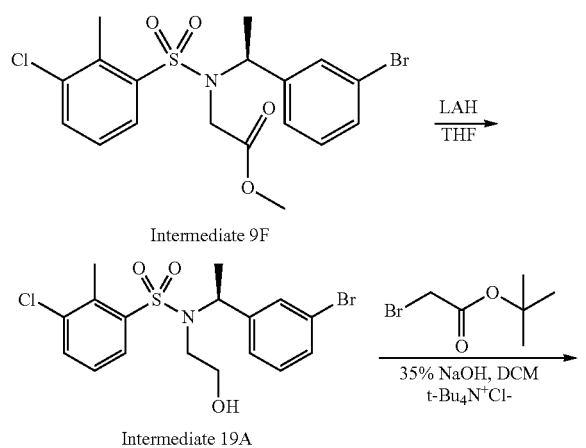

(S)—N-(1-(3-Bromophenyl)ethyl)-3-chloro-N-(2-hydroxyethyl)-2-methylbenzenesulfonamide (Intermediate 19A Under an atmosphere of nitrogen, Intermediate 9F (0.59 g, 1.3 mmol) was dissolved in anhydrous tetrahydrofuran (5 mL) and cooled to 0° C. in an ice bath. A solution of 1M lithium aluminum hydride in toluene (3.0 mL, 3.0 mmol) was added and the yellow solution was stirred at 0° C. for 1 hour. The reaction was quenched with a 1M hydrochloric acid solution until no more gas evolution was observed. The reaction was extracted with EtOAc (3X). The combined organic layers were washed with brine (1x) and dried over magnesium sulfate. The reaction was filtered and concentrated in vacuo which gave clear oil. The oil was purified by flash chromatography (EtOAc/hexanes) to afford Intermediate 19A (0.45 g, 81%) as a clear oil. ¹H NMR (CD₃OD): δ 8.00 (dd, 1H), 7.70 (dd, 1H), 7.46-7.35 (m, 2H), 7.32-7.20 (m, 3H), 4.97 (q, 1H), 3.51-3.14 (br m, 4H), 2.61 (s, 3H), 1.51 (d, 3H).

(S)-tert-Butyl 2-(2-(N-(1-(3-bromophenyl)ethyl)-3-chloro-2-methylphenylsulfonamido) ethoxy)acetate (Intermediate 19)

35% sodium hydroxide solution (2.5 mL) was added to a stirring solution of Intermediate 19A (0.45 g, 1.0 mmol) and tert-butyl ammonium chloride (0.086 g, 3.1 mmol) in DCM (2.5 mL) and stirred vigorously at room temperature for 1 hour. The reaction was partitioned between DCM and H₂O and the organic layer was dried over magnesium sulfate. The reaction was filtered and concentrated in vacuo. The residue was purified by flash chromatography (EtOAc/hexanes) to afford Intermediate 19 (0.14 g, 25%) as a clear oil. ¹H NMR (CD₃OD): δ 7.98 (dd, 1H), 7.67 (dd, 1H), 7.46-7.26 (m, 3H), 7.25-7.20 (m, 1H), 5.00 (q, 1H), 3.48-3.19 (br m, 6H), 2.61 (s, 3H), 1.54 (d, 3H), 1.45 (s, 9H)

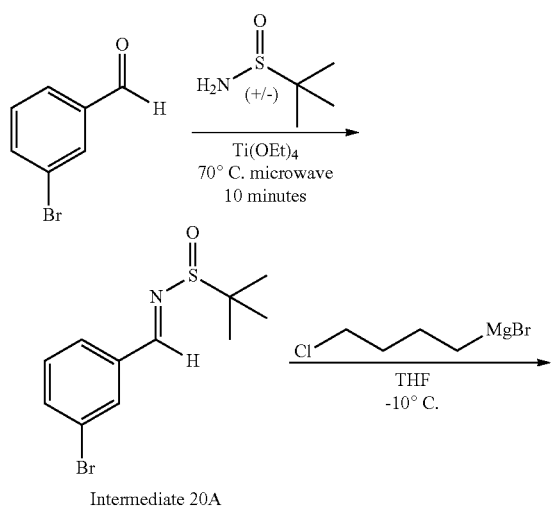

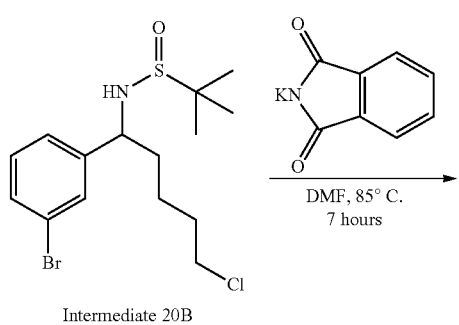

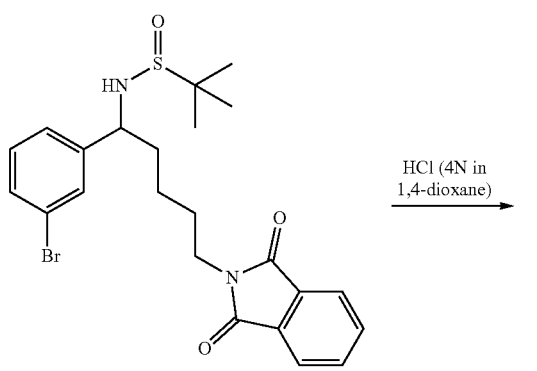

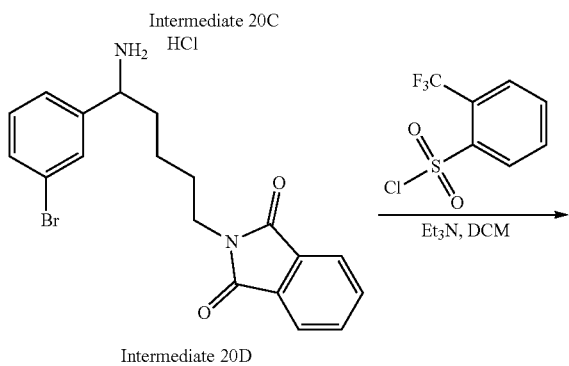

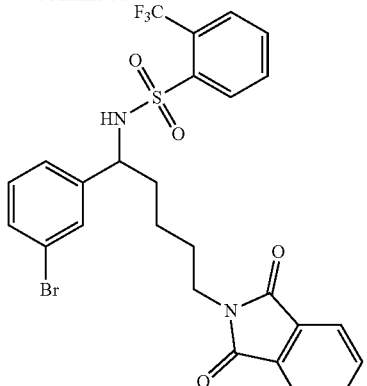

Intermediate 20

N-(3-bromobenzylidene)-2-methylpropane-2-sulfinamide (Intermediate 20A

Racemic 2-methylpropane-2-sulfinamide (0.36 g, 3.0 mmol) and 3-bromobenzaldehyde (0.56 g, 3.0 mmol) were weighed out into a Biotage microwave vessel, and stirred under nitrogen. Titanium(IV) ethoxide (1.3 mL, 6.0 mmol) was added and the mixture was stirred under nitrogen for 5 minutes, then irradiated to 70° C. for 10 minutes in a Biotage Initiator microwave. After cooling, the reaction mixture was diluted with EtOAc (15 mL), and added to a rapidly stirred brine solution (0.75 mL). The mixture was filtered through Celite, and the filtrate was concentrated in vacuo to give Intermediate 20A (0.85 g, 98% yield). $^1$H NMR (CDCl$_3$) δ 8.54 (s, 1H), 8.04 (m, 1H), 7.75 (m, 1H), 7.66 (m, 1H), 7.37 (t, 1H), 1.29 (s, 9H).

(4-chlorobutyl)magnesium Bromide

Magnesium filings (0.28 g, 11.5 mmol) were added to an oven-dried 3 necked flask fitted with an addition funnel, a reflux condenser and nitrogen line. Anhydrous THF (10 mL) and 2 iodine crystals were added. A solution of 1-bromo-4-chlorobutane (1.20 mL, 10 mmol dissolved in 24 mL THF) was added to the addition funnel. After the addition of 2 mL of the 1-bromo-4-chlorobutane solution to the Mg/THF mixture, a 40° C. water bath was applied until the reaction mixture turned clear. The reaction mixture was cooled to −10° C., and the remaining 1-bromo-4-chlorobutane solution was added dropwise over 30 minutes. The reaction mixture was allowed to warm to room temperature, and stirred for 90 minutes to form a solution of (4-chlorobutyl) magnesium bromide.

N-(1-(3-bromophenyl)-5-chloropentyl)-2-methylpropane-2-sulfinamide (Intermediate 20B The solution of (4-chlorobutyl)magnesium bromide was diluted with THF (40 mL) and cooled to −10° C. A solution of Intermediate 20A (0.84 g, 2.9 mmol) in THF (60 mL) was cooled to −10° C. The (4-chlorobutyl)magnesium bromide solution was added via cannula over 35 minutes to intermediate 20A. After the addition was complete, the reaction mixture was poured into a saturated ammonium chloride solution, and the layers were separated. The aqueous layer was extracted twice with EtOAc (40 mL). The combined organics were dried over sodium sulfate, filtered and evaporated to dryness. Purification by silica gel chromatography (0-50% EtOAc/DCM) yielded Intermediate 20B (0.81 g, 73%) as a mixture of diastereomer pairs. LCMS (method A): m/z 382.3/380.3 (M+H)+.

N-(1-(3-bromophenyl)-5-(1,3-dioxoisoindolin-2-yl) pentyl)-2-methylpropane-2-sulfinamide (Intermediate 20C Potassium phthalimide (0.72 g, 3.9 mmol) was added to a solution of Intermediate 20B (0.67 g, 1.8 mmol) in DMF (8 mL). The reaction mixture was heated to 85° C. for 7 hours. The reaction mixture was diluted with EtOAc (50 mL) and filtered through a pad of Celite. The filtrate was washed with water (30 mL×3), brine (30 mL×1), and dried over sodium sulfate. The mixture was filtered and concentrated in vacuo. Purification by silica gel chromatography (0-50% EtOAc/DCM) gave Intermediate 20C (0.24 g of first eluting enantiomer pair and 0.33 g of second eluting enantiomer pair). First eluting enantiomer pair: $^1$H NMR (CDCl$_3$) δ 7.85 (m, 2H), 7.72 (m, 2H), 7.45 (m, 1H), 7.40 (m, 1H), 7.23 (m, 2H), 4.28 (m, 1H), 3.64 (t, 2H), 3.38 (d, 1H), 2.03 (m, 1H), 1.77 (m, 1H), 1.69 (m, 2H), 1.34 (m, 1H), 1.21 (s, 9H), 1.20 (m, 1H). Second eluting enantiomer pair: $^1$H NMR (CDCl$_3$) δ 7.84 (m, 2H), 7.73 (m, 2H), 7.44 (m, 1H), 7.38 (m, 1H), 7.21 (m, 2H), 4.35 (m, 1H), 3.65 (t, 2H), 3.48 (m, 1H), 1.83 (m, 2H), 1.66 (m, 2H), 1.36 (m, 1H), 1.31 (m, 1H), 1.21 (s, 9H).

2-(5-amino-5-(3-bromophenyl)pentyl)isoindoline-1, 3-dione hydrochloride (Intermediate 20D A solution was made of the combined diastereomer pairs Intermediate 20C (0.50 g, 1.0 mmol) in diethyl ether (4 mL). A solution of HCl in dioxane (4 M, 0.76 mmol) was added dropwise. A white precipitate formed immediately. The mixture was cooled to 0° C., and diluted with diethyl ether (15 mL). The white precipitate was collected by vacuum filtration, and dried in vacuo to yield Intermediate 20D (0.43 g, 98%). $^1$H NMR (DMSO-d6) δ 8.46 (m, 3H), 7.85 (m, 4H), 7.73 (m, 1H), 7.55 (m, 1H), 7.46 (m, 1H), 7.36 (m, 1H), 4.22 (m, 1H), 3.52 (t, 1H), 1.92 (m, 1H), 1.84 (m, 1H), 1.58 (m, 2H), 1.22 (m, 1H), 1.07 (m, 1H).

N-(1-(3-bromophenyl)-5-(1,3-dioxoisoindolin-2-yl) pentyl)-2-(trifluoromethyl)Benzenesulfonamide (Intermediate 20)

Intermediate 20D was reacted with 2-(trifluoromethyl) benzene-1-sulfonyl chloride in a manner similar to the preparation of intermediate 1 but using Et$_3$N as the base to afford Intermediate 20. $^1$H NMR (CDCl$_3$) δ 7.87 (m, 2H), 7.81 (d, 1H), 7.74 (m, 3H), 7.53 (t, 1H), 7.42 (t, 1H), 7.16 (m, 1H), 7.01 (m, 1H), 6.95 (m, 2H), 5.20 (d, 1H), 4.34 (q, 1H), 3.65 (t, 2H), 1.90 (m, 1H), 1.67 (m, 3H), 1.41 (m, 1H), 1.26 (m, 1H).

Example 1

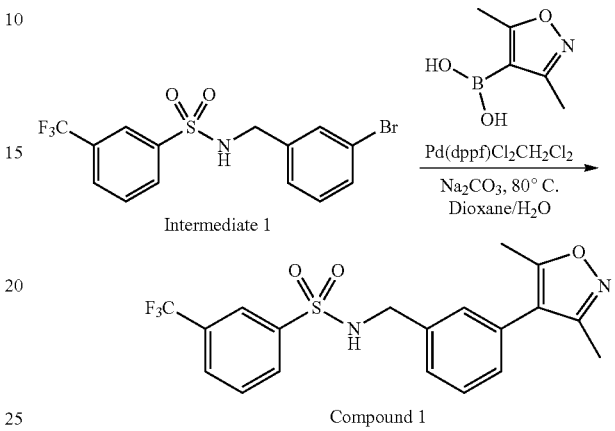

N-(3-(3,5-dimethylisoxazol-4-yl)benzyl)-3-(trifluoromethyl)benzenesulfonamide (Compound 1)

To a mixture of N-(3-bromobenzyl)-3-(trifluoromethyl) benzenesulfonamide (0.10 g, 0.25 mmol), (3,5-dimethylisoxazol-4-yl)boronic acid (72 mg, 0.51 mmol), and Na$_2$CO$_3$ (54 mg, 0.51 mmol) in dioxane/H$_2$O (1.6 mL/0.4 mL) was added Pd(dppf)Cl$_2$—CH$_2$Cl$_2$ (21 mg, 0.025 mmol). The reaction was degassed with N$_2$ and stirred at 80° C. for 4 hours. The reaction was cooled to room temperature and DCM was added. The mixture was washed with brine (1X) and water (2X). The organic layer was dried over sodium sulfate, filtered, and concentrated in vacuo. The residue was purified by silica gel chromatography (0-35% EtOAc/Hexanes, 2 cycles) to afford the title compound (35 mg, 34%). LCMS (method A): m/z 411.2 (M+H)+. $^1$H NMR (CDCl$_3$) δ 8.10 (s, 1H), 8.05 (d, 1H), 7.82 (d, 1H), 7.64 (t, 1H), 7.35 (t, 1H), 7.20 (d, 1H), 7.14 (d, 1H), 7.11 (s, 1H), 5.42 (t, 1H), 4.26 (d, 2H), 2.35 (s, 3H), 2.20 (s, 3H).

Following the method described above for Example 1 and substituting the appropriate intermediates and reagents, the following compounds were prepared as indicated in Table 1.

Reactions were monitored by LCMS.

TABLE 1

| Compound No | Structure | Intermediate | Reagent | MS (M + H)+ |
|---|---|---|---|---|
| 1AA | N-(3-(3,5-dimethylisoxazol-4-yl)benzyl)-4-(trifluoromethyl)-benzenesulfonamide | 1B | (3,5-dimethylisoxazol-4-yl)boronic acid | 411.2 (method A) |

TABLE 1-continued

| Compound No | Structure | Intermediate | Reagent | MS (M + H)+ |
|---|---|---|---|---|
| 1AB | 4-chloro-N-(3-(3,5-dimethylisoxazol-4-yl)benzyl)benzenesulfonamide | 1C | | 377.1/ 379.2 (method A) |
| 1AC | N-(2-(3-(3,5-dimethylisoxazol-4-yl)phenyl)propan-2-yl)-3-(trifluoromethyl)benzenesulfonamide | 1D | | 439.3 (method A) |
| 1AD | N-(2-(3-(pyridin-4-yl)phenyl)propan-2-yl)-3-(trifluoromethyl)benzenesulfonamide | 1D | | 421.3 (method A) |
| 1AE | N-(2-(3-(3-fluoropyridin-4-yl)phenyl)propan-2-yl)-3-(trifluoromethyl)benzenesulfonamide | 1D | | 439.3 (method A) |
| 1AF | N-(2-(3-(3-chloropyridin-4-yl)phenyl)propan-2-yl)-3-(trifluoromethyl)benzenesulfonamide | 1D | | 455.3/ 457.3 (method A) |

TABLE 1-continued

| Compound No | Structure | Intermediate | Reagent | MS (M + H)+ |
|---|---|---|---|---|
| 1AG | N-(2-(3-(2-chloro pyridin-4-yl)phenyl)propan-2-yl)-3-(trifluoromethyl)benzenesulfonamide | 1D | 2-chloropyridin-4-yl boronic acid | 455.3/457.3 (method A) |
| 1AH | 3-(trifluoromethyl)-N-(2-(3-(2-(trifluoromethyl)pyridin-4-yl)phenyl)propan-2-yl)benzenesulfonamide | 1D | 2-(trifluoromethyl)pyridin-4-yl boronic acid | 489.2 (method A) |
| 1AI | N-(2-(3-(3-methoxypyridin-4-yl)phenyl)propan-2-yl)-3-(trifluoromethyl)benzenesulfonamide | 1D | 3-methoxypyridin-4-yl boronic acid pinacol ester | 451.3 (method A) |
| 1AJ | N-(2-(3-(quinolin-4-yl)phenyl)propan-2-yl)-3-(trifluoromethyl)benzenesulfonamide | 1D | quinolin-4-yl boronic acid | 471.3 (method A) |
| 1AK | N-(2-(3-(2-methylpyridin-4-yl)phenyl)propan-2-yl)-3-(trifluoromethyl)benzenesulfonamide | 1D | 2-methylpyridin-4-yl boronic acid pinacol ester | 435.3 (method A) |

TABLE 1-continued

| Compound No | Structure | Intermediate | Reagent | MS (M + H)+ |
|---|---|---|---|---|
| 1AL | 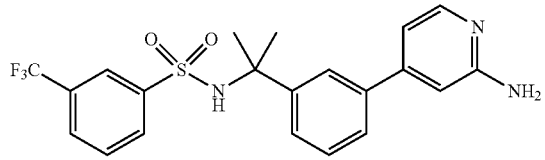<br>N-(2-(3-(2-aminopyridin-4-yl)phenyl)propan-2-yl)-3-(trifluoromethyl)benzene-sulfonamide | 1D | 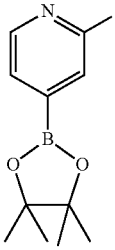 | 436.3 (method A) |
| 1AM | 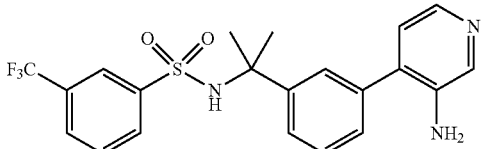<br>N-(2-(3-(3-aminopyridin-4-yl)phenyl)propan-2-yl)-3-(trifluoromethyl)benzene-sulfonamide | 1D | 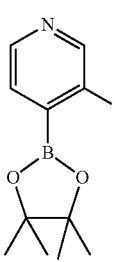 | 436.5 (method A) |
| 1AN | 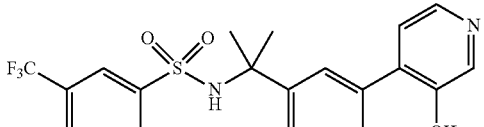<br>N-(2-(3-(3-hydroxypyridin-4-yl)phenyl)propan-2-yl)-3-(trifluoromethyl)benzene-sulfonamide | 1D | 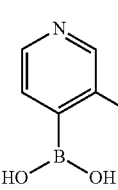<br>Intermediate 4 | 437.2 (method A) |
| 1AO | 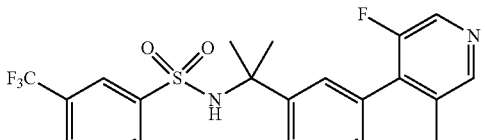<br>N-(2-(3-(3-fluoro-5-methylpyridin-4-yl)phenyl)propan-2-yl)-3-(trifluoromethyl)benzene-sulfonamide | 1D | 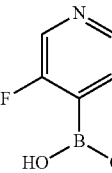 | 453.3 (method A) |
| 1AP | 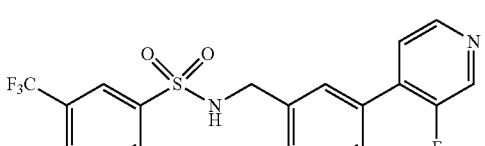<br>N-(3-(3-fluoropyridin-4-yl)benzyl)-3-(trifluoromethyl)-benzenesulfonamide | 1 | 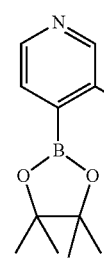 | 411.3 (method A) |

TABLE 1-continued

| Compound No | Structure | Intermediate | Reagent | MS (M + H)+ |
|---|---|---|---|---|
| 1AQ | N-(3-(3-chloropyridin-4-yl)benzyl)-3-(trifluoromethyl)-benzenesulfonamide | 1 | | 427.2/ 429.2 (method A) |
| 1AR | N-(3-(pyridin-4-yl)benzyl)-3-(trifluoromethyl)benzene-sulfonamide | 1 | | 393.3 (method A) |
| 1AS | N-(4-fluoro-3-(pyridin-4-yl)benzyl)-3-(trifluoromethyl)-benzenesulfonamide | 1E | | 411.3 (method A) |
| 1AT | N-(3-(3-chloropyridin-4-yl)-4-fluorobenzyl)-3-(trifluoromethyl)-benzenesulfonamide | 1E | | 445.2/ 447.1 (method A) |
| 1AU | N-(2-fluoro-5-(pyridin-4-yl)benzyl)-3-(trifluoromethyl)-benzenesulfonamide | 1F | | 411.3 (method A) |
| 1AV | N-(5-(3-chloropyridin-4-yl)-2-fluorobenzyl)-3-(trifluoromethyl)-benzenesulfonamide | 1F | | 445.2/ 447.1 (method A) |

TABLE 1-continued

| Compound No | Structure | Intermediate | Reagent | MS (M + H)+ |
|---|---|---|---|---|
| 1AW | (S)-N-(1-(3-pyridin-4-yl)phenyl)ethyl)-3-(trifluoromethyl)benzenesulfonamide | 1G | | 407.3 (method A) |
| 1AX | (S)-N-(1-(3-(3-chloropyridin-4-yl)phenyl)ethyl)-3-(trifluoromethyl)benzenesulfonamide | 1G | | 441.2/ 443.2 (method A) |
| 1AY | (S)-N-(1-(3-(3-floropyridin-4-yl)phenyl)ethyl)-3-(trifluoromethyl)benzenesulfonamide | 1G | | 425.2 (method A) |
| 1AZ | (S)-N-(1-(3-(3-methoxypyridin-4-yl)phenyl)ethyl)-3-(trifluoromethyl)benzenesulfonamide | 1G | | 437.2 (method A) |
| 1BB | (R)-N-(1-(3-(pyridin-4-yl)phenyl)ethyl)-3-(trifluoromethyl)benzenesulfonamide | 1H | | 407.3 (method A) |

TABLE 1-continued

| Compound No | Structure | Intermediate | Reagent | MS (M + H)+ |
|---|---|---|---|---|
| 1BC | 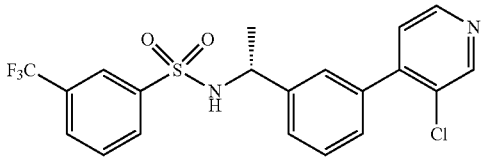<br>(R)-N-(1-(3-(3-chloropyridin-4-yl)phenyl)ethyl)-3-(trifluoromethyl)benzenesulfonamide | 1H | 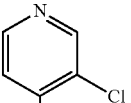 | 441.2/ 443.2 (method A) |
| 1BD | 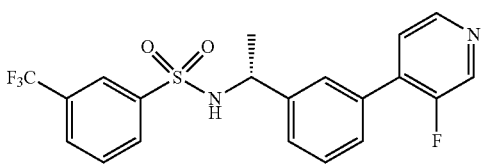 [SMILES: Cc1cnccc1-c1cccc([C@@H](C)NS(=O)(=O)c2cccc(C(F)(F)F)c2)c1]<br>(R)-N-(1-(3-(3-fluoropyridin-4-yl)phenyl)ethyl)-3-(trifluoromethyl)benzenesulfonamide | 1H | 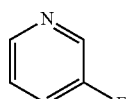 | 425.2 (method A) |
| 1BE | 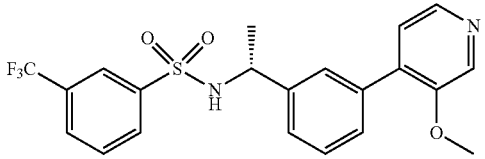<br>(R)-N-(1-(3-(3-methoxypyridin-4-yl)phenyl)ethyl)-3-(trifluoromethyl)benzenesulfonamide | 1H | 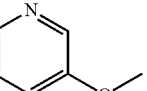 | 437.2 (method A) |
| 1BF | 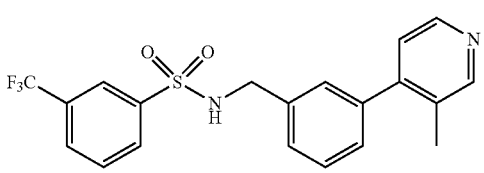<br>N-(3-(3-methylpyridin-4-yl)benzyl)-3-(trifluoromethyl)benzenesulfonamide | 1I | 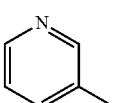 | 407.2 (method A) |
| 1BG | 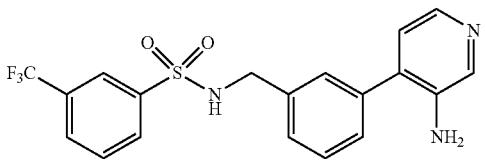<br>N-(3-(3-aminopyridin-4-yl)benzyl)-3-(trifluoromethyl)benzenesulfonamide | 1I | 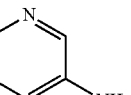 | (See NMR below) |
| 1BH | 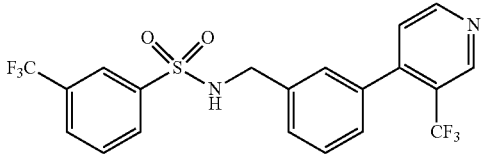<br>3-(trifluoromethyl)-N-(3-(3-(trifluoromethyl)pyridin-4-yl)benzyl)benzenesulfonamide | 1I | 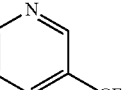 | 461.2 (method A) |

TABLE 1-continued

| Compound No | Structure | Intermediate | Reagent | MS (M + H)+ |
|---|---|---|---|---|
| 1BI | N-(3-(6-methylpyrimidin-4-yl)benzyl)-3-(trifluoromethyl)-benzenesulfonamide | 1I | 4-chloro-6-methylpyrimidine | 408.2 (method A) |
| 1BJ | 3-(trifluoromethyl)-N-(3-(6-(trifluoromethyl)pyrimidin-4-yl)benzyl)benzenesulfonamide | 1I | 4-chloro-6-(trifluoromethyl)pyrimidine | 462.2 (method A) |
| 1BK | N-(3-(pyrimidin-4-yl)benzyl)-3-(trifluoromethyl)benzene-sulfonamide | 1I | 4-chloropyrimidine | 394.2 (method A) |
| 1BL | N-(2-(3-(pyridazin-4-yl)phenyl)propan-2-yl)-2-(trifluoromethyl)benzene-sulfonamide | 1J | pyridazin-4-yl boronic acid pinacol ester | 422.4 (method A) |
| 1BM | N-(2-(3-(3-hydroxypyridin-4-yl)phenyl)propan-2-yl)-2-(trifluoromethyl)benzene-sulfonamide | 1J | Intermediate 5 | 437.3 (method A) |

TABLE 1-continued

| Compound No | Structure | Intermediate | Reagent | MS (M + H)+ |
|---|---|---|---|---|
| 1BN | N-(1-(3-(3-methoxypyridin-4-yl)phenyl)cyclopropyl-3-(trifluoromethyl)benzenesulfonamide | 1K | | 449.3 (method A) |
| 1BO | N-(2-(3-(3-methoxypyridin-4-yl)phenyl)propan-2-yl)-2-nitrobenzenesulfonamide | 1L | | 428.4 (method A) |
| 1BP | (S)-3-chloro-2-methyl-N-(1-(3-(pyridazin-4-yl)phenyl)ethyl)-benzenesulfonamide | 1O | | 388.4/ 390.4 (method A) |
| 1BQ | N-((3'-methoxy-[2,4'-bipyridin]-6-yl)methyl)-3-(trifluoromethyl)-benzenesulfonamide | 1V | | 424.4 (method A) |
| 1BR | N-((3'-methoxy-[4,4'-bipyridin]-2-yl)methyl)-3-(trifluoromethyl)-benzenesulfonamide | 1W | | 424.4 (method A) |
| 1BS | N-((3'-methoxy-[2,4'-bipyridin]-4-yl)methyl)-3-(trifluoromethyl)-benzenesulfonamide | 1X | | 424.4 (method A) |

TABLE 1-continued

| Compound No | Structure | Intermediate | Reagent | MS (M + H)+ |
|---|---|---|---|---|
| 1BT | 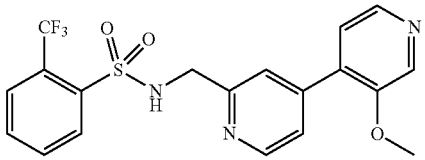 [SMILES: CCc1cnccc1-c1cccc([C@@H](C)NS(=O)(=O)c2ccccc2C(F)(F)F)c1]<br>N-((3'-methoxy-[4,4'-bipyridin]-2-yl)methyl)-3-(trifluoromethyl)-benzenesulfonamide | 1Y | 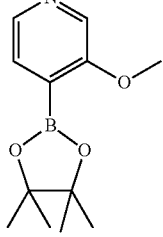 | 424.4 (method A) |
| 1BU | 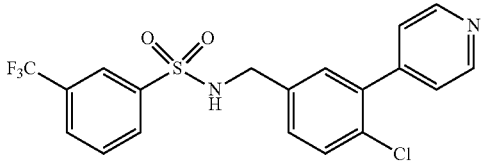<br>N-(4-chloro-3-(pyridin-4-yl)benzyl)-3-(trifluoromethyl)-benzenesulfonamide | 6 | 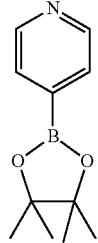 | 427.2/ 429.2 (method A) |
| 1BV | 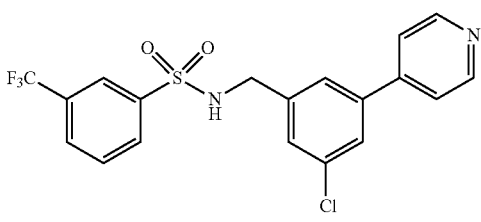<br>N-(3-chloro-5-(pyridin-4-yl)benzyl)-3-(trifluoromethyl)-benzenesulfonamide | 6B | 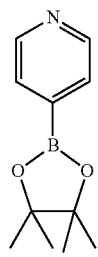 | 427.2/ 429.2 (method A) |
| 1BW | 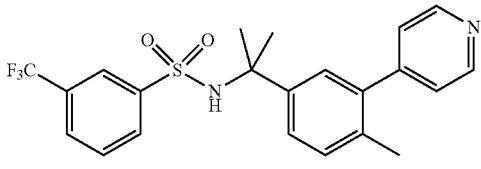<br>N-(2-(4-methyl-3-(pyridin-4-yl)phenyl)propan-2-yl)-3-(trifluoromethyl)benzene sulfonamide | 7 | 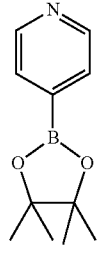 | 435.2 (method A) |
| 1BX | 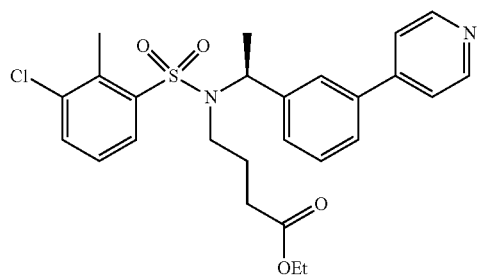<br>(S)-ethyl 4-(3-chloro-2-methyl-N-(1-(3-(pyridin-4-yl)phenyl)ethyl)-phenylsulfonamido)butanoate | 9A | 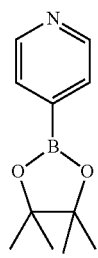 | 501.5/ 503.5 (method A) |

TABLE 1-continued

| Compound No | Structure | Intermediate | Reagent | MS (M + H)+ |
|---|---|---|---|---|
| 1BY | 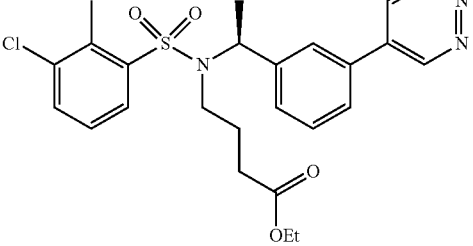<br>(S)-ethyl 4-(3-chloro-2-methyl-N-(1-(3-(pyridazin-4-yl)phenyl)-ethyl)phenylsulfonamido) butanoate | 9A | 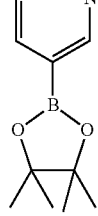 | 502.5/ 504.5 (method A) |
| 1BZ | 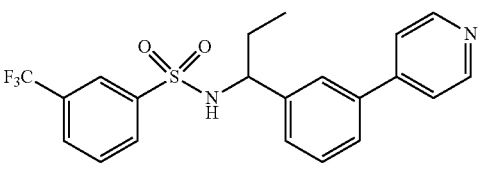 [SMILES: CCC(NS(=O)(=O)c1cccc(C(F)(F)F)c1)c1cccc(-c2ccncc2C)c1]<br>(+/−)N-(1-(3-(pyridin-4-yl)phenyl)propyl)-3-(trifluoromethyl)benzene-sulfonamide | 10 | 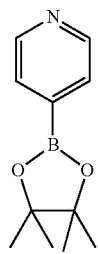 | 421.3 (method A) |
| 1CC | 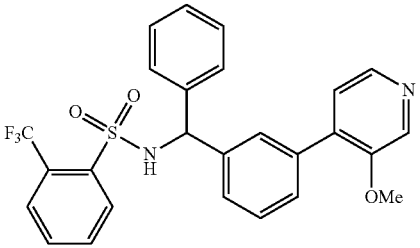<br>(+/−)N-((3-(3-methoxypyridin-4-yl)phenyl)(phenyl)methyl)-2-(trifluoromethyl)benzene-sulfonamide | 10B | 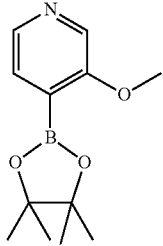 | 499.5 (method A) |
| 1CD | 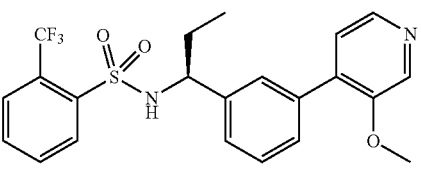<br>(S)-N-(1-(3-(3-methoxypyridin-4-yl)phenyl)propyl)-2-(trifluoromethyl)benzene Sulfonamido) | 11 | 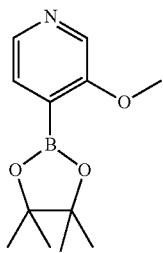 | 451.4 (method A) |
| 1CE | 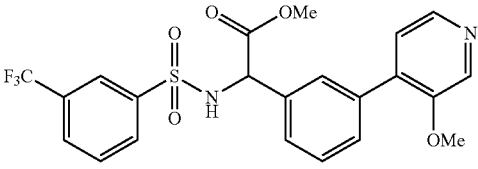<br>methyl 2-(3-(3-methoxypyridin-4-yl)phenyl)-2-(3-(trifluoromethyl)phenyl sulfonamido)acetate | 12 | 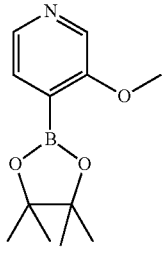 | 481.4 (method A) |

| Compound No | Structure | Intermediate | Reagent | MS (M + H)+ |
|---|---|---|---|---|
| 1CF | 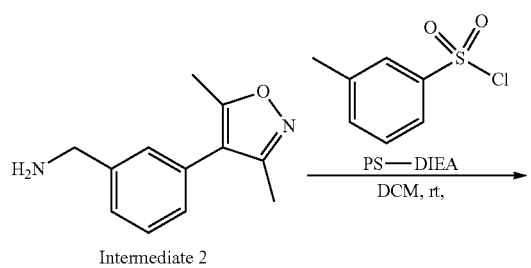<br>N-(3-(3-methoxypyridin-4-yl)phenethyl)-2-(trifluoromethyl)benzenesulfonamide | 1T | 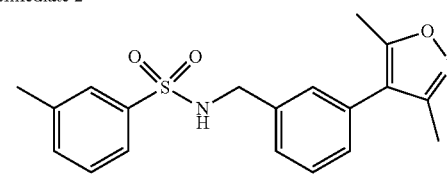 | 437.4 (method A) |

Compound 1BG

¹H NMR (CDCl₃) δ 8.09 (s, 1H), 8.07 (s, 1H), 8.04 (d, 1H), 7.95 (d, 1H), 7.79 (d, 1H), 7.62 (t, 1H), 7.38 (q, 1H), 7.33 (d, 1H), 7.26 (d, 2H), 6.88 (d, 1H), 6.23 (s, 1H), 4.27 (s, 2H), 3.76 (s, 2H).

Example 2

N-(3-(3,5-dimethylisoxazol-4-yl)benzyl)-3-methyl-benzenesulfonamide (Compound 2)

3-Methylbenzene-1-sulfonyl chloride (26 µL, 0.18 mmol) was added into a mixture of Intermediate 2 (30 mg, 0.15 mmol) and PS-DIEA (3.68 mmol/g, 0.19 g, 0.71 mmol) in DCM (2 mL). The reaction was stirred at room temperature overnight and PS-trisamine (3.95 mmol/g, 37 mg, 0.15 mmol) was added. The reaction was stirred at room temperature gently for 2 hours, filtered, and concentrated in vacuo. The residue was purified by MS-HPLC to afford the title compound (22 mg, 41%). LCMS (method A): m/z 357.3 (M+H)+. ¹H NMR (CDCl₃) δ 7.68 (s, 1H), 7.67 (d, 1H), 7.38~7.34 (m, 3H), 7.22 (d, 1H), 7.14 (d, 1H), 7.10 (s, 1H), 5.07 (t, 1H), 4.19 (d, 2H), 2.40 (s, 3H), 2.36 (s, 3H), 2.21 (s, 3H).

Following the method described above for Example 2 and substituting the appropriate intermediates and reagents, the following compounds were prepared as indicated in Table 2. For compounds 2AI-2BT, DIEA (0.10 mL) was used in place of PS-DIEA

TABLE 2

| Compound No | Structure | Intermediate | Reagent | MS (M + H)+ |
|---|---|---|---|---|
| 2AA | 3-chloro-N-(3-(3,5-dimethylisoxazol-4-yl)benzyl)benzenesulfonamide | 2 | | 377.2/ 379.2 (method A) |

TABLE 2-continued

| Compound No | Structure | Intermediate | Reagent | MS (M + H)+ |
|---|---|---|---|---|
| 2AB | N-(3-(3,5-dimethylisoxazol-4-yl)benzyl)-3-methoxybenzene-sulfonamide | 2 | | 373.3 (method A) |
| 2AC | N-(3-(3,5-dimethylisoxazol-4-yl)benzyl)-2-(trifluoromethyl)-benzenesulfonamide | 2 | | 411.3 (method A) |
| 2AD | 4-chloro-N-(3-(3,5-dimethylisoxazol-4-yl)benzyl)-3-(trifluoromethyl)benzene-sulfonamide | 2 | | 445.2/ 447.2 (method A) |
| 2AE | N-(3-(3,5-dimethylisoxazol-4-yl)benzyl)-4-fluoro-3-(trifluoromethyl)benzene-sulfonamide | 2 | | 429.3 (method A) |
| 2AF | N-(3-(3,5-dimethylisoxazol-4-yl)benzyl)-2-fluoro-5-(trifluoromethyl)benzene-sulfonamide | 2 | | 429.3 (method A) |

TABLE 2-continued

| Compound No | Structure | Intermediate | Reagent | MS (M + H)+ |
|---|---|---|---|---|
| 2AG | N-(3-(3,5-dimethylisoxazol-4-yl)benzyl)-3-fluoro-5-(trifluoromethyl)-benzenesulfonamide | 2 | 3-fluoro-5-(trifluoromethyl)benzenesulfonyl chloride | 429.3 (method A) |
| 2AH | N-(3-(3,5-dimethylisoxazol-4-yl)benzyl)-3,5-bis(trifluoromethyl)-benzenesulfonamide | 2 | 3,5-bis(trifluoromethyl)benzenesulfonyl chloride | 479.3 (method A) |
| 2AI | 3-methyl-N-(3-(pyridin-4-yl)benzyl)benzenesulfonamide | 3C | 3-methylbenzenesulfonyl chloride | 339.3 (method A) |
| 2AJ | 3-chloro-N-(3-(pyridin-4-yl)benzyl)benzenesulfonamide | 3C | 3-chlorobenzenesulfonyl chloride | 359.2/ 361.2 (method A) |
| 2AK | 3-fluoro-N-(3-(pyridin-4-yl)benzyl)benzenesulfonamide | 3C | 3-fluorobenzenesulfonyl chloride | 343.2 (method A) |

TABLE 2-continued

| Compound No | Structure | Intermediate | Reagent | MS (M + H)+ |
|---|---|---|---|---|
| 2AL | 3-methoxy-N-(3-(pyridin-4-yl)benzyl)benzenesulfonamide | 3C | | 355.3 (method A) |
| 2AM | N-(3-(pyridin-4-yl)benzyl)-2-(trifluoromethyl)benzene-sulfonamide | 3C | | 393.3 (method A) |
| 2AN | 3-nitro-N-3-(pyridin-4-yl)benzyl)benzenesulfonamide | 3C | | 370.3 (method A) |
| 2AO | 2-nitro-N-(3-(pyridin-4-yl)benzyl)benzenesulfonamide | 3C | | 370.3 (method A) |
| 2AP | 2-methyl-N-(3-(pyridin-4-yl)benzyl)benzenesulfonamide | 3C | | 339.3 (method A) |
| 2AQ | 3-bromo-N-3-(pyridin-4-yl)benzyl)benzenesulfonamide | 3C | | 403.2/ 405.2 (method A) |

TABLE 2-continued

| Compound No | Structure | Intermediate | Reagent | MS (M + H)+ |
|---|---|---|---|---|
| 2AR | 2-chloro-N-3-(pyridin-4-yl)benzyl)benzenesulfonamide | 3C | (2-chlorobenzenesulfonyl chloride) | 359.2/ 361.2 (method A) |
| 2AS | 2-fluoro-N-3-(pyridin-4-yl)benzyl)benzenesulfonamide | 3C | (2-fluorobenzenesulfonyl chloride) | 343.3 (method A) |
| 2AT | 3-bromo-N-(2-(3-(3-methoxypyridin-4-yl)-phenyl)propan-2-yl)-benzenesulfonamide | 3 | (3-bromobenzenesulfonyl chloride) | 461.2/ 463.2 (method A) |
| 2AU | N-(2-(3-(3-methoxypyridin-4-yl)phenyl)propan-2-yl)-2-nitrobenzenesulfonamide | 3 | (2-nitrobenzenesulfonyl chloride) | 428.3 (method A) |
| 2AV | N-(3-(pyridin-4-yl)benzyl)-2-(trifluoromethyl)benzene-sulfonamide | 3 | (2-(trifluoromethyl)benzenesulfonyl chloride) | 451.3 (method A) |
| 2AW | 2-methoxy-N-(2-(3-(3-methoxypyridin-4-yl)-phenyl)propan-2-yl)-5-(trifluoromethyl)benzene-sulfonamide | 3 | (2-methoxy-5-(trifluoromethyl)benzenesulfonyl chloride) | 481.2 (method A) |

TABLE 2-continued

| Compound No | Structure | Intermediate | Reagent | MS (M + H)+ |
|---|---|---|---|---|
| 2AX | 2-chloro-N-(2-(3-(3-methoxypyridin-4-yl)phenyl)propan-2-yl)benzenesulfonamide | 3 | | 417.3/ 419.3 (method A) |
| 2AY | 3-chloro-N-(2-(3-(3-methoxypyridin-4-yl)phenyl)propan-2-yl)benzenesulfonamide | 3 | | 417.4/ 419.3 (method A) |
| 2AZ | N-(2-(3-(3-methoxypyridin-4-yl)phenyl)propan-2-yl)-3-methylbenzenesulfonamide | 3 | | 397.3 (method A) |
| 2BB | 3-bromo-N-(2-(3-(3-methoxypyridin-4-yl)phenyl)propan-2-yl)-5-(trifluoromethyl)benzenesulfonamide | 3 | | 529.2/ 531.2 (method A) |
| 2BC | 2,3-dichloro-N-(2-(3-(3-methoxypyridin-4-yl)phenyl)propan-2-yl)benzenesulfonamide | 3 | | 451.4/ 453.4 (method A) |

TABLE 2-continued

| Compound No | Structure | Intermediate | Reagent | MS (M + H)+ |
|---|---|---|---|---|
| 2BD | 4-fluoro-N-(2-(3-(3-methoxypyridin-4-yl)-phenyl)propan-2-yl)-2-(trifluoromethyl)benzene-sulfonamide | 3 | | 469.5 (method A) |
| 2BE | 2,5-dichloro-N-(2-(3-(3-methoxypyridin-4-yl)phenyl)propan-2-yl)benzenesulfonamide | 3 | | 451.4/ 453.4 (method A) |
| 2BF | 4-chloro-N-(2-(3-(3-methoxypyridin-4-yl)phenyl)propan-2-yl)-2-(trifluoromethyl)benzene-sulfonamide | 3 | | 485.4/ 487.4 (method A) |
| 2BG | 2,4-dichloro-N-(2-(3-(3-methoxypyridin-4-yl)phenyl)propan-2-yl)benzenesulfonamide | 3 | | 451.4/ 453.4 (method A) |
| 2BH | 5-chloro-N-(2-(3-(3-methoxypyridin-4-yl)phenyl)propan-2-yl)-2-nitrobenzenesulfonamide | 3 | | 462.4/ 464.4 (method A) |

TABLE 2-continued

| Compound No | Structure | Intermediate | Reagent | MS (M + H)+ |
|---|---|---|---|---|
| 2BI | 2,4-dichloro-N-(2-(3-(3-methoxypyridin-4-yl)phenyl)propan-2-yl)benzenesulfonamide | 3 | | 462.4/ 464.4 (method A) |
| 2BJ | N-(2-(3-(3-methoxypyridin-4-yl)phenyl)propan-2-yl)-2-nitro-4-(trifluoromethyl)benzenesulfonamide | 3 | | 496.5 (method A) |
| 2BK | N-(2-(3-(3-methoxypyridin-4-yl)phenyl)propan-2-yl)-2,5-bis(trifluoromethyl)benzenesulfonamide | 3 | | 519.5 (method A) |
| 2BL | 3-chloro-N-(2-(3-(3-methoxypyridin-4-yl)phenyl)propan-2-yl)-2-methylbenzenesulfonamide | 3 | | 431.4/ 433.4 (method A) |
| 2BM | N-(2-(3-(3-methoxypyridin-4-yl)phenyl)propan-2-yl)-2-methyl-3-(trifluoromethyl)-benzenesulfonamide | 3 | | 465.5 (method A) |

TABLE 2-continued

| Compound No | Structure | Intermediate | Reagent | MS (M + H)⁺ |
|---|---|---|---|---|
| 2BN | 2-chloro-4-cyano-N-(2-(3-(3-methoxypyridin-4-yl)phenyl)propan-2-yl)benzenesulfonamide | 3 | (2-chloro-4-cyanobenzenesulfonyl chloride) | 442.4/ 444.4 (method A) |
| 2BO | (S)-3-bromo-N-(1-(3-(3-methoxypyridin-4-yl)-phenyl)ethyl)benzene-sulfonamide | 3D | (3-bromobenzenesulfonyl chloride) | 447.2/ 449.2 (method A) |
| 2BP | (S)-N-(1-(3-(3-methoxypyridin-4-yl)-phenyl)ethyl)-2-nitrobenzenesulfonamide | 3D | (2-nitrobenzenesulfonyl chloride) | 414.2 (method A) |
| 2BQ | (S)-N-(1-(3-(3-methoxypyridin-4-yl)phenyl)ethyl)-2-(trifluoromethyl)benzene-sulfonamide | 3D | (2-(trifluoromethyl)benzenesulfonyl chloride) | 437.3 (method A) |
| 2BR | (S)-3-bromo-N-(1-(3-(3-chloropyridin-4-yl)-phenyl)ethyl)benzene-sulfonamide | 3E | (3-bromobenzenesulfonyl chloride) | 451.1/ 453.1 (method A) |

TABLE 2-continued

| Compound No | Structure | Intermediate | Reagent | MS (M + H)+ |
|---|---|---|---|---|
| 2BS | (S)-N-(1-(3-(3-chloropyridin-4-yl)phenyl)ethyl)-2-nitrobenzenesulfonamide | 3E | | 418.2/ 420.2 (method A) |
| 2BT | (S)-N-(1-(3-(3-chloropyridin-4-yl)phenyl)ethyl)-2-(trifluoromethyl)benzene-sulfonamide | 3E | | 441.2/ 443.2 (method A) |
| 2BU | 3-chloro-2-methyl-N-(2-(3-(3-methylpyridin-4-yl)phenyl)-propan-2-yl)benzenesulfonamide | 4 | | 415.4/ 417.5 (method A) |
| 2BV | 2,3-dichloro-N-(2-(3-(3-methylpyridin-4-yl)phenyl)-propan-2-yl)benzenesulfonamide | 4 | | 435.4/ 437.4 (method A) |
| 2BW | 5-bromo-2-methyl-N-(2-(3-(3-methylpyridin-4-yl)phenyl)-propan-2-yl)benzenesulfonamide | 4 | | 459.4/ 461.4 (method A) |
| 2BX | 2-methyl-N-(2-(3-(3-methylpyridin-4-yl)phenyl)-propan-2-yl)benzenesulfonamide | 4 | | 381.3 (method A) |

TABLE 2-continued

| Compound No | Structure | Intermediate | Reagent | MS (M + H)+ |
|---|---|---|---|---|
| 2BY | 3-chloro-N-(2-(3-(3-ethylpyridin-4-yl)phenyl)propan-2-yl)-2-methylbenzenesulfonamide | 4C | (3-chloro-2-methylbenzenesulfonyl chloride) | 429.5/ 431.5 (method A) |
| 2BZ | (S)-3-chloro-N-(4-cyano-1-(3-(3-methylpyridin-4-yl)phenyl)butyl)-2-methylbenzenesulfonamide | 14 | (3-chloro-2-methylbenzenesulfonyl chloride) | 454.4 456.4 (method A) |
| 2CC | N-(2-(3-(benzyloxy)-5-(3-ethylpyridin-4-yl)phenyl)propan-2-yl)-2-(trifluoromethyl)benzenesulfonamide | 17 | (2-(trifluoromethyl)benzenesulfonyl chloride) | Used directly to make Compound 22 |
| 2CD | N-(2-(3-(3-ethylpyridin-4-yl)-5-methoxyphenyl)propan-2-yl)-2-(trifluoromethyl)benzenesulfonamide | 17E | (2-(trifluoromethyl)benzenesulfonyl chloride) | 479.1 (method C) |
| 2CE | 3-chloro-2-methyl-N-(3-(3-methylpyridin-4-yl)benzyl)benzenesulfonamide | 4D | (3-chloro-2-methylbenzenesulfonyl chloride) | 387.2/ 389.3 (method A) |

Example 3

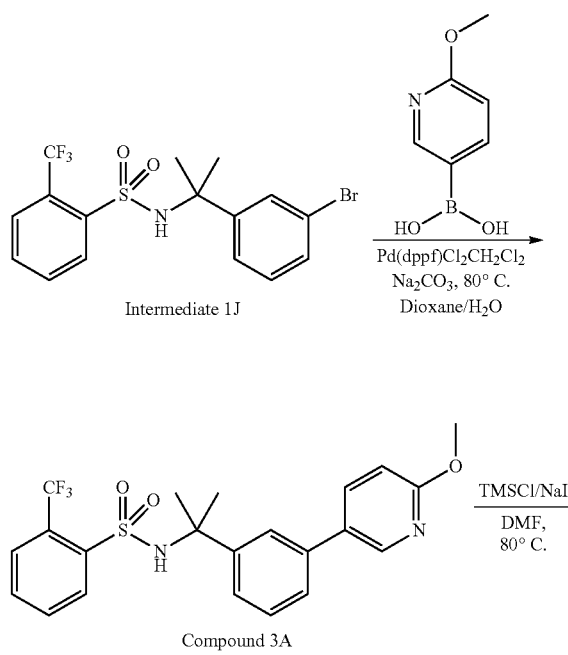

Compound 3A

N-(2-(3-(6-methoxypyridin-3-yl)phenyl)propan-2-yl)-2-(trifluoromethyl)benzenesulfonamide (Compound 3A)

Intermediate 1J (150 mg, 0.36 mmol) was converted to Compound 3A (140 mg, 89%) following the procedure as described in Example 1. LCMS (method A): m/z 451.4 (M+H)$^+$.

N-(2-(3-(6-oxo-1,6-dihydropyridin-3-yl)phenyl)propan-2-yl)-2-(trifluoromethyl)benzenesulfonamide (Compound 3)

TMSCl (42 µL, 0.33 mmol) was added into a mixture of Compound 3A (50 mg, 0.11 mmol) and NaI (50 mg, 0.33 mmol) in DMF (1 mL). The reaction was heated to 80° C. for approximately 1 hour and concentrated in vacuo to give a residue which was purified by MS-HPLC to afford the title compound (37 mg, 76%). LCMS (method A): m/z 437.4 (M+H)$^+$. $^1$H NMR (CDCl$_3$) δ 8.13 (s, 1H), 7.75 (d, 1H), 7.74 (d, 1H), 7.69 (dd, 1H), 7.54 (t, 1H), 7.51 (d, 1H), 7.41 (t, 1H), 7.33 (t, 1H), 7.30–7.18 (m, 3H), 6.75 (d, 1H), 5.44 (s, 1H), 1.71 (s, 6H).

Example 4

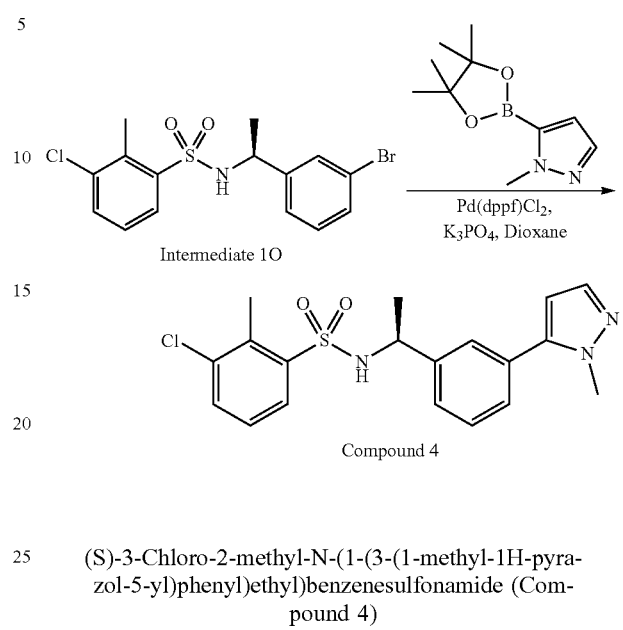

Compound 4

(S)-3-Chloro-2-methyl-N-(1-(3-(1-methyl-1H-pyrazol-5-yl)phenyl)ethyl)benzenesulfonamide (Compound 4)

In a microwave vial, Intermediate 1O (0.10 g, 0.26 mmol), 1-methyl-5-(4,4,5,5-tetramethyl-1,3,2-dioxaborolan-2-yl)-1H-pyrazole (49 mg, 0.23 mmol) and [1,1'Bis(diphenylphosphino) ferrocene]palladium(II) dichloride (19 mg, 0.02 mmol) were suspended in acetonitrile (2 mL), followed by addition of 1M tribasic potassium phosphate solution (1 mL). The mixture was heated in the microwave at 120° C. for 5 minutes. The acetonitrile was decanted and the residue was concentrated in vacuo to give a black oil. Purification by flash chromatography using EtOAc in hexanes as the eluent afforded Compound 4 (57 mg, 57%) as an off-white solid. LCMS (method A): m/z 390.4/392.4 (M+H)$^+$. $^1$H NMR (CD$_3$OD): δ 7.76 (dd, 1H), 7.48 (d, 1H), 7.43 (dd, 1H), 7.26 (t, 1H), 7.22 (dt, 1H), 7.17-7.10 (m, 3H), 6.28 (d, 1H), 4.46 (q, 1H), 3.79 (s, 3H), 2.50 (s, 3H), 1.46 (d, 3H).

Example 5

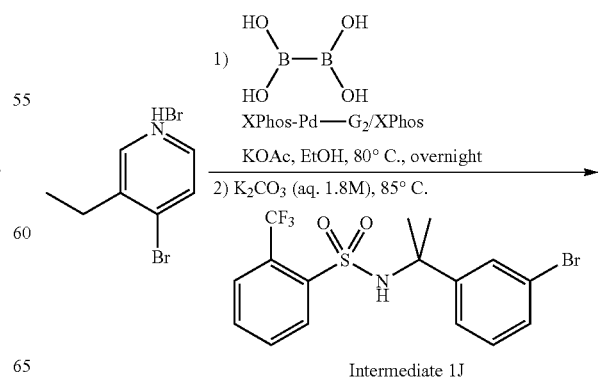

Intermediate 1J

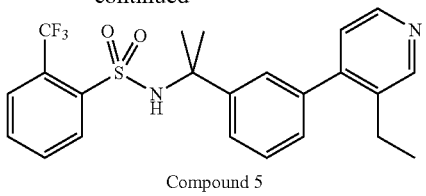

Compound 5

N-(2-(3-(3-ethylpyridin-4-yl)phenyl)propan-2-yl)-2-(trifluoromethyl)benzenesulfonamide (Compound 5)

EtOH (1.8 mL) was added into a mixture of 4-bromo-3-ethylpyridine hydrobromide (49 mg, 0.18 mmol), B₂(OH)₄ (49 mg, 0.55 mmol), XPhos-Pd-G₂ (14 mg, 0.018 mmol), XPhos (17 mg, 0.037 mmol), and KOAc (54 mg, 0.55 mmol). The reaction was degassed via N₂ and stirred at 80° C. overnight. After cooling to room temperature, solutions of N-(2-(3-bromophenyl)propan-2-yl)-2-(trifluoromethyl)benzenesulfonamide (Intermediate 1J) (100 mg, 0.24 mmol) in EtOH/THF (0.3 mL/0.3 mL) and K₂CO₃ (1.8 M, 0.31 mL, 0.55 mmol) were added respectively into the reaction. The mixture was degassed via N₂ again and stirred at 85° C. overnight. The reaction was cooled to room temperature, filtered through celite, washed with EtOAc (3X), and concentrated in vacuo to give a residue which was dissolved into EtOAc. This solution was washed with brine (1X), dried over sodium sulfate, filtered, and concentrated in vacuo. The residue was purified by MS-HPLC to afford the title compound (16 mg, 20%). LCMS (method A): m/z 449.3 (M+H)⁺. ¹H NMR (CDCl₃) δ 8.54 (s, 1H), 8.46 (d, 1H), 7.83 (d, 1H), 7.79 (d, 1H), 7.59 (t, 1H), 7.47 (t, 1H), 7.31 (m, 2H), 7.21 (t, 1H), 7.11 (dt, 1H), 7.03 (d, 1H), 5.28 (s, 1H), 2.63 (q, 2H), 1.69 (s, 6H), 1.13 (t, 3H).

Following the method described above for Example 5 and substituting the appropriate intermediates and reagents, the following compounds were prepared as indicated in Table 3.

TABLE 3

| Compound No | Structure | Intermediate | Reagent | MS (M+H)⁺ |
|---|---|---|---|---|
| 5AA | N-(2-(3-(3-methylpyridin-4-yl)phenyl)propan-2-yl)-3-(trifluoromethyl)benzenesulfonamide | 1D | | 435.3 (method A) |
| 5AB | N-(2-(3-(3-ethylpyridin-4-yl)phenyl)propan-2-yl)-3-(trifluoromethyl)benzenesulfonamide | 1D | | 449.4 (method A) |
| 5AC | N-(2-(3-(2,3-dimethylpyridin-4-yl)phenyl)propan-2-yl)-3-(trifluoromethyl)-benzenesulfonamide | 1D | | 449.4 (method A) |
| 5AD | N-(2-(3-(3,5-dimethylpyridin-4-yl)phenyl)propan-2-yl)-3-(trifluoromethyl)benzenesulfonamide | 1D | | 449.3 (method A) |

TABLE 3-continued

| Compound No | Structure | Intermediate | Reagent | MS (M +H)+ |
|---|---|---|---|---|
| 5AE | N-(2-(3-(3-(hydroxymethyl)-pyridin-4-yl)phenyl)propan-2-yl)-3-(trifluoromethyl)benzenesulfonamide | 1D | 4-bromo-3-(hydroxymethyl)pyridine | 451.4 (method A) |
| 5AF | N-(2-(3-(imidazo[1,2-a]pyridin-6-yl)phenyl)propan-2-yl)-3-(trifluoromethyl)benzenesulfonamide | 1D | 6-chloroimidazo[1,2-a]pyridine HCl | 460.4 (method A) |
| 5AG | (S)-N-(1-(3-(3-methylpyridin-4-yl)phenyl)ethyl)-3-(trifluoromethyl)benzenesulfonamide | 1G | 4-bromo-3-methylpyridine | 421.3 (method A) |
| 5AH | (R)-N-(1-(3-(3-methylpyridin-4-yl)phenyl)ethyl)-3-(trifluoromethyl)benzenesulfonamide | 1H | 4-bromo-3-methylpyridine | 421.3 (method A) |
| 5AI | N-(2-(3-(3-methylpyridin-4-yl)phenyl)propan-2-yl)-2-(trifluoromethyl)benzenesulfonamide | 1J | 4-bromo-3-methylpyridine | 435.4 (method A) |
| 5AJ | N-(2-(3-(imidazo[1,2-a]pyridin-6-yl)phenyl)propan-2-yl)-2-(trifluoromethyl)benzenesulfonamide | 1J | 6-bromoimidazo[1,2-a]pyridine | 460.5 (method A) |

TABLE 3-continued

| Compound No | Structure | Intermediate | Reagent | MS (M +H)+ |
|---|---|---|---|---|
| 5AK | N-(2-(3-(7-methylimidazo[1,2-a]pyridin-6-yl)phenyl)propan-2-yl)-2-(trifluoromethyl)benzenesulfonamide | 1J | (6-bromo-7-methylimidazo[1,2-a]pyridine) | 474.5 (method A) |
| 5AL | N-(2-(3-(1H-benzo[d]imidazol-5-yl)phenyl)propan-2-yl)-2-(trifluoromethyl)benzenesulfonamide | 1J | (5-chloro-1H-benzimidazole) | 460.5 (method A) |
| 5AM | N-(2-(3-(imidazo[1,2-a]pyrimidin-6-yl)phenyl)propan-2-yl)-2-(trifluoromethyl)benzenesulfonamide | 1J | (6-bromoimidazo[1,2-a]pyrimidine) | 461.5 (method A) |
| 5AN | N-(2-(3-(3-(hydroxymethyl)pyridin-4-yl)phenyl)propan-2-yl)-2-(trifluoromethyl)benzenesulfonamide | 1J | (4-bromo-3-(hydroxymethyl)pyridine) | 451.4 (method A) |
| 5AO | N-(2-(3-(3-ethylpyridin-4-yl)phenyl)propan-2-yl)-2-nitrobenzenesulfonamide | 1L | (4-bromo-3-ethylpyridine) | 426.5 (method A) |
| 5AP | N-(2-(3-(3-methylpyridin-4-yl)phenyl)propan-2-yl)-2-nitrobenzenesulfonamide | 1L | (4-bromo-3-methylpyridine) | 412.4 (method A) |

TABLE 3-continued

| Compound No | Structure | Intermediate | Reagent | MS (M +H)+ |
|---|---|---|---|---|
| 5AQ | (S)-N-(1-(3-(3-ethylpyridin-4-yl)phenyl)ethyl)-2-(trifluoromethyl)benzenesulfonamide | 1M | 4-bromo-3-ethylpyridine | 435.5 (method A) |
| 5AR | (S)-N-(1-(3-(3-methylpyridin-4-yl)phenyl)ethyl)-2-(trifluoromethyl)benzenesulfonamide | 1M | 4-bromo-3-methylpyridine | 421.4 (method A) |
| 5AS | (R)-N-(1-(3-(3-ethylpyridin-4-yl)phenyl)ethyl)-2-(trifluoromethyl)benzenesulfonamide | 1N | 4-bromo-3-ethylpyridine | 435.4 (method A) |
| 5AT | (R)-N-(1-(3-(3-methylpyridin-4-yl)phenyl)ethyl)-2-(trifluoromethyl)benzenesulfonamide | 1N | 4-bromo-3-methylpyridine | 421.4 (method A) |
| 5AU | (+/−)N-(1-(3-(3-methylpyridin-4-yl)phenyl)propyl)-3-(trifluoromethyl)benzenesulfonamide | 1O | 4-bromo-3-methylpyridine | 435.3 (method A) |
| 5AV | (+/−)N-(cyclopropyl(3-(3-methylpyridin-4-yl)phenyl)methyl)-2-(trifluoromethyl)benzenesulfonamide | 10C | 4-chloro-3-methylpyridine | 447.5 (method A) |

TABLE 3-continued

| Compound No | Structure | Intermediate | Reagent | MS (M +H)+ |
|---|---|---|---|---|
| 5AW | (S)-N-(1-(3-(3-methylpyridin-4-yl)phenyl)propyl)-2-(trifluoromethyl)benzenesulfonamide | 11 | 4-bromo-3-methylpyridine | 435.4 (method A) |
| 5AX | (S)-N-(1-(3-(imidazo[1,2-a]pyridin-6-yl)phenyl)propyl)-2-(trifluoromethyl)benzenesulfonamide | 11 | 6-bromoimidazo[1,2-a]pyridine | 460.5 (method A) |
| 5AY | (S)-N-(1-(3-(3-methylpyridin-4-yl)phenyl)propyl)-3-(trifluoromethyl)benzenesulfonamide | 11C | 4-bromo-3-methylpyridine | 435.4 (method A) |
| 5AZ | (S)-N-methyl-3-(3-(3-methylpyridin-4-yl)phenyl)-3-(2-(trifluoromethyl)phenylsulfonamido)propanamide | 13 | 4-chloro-3-methylpyridine | 478.4 (method A) |
| 5BB | (S)-N,N-dimethyl-3-(3-(3-methylpyridin-4-yl)phenyl)-3-(2-(trifluoromethyl)phenylsulfonamido)propanamide | 13B | 4-chloro-3-methylpyridine | 492.5 (method A) |

TABLE 3-continued

| Compound No | Structure | Intermediate | Reagent | MS (M+H)+ |
|---|---|---|---|---|
| 5BC | (S)-N-(4-cyano-1-(3-(3-methylpyridin-4-yl)phenyl)-butyl)-2-(trifluoromethyl)benzenesulfonamide | 11E | 4-chloro-3-methylpyridine | 474.5 (method A) |
| 5BD | N-(3-(3-methylpyridin-4-yl)phenethyl)-2-(trifluoromethyl)benzenesulfonamide | 1T | 4-chloro-3-methylpyridine | 421.4 (method A) |
| 5BE | 3-chloro-2-methyl-N-(3-(3-methylpyridin-4-yl)phenethyl)benzenesulfonamide | 1U | 4-chloro-3-methylpyridine | 401.9/ 403.9 (method A) |

Example 6

Methyl 4-(3-(2-(2-(trifluoromethyl)phenylsulfonamido)propan-2-yl)phenyl)nicotinate (Compound 6)

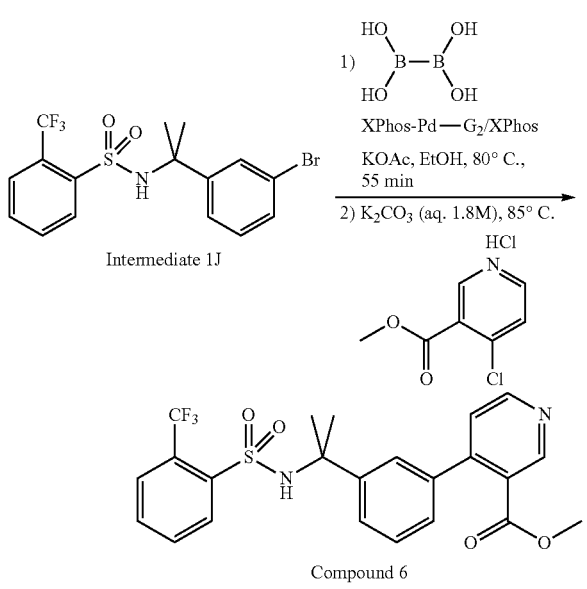

EtOH (1.9 mL) was added into a mixture of Intermediate 1J (100 mg, 0.24 mmol), B₂(OH)₄ (64 mg, 0.71 mmol), XPhos-Pd-G₂ (19 mg, 0.024 mmol), XPhos (23 mg, 0.048 mmol), and KOAc (70 mg, 0.71 mmol). The reaction was degassed with N₂ and stirred at 80° C. for approximately 55 minutes. After cooling to room temperature, methyl 4-chloronicotinate hydrochloride (64 mg, 0.31 mmol) and K₂CO₃ (1.8 M, 400 μL, 0.71 mmol) were added respectively. The reaction was degassed with N₂ again, stirred at 85° C. for approximately 3 hours, and cooled to room temperature. The reaction was filtered through celite and washed with EtOAc (3X). The combined organic layers were washed with brine (1X), dried over sodium sulfate, filtered, and concentrated in vacuo. The residue was purified by silica gel chromatography (0-100% EtOAc/Hexanes) to afford the title compound (70 mg, 61%). LCMS (method A): m/z 479.5 (M+H)⁺. ¹H NMR (CDCl₃) δ 9.00 (s, 1H), 8.72 (d, 1H), 7.82 (d, 1H), 7.77 (d, 1H), 7.55 (t, 1H), 7.47 (t, 1H), 7.29 (m, 2H), 7.21~7.14 (m, 3H), 5.18 (s, 1H), 3.77 (s, 3H), 1.68 (s, 6H).

Following the method described above for Example 6 and substituting the appropriate intermediates and reagents, the following compounds were prepared as indicated in Table 4.

TABLE 4

| Compound No | Structure | Intermediate | Reagent | MS (M + H)+ |
|---|---|---|---|---|
| 6AA | N-(2-(3-(5-methylpyrimidin-4-yl)phenyl)propan-2-yl)-2-(trifluoromethyl)benzenesulfonamide | 1J | 4-chloro-5-methylpyrimidine | 436.4 (method A) |
| 6AB | N-(2-(3-(2-(dimethylamino)-pyridin-4-yl)phenyl)propan-2-yl)-2-(trifluoromethyl)benzenesulfonamide | 1J | 4-bromo-N,N-dimethylpyridin-2-amine | 464.5 (method A) |
| 6AC | (S)-N-(4-cyano-1-(3-(3-ethylpyridin-4-yl)phenyl)butyl)-2-(trifluoromethyl)benzenesulfonamide | 11E | 4-bromo-3-ethylpyridine | 488.4 (method A) |
| 6AD | N-(3-cyano-1-(3-(3-methylpyridin-4-yl)phenyl)-propyl)-2-(trifluoromethyl)benzenesulfonamide | 11F | 4-chloro-3-methylpyridine | 460.4 (method A) |
| 6AE | N-(5-(1,3-dioxoisoindolin-2-yl)-1-(3-(3-methylpyridin-4-yl)phenyl)pentyl)-2-(trifluoromethyl)benzenesulfonamide | 20 | 4-chloro-3-methylpyridine | 608.5 (method A) |

Example 7

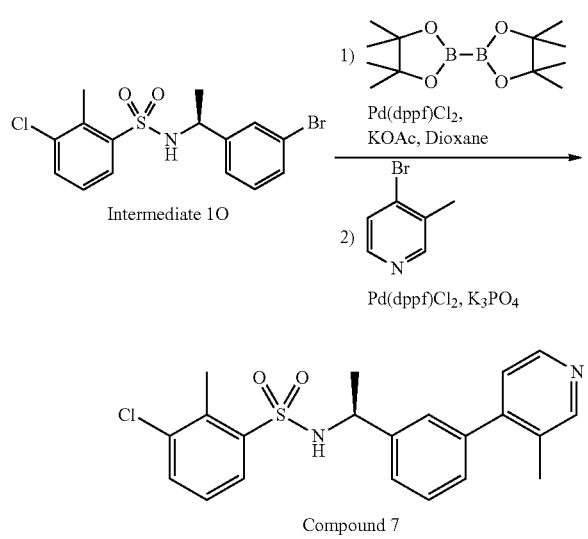

(S)-3-Chloro-2-methyl-N-(1-(3-(3-methylpyridin-4-yl)phenyl)ethyl)benzenesulfonamide (Compound 7)

Intermediate 1O (0.1 g, 0.26 mmol), bispinacolatodiboron (0.13 g, 0.52 mmol), [1,1'Bis(diphenylphosphino) ferrocene]palladium(II) dichloride (0.042 g, 0.052 mmol), and potassium acetate (0.076 g, 0.77 mmol) were mixed in dioxane (2 mL) in a pressure vessel and heated to 80° C. for 18 hours. The reaction was cooled to room temperature and 4-bromo-2-methylpyridine hydrochloride (0.081 g, 0.39 mol) and [1,1'-Bis(diphenylphosphino)ferrocene]-palladium (II) dichloride (0.042 g, 0.052 mmol) were added, followed by addition of 1M tribasic potassium phosphate solution (1 mL). The reaction was heated to 80° C. overnight. The resultant mixture was filtered over celite and diluted with DCM, and washed with $H_2O$ (1x) and brine (1x). The organic layer was dried over magnesium sulfate, filtered and concentrated in vacuo. The residue was purified by flash chromatography (10-70% EtOAc/hexanes) to afford Compound 7 (0.65 g, 65%). LCMS (method A): m/z 401.4/403.4 (M+H)$^+$. $^1$H NMR (CD$_3$OD): δ 8.42 (s, 1H), 8.38 (d, 1H), 7.75 (dd, 1H), 7.45 (dd, 1H), 7.26 (t, 1H), 7.18-7.10 (m, 4H), 7.02 (t, 1H), 4.48 (q, 1H), 2.51 (s, 3H), 2.21 (s, 3H), 1.46 (d, 3H)

Following the method described above for Example 7 and substituting the appropriate intermediates and reagents, the following compounds were prepared as indicated in Table 5.

TABLE 5

| Compound No | Structure | Intermediate | Reagent | MS (M + H)$^+$ |
|---|---|---|---|---|
| 7AA | (S)-3-chloro-2-methyl-N-(1-(3-(4-methylisothiazol-5-yl)-phenyl)ethyl)benzenesulfonamide | 1O | | 407.3/ 409.3 (method A) |
| 7AB | (S)-3-chloro-N-(1-(3-(2,3-dimethylpyridin-4-yl)phenyl)ethyl)-2-methylbenzenesulfonamide | 1O | | 415.3/ 417.3 (method A) |
| 7AC | 3-chloro-2-methyl-N-(3-(3-(3-methylpyridin-4-yl)phenyl)oxetan-3-yl)benzenesulfonamide | 8 | | 429.3/ 431.3 (method A) |

TABLE 5-continued

| Compound No | Structure | Intermediate | Reagent | MS (M + H)+ |
|---|---|---|---|---|
| 7AD | (S)-N-(1-(3-(3-methylpyridin-4-yl)phenyl)ethyl)-2-nitrobenzenesulfonamide | 1S | | 398.4 (method A) |
| 7AE | (S)-3-chloro-N-(4-(1,3-dioxoisoindolin-2-yl)butyl)-N-(1-(3-(3-ethylpyridin-4-yl)phenyl)ethyl)-2-methylbenzenesulfonamide | 9H | | 616.4/ 618.4 (method A) |

Example 8

N-(2-(3-(3-(2-methoxyethoxy)pyridin-4-yl)phenyl)propan-2-yl)-3-(trifluoromethyl)benzenesulfonamide (Compound 8)

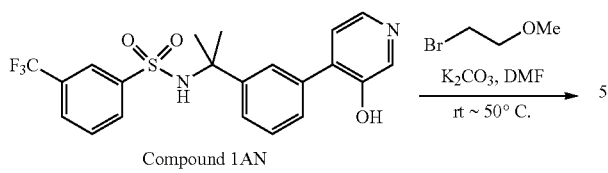

Compound 1AN

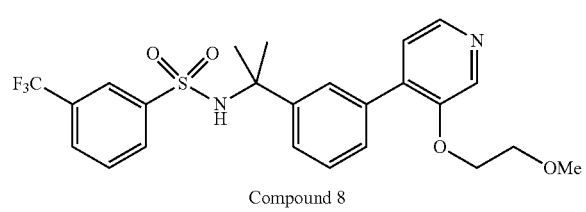

Compound 8

1-bromo-2-methoxyethane (4.0 μL, 0.044 mmol) was added into a mixture of Compound IAN (17 mg, 0.04 mmol) and K$_2$CO$_3$ (17 mg, 0.12 mmol) in DMF (1 mL). The reaction was stirred at room temperature for approximately 1 hour and heated to 50° C. for approximately 5 hours. The reaction was cooled to room temperature and filtered to give a solution which was purified directly by MS-HPLC to afford the title compound (6 mg, 30%). LCMS (method A): m/z 495.3 (M+H)+. $^1$H NMR (CDCl$_3$) δ 8.41 (s, 1H), 8.33 (s, 1H), 7.81 (s, 2H), 7.74 (d, 1H), 7.57 (d, 1H), 7.34 (m, 2H), 7.22 (s, 1H), 7.12 (d, 2H), 5.66 (s, 1H), 4.28 (t, 2H), 3.82 (t, 2H), 3.43 (s, 3H), 1.73 (s, 6H).

Following the method described above for Example 8 and substituting the appropriate starting materials and reagents, the following compounds were prepared as indicated in Table 6.

TABLE 6

| Compound No | Structure | Starting material | Reagent | MS (M + H)+ |
|---|---|---|---|---|
| 8AA | ![structure] N-(2-(3-(3-isopropoxypyridin-4-yl)phenyl)propan-2-yl)-3-(trifluoromethyl)benzenesulfonamide | 1AN | Br–iPr | 479.3 (method A) |
| 8AB | ![structure] N-(2-(3-(3-ethoxypyridin-4-yl)phenyl)propan-2-yl)-3-(trifluoromethyl)benzenesulfonamide | 1AN | Br–Et | 465.3 (method A) |
| 8AC | ![structure] N-(2-(3-(3-ethoxypyridin-4-yl)phenyl)propan-2-yl)-2-(trifluoromethyl)benzenesulfonamide | 1BM | Br–Et | 465.4 (method A) |

Example 9

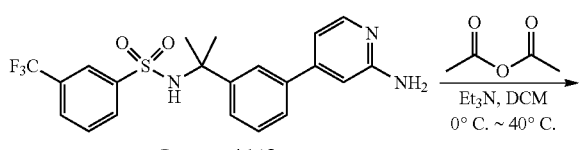

Compound 1AL

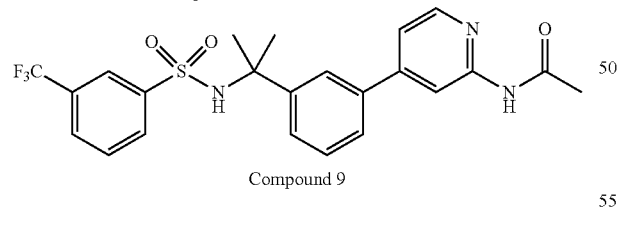

Compound 9

N-(4-(3-(2-(3-(trifluoromethyl)phenylsulfonamido)propan-2-yl)phenyl)pyridin-2-yl)acetamide (Compound 9)

Ac$_2$O (5.0 µL, 0.051 mmol) was added into a mixture of Compound 1AL (20 mg, 0.046 mmol) and Et$_3$N (7.0 µL, 0.051 mmol) in DCM (1 mL) under 0° C. The reaction was heated at 40° C. for 3 days, diluted with DCM, and washed with 1N HCl (1X) and brine (2X). The organic layer was dried over sodium sulfate, filtered, and concentrated in vacuo. The residue was purified by silica gel chromatography (0-90% EtOAc/Hexanes) to afford the title compound (9 mg, 41%). LCMS (method A): m/z 478.5 (M+H)+. $^1$H NMR (CDCl$_3$) δ 8.28 (s, 1H), 8.23 (d, 1H), 8.16 (s, 1H), 7.75 (s, 1H), 7.71 (d, 1H), 7.55 (d, 1H), 7.41 (t, 2H), 7.35 (m, 2H), 7.27 (t, 1H), 7.05 (dd, 1H), 5.44 (s, 1H), 2.26 (s, 3H), 1.76 (s, 6H).

Example 10

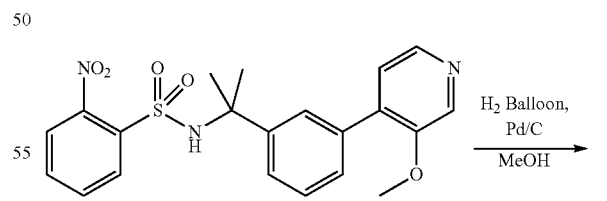

Compound 1BO

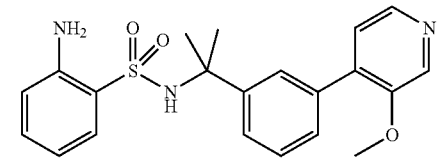

Compound 10

2-amino-N-(2-(3-(3-methoxypyridin-4-yl)phenyl)propan-2-yl)benzenesulfonamide (Compound 10)

Pd/C (10%) (45 mg, 0.043 mmol) was added into a mixture of Compound 1BO (0.18 g, 0.43 mmol) in MeOH (10 mL). The reaction was degassed with $H_2$, and stirred under $H_2$ at room temperature for approximately 6 hours. The resultant mixture was filtered through celite and concentrated in vacuo. The residue was purified by silica gel chromatography (0-100% EtOAc/Hexanes) to afford the title compound (0.17 g, 100%). LCMS (method A): m/z 398.5 (M+H)$^+$. $^1$H NMR (CDCl$_3$) δ 8.34 (s, 1H), 8.29 (d, 1H), 7.58 (t, 1H), 7.45 (dd, 1H), 7.40~7.34 (m, 2H), 7.24 (q, 1H), 7.18 (d, 1H), 7.17 (t, 1H), 6.63~6.59 (m, 2H), 5.51 (s, 1H), 4.77 (s, 2H), 3.90 (s, 3H), 1.64 (s, 6H).

Following the method described above for Example 10 and substituting the appropriate starting material, the following compound was prepared as indicated in Table 7.

TABLE 7

| Compound No | Structure | Starting material | MS (M + H)$^+$ |
|---|---|---|---|
| 10AA | 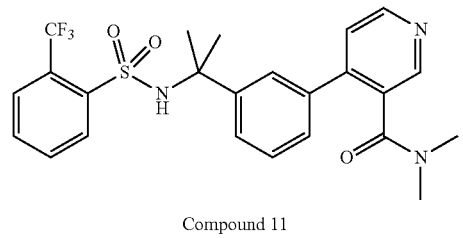<br>(S)-2-amino-N-(1-(3-(3-methylpyridin-4-yl)phenyl)ethyl)benzenesulfonamide | 7AD | 368.4 (method A) |

4-(3-(2-(2-(trifluoromethyl)phenylsulfonamido)propan-2-yl)phenyl)nicotinic acid (Compound 11A)

LiOH.H$_2$O (15 mg, 0.35 mmol) was added into a mixture of Compound 6 (54 mg, 0.11 mmol) in THF/H$_2$O (1.0 mL/0.5 mL) and the reaction was stirred at room temperature overnight. THF was removed under reduced pressure and the pH of remaining aqueous solution was adjusted to about 3~4 by adding HCl (1N) dropwise. EtOAc was added to extract the desired product. The resultant organic layer was washed with brine (1X), dried over sodium sulfate, filtered, and concentrated in vacuo. The residue was purified by MS-HPLC to afford the title compound (18 mg, 34%). LCMS (method A): m/z 465.5 (M+H)$^+$. $^1$H NMR (DMSO) δ 13.28 (br s, 1H), 8.85 (s, 1H), 8.73 (d, 1H), 7.40 (s, 1H), 7.89 (m, 1H), 7.82 (m, 1H), 7.68 (m, 2H), 7.40 (d, 2H), 7.33 (d, 1H), 7.26 (t, 1H), 7.22 (t, 1H), 1.56 (s, 6H).

Example 11

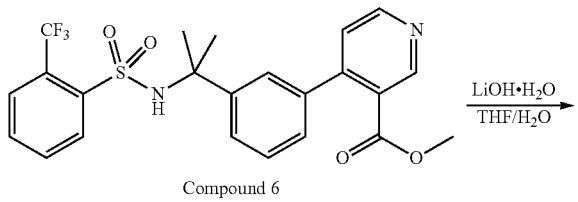

Compound 6

LiOH·H$_2$O / THF/H$_2$O

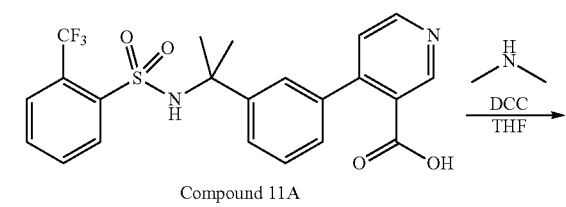

Compound 11A

DCC / THF

N,N-dimethyl-4-(3-(2-(2-(trifluoromethyl)phenylsulfonamido)propan-2-yl)phenyl)nicotinamide (Compound 11)

Dimethylamine (2 M in THF, 20 μL, 0.04 mmol) was added into a mixture of Compound 11A (16 mg, 0.03 mmol) and DCC (8.0 mg, 0.04 mmol) in THF (1 mL). The reaction was stirred at room temperature for 4 days and concentrated in vacuo. The residue was purified by silica gel chromatography (0-100% EtOAc/Hexanes), and purified again by MS-HPLC to afford the title compound (5.0 mg, 31%). LCMS (method A): m/z 492.5 (M+H)$^+$. $^1$H NMR (CDCl$_3$) δ 8.69 (d, 1H), 8.64 (s, 1H), 7.83 (d, 1H), 7.81 (d, 1H), 7.60 (t, 1H), 7.51 (t, 1H), 7.48 (t, 1H), 7.40 (dt, 1H), 7.32 (s, 1H), 7.31 (s, 1H), 7.26 (m, 1H), 5.28 (s, 1H), 2.97 (s, 3H), 2.56 (s, 3H), 1.64 (s, 6H).

Example 12

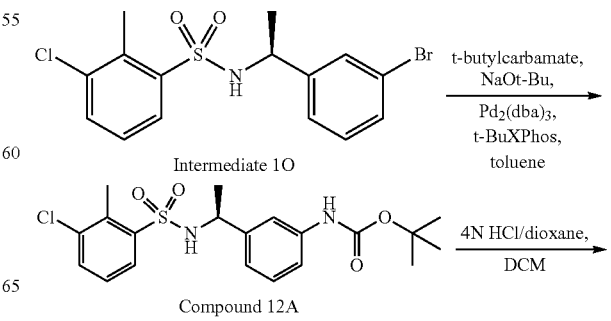

Intermediate 1O t-butylcarbamate, NaOt-Bu, Pd$_2$(dba)$_3$, t-BuXPhos, toluene

Compound 12A

4N HCl/dioxane, DCM

Compound 11

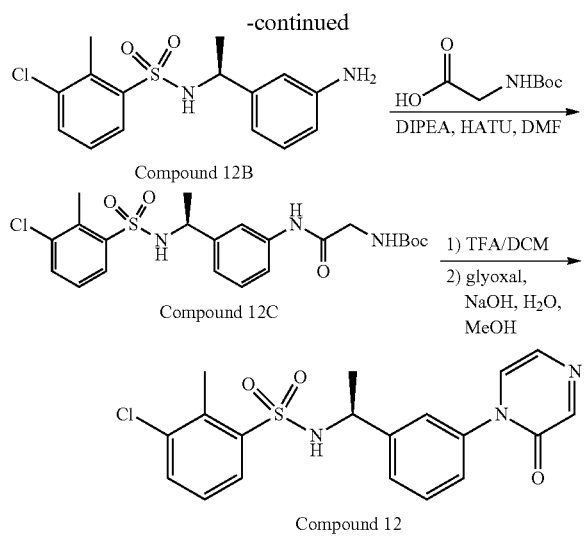

Compound 12B

Compound 12C

Compound 12

(S)-tert-butyl (3-(1-(3-chloro-2-methylphenylsulfonamido)ethyl)phenyl)carbamate (Compound 12A)

To a solution of Intermediate 1O (210 mg, 0.54 mmol) in toluene (5 mL) were added t-butylcarbamate (89 mg, 0.76 mmol) and NaOt-Bu (78 mg, 0.82 mmol). The resultant mixture was degassed by nitrogen and then $Pd_2(dba)_3$ (75 mg, 0.082 mmol) was added followed by t-BuXPhos (0.10 g, 0.24 mmol). Nitrogen gas was then bubbled through the reaction mixture for an additional 5 min and then the reaction vessel was tightly sealed and stirred under nitrogen atmosphere for 16 hours at room temperature. The mixture was diluted with EtOAc (10 mL) and 0.5 N HCl (aq) (10 mL) was added. The layers were partitioned and the aqueous phase was extracted with EtOAc (2×10 mL). The combined organic layers were washed with brine (1×15 mL), dried ($Na_2SO_4$), filtered and concentrated in vacuo. The residue was purified by silica gel chromatography (12 g, 0-20% EtOAc/hexanes) to give 0.23 g (100%) of Compound 12A. LCMS (Method A): m/z 447.3/449.3 (M+Na)$^+$. $^1$H NMR (CDCl$_3$) δ 7.76 (d, 1H), 7.44 (d, 1H), 7.16 (s, 1H), 7.11-7.04 (m, 2H), 6.99 (m, 1H), 6.67 (d, 1H), 6.35 (s, 1H), 4.79 (d, 1H), 4.42 (m, 1H), 2.56 (s, 3H), 1.53 (s, 9H), 1.46 (d, 3H).

Step 2: (S)—N-(1-(3-aminophenyl)ethyl)-3-chloro-2-methylbenzenesulfonamide (Compound 12B)

To a solution of Compound 12A (230 mg, 0.54 mmol) in DCM (3 mL) was added 4 N HCl/dioxane (1.5 mL) and the reaction mixture was stirred at room temperature for 2 hours. More 4 N HCl/dioxane (1.5 mL) was added and the mixture was stirred at room temperature for an additional 2 hours. The mixture was concentrated in vacuo and crude Compound 12B was used in the next step without further purification.

Step 3: (S)-tert-butyl (2-((3-(1-(3-chloro-2-methylphenylsulfonamido)ethyl)phenyl)amino)-2-oxoethyl)carbamate (Compound 12C)

To a mixture of crude Compound 12B and Boc-glycine (101 mg, 0.54 mmol) in DMF (5 mL) were added DIEA (0.21 mL, 1.2 mmol) and HATU (0.23 g, 0.60 mmol). The reaction mixture was stirred at room temperature for 2 hours. The reaction was diluted with EtOAc (20 mL) and washed with 1 N HCl (aq) (1×20 mL), saturated NaHCO$_3$ (aq) (1×20 mL) and brine (1×20 mL). The organic layer was dried (Na$_2$SO$_4$), filtered and concentrated in vacuo. The crude residue was purified by silica gel chromatography (12 g, 0-70% EtOAc/hexanes) to provide 0.24 g (92% for 2 steps) of Compound 12C. LCMS (Method A): m/z 482.4/484.4 (M+H)$^+$.

Steps 4 and 5: (S)-3-chloro-2-methyl-N-(1-(3-(2-oxopyrazin-1(2H)-yl)phenyl)ethyl)benzenesulfonamide (Compound 12)

Compound 12C (0.24 g, 0.51 mmol) was treated with 50% TFA/DCM (6 mL) and allowed to stand at room temperature for 1 h. After concentrating in vacuo, the crude residue was dissolved in MeOH (2 mL) and the resultant solution cooled to –40° C. To this mixture was added glyoxal (40 wt. % in H$_2$O, 0.29 mL, 2.5 mmol) followed by 3 N NaOH (aq) (0.25 mL, 0.75 mmol). The reaction mixture was stirred at –40° C. for 30 min and additional MeOH (1 mL) and 3 N NaOH (aq) (0.25 mL, 0.75 mmol) were added. This mixture was stirred at –40° C. for 5 min, warmed to 0° C., and stirred at this temperature for 1.5 h. More glyoxal (40 wt. % in H$_2$O, 0.29 mL, 2.5 mmol) and MeOH (1 mL) were added and the mixture was warmed to room temperature and stirred for 16 h. The pH of the mixture was then brought to 3 by the addition of 2 N HCl (aq). After dilution with H$_2$O (20 mL), the mixture was extracted with EtOAc (3×20 mL) and the combined organic extracts were washed with saturated NaHCO$_3$ (aq) (1×20 mL) and brine (1×20 mL). The organic layer was dried (Na$_2$SO$_4$), filtered and concentrated in vacuo. The residue was purified by silica gel chromatography (12 g, 0-5% MeOH/DCM) and further purified by silica gel chromatography (4 g, 0-100% EtOAc/hexanes) to provide 67 mg (33% for 2 steps) of Compound 12. LCMS (Method A): m/z 404.3/406.3 (M+H)$^+$. $^1$H NMR (CDCl$_3$) δ 8.25 (d, 1H), 7.78 (dd, 1H), 7.49 (dd, 1H), 7.40 (d, 1H), 7.35 (t, 1H), 7.23 (m, 1H), 7.19 (d, 1H), 7.16-7.12 (m, 2H), 7.01 (dd, 1H), 4.84 (br d, 1H), 4.57 (m, 1H), 2.62 (s, 3H), 1.49 (d, 3H).

Example 13

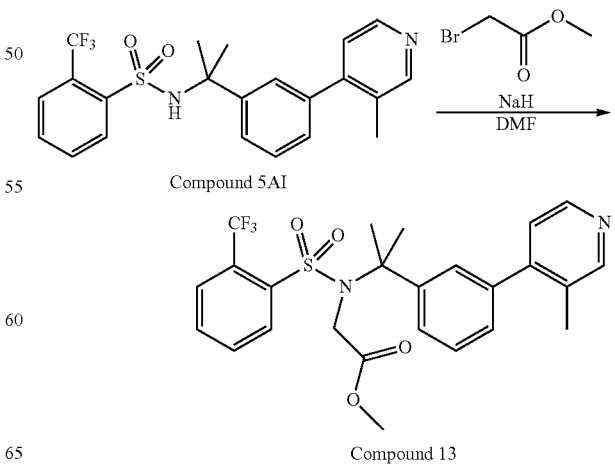

Compound 5AI

Compound 13

Methyl 2-(N-(2-(3-(3-methylpyridin-4-yl)phenyl)propan-2-yl)-2-(trifluoromethyl)phenylsulfonamido)acetate (Compound 13)

Methyl 2-bromoacetate (8.0 µL, 0.08 mmol) was added into a mixture of Compound 5AI (30 mg, 0.07 mmol) and NaH (60% in oil, 4 mg, 0.08 mmol) in DMF (0.5 mL). The reaction was stirred at room temperature overnight and heated to 80° C. for a second day. The reaction was cooled to room temperature, quenched with water, and EtOAc was added. The mixture was washed with water (1X), dried over sodium sulfate, filtered, and concentrated in vacuo. The residue was purified by silica gel chromatography (0-80% EtOAc/Hexanes) to afford Compound 13 (3 mg, 9%). LCMS (method A): m/z 507.5 (M+H)$^+$. $^1$H NMR (CDCl$_3$) δ 8.95 (d, 1H), 8.52 (s, 1H), 8.50 (d, 1H), 7.85 (d, 1H), 7.72 (t, 1H), 7.66 (t, 1H), 7.51 (d, 1H), 7.44 (s, 1H), 7.38 (t, 1H), 7.24 (t, 1H), 7.15 (d, 1H), 4.08 (s, 2H), 3.65 (s, 3H), 2.27 (s, 3H), 1.72 (s, 6H).

Following the method described above for Example 13 and substituting the appropriate starting material and reagent, the following compound was prepared as indicated in Table 8.

TABLE 8

| Compound No | Structure | Starting material | Reagent | MS (M + H)$^+$ |
|---|---|---|---|---|
| 13AA | ![structure] N-(2-methoxyethyl)-N-(2-(3-(3-methylpyridin-4-yl)phenyl)propan-2-yl)-2-(trifluoromethyl)benzenesulfonamide | 5AI | Br~~~O~ | 493.5 (method A) |

Example 14

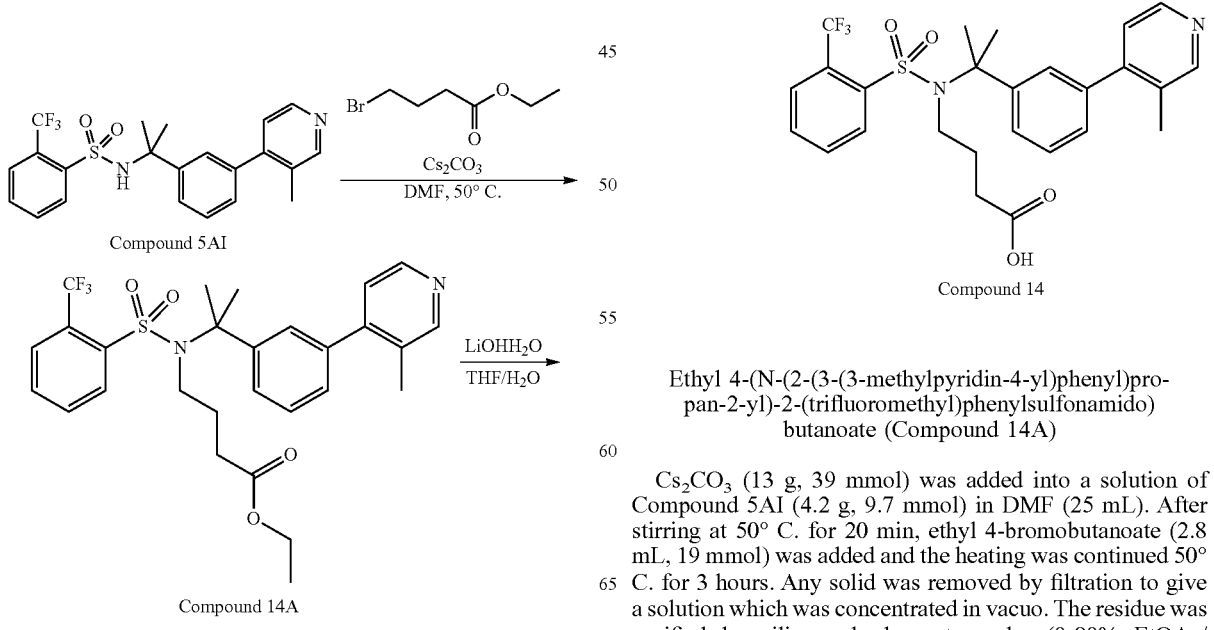

Ethyl 4-(N-(2-(3-(3-methylpyridin-4-yl)phenyl)propan-2-yl)-2-(trifluoromethyl)phenylsulfonamido)butanoate (Compound 14A)

Cs$_2$CO$_3$ (13 g, 39 mmol) was added into a solution of Compound 5AI (4.2 g, 9.7 mmol) in DMF (25 mL). After stirring at 50° C. for 20 min, ethyl 4-bromobutanoate (2.8 mL, 19 mmol) was added and the heating was continued 50° C. for 3 hours. Any solid was removed by filtration to give a solution which was concentrated in vacuo. The residue was purified by silica gel chromatography (0-80% EtOAc/

Hexanes) to afford Compound 14A (3.4 g, 64%). LCMS (method A): m/z 549.5 (M+H)+. $^1$H NMR (CDCl$_3$) δ 8.51 (s, 1H), 8.48 (d, 1H), 8.04~8.01 (m, 1H), 7.86~7.84 (m, 1H), 7.68~7.64 (m, 2H), 7.53 (d, 1H), 7.50 (s, 1H), 7.37 (t, 1H), 7.21 (d, 1H), 7.15 (d, 1H), 4.06 (q, 2H), 3.47~3.44 (m, 2H), 2.29 (s, 3H), 2.21 (t, 2H), 1.98~1.94 (m, 2H), 1.81 (s, 6H), 1.20 (t, 3H).

4-(N-(2-(3-(3-methylpyridin-4-yl)phenyl)propan-2-yl)-2-(trifluoromethyl)phenylsulfonamido)butanoic acid (Compound 14)

Following the procedure as described in Example 11, step 1, compound 14A (3.9 g, 6.2 mmol) was hydrolyzed and purified by reverse phase ISCO (0-100% CH$_3$CN/H$_2$O with 0.25% formic acid) to afford Compound 14 (2.9 g, 83%). LCMS (method A): m/z 521.4 (M+H)+. $^1$H NMR (DMSO) δ 12.24 (br s, 1H), 8.52 (s, 1H), 8.47 (d, 1H), 8.10 (d, 1H), 7.97 (d, 1H), 7.92 (t, 1H), 7.83 (t, 1H), 7.57 (d, 1H), 7.53 (s, 1H), 7.44 (t, 1H), 7.30 (d, 1H), 7.23 (d, 1H), 3.46~3.42 (m, 2H), 2.25 (s, 3H), 2.13 (t, 2H), 1.84~1.76 (m, 2H), 1.75 (s, 6H).

Following the method described above for Example 14 and substituting the appropriate starting materials and reagents, the following compounds were prepared as indicated in Table 9.

TABLE 9

| Compound No | Structure | Starting material | Reagent | MS (M + H)+ |
| --- | --- | --- | --- | --- |
| 14AA | 4-(N-(2-(3-(3-ethylpyridin-4-yl)phenyl)propan-2-yl)-2-(trifluoromethyl)phenylsulfonamido)butanoic acid | Compound 5 | Br~~~COOEt | 535.4 (method A) |
| 14AB | 4-(3-chloro-N-(2-(3-(3-ethylpyridin-4-yl)phenyl)-propan-2-yl)-2-methylphenyl-sulfonamido)butanoic acid | 2BY | Br~~~COOEt | 515.4/ 517.4 (method A) |
| 14AC | 4-(3-chloro-2-methyl-N-(2-(3-(3-methylpyridin-4-yl)-phenyl)-propan-2-yl)phenyl-sulfonamido)butanoic acid | 2BU | Br~~~COOEt | 501.4/ 503.4 (method A) |

TABLE 9-continued

| Compound No | Structure | Starting material | Reagent | MS (M + H)+ |
|---|---|---|---|---|
| 14AD | (S)-4-(3-chloro-2-methyl-N-(1-(3-(pyridin-4-yl)phenyl)ethyl)phenylsulfonamido)butanoic acid | 1BX | Only step 2 hydrolysis | 473.4/ 475.4 (method A) |
| 14AE | (S)-4-(3-chloro-2-methyl-N-(1-(3-(pyridazin-4-yl)phenyl)ethyl)phenylsulfonamido)butanoic acid | 1BY | Only step 2 hydrolysis | 474.4/ 476.4 (method A) |
| 14AF | 4-(3-chloro-2-methyl-N-(3-(3-methylpyridin-4-yl)phenethyl)phenylsulfonamido)butanoic acid | 5BE | Br-CH2CH2CH2-C(=O)-O-Et | 487.3/ 488.3 (method A) |
| 14AG | (S)-4-(3-chloro-N-(1-(3-(2,3-dimethylpyridin-4-yl)phenyl)ethyl)-2-methylphenylsulfonamido)butanoic acid | 7AB | Br-CH2CH2CH2-C(=O)-O-Et | 501.4/ 503.4 (method A) |

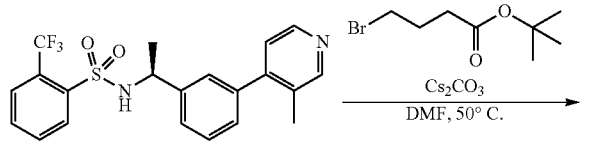

Compound 5AR

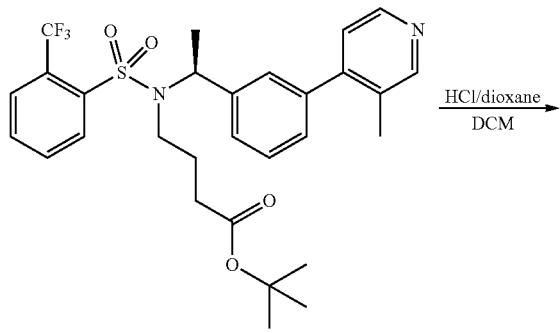

Compound 15A

Compound 15

(S)-tert-butyl 4-(N-(1-(3-(3-methylpyridin-4-yl)phenyl)ethyl)-2-(trifluoromethyl)phenylsulfonamido)butanoate (Compound 15A)

Compound 5AR (420 mg, 1.5 mmol) was converted to Compound 15A (0.56 g, 100%) following the method described in Example 14, step 1. LCMS (method A): m/z 563.5 (M+H)$^+$.

(S)-4-(N-(1-(3-(3-methylpyridin-4-yl)phenyl)ethyl)-2-(trifluoromethyl)phenylsulfonamido)-butanoic acid (Compound 15)

To Compound 15A (0.56 g, 1 mmol) in DCM (15 mL) was added HCl (2 mL, 4 N in diaoxane) and the mixture was stirred overnight. Volatiles were removed to afford the desired product (0.5 g, 99%). LCMS (method A): m/z 507.5 (M+H)$^+$. $^1$H NMR (CD$_3$OD): δ 8.76 (s, 1H), 8.74 (dd, 1H), 8.20 (dd, 1H), 7.99-7.36 (m, 2H), 7.88-7.81 (m, 2H), 7.65-7.57 (m, 3H), 7.49-7.47 (dd, 1H), 5.35 (q, 1H), 2.50 (s, 3H), 2.16-2.08 (m, 2H), 1.66-1.53 (m, 5H), 1.39-1.14 (m, 2H).

Following the method described above for Example 15 and substituting the appropriate starting materials and reagents, the following compounds were prepared as indicated in Table 10

TABLE 10

| Compound No | Structure | Starting material | Reagent | MS (M + H)$^+$ |
|---|---|---|---|---|
| 15AA | 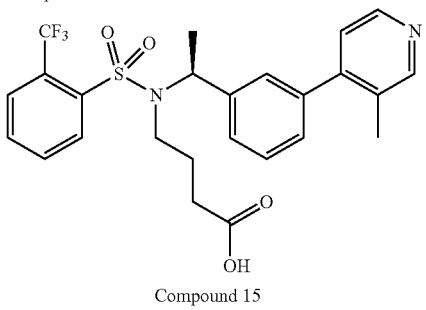<br>(S)-5-(N-(1-(3-(3-methylpyridin-4-yl)phenyl)ethyl)-2-(trifluoromethyl)phenylsulfonamido)pentanoic acid | 5AR | Br~~~~CO$_2$tBu | 521.5 (method A) |
| 15AB | (S)-4-(N-(1-(3-(3-ethylpyridin-4-yl)phenyl)ethyl)-2-(trifluoromethyl)phenylsulfonamido)butanoic acid | 5 | Br~~~CO$_2$tBu | 521.4 (method A) |

TABLE 10-continued

| Compound No | Structure | Starting material | Reagent | MS (M + H)+ |
|---|---|---|---|---|
| 15AC | 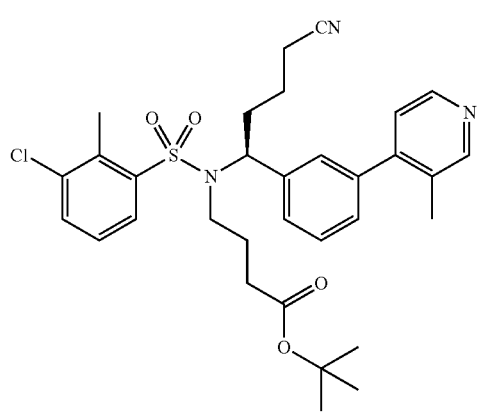 [SMILES: Cc1cnccc1-c1cccc([C@H](CCCC#N)N(CCCC(=O)OC(C)(C)C)S(=O)(=O)c2cccc(Cl)c2C)c1]<br>(S)-tert-butyl 4-(3-chloro-N-(4-cyano-1-(3-(3-methylpyridin-4-yl)phenyl)butyl)-2-methylphenylsulfonamido) butanoate | 2BZ | Br reagent, Only step 1 | 596.6/ 598.6 (method A) |
| 15AD | 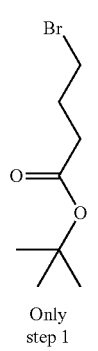<br>(S)-4-(3-chloro-N-(4-cyano-1-(3-(3-methylpyridin-4-yl)phenyl)butyl)-2-methylphenylsulfonamido) butanoic acid | 15AC | Treated with formic acid as Intermediate 16, step 3 | 540.5/ 542.5 (method A) |

Example 16

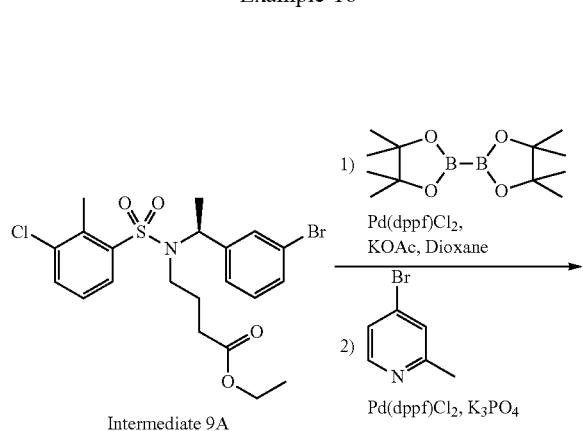

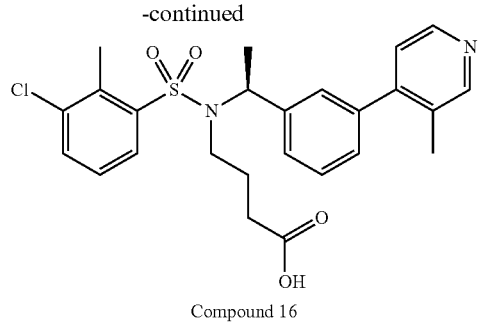

Compound 16

(S)-Ethyl 4-(3-chloro-2-methyl-N-(1-(3-(3-methylpyridin-4-yl)phenyl)ethyl)-phenylsulfonamido) butanoate (Compound 16A)

Following similar procedure as described in Example 7, Intermediate 9A (2.9 g, 5.9 mmol), was converted to Compound 16A (1.8 g, 60%) as a brown oil. LCMS (method A): m/z 515.5/517.5 (M+H)$^+$. $^1$H NMR (CD$_3$OD): δ 8.44 (s, 1H), 8.39 (d, 1H), 8.00 (dd, 1H), 7.62 (dd, 1H), 7.45 (t, 1H), 7.42-7.33 (m, 2H), 7.33-7.29 (m, 1H), 7.20 (d, 1H), 7.09 (s 1H), 5.07 (q, 1H), 4.04 (q, 2H), 3.29-3.19 (m, 2H), 2.56 (s, 3H), 2.23 (s, 1H), 2.21-2.06 (m, 2H), 1.76-1.65 (m, 1H), 1.59 (d, 3H), 1.57-1.46 (m, 1H), 1.18 (t, 3H)

(S)-4-(3-Chloro-2-methyl-N-(1-(3-(3-methylpyridin-4-yl)phenyl)ethylphenylsulfonamido) butanoic acid (Compound 16)

Compound 16A (0.15 g, 0.30 mmol) was converted into Compound 16 (0.14 g, 94%) according to the procedure for Example 11, step 1. LCMS (method A): m/z 487.4/489.4 (M+H)$^+$. $^1$H NMR (CD$_3$OD): δ 8.44 (s, 1H), 8.39 (d, 1H), 8.00 (dd, 1H), 7.62 (dd, 1H), 7.45 (t, 1H), 7.42-7.39 (m, 1H), 7.35 (t, 1H), 7.32-7.28 (m, 1H), 7.20 (d, 1H), 7.08 (s 1H), 5.07 (q, 1H), 4.04 (q, 2H), 3.29-3.21 (m, 2H), 2.56 (s, 3H), 2.23 (s, 1H), 2.21-2.05 (m, 2H), 1.76-1.65 (m, 1H), 1.60 (d, 3H), 1.57-1.46 (m, 1H).

Following the method described above for Example 16 and substituting the appropriate intermediates and reagents, the following compounds were prepared as indicated in Table 11.

TABLE 11

| Compound No | Structure | Intermediate | Reagent | MS (M + H)$^+$ |
|---|---|---|---|---|
| 16AA | (R)-4-(3-chloro-2-methyl-N-(1-(3-(3-methylpyridin-4-yl)-phenyl)ethyl)phenylsulfonamido)butanoic acid | 9C | 3-methyl-4-bromopyridine | 487.5/489.5 (method A) |

TABLE 11-continued

| Compound No | Structure | Intermediate | Reagent | MS (M + H)+ |
|---|---|---|---|---|
| 16AB | (S)-4-(3-chloro-N-(1-(3-(3-ethylpyridin-4-yl)phenyl)ethyl)-2-methylphenyl-sulfonamido)butanoic acid | 9A | | 501.5/503.5 (method A) |
| 16AC | 4-(3-chloro-N-(2-(3-(3-(hydroxymethyl)pyridin-4-yl)-phenyl)propan-2-yl)-2-methylphenylsulfonamido)butanoic acid | 9B | | 517.5/519.5 (method A) |
| 16AD | (S)-4-(2-methyl-N-(1-(3-(3-methylpyridin-4-yl)phenyl)-ethyl)phenylsulfonamido)butanoic acid | 9D | | 453.5 (method A) |
| 16AE | (S)-4-(N-(1-(3-(3-ethylpyridin-4-yl)phenyl)ethyl)-2-methylphenylsulfonamido) butanoic acid | 9D | | 467.4 (method A) |

TABLE 11-continued

| Compound No | Structure | Intermediate | Reagent | MS (M + H)+ |
|---|---|---|---|---|
| 16AF | (S)-5-(3-chloro-2-methyl-N-(1-(3-(3-methylpyridin-4-yl)phenyl)ethyl)phenylsulfonamido)pentanoic acid | 9 | 3-methyl-4-bromopyridine | 501.5/503.5 (method A) |
| 16AG | (S)-5-(3-chloro-N-(1-(3-(3-ethylpyridin-4-yl)phenyl)-ethyl)-2-methylphenyl-sulfonamido)pentanoic acid | 9 | 3-ethyl-4-bromopyridine | 515.4/517.4 (method A) |
| 16AH | (S)-4-(N-(1-(3-(3-(benzyloxy)-pyridin-4-yl)phenyl)ethyl)-3-chloro-2-methylphenyl-sulfonamido)butanoic acid | 9A | 3-(benzyloxy)-4-bromopyridine | 579.5 (method A) |
| 16AI | (S)-4-(3-chloro-N-(1-(3-(3-(hydroxymethyl)pyridin-4-yl)phenyl)ethyl)-2-methylphenylsulfonamido)butanoic acid | 9A | (4-bromopyridin-3-yl)methanol | 503.4/505.4 (method A) |

TABLE 11-continued

| Compound No | Structure | Intermediate | Reagent | MS (M + H)+ |
|---|---|---|---|---|
| 16AJ | (S)-4-(3-chloro-2-methyl-N-(1-(3-(4-methylisothiazol-5-yl)phenyl)ethyl)phenyl-sulfonamido)butanoic acid | 9A | 5-bromo-4-methylisothiazole | 493.4/495.4 (method A) |
| 16AK | (S)-3-(3-chloro-2-methyl-N-(1-(3-(3-methylpyridin-4-yl)phenyl)ethyl)phenylsulfonamido)propanoic acid | 9E | 4-bromo-3-methylpyridine | 473.3/475.3 (method A) |
| 16AL | 4-(3-chloro-2-methyl-N-(3-(3-(3-methylpyridin-4-yl)phenyl)-oxetan-3-yl)phenyl-sulfonamido)butanoic acid | 9G | 4-bromo-3-methylpyridine | 515.4/517.4 (method A) |
| 16AM | (S)-2-(2-(3-chloro-2-methyl-N-(1-(3-(3-methylpyridin-4-yl)phenyl)ethyl)phenylsulfonamido)ethoxy)acetic acid | 19 | 4-bromo-3-methylpyridine Followed by formic acid as in Intermediate 16, step 3 | 503.5/505.5 (method A) |

Example 17

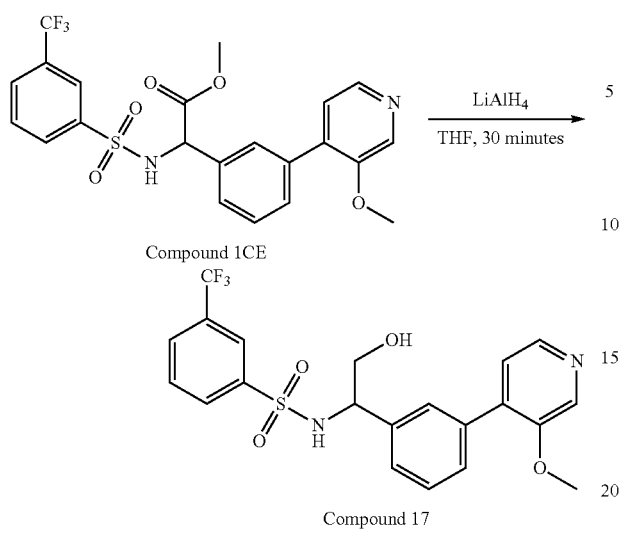

Compound 1CE

Compound 17

(+/−) N-(2-hydroxy-1-(3-(3-methoxypyridin-4-yl)phenyl)ethyl)-3-(trifluoromethyl)benzenesulfonamide (Compound 17)

A solution was prepared of Compound 10E (30 mg, 0.06 mmol) in anhydrous THF (1 mL) and cooled to 0° C. A solution of lithium aluminum hydride in THF (1M, 0.13 mL, 0.13 mmol) was added slowly. After 30 minutes, the reaction was quenched by the sequential addition of water (5 µL), 1N NaOH (20 µL), and water (15 µL). The reaction mixture was diluted with 10 mL diethyl ether, and allowed to stand overnight. The mixture was filtered, and then evaporated to dryness. Purification by silica gel chromatography (30-100% EtOAc/hexanes) yielded Compound 17 (6.2 mg, 21%). LCMS (method A): m/z 453.4 (M+H)+. $^1$H NMR (CDCl$_3$) δ 8.28 (m, 2H), 7.89 (m, 2H), 7.63 (d, 1H), 7.42 (m, 2H), 7.26 (m, 2H), 7.10 (m, 2H), 6.19 (m, 1H), 4.63 (m, 1H), 3.91 (m, 1H), 3.89 (s, 3H), 3.81 (m, 1H).

Example 18

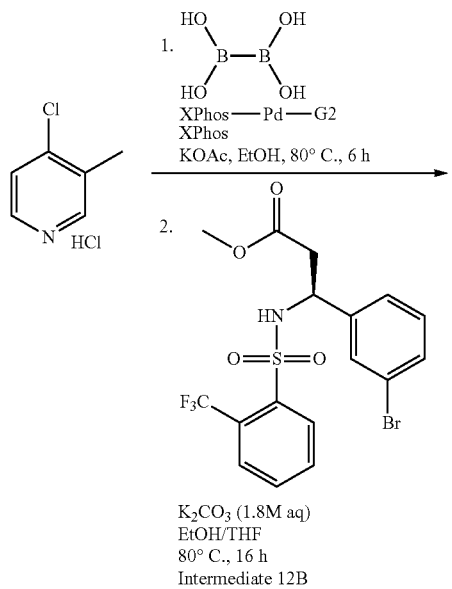

K$_2$CO$_3$ (1.8M aq)
EtOH/THF
80° C., 16 h
Intermediate 12B

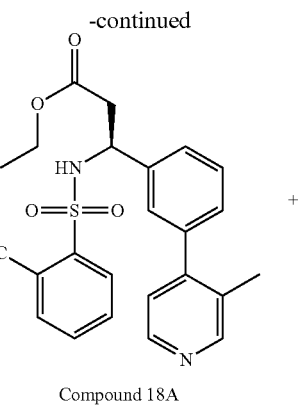

Compound 18A

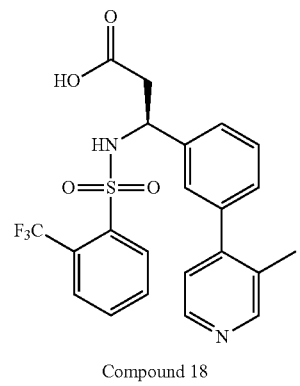

Compound 18

(S)-ethyl 3-(3-(3-methylpyridin-4-yl)phenyl)-3-(2-(trifluoromethyl)phenylsulfonamido)-propanoate (Compound 18A) and (S)-3-(3-(3-methylpyridin-4-yl)phenyl)-3-(2-(trifluoromethyl)phenylsulfonamido) propanoic acid (Compound 18)

Tetrahydroxydiborane (70 mg, 0.78 mmol), 4-chloro-3-methylpyridine hydrochloride (42 mg, 0.26 mmol), chloro(2-dicyclohexylphosphino-2',4',6'-triisopropyl-1,1'-biphenyl)[2-(2'-amino-1,1'-biphenyl)]palladium(II) (XPhos-Pd-G2, 10 mg, 0.01 mmol), 2-dicyclohexylphosphino-2',4',6'-triisopropylbiphenyl (XPhos, 12 mg, 0.02 mmol), and potassium acetate (77 mg, 0.78 mmol) were weighed out into a Biotage microwave vessel. Absolute ethanol (3 mL) was added and the mixture was degassed with nitrogen for 10 minutes. The vessel was capped, and the reaction mixture was heated to 80° C. via heating block for 6 hours. The reaction mixture was cooled to room temperature, and a degassed solution of Intermediate 12B (120 mg, 0.26 mmol) in 0.3 mL THF and 0.3 mL ethanol was added, followed by a degassed potassium carbonate solution (0.52 mL, 1.8 M aqueous). The reaction mixture was heated to 80° C. for 16 hours via heating block. After cooling to room temperature, the mixture was diluted with ethanol (8 mL), and filtered through a pad of Celite. The filtrate was diluted with EtOAc (20 mL). The solution was washed with water (10 mL) and saturated aqueous sodium bicarbonate (10 mL). The organic layer was dried over sodium sulfate, filtered, and evaporated to dryness. Purification by silica gel chromatography (15-

90% EtOAc/hexanes) yielded Compound 18A (19 mg, 15% yield). LCMS (method A): m/z 493.5 (M+H)+. $^1$H NMR (CDCl$_3$) δ 8.49 (m, 2H), 8.00 (d, 1H), 7.73 (d, 1H), 7.52 (m, 2H), 7.24 (m, 1H), 7.14 (m, 2H), 7.06 (m, 1H), 6.96 (d, 1H), 6.22 (m, 1H), 4.93 (q, 1H), 4.07 (q, 2H), 2.85 (m, 2H), 2.18 (s, 3H), 1.16 (t, 3H).

The combined aqueous washings were acidified to pH-2 with 2M HCl and evaporated to dryness. The residue was stirred with acetonitrile/water (3:1 ratio, 5 mL) and filtered. The filtrate was dissolved in a 2:1 mixture of acetonitrile/water (1.2 mL), and purified by MS-HPLC to afford Compound 18 (4.3 mg, 4% yield). LCMS (method A): m/z 465.4 (M+H)+. $^1$H NMR (CD$_3$OD) δ 8.41 (m, 2H), 8.01 (d, 1H), 7.73 (d, 1H), 7.58 (m, 2H), 7.32 (m, 1H), 7.22 (m, 2H), 7.15 (m, 3H), 4.91 (m, 1H, overlapping with CD$_3$OD), 2.81 (m, 2H), 2.21 (s, 3H).

Example 19

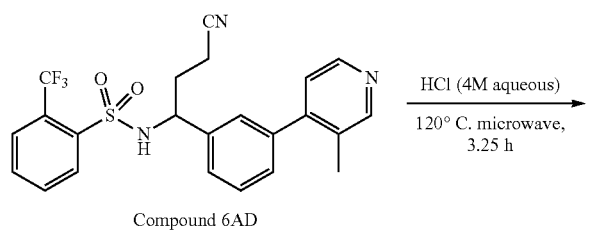

Compound 6AD

HCl (4M aqueous)
120° C. microwave,
3.25 h

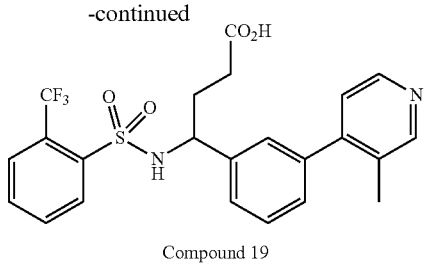

Compound 19

4-(3-(3-methylpyridin-4-yl)phenyl)-4-(2-(trifluoromethyl)phenylsulfonamido)butanoic acid (Compound 19)

A mixture of Compound 6AD (46 mg, 0.10 mmol) and hydrochloric acid (4M aqueous, 3.5 mL) was irradiated to 120° C. for 3.25 hours in a Biotage Initiator microwave. The reaction mixture was evaporated to dryness, and the crude product was purified by MS-HPLC to give Compound 19 (20 mg, 41%). LCMS (method A): m/z 479.4 (M+H)+. $^1$H NMR (CD$_3$OD) δ 8.44 (s, 1H), 8.40 (d, 1H), 8.00 (m, 1H), 7.71 (m, 1H), 7.56 (m, 2H), 7.27 (m, 1H), 7.19 (m, 1H), 7.14-7.10 (m, 3H), 4.53 (m, 1H), 2.36 (m, 2H), 2.21 (s, 3H), 2.10-1.97 (m, 2H).

Following the method described above for Example 19 but using heating block instead of microwave, the following compound was prepared as indicated in Table 12.

TABLE 12

| Compound No | Structure | Starting material | Condition | MS (M + H)+ |
|---|---|---|---|---|
| 19AA | 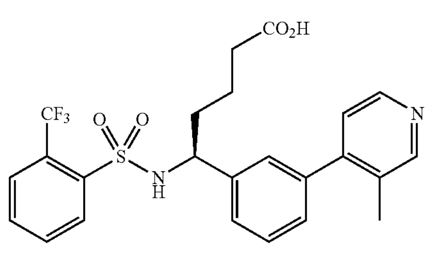 [SMILES: Cc1cnccc1-c1cccc([C@H](CCCC(=O)O)NS(=O)(=O)c2ccccc2C(F)(F)F)c1] | 5BC | Heating (no microwave) 100° C.+n 24 h | 493.5 (method A) |

(S)-5-(3-(3-methylpyridin-4-yl)phenyl)-5-(2-(trifluoromethyl)phenylsulfonamido)pentanoic acid

Example 20

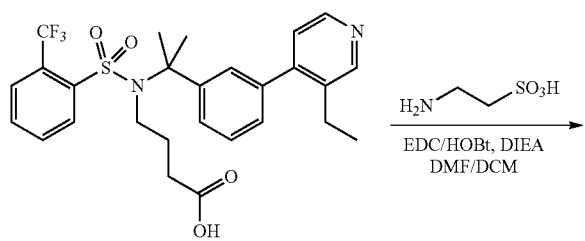

Compound 14AA

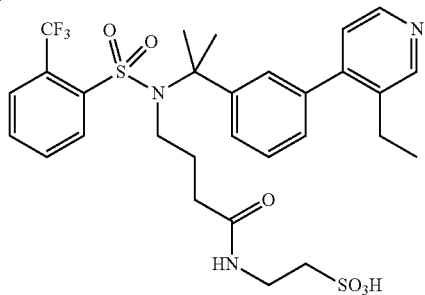

Compound 20

2-(4-(N-(2-(3-(3-ethylpyridin-4-yl)phenyl)propan-2-yl)-2-(trifluoromethyl)-phenylsulfonamido)butanamido)ethanesulfonic acid (Compound 20)

DIEA (36 μL, 0.2 mmol) was added into a mixture of Compound 14AA (36 mg, 0.07 mmol),1-ethyl-3-(3-dimethylaminopropyl) carbodiimide (26 mg, 0.14 mmol), hydroxybenzotriazole (18 mg, 0.14 mmol), and 2-aminoethanesulfonic acid (17 mg, 0.14 mmol) in DMF/DCM (0.5 mL/0.5 mL). The reaction was stirred at room temperature for 3 days. The reaction was concentrated in vacuo and purified by MS-HPLC to afford the title compound (32 mg, 72%). LCMS (method A): m/z 642.4 $(M+H)^+$. $^1$H NMR (MeOD) δ 8.80 (s, 1H), 8.75 (d, 1H), 8.15 (d, 1H), 8.00 (d, 1H), 7.94 (d, 1H), 7.88 (t, 1H), 7.79 (t, 1H), 7.74~7.71 (m, 2H), 7.56 (t, 1H), 7.40 (d, 1H), 3.50~3.42 (m, 4H), 2.92~2.84 (m, 4H), 2.06 (t, 2H), 1.90 (m, 2H), 1.79 (s, 6H), 1.20 (t, 3H), Following the method described above for Example 20 and substituting the appropriate starting materials and reagents, the following compounds were prepared using EDC as the coupling reagent, unless specified as indicated in Table 13.

TABLE 13

| Compound No | Structure | Starting material | Reagent | MS $(M + H)^+$ |
|---|---|---|---|---|
| 20AA | ![structure]<br><br>2-(4-(N-(2-(3-(3-methylpyridin-4-yl)phenyl)propan-2-yl)-2-(trifluoromethyl)phenylsulfonamido)butanamido)ethanesulfonic acid | Compound 14 | H₂N–CH₂CH₂–SO₃H | 628.4 (method A) |
| 20AB | ![structure]<br><br>(4-(N-(2-(3-(3-methylpyridin-4-yl)phenyl)propan-2-yl)-2-(trifluoromethyl)phenylsulfonamido)butanamido)methanesulfonic acidtrifluoromethyl)benzenesulfonamide | Compound 14 | H₂N–CH₂–SO₃H | 614.4 (method A) |

TABLE 13-continued

| Compound No | Structure | Starting material | Reagent | MS (M + H)+ |
|---|---|---|---|---|
| 20AC | 2-(4-(3-chloro-N-(2-(3-(3-ethylpyridin-4-yl)phenyl)propan-2-yl)-2-methylphenylsulfonamido)butanamido)ethanesulfonic acid | 14AB | H₂N–CH₂CH₂–SO₃H | 622.4/ 624.4 (method A) |
| 20AD | 3-(4-(3-chloro-2-methyl-N-(2-(3-(3-methylpyridin-4-yl)phenyl)propan-2-yl)phenylsulfonamido)butanamido)propane-1-sulfonic acid | 14AC | H₂N–(CH₂)₃–SO₃H | 622.5/ 624.5 (method A) |
| 20AE | 4-(3-chloro-2-methyl-N-(2-(3-(3-methylpyridin-4-yl)phenyl)propan-2-yl)phenylsulfonamido)-N-(2-sulfamoylethyl)butanamide | 14AC | H₂N–CH₂CH₂–SO₂NH₂ | 607.5/ 609.5 (method A) |
| 20AF | 4-(3-chloro-2-methyl-N-(2-(3-(3-methylpyridin-4-yl)phenyl)propan-2- | 14AC | NH₂–CH₂–CH(OH)–CH(OH)–CH(OH)–CH(OH)–CH₂OH | 664.6/ 666.6 (method A) |

TABLE 13-continued

| Compound No | Structure | Starting material | Reagent | MS (M + H)+ |
|---|---|---|---|---|
| | yl)phenylsulfonamido)-N-((2R,3S,4S,5S)-2,3,4,5,6-pentahydroxyhexyl)butanamide | | | |
| 20AG | 2-(4-(3-chloro-2-methyl-N-(2-(3-(3-methylpyridin-4-yl)phenyl)propan-2-yl)phenylsulfonamido)butanamido)ethanesulfonic acid | 14AC | H₂N–CH₂CH₂–SO₃H | 608.5/ 610.5 (method A) |
| 20AH | (S)-2-(5-(3-chloro-2-methyl-N-(1-(3-(3-methylpyridin-4-yl)phenyl)ethyl)phenylsulfonamido)pentanamido)ethanesulfonic acid | 16AF | H₂N–CH₂CH₂–SO₃H | 608.5/ 610.5 (method A) |
| 20AI | 5-(3-chloro-2-methyl-N-((S)-1-(3-(3-methylpyridin-4-yl)phenyl)ethyl)phenylsulfonamido)-N-((2R,3S,4S,5S)-2,3,4,5,6-pentahydroxyhexyl)pentanamide | 16AF | 1-amino-1-deoxy sugar (pentahydroxyhexylamine) | 664.6/ 666.6 (method A) |
| 20AJ | 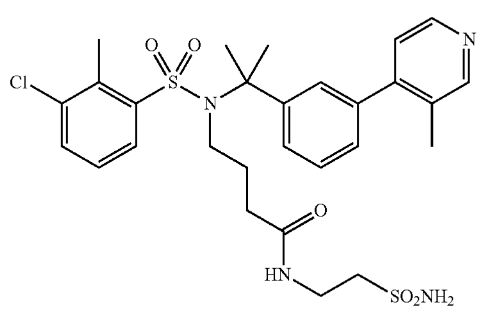 [SMILES: Cc1cnccc1-c1cccc(C(C)(C)N(CCCC(=O)NCCS(N)(=O)=O)S(=O)(=O)c2cccc(Cl)c2C)c1] | Compound 16 | H₂N–CH₂CH₂–SO₂NH₂ | 593.5/ 595.5 (method A) |

TABLE 13-continued

| Compound No | Structure | Starting material | Reagent | MS (M + H)+ |
|---|---|---|---|---|
|  | (S)-4-(3-chloro-2-methyl-N-(1-(3-(3-methylpyridin-4-yl)phenyl)ethyl)phenylsulfonamido)-N-(2-sulfamoylethyl)butanamide | | | |
| 20AK | 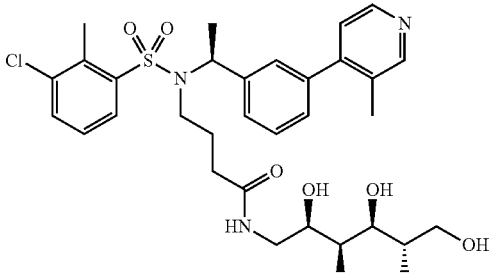<br>4-(3-chloro-2-methyl-N-((S)-1-(3-(3-methylpyridin-4-yl)phenyl)ethyl)phenylsulfonamido)-N-((2R,3S,4S,5S)-2,3,4,5,6-pentahydroxyhexyl)butanamide | Compound 16 | 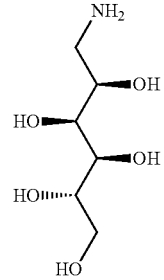 | 650.6/ 652.6 (method A) |
| 20AL | 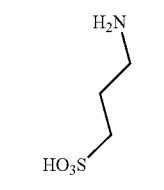<br>(S)-3-(4-(3-chloro-2-methyl-N-(1-(3-(3-methylpyridin-4-yl)phenyl)ethyl)phenylsulfonamido)butanamido)propane-1-sulfonic acid | Compound 16 | H$_2$N~~~SO$_3$H | 608.5/ 610.5 (method A) |
| 20AM | 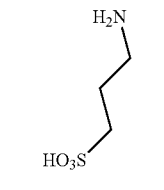<br>(S)-3-(4-(3-chloro-N-(1-(3-(3-ethylpyridin-4-yl)phenyl)ethyl)-2-methylphenylsulfonamido)butanamido)propane-1-sulfonic acid | 16AB | H$_2$N~~~SO$_3$H | 622.5/ 624.6 (method A) |

TABLE 13-continued

| Compound No | Structure | Starting material | Reagent | MS (M + H)+ |
|---|---|---|---|---|
| 20AN | 4-(3-chloro-N-((S)-1-(3-(3-ethylpyridin-4-yl)phenyl)ethyl)-2-methylphenylsulfonamido)-N-((2R,3S,4S,5S)-2,3,4,5,6-pentahydroxyhexyl)butanamide | 16AB | | 664.6/ 666.5 (method A) |
| 20AO | 2-(4-(3-chloro-N-(2-(3-(3-(hydroxymethyl)pyridin-4-yl)phenyl)propan-2-yl)-2-methylphenylsulfonamido)butanamido)ethanesulfonic acid | 16AC | | 624.5/ 626.5 (method A) |
| 20AP | (S)-2-(4-(3-chloro-N-(1-(3-(3-(hydroxymethyl)pyridin-4-yl)phenyl)ethyl)-2-methylphenylsulfonamido)butanamido)ethanesulfonic acid | 16AI | | 610.4/ 612.4 (method A) |
| 20AQ | 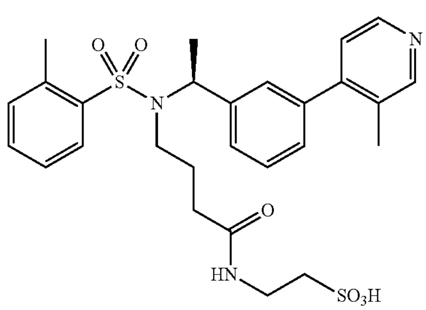 [SMILES: Cc1cnccc1-c1cccc([C@H](C)N(CCCC(=O)NCCS(=O)(=O)O)S(=O)(=O)c2ccccc2C)c1] | 16AD | | 560.6 (method A) |

TABLE 13-continued

| Compound No | Structure | Starting material | Reagent | MS (M + H)+ |
|---|---|---|---|---|
| | (S)-2-(4-(2-methyl-N-(1-(3-(3-methylpyridin-4-yl)phenyl)ethyl)phenylsulfonamido)butanamido)ethanesulfonic acid | | | |
| 20AR | (S)-2-(4-(N-(1-(3-(3-ethylpyridin-4-yl)phenyl)ethyl)-2-methylphenyl-sulfonamido)butanamido)ethane sulfonic acid | 16AE | H2N-CH2CH2-SO3H | 574.5 (method A) |
| 20AS | (S)-2-(5-(3-chloro-N-(1-(3-(3-ethylpyridin-4-yl)phenyl)ethyl)-2-methylphenylsulfonamido)pentanamido)ethanesulfonic acid | 16AG | H2N-CH2CH2-SO3H | 622.5/ 624.5 (method A) |
| 20AT | (S)-N-(2-(2-aminoethoxy)ethyl)-5-(3-chloro-2-methyl-N-(1-(3-(3-methylpyridin-4-yl)phenyl)ethyl)phenylsulfonamido)pentanamide | 16AF | H2N-CH2CH2-O-CH2CH2-NH-Boc; Coupling followed by HCl as Intermediate 3, step 3 | 587.6/ 589.6 (method A) |

TABLE 13-continued

| Compound No | Structure | Starting material | Reagent | MS (M + H)+ |
|---|---|---|---|---|
| 20AU | 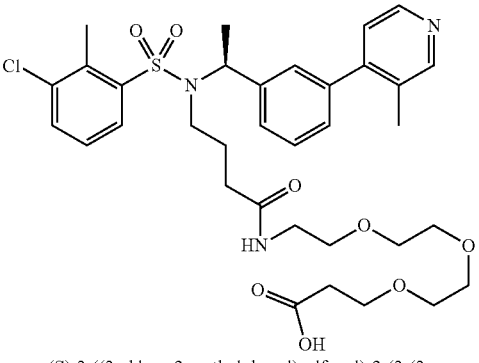<br>(S)-3-((3-chloro-2-methylphenyl)sulfonyl)-2-(3-(3-methylpyridin-4-yl)phenyl)-7-oxo-11,14,17-trioxa-3,8-diazaicosan-20-oic acid | Compound 16 | 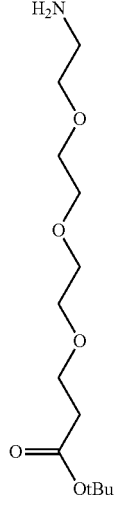 [SMILES: CC(C)(C)OC(=O)CCOCCOCCOCCN]<br>Coupling followed by formic acid as Intermediate 16, step 3 | 690.6/ 692.6 (method A) |
| 20AV | 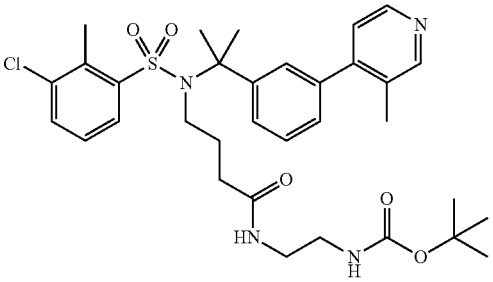 [SMILES: Cc1cnccc1-c1cccc(C(C)(C)N(CCCC(=O)NCCNC(=O)OC(C)(C)C)S(=O)(=O)c2cccc(Cl)c2C)c1]<br>tert-butyl (2-(4-(3-chloro-2-methyl-N-(2-(3-(3-methylpyridin-4-yl)phenyl)propan-2-yl)phenyl sulfonamido)butanamido)ethyl)carbamate | 14AC | 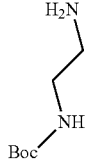 | 643.6 (method A) |
| 20AW | 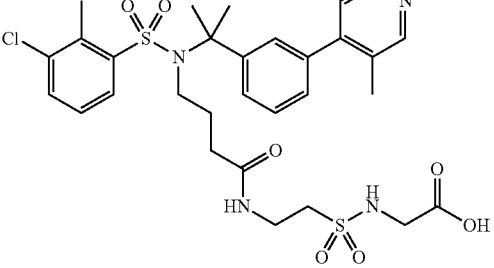<br>(4-(3-chloro-2-methyl-N-(2-(3-(3-methylpyridin-4-yl)phenyl)propan-2-yl)phenyl sulfonamido)-N-butanamido ethylsulfonamido)acetic acid | 14AC | Coupling with Intermediate 18 followed by LiOH as Example 11, step 1 | 665.5/ 667.5 (method A) |

TABLE 13-continued

| Compound No | Structure | Starting material | Reagent | MS (M + H)+ |
|---|---|---|---|---|
| 20AX | (S)-2-(4-(2-methyl-N-(1-(3-(3-methylpyridin-4-yl)phenyl)ethyl)phenylsulfonamido)butanamidoethylsulfonamido)acetate | 16AD | Coupling with Intermediate 18B followed by formic acid as Intermediate 16, step 3 | 673.6 (method A) |
| 20AY | (S)-4-(3-Chloro-2-methyl-N-(1-(3-(3-methylpyridin-4-yl)phenyl)ethyl)phenylsulfonamido)butanamide | Compound 16 | NH₄Cl and PyBOP | 486.4 (method A) |
| 20AZ | (S)-N-(2-aminoethyl)-4-(3-chloro-2-methyl-N-(1-(3-(3-methylpyridin-4-yl)phenyl)ethyl)phenylsulfonamido)butanamide | Compound 16 | H₂N-CH₂CH₂-NHBoc and HATU coupling followed by HCl as Intermediate 3, step 3 | 529.5/ 531.6 (method A) |
| 2OBB | (S) 2-(3-(4-(3-chloro-2-methyl-N-(1-(3-(3-ethylpyridin-4-yl)phenyl)ethyl)phenylsulfonamido)butanamido)ethylsulfonamido)propanoic acid | 16AB | HATU coupling with Intermediate 18B followed by formic acid as Intermediate 16, step 3 | 679.5/ 681.5 (method A) |

TABLE 13-continued

| Compound No | Structure | Starting material | Reagent | MS (M + H)+ |
|---|---|---|---|---|
| 20BC | 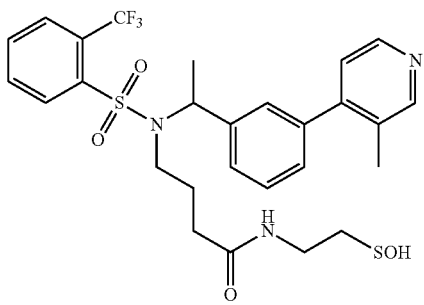<br>N-(2-(hydroxythio)ethyl)-4-(N-(1-(3-(3-methylpyridin-4-yl)phenyl)ethyl)-2-(trifluoromethyl)phenylsulfonamido)butanamide | Intermediate 16 |  | 614.5 (method A) |
| 20BD | 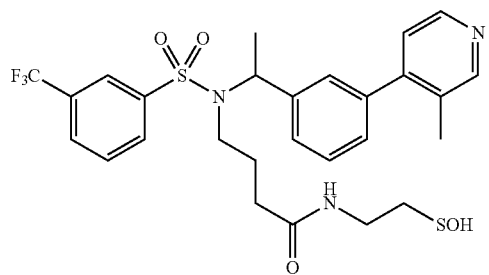<br>N-(2-(hydroxythio)ethyl)-4-(N-(1-(3-(3-methylpyridin-4-yl)phenyl)ethyl)-3-(trifluoromethyl)phenylsulfonamido)butanamide | Intermediate 16 |  | 614.5 (method A) |
| 20BE | 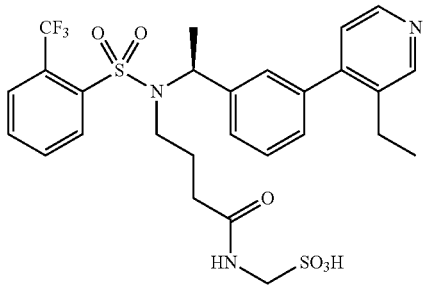 [SMILES: CCc1cnccc1-c1cccc([C@H](C)N(CCCC(=O)NCS(=O)(=O)O)S(=O)(=O)c2ccccc2C(F)(F)F)c1]<br>(S)-(4-(N-(1-(3-(3-ethylpyridin-4-yl)phenyl)ethyl)-2-(trifluoromethyl)phenylsulfonamido)butanamido)methanesulfonic acid | 15AB | 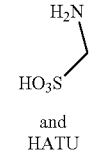<br>and<br>HATU | 614.5 (method A) |
| 20BF | 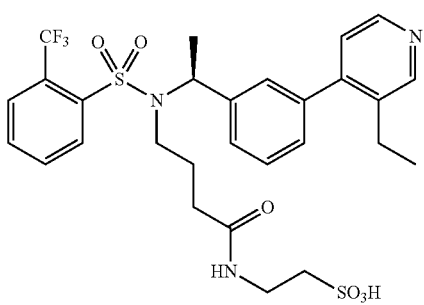 [SMILES: CCc1cnccc1-c1cccc([C@H](C)N(CCCC(=O)NCCS(=O)(=O)O)S(=O)(=O)c2ccccc2C(F)(F)F)c1] | 15AB | <br>and<br>HATU | 628.5 (method A) |

TABLE 13-continued

| Compound No | Structure | Starting material | Reagent | MS (M + H)+ |
|---|---|---|---|---|
| | (S)-2-(4-(N-(1-(3-(3-ethylpyridin-4-yl)phenyl)ethyl)-2-(trifluoromethyl)phenylsulfonamido)butanamido)ethanesulfonic acid | | | |
| 20BG | (S) 2-(4-(N-(1-(3-(3-ethylpyridin-4-yl)phenyl)ethyl)-2-(trifluoromethyl)phenylsulfonamido)butanamido)ethylsulfonamido)acetic acid | 15AB | HATU Coupling with Intermediate 18B followed by TFA as Intermediate 16, step 3 | 685.6 (method A) |
| 20BH | (S)-2-(4-(N-(1-(3-(3-ethylpyridin-4-yl)phenyl)ethyl)-2-(trifluoromethyl)phenylsulfonamido)butanamido)ethanesulfonic acid | Compound 15 | H$_2$N-CH$_2$CH$_2$-SO$_3$H and HATU | 614.5 (method A) |
| 20BI | (S) 2-(4-(N-(1-(3-(3-methylpyridin-4-yl)phenyl)ethyl)-2-(trifluoromethyl)phenylsulfonamido)butanamido)ethylsulfonamido)propanoic acid | Compound 15 | HATU Coupling with Intermediate 18C followed by TFA as Intermediate 16, step 3 | 685.5 (method A) |

TABLE 13-continued

| Compound No | Structure | Starting material | Reagent | MS (M + H)+ |
|---|---|---|---|---|
| 2OBJ | (S) 2-(4-(N-(1-(3-(3-methylpyridin-4-yl)phenyl)ethyl)-2-(trifluoromethyl)phenylsulfonamido)butanamido)ethylsulfonamido)acetic acid | Compound 15 | HATU coupling with Intermediate 18B followed by TFA as Intermediate 16, step 3 | 671.5 (method A) |
| 20BK | (S) 2-(4-(N-(1-(3-(3-methylpyridin-4-yl)phenyl)ethyl)-2-(trifluoromethyl)phenylsulfonamido)butanamido)ethylsulfonamido)butanoic acid | Compound 15 | HATU Coupling with Intermediate 18D followed by TFA as Intermediate 16, step 3 | 699.6 (method A) |
| 20BL | (S) 2-(4-(N-(1-(3-(3-methylpyridin-4-yl)phenyl)ethyl)-2-(trifluoromethyl)phenylsulfonamidopentanamido)ethylsulfonamido)acetic acid | 15AA | HATU Coupling with Intermediate 18B followed by TFA as Intermediate 16, step 3 | 685.5 (method A) |
| 20BM | 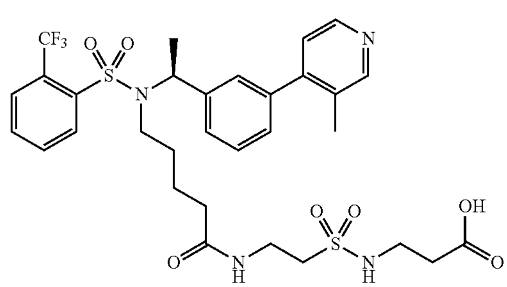 [SMILES: Cc1cnccc1-c1cccc([C@H](C)N(CCCCC(=O)NCCS(=O)(=O)NCCC(=O)O)S(=O)(=O)c2ccccc2C(F)(F)F)c1] | 15AA | HATU Coupling with Intermediate 18C followed by TFA as Intermediate 16, step 3 | 699.6 (method A) |

TABLE 13-continued

| Compound No | Structure | Starting material | Reagent | MS (M + H)+ |
|---|---|---|---|---|
| | (S) 2-(4-(N-(1-(3-(3-methylpyridin-4-yl)phenyl)ethyl)-2-(trifluoromethyl)phenylsulfonamidopentanamido)ethylsulfonamido)propanoic acid | | | |
| 20BN | [structure] 2-(4-(3-chloro-2-methyl-N-(3-(3-(3-methylpyridin-4-yl)phenyl)oxetan-3-yl)phenylsulfonamido)butanamido)ethanesulfonic acid | 16AL | H₂N—CH₂CH₂—SO₃⁻ Bu₄N⁺ | 622.4/ 624.4 (method A) |
| 20BO | [structure] (S)-2-(4-(3-chloro-2-methyl-N-(1-(3-(pyridazin-4-yl)phenyl)ethyl)phenylsulfonamido)butanamido)ethanesulfonic acid | 14AE | H₂N—CH₂CH₂—SO₃H | No MS (see NMR below) |
| 20BP | [structure] (S)-2-(4-(3-chloro-2-methyl-N-(1-(3-(4-methylisothiazol-5-yl)phenyl)ethyl)phenylsulfonamido)butanamido)ethanesulfonic acid | 16AJ | H₂N—CH₂CH₂—SO₃H | 600.4/ 602.4 (method A) |

TABLE 13-continued

| Compound No | Structure | Starting material | Reagent | MS (M + H)+ |
|---|---|---|---|---|
| 20BQ | (S)-2-(4-(N-(1-(3-(3-(benzyloxy)pyridin-4-yl)phenyl)ethyl)-3-chloro-2-methylphenylsulfonamido)butanamido)ethanesulfonic acid | 16AH | H₂N–CH₂CH₂–SO₃H | 686.4/ 688.4 (method A) |
| 20BR | (S)-(5-(3-(3-methylpyridin-4-yl)phenyl)-5-(2-(trifluoromethyl)phenylsulfonamido)pentanamido)methanesulfonic acid | 19AA | H₂N–CH₂–SO₃H | 586.4 (method A) |
| 20BS | (S)-2-(4-(3-chloro-N-(1-(3-(3-(hydroxymethyl)pyridin-4-yl)phenyl)ethyl)-2-methylphenylsulfonamido)butanamido)ethanesulfonamido acetic acid | 20AP | coupling with Intermediate 18B followed by formic acid as Intermediate 16, step 3 | 667.3/ 669.3 (method A) |
| 20BT | 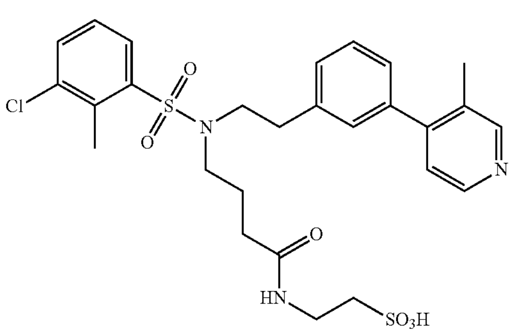 [SMILES: Cc1cnccc1-c1cccc(CCN(CCCC(=O)NCCS(=O)(=O)O)S(=O)(=O)c2cccc(Cl)c2C)c1] | 14AF | H₂N–CH₂CH₂–SO₃H | 594.3/ 596.3 (method A) |

TABLE 13-continued

| Compound No | Structure | Starting material | Reagent | MS (M + H)+ |
|---|---|---|---|---|
| | 2-(4-(3-chloro-2-methyl-N-(3-(3-methylpyridin-4-yl)phenethyl)phenylsulfonamido)butanamido)ethanesulfonic acid | | | |
| 20BU | (S)-2-(4-(2-methyl-N-(1-(3-(3-ethylpyridin-4-yl)phenyl)ethyl)phenylsulfonamido)butanamidoethylsulfonamido)acetate | 16AD | coupling with Intermediate 18B followed by formic acid as Intermediate 16, step 3 | 631.4 (method A) |
| 20BV | (S)-2-(3-(3-chloro-2-methyl-N-(1-(3-(3-methylpyridin-4-yl)phenyl)ethyl)phenylsulfonamido)propanamido)ethanesulfonic acid | 16AK | H$_2$N\~\~SO$_3$$^-$ Bu$_4$N$^+$ Coupling with HATU | 580.5/ 582.5 (method A) |
| 20BW | (S)-3-(N-(4-(3-chloro-2-methyl-N-(1-(3-(3-methylpyridin-4-yl)phenyl)ethyl)phenylsulfonamido)butanoyl)sulfamoyl)propanoic acid | 16 | HATU coupling with Intermediate 18E followed by LiOH as Example 11, step 1 | 622.4/ 624.4 (method A) |

TABLE 13-continued

| Compound No | Structure | Starting material | Reagent | MS (M + H)+ |
|---|---|---|---|---|
| 20BX | 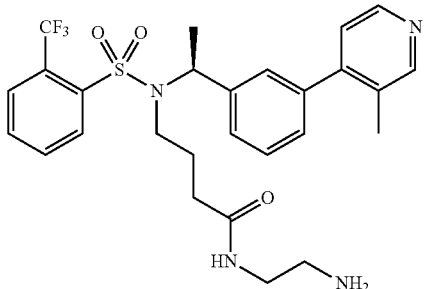<br>((S)-N-(2-aminoethyl)-4-(N-(1-(3-(3-methylpyridin-4-yl)phenyl)ethyl)-2-(trifluoromethyl)phenylsulfonamido)butanamide | Compound 15 | <br>and HATU coupling followed by HCl as Intermediate 3, step 3 | 549.4 (method A) |

Compound 20BO $^1$H NMR (CD$_3$OD) δ 10.0 (s, 1H), 9.60 (d, 1H), 8.85 (d, 1H), 8.0 (m, 3H), 7.70 (d, 1H), 7.65 (t, 1H), 7.55 (d, 1H), 7.40 (t, 1H), 5.07 (q, 1H), 3.45 (m, 2H), 3.30 (m, 2H), 2.85 (m, 2H), 2.60 (s, 3H), 2.00 (m, 2H), 1.77 (m, 1H), 1.65 (d, 3H), 1.40 (m, 1H).

Example 21

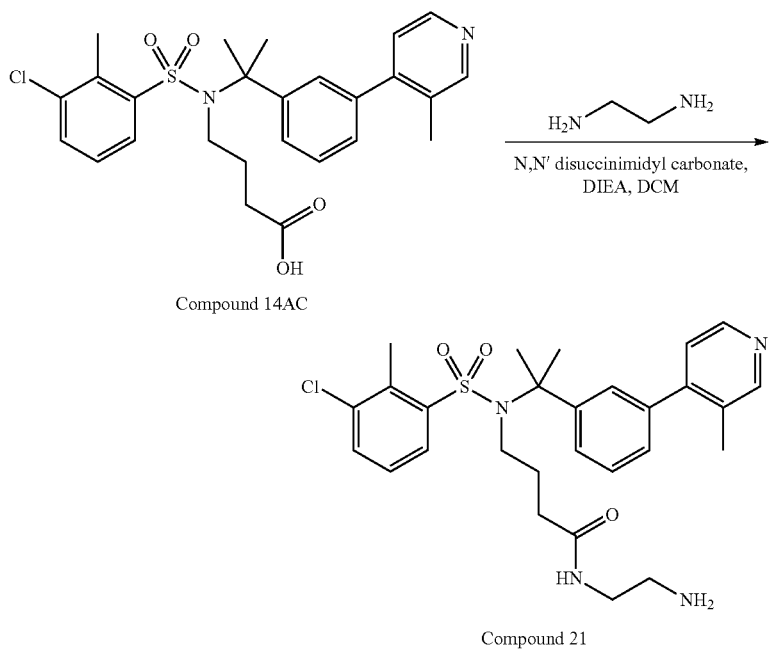

N-(2-Aminoethyl)-4-(3-chloro-2-methyl-N-(2-(3-(3-methylpyridin-4-yl)phenyl)propan-2-yl)-phenylsulfonamido)butanamide (Compound 21)

Compound 14AC (0.10 g, 0.20 mmol), and N,N' disuccinimidyl carbonate (0.62 g, 0.24 mmol) were suspended in DCM. DIEA (0.04 mL, 0.24 mmol) was added and the reaction was stirred at room temperature for 1 hour. Ethylene diamine (0.13 mL, 2.0 mmol) was added to the yellow solution and stirred at room temperature for 1 hour. The reaction was diluted with DCM and washed with H$_2$O (lx), brine (lx) and dried over magnesium sulfate. The reaction was filtered and concentrated in vacuo which gave the crude material as an yellow oil. The oil was purified by reverse phase flash chromatography (acetonitrile in H$_2$O with 0.25% formic acid) to afford Compound 21 (0.1 g, 89%) as white solid. LCMS (method A): m/z 543.5/545.5 (M+H)+. $^1$H NMR (CD$_3$OD): δ 8.45 (s, 1H), 8.41 (d, 1H), 7.82 (d, 1H), 7.61 (d, 1H), 7.51-7.46 (m, 1H), 7.42-7.37 (br m, 2H), 7.32-7.21 (m, 3H), 3.48-3.38 (m, 2H), 3.35 (t, 2H), 2.95 (t, 2H), 2.58 (s, 3H), 2.25 (s, 3H), 2.12 (t, 2H), 1.99-1.91 (m, 2H), 1.78 (s, 6H).

Following the method described above for Example 21 and substituting the appropriate starting materials and reagents, the following compounds were prepared as indicated in Table 14.

TABLE 14

| Cmpd No | Structure | Starting material | Reagent | MS (M + H)+ |
|---|---|---|---|---|
| 21AA | (R)-2-(4-(3-chloro-2-methyl-N-(2-(3-(3-methylpyridin-4-yl)phenyl)propan-2-yl)phenylsulfonamido)butanamido)-3-sulfopropanoic acid | 14AC | | 652.5/ 654.5 (method A) |
| 21AB | 2-(4-(3-chloro-2-methyl-N-(2-(3-(3-methylpyridin-4-yl)phenyl)propan-2-yl)phenylsulfonamido)butanamido) acetic acid | 14AC | | 558.5/ 560.5 (method A) |
| 21AC | N-(2-amino-2-oxoethyl)-4-(3-chloro-2-methyl-N-(2-(3-(3-methylpyridin-4-yl)phenyl)propan-2-yl) phenylsulfonamido)butanamide | 14AC | | 557.5/ 559.5 (method A) |

TABLE 14-continued

| Cmpd No | Structure | Starting material | Reagent | MS (M + H)+ |
|---|---|---|---|---|
| 21AD | 4-(3-chloro-2-methyl-N-(2-(3-(3-methylpyridin-4-yl)phenyl)propan-2-yl)phenylsulfonamido)-N-(2-(dimethylamino)ethyl)butanamide | 14AC | H2N–CH2CH2–N(CH3)2 | 571.5/ 573.5 (method A) |
| 21AE | (R)-2-(4-(3-chloro-2-methyl-N-(2-(3-(3-methylpyridin-4-yl)phenyl)propan-2-yl)phenylsulfonamido)butanamido)propanoic acid | 14AC | D-alanine | 572.5/ 574.5 (method A) |
| 21AF | (S)-2-(4-(3-chloro-2-methyl-N-(2-(3-(3-methylpyridin-4-yl)phenyl)propan-2-yl)phenylsulfonamido)butanamido)propanoic acid | 14AC | L-alanine | 572.5/ 574.5 (method A) |
| 21AG | 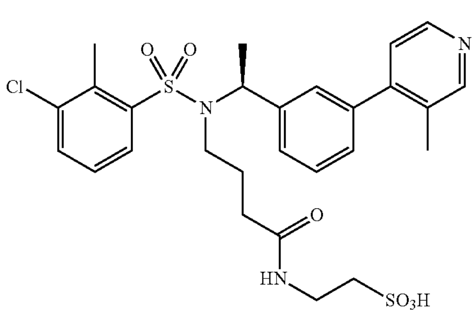 | 16 | H2N–CH2CH2–SO3H | 594.5/ 596.5 (method A) |

TABLE 14-continued

| Cmpd No | Structure | Starting material | Reagent | MS (M + H)+ |
|---|---|---|---|---|
| | (S)-2-(4-(3-chloro-2-methyl-N-(1-(3-(3-methylpyridin-4-yl)phenyl)ethyl)phenylsulfonamido)butanamido) ethanesulfonic acid | | | |
| 21AH | (structure) | 16 | H2N-CH2CH2-CO2H | 558.5/ 560.5 (method A) |
| | (S)-3-(4-(3-chloro-2-methyl-N-(1-(3-(3-methylpyridin-4-yl)phenyl)ethyl)phenylsulfonamido)butanamido) propanoic acid | | | |
| 21AI | (structure) | 16 | HO-CH2-CH(NH2)-COOH (serine) | 574.5/ 576.6 (method A) |
| | (S)-2-(4-(3-chloro-2-methyl-N-((S)-1-(3-(3-methylpyridin-4-yl)phenyl)ethyl)phenylsulfonamido) butanamido)-3-hydroxypropanoic acid | | | |
| 21AJ | (structure) | 16 | proline | 584.5/ 586.5 (method A) |
| | (S)-1-(4-(3-chloro-2-methyl-N-((S)-1-(3-(3-methylpyridin-4-yl)phenyl)ethyl)phenylsulfonamido) butanoyl)pyrrolidine-2-carboxylic acid | | | |

TABLE 14-continued

| Cmpd No | Structure | Starting material | Reagent | MS (M + H)+ |
|---|---|---|---|---|
| 21AK | (S)-2,2'-((4-(3-chloro-2-methyl-N-(1-(3-(3-methylpyridin-4-yl)phenyl)ethyl)phenylsulfonamido)butanoyl)azanediyl)diacetic acid | 16 | iminodiacetic acid (HOOC-CH2-NH-CH2-COOH) | 602.5/ 604.5 (method A) |
| 21AL | (S) 2-(3-(4-(3-chloro-2-methyl-N-(1-(3-(3-methylpyridin-4-yl)phenyl)ethyl)phenylsulfonamido)butanamido)ethylsulfonamido) propanoic acid | 16 | Coupling with Intermediate 18C followed by formic acid as Intermediate 16, step 3 | 665.5/ 667.4 (method A) |
| 21AM | (S)-2-(3-(4-(3-chloro-2-methyl-N-(1-(3-(3-methylpyridin-4-yl)phenyl)ethyl)phenylsulfonamido)butanamido)propanamido)acetic acid | 21AH | glycine (H2N-CH2-COOH) | 615.6/ 617.5 (method A) |
| 21AN | 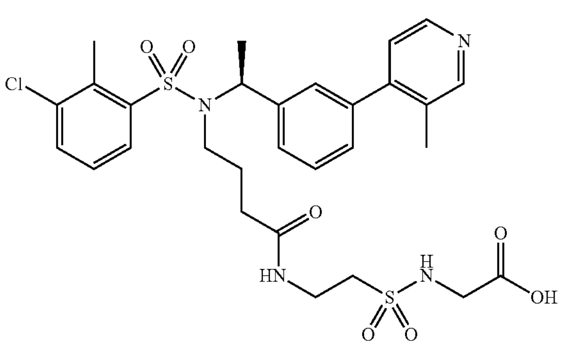 [SMILES: Cc1cnccc1-c1cccc([C@H](C)N(CCCC(=O)NCCS(=O)(=O)NCC(=O)O)S(=O)(=O)c2cccc(Cl)c2C)c1] | 16 | Coupling with Intermediate 18 followed by LiOH as Example 11, step 1 | 651.5/ 653.5 (method A) |

TABLE 14-continued

| Cmpd No | Structure | Starting material | Reagent | MS (M + H)+ |
|---|---|---|---|---|
| | (S) 2-(3-(4-(3-chloro-2-methyl-N-(1-(3-(3-methylpyridin-4-yl)phenyl)ethyl)phenylsulfonamido)butanamido)ethylsulfonamido) acetic acid | | | |
| 21AO | 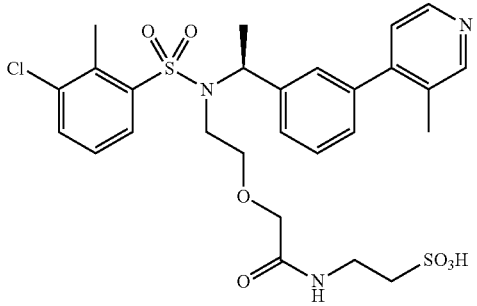 [SMILES: Cc1cnccc1-c1cccc([C@H](C)N(CCOCC(=O)NCCS(=O)(=O)O)S(=O)(=O)c2cccc(Cl)c2C)c1] <br> (S)-2-(2-(2-(3-Chloro-2-methyl-N-(1-(3-(3-methylpyridin-4-yl)phenyl)ethyl)phenylsulfonamido) ethoxy)acetamido)ethanesulfonic acid | 16AM | 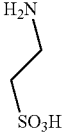 | 610.5/ 612.5 (method A) |
| 21AP | 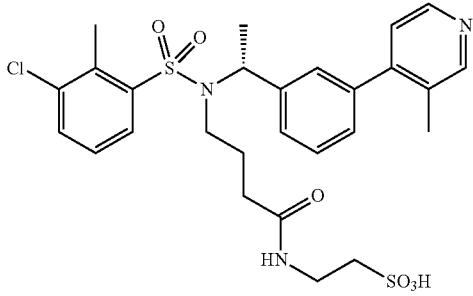 [SMILES: Cc1cnccc1-c1cccc([C@@H](C)N(CCCC(=O)NCCS(=O)(=O)O)S(=O)(=O)c2cccc(Cl)c2C)c1] <br> (R)-2-(4-(3-Chloro-2-methyl-N-(1-(3-(3-methylpyridin-4-yl)phenyl)ethyl)phenylsulfonamido)butanamido)ethane-sulfonic acid | 16AA | 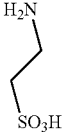 | 594.5/ 596.5 (method A) |
| 21AQ | 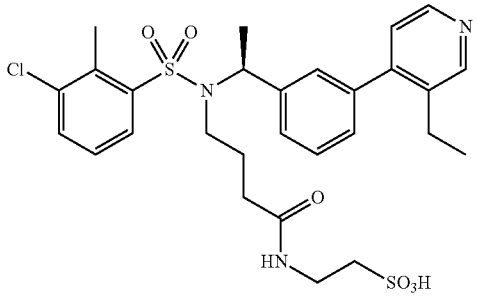 [SMILES: CCc1cnccc1-c1cccc([C@H](C)N(CCCC(=O)NCCS(=O)(=O)O)S(=O)(=O)c2cccc(Cl)c2C)c1] <br> (S)-2-(4-(3-chloro-N-(1-(3-(3-ethylpyridin-4-yl)phenyl)ethyl)-2-methylphenylsulfonamido)butanamido)ethanesulfonic acid | 16AB |  | 608.5/ 610.5 (method A) |
| 21AR | 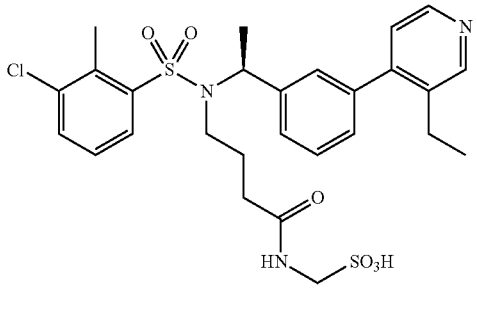 [SMILES: CCc1cnccc1-c1cccc([C@H](C)N(CCCC(=O)NCS(=O)(=O)O)S(=O)(=O)c2cccc(Cl)c2C)c1] | 16AB | 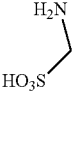 | 594.5/ 596.5 (method A) |

TABLE 14-continued

| Cmpd No | Structure | Starting material | Reagent | MS (M + H)+ |
|---|---|---|---|---|
| 21AS |  (S)-(4-(3-chloro-N-(1-(3-(3-ethylpyridin-4-yl)phenyl)ethyl)-2-methylphenylsulfonamido)butanamido)methanesulfonic acid | 16AB | H$_2$N-CH$_2$CH$_2$-NH-Boc Coupling followed by HCl as Intermediate 3, step 3 | 543.6/ 545.6 (method A) |
| 21AT | (S)-N-(2-aminoethyl)-4-(3-chloro-N-(1-(3-(3-ethylpyridin-4-yl)phenyl)ethyl)-2-methylphenylsulfonamido) butanamide (S) 2-(3-(4-(3-chloro-2-methyl-N-(1-(3-(3-ethylpyridin-4-yl)phenyl)ethyl)phenylsulfonamido)butanamido)ethylsulfonamido) acetic acid | 16AB | Coupling with Intermediate 18 followed by LiOH as Example 11, step 1 | 665.5/ 667.5 (method A) |

Example 22

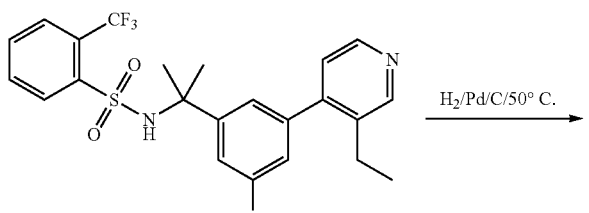

Compound 2CC

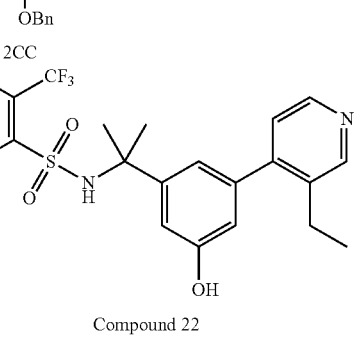

Compound 22

N-(2-(3-(3-Ethylpyridin-4-yl)-5-hydroxyphenyl) propan-2-yl)-2-(trifluoromethyl)benzenesulfonamide (Compound 22)

To a solution of Compound 2CC (600 mg, 1.1 mmol) in EtOH (50 mL) was added Pd/C (0.5 g, 50%) and the reaction mixture was stirred overnight at 50° C. under H$_2$ (50 psi). After LCMS showed the starting material was consumed completely, the mixture was filtered and the filtrate was concentrated to give the crude product, which was purified by preparative HPLC to give Compound 22. (250 mg, 50%). LCMS (method C): m/z 465.1 (M+H)+. $^1$H NMR (DMSO-d6): δ 9.47 (s, 1H), 8.48 (s, 1H), 8.38 (d, 1H), 8.30 (s, 1H), 7.97 (d, 1H), 7.84 (d, 1H), 7.22 (m, 2H), 7.03-7.04 (d, 1H), 6.80 (s, 1H), 6.76 (s, 1H), 6.49 (s, 1H), 2.54-2.59 (m, 2H), 1.47 (s, 6H), 1.02-1.06 (m, 3H).

Following the method described above for Example 22 and substituting the appropriate starting material, the following compound was prepared using conditions specified in Table 15

TABLE 15

| Cmpd No | Structure | Starting material | Reagent | MS (M + H)+ |
|---|---|---|---|---|
| 22AA | (S)-2-(4-(N-(1-(3-(3-hydroxypyridin-4-yl)phenyl)ethyl)-2-methylphenylsulfonamido)butanamido)ethanesulfonic acid | 20BQ | Pd/C H₂ (1 atm) Room temp. | 562.4 (method A) |

Example 23

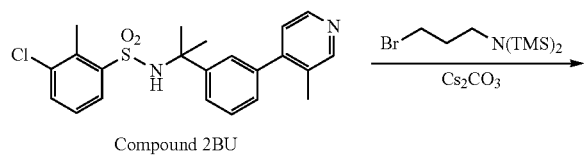

Compound 2BU

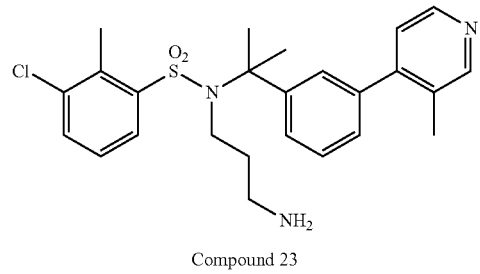

Compound 23

N-(3-aminopropyl)-3-chloro-2-methyl-N-(2-(3-(3-methylpyridin-4-yl)phenyl)propan-2-yl)benzenesulfonamide (Compound 23)

To a pressure tube was added Compound 2BU (0.50 g, 1.2 mmol), DMF (6 mL), cesium carbonate (1.4 g, 4.2 mmol) and 3-bromo-N,N'-bis(trimethylsilyl)propan-1-amine (0.48 g, 3.6 mmol). The mixture was degassed with nitrogen for approximately 2 minutes and the tube sealed with a septum. The mixture was stirred overnight at 90° C. using an aluminum heating block. Additional 3-bromo-N,N'-bis(trimethylsilyl)propan-1-amine (0.48 g, 3.6 mmol) was added and heating continued for eight hours. The mixture was cooled to room temperature, poured into water and extracted with EtOAc (3X). The combined extracts were washed with brine, dried with sodium sulfate, filtered and evaporated to dryness. Purification by silica gel chromatography (0-5% 7 M NH₃ in MeOH/DCM) yielded Compound 23 (0.32 g, 57%). LCMS (Method A): m/z 472.5/474.5 (M+H)+. ¹H NMR (CDCl₃) δ 8.52 (s, 1H), 8.49 (d, 1H), 7.87 (dd, 1H), 7.53 (d, 1H), 7.47-7.43 (m, 1H), 7.41-7.35 (m, 2H), 7.11 (d, 1H), 3.40-3.34 (m 2H), 2.68 (s, 3H), 2.54 (t, 2H), 2.26 (s, 3H), 1.68-1.57 (m, 8H).

Following the method described above for Example 23 and substituting the appropriate starting material, the following compound was prepared using conditions specified in Table 16.

TABLE 16

| Cmpd No | Structure | Starting material | MS (M + H)+ |
|---|---|---|---|
| 23AA | N-(3-aminopropyl)-3-chloro-2-methyl-N-(3-(3-methylpyridin-4-yl)benzyl)benzenesulfonamide | 2CE | 444.3/ 446.3 (method A) |

Example 24

Scheme 4

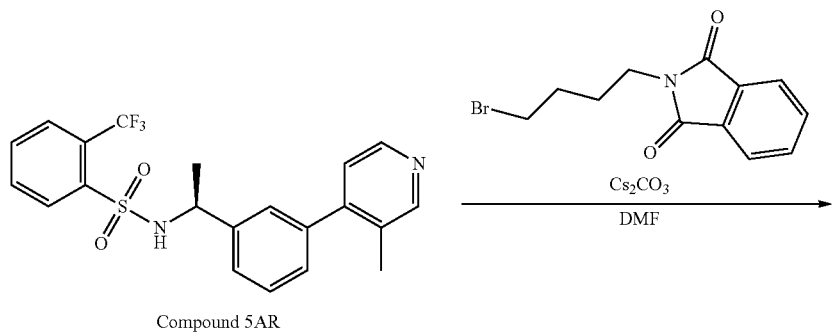

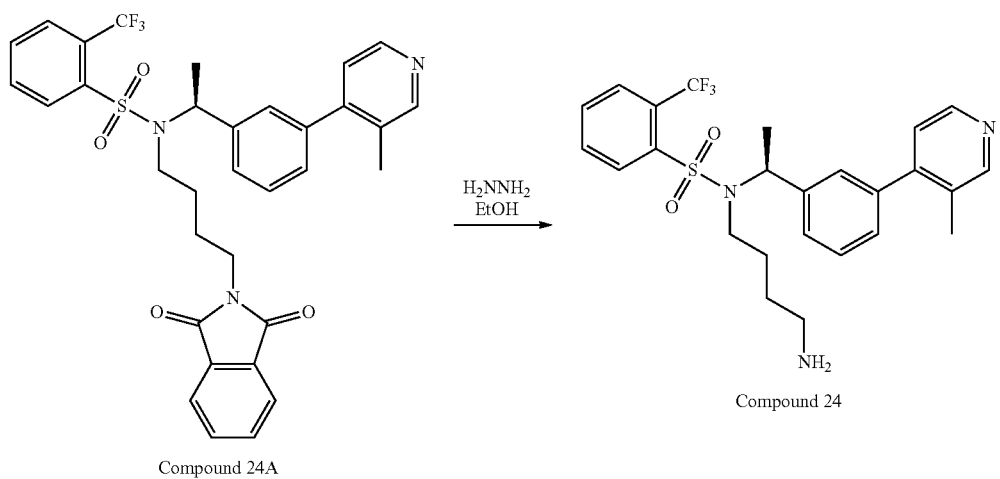

(S)—N-(4-(1,3-dioxoisoindolin-2-yl)butyl)-N-(1-(3-(3-methylpyridin-4-yl)phenyl)ethyl)-2-(trifluoromethyl)benzenesulfonamide (Compound 24A)

To a solution of Compound 5AR (0.47 g, 1.1 mmol) in DMF (4 mL) was added 2-(4-bromobutyl)isoindoline-1,3-dione (0.47 g, 1.68 mmol) and cesium carbonate (0.69 g, 2.24 mmol). The reaction mixture was stirred at room temperature overnight and was partitioned between EtOAc and water. The organic layer was washed with brine, dried over $Na_2SO_4$ and concentrated to a residue which was purified by silica gel chromatography (0-50% EtOAc/hexanes) to afford Compound 24A (0.53 g, 76%). LCMS (method A): m/z 622.2 $(M+H)^+$.

(S)—N-(4-aminobutyl)-N-(1-(3-(3-methylpyridin-4-yl)phenyl)ethyl)-2-(trifluoromethyl)Benzenesulfonamide (Compound 24)

To Compound 24A (0.53 g, 0.85 mmol) in EtOH (15 mL) was added hydrazine (0.5 mL). The reaction was stirred at room temperature overnight and filtered. The filtrate was concentrated. The residue was purified by silica gel chromatography (0-6% MeOH/DCM) to afford Compound 24 (0.29 g, 69%). LCMS (method A): m/z 492.5 $(M+H)^+$. $^1$H NMR (400 MHz, $d^4$-MeOD): δ 8.45 (s, 1H), 8.40 (d, 1H), 8.19 (dd, 1H), 7.94 (d, 1H), 7.78 (m, 2H), 7.47 (d, 2H), 7.32 (m, 1H), 7.25 (s, 1H), 7.20 (d, 1H), 5.25 (q, 1H), 2.48 (t, 2H), 2.25 (s, 3H), 1.54 (d, 3H), 1.51-1.12 (m, 4H).

Following the method described above for Example 24, step 2 and substituting the appropriate starting material, the following compounds were prepared using conditions specified in Table 17.

TABLE 17

| Cmpd No | Structure | Starting material | Reagent | MS (M + H)+ |
|---|---|---|---|---|
| 24AA | N-(5-amino-1-(3-(3-methylpyridin-4-yl)phenyl)pentyl)-2-(trifluoromethyl)benzenesulfonamide | 6AE | Only step 2 hydrazine | 478.5 (method A) |
| 24AB | (S)-N-(4-aminobutyl)-N-(1-(3-(3-ethylpyridin-4-yl)phenyl)ethyl)-2-(trifluoromethyl)benzenesulfonamide | 5AQ | Same as Example 24 | 506.3 (method A) |
| 24AC | (S)-N-(4-aminobutyl)-3-chloro-N-(1-(3-(3-ethylpyridin-4-yl)phenyl)ethyl)-2-methylbenzenesulfonamide | 7AE | Only step 2 hydrazine | 486.3/ 488.3 (method A) |

Example 25

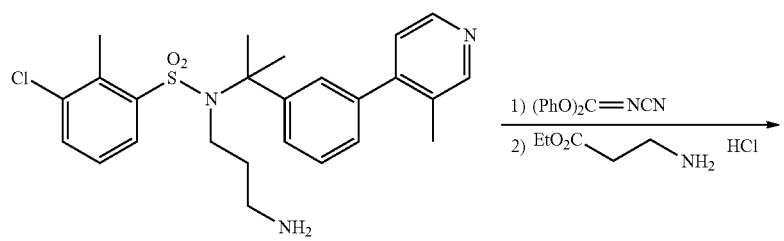

Compound 23

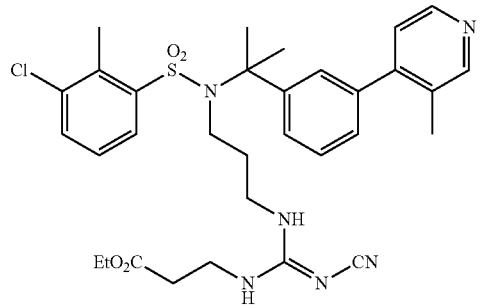

Compound 25A

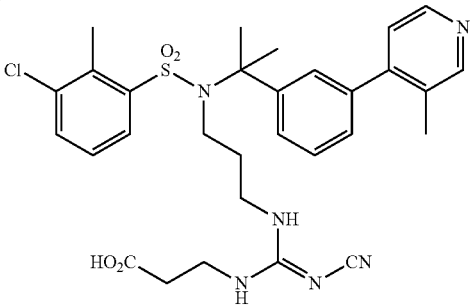

Compound 25

Ethyl (E)-3-(3-(3-((3-chloro-2-methyl-N-(2-(3-(3-methylpyridin-4-yl)phenyl)propan-2-yl)phenyl)sulfonamido)propyl)-2-cyanoguanidino)propanoate (Compound 25A)

To a vial was added Compound 23 (27 mg, 0.06 mmol), acetonitrile (1 mL), diisopropylethyl amine (15 mg, 0.14 mmol) and diphenyl N-cyanocarbodiimidate (14 mg, 0.06 mmol). The vial was capped and the mixture stirred for 90 minutes. β-alanine ethylester hydrochloride (13 mg, 0.086 mmol) was added and the mixture stirred for five hours. Additional β-alanine ethylester hydrochloride (26 mg, 0.18 mmol) and diisopropylethyl amine (30 mg, 0.28 mmol) were added and the mixture stirred overnight. The reaction mixture was concentrated in vacuo and the residue purified by silica gel chromatography (0-5% 2 M $NH_3$ in MeOH/DCM) followed by purification by reversed phase HPLC (19×100 mm C-18, 10 to 80% acetonitrile in water with 0.1% formic acid) to yield Compound 25A (12 mg, 33%). LCMS (Method A): m/z 639.6/641.6 (M+H)$^+$. $^1$H NMR (CDCl$_3$) δ 8.52 (bs, 1H), 7.86 (d, 1H), 7.50 (d, 1H), 7.46-7.09 (m, 7H), 6.01 (bs, 1H), 5.74 (s, 1H), 4.12 (q, 2H), 3.50-3.30 (m 4H), 3.11 (d, 2H), 2.63 (s, 3H), 2.55 (t, 2H), 2.25 (s, 6H), 1.83-1.68 (m, 8H), 1.58-1.41 (m, 2H), 1.24 (t, 4H).

(E)-3-(3-(3-((3-chloro-2-methyl-N-(2-(3-(3-methylpyridin-4-yl)phenyl)propan-2-yl)phenyl)sulfonamido)propyl)-2-cyanoguanidino)propanoic acid (Compound 25)

Following procedure as described in Example 11, step 1, Compound 25A (56 mg, 0.09 mmol) was converted to Compound 25 (12 mg, 23%). LCMS (method A): m/z 611.6/613.5 (M+H)$^+$. $^1$H NMR (DMSO-d6) δ 8.51 (s, 1H), 8.47 (d, 1H), 7.79 (d, 1H), 7.71 (d, 1H), 7.49-7.44 (m, 1H), 7.44-7.36 (m, 3H), 7.30-7.26 (m, 1H), 7.20 (d, 1H), 7.04 (m, 1H), 6.88 (t, 1H), 3.30-3.20 m, 4H), 2.99-2.92 (m, 2H), 2.55 (s, 3H), 2.40 (t, 2H), 2.22 (s, 3H), 1.77-1.67 (m, 8H).

Example 26

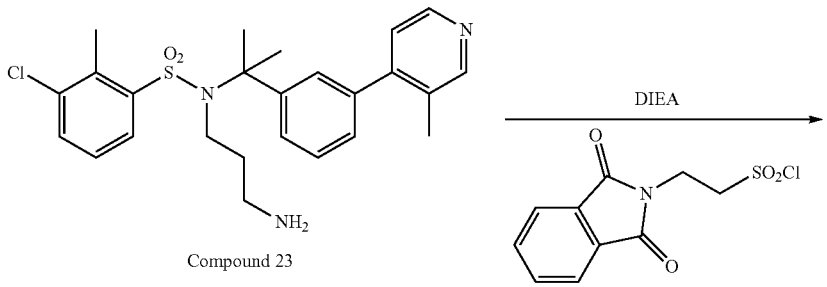

Compound 23

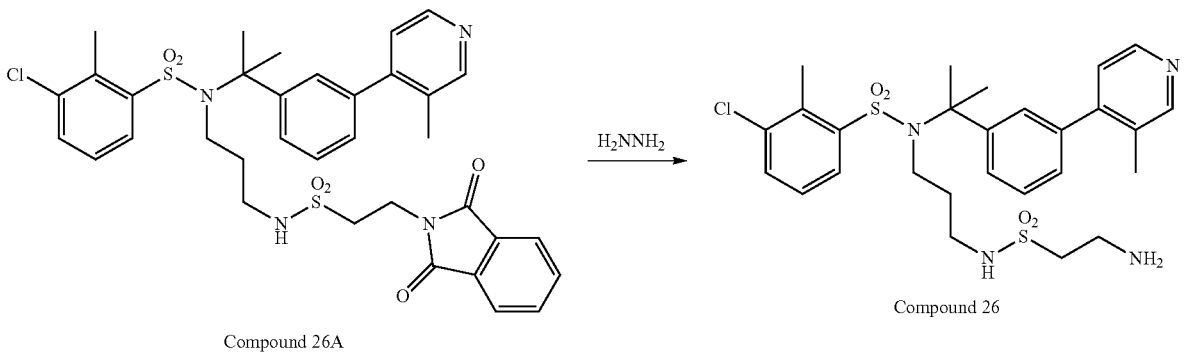

Compound 26A → Compound 26

253

3-Chloro-N-(3-((2-(1,3-dioxoisoindolin-2-yl)ethyl) sulfonamido)propyl)-2-methyl-N-(2-(3-(3-methylpyridin-4-yl)phenyl)propan-2-yl)benzenesulfonamide (Compound 26A)

To Compound 23 (0.10 g, 0.21 mmol) in DCM (2 mL) at 0° C. was added diisopropyl ethylamine (0.41 g, 0.32 mmol) followed by 2-phthalimidoethane sulfonylchloride (0.064 g, 0.23 mmol) and the mixture stirred under nitrogen for 40 minutes. The reaction mixture was poured into water and extracted with DCM (3X). The combined extracts were washed with brine, dried with sodium sulfate, filtered and evaporated to dryness. Purification by silica gel chromatography (0-75% EtOAc/hexanes) yielded Compound 26A (0.13 g, 86%). LCMS (Method A): m/z 709.5/711.5 (M+H)+. 1H NMR (CDCl3) δ 8.51 (s, 1H), 8.47 (d, 1H), 7.89-7.80 (m, 3H), 7.76-7.70 (m, 2H), 7.5 (d, 1H), 7.47-7.36 (m, 3H), 7.28-7.19 (m, 2H), 7.12 (d, 1H), 4.88 (t, 1H), 4.12-4.04 (m, 2H), 3.45 (t, 2H), 3.31 (t, 2H), 3.04 (q, 2H), 2.65 (s, 3H), 2.25 (s, 3H), 1.84-1.70 (m, 7H), 1.63 (s, 1H).

254

N-(3-((2-aminoethyl)sulfonamido)propyl)-3-chloro-2-methyl-N-(2-(3-(3-methylpyridin-4-yl)phenyl) propan-2-yl)benzenesulfonamide (Compound 26)

To Compound 26A (0.41 g, 0.58 mmol) in ethanol (5 mL) was added hydrazine (100 uL, 3.1 mmol) and the mixture stirred under nitrogen overnight. A thick white precipitate had formed. The reaction mixture was evaporated to dryness and the residue triturated in DCM then filtered. The filtrate was evaporated to dryness yielding Compound 26 (0.34 g, 100%). LCMS (method A): m/z 579.5/581.5 (M+H)+. 1H NMR (CDCl3) δ 8.53 (s, 1H), 8.51 (d, 1H), 7.85 (d, 1H), 7.56 (d, 1H), 7.45-7.35 (m, 3H), 7.25-7.19 (m, 2H), 7.12 (d, 1H), 3.45 (t, 2H), 3.20-3.14 (m, 2H), 3.08-2.98 (m, 4H), 2.64 (s, 3H), 2.25 (s, 3H), 1.81-1.69 (m, 8H).

Following the method described above for Example 26 and substituting the appropriate starting materials and reagents, the following compounds were prepared as indicated in Table 18.

TABLE 18

| Compound No | Structure | Starting material | Reagent | MS (M + H)+ |
|---|---|---|---|---|
| 26AA | (S)-4-(3-chloro-2-methyl-N-(1-(3-(3-methylpyridin-4-yl)phenyl)ethyl)phenylsulfonamido)butanamido-2-(N-ethylsulfamoyl)acetic acid | 20AZ | Cl-S(=O)(=O)-CH2-C(=O)-O-CH3 And LiOH in step 2 as described in Exmple 11, step 1 | 651.5/ 653.5 (method A) |
| 26AB | (S)-4-(3-chloro-2-methyl-N-(1-(3-(3-methylpyridin-4-yl)phenyl)ethyl)phenylsulfonamido)butanamido-2-(N-ethylsulfamoyl)propanoic acid | 20AZ | Cl-S(=O)(=O)-CH2CH2-C(=O)-O-CH3 And LiOH in step 2 as described in Exmple 11, step 1 | 665.5/ 667.5 (method A) |

TABLE 18-continued

| Compound No | Structure | Starting material | Reagent | MS (M + H)+ |
|---|---|---|---|---|
| 26AC | (S)-Methyl-4-(3-chloro-2-methyl-N-(1-(3-(3-methylpyridin-4-yl)phenyl)ethyl)phenylsulfonamido)butanamido-2-(N-(2-(2-aminoethoxy)ethylsulfamoyl)acetate | 20AT | (chlorosulfonyl acetate methyl ester structure) Only step 1 | 723.6/ 725.6 (method A) |
| 26AD | (S)-4-(3-chloro-2-methyl-N-(1-(3-(3-methylpyridin-4-yl)phenyl)ethyl)phenylsulfonamido)butanamido-2-(N-(2-(2-aminoethoxy)ethylsulfamoyl)acetic acid | 26AC | LiOH Only step 2 | 709.6/ 711.6 (method A) |
| 26AE | (S)-3-(N-(4-(3-chloro-N-(1-(3-(3-ethylpyridin-4-yl)phenyl)ethyl)-2-methylphenylsulfonamido)butyl)sulfamoyl) propanoic acid | 24AC | (3-chlorosulfonyl propanoate methyl ester structure) And LiOH in step 2 as described in Exmple 11, step 1 | 622.5/ 624.4 (method A) |

Example 27

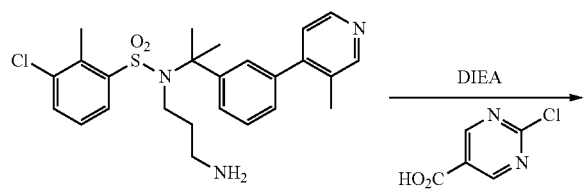

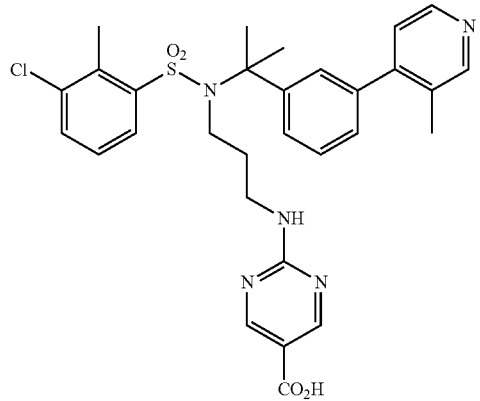

Compound 27

2-((3-((3-chloro-2-methyl-N-(2-(3-(3-methylpyridin-4-yl)phenyl)propan-2-yl)phenyl)sulfonamido)propyl)amino)pyrimidine-5-carboxylic acid (Compound 27)

To Compound 23 (75 mg, 0.16 mmol) in a vial was added acetonitrile (1 mL), 2-chloro-5-carpoxypurimidine (30 mg, 0.19 mmol) and diisopropyl ethylamine (0.10 g, 0.79 mmol). The vial was capped and the mixture heated to 80° C. while stirring overnight.

The mixture was evaporated to dryness and the residue purified by silica gel chromatography (0-10% MeOH/DCM with 0.5% HOAc). The crude product was taken up in 95:5 DCM/MeOH and washed with water while the pH was adjusted to 7.0 using saturated aqueous sodium bicarbonate. The aqueous phase was extracted with DCM (3X). The combined organic phases were washed with brine, dried with sodium sulfate, filtered, and concentrated in vacuo. The resulting yellow solid was purified by silica gel chromatography (0-5% MeOH/DCM) yielding Compound 27 (27 mg, 29%). LCMS (Method A): m/z 594.5/596.5 (M+H)$^+$. $^1$H NMR (CDCl$_3$) δ 8.81 (d, 2H), 8.56 (s, 1H), 8.51 (d, 1H), 7.91 (d, 1H), 7.54 (d, 1H), 7.46-7.41 (m, 1H), 7.38-7.32 (m, 2H), 7.28-7.14 (m, 3H), 3.44-3.31 (m 4H), 2.67 (s, 3H), 1.94-1.84 (m, 2H), 1.74 (s, 6H).

Following the method described above for Example 27 and substituting the appropriate starting materials and reagents, the following compounds were prepared as indicated in Table 19

TABLE 19

| Compound No | Structure | Starting material | Reagent | MS (M + H)$^+$ |
|---|---|---|---|---|
| 27AA | 2-((2-(4-(3-chloro-2-methyl-N-(2-(3-(3-methylpyridin-4-yl)Phenyl)propan-2-yl)phenylsulfonamido)butanamido)ethyl)amino)pyrimidine-5-carboxylic acid | 21 | CO$_2$H, Cl-pyrimidine | 665.6/ 667.6 (method A) |
| 27AB | 4-(3-chloro-2-methyl-N-(2-(3-(3-methylpyridin-4-yl)phenyl)propan-2-yl)phenylsulfonamido)-N-(2-guanidinoethyl)butanamide | 21 | H$_2$N-C(=NH)-pyrazole | 585.6/ 587.6 (method A) |

TABLE 19-continued

| Compound No | Structure | Starting material | Reagent | MS (M + H)+ |
|---|---|---|---|---|
| 27AC | 3-chloro-N-(3-((2-guanidinoethyl)sulfonamido)propyl)-2-methyl-N-(2-(3-(3-methylpyridin-4-yl)phenyl)propan-2-yl)benzenesulfonamide | 26 | H2N-C(=NH)-N(pyrazole) | 621.6/ 623.6 (method A) |
| 27AD | 2-(4-(3-chloro-2-methyl-N-(2-(3-(3-methylpyridin-4-yl)phenyl)propan-2-yl)phenylsulfonamido)butanamido)-N,N,N-trimethylethanaminium | 21 | MeI | 585.4/ 587.6 (method A) |
| 27AE | (S)-2-(4-(3-chloro-N-(1-(3-(3-ethylpyridin-4-yl)phenyl)ethyl)-2-methylphenylsulfonamido)butanamido)-N,N,N-trimethylethanaminium | 21AS | MeI | 585.6/ 587.6 (method A) |

Example 28

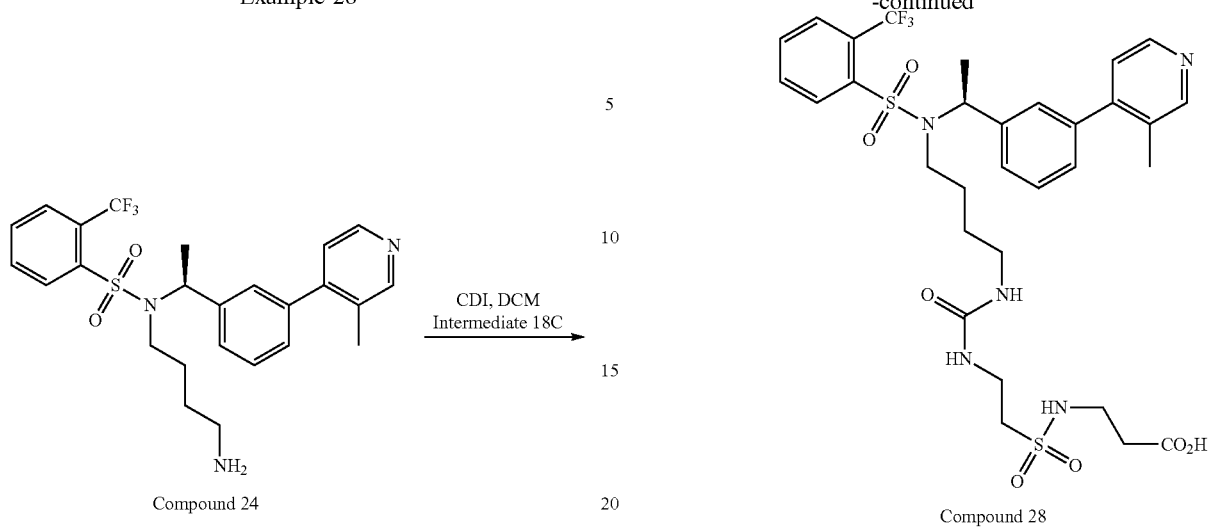

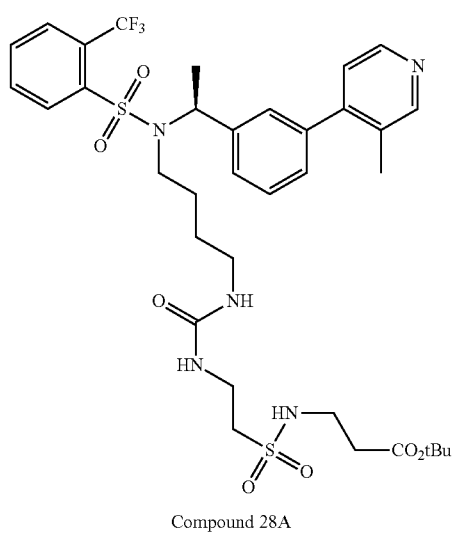

(S)-tert-butyl-2-(3-(4-(N-(1-(3-(3-methylpyridin-4-yl)phenyl)ethyl)-2-(trifluoromethyl)phenylsulfonamido)butyl)ureido)ethanesulfonamidopropanoate (Compound 28A)

To Compound 24 (80 mg, 0.16 mmol) in DCM (1 mL) was added CDI (32 mg, 0.2 mmol) and the reaction was stirred at room temperature for 45 minutes. After the solvent was removed in vacuo, half of the residue was dissolved in DMF (1 mL), followed by the addition of Intermediate 18C (24 mg, 0.1 mmol) and DIEA (0.02 mL, 0.12 mmol). The reaction mixture was stirred at room temperature overnight and partitioned between EtOAc and water. The organic layer was washed with water and brine, dried over $Na_2SO_4$, and concentrated. The residue was purified by silica gel chromatography (0-5% MeOH/DCM) to afford Compound 28A (42 mg, 68%). LCMS (method A): m/z 770.6 (M+H)$^+$.

(S)-2-(3-(4-(N-(1-(3-(3-methylpyridin-4-yl)phenyl)ethyl)-2-(trifluoromethyl)phenylsulfonamido)butyl)ureido)ethanesulfonamidopropanoic acid (Compound 28)

Following the procedure described in Intermediate 16, step 3, using TFA, Compound 28A (42 mg) was converted to Compound 28. The residue was purified by reverse phase HPLC. The fractions containing desired product were combined, an HCl solution (0.2 mL, 4 M in dioxane) was added and the mixture was concentrated. The residue was dissolved in water, and washed with ethyl ether. The aqueous layer was lyophilized to afford the desired product (10 mg, 26%). LCMS (method A): m/z 714.6 (M+H)$^+$. $^1$H NMR (CD$_3$OD): δ 8.45 (s, 1H), 8.40 (d, 1H), 8.17 (dd, 1H), 7.92 (dd, 1H), 7.77 (m, 2H), 7.47 (d, 2H), 7.31 (m, 1H), 7.26 (s, 1H), 7.21 (d, 1H), 5.25 (q, 1H), 3.50 (t, 2H), 3.17 (t, 2H), 2.93 (m, 2H), 2.53 (t, 2H), 2.25 (s, 3H), 1.54 (d, 3H), 1.49-1.14 (m, 2H).

Following the method described above for Example 28 and substituting the appropriate starting materials and reagents, the following compounds were prepared as indicated in Table 20.

TABLE 20

| Compound No | Structure | Starting Material | Reagent | MS (M + H)+ |
|---|---|---|---|---|
| 28AA | (S)-2-(3-(4-(N-(1-(3-(3-methylpyridin-4-yl)phenyl)ethyl)-2-(trifluoromethyl) phenylsulfonamido)butyl)ureido) ethanesulfonamido acetic acid | Compound 24 | Intermediate 18B Followed by formic acid as Intermediate 16, step 3 | 700.2 (Method A) |
| 28AB | (S)-2-(3-(4-(N-(1-(3-(3-methylpyridin-4-yl)phenyl)ethyl)-2-(trifluoromethyl)phenyl-sulfonamido)butyl)ureido)ethanesulfonic acid | 24 | H₂N-CH₂CH₂-SO₃H  Only step 1 | 643.5 (Method A) |
| 28AC | (S)-(3-(4-(N-(1-(3-(3-methylpyridin-4-yl)phenyl)ethyl)-2-(trifluoromethyl)phenyl-sulfonamido)butyl)ureido)methanesulfonic acid | 24 | H₂N-CH₂-SO₃H  Only step 1 | 629.5 (Method A) |

TABLE 20-continued

| Compound No | Structure | Starting Material | Reagent | MS (M + H)+ |
|---|---|---|---|---|
| 28AD | 2-(3-(2-(N-(3-((3-chloro-2-methyl-N-(2-(3-(3-methylpyridin-4-yl)phenyl)propan-2-yl)phenyl)sulfonamido)propyl)sulfamoyl)ethyl)ureido)ethane-1-sulfonic acid | 26 | H₂N–CH₂CH₂–SO₃H  Only step 1 | 730.5/ 732.5 (Method A) |
| 28AE | 3-(3-(2-(N-(3-((3-chloro-2-methyl-N-(2-(3-(3-methylpyridin-4-yl)phenyl)-propan-2-yl)phenyl)sulfonamido)-propyl)sulfamoyl)ethyl)ureido)propane-1-sulfonic acid | 26 | H₂N–(CH₂)₃–SO₃H  Only step 1 | 744.5/ 746.5 (Method A) |
| 28AF | (S)-17-((3-chloro-2-methylphenyl)sulfonyl)-18-(3-(3-methylpyridin-4-yl)phenyl)-4,12-dioxo-8-oxa-3,5,11,17-tetraazanonadecane-1-sulfonic acid | 20AT | H₂N–CH₂CH₂–SO₃H  Only step 1 | 738.6/ 740.6 (Method A) |

TABLE 20-continued

| Compound No | Structure | Starting Material | Reagent | MS (M + H)+ |
|---|---|---|---|---|
| 28AG | 2-(3-(5-(3-(3-methylpyridin-4-yl)phenyl)-5-(2-(trifluoromethyl)phenylsulfonamido)pentyl)ureido)ethanesulfonic acid | 24AA | H₂N-CH₂CH₂-SO₃H<br>Only step 1 | 629.5 (Method A) |
| 28AH | (S)-(3-(4-(N-(1-(3-(3-ethylpyridin-4-yl)phenyl)ethyl)-2-(trifluoromethyl)phenylsulfonamido)butyl)ureido)methanesulfonic acid | 24AB | H₂N-CH₂-SO₃H<br>Only step 1 | 643.3 (Method A) |
| 28AI | (3-(3-(3-chloro-2-methyl-N-(3-(3-methylpyridin-4-yl)benzyl)phenylsulfonamido)propyl)ureido)methanesulfonic acid | 23AA | H₂N-CH₂-SO₃H<br>Only step 1 | 581.4/583.4 (Method A) |

Example 29

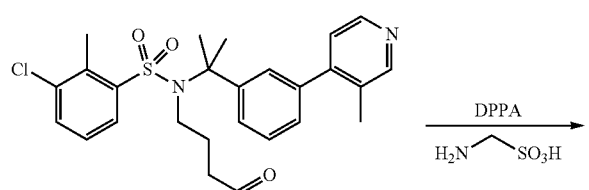

Compound 14AC

→ DPPA, $H_2N\text{-}SO_3H$

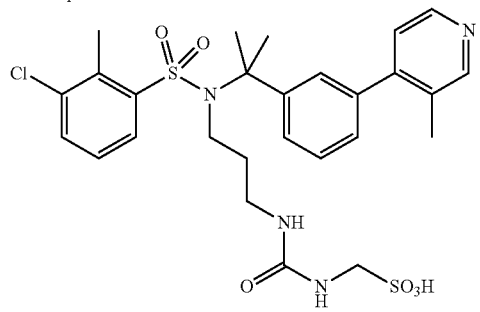

Compound 29

(3-(3-((3-Chloro-2-methyl-N-(2-(3-(3-methylpyridin-4-yl) phenyl) propan-2-yl) phenyl) sulfonamide) propyl) ureido) methanesulfonic acid (Compound 29)

A mixture of Compound 14AC (0.12 g, 0.20 mmoles), diphenyl phosphoryl azide (0.05 mL, 0.24 mmole), and TEA (0.14 mL, 1 mmole) in toluene (5 mL) was heated to 80° C. After 2 hours, aminomethanesulfonic acid (0.053 g, 0.4 mmol) was added and stirring was continued at 80° C. overnight. Reaction mixture was cooled to room temperature and concentrated in vacuo. The residue was dissolved in 1 mL DMSO and purified by MS-HPLC to afford the title compound (0.025 g, 21%). LCMS (method A) m/z 609.3/611.3 (M+H)$^+$. $^1$H NMR (CD$_3$OD) δ 8.78 (m, 2H), 7.99 (d, 1H), 7.87 (d, 1H), 7.65 (m, 3H), 7.54 (m, 1H), 7.42 (m, 1H), 7.33 (m, 1H), 5.5 (s, 2H), 4.15 (d, 1H), 3.41 (m, 2H), 2.92 (m, 2H), 2.63 (s, 3H), 2.49 (s, 3H), 1.79 (m, 5H), 1.7 (m, 2H).

Following the method described above for Example 29 and substituting the appropriate starting materials and reagents, the following compounds were prepared as indicated in Table 21.

TABLE 21

| Compound No | Structure | Starting Material | Reagent | MS (M + H)$^+$ |
|---|---|---|---|---|
| 29AA | 2-(3-(3-((3-Chloro-2-methyl-N-(2-(3-(3-methylpyridin-4-yl)phenyl)propan-2-yl)phenyl) sulfonamide)propyl)ureido)ethane-1-sulfonic acid | 14AC | H$_2$N~SO$_3$H | 623.3/ 625.3 (Method A) |
| 29AB | 3-Chloro-2-methyl-N-(2-(3-methylpyridin-4-yl)phenyl)propan-2-yl)-N-(3-(3-(2-sulfamoylethyl)ureido)propyl)benzenesulfonamide | 14AC | H$_2$N~SO$_2$NH$_2$ | 622.3/ 624.3 (Method A) |

TABLE 21-continued

| Compound No | Structure | Starting Material | Reagent | MS (M + H)+ |
|---|---|---|---|---|
| 29AC | ![structure] 3-(3-(3-((3-Chloro-2-methyl-N-(2-(3-(3-methylpyridin-4-yl)phenyl)sulfonamide) propyl)ureido)propane-1-sulfonic acid | 14AC | H₂N–CH₂CH₂CH₂–SO₃H | 637.3/ 639.3 (Method A) |
| 29AD | ![structure] (3-(3-(3-chloro-2-methyl-N-(3-(3-methylpyridin-4-yl)phenethyl)phenylsulfonamido) propyl)ureido)methanesulfonic acid | 14AF | H₂N–CH₂–SO₃H | 595.3/ 597.3 (Method A) |

Example 30

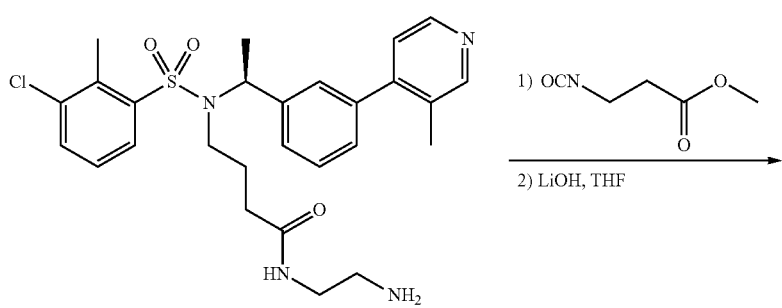

Compound 20AZ

1) OCN–CH₂CH₂–C(O)–O–CH₃
2) LiOH, THF

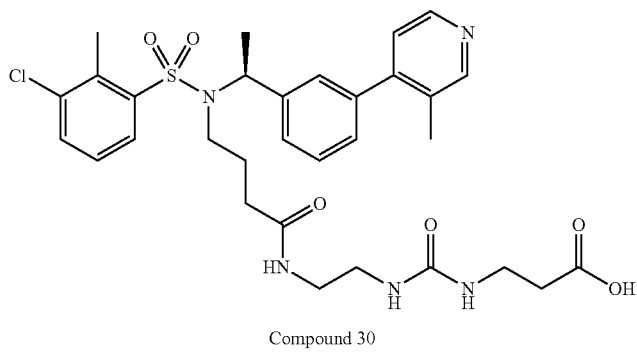

Compound 30

(S)-3-((3-Chloro-2-methylphenyl)sulfonyl)-2-(3-(3-methylpyridin-4-yl)phenyl)-7,12-dioxo-3,8,11,13-tetraazahexadecan-16-oic acid (Compound 30)

Ethyl 3-isocyanatopropionate (0.013 mL, 0.095 mmol) was added to a solution of Compound 20AZ (0.050 g, 0.095 mmol) in DCM (0.5 mL) and stirred at room temperature for 3 hours. The reaction was concentrated in vacuo. The residue was dissolved in tetrahydrofuran (0.5 mL) and followed by addition of a 1 M lithium hydroxide solution (0.25 mL) and stirring was continued at 50° C. for 2 hours. The crude reaction was concentrated in vacuo to give a brown oil which was dissolved in H$_2$O and purified by reverse phase flash chromatography (acetonitrile/H$_2$O with 0.25% formic acid) to afford Compound 30 (0.024 g, 39%) as a white solid. LCMS (method A): m/z 644.5/646.5 (M+H)$^+$. $^1$H NMR (CD$_3$OD): δ 8.45 (s, 1H), 8.40 (d, 1H), 7.99 (dd, 1H), 7.61 (dd, 1H), 7.45 (t, 1H), 7.41-7.28 (m, 3H), 7.20 (d, 1H), 7.01 (s, 1H), 5.04 (q, 1H), 3.34 (t 2H), 3.24-3.11 (m, 6H), 2.54 (s, 3H), 2.45, (t, 2H), 2.22 (s, 3H), 2.14-1.98 (m, 2H), 1.86-1.73 (m, 1H), 1.62 (d, 3H), 1.60-1.52 (m, 1H).

Example 31

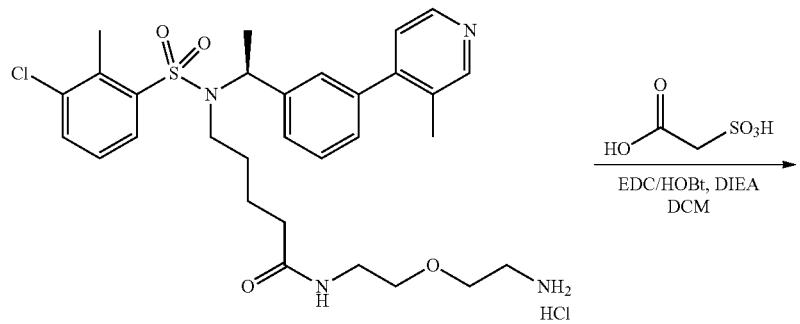

Compound 20AT

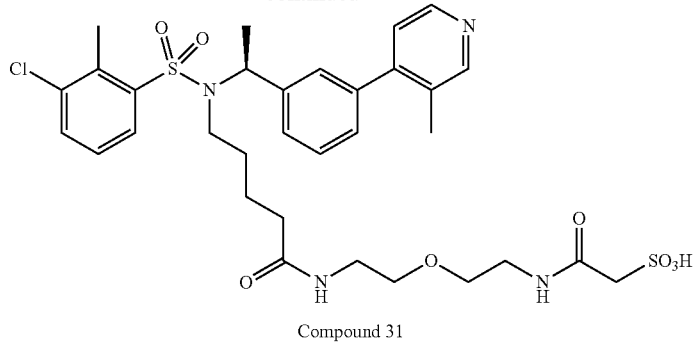

Compound 31

(S)-15-((3-chloro-2-methylphenyl)sulfonyl)-16-(3-(3-methylpyridin-4-yl)phenyl)-2,10-dioxo-6-oxa-3,9,15-triazaheptadecane-1-sulfonic acid (Compound 31)

DIEA (26 μL, 0.15 mmol) was added into a mixture of Compound 20AT (58 mg, 0.10 mmol), 1-ethyl-3-(3-dimethylaminopropyl)carbodiimide (23 mg, 0.12 mmol), hydroxybenzotriazole (16 mg, 0.12 mmol), and 2-sulfoacetic acid (15 mg, 0.12 mmol) in DCM (1.5 mL). The reaction was stirred at room temperature overnight. The reaction was concentrated in vacuo. The residue was purified by reverse phase silica gel chromatography (0-100% MeCN/H$_2$O) and further purified by MS-HPLC to afford the title compound (4 mg, 6%). LCMS (method A): m/z 709.6/711.6 (M+H)$^+$. $^1$H NMR (CD$_3$OD) δ 8.80 (s, 1H), 8.75 (d, 1H), 8.00 (dd, 1H), 7.93 (d, 1H), 7.66 (dd, 1H), 7.59~7.54 (m, 2H), 7.51~7.46 (m, 2H), 7.38 (t, 1H), 5.14 (q, 1H), 3.68 (s, 2H), 3.51 (t, 2H), 3.47 (t, 2H), 3.39 (t, 2H), 3.28~3.24 (m, 4H), 2.63 (s, 3H), 2.48 (s, 3H), 2.10~2.03 (m, 2H), 1.56 (d, 3H), 1.45~1.35 (m, 3H), 1.09~1.04 (m, 1H).

Following the method described above for Example 31 and substituting the appropriate starting materials and reagents, the following compounds were prepared as indicated in Table 22.

TABLE 22

| Compound No | Structure | Starting Material | Reagent | MS (M + H)$^+$ |
|---|---|---|---|---|
| 31AA | ![structure] (S)-2-((4-(N-(1-(3-(3-methylpyridin-4-yl)phenyl)ethyl)-2-(trifluoromethyl)phenylsulfonamido)butyl)amino)-2-oxoethanesulfonic acid | 24 | HO-C(=O)-CH$_2$-SO$_3$H | 614.5 (Method A) |
| 31AB | ![structure] 2-((3-(3-chloro-2-methyl-N-(2-(3-(3-methylpyridin-4-yl)phenyl)propan-2-yl)phenylsulfonamido)propyl)amino)-2-oxoethanesulfonic acid | 23 | HO-C(=O)-CH$_2$-SO$_3$H | 594.3/ 596.3 (Method A) |

TABLE 22-continued

| Compound No | Structure | Starting Material | Reagent | MS (M + H)+ |
|---|---|---|---|---|
| 31AC | (R)-2-amino-3-((4-(N-((S)-1-(3-(3-methylpyridin-4-yl)phenyl)ethyl)-2-(trifluoromethyl)phenyl-sulfonamido)butyl)amino)-3-oxopropane-1-sulfonic acid | 24 | BocHN-CH(SO$_3$H)-COOH (R) followed by TFA Removal of Boc group | 643.4 (Method A) |
| 31AD | (R)-2-amino-3-((4-(3-chloro-N-((S)-1-(3-(3-ethylpyridin-4-yl)phenyl)ethyl)-2-methylphenylsulfonamido)butyl)amino)-3-oxopropane-1-sulfonic acid | 24AC | BocHN-CH(SO$_3$H)-COOH (R) followed by TFA Removal of Boc group | 637.4/ 639.4 (Method A) |
| 31AE | (S)-2-((2-(4-(N-(1-(3-(3-methylpyridin-4-yl)phenyl)ethyl)-2-(trifluoromethyl)phenylsulfonamido)butanamido)ethyl)amino)-2-oxoethanesulfonic acid | 20BX | HOOC-CH$_2$-SO$_3$H | 671.3 (Method A) |

TABLE 22-continued
| Compound No | Structure | Starting Material | Reagent | MS (M + H)+ |
|---|---|---|---|---|
| 31AF | 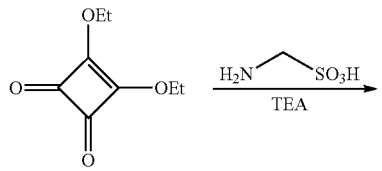<br>(R)-2-amino-3-((2-(4-(N-((S)-1-(3-(3-methylpyridin-4-yl)phenyl)ethyl)-2-(trifluoromethyl)phenyl-sulfonamido)butanamido)ethyl)amino)-3-oxopropane-1-sulfonic acid | 20BX | BocHN—(R)—SO₃H / HO—C(=O)<br>followed by TFA Removal of Boc group | 700.5 (Method A) |
Example 32
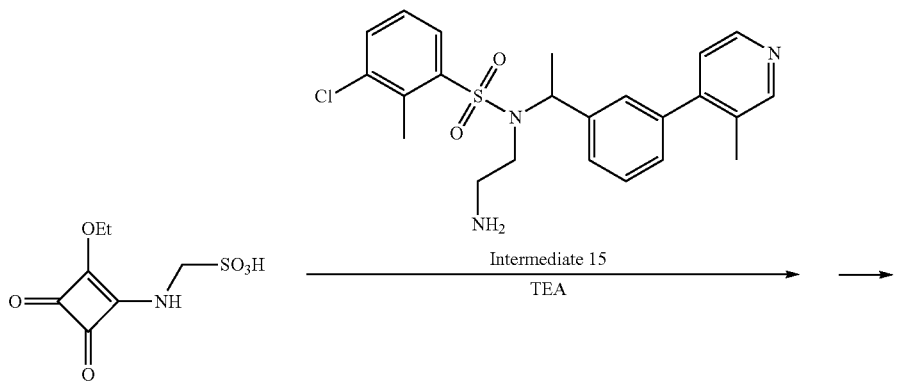

-continued

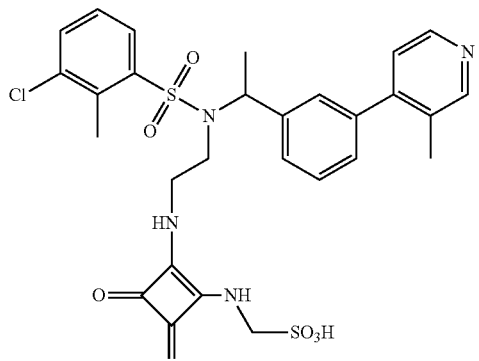

Compound 32

2-((2-((2-(3-chloro-2-methyl-N-(1-(3-(3-methylpyridin-4-yl)phenyl)ethyl)phenylsulfonamido)ethyl)amino)-3,4-dioxocyclobut-1-en-1-yl)amino)methanesulfonic acid (Compound 32)

To a suspension of aminomethylsulfonic acid (37 mg, 0.33 mmol) and TEA (0.07 mL, 0.51 mmol) in acetonitrile (1 mL) at 0° C. was added 3,4-diethoxycyclobut-3-ene-1,2-dione (0.05 mL, 0.33 mmol). The reaction mixture was stirred at room temperature and progress was monitored by LC-MS until all the diethoxycyclobut-3-ene-1,2-dione was consumed. After 30 hours, Intermediate 15 (0.12 g, 0.22 mmol) and TEA (0.07 mL, 0.51 mmol) were added to the reaction mixture which was further stirred for 3 days. After concentration in vacuo, the residue was purified by HPLC to afford Compound 32 (60 mg, 43%). LCMS (method A): m/z 633.4/635.4 (M+H)$^+$. $^1$H NMR (400 MHz, d$^6$-D): δ 8.85 (s, 1H), 8.78 (d, 1H), 7.95 (d, 1H), 7.85 (br, 1H), 7.74 (d, 2H), 7.54-7.40 (m, 5H), 7.26 (br, 1H), 5.08 (m, 1H), 4.23 (br 2H), 4.43 (br, 2H), 3.565-3.25 (m, 7H), 2.32 (s, 3H), 1.58 (m, 3H).

Following the method described above for Example 32 and substituting the appropriate starting materials and reagents, the following compounds were prepared as indicated in Table 23.

TABLE 23

| Compound No | Structure | Starting Material | Reagent | MS (M + H)$^+$ |
|---|---|---|---|---|
| 32AA | ((2-((3-(3-chloro-2-methyl-N-(1-(3-(3-methylpyridin-4-yl)phenyl)ethyl)phenylsulfonamido)propyl)amino)-3,4-dioxocyclobut-1-en-1-yl)amino)methanesulfonic acid | Intermediate 15D | NH$_2$–CH$_2$–SO$_3$H | 647.5/ 649.5 (Method A) |

TABLE 23-continued

| Compound No | Structure | Starting Material | Reagent | MS (M + H)+ |
|---|---|---|---|---|
| 32AB | 3-((2-((2-(3-chloro-2-methyl-N-(1-(3-(3-methyl-pyridin-4-yl)phenyl)ethyl)phenylsulfonamido)ethyl)amino)-3,4-dioxocyclobut-1-en-1-yl)amino)propanoic acid | Intermediate 15D | NH2–CH2CH2–C(=O)OtBu<br><br>Followed by HCl as Example 15, step 2 | 625.5/ 627.5 (Method A) |
| 32AC | ((2-((3-(3-chloro-2-methyl-N-(1-(3-(3-methylpyridin-4-yl)phenyl)ethyl)phenylsulfonamido)propyl)amino)-3,4-dioxocyclobut-1-en-1-yl)amino)methanesulfonic acid | Compound 24 | H2N–CH2CH2–SO3H | 695.5 (Method A) |

(S)-tert-butyl 3-((4-(3-chloro-2-methyl-N-(1-(3-(3-methylpyridin-4-yl)phenyl)ethyl)phenylsulfonamido)butyl)amino)propanoate (Compound 33A)

A solution of dppe (4.0 mg, 0.01 mmol) in dioxane (1 mL) was degassed via $N_2$ (g) for 5 min. To this solution was added Pt (0)-1,3-divinyl-1,1,3,3-tetramethyldisiloxane complex solution (Karstedt's catalyst) (0.1 M in poly(dimethylsiloxane), vinyl terminated, 0.10 mL, 0.010 mmol) and the $N_2$ (g) sparge was continued for an additional 5 min. After stirring for 10 min, $PhSiH_3$ (0.10 mL, 0.82 mmol) was added (vigorous bubbling observed) followed immediately by t-Bu-beta-alanine hydrochloride (75 mg, 0.41 mmol), triethylamine (0.11 mL, 0.82 mmol) and Compound 16 (100 mg, 0.21 mmol). The reaction vessel was sealed and the reaction mixture was stirred at 60° C. for 16 hours. The reaction temperature was increased to 110° C. and stirring continued at this temperature for an additional 3 hours. Additional $PhSiH_3$ (0.10 mL, 0.82 mmol) was added and stirring continued at 110° C. for 1 hour. The reaction mixture was cooled to room temperature and partitioned between EtOAc (3X) and 1 N NaOH (aq). The combined organic layers were washed with brine (1X), dried ($Na_2SO_4$), filtered, and concentrated in vacuo. The residue was purified by silica gel chromatography (4 g, 0-10% MeOH/DCM) to provide Compound 33A (33 mg, 27%). LCMS (Method A): m/z 600.6/ 602.6 (M+H)+.

285

(S)-3-((4-(3-chloro-2-methyl-N-(1-(3-(3-methylpyridin-4-yl)phenyl)ethyl)phenylsulfonamido)butyl)amino)propanoic acid (Compound 33)

Following a procedure similar to Intermediate 16, step 3, compound 33A (13 mg, 0.022 mmol) was converted to Compound 33 (6 mg, 50%). LCMS (Method A): m/z 544.5/546.5 (M+H)$^+$. $^1$H NMR (d$_6$-DMSO) δ 8.51 (s, 1H), 8.47 (d, 1H), 8.15 (br s, 1H), 7.93 (d, 1H), 7.73 (d, 1H), 7.44 (m, 2H), 7.34 (m, 2H), 7.13 (d, 1H), 7.10 (s, 1H), 4.98 (q, 1H), 3.29 (m, 1H, partially obscured by water peak), 3.15 (m, 1H), 2.94 (m, 2H), 2.67 (m, 2H), 2.50 (s, 3H, completely obscured by solvent peak), 2.19 (s, 3H), 1.53 (d, 3H), 1.47-1.13 (m, 4H).

Example 34

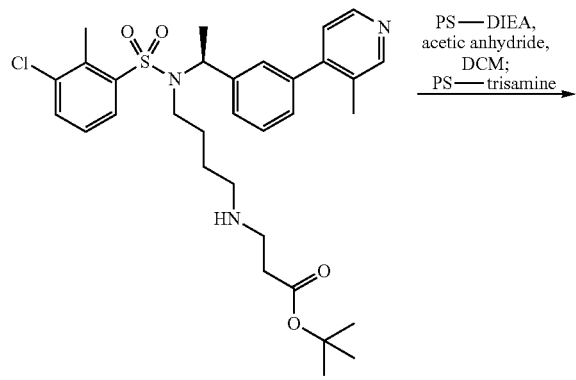

Compound 33A

PS—DIEA, acetic anhydride, DCM; PS—trisamine

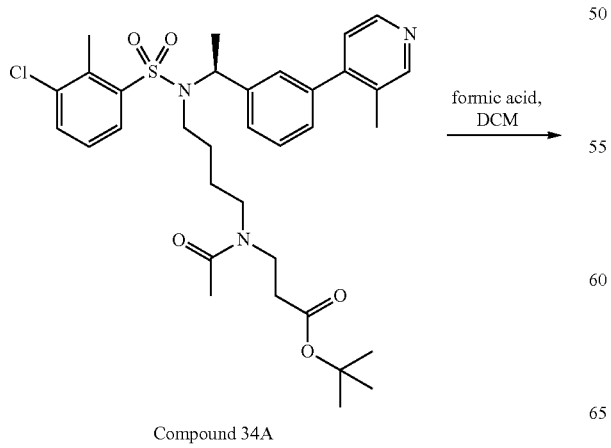

Compound 34A formic acid, DCM

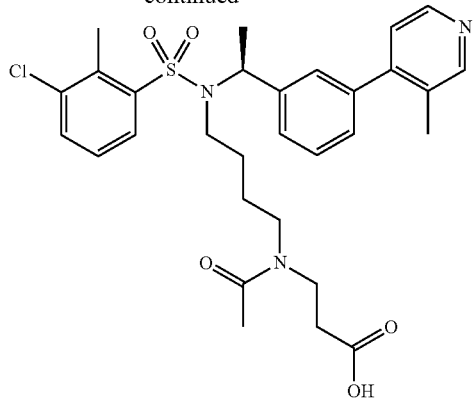

Compound 34

286

(S)-tert-butyl 3-(N-(4-(3-chloro-2-methyl-N-(1-(3-(3-methylpyridin-4-yl)phenyl)ethyl)phenylsulfonamido)butyl)acetamido)propanoate (Compound 34A)

To a solution of Compound 33A (33 mg, 0.055 mmol) in DCM (1 mL) were added PS-DIEA (loading 3.68 mmol/g, 44 mg, 0.17 mmol) and acetic anhydride (8 μL, 0.08 mmol) and the resultant mixture was stirred for 2 hours. PS-trisamine (loading 3.95 mmol/g, 70 mg, 0.28 mmol) was added and stirring was continued for 1.5 hours. The mixture was filtered and the resin rinsed with additional DCM (10 mL). The combined filtrates were concentrated in vacuo and crude Compound 34A was used directly in the next step without further purification. LCMS (Method A): m/z 642.6/644.6 (M+H)$^+$.

(S)-3-(N-(4-(3-chloro-2-methyl-N-(1-(3-(3-methylpyridin-4-yl)phenyl)ethyl)phenylsulfonamido)butyl)acetamido)propanoic acid (Compound 34)

Following a procedure similar to Intermediate 16, step 3, crude Compound 34A from step 1 was converted to Compound 34 (8 mg, 25%). LCMS (Method A): m/z 586.6/588.6 (M+H)$^+$. $^1$H NMR (CD$_3$OD; 1.2:1 mixture of 3° amide rotamers observed) δ8.45 (s, 1H), 8.41 (d, 1H), 8.01 (t, 1H), 7.50-7.43 (m, 2H), 7.39-7.31 (m, 2H), 7.22-7.13 (m, 2H), 5.09 (m, 1H), 3.54-3.11 (m, 6H, partially obscured by solvent peak), 2.60 and 2.59 (2 s, 3H), 2.49 (m, 2H), 2.25 (2 s, 3H), 2.08 and 1.96 (2 s, 3H), 1.58 and 1.56 (2 d, 3H), 1.42-1.08 (m, 4H).

Example 35

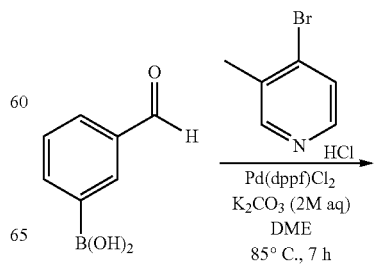

Pd(dppf)Cl$_2$
K$_2$CO$_3$ (2M aq)
DME
85° C., 7 h

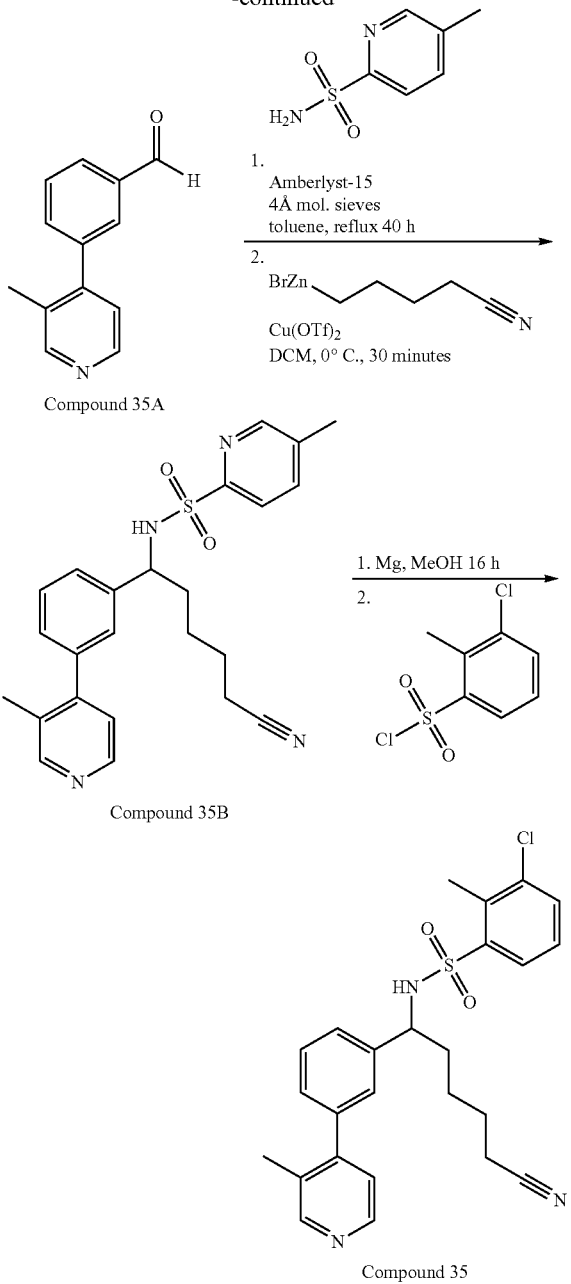

3-(3-methylpyridin-4-yl)benzaldehyde (Compound 35A)

A mixture of (3-formylphenyl)boronic acid (2.1 g, 14 mmol) and 4-bromomethylpyridine hydrochloride (2.4 g, 12 mmol) in 1,2-dimethoxyethane (48 mL) was degassed with nitrogen for 10 minutes. Aqueous potassium carbonate (2.5 M, 14 mL) was added, followed by [1,1'-bis(diphenylphosphino)ferrocene]dichloropalladium(II) complex with DCM (0.38 g, 0.46 mmol). The reaction mixture was heated to 85° C. for 6 hours under nitrogen. The reaction mixture was diluted with EtOAc (100 mL), and washed with water (60 mL) and brine (60 mL). The organic layer was dried over sodium sulfate, filtered and concentrated in vacuo. Purification by silica gel chromatography (20-90% EtOAc/hexanes) gave Compound 35A (1.35 g, 50%). $^1$H NMR (CDCl$_3$) δ 10.10 (s, 1H), 8.57 (s, 1H), 8.53 (d, 1H), 7.95 (m, 1H), 7.87 (m, 1H), 7.63 (m, 2H), 7.18 (d, 1H), 2.30 (s, 3H).

N-(5-cyano-1-(3-(3-methylpyridin-4-yl)phenyl)pentyl)-5-methylpyridine-2-sulfonamide (Compound 35B)

A mixture was made of Compound 35A (0.66 g, 3.30 mmol), 5-methylpyridine-2-sulfonamide (0.49 g, 2.8 mmol), Amberlyst-15 (80 mg), and ground 4 Å molecular sieves (0.70 g) in a flask fitted with a Dean-Stark trap and a reflux condenser. Anhydrous toluene (5 mL) was added, and the mixture was heated to reflux for 40 hours. The mixture was filtered through a pad of Celite, and the Celite pad was washed with toluene (20 mL). The combined filtrates were concentrated in vacuo, and the crude compound was used in the following step.

A solution was made of the crude imine (0.86 g crude, approximately 2.4 mmol) in anhydrous DCM (24 mL). The addition of copper(II) trifluoromethanesulfonate (0.12 g, 0.33 mmol) resulted in a blue solution which was cooled to 0° C. After the addition of 4-cyanobutylzinc bromide (0.5 M in THF, 7.2 mL, 3.6 mmol), the reaction was stirred at 0° C. for 20 minutes. The reaction was quenched by the addition of 30 mL water. The layers were separated, and the aqueous layer was extracted with DCM (3×20 mL). The combined organics were washed with saturated aqueous sodium bicarbonate solution, dried over sodium sulfate, filtered and concentrated in vacuo. Purification by silica gel chromatography (40-100% EtOAc/hexanes) gave Compound 35B (0.26 g, 25% over two steps). LCMS (method A): m/z 435.4 (M+H)$^+$. $^1$H NMR (CDCl$_3$) δ 8.49 (m, 2H), 8.30 (m, 1H), 7.71 (d, 1H), 7.53 (m, 1H), 7.25 (m, 1H), 7.13 (m, 2H), 7.02 (m, 2H), 5.39 (d, 1H), 4.44 (q, 1H), 2.34 (s, 3H), 2.32 (t, 2H), 2.22 (s, 3H), 1.94 (m, 1H), 1.81 (m, 1H), 1.66 (m, 2H), 1.55 (m, 1H), 1.51 (m, 1H).

3-chloro-N-(5-cyano-1-(3-(3-methylpyridin-4-yl)phenyl)pentyl)-2-methylbenzenesulfonamide (Compound 35)

Magnesium turnings (140 mg, 5.7 mmol) were added to a solution of Compound 35B (0.25 g, 0.57 mmol) in anhydrous methanol (8 mL). The mixture was stirred overnight at room temperature. After filtration through Celite, the filtrate was concentrated in vacuo. The residue was dissolved in DCM (4 mL), and DIEA (160 µL, 0.91 mmol) was added. The resulting mixture was cooled to 0° C. After the addition of 3-chloro-2-methylbenzene-1-sulfonyl chloride (0.18 g, 0.80 mmol), the mixture was stirred overnight at room temperature. The reaction mixture was diluted with DCM (15 mL) and washed with saturated aqueous sodium bicarbonate solution, dried over sodium sulfate, filtered and concentrated in vacuo. Purification by silica gel chromatography (5-100% EtOAc/hexanes) gave Compound 35 (22 mg, 8% yield over 2 steps). LCMS (method A): m/z 468.4/470.4 (M+H)$^+$. $^1$H NMR (CDCl$_3$) δ 8.49 (m, 2H), 7.79 (m, 1H), 7.42 (m, 1H), 7.25 (m, 1H), 7.14 (m, 2H), 7.00 (m, 2H), 6.89 (m, 1H), 5.25 (m, 1H), 4.29 (q, 1H), 2.48 (s, 3H), 2.32 (t, 2H), 2.20 (s, 3H), 1.94 (m, 1H), 1.82 (m, 1H), 1.66 (m, 2H), 1.53 (m, 1H), 1.40 (m, 1H).

Example 36

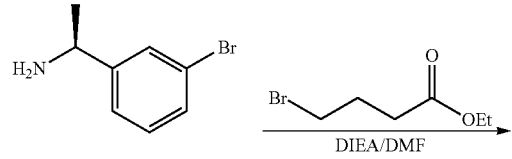

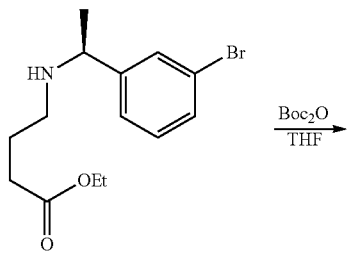

Compound 36A

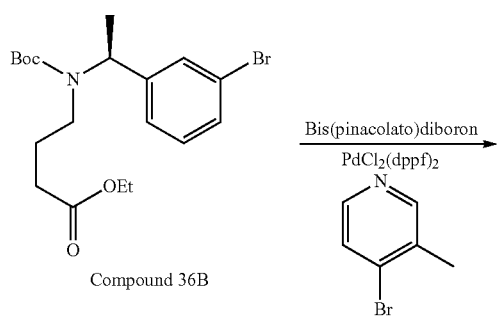

Compound 36B

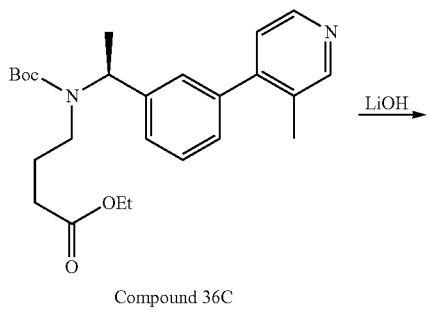

Compound 36C

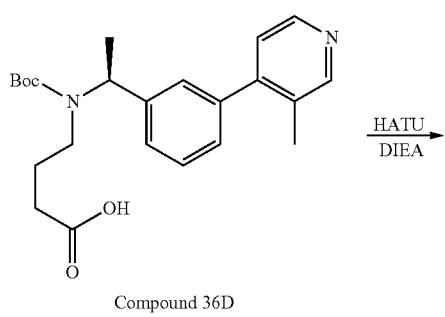

Compound 36D

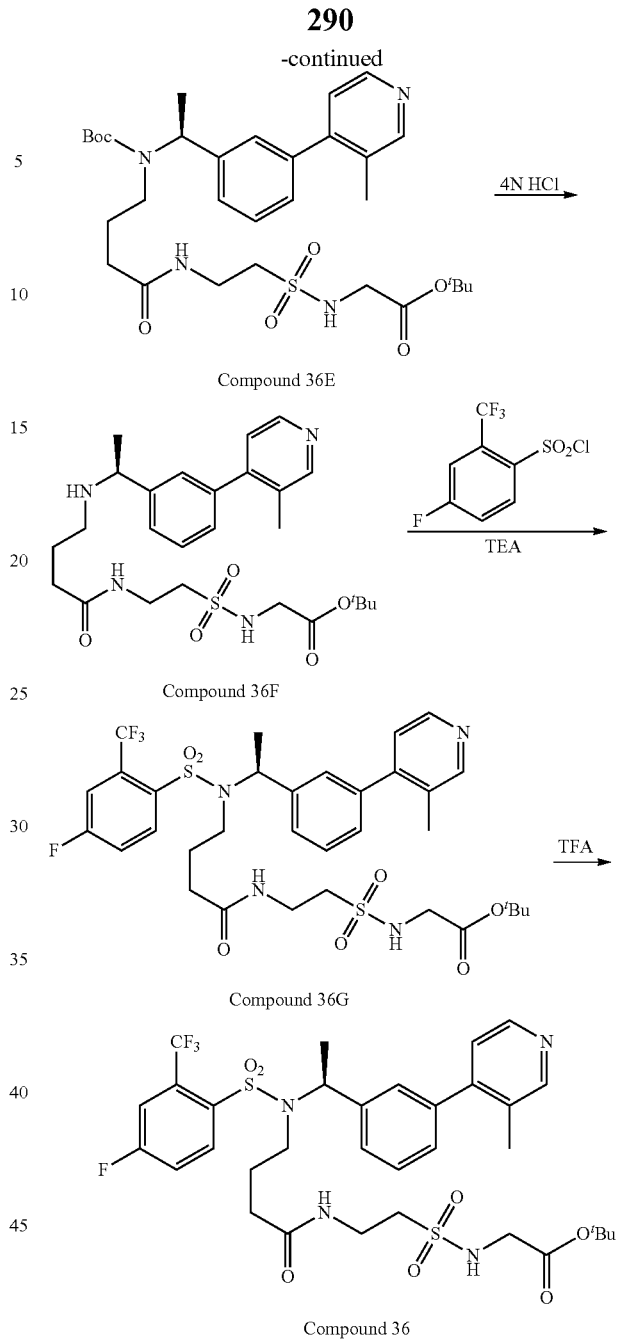

(S)-ethyl 4-((1-(3-bromophenyl)ethyl)amino)butanoate (Compound 36A)

To a solution of (S)-1-(3-bromophenyl)ethanamine hydrochloride salt (2.3 g, 10 mmol) in DMF (30 mL) was added DIEA (3.5 mL, 20 mmol) and ethyl 4-bromobutanoate (0.95 mL, 6.7 mmol). The reaction mixture was stirred overnight and partitioned between EtOAc and water. Organic layer was washed with brine, dried over $Na_2SO_4$ and concentrated in vacuo. Silica gel chromatography purification (0-50% EtOAc/hexanes) gave a mixture of desired product and starting material (5.1 g). The mixture was used in the next step without further purification. LCMS (method A): m/z 314.3/316.3 $(M+H)^+$.

(S)-ethyl 4-((1-(3-bromophenyl)ethyl)(tert-butoxycarbonyl)amino)butanoate (Compound 36B)

A mixture of the previous reaction containing compound 36A (5.1 g)), (Boc)$_2$O (4.4 g, 20 mmol) and NaHCO$_3$ (3.4 g, 40 mmol) in THF (60 mL) and water (30 mL) was stirred at room temperature overnight. Solvent was removed in vacuo. The residue was partitioned between EtOAc and water. The organic layer was washed with brine, dried over Na$_2$SO$_4$, and concentrated in vacuo to afford Compound 36B.

(S)-ethyl 4-((tert-butoxycarbonyl)(1-(3-(3-methylpyridin-4-yl)phenyl)ethyl)amino) butanoate (Compound 36C)

Following similar procedure as described in Example 7, Compound 36B was converted to Compound 36C, followed by silica gel chromatography (0-5% MeOH/DCM) to afford a mixture (2.8 g desired product and by-product). LCMS (method A): m/z 427.4 (M+H)$^+$. The mixture was used in the next step without further purification.

(S)-4-((tert-butoxycarbonyl)(1-(3-(3-methylpyridin-4-yl)phenyl)ethyl)amino)butanoic acid (Compound 36D)

The mixture of Compound 36C was dissolved in dioxane (30 mL) and a solution of LiOH (10 mL, 10%) was added. The reaction was stirred overnight, and water was added. The mixture was washed with ether. The aqueous layer was acidified with HCl (aq.) to pH 3~4 and extracted with CHCl$_3$ (3X). The organic layers were concentrated in vacuo to afford Compound 36D (0.32 g, 8% for 4 steps). LCMS (method A): m/z 399.4 (M+H)$^+$.

(S)-tert-butyl 4-((tert-butoxycarbonyl)(1-(3-(3-methylpyridin-4-yl)phenyl)ethyl)amino) butanamidoethylsulfonamido)acetate (Compound 36E)

To a solution of Compound 36D (320 mg, 0.8 mmol) in DCM (8 mL) was added HATU (0.37 g mg, 0.96 mmol). The mixture was stirred at room temperature for 10 minutes, followed by the addition of Intermediate 18A (0.23 g, 0.96 mmol) and DIEA (0.41 mL, 0.29 mmol). The reaction was stirred at room temperature for 1 hour. Solvent was removed in vacuo. The residue was partitioned between EtOAc and water. The organic layer was washed with brine, dried over Na$_2$SO$_4$ and concentrated in vacuo. The residue was purified by silica gel chromatography (0-3% MeOH/DCM) to afford Compound 36E (0.19 g, 39%). LCMS (method A): m/z 619.5 (M+H)$^+$.

(S)-tert-butyl-4-((1-(3-(3-methylpyridin-4-yl)phenyl)ethyl)amino) butanamidoethylsulfonamido)acetate (Compound 36F)

Following similar procedure as in Intermediate 3, step 3, Compound 36E (0.11 g, 0.18 mmol) was converted to Compound 36F (58 mg, 62%). LCMS (method A): m/z 519.4 (M+H)$^+$.

(S)-tert-butyl-2-(4-(4-fluoro-N-(1-(3-(3-methylpyridin-4-yl)phenyl)ethyl)-2-(trifluoromethyl)phenylsulfonamido)butanamido)ethanesulfonamido acetate (Compound 36G)

Following similar procedure as Intermediate 7, step 2, Compound 36F (56 mg, 0.054 mmol) was converted to Compound 36G (20 mg, 48%). LCMS (method A): m/z 745.4 (M+H)$^+$.

(S)-2-(4-(4-fluoro-N-(1-(3-(3-methylpyridin-4-yl)phenyl)ethyl)-2-(trifluoromethyl)phenylsulfonamido)butanamido)ethanesulfonamido acetic acid (Compound 36)

To a solution of Compound 36G (20 mg, 0.026 mmol) in DCM (0.5 mL) was added TFA (0.25 mL). The reaction was stirred at room temperature for 90 minutes. The mixture was concentrated in vacuo. The residue was treated with HCl (4 N in dioxane) to afford Compound 36 as the HCl salt (18 mg, 96%). LCMS (method A): m/z 689.3 (M+H)$^+$. $^1$H NMR (400 MHz, d$^4$-MeOD): δ 8.76 (s, 1H), 8.71 (d, 1H), 8.20 (dd, 1H), 7.91 (d, 1H), 7.75 (dd 1H), 7.63 (m, 4H), 7.48 (m, 1H), 5.31 (q, 1H), 3.85 (s, 2H), 3.66 (m, 2H), 3.56 (m, 2H), 3.20 (t, 2H), 2.47 (s, 3H), 2.03 (m, 2H), 1.58 (d, 3H), 1.76-1.37 (2br, 2H).

Following the method described above for Example 36 and substituting the appropriate intermediates and reagent, the following compound was prepared as indicated in Table 24.

TABLE 24

| Compound No | Structure | Starting material | Reagent | MS (M + H)$^+$ |
|---|---|---|---|---|
| 36AA | (S)-2-(4-(3-chloro-N-(1-(3-(3-methylpyridin-4-yl)phenyl)ethyl)-2-chloro-phenylsulfonamido)butanamido)ethanesulfonamido acetic acid | 36F | (dichlorophenylsulfonyl chloride) | 671.2/ 673.2 (Method A) |

Example 37

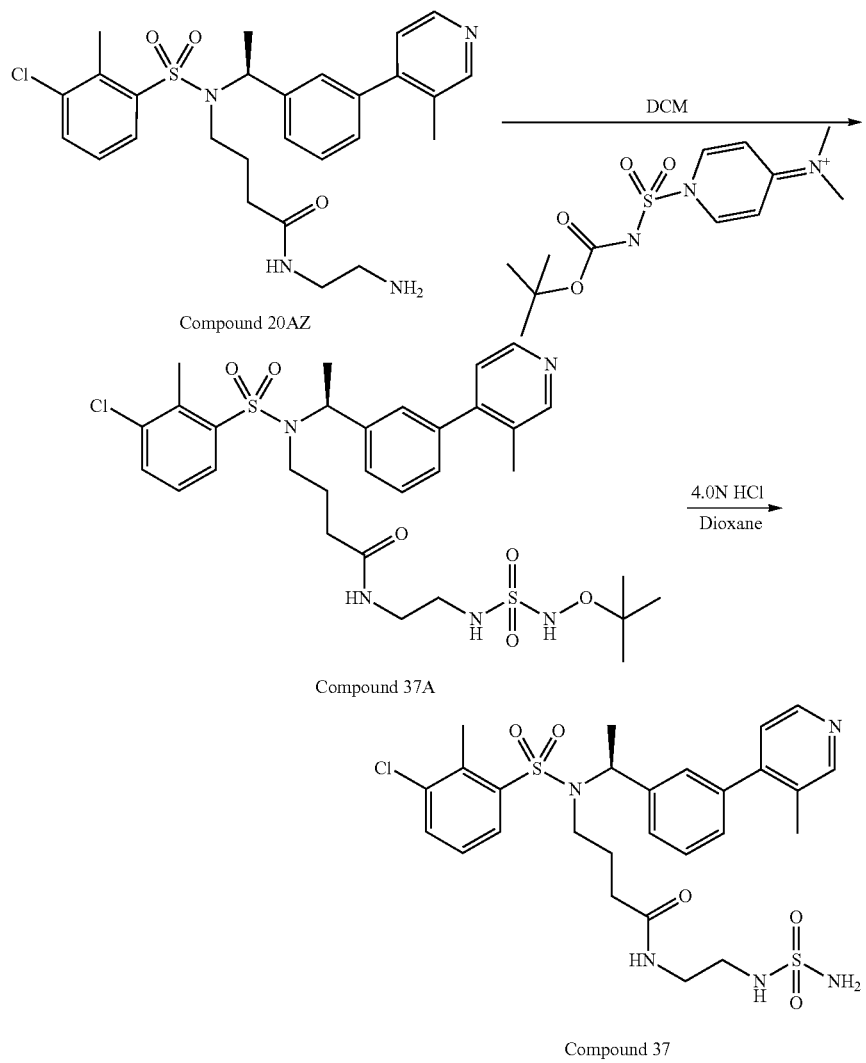

(S)—N-(2-4N-(tert-butoxy)sulfamoyl)amino)ethyl)-4-(3-chloro-2-methyl-N-(1-(3-(3-methylpyridin-4-yl)phenyl)ethyl)phenylsulfonamido)butanamide (Compound 37A)

To a solution of Compound 20AZ (340 mg, 0.64 mmol) in DCM (5 mL) was added (tert-butoxycarbonyl)((4-(dimethyliminio)pyridin-1(4H)-yl)sulfonyl)amide (250 mg, 0.84 mmol) and the mixture was stirred for 18 hours. The mixture was diluted with EtOAc, and washed with NH$_4$Cl (sat., aq.) and brine. The organic layer was dried (Na$_2$SO$_4$), filtered and concentrated in vacuo. The residue was purified by silica gel chromatography (0-10% MeOH/DCM) to afford Compound 37A (410 mg, 91%). LCMS (method A): m/z 708.5/710.4 (M+H)$^+$. $^1$H NMR (CDCl$_3$) δ10.89 (s, 1H), 8.50 (s, 1H), 8.45 (d, 1H), 7.92 (d, 1H), 7.79 (t, 1H), 7.72 (d, 1H), 7.58 (m, 1H), 7.45 (q, 2H), 7.35-7.30 (m, 2H), 7.13 (d, 1H), 7.08 (m, 1H), 5.00 (m, 1H), 3.31 (s, 1H), 3.28-3.03 (m, 4H), 2.87 (q, 2H), 2.18 (s, 3H), 1.92 (m, 2H), 1.67-1.57 (m, 1H), 1.55 (d, 3H), 1.41 (s, 9H).

(S)-4-(3-chloro-2-methyl-N-(1-(3-(3-methylpyridin-4-yl)phenyl)ethyl)phenylsulfonamido)-N-(2-(sulfamoylamino)ethyl)butanamide (Compound 37)

Compound 37A (50 mg, 0.071 mmol) was dissolved in 4 N HCl (in dioxane, 2 mL) and the mixture was stirred for 2 hours. The mixture was concentrated and the residue was dissolved in water and lyophilized. The resulting solid was purified by prep HPLC, concentrated, then dissolved in water with 1 drop conc. HCl. The solution was lyophilized to afford Compound 37 (27 mg, 63%). LCMS (method A): m/z 608.5/610.5 (M+H)$^+$. $^1$H NMR (CDCl$_3$) δ 8.92 (s, 1H), 8.84 (d, 1H), 7.92 (d, 1H), 7.80 (d, 1H), 7.79 (t, 1H), 7.73 (d, 1H), 7.58-7.41 (m, 4H), 7.22 (s, 1H), 6.53 (bs, 2H), 5.05 (q, 1H), 3.31-3.06 (m, 4H), 2.86 (m, 2H), 2.37 (s, 3H), 1.93 (m, 2H), 1.67-1.57 (m, 1H), 1.56 (d, 2H), 1.42-1.28 (m, 1H).

Following the method described above for Example 37 and substituting the appropriate intermediates and reagent, the following compound was prepared as indicated in Table 25.

TABLE 25
| Compound No | Structure | Starting material | Reagent | MS (M + H)+ |
|---|---|---|---|---|
| 37AA | 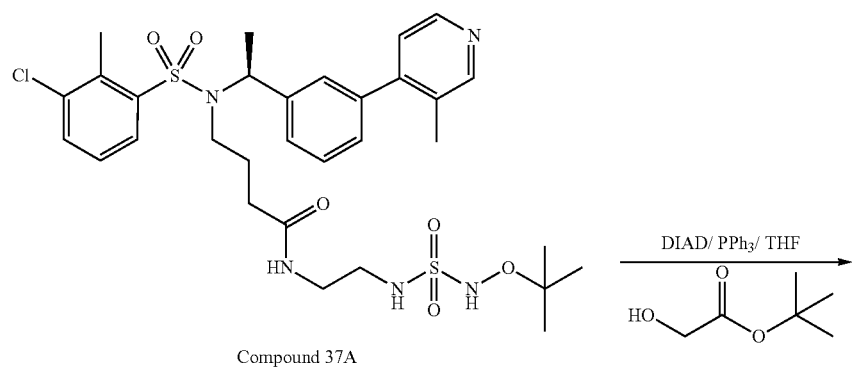
(S)-4-(3-chloro-N-(1-(3-(3-ethylpyridin-4-yl)phenyl)ethyl)-2-methylphenylsulfonamido)-N-(2-(sulfamoylamino)ethyl)butanamide | 21AS | Same as Example 37 | 622.3/ 624.3 (Method A) |
Example 38
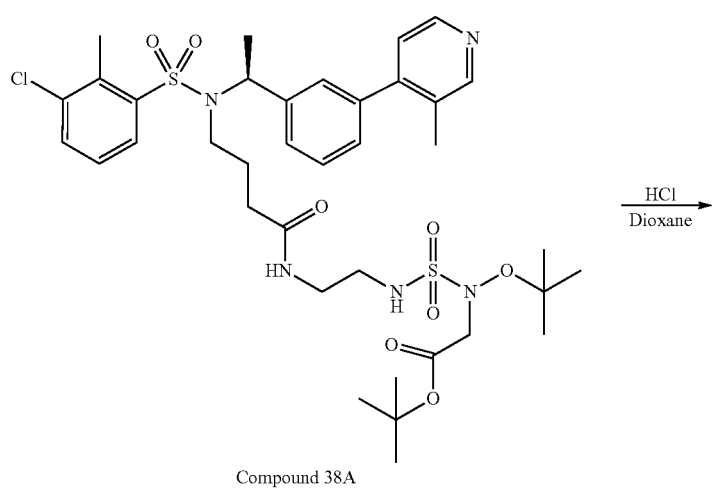
Compound 38A

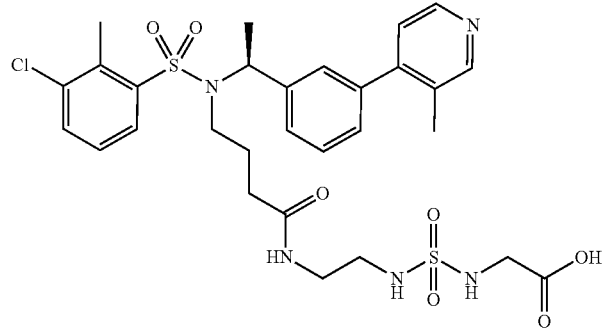 [SMILES: CCc1cnccc1-c1cccc([C@H](C)N(CCCC(=O)NCCNS(=O)(=O)NCC(=O)O)S(=O)(=O)c2cccc(Cl)c2C)c1]

Compound 38

(S)-2-((N-(2-(4-(3-chloro-2-methyl-N-(1-(3-(3-methylpyridin-4-yl)phenyl)ethyl)phenylsulfonamido)butanamido)ethyl)sulfamoyl)amino)acetic acid (Compound 38A)

To a solution of Compound 37A (200 mg, 0.28 mmol) and DIAD (60 mg, 0.30 mmol) in THF (0.5 mL) was added a solution of triphenylphospine (78 mg, 0.30 mmol) and t-butyl-2-hydroxy acetate in THF (0.5 mL) dropwise. The resulting mixture was stirred for 18 hours and concentrated in vacuo. The residue was purified by silica gel chromatography (0-100% EtOAc/Hexanes) to afford Compound 38A (170 mg, 75%).

S)-2-((N-(2-(4-(3-chloro-2-methyl-N-(1-(3-(3-methylpyridin-4-yl)phenyl)ethyl)phenylsulfonamido)butanamido)ethyl)sulfamoyl)amino)acetic acid (Compound 38)

Compound 38A (170 mg, 0.21 mmol) was dissolved in 4 N HCl (dioxane, 6 mL) and stirred for 2 hours. The mixture was partioned between EtOAc and water. The organic layers were concentrated in vacuo and the residue was purified by reverse phase chromatography (5-100% water/AcN 0.25% formic acid) to afford Compound 38 as the formate salt (41 mg, 29%). LCMS (method A): m/z 666.4/668.4 (M+H)+. 1H NMR (CDCl3) δ 12.66 (bs, 1H), 8.44 (bs, 1H), 8.39 (d, 1H), 7.85 (d, 1H), 7.70 (t, 1H), 7.65 (d, 1H), 7.37 (q, 2H), 7.29-7.23 (m, 2H), 7.12 (t, 1H), 7.07 (d, 1H), 7.01 (s, 1H), 6.82 (bs, 1H), 4.93 (q, 1H), 3.48 (d, 2H), 3.22-2.93 (m, 4H), 2.76 (m, 2H), 2.11 (s, 3H), 1.91-1.79 (m, 2H), 1.62-1.51 (m, 1H), 1.49 (d, 3H), 1.38-1.24 (m, 1H).

Following the method described above for Example 38 and substituting the appropriate starting material and reagent, the following compound was prepared as indicated in Table 26.

TABLE 26

| Compound No | Structure | Starting material | Reagent | MS (M + H)+ |
|---|---|---|---|---|
| 38AA | (S)-2-((N-(2-(4-(3-chloro-N-(1-(3-(3-ethylpyridin-4-yl)phenyl)ethyl)-2-methylphenylsulfonamido)butanamido)ethyl)sulfamoyl)amino)acetic acid | Boc precursor of 37AA | Same as Example 38 | 680.3/ 682.3 (Method A) |

Example 39

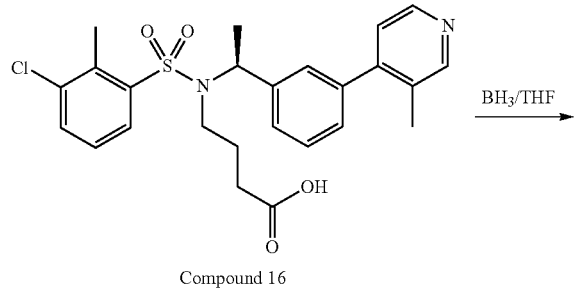

Compound 16

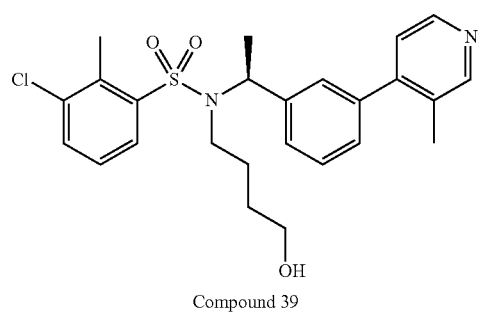

Compound 39

(S)-3-chloro-N-(4-hydroxybutyl)-2-methyl-N-(1-(3-(3-methylpyridin-4-yl)phenyl)ethyl)Benzenesulfonamide (Compound 39)

Following procedure similar to Intermediate 6, step 1, keeping reaction at room temperature, Compound 16 (0.30 g, 0.62 mmol) was converted to Compound 39, and purified by flash column chromatography (1-7% MeOH/DCM) to afford the title compound (0.21 g, 95%). LCMS (method A): m/z 473.4/475.3 (M+H)+. $^1$H NMR (CD$_3$OD) δ 8.45 (s, 1H), 8.39 (d, 1H), 7.88 (d, 1H), 7.63 (d, 1H), 7.48-7.30 (m, 4H), 7.19 (d, 1H), 7.08 (s, 1H), 5.06 (q, 1H), 3.39-3.33 (m, 2H), 3.30-3.18 (m, 2H), 2.58 (s, 3H), 2.24 (s, 3H), 1.59 (d, 3H), 1.54 (m, 1H), 1.37-1.31 (m, 3H).

Experimental for Formula (II)

Intermediate 21

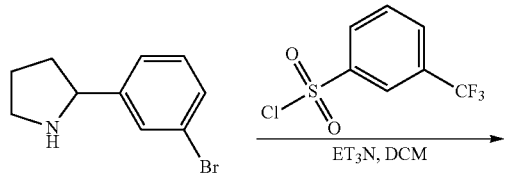

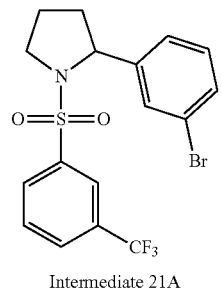

Intermediate 21A (+/−)2-(3-bromophenyl)-1-((3-(trifluoromethyl)phenyl)sulfonyl)pyrrolidine (Intermediate 21A A mixture of triethylamine (0.22 mL, 1.60 mmol) and (+/−) 2-(3-bromophenyl)pyrrolidine (0.20 g, 0.76 mmol) in DCM (8 mL) was stirred at 0° C. A solution of 3-(trifluoromethyl)benzene-1-sulfonyl chloride (0.13 mL, 0.80 mmol) in DCM (1 mL) was added, and the reaction mixture was stirred overnight at room temperature. The reaction mixture was diluted with DCM (15 mL), washed with aqueous HCl (0.2 N solution, 10 mL) and saturated aqueous sodium bicarbonate solution (10 mL). The organics were dried over sodium sulfate, filtered, and concentrated in vacuo. Purification by silica gel chromatography (0-40% EtOAc/hexanes) yielded Intermediate 21A (0.29 g, 88%). LCMS (method A): m/z 434.3/436.3 (M+H)+. $^1$H NMR (CDCl$_3$) δ 8.93 (s, 1H), 7.89 (d, 1H), 7.81 (d, 1H), 7.62 (t, 1H), 7.34 (m, 1H), 7.26 (m, 1H), 7.15 (m, 2H), 4.82 (m, 1H), 3.68-3.55 (m, 2H), 2.16 (m, 1H), 1.95 (m, 1H), 1.89-1.80 (m, 2H).

Following the method described above for Intermediate 21A and substituting the appropriate starting reagent, the following intermediate was prepared as indicated in Intermediate Table 15.

TABLE 15

| Intermediate | | | |
|---|---|---|---|
| Intermediate | Structure | Reagent | MS (M + H)+ |
| Intermediate 21B | 2-(3-bromophenyl)-1-((2-(trifluoromethyl)phenyl)sulfonyl)pyrrolidine | | 434.3/ 436.3 (method A) |

Intermediate 22

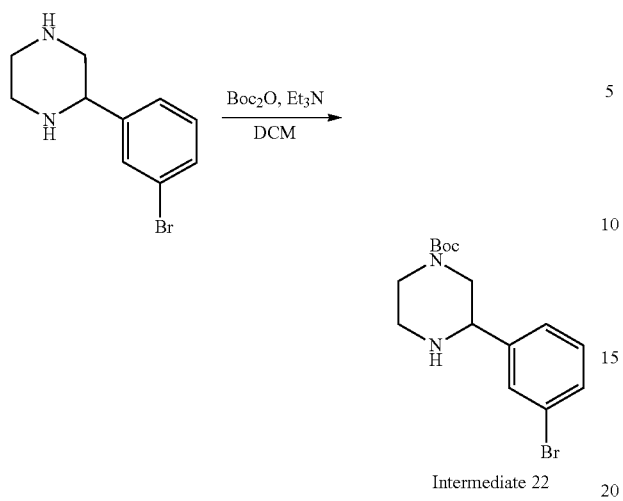

(+/−) tert-butyl 3-(3-bromophenyl)piperazine-1-carboxylate (Intermediate 22)

To a 0° C. suspension of racemic 2-(3-bromophenyl)piperazine (2.00 g, 8.29 mmol) in triethylamine (2.50 mL, 18.2 mmol), and DCM (15 mL) was added di-tert-butyl dicarbonate (1.81 g, 8.29 mmol) in three portions. The reaction mixture was allowed to warm to room temperature and stir for 16 hours. The reaction mixture was concentrated in vacuo. Purification by silica gel chromatography (0-100% EtOAc/hexanes) yielded Intermediate 22 (2.16 g, 76%). $^1$H NMR (CDCl$_3$) δ 7.61 (s, 1H), 7.43 (d, 1H), 7.33 (d, 1H), 7.22 (t, 1H), 4.05 (m, 2H), 3.69 (d, 1H), 3.08 (d, 1H), 2.87 (m, 2H), 2.70 (m, 1H), 1.48 (s, 9H).

Intermediate 23

(+/−)tert-butyl 3-(3-bromophenyl)-4-((3-chloro-2-methylphenyl)sulfonyl)piperazine-1-carboxylate (Intermediate 23A)

To a solution of (+/−) tert-butyl 3-(3-bromophenyl)piperazine-1-carboxylate (2.16 g, 6.33 mmol) in DCM (12 mL) was added triethylamine (1.80 mL, 12.7 mmol). The mixture was cooled to 0° C. and 3-chloro-2-methylbenzene-1-sulfonyl chloride (1.71 g, 7.60 mmol) was added in three portions. The reaction mixture was allowed to warm to room temperature and stir for 16 hours. The reaction mixture was diluted with DCM (60 mL), and washed with 1 N HCl (30 mL), saturated aqueous sodium bicarbonate (30 mL), and brine (30 mL). The organic layer was dried with sodium sulfate, filtered, and concentrated in vacuo. Purification by silica gel chromatography (0-70% EtOAc/hexanes) yielded Intermediate 23A (2.84 g, 84%). $^1$H NMR (CDCl$_3$) δ 7.87 (m, 1H), 7.60 (d, 1H), 7.37-7.14 (m, 5H), 4.90 (m, 1H), 4.39 (m, 1H), 3.98-3.69 (m, 2H), 3.43 (m, 1H), 3.26-3.01 (m, 2H), 2.65 (s, 3H), 1.46 (s, 9H).

Following the method described above for Intermediate 23A and substituting the appropriate starting reagents, the following compounds were prepared as indicated in Intermediate Table 16.

TABLE 16

| Intermediate | | | |
|---|---|---|---|
| Intermediate | Structure | Reagent | MS (M + H)$^+$ |
| Intermediate 23B | [structure] | [structure] | 493.3/ 495.3 (M-tBu)$^+$ (method A) | tert-butyl 3-(3-bromophenyl)-4-

TABLE 16-continued

| Intermediate | Structure | Reagent | MS (M + H)⁺ |
|---|---|---|---|
| | ((2-(trifluoromethyl)-phenyl)sulfonyl)piperazine-1-carboxylate | | |
| Intermediate 23C | tert-butyl 3-(3-bromophenyl)-4-(o-tolylsulfonyl)piperazine-1-carboxylate | 2-methylbenzenesulfonyl chloride | 395.3/ 397.2 (M-Boc)⁺ (method A) |
| Intermediate 23D | tert-butyl 3-(3-bromophenyl)-4-((3-methoxyphenyl)sulfonyl)-piperazine-1-carboxylate | 3-methoxybenzenesulfonyl chloride | 455.3 (M-tBu)⁺ (method A) |
| Intermediate 23E | tert-butyl 3-(3-bromophenyl)-4-((2,3-dichlorophenyl)sulfonyl)-piperazine-1-carboxylate | 2,3-dichlorobenzenesulfonyl chloride | 495.1 (M-tBu)⁺ (method A) |

TABLE 16-continued

Intermediate

| Intermediate | Structure | Reagent | MS (M + H)+ |
|---|---|---|---|
| Intermediate 23F | 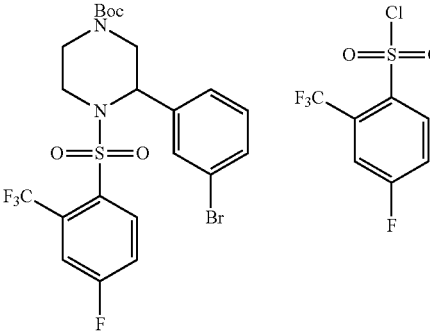<br>tert-butyl 3-(3-bromophenyl)-4-((4-fluoro-2-(trifluoromethyl)phenyl)sulfonyl)piperazine-1-carboxylate | 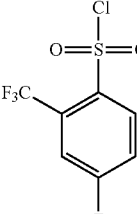 | 580.5/ 581.5 (method A) |

Intermediate 24

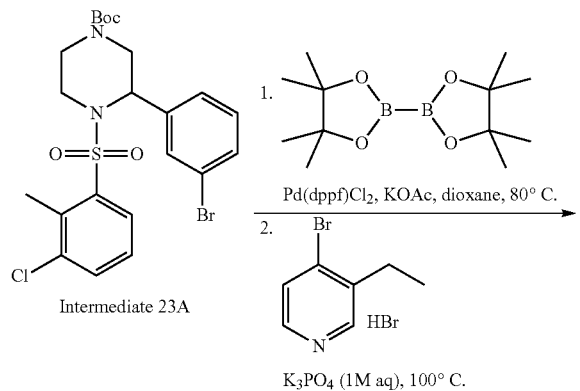

(+/−) tert-butyl 4-((3-chloro-2-methylphenyl)sulfonyl)-3-(3-(3-ethylpyridin-4-yl)phenyl)piperazine-1-carboxylate (Intermediate 24A To tert-butyl 3-(3-bromophenyl)-4-((3-chloro-2-methylphenyl)sulfonyl)piperazine-1-carboxylate (1.20 g, 2.27 mmol) in a Biotage microwave vessel was added 1,4-dioxane (6.6 mL). While the resulting solution was bubbled with nitrogen, bis(pinacolato)diboron (1.15 g, 4.53 mmol), [1,1'-Bis(diphenylphosphino)ferrocene]dichloropalladium (II), complex with DCM (0.19 g, 0.23 mmol), and potassium acetate (0.67 g, 6.84 mmol) were added. The vessel was capped and heated to 80° C. in a heated block for 16 hours. After cooling to room temperature, 4-bromo-3-ethylpyridine hydrobromide (0.91 g, 3.41 mmol) and a potassium phosphate solution (1 M aqueous, 6.81 mL, 6.81 mmol) were added and the mixture was heated to 100° C. for 23 hours. An additional portion of 4-bromo-3-ethylpyridine hydrobromide (0.30 g, 1.12 mmol) and a potassium phosphate solution (1 M aqueous, 2.00 mL, 2.00 mmol) were added and the mixture was heated for an additional 62 hours. After cooling, the mixture was diluted with 40 mL EtOAc, and filtered through a pad of Celite. The layers of the filtrate were separated, and the aqueous layer was extracted twice with EtOAc (10 mL). The combined organics were washed with water (20 mL), brine (20 mL), dried with sodium sulfate, filtered and concentrated in vacuo. Purification by silica gel chromatography (5-70% EtOAc/hexanes) yielded Intermediate 24A (1.06 g, 84%). LCMS (method A): m/z 556.5 (M+H)+. $^1$H NMR (CDCl$_3$) δ 8.53 (s, 1H), 8.46 (d, 1H), 7.92 (m, 1H), 7.54 (m, 1H), 7.35-7.19 (m, 4H), 7.08 (m, 1H), 7.00 (m, 1H), 5.02 (m 1H), 4.52 (m, 1H), 4.03-3.83 (m, 1H), 3.73 (m, 1H), 3.45 (m, 1H), 3.23 (m, 1H), 3.20-2.93 (m, 1H), 2.61 (s, 3H), 2.57 (q, 2H), 1.35 (bs, 9H), 1.07 (t, 3H).

Following the method described above for Intermediate 24A and substituting the appropriate starting reagents, the following intermediates were prepared as indicated in Intermediate Table 17.

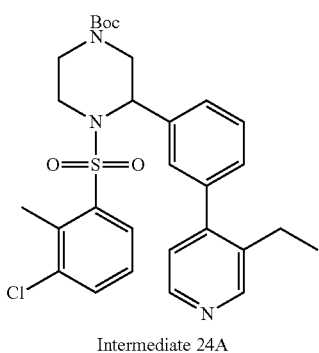

Intermediate 24A

TABLE 17

| Intermediate | Structure | Intermediate | Reagent | MS (M + H)+ |
|---|---|---|---|---|
| Intermediate 24B | tert-butyl 3-(3-(3-methylpyridin-4-yl)phenyl)-4-(o-tolylsulfonyl)piperazine-1-carboxylate | 23C | Br, 3-methylpyridine HCl | 508.4 (method A) |
| Intermediate 24C | tert-butyl 4-((3-methoxyphenyl)sulfonyl)-3-(3-(3-methylpyridin-4-yl)phenyl)piperazine-1-carboxylate | 23D | Br, 3-methylpyridine HCl | 524.4/ 525.4 (method A) |
| Intermediate 24D | tert-butyl 4-((2,3-dichlorophenyl)sulfonyl)-3-(3-(3-methylpyridin-4-yl)phenyl)piperazine-1-carboxylate | 23E | Br, 3-methylpyridine HCl | 562.4/ 564.4 (method A) |

TABLE 17-continued

| Intermediate | Structure | Intermediate | Reagent | MS (M + H)+ |
|---|---|---|---|---|
| Intermediate 24E | tert-butyl 4-((4-fluoro-2-(trifluoromethyl)phenyl)sulfonyl)-3-(3-(3-methylpyridin-4-yl)phenyl)piperazine-1-carboxylate | 23F | Br-pyridine·HCl (3-methyl) | 581.5/580.5 (method A) |
| Intermediate 24F | tert-butyl 4-((3-chloro-2-methylphenyl)sulfonyl)-3-(3-(3-methylpyridin-4-yl)phenyl)piperazine-1-carboxylate | 23A | Br-pyridine·HCl (3-methyl) | 542.5/544.5 (method A) |

Intermediate 25

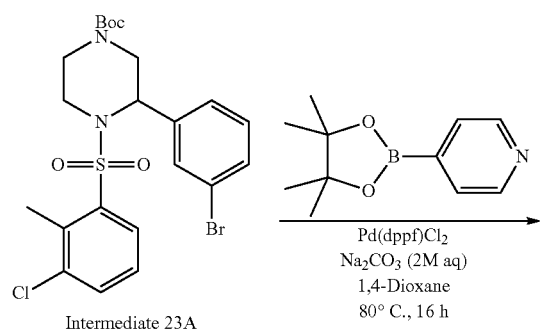

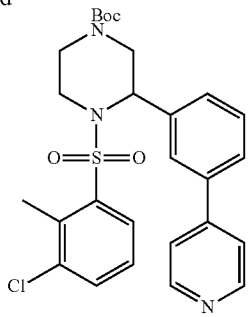

Intermediate 25A (+/−) tert-butyl 4-((3-chloro-2-methylphenyl)sulfonyl)-3-(3-(3-ethylpyridin-4-yl)phenyl)piperazine-1-carboxylate (Intermediate 25A To (+/−) tert-butyl 4-((3-chloro-2-methylphenyl)sulfonyl)-3-(3-(pyridin-4-yl)phenyl)piperazine-1-carboxylate (0.25 g, 0.47 mmol) in a Biotage microwave vessel was added 1,4-dioxane (2.8 mL). While the resulting solution was bubbled with nitrogen, [1,1'-bis(diphenylphosphino)ferrocene]dichloropalladium(II), complex with DCM (31 mg, 0.04 mmol), and a degassed solution of sodium carbonate (2 M aqueous, 0.70 mL, 1.40 mmol) were added. The vessel was capped and heated to 80° C. in a heated block for 16 hours. After cooling, the mixture was diluted with 25 mL EtOAc, and filtered through a pad of celite. The filtrate was washed with a saturated aqueous sodium bicarbonate solution (25 mL). The organic layer was dried with sodium sulfate, filtered and concentrated in vacuo. Purification by silica gel chromatography (15-70% EtOAc/hexanes) yielded Intermediate 25A (0.20 g, 80%). LCMS: (method A), m/z 528.4/530.4 (M+H)$^+$. $^1$H NMR (CDCl$_3$) δ 8.65 (m, 2H), 7.91 (d, 1H), 7.54 (m, 2H), 7.40 (m, 5H), 7.21 (m, 1H), 5.01 (m 1H), 4.57 (m, 1H), 3.98 (m, 1H), 3.85 (m, 1H), 3.72 (m, 1H), 3.16 (m, 2H), 2.66 (s, 3H), 1.41 (s, 9H).

Following the method described above for Intermediate 25A and substituting the appropriate starting reagents, the following intermediates were prepared as indicated in Intermediate Table 18.

TABLE 18

Intermediate

| Intermediate | Structure | Reagent | MS (M + H)$^+$ |
|---|---|---|---|
| Intermediate 25B | tert-butyl 4-((3-chloro-2-methylphenyl)sulfonyl)-3-(3-(3-chloropyridin-4-yl)phenyl)piperazine-1-carboxylate | | 562.3/564.3 (method A) |
| Intermediate 25C | tert-butyl 4-((3-chloro-2-methylphenyl)sulfonyl)-3-(3-(3-methoxypyridin-4-yl)phenyl)piperazine-1-carboxylate | | 558.3/560.3 (method A) |

Example 40

3-methoxy-4-(3-(1-((3-(trifluoromethyl)phenyl)sulfonyl)pyrrolidin-2-yl)phenyl)pyridine (Compound 40)

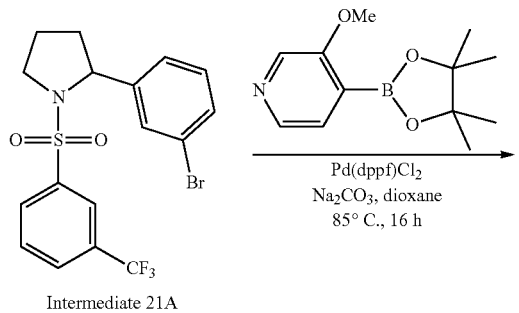

Intermediate 21A

A mixture of Intermediate 21A (62 mg, 0.14 mmol) and 3-methoxy-4-(4,4,5,5-tetramethyl-1,3,2-dioxaborolan-2-yl)pyridine (35 mg, 0.15 mmol) in 1,4-dioxane (1.0 mL) in a Biotage microwave vessel was degassed with nitrogen for 10 minutes. To this mixture [1,1'-bis(diphenylphosphino)ferrocene]dichloropalladium(II), complex with DCM (11 mg, 0.014 mmol), and a sodium carbonate solution (2 M aqueous, 0.2 5 mL, 0.50 mmol) were added. After degassing with nitrogen for 2 minutes, the vessel was capped and heated to 85° C. in a heating block for 16 hours. After cooling, the mixture was diluted with 5 mL EtOAc, and 5 mL water. The layers were separated, and the organic layer was washed with saturated sodium bicarbonate solution (10 mL), dried over sodium sulfate, filtered, and concentrated in vacuo. Purification by silica gel chromatography (20-80% EtOAc/hexanes) yielded Compound 40 (60 mg, 92%). LCMS (method A): m/z 453.3 (M+H)$^+$. $^1$H NMR (CDCl$_3$) δ 8.38 (s, 1H), 8.323 (d, 1H), 7.95 (s, 1H), 7.90 (d, 1H), 7.76 (d, 1H), 7.57 (t, 1H), 7.44 (m, 2H), 7.34 (m, 1H), 7.23 (m, 1H), 7.19 (m, 1H), 4.92 (m, 1H), 3.93 (m, 3H), 3.66 (m, 1H), 3.60 (m, 1H), 2.17 (m, 1H), 2.01-1.83 (m, 3H).

Following the method described above for Example 40 and substituting the appropriate intermediate, the following compound was prepared as indicated in Table 27.

TABLE 27

| Compound No. | Structure | Intermediate | MS (M + H)$^+$ |
|---|---|---|---|
| 40AA | 3-methoxy-4-(3-(1-((2-(trifluoromethyl)phenyl)sulfonyl)pyrrolidin-2-yl)phenyl)pyridine | Intermediate 21B | 463.5 (method A) |

Example 41

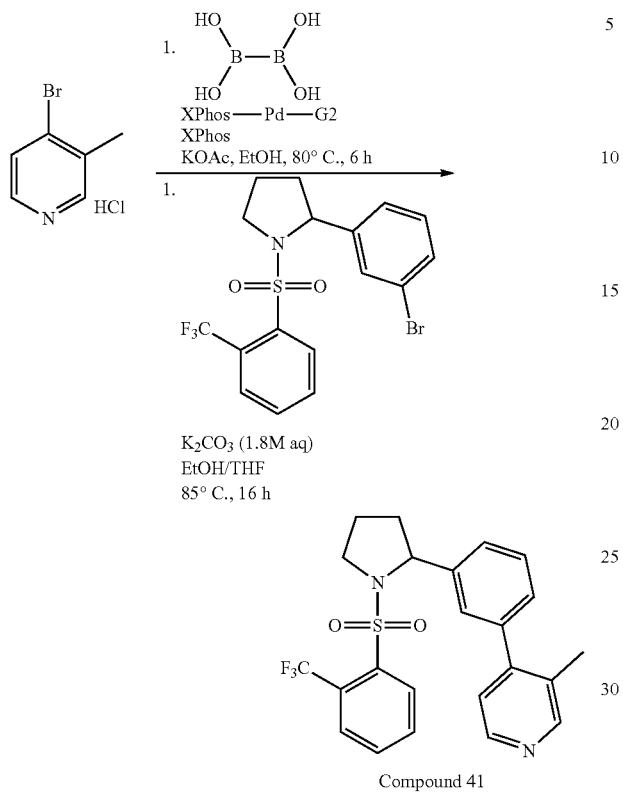

Compound 41

(+/−) 3-Methyl-4-(3-(1-((2-(trifluoromethyl)phenyl)
sulfonyl)pyrrolidin-2-yl)phenyl)pyridine (Compound 41)

Tetrahydroxydiborane (56 mg, 0.63 mmol), 4-bromo-3-methylpyridine hydrochloride (44 mg, 0.21 mmol), chloro (2-dicyclohexylphosphino-2',4',6'-triisopropyl-1,1'-biphenyl)[2-(2'-amino-1,1'-biphenyl)]palladium(II) (XPhos-Pd-G2, 8.0 mg, 0.01 mmol), 2-dicyclohexylphosphino-2',4',6'-triisopropylbiphenyl (XPhos, 10.0 mg, 0.02 mmol), and potassium acetate (62 mg, 0.63 mmol) were weighed out into a Biotage microwave vessel. Absolute ethanol (2.5 mL) was added and the mixture was degassed with nitrogen for 10 minutes. The vessel was capped, and the reaction mixture was heated to 80° C. via heating block for 6 hours. The reaction mixture was cooled to room temperature, and a degassed solution of Intermediate 21B (80 mg, 0.18 mmol) in 0.3 mL THF and 0.3 mL ethanol was added, followed by a degassed potassium carbonate solution (0.42 mL, 1.8M aqueous). The reaction mixture was heated to 85° C. for 16 hours via heating block. After cooling to room temperature, the reaction mixture was diluted with EtOAc (10 mL), and filtered through a pad of Celite. The filtrate was concentrated in vacuo. Purification by silica gel chromatography (20-90% EtOAc/hexanes) yielded Compound 41 (22 mg, 27%). LCMS (Method A): m/z 447.4 (M+H)$^+$. $^1$H NMR (CDCl$_3$) δ 8.51 (s, 1H), 8.47 (d, 1H), 7.83 (d, 1H), 7.75 (d, 1H), 7.52 (t, 1H), 7.40 (t, 1H), 7.24 (m, 1H), 7.16 (m, 1H), 7.10 (m, 2H), 7.01 (m, 1H), 5.07 (m, 1H), 3.83 (m, 1H), 3.69 (m, 1H), 2.43 (m, 1H), 2.24 (s, 3H), 2.07-1.95 (m, 3H).

Example 42

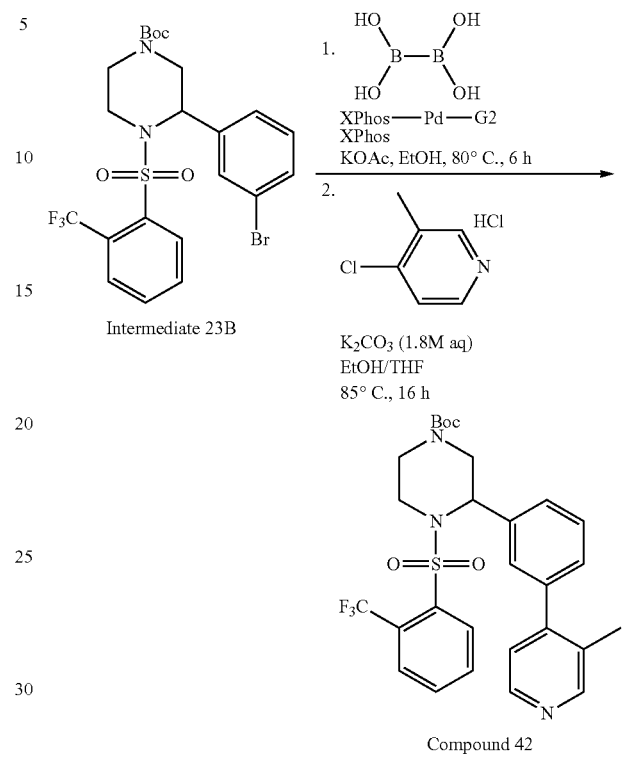

Compound 42

(+/−) tert-butyl 3-(3-(3-methylpyridin-4-yl)phenyl)-
4-((2-(trifluoromethyl)phenyl)sulfonyl)-piperazine-
1-carboxylate (Compound 42)

Tetrahydroxydiborane (102 mg, 1.14 mmol), tert-butyl 3-(3-bromophenyl)-4-((2-(trifluoromethyl)phenyl)sulfonyl) piperazine-1-carboxylate (213 mg, 0.38 mmol), chloro(2-dicyclohexylphosphino-2',4',6'-triisopropyl-1,1'-biphenyl) [2-(2'-amino-1,1'-biphenyl)]palladium(II) (XPhos-Pd-G2, 15 mg, 0.019 mmol), 2-dicyclohexylphosphino-2',4',6'-triisopropylbiphenyl (XPhos, 18 mg, 0.038 mmol), and potassium acetate (112 mg, 1.14 mmol) were weighed out into a Biotage microwave vessel. Absolute ethanol (2.5 mL) was added and the mixture was degassed with nitrogen for 10 minutes. The vessel was capped, and the reaction mixture was heated to 80° C. via heating block for 5 hours. The reaction mixture was cooled to room temperature, and 4-chloro-3-methylpyridine hydrochloride (62 mg, 0.38 mmol), was added, followed by a degassed potassium carbonate solution (0.76 mL, 1.8M aqueous). The reaction mixture was heated to 85° C. for 16 hours via heating block. After cooling to room temperature, the reaction mixture was diluted with EtOAc (10 mL), and filtered through a pad of celite. The resultant solution was washed with water (10 mL) and brine (10 mL), dried over Na$_2$SO$_4$, and concentrated in vacuo. Purification by silica gel chromatography (0-100% EtOAc/hexanes) and silica gel chromatography (0-5% MeOH/DCM) yielded Compound 42 (126 mg, 22%). LCMS (Method A): m/z 562.5 (M+H)$^+$. $^1$H NMR (CDCl$_3$) δ 8.48 (s, 1H), 8.44 (d, 1H), 8.16 (bs, 1H), 7.84 (m, 1H), 7.65 (m, 2H), 7.32 (bs, 2H), 7.20 (d, 1H), 7.12 (s, 1H), 7.01 (d, 1H), 5.17 (s, 1H), 5.56 (d, 1H), 4.03 (m, 2H), 3.34 (m, 1H), 3.22 (m, 1H), 2.86 (m, 1H), 1.32 (bs, 9H).

Example 43

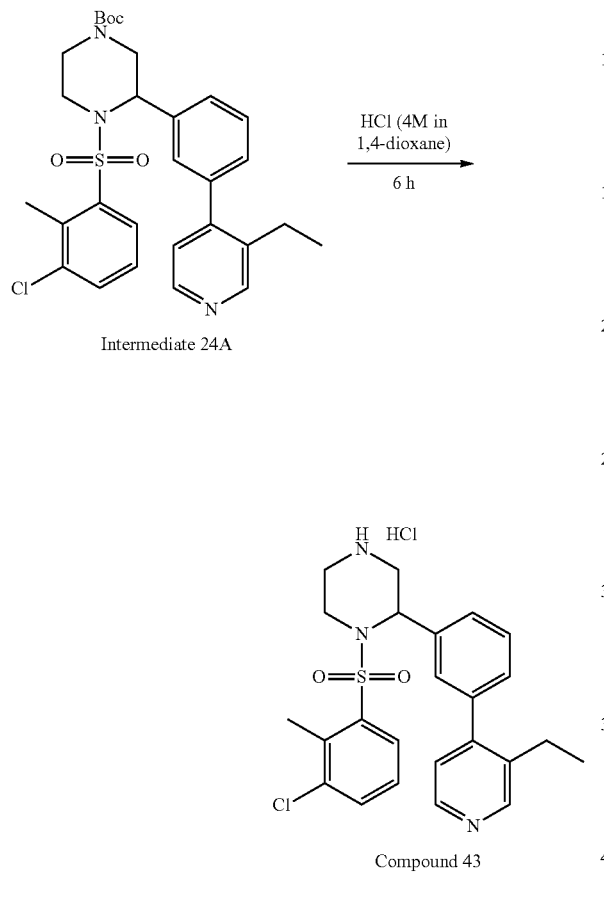

Intermediate 24A

Compound 43

(+/−) 1-((3-chloro-2-methylphenyl)sulfonyl)-2-(3-(3-ethylpyridin-4-yl)phenyl)piperazine hydrochloride (Compound 43)

A solution was made of (+/−) tert-butyl 4-((3-chloro-2-methylphenyl)sulfonyl)-3-(3-(3-ethylpyridin-4-yl)phenyl)piperazine-1-carboxylate (0.60 g, 1.1 mmol) in 1,4-dioxane (4 mL). A solution of HCl in 1,4-dioxane (4 M, 2.7 mL, 11 mmol) was added. After 3 hours at room temperature, the reaction mixture was heated to 35° C. for an additional 3 hours. The reaction mixture was cooled to room temperature, and diethyl ether (60 mL) was added. After cooling to 0° C. for 15 minutes, the resulting white solid was collected by vacuum filtration, and dried under vacuum to give Compound 43 (0.48 g, 90%). LCMS (Method A): m/z 456.4 (M+H)$^+$. $^1$H NMR (DMSO-d6) δ 9.98 (s, 1H), 9.42 (s, 1H), 8.92 (s, 1H), 8.82 (d, 1H), 8.70 (m, 2H), 7.48 (d, 1H), 7.40 (m, 3H), 7.25 (m, 2H), 5.14 (m, 1H), 3.81-3.68 (m, 3H), 3.43-3.23 (m, 3H), 2.75 (q, 2H), 2.57 (s, 3H), 1.10 (t, 3H).

Following the method described above for Example 43 and substituting the appropriate starting reagents, the following compounds were prepared as indicated in Table 28.

TABLE 28

| Compound No. | Structure | Intermediate | MS (M + H)$^+$ |
|---|---|---|---|
| 43AA | 2-(3-(3-methylpyridin-4-yl)phenyl)-1-(o-tolylsulfonyl)piperazine | 24B | 508.4/510.4 (method A) |
| 43AB | 1-((3-methoxyphenyl)sulfonyl)-2-(3-(3-methylpyridin-4-yl)phenyl)piperazine | 24C | 424.4 (method A) |
| 43AC | 1-((2,3-dichlorophenyl)sulfonyl)-2-(3-(3-methylpyridin-4-yl)phenyl)piperazine | 24D | 462.3/464.3 (method A) |

TABLE 28-continued

| Compound No. | Structure | Intermediate | MS (M + H)+ |
|---|---|---|---|
| 43AD | 1-((4-fluoro-2-(trifluoromethyl)phenyl)sulfonyl)-2-(3-(3-methylpyridin-4-yl)phenyl)piperazine | 24E | 480.4/ 481.4 (method A) |
| 43AE | 1-((3-chloro-2-methylphenyl)sulfonyl)-2-(3-(3-methylpyridin-4-yl)phenyl)piperazine | 24F | 442.4/ 444.4 (method A) |
| 43AF | 1-((3-chloro-2-methylphenyl)sulfonyl)-2-(3-(pyridin-4-yl)phenyl)piperazine | 25A | 428.3/ 430.3 (method A) |
| 43AG | 1-((3-chloro-2-methylphenyl)sulfonyl)-2-(3-(3-chloropyridin-4-yl)phenyl)piperazine | 25B | 462.2/ 464.2 (method A) |
| 43AH | 1-((3-chloro-2-methylphenyl)sulfonyl)-2-(3-(3-methoxypyridin-4-yl)phenyl)piperazine | 25C | 458.3/ 460.3 (method A) |

Example 44

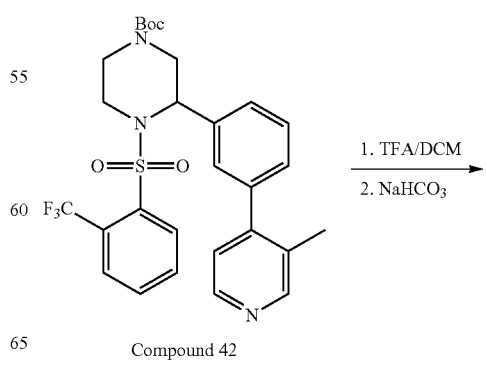

1. TFA/DCM
2. NaHCO₃

Compound 42

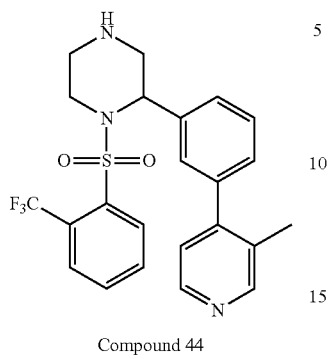

Compound 44

(+/−) 2-(3-(3-methylpyridin-4-yl)phenyl)-1-((2-(trifluoromethyl)phenyl)sulfonyl)piperazine (Compound 44)

To a solution of Compound 42 in DCM (3 mL) was added TFA (1 mL). After stirring at room temperature for 2 hours, the reaction was concentrated in vacuo. The residue was dissolved in EtOAc (10 mL) and neutralized by washing with saturated NaHCO$_3$. The aqueous layer was further extracted with EtOAc (10 mL) and the combined EtOAc layers were washed with brine, dried over Na$_2$SO$_4$, and concentrated in vacuo. Purification by silica gel chromatography (0-5% MeOH/DCM) yielded Compound 44 (78 mg, 81%). LCMS (Method A): m/z 462.4 (M+H)$^+$. $^1$H NMR (CDCl$_3$) δ 8.48 (s, 1H), 8.44 (d, 1H), 8.06 (m, 1H), 7.81 (m, 1H), 7.60 (m, 2H), 7.37 (m, 2H), 7.20 (m, 2H), 7.03 (d, 1H), 5.05 (s, 1H), 3.67 (m, 1H), 3.51 (m, 1H), 3.35 (m, 1H), 3.21 (m, 1H), 2.95 (m, 1H), 2.82 (m, 1H), 2.24 (s, 3H).

Example 45

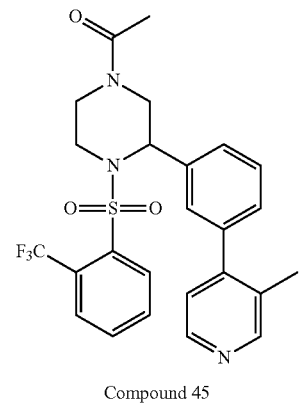

Compound 45

1-(3-(3-(3-methylpyridin-4-yl)phenyl)-4-((2-(trifluoromethyl)phenyl)sulfonyl)piperazin-1-yl)ethanone (Compound 45)

To a solution of Compound 44 (31 mg, 0.67 mmol) in DCM (1 mL) was added TEA (28 μL, 0.20 mmol) and acetic anhydride (13 μL, 0.134 mmol). After stirring at room temperature for 16 hours the mixture was directly purified by silica gel chromatography (0-5% MeOH/DCM) to yield Compound 45 (29.7 mg, 88%). LCMS (method A): m/z 504.4 (M+H)$^+$. $^1$H NMR (CDCl$_3$; mixture of conformational isomers/rotamers) δ 8.46 (m, 2H), 8.14-8.06 (m, 1H), 7.81 (m, 1H), 7.61 (m, 2H), 7.36-6.96 (m, 4H), 6.95 (m, 1H), 5.21-5.14 (m, 1H), 4.90, 4.38 (2m, 1H), 4.13, 3.96 (2m, 1H), 3.75-3.28 (m, 3H), 3.25, 2.95 (m, 1H), 2.24-2.17 (3s, 3H), 2.10-1.94 (3s, 3H).

Example 46

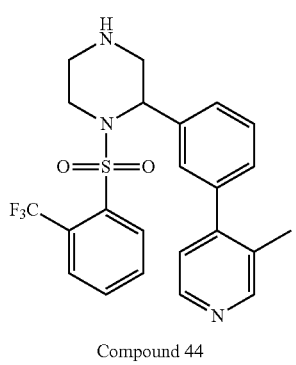

Compound 44

Ac$_2$O/Et$_3$N/DCM →

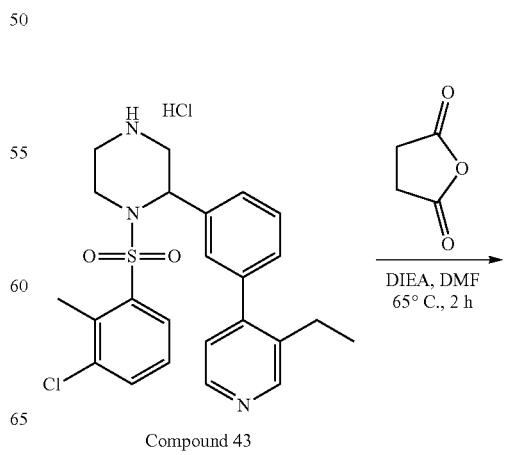

Compound 43

DIEA, DMF
65° C., 2 h

(+/−) 4-(4-((3-Chloro-2-methylphenyl)sulfonyl)-3-(3-(3-ethylpyridin-4-yl)phenyl)piperazin-1-yl)-4-oxobutanoic acid (Compound 46)

DMF (0.5 mL) was added to a mixture of (+/−) 1-((3-chloro-2-methylphenyl)sulfonyl)-2-(3-(3-ethylpyridin-4-yl)phenyl)piperazine hydrochloride (74 mg, 0.15 mmol) and succinic anhydride 22 mg, 0.22 mmol) in a Biotage microwave vessel. The mixture was stirred until the reactants were dissolved. N,N-Diisopropylethylamine (78 µL, 0.45 mmol) was added to the reaction mixture and the vessel was capped and heated to 65° C. for 2 hours in a heating block. Upon cooling, the volatiles were removed in vacuo, and the residue was purified by reverse phase chromatography (30 g C18 column, 5-50% acetonitrile in water with 0.25% formic acid). The product was isolated by lyophilization to give Compound 46 (56 mg, 68%). LCMS (Method A): m/z 556.5/558.5 (M+H)+. $^1$H NMR (CD$_3$OD, 1.8:1 mixture of 3° amide rotamers) δ 8.44 (m, 2H), 7.94-7.81 (m, 1H), 7.60 (m, 1H), 7.40-7.22 (m, 4H), 7.17-6.97 (m, 2H), 5.12 (m, 1H), 4.73 (m, 1H), 4.25-3.22 (m, 5H, overlapping with CD$_3$OD), 2.66-2.29 (m, 6H), 2.58 (m, 3H), 1.02 (m, 3H).

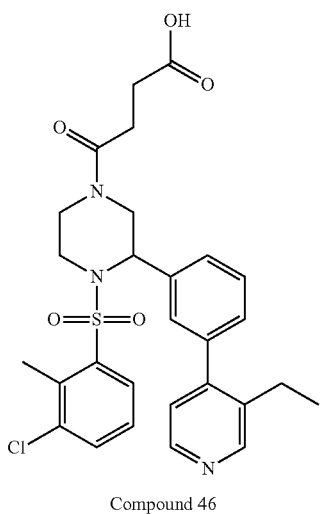

Compound 46

Following the method described above for Example 46 and substituting the appropriate intermediates and reagents, the following compounds were prepared as indicated in Table 29.

TABLE 29

| Compound No | Structure | Starting Material | Reagent | MS (M + H)+ |
|---|---|---|---|---|
| 46AA | [structure shown below] | Compound 43 | [glutaric anhydride structure] | 570.6/ 572.5 (method A) |

5-(4-((3-chloro-2-methylphenyl)sulfonyl)-3-(3-ethylpyridin-4-yl)phenyl)piperazin-1-yl)-5-oxopentanoic acid

TABLE 29-continued
| Compound No | Structure | Starting Material | Reagent | MS (M + H)+ |
|---|---|---|---|---|
| 46AB | 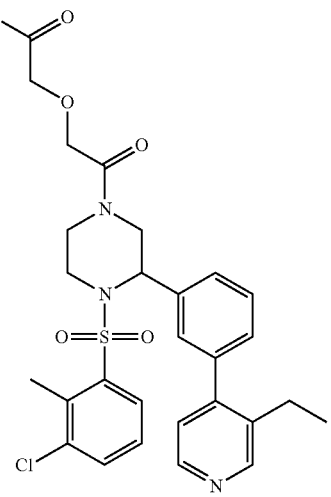<br>2-(2-(4-((3-chloro-2-methylphenyl)sulfonyl)-3-(3-(3-ethylpyridin-4-yl)phenyl)piperazin-1-yl)-2-oxoethoxy)acetic acid | Compound 43 | 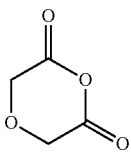 | 572.5/ 574.5 (method A) |
| 46AC | 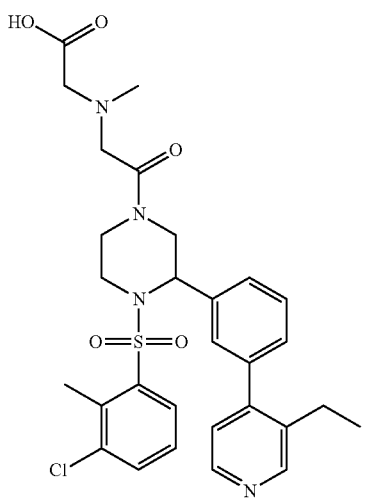 [SMILES: CCc1cnccc1-c1cccc(C2CN(C(=O)CN(C)CC(=O)O)CCN2S(=O)(=O)c2cccc(Cl)c2C)c1]<br>2-((2-(4-((3-chloro-2-methylphenyl)sulfonyl)-3-(3-(3-ethylpyridin-4-yl)phenyl)piperazin-1-yl)-2-oxoethyl)(methyl)amino)acetic acid | Compound 43 | 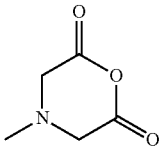 | 585.5/ 587.5 (method A) |

TABLE 29-continued
| Compound No | Structure | Starting Material | Reagent | MS (M + H)+ |
|---|---|---|---|---|
| 46AD | 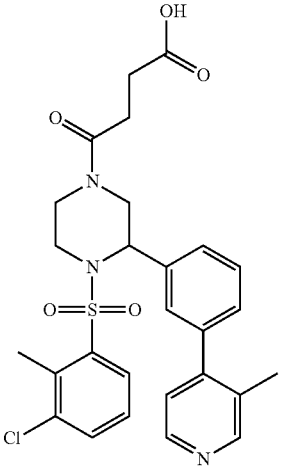 [SMILES: Cc1cnccc1-c1cccc(C2CN(C(=O)CCC(=O)O)CCN2S(=O)(=O)c2cccc(Cl)c2C)c1]<br>4-(4-((3-chloro-2-methylphenyl)sulfonyl)-3-(3-(3-methylpyridin-4-yl)phenyl)piperazin-1-yl)-4-oxobutanoic acid | Compound 43AE | 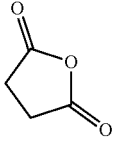 | 542.5/ 544.5 (method A) |
| 46AE | 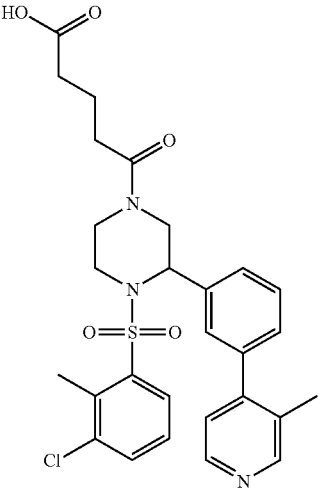 [SMILES: Cc1cnccc1-c1cccc(C2CN(C(=O)CCCC(=O)O)CCN2S(=O)(=O)c2cccc(Cl)c2C)c1]<br>5-(4-((3-chloro-2-methylphenyl)sulfonyl)-3-(3-(3-methylpyridin-4-yl)phenyl)piperazin-1-yl)-5-oxopentanoic acid | Compound 43AE | 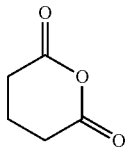 | 556.5/ 558.5 (method A) |

TABLE 29-continued

| Compound No | Structure | Starting Material | Reagent | MS (M + H)+ |
|---|---|---|---|---|
| 46AF | 4-(4-((3-chloro-2-methylphenyl)sulfonyl)-3-(3-(pyridin-4-yl)phenyl)piperazin-1-yl)-4-oxobutanoic acid | Compound 43AF | succinic anhydride | 528.3/ 530.3 (method A) |
| 46AG | 4-(4-((3-chloro-2-methylphenyl)sulfonyl)-3-(3-(3-chloropyridin-4-yl)phenyl)piperazin-1-yl)-4-oxobutanoic acid | Compound 43AG | succinic anhydride | 562.3/ 564.3 (method A) |

TABLE 29-continued
| Compound No | Structure | Starting Material | Reagent | MS (M + H)+ |
|---|---|---|---|---|
| 46AH | 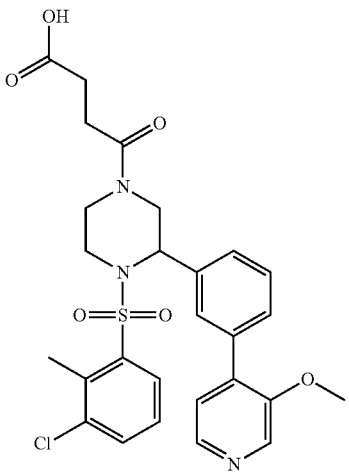 [SMILES: COc1cnccc1-c1cccc(C2CN(C(=O)CCC(=O)O)CCN2S(=O)(=O)c2cccc(Cl)c2C)c1]<br>4-(4-((3-chloro-2-methylphenyl)sulfonyl)-3-(3-(3-methoxypyridin-4-yl)phenyl)piperazin-1-yl)-4-oxobutanoic acid | Compound 43AH | 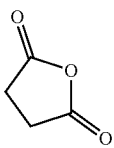 | 558.3/ 560.3 (method A) |
| 46AI | 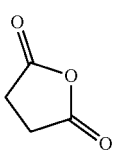<br>4-(3-(3-(3-methylpyridin-4-yl)phenyl)-4-(o-tolylsulfonyl)piperazin-1-yl)-4-oxobutanoic acid | Compound 43AA | 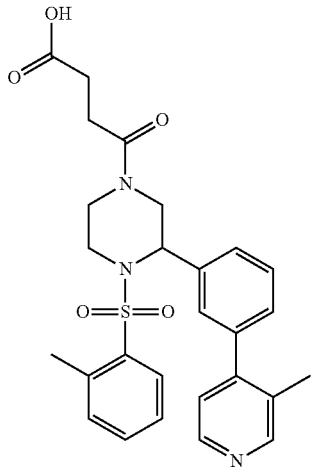 [SMILES: Cc1cnccc1-c1cccc(C2CN(C(=O)CCC(=O)O)CCN2S(=O)(=O)c2ccccc2C)c1] | 508.4/ 509.5 (method A) |

TABLE 29-continued

| Compound No | Structure | Starting Material | Reagent | MS (M + H)+ |
|---|---|---|---|---|
| 46AJ | 4-(4-((3-methoxyphenyl)sulfonyl)-3-(3-(3-methylpyridin-4-yl)phenyl)piperazin-1-yl)-4-oxobutanoic acid | Compound 43AB | succinic anhydride | 524.5/ 525.5 (method A) |
| 46AK | 4-(4-((2,3-dichlorophenyl)sulfonyl)-3-(3-(3-methylpyridin-4-yl)phenyl)piperazin-1-yl)-4-oxobutanoic acid | Compound 43AC | succinic anhydride | 562.4/ 564.4 (method A) |

TABLE 29-continued

| Compound No | Structure | Starting Material | Reagent | MS (M + H)+ |
|---|---|---|---|---|
| 46AL | 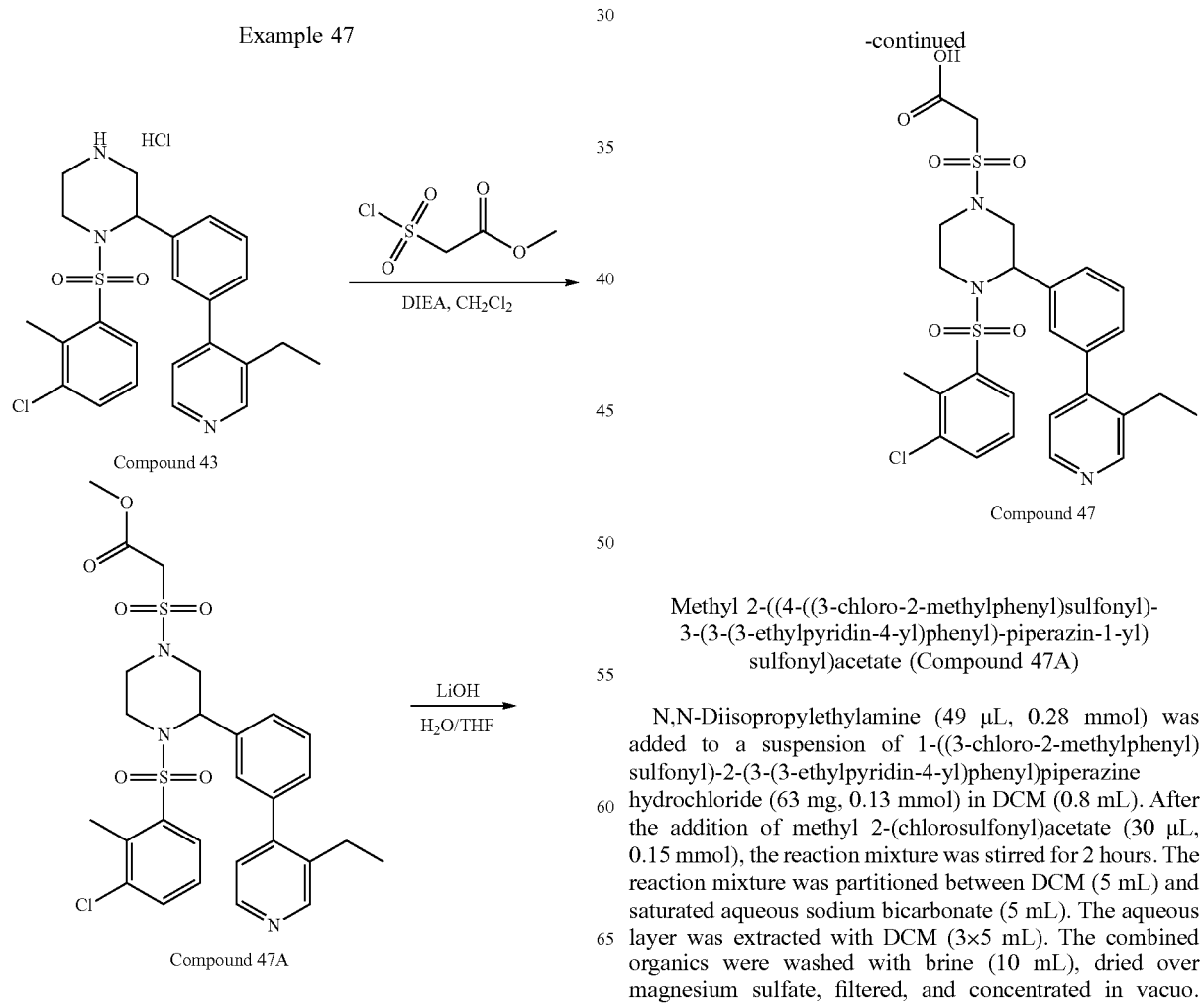

4-(4-((4-fluoro-2-(trifluoromethoxy)phenyl)sulfonyl)-3-(3-(3-methylpyridin-4-yl)phenyl)piperazin-1-yl)-4-oxobutanoic acid | Compound 43AD | | 580.5/ 581.5 (method A) |

Example 47

Methyl 2-((4-((3-chloro-2-methylphenyl)sulfonyl)-3-(3-(3-ethylpyridin-4-yl)phenyl)-piperazin-1-yl)sulfonyl)acetate (Compound 47A)

N,N-Diisopropylethylamine (49 μL, 0.28 mmol) was added to a suspension of 1-((3-chloro-2-methylphenyl)sulfonyl)-2-(3-(3-ethylpyridin-4-yl)phenyl)piperazine hydrochloride (63 mg, 0.13 mmol) in DCM (0.8 mL). After the addition of methyl 2-(chlorosulfonyl)acetate (30 μL, 0.15 mmol), the reaction mixture was stirred for 2 hours. The reaction mixture was partitioned between DCM (5 mL) and saturated aqueous sodium bicarbonate (5 mL). The aqueous layer was extracted with DCM (3×5 mL). The combined organics were washed with brine (10 mL), dried over magnesium sulfate, filtered, and concentrated in vacuo.

Purification by silica gel chromatography (0-8% MeOH in DCM) yielded Compound 47A (31 mg, 41%). $^1$H NMR (CDCl$_3$) δ 8.53 (s, 1H), 8.46 (d, 1H), 7.92 (d, 1H), 7.55 (d, 1H), 7.38 (m, 2H), 7.22 (m, 2H), 6.95 (d, 2H), 5.03 (m, 1H), 4.32 (m, 1H), 3.96 (m, 3H), 3.82 (s, 3H), 3.70 (m, 2H), 3.30 (m, 2H), 2.57 (s, 3H), 2.54 (m, 2H), 1.04 (t, 3H).

2-((4-((3-Chloro-2-methylphenyl)sulfonyl)-3-(3-(3-ethylpyridin-4-yl)phenyl)piperazin-1-yl)sulfonyl) acetic acid (Compound 47)

An aqueous lithium hydroxide solution (4 mg, 0.16 mmol, in 0.3 mL water) was added to a solution of methyl 2-((4-((3-chloro-2-methylphenyl)sulfonyl)-3-(3-(3-ethylpyridin-4yl)phenyl)piperazin-1-yl)sulfonyl)acetate (31 mg, 0.05 mmol) in THF (0.5 mL). The reaction mixture was stirred for 16 hours at room temperature. After adding formic acid (50 µL) to the reaction mixture, the mixture was concentrated in vacuo. The residue was purified by reverse phase chromatography (30 g C18 column, 5-20% acetonitrile in water with 0.25% formic acid). The product was isolated by lyophilization to give Compound 47 (19 mg, 63%). LCMS (Method A): m/z 578.4/580.4 (M+H)$^+$. $^1$H NMR (CD$_3$OD) δ 8.52 (m, 2H), 7.96 (m, 1H), 7.63 (m, 1H), 7.50 (m, 1H), 7.43 (t, 1H), 7.36-7.23 (m, 3H), 7.15 (m, 1H), 5.17 (m, 1H), 4.33 (d, 1H), 4.07 (s, 2H), 3.88 (d, 1H), 3.71 (d, 1H), 3.60 (m, 1H), 3.37-3.13 (m, 2H, overlapping with CD$_3$OD), 2.67 (q, 2H), 2.59 (s, 3H), 1.05 (t, 3H).

Example 48

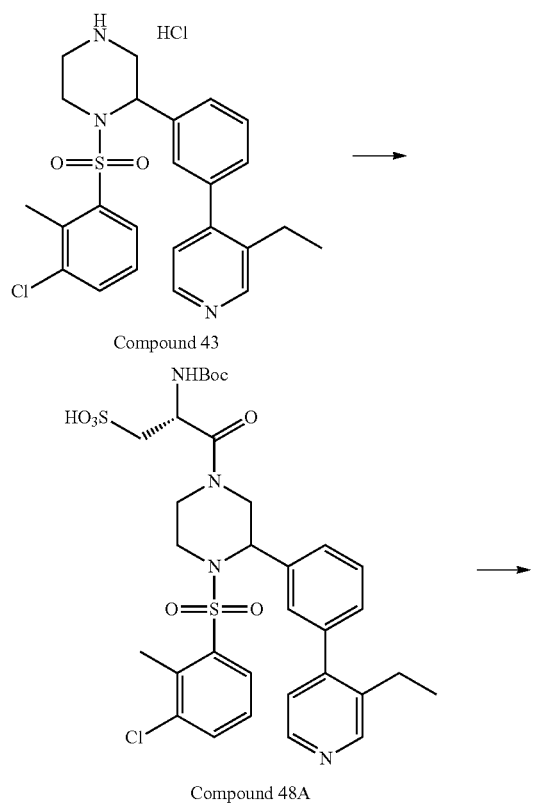

Compound 43

Compound 48A

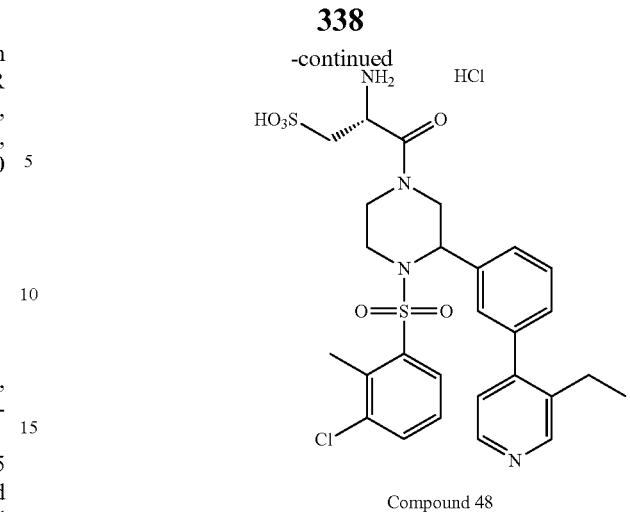

Compound 48

(2R)-2-((tert-butoxycarbonyl)amino)-3-(4-((3-chloro-2-methylphenyl)sulfonyl)-3-(3-(3-ethylpyridin-4-yl)phenyl)piperazin-1-yl)-3-oxopropane-1-sulfonic acid (Compound 48A)

A mixture of Boc-L-cysteic acid (98 mg, 0.36 mmol), 1-hydroxybenzotriazole hydrate (49 mg, 0.36 mmol), and N-(3-dimethylaminopropyl)-N'-ethylcarbodiimide hydrochloride (70 mg, 0.36 mmol) in DCM (2.5 mL) and DMF (0.4 mL) was stirred for 5 minutes. N,N-Diisopropylethylamine (0.38 mL, 3.9 mmol) and 1-((3-chloro-2-methylphenyl)sulfonyl)-2-(3-(3-ethylpyridin-4-yl)phenyl)piperazine hydrochloride (112 mg, 0.23 mmol) were added to the reaction mixture. After stirring overnight the volatiles were removed in vacuo to yield Compound 48A which was carried forward as a crude mixture of diastereomers. LCMS (Method A): Peak A m/z 707.5/709.5 (M+H)$^+$, Peak B m/z=707.5/709.5 (M+H)$^+$.

(2R)-2-amino-3-(4-((3-chloro-2-methylphenyl)sulfonyl)-3-(3-(3-ethylpyridin-4-yl)phenyl)piperazin-1-yl)-3-oxopropane-1-sulfonic acid hydrochloride (Compound 48)

Hydrogen chloride solution (4 M in 1,4-dioxane, 2 mL) was added to a suspension of crude Compound 48A (approximately 0.23 mmol) in 1,4-dioxane (2 mL). After 80 minute, the volatiles were removed in vacuo, and the residue was taken up in water (1.2 mL), acetonitrile (0.5 mL), and formic acid (0.10 mL). The mixture was filtered through a cotton plug, and purified by reverse phase chromatography (30 g C18 column, 5-50% acetonitrile in water with 0.25% formic acid). The product was isolated by lyophilization to give Compound 48 as a mixture of diastereomers (61 mg, 44%). LCMS (Method A): m/z 607.3/609.3 (M+H)$^+$. $^1$H NMR (CD$_3$OD, mixture of diastereomers and 3° amide rotomers) δ 8.48 (m, 1H), 8.41 (m, 1H), 7.97-7.56 (m, 2H), 7.45-6.94 (m, 6H), 5.18 (m, 1H), 4.84-4.48 (m, 2H), 4.13-3.77 (m, 3H), 3.67-3.26 (m, 3H), 3.14-2.77 (m, 1H), 2.65-2.56 (m, 5H), 1.12-1.00 (m, 3H).

Example 49

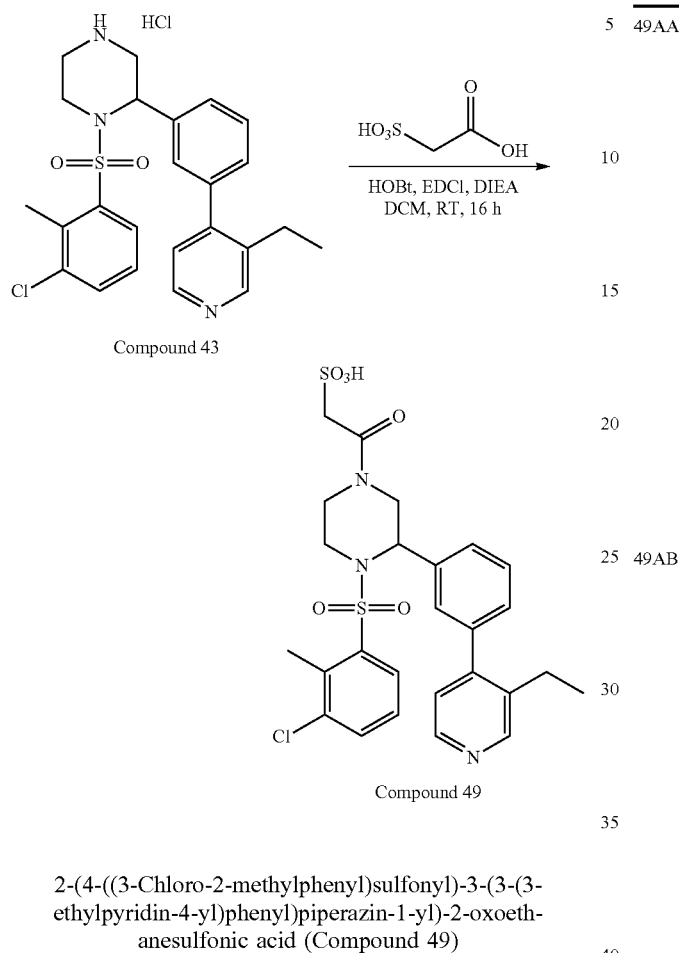

Compound 43

Compound 49

2-(4-((3-Chloro-2-methylphenyl)sulfonyl)-3-(3-(3-ethylpyridin-4-yl)phenyl)piperazin-1-yl)-2-oxoethanesulfonic acid (Compound 49)

A mixture of 2-sulfoacetic acid (38 mg, 0.27 mmol), 1-hydroxybenzotriazole hydrate (36 mg, 0.27 mmol), and N-(3-dimethylaminopropyl)-N'-ethylcarbodiimide hydrochloride (51 mg, 0.27 mmol) in DCM (1.5 mL) was stirred for 5 minutes at room temperature. N,N-Diisopropylethylamine (0.14 mL, 0.80 mmol) and Compound 43 (66 mg, 0.13 mmol) were added to the reaction mixture. After the reaction mixture was stirred overnight at room temperature, the mixture was concentrated in vacuo. The residue was taken up in water (2 mL), acetonitrile (2 mL), and formic acid (0.5 mL), and concentrated in vacuo. The crude compound was purified by reverse phase chromatography (30 g C18 column, 5-60% acetonitrile in water with 0.25% formic acid). The product was isolated by lyophilization to give Compound 49 (43 mg, 55%). LCMS (Method A): m/z 578.5/580.5 (M+H)$^+$. $^1$H NMR (CD$_3$OD+CD$_3$CN, 5:1 ratio of 3° amide rotamers) δ 8.69 (m, 2H), 7.97 (major rotamer, m, 2H), 7.82 (minor rotamer, d, 1H), 7.69 (m, 1H), 7.58 (minor rotamer, d, 1H), 7.49-7.34 (m, 5H), 7.20 (minor rotamer, t, 1H), 5.19 (m, 1H), 4.95 (m, 1H), 4.24 (m, 1H), 4.11 (m, 1H), 3.89-3.68 (m, 3H), 3.44 (m, 1H), 3.28 (m, 1H, overlapping with CD$_3$OD), 2.85 (m, 2H), 2.62 (s, 3H), 1.20 (minor rotamer, t, 3H), 1.15 (t, 3H).

Following the method described above for Example 49 and substituting the appropriate starting reagents, the following compound was prepared as indicated in Table 30.

TABLE 30

| Compound No. | Structure | Starting material | MS (M + H)$^+$ |
|---|---|---|---|
| 49AA | 2-(3-(3-(3-methylpyridin-4-yl)phenyl)-4-(o-tolylsulfonyl)piperazin-1-yl)-2-oxoethanesulfonic acid | 43AA | 530.4 (method A) |
| 49AB | 2-(4-((3-methoxyphenyl)sulfonyl)-3-(3-(3-methylpyridin-4-yl)phenyl)piperazin-1-yl)-2-oxoethanesulfonic acid | 43AB | 546.4 (method A) |
| 49AC | 2-(4-((2,3-dichlorophenyl)sulfonyl)-3-(3-(3-methylpyridin-4-yl)phenyl)piperazin-1-yl)-2-oxoethanesulfonic acid | 43AC | 584.3/ 586.4 (method A) |

TABLE 30-continued

| Compound No. | Structure | Starting material | MS (M + H)+ |
|---|---|---|---|
| 49AD | [structure] 2-(4-((3-chloro-2-methylphenyl)sulfonyl)-3-(3-(pyridin-4-yl)phenyl)piperazin-1-yl)-2-oxoethanesulfonic acid | 43AF | 550.3/552.3 (method A) |
| 49AE | [structure] 2-(4-((3-chloro-2-methylphenyl)sulfonyl)-3-(3-(3-chloropyridin-4-yl)phenyl)piperazin-1-yl)-2-oxoethanesulfonic acid | 43AG | 584.3/586.3 (method A) |
| 49AF | [structure] 2-(4-((3-chloro-2-methylphenyl)sulfonyl)-3-(3-(3-methoxypyridin-4-yl)phenyl)piperazin-1-yl)-2-oxoethanesulfonic acid | 43AH | 580.3/582.3 (method A) |

TABLE 30-continued

| Compound No. | Structure | Starting material | MS (M + H)+ |
|---|---|---|---|
| 49AG | [structure] 2-(3-(3-(3-methylpyridin-4-yl)phenyl)-4-((2-(trifluoromethyl)phenyl)sulfonyl)piperazin-1-yl)-2-oxoethanesulfonic acid | 43AI | 584.4 (method A) |

Example 50

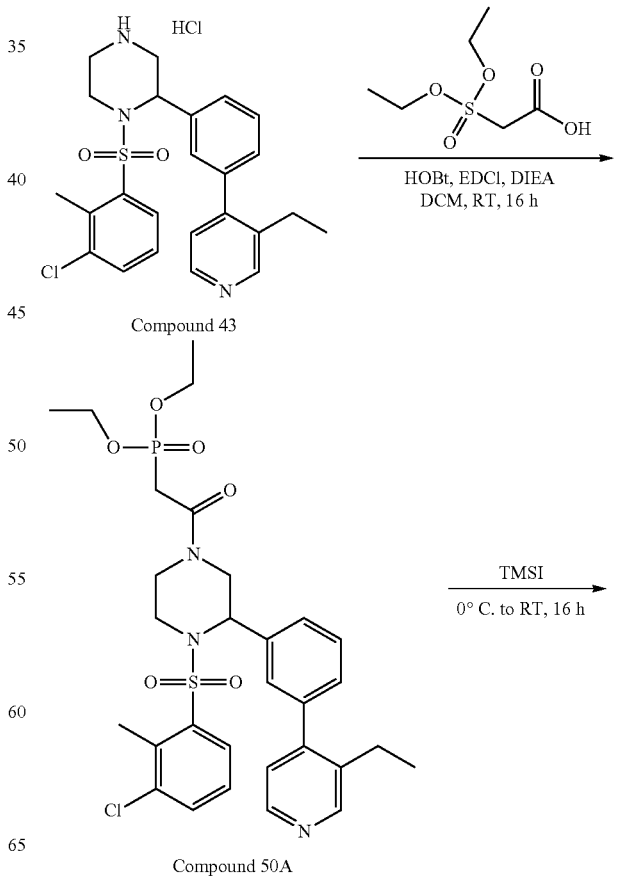

Compound 43

HOBt, EDCl, DIEA
DCM, RT, 16 h

Compound 50A

TMSI
0° C. to RT, 16 h

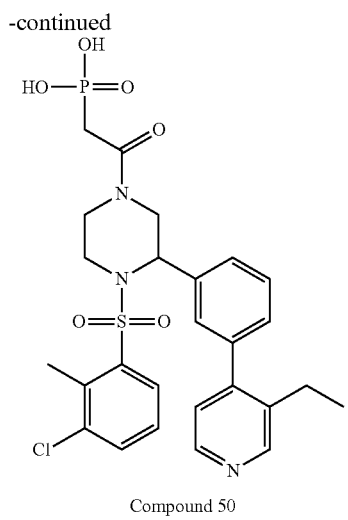

Compound 50

Diethyl (2-(4-((3-chloro-2-methylphenyl)sulfonyl)-3-(3-(3-ethylpyridin-4-yl)phenyl)piperazin-1-yl)-2-oxoethyl)phosphonate (Compound 50A)

A mixture of 2-(diethoxyphosphoryl)acetic acid (38 µL, 0.23 mmol) and 1-hydroxybenzotriazole hydrate (31 mg, 0.23 mmol) in dichloromethane (1.0 mL) was cooled to 0° C. After the addition of N-(3-dimethylaminopropyl)-N'-ethylcarbodiimide hydrochloride (45 mg, 0.23 mmol), the mixture was stirred at 0° C. for 5 minutes. N,N-Diisopropylethylamine (64 µL, 0.37 mmol) and Compound 43 (72 mg, 0.15 mmol) were added to the reaction mixture. After the reaction mixture was stirred overnight at room temperature, the mixture was evaporated to dryness. The residue was taken up in water (2 mL), acetonitrile (2 mL), and formic acid (0.5 mL), and evaporated to dryness. Purification by silica gel chromatography (0-8% methanol in dichloromethane) yielded Compound 50A (65 mg, 70%). LCMS (Method A): m/z 634.4/636.4 (M+H)+.

2-(4-((3-chloro-2-methylphenyl)sulfonyl)-3-(3-(3-ethylpyridin-4-yl)phenyl)piperazin-1-yl)-2-oxoethanesulfonic acid (Compound 50)

A solution of diethyl (2-(4-((3-chloro-2-methylphenyl)sulfonyl)-3-(3-(3-ethylpyridin-4-yl)phenyl)piperazin-1-yl)-2-oxoethyl)phosphonate (59 mg, 0.09 mmol) in acetonitrile (1.2 mL) was cooled to 0° C. Iodotrimethylsilane (79 µL, 0.56 mmol) was added in two portions. The reaction mixture was allowed to warm to room temperature and stir overnight. Upon cooling, the volatiles were removed in vacuo, and the resulting residue was purified by reverse phase chromatography (30 g C18 column, 5-50% acetonitrile in water with 0.25% formic acid). The product was isolated by lyophilization to give Compound 50 (35 mg, 65%). LCMS (Method A): m/z 578.4/580.4 (M+H)+. 1H NMR (CD3CN+CD3OD, mixture of 3° amide rotomers) δ 8.55 (m, 2H), 7.90-7.55 (m, 3H), 7.42-7.18 (m, 5H), 5.09 (m, 1H), 4.80 (m, 1H), 4.07-3.73 (m, 3H), 3.44-3.30 (m, 3H), 2.96 (m, 2H), 2.71 (m, 2H), 2.60 (m, 3H), 1.10 (m, 3H).

Example 51

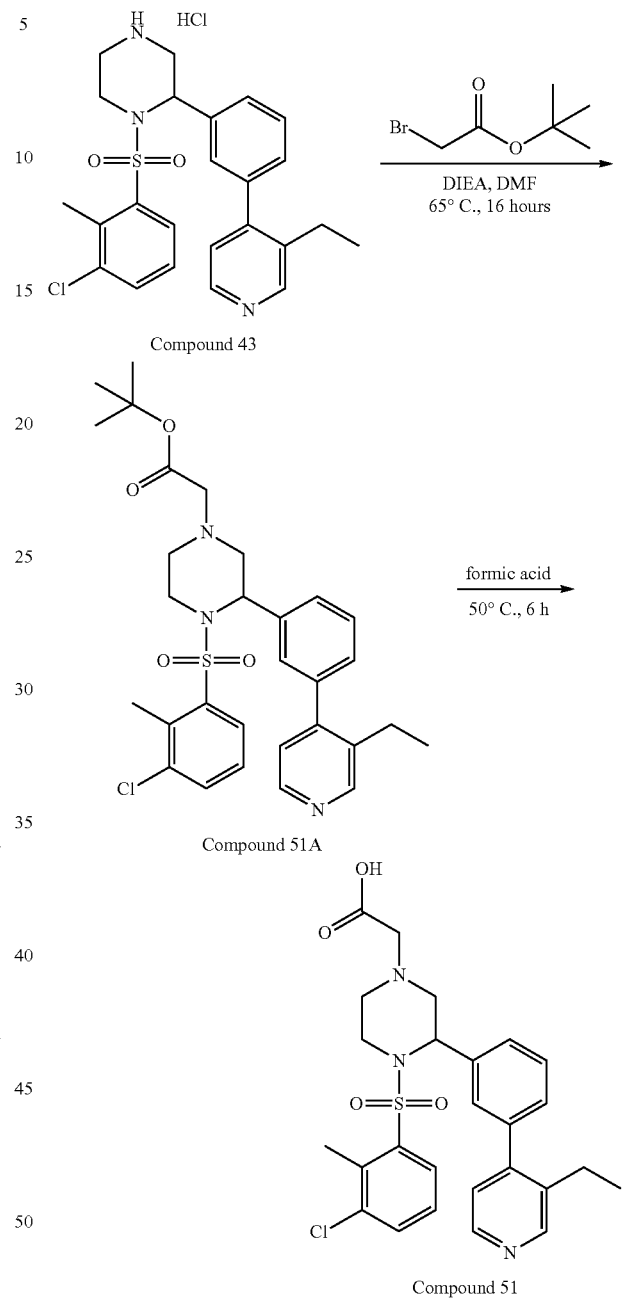

tert-Butyl 2-(4-((3-chloro-2-methylphenyl)sulfonyl)-3-(3-(3-ethylpyridin-4-yl)phenyl)piperazin-1-yl)acetate (Compound 51A)

A solution was made of 1-((3-chloro-2-methylphenyl)sulfonyl)-2-(3-(3-ethylpyridin-4-yl)phenyl)piperazine hydrochloride (67 mg, 0.14 mmol) and N,N-diisopropylethylamine (60 µL, 0.34 mmol) in DMF (0.5 mL). tert-Butyl 2-bromoacetate (24 µL, 0.16 mmol) was added to the reaction mixture, followed by heating to 65° C. for 16 hours. The reaction mixture was diluted with EtOAc (20 mL), washed with water (10 mL) and brine (10 mL), dried over sodium sulfate, filtered, and concentrated in vacuo. Purification by silica gel chromatography (5-80% EtOAc/hexanes) yielded Compound 51A (23 mg, 30%). $^1$H NMR (CDCl$_3$) δ 8.53 (s, 1H), 8.45 (d, 1H), 7.82 (m, 1H), 7.63 (d, 1H), 7.50 (m, 1H), 7.34 (t, 1H), 7.27 (s, 1H, overlapping with CDCl3), 7.18 (m, 2H), 7.02 (d, 1H), 4.93 (m, 1H), 3.66 (m, 1H), 3.42 (m, 2H), 3.15 (dd, 2H), 2.83 (m, 2H), 2.61 (m, 3H), 2.57 (s, 3H), 1.45 (s, 9H), 1.08 (t, 3H).

2-(4-((3-Chloro-2-methylphenyl)sulfonyl)-3-(3-(3-ethylpyridin-4-yl)phenyl)piperazin-1-yl)acetic acid (Compound 51)

A mixture of tert-butyl 2-(4-((3-chloro-2-methylphenyl)sulfonyl)-3-(3-(3-ethylpyridin-4-yl)phenyl)piperazin-1-yl)acetate (23 mg, 0.04 mmol) and formic acid (88%, 2 mL) was stirred at room temperature for 16 hours. An additional portion of formic acid (5 mL) was added, and the reaction mixture was stirred at room temperature for 4 hours, then 50° C. for 6 hours. The volatiles were removed in vacuo. The residue was suspended in water (2 mL) and acetonitrile (0.4 mL), and frozen. Lyophilization provided Compound 51 (18.5 mg, 90%) as a white powder. LCMS (method A): m/z 514.4/516.4 (M+H)$^+$. $^1$H NMR (CD$_3$OD) δ 8.48 (s, 1H), 8.40 (d, 1H), 7.81 (d, 1H), 7.60 (m, 2H), 7.36 (t, 1H), 7.27 (m, 3H), 7.17 (d, 1H), 5.01 (m, 1H), 3.73 (m, 1H), 3.59 (m, 1H), 3.46 (m, 1H), 3.35 (m, 2H, overlapping with CD$_3$OD), 2.94 (m, 2H), 2.66 (m, 3H), 2.57 (s, 3H), 1.06 (t, 3H).

Example 52

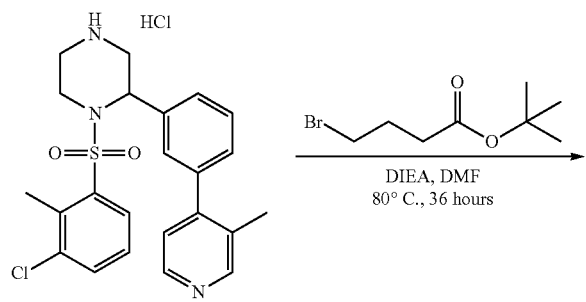

Compound 43AE

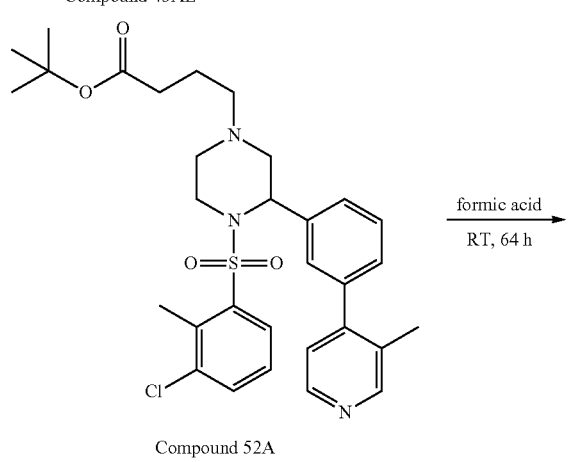

Compound 52A

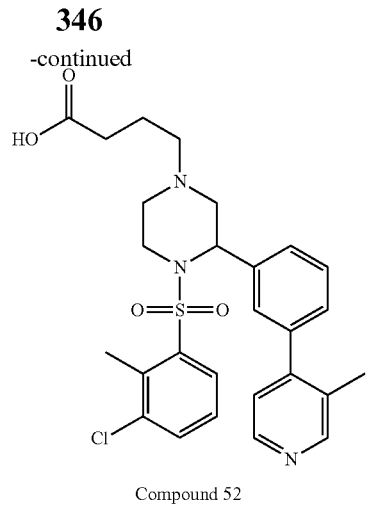

Compound 52 tert-Butyl 4-(4-((3-chloro-2-methylphenyl)sulfonyl)-3-(3-(3-methylpyridin-4-yl)phenyl)piperazin-1-yl)butanoate (Compound 52A)

N,N-Diisopropylethylamine (0.24 mL, 1.40 mmol) was added to a suspension of 1-((3-chloro-2-methylphenyl)sulfonyl)-2-(3-(3-methylpyridin-4-yl)phenyl)piperazine hydrochloride (0.26 g, 0.54 mmol) in DMF (2 mL). The mixture was stirred for 5 minutes. After tert-butyl 4-bromobutanoate (124 μL, 0.70 mmol) was added, the reaction vessel was capped and heated to 70° C. for 20 hours. Additional portions of N,N-diisopropylethylamine (45 μL) and tert-butyl 4-bromobutanoate (35 μL) were added, and the reaction mixture was heated to 80° C. for an additional 16 hours. The reaction mixture was diluted with EtOAc (40 mL), washed with water (25 mL), brine (25 mL), dried over sodium sulfate, filtered, and concentrated in vacuo. Purification by silica gel chromatography (5-70% EtOAc/hexanes) yielded Compound 52A (122 mg, 39%). $^1$H NMR (CDCl$_3$) δ 8.48 (m, 2H), 7.78 (d, 1H), 7.49 (m, 2H), 7.29 (m, 2H, overlapping with CDCl$_3$), 7.16 (m, 2H), 7.02 (d, 1H), 4.91 (m, 1H), 3.62 (m, 1H), 3.40 (m, 1H), 3.18 (m, 1H), 2.78 (m, 1H), 2.65 (m, 1H), 2.57 (s, 3H), 2.40-2.22 (m, 5H), 2.24 (s, 3H), 1.78 (m, 2H), 1.43 (s, 9H).

4-(4-((3-chloro-2-methylphenyl)sulfonyl)-3-(3-(3-methylpyridin-4-yl)phenyl)piperazin-1-yl)butanoic acid (Compound 52)

A mixture of tert-butyl 4-(4-((3-chloro-2-methylphenyl)sulfonyl)-3-(3-(3-methylpyridin-4-yl)phenyl)piperazin-1-yl)butanoate (87 mg, 0.15 mmol) and formic acid (88%, 10 mL) was stirred at room temperature for 36 hours. The volatiles were removed in vacuo to provide Compound 52 (77 mg, 98%). LCMS (Method A): m/z 528.5/530.5 (M+H)$^+$. $^1$H NMR (CD$_3$OD) δ 8.40 (m, 2H), 7.77 (d, 1H), 7.55 (d, 1H), 7.49 (d, 1H), 7.34 (m, 1H), 7.23 (m, 3H), 7.16 (d, 1H), 4.95 (m, 1H, overlapping with CD$_3$OD), 3.64 (m, 1H), 3.47 (m, 1H), 3.26 (m, 1H, overlapping with CD$_3$OD), 2.85 (m, 1H), 2.65 (m, 1H), 2.55 (s, 3H), 2.44 (m, 2H), 2.30 (m, 3H), 2.25 (s, 3H), 1.78 (m, 2H).

Following the method described above for Example 52 and substituting the appropriate starting reagent, the following compound was prepared as indicated in Table 31.

TABLE 31

| Compound No. | Structure | Starting material | MS (M + H)+ |
|---|---|---|---|
| 52AA | 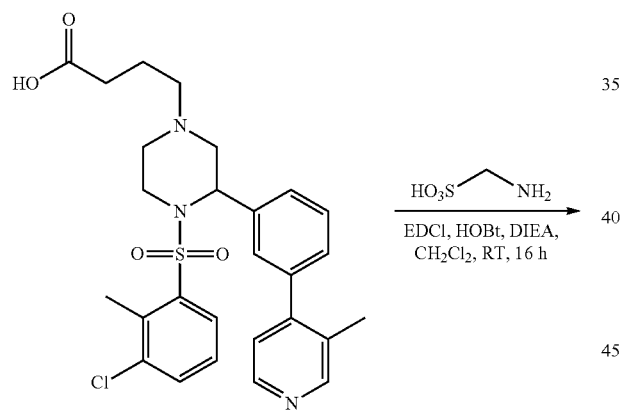  4-(4-((3-chloro-2-methylphenyl)sulfonyl)-3-(3-(3-ethylpyridin-4-yl)phenyl)piperazin-1-yl)butanoic acid | Compound 43 | 542.5/ 544.5 (M + H)+ (method A) |

Example 53

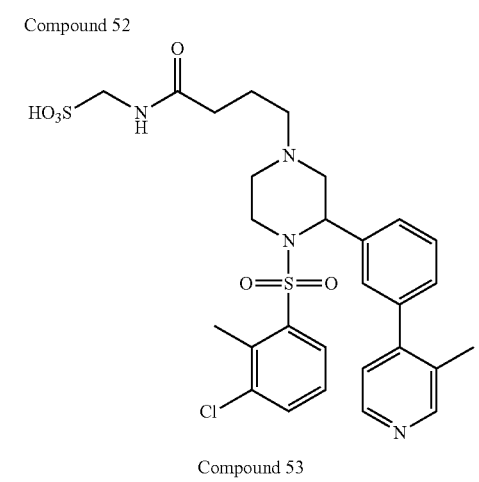

(4-(4-((3-Chloro-2-methylphenyl)sulfonyl)-3-(3-(3-methylpyridin-4-yl)phenyl)piperazin-1-yl)butanamido)methanesulfonic acid (Compound 53)

A mixture was made of 4-(4-((3-chloro-2-methylphenyl)sulfonyl)-3-(3-(3-methylpyridin-4-yl)phenyl)piperazin-1-yl)butanoic acid (61 mg, 0.12 mmol), aminomethanesulfonic acid (76 mg, 1-hydroxybenzotriazole hydrate (22 mg, 0.16 mmol), and N,N-diisopropylethylamine (80 µL, 0.46 mmol) in DCM (0.5 mL). N-(3-dimethylaminopropyl)-N-ethylcarbodiimide hydrochloride (31 mg, 0.16 mmol) was added, and the reaction mixture was stirred overnight at room temperature. The reaction mixture was diluted with acetonitrile (3 mL) and formic acid (100 µL), and filtered through a cotton plug. The filtrate was purified by reverse phase chromatography (30 g C18 column, 5-30% acetonitrile in water with 0.25% formic acid). The product was isolated by lyophilization to give Compound 53 (57 mg, 80%). LCMS (Method B): m/z 621.5/623.5 (M+H)+. $^1$H NMR (CD$_3$OD) δ 8.53 (s, 1H), 8.49 (d, 1H), 7.57 (m, 2H), 7.36-7.27 (m, 5H), 7.16 (m, 1H), 5.14 (m, 1H), 4.24 (dd, 2H), 3.92-3.77 (m, 3H), 3.43-3.26 (m, 3H, overlapping with CD$_3$OD), 3.14 (m, 2H), 2.64 (s, 3H), 2.44 (t, 2H), 2.32 (s, 3H), 2.02 (m, 2H).

Following the method described above for Example 53 and substituting the appropriate starting materials, the following compounds were prepared as indicated in Table 32.

TABLE 32
| Compound No | Structure | Starting material | Amine | MS (M + H)+ |
|---|---|---|---|---|
| 53AA | 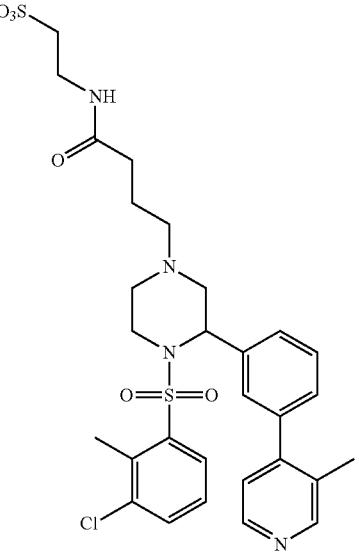<br>2-(4-(4-((3-chloro-2-methylphenyl)sulfonyl)-3-(3-(3-methylpyridin-4-yl)phenyl)piperazin-1-yl)butanamido)ethanesulfonic acid | 52 | 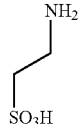 | 635.5/637.5 (M + H)+ (method A) |
| 53AB | 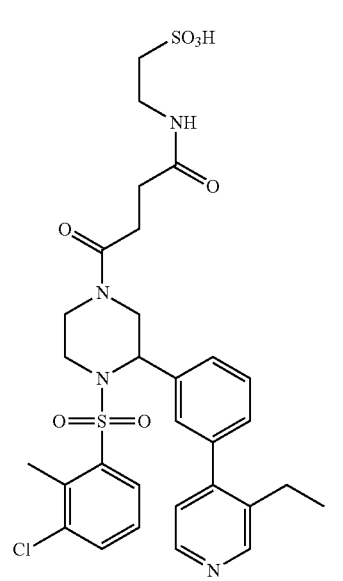 [SMILES: CCc1cnccc1-c1cccc(C2CN(C(=O)CCC(=O)NCCS(=O)(=O)O)CCN2S(=O)(=O)c2cccc(Cl)c2C)c1]<br>2-(4-(4-((3-chloro-2-methylphenyl)sulfonyl)-3-(3-(3-ethylpyridin-4-yl)phenyl)piperazin-1-yl)-4-oxobutanamido)ethanesulfonic acid | 52AA | 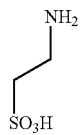 | 663.5/665.5 (M + H)+ (method A) |

TABLE 32-continued
| Compound No | Structure | Starting material | Amine | MS (M + H)+ |
|---|---|---|---|---|
| 53AC | 3-(4-(4-((3-chloro-2-methylphenyl)sulfonyl)-3-(3-(3-ethylpyridin-4-yl)phenyl)piperazin-1-yl)-4-oxobutanamido)propane-1-sulfonic acid | 52AA | NH₂–(CH₂)₃–SO₃H | 677.5/679.5 (M + H)+ (method A) |
Example 54
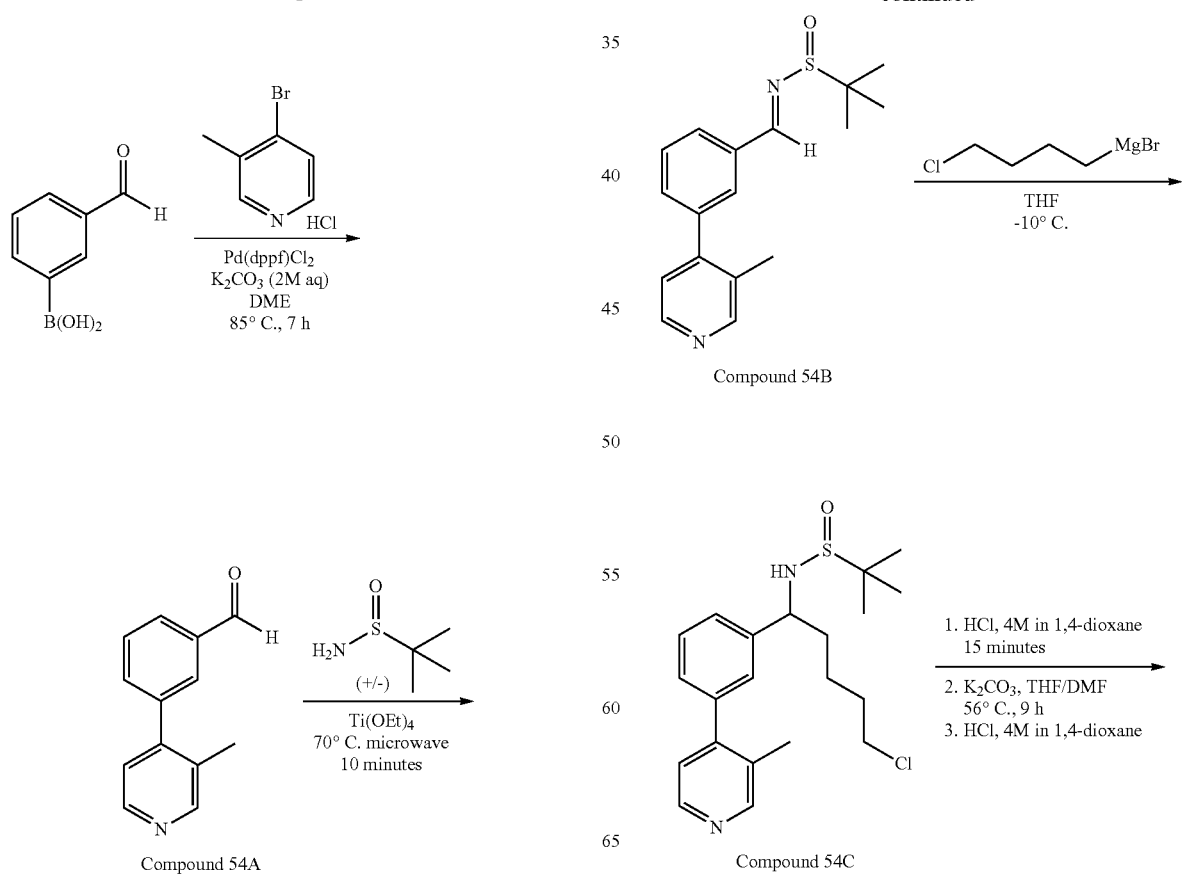

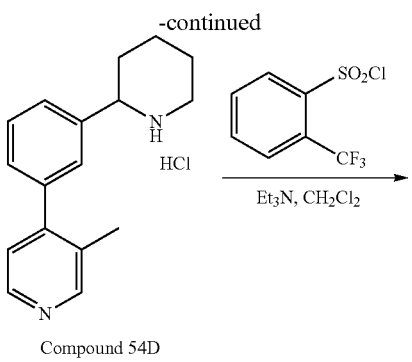

Compound 54D

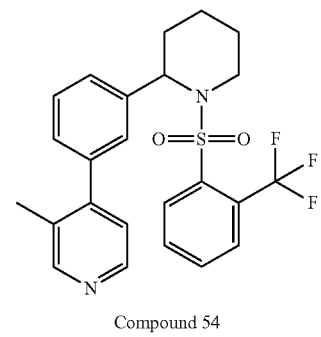

Compound 54

3-(3-Methylpyridin-4-yl)benzaldehyde (Compound 54A)

A mixture of (3-formylphenyl)boronic acid (2.1 g, 14 mmol) and 4-bromo-3-methylpyridine hydrochloride (2.4 g, 12 mmol) in 1,2-dimethoxyethane (48 mL) was degassed with nitrogen for 10 minutes. Aqueous potassium carbonate (2.5 M, 13.8 mL) was added, followed by [1,1'-bis(diphenylphosphino)ferrocene]dichloropalladium(II), complex with DCM (0.38 g, 0.46 mmol). The reaction mixture was heated to 85° C. for 6 hours under nitrogen. The reaction mixture was diluted with EtOAc (100 mL), and washed with water (60 mL) and brine (60 mL). The organic layer was dried over sodium sulfate, filtered and concentrated in vacuo. Purification by silica gel chromatography (20-90% EtOAc/hexanes) gave Compound 54A (1.35 g, 50%). $^1$H NMR (CDCl$_3$) δ 10.10 (s, 1H), 8.57 (s, 1H), 8.53 (d, 1H), 7.95 (m, 1H), 7.87 (m, 1H), 7.63 (m, 2H), 7.18 (d, 1H), 2.30 (s, 3H).

2-Methyl-N-(3-(3-methylpyridin-4-yl)benzylidene)propane-2-sulfinamide (Compound 54B)

Racemic 2-methylpropane-2-sulfinamide (0.93 g, 7.7 mmol) and Compound 54A (1.5 g, 7.7 mmol) were weighed out into a Biotage microwave vessel, and stirred under nitrogen. Titanium(IV) ethoxide (3.2 mL, 15.3 mmol) was added and the mixture was irradiated to 70° C. for 10 minutes in a Biotage Initiator microwave. After cooling, the reaction mixture was diluted with EtOAc (40 mL), and added to a rapidly stirred brine solution (1.7 mL). The mixture was filtered through Celite, and the filtrate was concentrated in vacuo to give Compound 54B (1.97 g, 86%). $^1$H NMR (CDCl$_3$) δ 8.66 (s, 1H), 8.56 (s, 1H), 8.52 (m, 1H), 7.90 (m, 1H), 7.84 (m, 1H), 7.60 (t, 1H), 7.50 (m, 1H), 7.19 (d, 1H), 2.31 (s, 3H), 1.29 (s, 9H).

N-(5-chloro-1-(3-(3-methylpyridin-4-yl)phenyl)pentyl)-2-methylpropane-2-sulfinamide (Compound 54C)

Magnesium filings (0.26 g, 10.7 mmol) were added to an oven-dried 3 necked flask fitted with dropping funnel, reflux condenser and nitrogen line. Anhydrous THF (8 mL) and 2 iodine crystals were added. A solution of 1-bromo-4-chlorobutane (1.07 mL, 9.3 mmol in 22 mL THF) was added to the dropping funnel. After the addition of 2 mL of the 1-bromo-4-chlorobutane solution to the Mg/THF mixture, a 40° C. water bath was applied until the reaction mixture turned clear. The reaction mixture was cooled to −10° C., and the 1-bromo-4-chlorobutane solution was added drop wise over 25 minutes. The reaction mixture was allowed to warm to room temperature, and stirred for 60 minutes to form a solution of (4-chlorobutyl)magnesium bromide. The mixture was cooled to −10° C.

A solution of Compound 54B (0.85 g, 2.8 mmol) in THF (16 mL) was cooled to −10° C. The (4-chlorobutyl)magnesium bromide solution was added via cannula over 10 minutes. After the addition was complete, the reaction mixture was poured into a saturated ammonium chloride solution (90 mL), and the layers were separated. The aqueous layer was extracted twice with 50 mL EtOAc. The combined organics were dried over sodium sulfate, filtered and concentrated in vacuo. Purification by silica gel chromatography (75-100% EtOAc in DCM) yielded Compound 54C (0.78 g, 84%) as a mixture of diastereomer pairs. $^1$H NMR (CDCl$_3$) δ 8.52 (s, 1H), 8.49 (m, 1H), 7.45 (m, 1H), 7.36 (m, 1H), 7.26 (m, 3H, overlapping with CDCl$_3$), 7.16 (m, 1H), 4.44 (m, 1H), 3.50 (t, 2H), 3.43 (m, 1H), 2.29, 2.28 (s, 3H, minor and major diastereomers), 1.89-1.74 (m, 4H), 1.47 (m, 1H), 1.36 (m, 1H), 1.25, 1.21 (s, 9H, minor and major diastereomers).

3-methyl-4-(3-(piperidin-2-yl)phenyl)pyridine hydrochloride (Compound 54D)

A solution of N-(1-(3-bromophenyl)-5-chloropentyl)-2-methylpropane-2-sulfinamide (120 mg, 0.31 mmol) in diethyl ether (4 mL) was cooled to 0° C. Hydrogen chloride solution (4 M in 1,4-dioxane, 0.31 mL) was added. After 5 minutes, an additional portion of hydrogen chloride solution (0.20 mL) was added, and the mixture was allowed to warm to room temperature. After 10 minutes, the solvent was decanted off, and the remaining white residue was dried in vacuo to give 5-chloro-1-(3-(3-methylpyridin-4-yl)phenyl) pentan-1-amine hydrochloride (105 mg, quantitative yield). $^1$H NMR (CD$_3$OD) δ 8.87 (s, 1H), 8.80 (d, 1H), 8.00 (d, 1H), 7.77-7.69 (m, 3H), 7.64 (m, 1H), 4.44 (s, 1H), 3.57 (m, 2H), 2.54 (s, 3H), 2.09 (m, 2H), 1.83 (m, 2H), 1.51 (m, 1H), 1.37 (m, 1H).

Tetrahydrofuran (6 mL) and DMF (2 mL) were added to 5-chloro-1-(3-(3-methylpyridin-4-yl)phenyl)pentan-1-amine hydrochloride (105 mg, 0.31 mmol). Potassium carbonate (0.86 g, 6.3 mmol) was added and the mixture was stirred for 10 minutes. The reaction mixture was heated to 56° C. for 9 hours. The reaction mixture was filtered through Celite, and concentrated in vacuo. The crude product was purified by reverse phase chromatography (30 g C18 column, 0-20% acetonitrile in water with 0.25% formic acid) to provide 3-methyl-4-(3-(piperidin-2-yl)phenyl)pyridine formate (60 mg, 65%). LCMS (Method B): m/z 253.4 (M+H)$^+$. $^1$H NMR (CD$_3$OD) δ 8.41 (m, 3H), 7.59 (m, 2H), 7.48 (m, 2H), 7.29 (d, 1H), 4.32 (dd, 1H), 3.48 (m, 1H), 3.20 (m, 1H), 2.30 (s, 3H), 2.14 (m, 1H), 2.02 (m, 3H), 1.81 (m, 2H).

Hydrogen chloride solution (4 M in 1,4-dioxane, 1 mL) was added to 3-methyl-4-(3-(piperidin-2-yl)phenyl)pyridine formate and stirred for 30 minutes, then concentrated in vacuo to provide Compound 54D.

3-methyl-4-(3-(1-((2-(trifluoromethyl)phenyl)sulfonyl)piperidin-2-yl)phenyl)pyridine (Compound 54)

The conversion of Compound 54D to Compound 54 (21 mg, 41%) was accomplished using the conditions outlined for Intermediate 21A. LCMS (Method A): m/z 461.4 (M+H)+. $^1$H NMR (CD$_3$OD) δ 8.45 (s, 1H), 8.39 (d, 1H), 8.23 (m, 1H), 7.88 (m, 1H), 7.75 (m, 2H), 7.44 (t, 1H), 7.38 (d, 1H), 7.24 (d, 1H), 7.15 (m, 2H), 5.31 (m, 1H), 3.88 (m, 1H), 3.13 (m, 1H), 2.41 (m, 1H), 2.24 (s, 3H), 1.97 (m, 1H), 1.61 (m, 2H), 1.46 (m, 2H).

Example 55

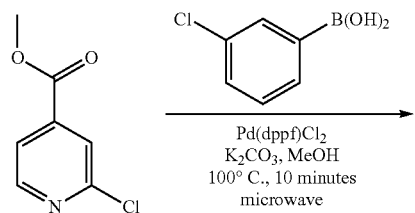

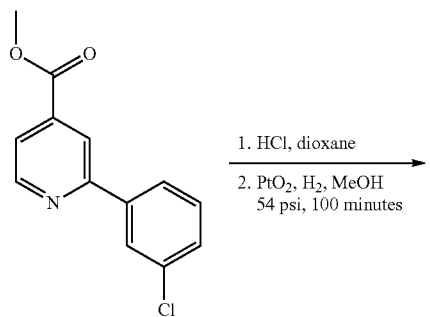

Compound 55A

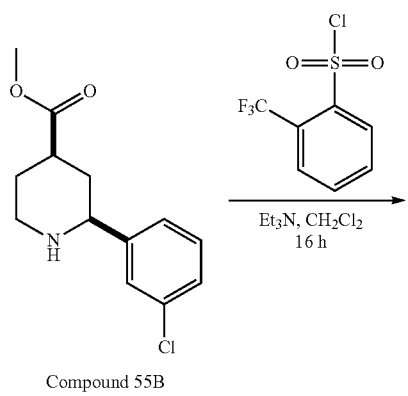

Compound 55B

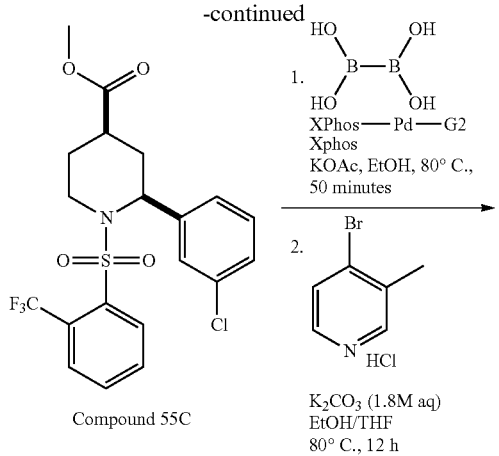

Compound 55C

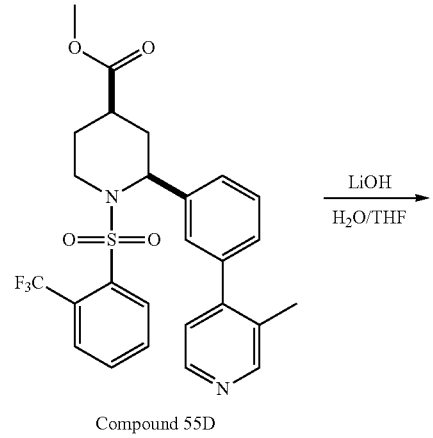

Compound 55D

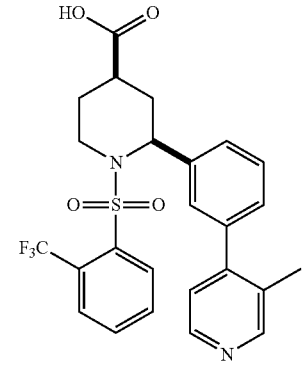

Compound 55

Methyl 2-(3-chlorophenyl)isonicotinate (Compound 55A)

Methyl 2-chloroisonicotinate (1.00 g, 5.83 mmol), (3-chlorophenyl)boronic acid (0.91 g, 5.83 mmol), and potassium carbonate (1.21 g, 8.75 mmol) were weighed out into a Biotage microwave tube. Methanol (6 mL) was added and the mixture was bubbled with nitrogen for 5 minutes. After two drops of water and [1,1'-bis(diphenylphosphino)ferrocene]-dichloropalladium(II) complex with DCM (190 mg, 0.23 mmol) were added, the vessel was capped and irradiated to 100° C. for 10 minutes in a Biotage Initiator microwave. The reaction mixture was diluted with dichloromethane (100 mL) and filtered through a pad of Celite. The filtrate was washed twice with saturated aqueous sodium bicarbonate (60 mL), dried over magnesium sulfate, filtered, and evaporated to dryness. Purification by silica gel chromatography (5-30% ethyl acetate in hexanes) yielded Compound 55A (0.75 g, 52%). $^1$H NMR (CDCl$_3$) δ 8.85 (m, 1H), 8.29 (m, 1H), 8.09 (m, 1H), 7.94 (m, 1H), 7.82 (m, 1H), 7.44 (m, 2H), 4.01 (s, 1H).

cis-Methyl
2-(3-chlorophenyl)piperidine-4-carboxylate
(Compound 55B)

Methyl 2-(3-chlorophenyl)isonicotinate (0.52 g, 2.10 mmol) was dissolved in MTBE (6 mL). A solution of HCl in 1,4-dioxane (4 N, 0.53 mL) was added. The mixture was stirred for 40 minutes at room temperature, and cooled to 0° C. The hydrochloride salt of methyl 2-(3-chlorophenyl) isonicotinate (0.43 g) was collected by vacuum filtration as a white solid. A solution of methyl 2-(3-chlorophenyl) isonicotinate hydrochloride (0.43 g) in methanol (35 mL) was degassed with nitrogen. Platinum oxide (25 mg) was added. The mixture was shaken on a Parr hydrogenation apparatus at 54 psi for 100 minutes. The reaction mixture was filtered through Celite, and the filter cake was washed with methanol (50 mL). The combined filtrates were evaporated to dryness. A portion (0.29 g) of the crude material was dissolved in saturated aqueous sodium bicarbonate (20 mL), and extracted twice with dichloromethane (80 mL). The combined organics were dried over magnesium sulfate, filtered, and concentrated in vacuo. Purification by silica gel chromatography (0.5-5% methanol and 0.1% ammonia in dichloromethane) yielded Compound 55B (127 mg). $^1$H NMR (CDCl$_3$) δ 7.40 (m, 1H), 7.25 (m, 3H), 3.69 (s, 3H), 3.62 (dd, 1H), 3.31 (m, 1H), 2.82 (m, 1H), 2.56 (m, 1H), 2.09 (m, 1H), 1.99 (m, 1H), 1.75-1.63 (m, 2H).

cis-Methyl 2-(3-chlorophenyl)-1-((2-(trifluoromethyl)phenyl)sulfonyl)piperidine-4-carboxylate
(Compound 55C)

Triethylamine (0.14 mL, 1.0 mmol) was added to a solution of cis-methyl 2-(3-chlorophenyl)piperidine-4-carboxylate (127 mg, 0.50 mmol) in dichloromethane (2 mL). The solution was cooled to 0° C. A solution of 2-(trifluoromethyl)benzene-1-sulfonyl chloride (93 μL, 0.60 mmol) in dichloromethane (0.5 mL) was added, and the reaction mixture was allowed to stir at room temperature for 16 hours. The reaction mixture was cooled to 0° C. and an additional portion of 2-(trifluoromethyl)benzene-1-sulfonyl chloride (93 μL, 0.60 mmol in 0.5 mL dichloromethane) was added. The reaction mixture was allowed to stir at room temperature for an additional night. The reaction mixture was diluted with dichloromethane (30 mL), washed with hydrochloric acid (0.5 M aqueous, 15 mL) and saturated aqueous sodium bicarbonate (15 mL). The organic layer was dried over sodium sulfate, filtered, and concentrated in vacuo. Purification by silica gel chromatography (5-40% ethyl acetate in hexanes) yielded Compound 55C (120 mg, 52%). $^1$H NMR (CDCl$_3$) δ 7.79 (d, 1H), 7.52 (m, 2H), 7.30 (t, 1H), 7.05-6.97 (m, 4H), 4.56 (m, 1H), 4.10 (m, 1H), 3.57 (s, 3H), 3.43 (m, 1H), 2.64 (m, 1H), 2.28-2.15 (m, 2H), 2.19-2.07 (m, 1H), 2.00-1.91 (m, 1H).

cis-Methyl 2-(3-(3-methylpyridin-4-yl)phenyl)-1-((2-(trifluoromethyl)phenyl)sulfonyl)-piperidine-4-carboxylate (Compound 55D)

Compound 55C was coupled with 4-bromo-3-methylpyridine hydrochloride using the conditions outlined in Example 41 to form Compound 55D (44%). LCMS (Method A): m/z 519.4 (M+H)$^+$. $^1$H NMR (CDCl$_3$) δ 8.50 (s, 1H), 8.46 (d, 1H), 7.72 (d, 1H), 7.64 (d, 1H), 7.49 (t, 1H), 7.34 (t, 1H), 7.12-7.05 (m, 4H), 6.97 (d, 1H), 4.79 (m, 1H), 4.05 (m, 1H), 3.54 (m, 1H), 3.49 (s, 3H), 2.67 (m, 1H), 2.39 (m, 1H), 2.28 (m, 1H), 2.25 (s, 3H), 2.09-1.94 (m, 2H).

cis-2-(3-(3-Methylpyridin-4-yl)phenyl)-1-((2-(trifluoromethyl)phenyl)sulfonyl)piperidine-4-carboxylic acid (Compound 55)

A solution was made of Compound 55C (73 mg, 0.14 mmol) in THF (1 mL). A solution of lithium hydroxide (10 mg, 0.42 mmol) in 1 mL water was added. The reaction mixture was allowed to stir at room temperature over the weekend. After formic acid (150 μL) was added to the reaction mixture, the volatiles were removed in vacuo. The resulting residue was purified by reverse phase chromatography (30 g C18 column, 5% to 40% acetonitrile in water with 0.25% formic acid). The product was isolated by lyophilization to provide Compound 55 (45 mg, 63%). LCMS (Method A): m/z 505.3 (M+H)$^+$. $^1$H NMR (CD$_3$OD) δ 8.41 (m, 2H), 7.77 (d, 1H), 7.67 (d, 1H), 7.61 (t, 1H), 7.48 (t, 1H), 7.18 (m, 5H), 4.84 (m, 1H), 4.02 (m, 1H), 3.56 (m, 1H), 2.71 (m, 1H), 2.37 (m, 1H), 2.27 (s, 3H), 2.22 (m, 1H), 2.04 (m, 1H), 1.92 (m, 1H).

In Vitro and In Vivo Experimental Studies

Example 56

Human TGR5 cAMP Production Assay

We evaluated the Compounds of the present invention for their ability to induce cAMP production using CHO-K1 cells overexpressing the human TGR5 receptor. CHO-K1 cells stably expressing human TGR5 receptor (accession number NM_001077194.1 (hTGR5) (i.e., hTGR5-CHO cells) were purchased from DiscoveRx Corporation (Fremont, Calif.). hTGR5-CHO cells were grown in Ham's F-12 media supplemented with 10% Fetal Bovine Serum, 1% Penicillin-Streptomycin, 2 mM L-Alanine L-Glutamine (Glutamax), and 800 μg/mL Geneticin selection. The cAMP production assay was performed using DiscoveRx's cAMP XS+ kit (Catalog No. 90-0075XL) following the manufacturer's recommended protocol. Briefly, hTGR5-CHO cells were harvested using non-enzymatic cell dissociation buffer (Sigma-Aldrich, St. Louis, Mo.) and 1×10$^6$ cells were combined in Phosphate-Buffered Saline (PBS) to a final volume of 496 μL to which 4 μL of 125 mM IBMX (Sigma-Aldrich, St. Louis, Mo.) was added. 500 μL of cAMP antibody solution was added to the harvested cells and incubated at room temperature for 20 min.

Test compounds were serially diluted (half-log dilutions) in DMSO and then further diluted 1:50 in PBS, 10 mM HEPES buffer. 2 μL of serially diluted compound was added to a 384-well low volume plate (Greiner; cat #784075) and centrifuged briefly. 2 μL of the cell/cAMP antibody mixture was then added to each compound-containing well and allowed to incubate at room temperature for one hour. Following incubation, the XS+ kits' ED/Lysis/CL Substrate Working Solution was prepared following the manufacturer's recommended protocol and 4 μL was added to each well of the plate. The plate was then incubated for one hour at room temperature. Following incubation, 4 μL of Enzyme Acceptor reagent was added to the plate and allowed to incubate overnight at room temperature. Luminescent signal was then detected using the Viewlux instrument (Perkin- Elmer, Waltham, Mass.). $EC_{50}$ values were determined using GraphPad Prism analysis (GraphPad Software, Inc.) and the results are shown in Table 33.

Example 57

Mouse TGR5 cAMP Production Assay

We evaluated compounds of the present invention for their ability to induce cAMP production in HEK-EBNA cells overexpressing the mouse TGR5 receptor. Human embryonic kidney cells (HEK293-EBNA) stably expressing mouse TGR5 receptor were established using the following procedure. Specifically, a commercially-obtained gene encoding mouse TGR5 (accession number BC116914) from Thermo Scientific (Waltham, Mass.) was cloned into an episomal expression vector. The resulting expression plasmid was then transfected into 293 c18 (ATCC® CRL10852™) cells, which express the Epstein-Barr virus nuclear antigen EBNA1 and can support the replication of episomal vectors. Selection for the plasmid was maintained with Hygromycin B. Cells were cultured and maintained in DMEM (Sigma; cat #6429) supplemented with 10% Fetal Bovine Serum, 1% penicillin/streptomycin, 2 mM L-alanine L-glutamine (GlutaMax), and 250 μg/mL Hygromycin.

Two cAMP production assays were developed.

1. Luminescent cAMP Production Assay

In this first cAMP production assay, the cAMP production was measured using DiscoveRx's cAMP XS+ kit following the manufacturer's recommended protocol.

Briefly, HEK293-EBNA cells stably overexpressing mouse TGR5 were harvested using non-enzymatic cell dissociation buffer (Sigma-Aldrich, St. Louis, Mo.), spun down, then resuspended in serum-free DMEM with 500 μM IBMX at a density of $1.25 \times 10^6$ cells/mL. 500 μL of cAMP antibody solution was added to 5004 of cell suspension and incubated at room temperature for 20 min.

Test compounds were serially diluted (half-log dilutions) in DMSO and then further diluted 1:50 in PBS, 10 mM HEPES buffer. 2 μL of serially diluted compound was added to a 384-well low volume plate (Greiner cat #784075) and centrifuged briefly. 2 μL of the cell/cAMP antibody mixture was then added to each compound-containing well and allowed to incubate at room temperature for one (1) hour. Following incubation, the XS+ kits' ED/Lysis/CL Substrate Working Solution was prepared following the manufacturer's recommended protocol and 4 μL was added to each well of the plate. The plate was then incubated for one (1) hour at room temperature. Following incubation, 4 μL of (Enzyme Acceptor) EA reagent was added to the plate and allowed to incubate overnight at room temperature. Luminescent signal was then detected using the Viewlux instrument (Perkin-Elmer, Waltham, Mass.). $EC_{50}$ values were determined using GraphPad Prism analysis (GraphPad Software, Inc.) and the results are shown in Table 33.

2. HTRF cAMP Production Assay

In this second cAMP production assay, the cAMP production was measured in 384-well low volume plates (Greiner; cat #784075) using the Cisbio™ cAMP HiRange HTRF Assay Kit (Cisbio) according to the manufacturer's protocol.

Briefly, compounds were initially diluted in 100% DMSO (12-point serial dilution by half logs) in a 96-well plate and then were further diluted 1:50 in PBS containing 10 mM HEPES. 5 μL were transferred to the 384-well assay plate in duplicate. HEK293-EBNA cells stably overexpressing mouse TGR5 were harvested using non-enzymatic cell dissociation buffer (Sigma), spun down, then resuspended in serum-free DMEM with 500 μM IBMX at a density of 500,000 cells/mL. 5 μL of cell suspension was transferred to each well of the 384-well assay plate already containing compound. The plate was covered and incubated at room temperature for 1 hour. The d2-cAMP and anti-cAMP Ab-cryptate stock solutions were prepared as per kit instructions. Then 5 μL of each conjugate (d2 and cryptate) were added to each well of the assay plate. The plate was covered and incubated at room temperature for 1 hour. The plate was read on an Envision™ plate reader (Perkin Elmer). $EC_{50}$ values were determined using Graph Pad Prism (GraphPad Software, Inc.) and the results are shown in Table 33 (below).

Human and Mouse TGR5cAMP

In Table 33, $EC_{50}$ values for both human and mouse cells were determined according to the TGR5 cAMP assays described above. The $EC_{50}$ values are coded as A, B, C or D: A<100 nM; B=100-999 nM; C=1,000-30,000 nM; D>30,000 nM.

TABLE 33

| Compound No. | Human TGR5 Lum. cAMP Activity | Mouse TGR5 Lum. cAMP Activity | Mouse TGR5 HTRF cAMP Activity |
|---|---|---|---|
| 1 | C | C | |
| 1AA | C | D | |
| 1AB | C | D | |
| 1AC | C | C | |
| 1AD | A | C | |
| 1AE | A | C | |
| 1AF | B | B | |
| 1AG | B | C | |
| 1AH | C | D | |
| 1AI | A | B | |
| 1AJ | C | C | |
| 1AK | B | C | |
| 1AL | B | C | |
| 1AM | A | | B |
| 1AN | B | C | |
| 1AO | C | C | |
| 1AP | B | C | |
| 1AQ | B | C | |
| 1AR | B | C | |
| 1AS | B | C | |
| 1AT | C | C | |
| 1AU | C | C | |
| 1AV | C | C | |
| 1AW | B | C | |
| 1AX | B | B | |
| 1AY | B | C | |
| 1AZ | A | C | |
| 1BB | B | C | |
| 1BC | B | B | |
| 1BD | B | C | |
| 1BE | B | B | |
| 1BF | B | B | |
| 1BG | B | C | |
| 1BH | C | C | |
| 1BI | C | D | |
| 1BJ | C | D | |
| 1BK | C | D | |
| 1BL | B | | C |
| 1BM | A | B | |
| 1BN | B | B | |
| 1BP | B | | C |
| 1BQ | C | C | |
| 1BR | C | C | |
| 1BS | C | | C |
| 1BT | C | | C |
| 1BU | C | D | |

TABLE 33-continued

| Compound No. | Human TGR5 Lum. cAMP Activity | Mouse TGR5 Lum. cAMP Activity | Mouse TGR5 HTRF cAMP Activity |
|---|---|---|---|
| 1BV | C | D | |
| 1BW | C | D | |
| 1BZ | B | C | |
| 1CC | B | | B |
| 1CD | A | | B |
| 1CE | C | | C |
| 1CF | B | | C |
| 2 | C | C | |
| 2AA | C | C | |
| 2AB | C | C | |
| 2AC | C | C | |
| 2AD | C | D | |
| 2AE | C | D | |
| 2AF | C | D | |
| 2AG | C | D | |
| 2AH | C | D | |
| 2AI | C | C | |
| 2AJ | C | C | |
| 2AK | C | D | |
| 2AL | C | D | |
| 2AM | C | C | |
| 2AN | C | C | |
| 2AO | C | C | |
| 2AP | C | D | |
| 2AQ | B | D | |
| 2AR | C | D | |
| 2AS | C | D | |
| 2AT | B | C | |
| 2AU | A | A | |
| 2AV | A | B | |
| 2AW | C | C | |
| 2AX | B | B | |
| 2AY | B | B | |
| 2AZ | B | B | |
| 2BB | B | B | |
| 2BC | A | | A |
| 2BD | A | | B |
| 2BE | A | | B |
| 2BF | A | | B |
| 2BG | A | | A |
| 2BH | A | | A |
| 2BI | A | | B |
| 2BJ | A | | C |
| 2BK | B | | C |
| 2BL | A | | A |
| 2BM | A | | B |
| 2BN | B | | C |
| 2BO | B | C | |
| 2BP | A | B | |
| 2BQ | A | B | |
| 2BR | B | C | |
| 2BS | B | B | |
| 2BT | A | B | |
| 2BU | A | | A |
| 2BV | A | | A |
| 2BW | A | | B |
| 2BX | A | | A |
| 2BY | A | | A |
| 2BZ | A | | A |
| 2CD | B | | B |
| 3 | B | | C |
| 4 | B | | C |
| 5 | A | A | A |
| 5AA | A | A | |
| 5AB | A | B | |
| 5AC | C | | C |
| 5AD | C | C | |
| 5AE | A | | C |
| 5AF | B | | C |
| 5AG | A | B | |
| 5AH | A | B | |
| 5AI | A | B | |
| 5AJ | B | | C |
| 5AK | B | | C |
| 5AL | C | | D |
| 5AM | C | | C |
| 5AN | A | | B |
| 5AO | A | | A |
| 5AP | A | | B |
| 5AQ | A | | A |
| 5AR | A | | B |
| 5AS | A | | B |
| 5AT | A | | B |
| 5AU | B | B | |
| 5AV | A | | B |
| 5AW | A | | A |
| 5AX | C | | C |
| 5AY | A | | B |
| 5AZ | B | | B |
| 5BB | B | | B |
| 5BC | A | | A |
| 5BD | B | | C |
| 6 | A | | C |
| 6AA | C | | C |
| 6AB | C | | C |
| 6AC | A | | A |
| 6AD | A | | B |
| 7 | A | | A |
| 7AA | C | | D |
| 7AB | B | | C |
| 7AC | A | | A |
| 8 | B | C | |
| 8AA | B | B | |
| 8AB | A | B | |
| 8AC | A | B | |
| 9 | C | | C |
| 10 | B | | B |
| 10AA | B | | C |
| 11 | C | | C |
| 12 | B | | C |
| 13 | A | | B |
| 13AA | A | | B |
| 14 | A | | A |
| 14A | A | | B |
| 14AD | B | | B |
| 14AG | B | | B |
| 15 | A | | B |
| 15AB | A | | A |
| 15AC | B | | C |
| 15AD | B | | B |
| 16 | B | | A |
| 16AA | B | | C |
| 16AB | A | | A |
| 16AC | A | | B |
| 16AD | B | | B |
| 16AF | A | | B |
| 16AG | A | | A |
| 16AJ | C | | C |
| 16AK | C | | C |
| 16AL | B | | B |
| 16AM | B | | B |
| 17 | B | | C |
| 18 | C | | B |
| 18A | A | | A |
| 19 | C | | B |
| 19AA | B | | B |
| 20 | A | | A |
| 20AA | A | | A |
| 20AB | A | | A |
| 20AC | A | | A |
| 20AD | A | | A |
| 20AE | A | | A |
| 20AF | A | | A |
| 20AG | A | | A |
| 20AH | A | | A |
| 20AI | A | | B |
| 20AJ | A | | B |
| 20AK | A | | B |

TABLE 33-continued

| Compound No. | Human TGR5 Lum. cAMP Activity | Mouse TGR5 Lum. cAMP Activity | Mouse TGR5 HTRF cAMP Activity |
|---|---|---|---|
| 20AL | A | | A |
| 20AM | A | | A |
| 20AN | A | | A |
| 20AO | A | | B |
| 20AP | B | | B |
| 20AQ | A | | B |
| 20AR | A | | A |
| 20AS | A | | A |
| 20AT | A | | B |
| 20AU | A | | B |
| 20AV | A | | B |
| 20AW | A | | A |
| 20AX | A | | B |
| 20AY | A | | B |
| 20BB | A | | A |
| 20BC | A | | B |
| 20BD | B | | B |
| 20BE | A | | A |
| 20BF | A | | A |
| 20BG | A | | A |
| 20BH | A | | B |
| 20BI | A | | A |
| 20BJ | A | | A |
| 20BK | A | | A |
| 20BL | A | | A |
| 20BM | A | | A |
| 20BN | A | | B |
| 20BO | B | | D |
| 20BP | B | | C |
| 20BR | B | | B |
| 20BS | B | | A |
| 20BT | B | | C |
| 20BU | A | | A |
| 20BV | B | | A |
| 20BW | B | | A |
| 20BX | A | | B |
| 21 | A | | B |
| 21AA | B | | A |
| 21AB | A | | A |
| 21AC | A | | A |
| 21AD | A | | B |
| 21AE | A | | A |
| 21AF | A | | A |
| 21AG | A | | A |
| 21AH | A | | B |
| 21AI | A | | B |
| 21AJ | A | | B |
| 21AK | C | | C |
| 21AL | A | | A |
| 21AM | A | | B |
| 21AN | A | | A |
| 21AO | B | | B |
| 21AP | A | | C |
| 21AQ | A | | A |
| 21AR | A | | A |
| 21AS | A | | B |
| 21AT | A | | A |
| 22 | A | | A |
| 22AA | B | | C |
| 23 | A | | C |
| 24 | A | | C |
| 24AA | C | | B |
| 24AC | B | | A |
| 25 | A | | A |
| 25A | A | | B |
| 26 | A | | B |
| 26A | A | | B |
| 26AA | A | | A |
| 26AB | A | | A |
| 26AC | A | | B |
| 26AD | A | | A |
| 26AE | A | | A |
| 27 | A | | B |
| 27AA | A | | A |
| 27AB | A | | B |
| 27AC | A | | B |
| 27AD | A | | B |
| 27AE | A | | B |
| 28 | A | | A |
| 28AA | A | | B |
| 28AB | A | | B |
| 28AC | A | | A |
| 28AD | A | | A |
| 28AE | A | | B |
| 28AF | A | | B |
| 28AG | B | | B |
| 28AH | A | | A |
| 28AI | B | | B |
| 29 | A | | B |
| 29AA | A | | A |
| 29AB | A | | A |
| 29AC | A | | A |
| 29AD | B | | C |
| 30 | A | | B |
| 31 | A | | A |
| 31AA | A | | A |
| 31AB | A | | A |
| 31AC | A | | A |
| 31AD | A | | A |
| 31AE | A | | B |
| 31AF | A | | B |
| 32 | C | | C |
| 32AA | A | | B |
| 32AB | B | | B |
| 32AC | A | | B |
| 33 | B | | B |
| 34 | B | | B |
| 35 | B | | B |
| 35B | C | | C |
| 36 | A | | A |
| 36AA | A | | A |
| 37 | A | | A |
| 37A | A | | A |
| 37AA | A | | A |
| 38 | A | | A |
| 38AA | A | | A |
| 39 | A | | A |
| 40 | B | | C |
| 40AA | A | | C |
| 41 | A | | B |
| 42 | C | | C |
| 43 | A | | A |
| 43AE | B | | B |
| 44 | B | | B |
| 45 | B | | A |
| 46 | A | | A |
| 46AA | A | | A |
| 46AB | A | | A |
| 46AC | A | | A |
| 46AD | B | | A |
| 46AE | A | | A |
| 46AF | C | | C |
| 46AG | B | | A |
| 46AH | B | | A |
| 46AI | B | | A |
| 46AJ | C | | B |
| 46AK | B | | A |
| 46AL | B | | B |
| 47 | A | | A |
| 48 | B | | A |
| 49 | A | | A |
| 49AA | B | | A |
| 49AB | B | | A |
| 49AC | A | | A |
| 49AD | B | | B |
| 49AE | B | | A |
| 49AF | A | | A |
| 49AG | B | | A |

TABLE 33-continued

| Compound No. | Human TGR5 Lum. cAMP Activity | Mouse TGR5 Lum. cAMP Activity | Mouse TGR5 HTRF cAMP Activity |
|---|---|---|---|
| 50 | B | | A |
| 51 | B | | B |
| 52 | B | | B |
| 52AA | A | | A |
| 53 | B | | A |
| 53AA | B | | A |
| 53AB | B | | A |
| 53AC | B | | A |
| 54 | A | | B |
| 55 | B | | B |

Example 58

STC-1 GLP-1 Assay

We evaluated Compounds of the present invention for their ability to induce GLP-1 production in mouse intestinal neuroendocrine tumor cells. Mouse STC-1 cells were cultured and maintained in high glucose DMEM (Sigma #5796) supplemented with 15% horse serum, 5% Fetal Bovine Serum (FBS), 1% penicillin/streptomycin, and 2 mM L-alanine L-glutamine (GlutaMax). Two days prior to analysis of GLP-1 secretion cells were harvested using Accutase (Sigma), spun down then resuspended in high glucose DMEM media containing 2 mM L-alanine L-glutamine (GlutaMax), 10% charcoal-dextran stripped FBS, and 50 µg/mL Gentamicin, at a density of 100,000 cells/mL. 100 µL of cell suspension was added to each well of a 96-well Poly-D-Lysine coated culture plate (Sigma; cat #2382493) and was incubated at 37° C. with 5% $CO_2$.

Compounds were initially diluted in 100% DMSO (12-point serial dilution by half logs) in a 96-well plate and then were further diluted 1:500 in Hanks' Balanced Salt Solution (HBSS) containing protease inhibitor cocktail, DPP-IV inhibitor, and 0.1% fatty acid free bovine serum albumin. On the day of the experiment cells were washed once with HBSS. After wash, 100 µL of test compound was added to each well. The plate was incubated at 37° C. with 5% $CO_2$ for 2 h. Supernatants were collected and GLP-1 secretion was measured using the Cisbio™ Active GLP-1 HTRF Assay Kit (Cisbio). Briefly, Anti-GLP-1-d2 conjugate and Anti-GLP-1 Terbium Cryptate conjugate stock solutions were prepared as per kit instructions. The two solutions were pre-mixed and 10 µL were transferred to a 384-well low volume plate (Greiner; cat #784075). 10 µL of collected supernatants were added to wells already containing the conjugate solution. The plate was covered and incubated at room temperature overnight. The plate was read on an Envision™ plate reader (Perkin Elmer). $EC_{50}$ values were determined using Graph Pad Prism (GraphPad Software, Inc.) and the results are shown in Table 34.

STC-1 GLP-1

In Table 34, $EC_{50}$ values obtained from the STC-1 GLP-1 production assay for compounds of the present invention are summarized. The $EC_{50}$ values were coded as A, B, or C: A<100 nM; B=100-999 nM; and C=1,000-30,000 nM.

TABLE 34

| Compound No | Mouse STC-1 HTRF GLP-1 Activity |
|---|---|
| 2AU | C |
| 2AV | C |
| 2BC | C |
| 2BL | B |
| 2BQ | C |
| 5 | B |
| 5AA | B |
| 5AV | C |
| 5AW | C |
| 8AC | B |
| 13 | C |
| 13AA | B |
| 14 | B |
| 14A | B |
| 18A | C |
| 20 | A |
| 20AA | B |
| 20AB | B |
| 20AC | B |
| 20AF | B |
| 20AH | C |
| 20AM | B |
| 20AN | B |
| 20AR | B |
| 20BB | B |
| 20BF | B |
| 20BG | B |
| 20BK | C |
| 20BL | C |
| 20BM | C |
| 20BU | B |
| 21AL | B |
| 21AN | B |
| 21AQ | B |
| 21AT | B |
| 26AA | B |
| 26AB | B |
| 28AA | B |
| 28AC | C |
| 28AH | B |
| 29 | B |
| 29AA | B |
| 31AA | B |
| 31AC | B |
| 37AA | B |
| 38 | B |
| 46 | B |
| 49 | B |
| 53 | B |

Example 59

Pharmacokinetic Profile in Mice

In this series of studies, the pharmacokinetic profile characteristics of compounds of the present invention were evaluated. The plasma concentration levels of the compounds were monitored in the blood stream (i.e., plasma) after oral gavage using $C_{max}$, and area under the curve (AUC).

8 week old male Hilltop mice were fasted overnight. Animals were randomized into groups (n=9) by body weight. Mice were dosed with 10 mg/kg compound (in 20% PEG400/80% 0.5% carboxymethylcellulose (medium viscosity)+0.25% Tween-80) at a volume of 10 mL/kg through oral gavage. Blood was collected via orbital bleeding at 0, 0.25, 0.5, 1, 2, and 4 h post-dose, with no one mouse having more than 3 blood draws. Blood was collected in EDTA coated tubes. Samples were stored at −20° C. until analysis.

Quantitation of compound levels in plasma was accomplished by LC-MS/MS analysis. Standard curve and quality control samples were prepared in male CD-1 mouse plasma containing EDTA $K^{2+}$ as an anticoagulant at final concentrations ranging from 500 to 0.1 ng/mL. The plasma samples, calibration curve standards, and quality control samples were prepared in an identical method in a 96-well deep plate (1 mL) with a quenching solution (1:1 mixed acetonitrile:methanol containing the internal standard Reserpine @ 400 ng/mL). Low volume samples were supplemented with CD-1 mouse plasma. The plate was mixed on multi-tube votex for 1 min and centrifuged at 4000 rpm for 30 min at 4° C. (Sorvall® Super T21) before LC-MS/MS analysis. LC conditions were developed and optimized based on each compound as needed. The outlet of the column was coupled to AB Sciex 4000 QTrap Mass Spectrometer (AB Sciex, Brugg Switzerland). Detection was carried out using multiple reaction monitoring mode with positive-ion detection focusing. The pharmacokinetic parameters were derived from the plasma-time data and calculated using the standard non-compartmental method with WinNonlin (Pharsight, Mountain View, Calif.) or PK Solver (*Comp. Meth. Prog. Biomed.* (2010), 99, 306-314).

The $C_{max}$ (ng/mL) of compounds studied are listed in Table 35. Values reported are the mean plasma concentration of three mice. The data show that most of the compounds of the present invention exhibit low plasma exposure (<200 ng/mL). In other words, the compounds of the present invention do not substantially appear in the blood stream after oral gavage.

TABLE 35

| Compound No. | $C_{max}$ (ng/mL) |
|---|---|
| 5 | 3.1 |
| 5AA | 128 |
| 5AZ | 2,327 |
| 14 | 1,084 |
| 20 | 5.0 |
| 20AA | 7.2 |
| 20AB | 1.5 |
| 20AC | 7.8 |
| 20AD | 2.5 |
| 20AE | 128 |
| 20AF | 5.2 |
| 20AG | 1.4 |
| 20AH | 0.9 |
| 20AM | 0.9 |
| 20AN | 1.7 |
| 20AR | 3.2 |
| 20AS | 2.3 |
| 20AW | 2.8 |
| 2OBB | 2.1 |
| 20BF | 0.8 |
| 20BG | 0.3 |
| 20BK | 0.4 |
| 20BL | 1.2 |
| 20BM | 0.6 |
| 20BN | 478 |
| 20BU | 1.1 |
| 21AB | 19.4 |
| 21AC | 269 |
| 21AG | 14.3 |
| 21AL | 7.6 |
| 21AN | 1.9 |
| 21AQ | 4.2 |
| 21AT | 1.6 |
| 25 | 3.1 |
| 26AA | 1.4 |
| 26AB | 2.6 |
| 27AD | 25.4 |
| 28 | 0.8 |

TABLE 35-continued

| Compound No. | $C_{max}$ (ng/mL) |
|---|---|
| 28AA | 0.7 |
| 28AC | 0.8 |
| 28AH | 4.6 |
| 29 | 2.5 |
| 29AA | 1.5 |
| 29AB | 109 |
| 31AA | 4.4 |
| 31AB | 35.8 |
| 31AC | 1.8 |
| 36AA | 7.5 |
| 37 | 122 |
| 37AA | 39.4 |
| 38 | 3.6 |
| 46 | 436 |
| 46AA | 1.6 |
| 46AB | 4.5 |
| 47 | 228 |
| 49 | 2.1 |
| 52AA | 647 |

Example 60

In Vivo Mouse GLP-1 Study

After establishing that the compounds of the present invention exhibit low plasma exposure after single dose oral administration (i.e., do not substantially appear in the blood), to evaluate whether the compounds still produce a biological effect in a live animal consistent with the activation of the TGR5 receptor, GLP-1 levels in the blood of male C57BL/6NTac mice were measured after a single oral administration of the compounds.

12-14 week old male C57BL/6NTac (Taconic) mice were divided into experimental groups (n=6) by randomizing mice based on pre-fasting body weight and then were fasted overnight. On experiment day, all mice were dosed with 3 mg/kg sitagliptin via oral gavage exactly 1 hour before oral gavage dosing of vehicle (0.5% carboxymethylcellulose (medium viscosity)+0.25% Tween-80) or 10 mg/kg compound in vehicle. Four (4) hours following the administration of compound, blood was collected via cardiac puncture. For the GLP-1 assay, 200-250 µL of blood was placed in an EDTA $K^{2+}$ tube containing 5 µL of 40 mg/mL aprotinin (Sigma A1153) and 1 µL of 10 mM sitagliptin (Sigma S8576) and plasma was separated by centrifugation. Plasma samples were stored at −20° C. until analysis. The active form of GLP-1 [GLP-1 (7-36) amide] was analyzed using Meso Scale Discovery System according to the manufacturer's directions (item number K150HYC). Values of p<0.05 are considered statistically significant.

The active GLP-1 assay results from the mice in vivo study are shown in Table 36 and FIG. 1, expressed as fold change over vehicle. These results indicate that the compounds increase GLP-1 level in the circulating blood of experimental mice four (4) hours after the compound administration.

TABLE 36

| Compound | Fold Increase |
|---|---|
| 20 | 1.0 |
| 20AA | 3.3 |
| 20AC | 1.2 |
| 20AD | 1.9 |
| 20AF | 0.8 |

TABLE 36-continued

| Compound | Fold Increase |
|---|---|
| 20AM | 2.3 |
| 20AW | 1.1 |
| 20BB | 2.7 |
| 20BF | 2.9 |
| 20BG | 4.4 |
| 20BK | 1.3 |
| 20BL | 2.1 |
| 21AB | 3.0 |
| 21AQ | 2.0 |
| 21AT | 4.2 |

Example 61

Bile Weight after a Single Oral Administration of the Compound

Figure 2:
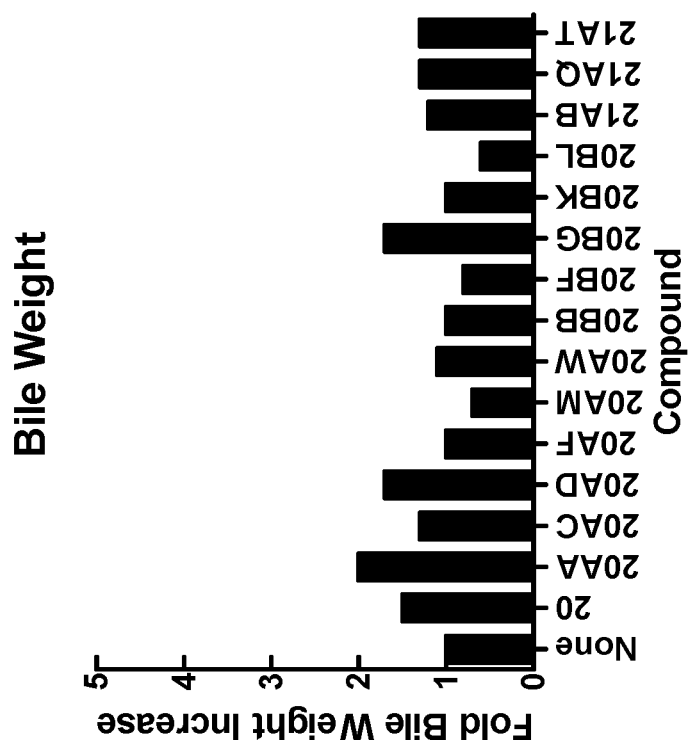
FIG. 2 depicts the fold increase of bile weight in C57BL/6NTac mice four (4) hours after a single 10 mg/kg oral administration of compounds 20, 20AA, 20AC, 20AD, 20AF, 20AM, 20AW, 20BB, 20BF, 20BG, 20BK, 20BL, 21AB, 21AQ, or 21AT. The mice were dosed with 3 mg/kg sitagliptin exactly 1 hour before oral administration of the compounds.

In the study, the association with gallbladder filling was evaluated in comparison to the observed GLP-1 elevation (induced by the compounds of the present invention). The mice were treated with compounds and the bile weight was monitored (a measure that indicated gallbladder filling) to determine if the compound retained more bile in the gallbladder as compared to the control mice (i.e., vehicle alone). The same animal protocol as described in Example 60 was utilized. After the mice were euthanized, bile was removed from the gallbladder and the bile was weighed to approximate volume of bile contained within the gallbladder. FIG. 2 shows the minimal effect by multiple compounds on the bile weight.

Example 62

Plasma Concentration of Compound in Mice

Figure 3:
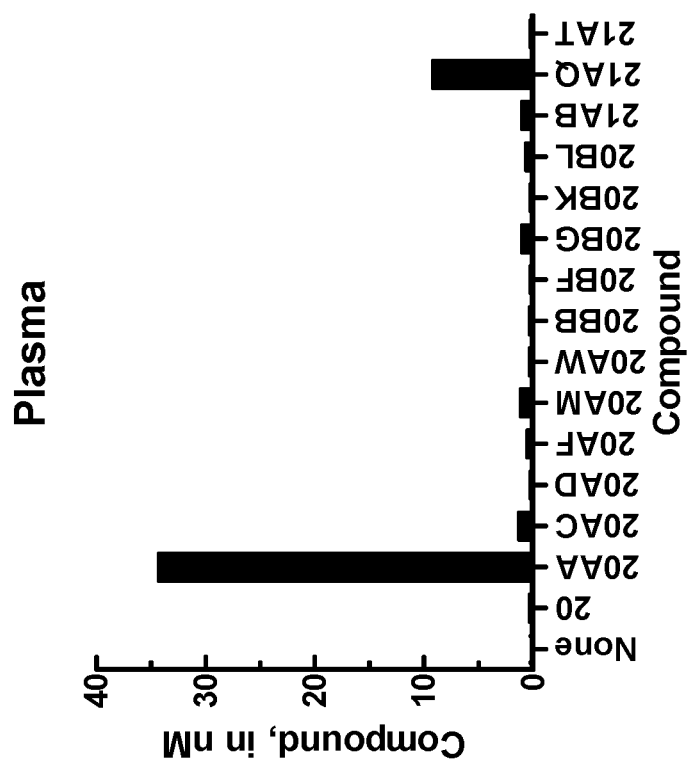
FIG. 3 depicts the compound plasma concentration in C57BL/6NTac mice four (4) hours after a single 10 mg/kg oral administration of compounds 20, 20AA, 20AC, 20AD, 20AF, 20AM, 20AW, 20BB, 20BF, 20BG, 20BK, 20BL, 21AB, 21AQ, or 21AT. The mice were dosed with 3 mg/kg sitagliptin exactly 1 hour before oral administration of the compounds.

In these studies, the plasma concentration of the compounds of the present invention was measured in mice. The same animal protocol as described in Example 59 was utilized. FIG. 3 shows the concentrations of compound in the plasma four (4) hours after oral administration. These plasma concentrations are well below the $EC_{50}$ concentration of GLP-1 stimulation in STC-1 cells as described in Example 57. These results indicate the compounds of the present invention can exhibit low exposure and exhibit a low concentration in the circulating blood.

Example 63

Low Level of Compounds is Attributed to Low Intestinal Absorption

In this study, it was determined if the low plasma level of the compounds of the present invention is due to low absorption in the gut, or due to the first pass effect (i.e., absorption followed by a rapid degradation of compounds by liver). Hepatic portal vein cannulated male CD (SD) rats obtained from Charles River Laboratory were utilized. In brief, Compound 20BG was administered orally at 10 mg/kg, and blood was obtained simultaneously from the portal vein and systemic circulation (retro-orbital sinus) at pre-dose, 0.25, 0.5, 1, 2, and 4 hours post-dose, in EDTA coated tubes. The samples were processed into plasma and quantification of compound levels in the plasma was accomplished by means of LC-MS/MS analysis as described in Example 59. The pharmacokinetic characteristics were determined and summarized in Table 37.

TABLE 37

| | $C_{max}$ (ng/mL) | $T_{max}$ (h) | AUC (0-7 h) (ng/mL * h) |
|---|---|---|---|
| Portal Vein bleed | 7.6 ± 3.6 | 0.25 – 2 | 30.1 ± 0.9 |
| Peripheral bleed | 1.3 ± 0.7 | 0.25 – 1 | 3.1 ± 10.8 |

The pharmacokinetic characteristics of Compound 20BG in the portal vein and systemic circulation (retro-orbital sinus) showed very low absorption of the compound. $C_{max}$, $T_{max}$ and AUC are consistent with low absorption of the compound in the intestine with fast first pass hepatic metabolism on any that does get absorbed.

Example 64

Absorption Vs. First Pass Metabolism

In this study, the absorption was examined as compared to first pass metabolism of the compounds of the present invention. ICR mice (Hilltop) were pre-treated with 1-aminobenzotriazole (ABT), a nonselective inhibitor of cytochrome P450 enzymes to inhibit Cyp450-mediated degradation of the compounds in liver.

ABT was administered at 150 mg/kg in 5 mL/kg of 0.04% ethanol in 0.5% methyl cellulose (w/v) by oral gavage, 2 hours prior to test compound administration. The compounds 20AA and 20AC were administered by oral gavage at 10 mg/kg in 10 mL/kg of 20% PEG400/80% (0.5% (w/v) CMC containing 0.25% (v/v) Tween 80) (v/v), 2 hours after the ABT treatment. Blood was collected via orbital bleeding at predose, 0.25, 0.5, 1, 2, and 4 hours post-dose and the quantification of compound levels in plasma was accomplished by means of LC-MS/MS analysis as described in Example 59. Reference compound "Propranolol" that is known to be metabolized by Cyp450 was used as a positive control.

Figure 4:
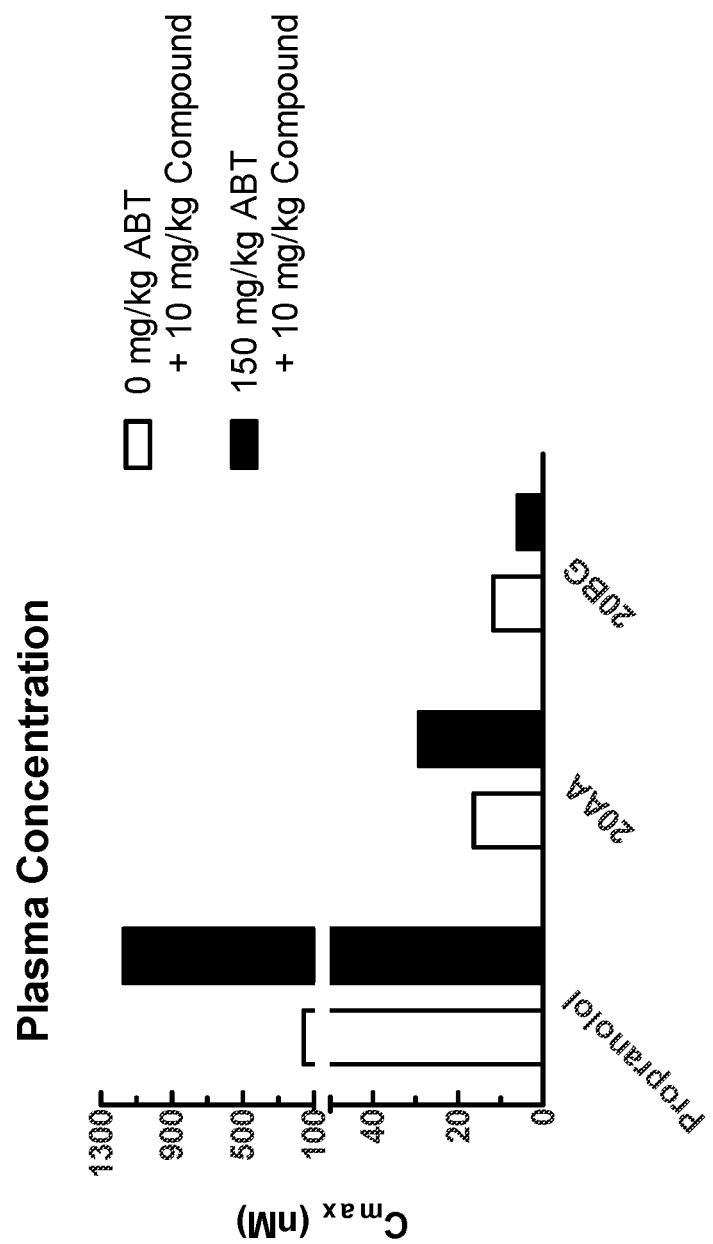
FIG. 4 depicts the $C_{max}$ (nM) of Compounds 20AA and 20BG (10 mg/kg) in ICR mice with and without 1-aminobenzotriazole pretreatment (150 mg/kg). Propranolol serves as a positive control.

FIG. 4 depicts the $C_{max}$ (nM) of the compounds of the present invention with and without ABT pre-treatment. As shown in FIG. 4, similar $C_{max}$ values were observed for the compounds of the present invention with or without ABT pre-treatment, indicating the lack of rapid Cyp450-mediated degradation of the compounds. In contrast, the $C_{max}$ value of the positive control propranolol was significantly higher in ABT pre-treated mice, as expected. All together, the data are consistent with the hypothesis that lower $C_{max}$ values exhibited by the compounds of the present invention are due to poor absorption in the intestine, rather than rapid degradation in first pass metabolism.

Example 65

Comparison of PK in DIO Mice and Lean Mice

The PK characteristics of Compound 20AA were examined in non-fasted lean C57BL/6N and DIO mice (Taconic). Compound 20AA was orally administered to both groups at 10 mg/kg by oral gavage and plasma concentration of the compound was determined as described in Example 59. The data are summarized in Table 38.

TABLE 38

| DIO mice, Non-fasted PK (10 mpk, p.o.) | | Lean mice, Non-fasted PK (10 mpk, p.o.) | |
|---|---|---|---|
| $C_{max}$ (nM) | $T_{max}$ (h) | $C_{max}$ (nM) | $T_{max}$ (h) |
| 1.7 | 1.0 | 3.0 | 1.0 |

The data show similar low $C_{max}$ values for Compound 20AA orally administered to lean mice as well as DIO mice. The results suggest the low plasma concentration of the compound does not depend on diet composition and animal adiposity.

In addition, PK parameters were determined for Compound 20AA (i.e., $C_{max}$, $T_{max}$ and AUC) following oral administration in four groups of mice: (i) fasted lean mice; (ii) non-fasted lean mice; (iii) non-fasted DIO mice; and (iv) lean mice receiving ABT.

TABLE 39

| Study | $C_{max}$ (nM) | $T_{max}$ (h) | AUC (0-4 h) (ng/mL * h) |
|---|---|---|---|
| Fasted Lean | 7.2 | 1.0 | 26 |
| Non-fasted Lean | 3.0 | 0.25 | 4.0 |
| Non-fasted DIO | 1.7 | 1.0 | 7.6 |
| ABT (150 mg/kg) | 2.6 | 0.25 | — |

The data clearly show that Compound 20AA has a low PK profile in lean and DIO mice, regardless the status of fasting or non-fasting. The ABT treatment confirms that the low $C_{max}$ value of Compound 20AA is attributed to low absorption.

Example 66

Monitoring of Weight Loss after Multiple Days of Dosing Compounds

Compounds of the present invention were dosed for multiple days and were evaluated for their ability to cause mice to lose weight. In the next series of studies (Examples 66-70), Male DIO mice were received at 12 weeks of age (from Taconic), and were single-housed at the testing facility and acclimated for at least 2 weeks. The mice were provided a high fat diet [Research Diet D12492 (60% Fat kcal)] while in the testing facility. Before the study initiation, the animals were randomized into 5 experimental groups by body weight. The vehicle group contained only 0.5% carboxymethylcellulose (medium viscosity)+0.25% Tween-80. The second group contained 10 mg/kg of the DPP-IV inhibitor Linagliptin while the third group contained 10 mg/kg Compound 20BG. The fourth group contained the combination of 10 mg/kg Linagliptin and 10 mg/kg Compound 20BG. The fifth group was the positive control for weight loss, Liraglutide. All mice, except the Liraglutide group, were dosed BID at approximately 6:00 am and again at approximately 4:00 μm. The positive control liraglutide was administered at a dose of 0.2 mg/kg subcutaneously in the afternoon.

Figure 5:
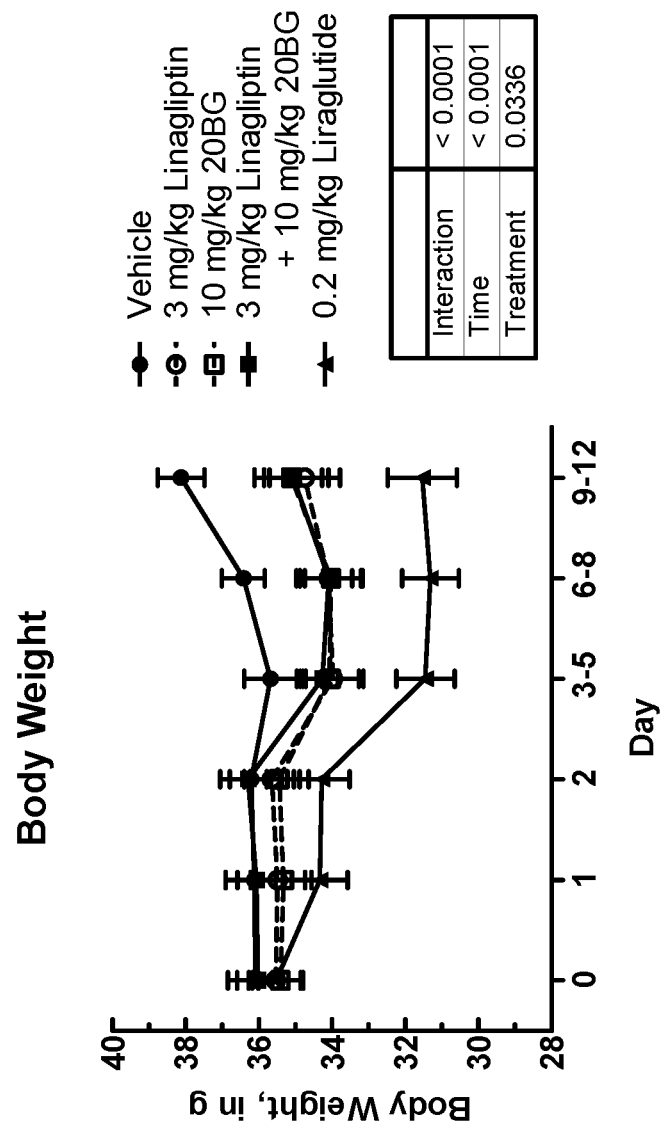
FIG. 5 depicts the body weight changes over 12 days in DIO mice receiving twice a day oral administration of vehicle, Compound 20BG (30 mg/kg), linagliptin (10 mg/kg), or Compound 20BG (30 mg/kg)+linagliptin (10 mg/kg). Liraglutide (0.2 mg/kg s.c. once a day) serves as the positive control.

Compounds of the present invention were evaluated for their ability to cause mice to lose weight. Mice were dosed compounds for 12 days and body weights were recorded twice a week. FIG. 5 shows that Compound 20BG was able to produce a modest weight loss in the mice.

Example 67

Monitoring of Food Intake after Multiple Days of Dosing Compounds

Compounds of the present invention were dosed for multiple days and were evaluated for their ability to cause mice to have a lower food intake. Mice were dosed compounds for 12 days as per the protocol in Example 66.

Figure 6:
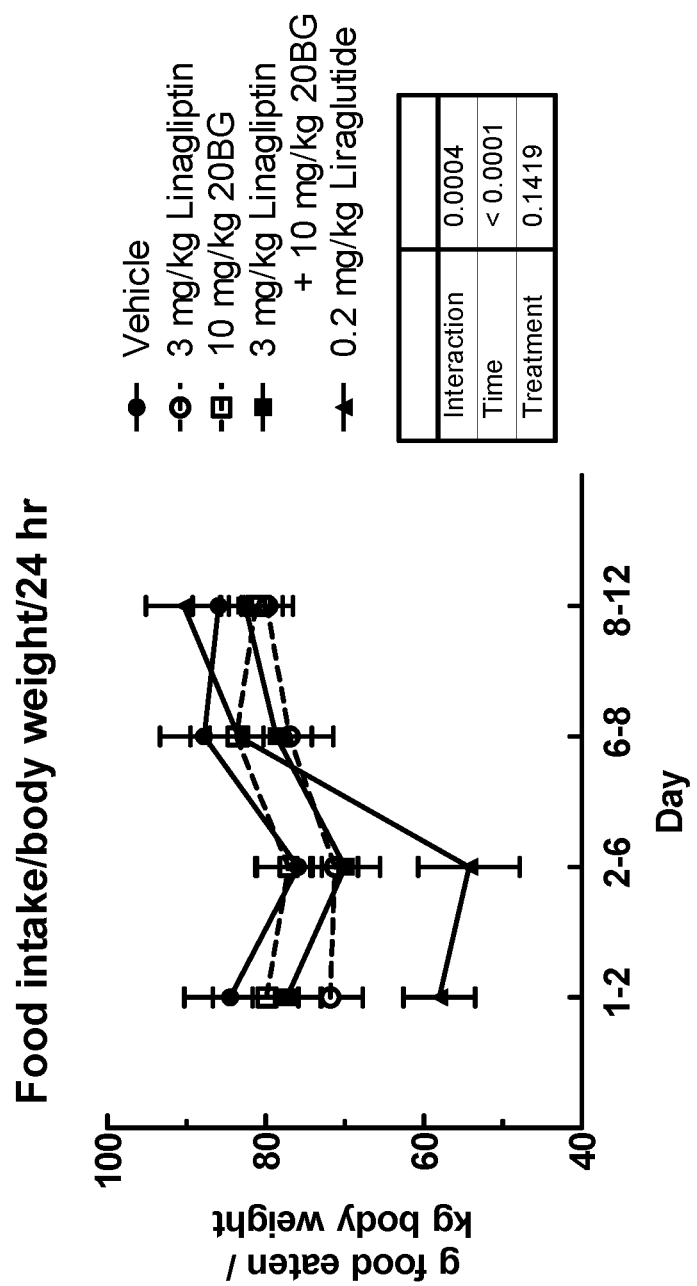
FIG. 6 depicts the food intake over 12 days in DIO mice receiving twice a day oral administration of vehicle, Compound 20BG (30 mg/kg), linagliptin (10 mg/kg), or Compound 20BG (30 mg/kg)+linagliptin (10 mg/kg). Liraglutide (0.2 mg/kg s.c. once a day) serves as the positive control.

The HFD (Research Diets, D12492, 60% fat kcal) is placed at the bottom of the cage of a singly-housed animal. The remaining food in each cage is recovered and weighed again at the same time of day 3 or 4 days later. The difference in the starting and ending food weight represents the amount of food consumed. Daily food intake is calculated by averaging over a 3 or 4 day period every week. FIG. 6 shows that Compound 20BG had no significant effect on food intake.

Example 68

GLP-1 Levels after Multiple Days of Dosing Compounds

Compounds of the present invention were dosed for multiple days and were evaluated to determine if they produce sustained GLP-1 levels. In this example, the protocol from Example 66 was utilized. In week 2 of the study, mice were euthanized and blood was collected 6 hours after the final dose of compound. For the GLP-1 assay, 200-250 μL of blood was placed in an EDTA $K^{2+}$ tube containing 5 μL of 40 mg/mL aprotinin (Sigma A1153) and 1 μL of 10 mM sitagliptin (Sigma S8576) and plasma was separated by centrifugation. Plasma samples were stored at −20° C. until analysis. The active form of GLP-1 [GLP-1 (7-36) amide] was analyzed using Meso Scale Discovery System according to the manufacturer's directions (item number K150HYC). Values of $p<0.05$ are considered statistically significant.

Figure 7:
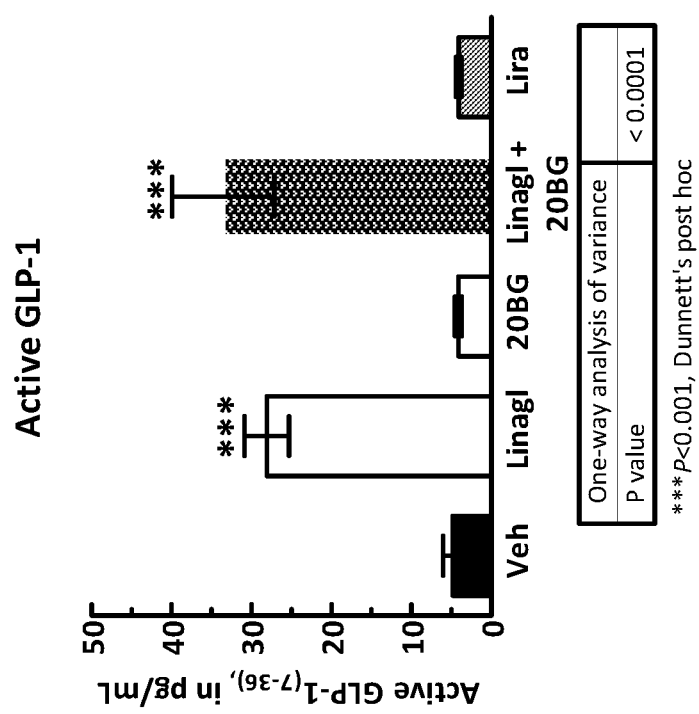
FIG. 7 depicts the GLP-1 increase after 12 days in DIO mice receiving twice a day oral administration of vehicle, linagliptin (10 mg/kg), Compound 20BG (30 mg/kg), or Compound 20BG (30 mg/kg)+linagliptin (10 mg/kg). Liraglutide (0.2 mg/kg s.c. once a day) serves as a control.

FIG. 7 depicts the GLP-1 plasma level increase following oral administration of Compound 20BG in DIO mice. Mice treated with Compound 20BG (in combination with linagliptin) exhibited a significantly increased level of GLP-1 as compared to the mice treated with vehicle alone. These data indicate that chronic dosing of compounds increases GLP-1 levels and shows no evidence of desensitization after 12 days of dosing compounds.

Example 69

Compound Concentration Levels in Plasma after Multiple Days of Dosing Compounds

Figure 8:
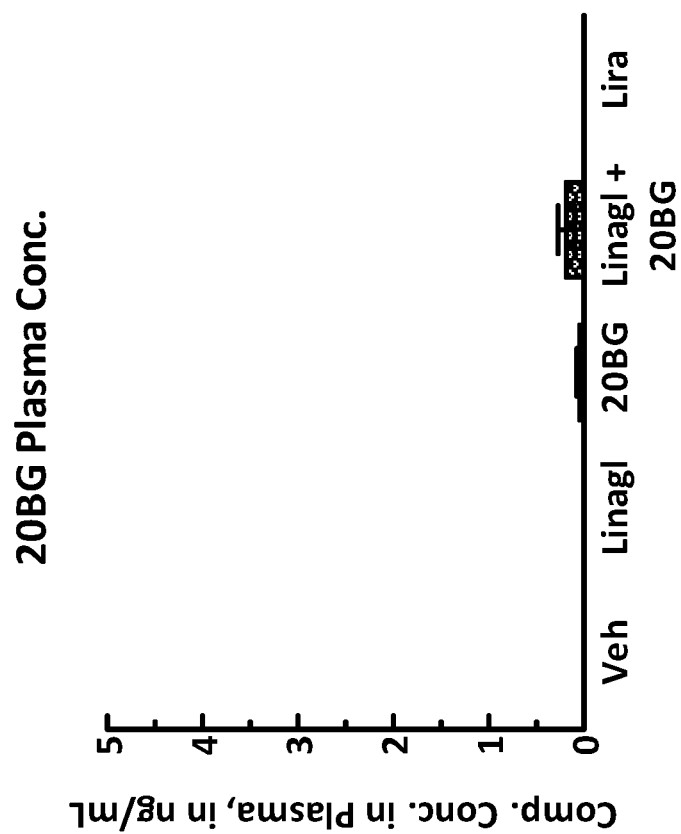
FIG. 8 depicts the plasma concentration of Compound 20BG after 12 days in DIO mice receiving twice a day oral administration of vehicle, Compound 20BG (30 mg/kg), linagliptin (10 mg/kg), or Compound 20BG (30 mg/kg)+ linagliptin (10 mg/kg). Liraglutide (0.2 mg/kg s.c. once a day) serves as a control.

Compounds of the present invention were dosed for multiple days and evaluated for plasma concentration of the compounds at the time mice were euthanized. In this example, the protocol from Example 66 was utilized. In week 2 of the study, mice were euthanized and blood was collected 6 hours after the final dose of compound. The collected blood (200-250 μL) was placed in an EDTA $K^{2+}$ tube containing 5 μL of 40 mg/mL aprotinin (Sigma A1153) and 1 μL of 10 mM sitagliptin (Sigma S8576) and plasma was separated by centrifugation. Plasma samples were stored at −20° C. until analysis. The plasma measurements were performed as described in Example 59. FIG. 8 shows the results and that the compound concentration is the blood is low. Overall, the results indicate that the compounds of the present invention are consistent with non-systemic TGR5 agonists.

Example 70

No Bile Weight Increase after Multiple Days of Dosing Compounds

Figure 9:
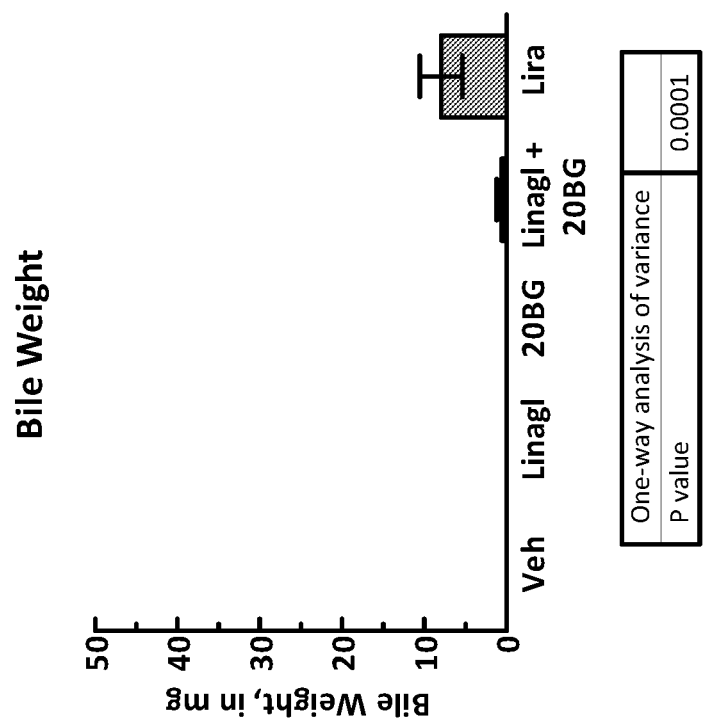
FIG. 9 depicts the bile weight change after 12 days in DIO mice receiving twice a day oral administration of vehicle, Compound 20BG (30 mg/kg), linagliptin (10 mg/kg), or Compound 20BG (30 mg/kg)+linagliptin (10 mg/kg). Liraglutide (0.2 mg/kg s.c. once a day) serves as a control.

Compounds of the present invention were dosed for multiple days and evaluated for an increase in bile weight within the gallbladder. In this example, the protocol from Example 66 was utilized. In week 2 of the study, mice were euthanized and bile was removed from the gallbladder about 6 hours after the final dose and the bile was weighed to approximate the volume of bile contained within the bladder. FIG. 9 depicts that the gallbladder does not show an increase in size even after 12 days of dosing Compound 20BG. These results indicate that the compounds of the present invention are consistent with non-systemic TGR5 agonists.

All references to the literature and all patents mentioned in this specification are incorporated herein by reference in their entirety. The present invention is not to be limited in terms of the particular embodiments described in this application, which are intended as single illustrations of individual aspects of the present invention. Functionally equivalent pharmaceutical compositions and methods of treatment within the scope of the present invention, in addition to those enumerated herein, will be apparent to those skilled in the art from the foregoing description. Such modifications and variations are intended to fall within the scope of the appended claims.

What is claimed is:

1. A compound of formula (I):

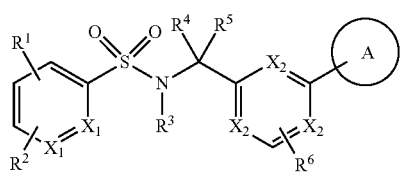

(I)

or a pharmaceutically acceptable salt thereof, wherein:
each $X_1$ is independently CH or N;
$R^1$ and $R^2$ are each independently H, halogen, $C_{1-6}$alkyl, $C_{1-6}$alkoxy, CN, $NO_2$ or $NH_2$, wherein alkyl is optionally substituted with 1-4 halogen;
each optionally mono-, di-, or tri-substituted with substituents independently selected from halogen and $C_{1-3}$alkyl, wherein alkyl is optionally substituted with 1-4 halogen;
$R^3$ is H,

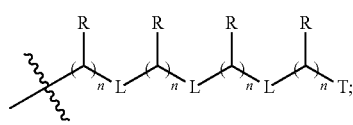

$R^4$ and $R^5$ are each independently H, $C_{1-6}$alkyl, phenyl, $C_{1-6}$alkyl-OH, $C_{1-6}$alkyl-CN, $C_{1-6}$alkyl-$NH_2$, $C_{0-6}$alkylC(O)O$C_{1-6}$alkyl, $C_{0-6}$alkylC(O)OH, $C_{0-6}$alkylC(O)NH$C_{1-6}$alkyl, $C_{0-6}$alkylC(O)N($C_{1-6}$ alkyl) ($C_{1-6}$alkyl), $C_{0-6}$alkylC(O)NH$C_{1-6}$alkylS(O)$_2$OH or $C_{0-6}$alkylNHC(O)NH$C_{1-6}$alkylS(O)$_2$OH,
or $R^4$ and $R^5$ together with the C to which they are attached form oxetanyl;
each $X_2$ is independently CH or N, and no more than one $X_2$ can be N;
$R^6$ is halogen, $C_{1-6}$alkyl, $C_{1-6}$alkoxy, OH or O$C_{1-6}$alkyl-C(O)OH;

A is

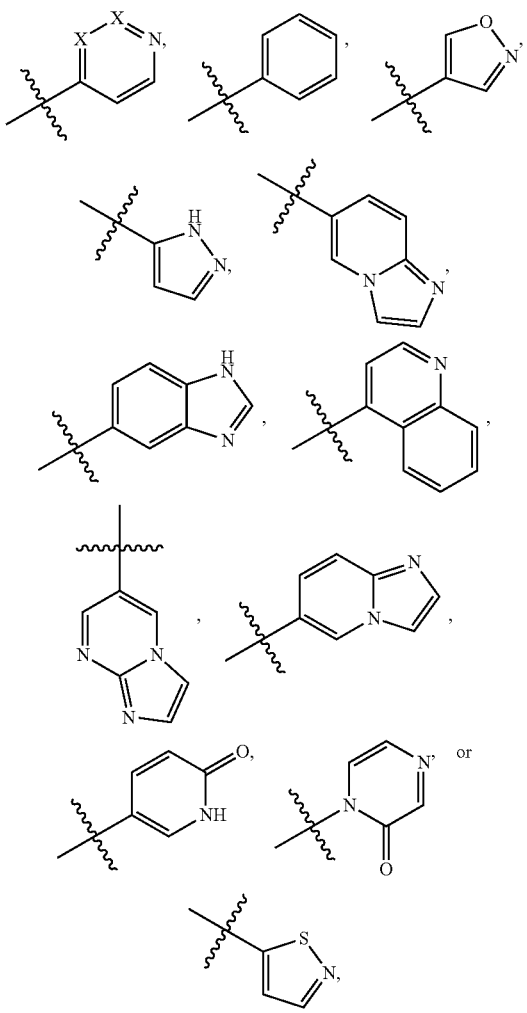

each optionally mono-, di-, or tri-substituted with substituents independently selected from halogen, $C_{1-3}$alkyl, $C_{1-3}$alkoxy, O$C_{1-3}$alkylO$C_{1-3}$alkyl, $C_{1-3}$alkylOH, OH, $NH_2$, N($C_{1-3}$alkyl)($C_{1-3}$alkyl), C(O)N($C_{1-3}$alkyl)($C_{1-3}$alkyl), NC(O)$C_{1-3}$alkyl, C(O)O$C_{1-3}$alkyl and $C_{1-3}$alkylC(O)NH$C_{1-3}$ alkylS(O)$_2$OH, wherein alkyl is optionally substituted with 1-4 halogen;

each L is independently absent,

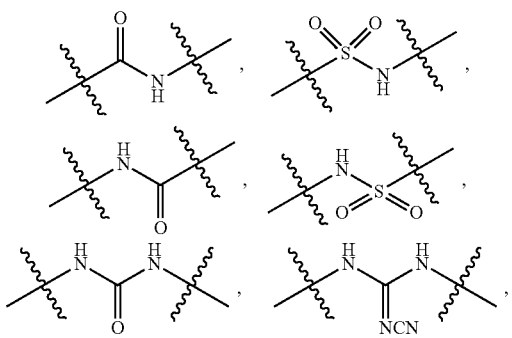

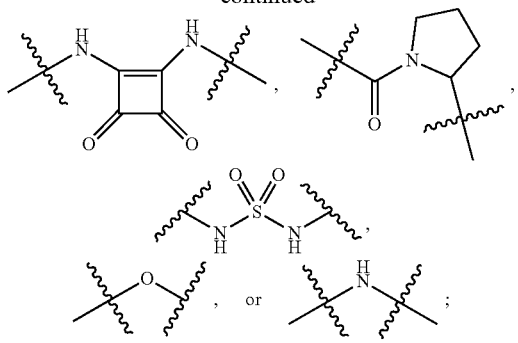

T is $NH_2$, $NH(C_{1-6}alkyl)$, $NH(C_{1-6}alkyl)(C_{1-6}alkyl)$,

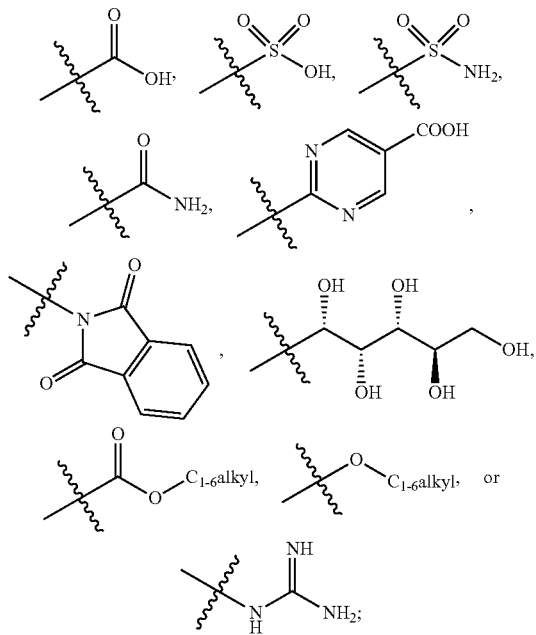

each n is independently 0, 1, 2, 3, 4 or 5, and at least one n is not 0;

each R is chosen from hydrogen, $C_{1-3}alkyl$, $C_{1-3}alkyl$-OH and $C_{0-3}alkyl$-C(O)OH; and each X is independently CH or N, and no more than two X can be N.

2. The compound of claim 1, or a pharmaceutically acceptable salt thereof, wherein
$R^1$ and $R^2$ are each independently H, halogen, $C_{1-3}alkyl$, CN, $NO_2$ or $NH_2$,
wherein alkyl is optionally substituted with 1-4 halogen.

3. The compound of claim 1, or a pharmaceutically acceptable salt thereof, wherein:
$R^3$ is each n is independently 0, 1, 2, 3 or 4, and at least one n is not 0.

4. The compound of claim 1, or a pharmaceutically acceptable salt thereof, wherein:
$R^4$ and $R^5$ are each independently H, $C_{1-3}alkyl$, $C_{1-3}alkyl$-CN, $C_{1-3}alkylC(O)OC_{1-3}alkyl$, $C_{1-3}alkylC(O)NHC_{1-3}alkyl$, $C_{1-3}alkylC(O)N(C_{1-3}alkyl)(C_{1-3}alkyl)$ or $C_{1-3}alkylC(O)NHC_{1-3}alkylS(O)_2OH$.

5. The compound of claim 1, or a pharmaceutically acceptable salt thereof, wherein:
$R^4$ and $R^5$ are each independently H, $CH_3$, $CH_2CH_3$, $CH_2CH_2CN$, $CH_2CH_2CH_2CN$, $CH_2C(O)OCH_2CH_3$, $CH_2C(O)NHCH_3$, $CH_2C(O)NH(CH_3)_2$ or $CH_2CH_2CH_2C(O)NHCH_2S(O)_2OH$.

6. The compound of claim 1, or a pharmaceutically acceptable salt thereof, wherein the C to which $R^4$ and R5 are attached form S configuration.

7. The compound of claim 1, or a pharmaceutically acceptable salt thereof, selected from the group consisting of:
1) N-(3-(3,5-dimethylisoxazol-4-yl)benzyl)-3-(trifluoromethyl)benzenesulfonamide;
2) N-(3-(3,5-dimethylisoxazol-4-yl)benzyl)-4-(trifluoromethyl)-benzene sulfonamide;
3) 4-chloro-N-(3-(3,5-dimethylisoxazol-4-yl)benzyl)benzenesulfonamide;
4) N-(2-(3-(3,5-dimethylisoxazol-4-yl)phenyl)propan-2-yl)-3-(trifluoromethyl)benzenesulfonamide;
5) N-(2-(3-(pyridin-4-yl)phenyl)propan-2-yl)-3-(trifluoromethyl)benzenesulfonamide;
6) N-(2-(3-(3-fluoropyridin-4-yl)phenyl)propan-2-yl)-3-(trifluoromethyl)benzenesulfonamide;
7) N-(2-(3-(3-chloropyridin-4-yl)phenyl)propan-2-yl)-3-(trifluoromethyl)benzene sulfonamide;
8) N-(2-(3-(2-chloropyridin-4-yl)phenyl)propan-2-yl)-3-(trifluoromethyl)benzene sulfonamide;
9) 3-(trifluoromethyl)-N-(2-(3-(2-(trifluoromethyl)pyridin-4-yl)phenyl)propan-2-yl)benzenesulfonamide;
10) N-(2-(3-(3-methoxypyridin-4-yl)phenyl)propan-2-yl)-3-(trifluoromethyl)benzenesulfonamide;
11) N-(2-(3-(quinolin-4-yl)phenyl)propan-2-yl)-3-(trifluoromethyl)benzene sulfonamide;
12) N-(2-(3-(2-methylpyridin-4-yl)phenyl)propan-2-yl)-3-(trifluoromethyl)benzenesulfonamide;
13) N-(2-(3-(2-aminopyridin-4-yl)phenyl)propan-2-yl)-3-(trifluoromethyl)benzene sulfonamide;
14) N-(2-(3-(3-aminopyridin-4-yl)phenyl)propan-2-yl)-3-(trifluoromethyl)benzene sulfonamide;
15) N-(2-(3-(3-hydroxypyridin-4-yl)phenyl)propan-2-yl)-3-(trifluoromethyl)benzenesulfonamide;
16) N-(2-(3-(3-fluoro-5-methylpyridin-4-yl)phenyl)propan-2-yl)-3-(trifluoromethyl)benzenesulfonamide;
17) N-(3-(3-fluoropyridin-4-yl)benzyl)-3-(trifluoromethyl)-benzenesulfonamide;
18) N-(3-(3-chloropyridin-4-yl)benzyl)-3-(trifluoromethyl)-benzenesulfonamide;
19) N-(3-(pyridin-4-yl)benzyl)-3-(trifluoromethyl)benzenesulfonamide;
20) N-(4-fluoro-3-(pyridin-4-yl)benzyl)-3-(trifluoromethyl)-benzenesulfonamide;
21) N-(3-(3-chloropyridin-4-yl)-4-fluorobenzyl)-3-(trifluoromethyl)-benzenesulfonamide;
22) N-(2-fluoro-5-(pyridin-4-yl)benzyl)-3-(trifluoromethyl)-benzenesulfonamide;
23) N-(5-(3-chloropyridin-4-yl)-2-fluorobenzyl)-3-(trifluoromethyl)-benzenesulfonamide;
24) (S)—N-(1-(3-(pyridin-4-yl)phenyl)ethyl)-3-(trifluoromethyl)benzenesulfonamide;

25) (S)—N-(1-(3-(3-chloropyridin-4-yl)phenyl)ethyl)-3-(trifluoromethyl)benzene sulfonamide;
26) (S)—N-(1-(3-(3-fluoropyridin-4-yl)phenyl)ethyl)-3-(trifluoromethyl)benzenesulfonamide;
27) (S)—N-(1-(3-(3-methoxypyridin-4-yl)phenyl)ethyl)-3-(trifluoromethyl)benzene sulfonamide;
28) (R)—N-(1-(3-(pyridin-4-yl)phenyl)ethyl)-3-(trifluoromethyl)benzenesulfonamide;
29) (R)—N-(1-(3-(3-chloropyridin-4-yl)phenyl)ethyl)-3-(trifluoromethyl)benzene sulfonamide;
30) (R)—N-(1-(3-(3-fluoropyridin-4-yl)phenyl)ethyl)-3-(trifluoromethyl)benzene sulfonamide;
31) (R)—N-(1-(3-(3-methoxypyridin-4-yl)phenyl)ethyl)-3-(trifluoromethyl)benzene sulfonamide;
32) N-(3-(3-methylpyridin-4-yl)benzyl)-3-(trifluoromethyl)-benzenesulfonamide;
33) N-(3-(3-aminopyridin-4-yl)benzyl)-3-(trifluoromethyl)-benzenesulfonamide;
34) 3-(trifluoromethyl)-N-(3-(3-(trifluoromethyl)pyridin-4-yl)benzyl)benzenesulfonamide;
35) N-(3-(6-methylpyrimidin-4-yl)benzyl)-3-(trifluoromethyl)-benzenesulfonamide;
36) 3-(trifluoromethyl)-N-(3-(6-(trifluoromethyl)pyrimidin-4-yl)benzyl)benzenesulfonamide;
37) N-(3-(pyrimidin-4-yl)benzyl)-3-(trifluoromethyl)benzenesulfonamide;
38) N-(2-(3-(pyridazin-4-yl)phenyl)propan-2-yl)-2-(trifluoromethyl)benzene sulfonamide;
39) N-(2-(3-(3-hydroxypyridin-4-yl)phenyl)propan-2-yl)-2-(trifluoromethyl)benzenesulfonamide;
41) (S)-3-chloro-2-methyl-N-(1-(3-(pyridazin-4-yl)phenyl)ethyl)benzenesulfonamide;
42) N-((3'-methoxy-[2,4'-bipyridin]-6-yl)methyl)-3-(trifluoromethyl)benzene sulfonamide;
43) N-((3'-methoxy-[4,4'-bipyridin]-2-yl)methyl)-3-(trifluoromethyl)benzenesulfonamide;
44) N-((3'-methoxy-[2,4'-bipyridin]-4-yl)methyl)-3-(trifluoromethyl)benzenesulfonamide;
45) N-((3'-methoxy-[4,4'-bipyridin]-2-yl)methyl)-2-(trifluoromethyl)benzene sulfonamide;
46) N-(4-chloro-3-(pyridin-4-yl)benzyl)-3-(trifluoromethyl)-benzenesulfonamide;
47) N-(3-chloro-5-(pyridin-4-yl)benzyl)-3-(trifluoromethyl)-benzenesulfonamide;
48) N-(2-(4-methyl-3-(pyridin-4-yl)phenyl)propan-2-yl)-3-(trifluoromethyl)benzenesulfonamide;
49) (+/−)N-(1-(3-(pyridin-4-yl)phenyl)propyl)-3-(trifluoromethyl)benzene sulfonamide;
50) (+/−)N-((3-(3-methoxypyridin-4-yl)phenyl)(phenyl)methyl)-2-(trifluoromethyl)benzenesulfonamide;
51) (S)—N-(1-(3-(3-methoxypyridin-4-yl)phenyl)propyl)-2-(trifluoromethyl)benzenesulfonamide;
52) methyl 2-(3-(3-methoxypyridin-4-yl)phenyl)-2-(3-(trifluoromethyl)phenyl sulfonamido)acetate;
53) N-(3-(3-methoxypyridin-4-yl)phenethyl)-2-(trifluoromethyl)benzene sulfonamide;
54) N-(3-(3,5-dimethylisoxazol-4-yl)benzyl)-3-methylbenzenesulfonamide;
55) 3-chloro-N-(3-(3,5-dimethylisoxazol-4-yl)benzyl) benzenesulfonamide;
56) N-(3-(3,5-dimethylisoxazol-4-yl)benzyl)-3-methoxybenzenesulfonamide;
57) N-(3-(3,5-dimethylisoxazol-4-yl)benzyl)-2-(trifluoromethyl)-benzene sulfonamide;
58) 4-chloro-N-(3-(3,5-dimethylisoxazol-4-yl)benzyl)-3-(trifluoromethyl)benzene sulfonamide;
59) N-(3-(3,5-dimethylisoxazol-4-yl)benzyl)-4-fluoro-3-(trifluoromethyl)benzene sulfonamide;
60) N-(3-(3,5-dimethylisoxazol-4-yl)benzyl)-2-fluoro-5-(trifluoromethyl)benzene sulfonamide;
61) N-(3-(3,5-dimethylisoxazol-4-yl)benzyl)-3-fluoro-5-(trifluoromethyl)benzene sulfonamide;
62) N-(3-(3,5-dimethylisoxazol-4-yl)benzyl)-3,5-bis(trifluoromethyl)benzene sulfonamide 63) 3-methyl-N-(3-(pyridin-4-yl)benzyl)benzenesulfonamide;
64) 3-chloro-N-(3-(pyridin-4-yl)benzyl)benzenesulfonamide;
65) 3-fluoro-N-(3-(pyridin-4-yl)benzyl)benzenesulfonamide;
66) 3-methoxy-N-(3-(pyridin-4-yl)benzyl)benzenesulfonamide;
67) N-(3-(pyridin-4-yl)benzyl)-2-(trifluoromethyl)benzenesulfonamide;
68) 3-nitro-N-(3-(pyridin-4-yl)benzyl)benzenesulfonamide;
69) 2-nitro-N-(3-(pyridin-4-yl)benzyl)benzenesulfonamide;
70) 2-methyl-N-(3-(pyridin-4-yl)benzyl)benzenesulfonamide;
71) 3-bromo-N-(3-(pyridin-4-yl)benzyl)benzenesulfonamide;
72) 2-chloro-N-(3-(pyridin-4-yl)benzyl)benzenesulfonamide;
73) 2-fluoro-N-(3-(pyridin-4-yl)benzyl)benzenesulfonamide;
74) 3-bromo-N-(2-(3-(3-methoxypyridin-4-yl)-phenyl)propan-2-yl)-benzene sulfonamide;
75) N-(2-(3-(3-methoxypyridin-4-yl)phenyl)propan-2-yl)-2-nitrobenzenesulfonamide;
76) N-(3-(pyridin-4-yl)benzyl)-2-(trifluoromethyl)benzenesulfonamide;
77) 2-methoxy-N-(2-(3-(3-methoxypyridin-4-yl)-phenyl)propan-2-yl)-5-(trifluoromethyl)benzenesulfonamide;
78) 2-chloro-N-(2-(3-(3-methoxypyridin-4-yl)phenyl)propan-2-yl)benzene sulfonamide;
79) 3-chloro-N-(2-(3-(3-methoxypyridin-4-yl)phenyl)propan-2-yl)benzene sulfonamide;
80) N-(2-(3-(3-methoxypyridin-4-yl)phenyl)propan-2-yl)-3-methyl benzenesulfonamide;
81) 3-bromo-N-(2-(3-(3-methoxypyridin-4-yl)phenyl)propan-2-yl)-5-(trifluoromethyl)benzenesulfonamide;
82) 2,3-dichloro-N-(2-(3-(3-methoxypyridin-4-yl)phenyl)propan-2-yl)benzenesulfonamide;
83) 4-fluoro-N-(2-(3-(3-methoxypyridin-4-yl)-phenyl)propan-2-yl)-2-(trifluoromethyl)benzenesulfonamide;
84) 2,5-dichloro-N-(2-(3-(3-methoxypyridin-4-yl)phenyl)propan-2-yl)benzenesulfonamide;
85) 4-chloro-N-(2-(3-(3-methoxypyridin-4-yl)phenyl)propan-2-yl)-2-(trifluoromethyl)benzenesulfonamide;
86) 2,4-dichloro-N-(2-(3-(3-methoxypyridin-4-yl)phenyl)propan-2-yl)benzenesulfonamide;
87) 5-chloro-N-(2-(3-(3-methoxypyridin-4-yl)phenyl)propan-2-yl)-2-nitrobenzenesulfonamide;
88) 2,4-dichloro-N-(2-(3-(3-methoxypyridin-4-yl)phenyl)propan-2-yl)benzenesulfonamide;
89) N-(2-(3-(3-methoxypyridin-4-yl)phenyl)propan-2-yl)-2-nitro-4-(trifluoromethyl)benzenesulfonamide;
90) N-(2-(3-(3-methoxypyridin-4-yl)phenyl)propan-2-yl)-2,5-bi s(trifluoromethyl)benzenesulfonamide;
91) 3-chloro-N-(2-(3-(3-methoxypyridin-4-yl)phenyl)propan-2-yl)-2-methylbenzenesulfonamide;
92) N-(2-(3-(3-methoxypyridin-4-yl)phenyl)propan-2-yl)-2-methyl-3-(trifluoromethyl)benzenesulfonamide;

93) 2-chloro-4-cyano-N-(2-(3-(3-methoxypyridin-4-yl)phenyl)propan-2-yl)benzenesulfonamide;
94) (S)-3-bromo-N-(1-(3-(3-methoxypyridin-4-yl)-phenyl)ethyl)benzenesulfonamide;
95) (S)—N-(1-(3-(3-methoxypyridin-4-yl)phenyl)ethyl)-2-nitrobenzenesulfonamide
96) (S)—N-(1-(3-(3-methoxypyridin-4-yl)phenyl)ethyl)-2-(trifluoromethyl)benzenesulfonamide;
97) (S)-3-bromo-N-(1-(3-(3-chloropyridin-4-yl)-phenyl)ethyl)benzenesulfonamide;
98) (S)—N-(1-(3-(3-chloropyridin-4-yl)phenyl)ethyl)-2-nitrobenzenesulfonamide;
99) (S)—N-(1-(3-(3-chloropyridin-4-yl)phenyl)ethyl)-2-(trifluoro-methyl)benzenesulfonamide;
100) 3-chloro-2-methyl-N-(2-(3-(3-methylpyridin-4-yl)phenyl)-propan-2-yl)benzenesulfonamide;
101) 2,3-dichloro-N-(2-(3-(3-methylpyridin-4-yl)phenyl)-propan-2-yl)benzenesulfonamide;
102) 5-bromo-2-methyl-N-(2-(3-(3-methylpyridin-4-yl)phenyl)-propan-2-yl)benzenesulfonamide;
103) 2-methyl-N-(2-(3-(3-methylpyridin-4-yl)phenyl)-propan-2-yl)benzenesulfonamide;
104) 3-chloro-N-(2-(3-(3-ethylpyridin-4-yl)phenyl)propan-2-yl)-2-methylbenzenesulfonamide;
105) (S)-3-chloro-N-(4-cyano-1-(3-(3-methylpyridin-4-yl)phenyl)butyl)-2-methyl benzenesulfonamide;
106) N-(2-(3-(3-ethylpyridin-4-yl)-5-methoxyphenyl)propan-2-yl)-2-(trifluoromethyl)benzenesulfonamide;
107) N-(2-(3-(6-oxo-1,6-dihydropyridin-3-yl)phenyl)propan-2-yl)-2-(trifluoromethyl)benzenesulfonamide;
108) (S)-3-Chloro-2-methyl-N-(1-(3-(1-methyl-1H-pyrazol-5-yl)phenyl)ethyl)benzenesulfonamide;
109) N-(2-(3-(3-ethylpyridin-4-yl)phenyl)propan-2-yl)-2-(trifluoromethyl)benzenesulfonamide;
110) N-(2-(3-(3-methylpyridin-4-yl)phenyl)propan-2-yl)-3-(trifluoromethyl)benzenesulfonamide;
111) N-(2-(3-(3-ethylpyridin-4-yl)phenyl)propan-2-yl)-3-(trifluoromethyl)benzenesulfonamide;
112) N-(2-(3-(2,3-dimethylpyridin-4-yl)phenyl)propan-2-yl)-3-(trifluoromethyl)benzenesulfonamide;
113) N-(2-(3-(3,5-dimethylpyridin-4-yl)phenyl)propan-2-yl)-3-(trifluoromethyl)benzenesulfonamide;
114) N-(2-(3-(3-(hydroxymethyl)-pyridin-4-yl)phenyl)propan-2-yl)-3-(trifluoromethyl)benzenesulfonamide;
115) N-(2-(3-(imidazo[1,2-a]pyridin-6-yl)phenyl)propan-2-yl)-3-(trifluoromethyl) benzenesulfonamide;
116) (S)—N-(1-(3-(3-methylpyridin-4-yl)phenyl)ethyl)-3-(trifluoromethyl)benzene sulfonamide;
117) (R)—N-(1-(3-(3-methylpyridin-4-yl)phenyl)ethyl)-3-(trifluoromethyl)benzene sulfonamide;
118) N-(2-(3-(3-methylpyridin-4-yl)phenyl)propan-2-yl)-2-(trifluoromethyl)benzenesulfonamide;
119) N-(2-(3-(imidazo[1,2-a]pyridin-6-yl)phenyl)propan-2-yl)-2-(trifluoromethyl)benzenesulfonamide;
120) N-(2-(3-(7-methylimidazo[1,2-a]pyridin-6-yl)phenyl)propan-2-yl)-2-(trifluoromethyl)benzenesulfonamide;
121) N-(2-(3-(1H-benzo[d]imidazol-5-yl)phenyl)propan-2-yl)-2-(trifluoromethyl)benzenesulfonamide;
122) N-(2-(3-(imidazo[1,2-a]pyrimidin-6-yl)phenyl)propan-2-yl)-2-(trifluoromethyl)benzenesulfonamide;
123) N-(2-(3-(3-(hydroxymethyl)pyridin-4-yl)phenyl)propan-2-yl)-2-(trifluoromethyl)benzenesulfonamide;
124) N-(2-(3-(3-ethylpyridin-4-yl)phenyl)propan-2-yl)-2-nitrobenzenesulfonamide;
125) N-(2-(3-(3-methylpyridin-4-yl)phenyl)propan-2-yl)-2-nitrobenzenesulfonamide;
126) (S)—N-(1-(3-(3-ethylpyridin-4-yl)phenyl)ethyl)-2-(trifluoromethyl)benzene sulfonamide;
127) (S)—N-(1-(3-(3-methylpyridin-4-yl)phenyl)ethyl)-2-(trifluoromethyl)benzene sulfonamide;
128) (R)—N-(1-(3-(3-ethylpyridin-4-yl)phenyl)ethyl)-2-(trifluoromethyl)benzene sulfonamide;
129) (R)—N-(1-(3-(3-methylpyridin-4-yl)phenyl)ethyl)-2-(trifluoromethyl)benzenesulfonamide;
130) (+/−)N-(1-(3-(3-methylpyridin-4-yl)phenyl)propyl)-3-(trifluoromethyl)benzenesulfonamide;
132) (S)—N-(1-(3-(3-methylpyridin-4-yl)phenyl)propyl)-2-(trifluoromethyl)benzenesulfonamide;
133) (S)—N-(1-(3-(imidazo[1,2-a]pyridin-6-yl)phenyl)propyl)-2-(trifluoromethyl)benzenesulfonamide;
134) (S)—N-(1-(3-(3-methylpyridin-4-yl)phenyl)propyl)-3-(trifluoromethyl)benzenesulfonamide;
135) (S)—N-methyl-3-(3-(3-methylpyridin-4-yl)phenyl)-3-(2-trifluoromethyl)phenyl sulfonamido)propanamide;
136) (S)—N,N-dimethyl-3-(3-(3-methylpyridin-4-yl)phenyl)-3-(2-(trifluoromethyl)phenyl sulfonamido)propanamide;
137) (S)—N-(4-cyano-1-(3-(3-methylpyridin-4-yl)phenyl)-butyl)-2-(trifluoromethyl)-benzenesulfonamide;
138) N-(3-(3-methylpyridin-4-yl)phenethyl)-2-(trifluoromethyl)benzenesulfonamide;
139) Methyl 4-(3-(2-(2-(trifluoromethyl)phenylsulfonamido)propan-2-yl)phenyl) nicotinate;
140) N-(2-(3-(5-methylpyrimidin-4-yl)phenyl)propan-2-yl)-2-(trifluoromethyl)benzenesulfonamide;
141) N-(2-(3-(2-(dimethylamino)-pyridin-4-yl)phenyl)propan-2-yl)-2-(trifluoromethyl)benzenesulfonamide;
142) (S)—N-(4-cyano-1-(3-(3-ethylpyridin-4-yl)phenyl)butyl)-2-(trifluoromethyl)benzenesulfonamide;
143) N-(3-cyano-1-(3-(3-methylpyridin-4-yl)phenyl)-propyl)-2-(trifluoromethyl)-benzenesulfonamide;
144) (S)-3-Chloro-2-methyl-N-(1-(3-(3-methylpyridin-4-yl)phenyl)ethyl)benzenesulfonamide;
145) (S)-3-chloro-2-methyl-N-(1-(3-(4-methylisothiazol-5-yl)-phenyl)ethyl)benzenesulfonamide;
146) (S)-3-chloro-N-(1-(3-(2,3-dimethylpyridin-4-yl)phenyl)ethyl)-2-methylbenzenesulfonamide;
147) 3-chloro-2-methyl-N-(3-(3-(3-methylpyridin-4-yl)phenyl)oxetan-3-yl)benzene sulfonamide;
148) N-(2-(3-(3-(2-methoxyethoxy)pyridin-4-yl)phenyl)propan-2-yl)-3-(trifluoromethyl)benzenesulfonamide;
149) N-(2-(3-(3-isopropoxypyridin-4-yl)phenyl)propan-2-yl)-3-(trifluoromethyl)benzenesulfonamide;
150) N-(2-(3-(3-ethoxypyridin-4-yl)phenyl)propan-2-yl)-3-(trifluoromethyl)benzene sulfonamide;
151) N-(2-(3-(3-ethoxypyridin-4-yl)phenyl)propan-2-yl)-2-(trifluoromethyl)benzene sulfonamide;
152) N-(4-(3-(2-(3-(trifluoromethyl)phenylsulfonamido)propan-2-yl)phenyl)pyridin-2-yl)acetamide;
153) 2-amino-N-(2-(3-(3-methoxypyridin-4-yl)phenyl)propan-2-yl)benzene sulfonamide;
154) (S)-2-amino-N-(1-(3-(3-methylpyridin-4-yl)phenyl)-ethyl)benzenesulfonamide 155) N,N-dimethyl-4-(3-(2-(2-(trifluoromethyl)phenylsulfonamido)propan-2-yl)phenyl)nicotinamide;
156) (S)-3-chloro-2-methyl-N-(1-(3-(2-oxopyrazin-1(21H)-yl)phenyl)ethyl)benzene sulfonamide;
157) Methyl 2-(N-(2-(3-(3-methylpyridin-4-yl)phenyl)propan-2-yl)-2-(trifluoromethyl)phenylsulfonamido) acetate;

158) N-(2-methoxyethyl)-N-(2-(3-(3-methylpyridin-4-yl)phenyl)propan-2-yl)-2-(trifluoromethyl)benzenesulfonamide;
159) 4-(N-(2-(3-(3-methylpyridin-4-yl)phenyl)propan-2-yl)-2-(trifluoromethyl)phenylsulfonamido)butanoic acid;
160) Ethyl 4-(N-(2-(3-(3-methylpyridin-4-yl)phenyl)propan-2-yl)-2-(trifluoromethyl)phenylsulfonamido)butanoate;
161) (S)-4-(3-chloro-2-methyl-N-(1-(3-(pyridin-4-yl)phenyl)ethyl)phenylsulfonamido) butanoic acid;
162) (S)-4-(3-chloro-N-(1-(3-(2,3-dimethylpyridin-4-yl)phenyl)ethyl)-2-methylphenyl sulfonamido)butanoic acid;
163) (S)-4-(N-(1-(3-(3-methylpyridin-4-yl)phenyl)ethyl)-2-(trifluoromethyl)phenyl sulfonamido)butanoic acid;
164) (S)-4-(N-(1-(3-(3-ethylpyridin-4-yl)phenyl)ethyl)-2-(trifluoromethyl)phenyl sulfonamido)butanoic acid;
165) (S)-tert-butyl 4-(3-chloro-N-(4-cyano-1-(3-(3-methylpyridin-4-yl)phenyl)butyl)-2-methylphenylsulfonamido)butanoate;
166) (S)-4-(3-chloro-N-(4-cyano-1-(3-(3-methylpyridin-4-yl)phenyl)butyl)-2-methylphenylsulfonamido)butanoic acid;
167) (S)-4-(3-Chloro-2-methyl-N-(1-(3-(3-methylpyridin-4-yl)phenyl)ethylphenyl sulfonamido) butanoic acid;
168) (R)-4-(3-chloro-2-methyl-N-(1-(3-(3-methylpyridin-4-yl)-phenyl)ethyl)phenyl-sulfonamido)butanoic acid;
169) (S)-4-(3-chloro-N-(1-(3-(3-ethylpyridin-4-yl)phenyl)-ethyl)-2-methylphenyl-sulfonamido)butanoic acid;
170) 4-(3-chloro-N-(2-(3-(3-(hydroxymethyl)pyridin-4-yl)-phenyl)propan-2-yl)-2-methylphenylsulfonamido)-butanoic acid;
171) (S)-4-(2-methyl-N-(1-(3-(3-methylpyridin-4-yl)phenyl)-ethyl)phenyl sulfonamido)-butanoic acid;
172) (S)-5-(3-chloro-2-methyl-N-(1-(3-(3-methylpyridin-4-yl)phenyl)ethyl)phenyl sulfonamido)pentanoic acid;
173) (S)-5-(3-chloro-N-(1-(3-(3-ethylpyridin-4-yl)phenyl)-ethyl)-2-methylphenyl-sulfonamido)pentanoic acid;
174) (S)-4-(3-chloro-2-methyl-N-(1-(3-(4-methylisothiazol-5-yl)phenyl)ethyl)phenyl-sulfonamido)butanoic acid;
175) (S)-3-(3-chloro-2-methyl-N-(1-(3-(3-methylpyridin-4-yl)phenyl)ethyl)phenyl sulfonamido)propanoic acid;
176) 4-(3-chloro-2-methyl-N-(3-(3-(3-methylpyridin-4-yl)phenyl)-oxetan-3-yl)phenyl-sulfonamido)butanoic acid;
177) (S)-2-(2-(3-chloro-2-methyl-N-(1-(3-(3-methylpyridin-4-yl)phenyl)ethyl)phenylsulfonamido)ethoxy)acetic acid;
178) (+/−)N-(2-hydroxy-1-(3-(3-methoxypyridin-4-yl)phenyl)ethyl)-3-(trifluoromethyl)benzenesulfonamide;
179) (S)-3-(3-(3-methylpyridin-4-yl)phenyl)-3-(2-(trifluoromethyl)phenyl sulfonamido)propanoic acid;
180) (S)-ethyl 3-(3-(3-methylpyridin-4-yl)phenyl)-3-(2-(trifluoromethyl)phenyl sulfonamido)propanoate;
181) 4-(3-(3-methylpyridin-4-yl)phenyl)-4-(2-(trifluoromethyl)phenyl sulfonamido)butanoic acid;
182) (S)-5-(3-(3-methylpyridin-4-yl)phenyl)-5-(2-(trifluoromethyl)phenyl sulfonamido)pentanoic acid;
183) 2-(4-(N-(2-(3-(3-ethylpyridin-4-yl)phenyl)propan-2-yl)-2-(trifluoromethyl)-phenylsulfonamido)butanamido)ethanesulfonic acid;
184) 2-(4-(N-(2-(3-(3-methylpyridin-4-yl)phenyl)propan-2-yl)-2-(trifluoromethyl)phenylsulfonamido)butanamido)ethanesulfonic acid;
185) (4-(N-(2-(3-(3-methylpyridin-4-yl)phenyl)propan-2-yl)-2-(trifluoromethyl)phenylsulfonamido)butanamido)methanesulfonicacid trifluoromethyl)benzene sulfonamide;
186) 2-(4-(3-chloro-N-(2-(3-(3-ethylpyridin-4-yl)phenyl)propan-2-yl)-2-methyl phenylsulfonamido)butanamido)ethanesulfonic acid;
187) 3-(4-(3-chloro-2-methyl-N-(2-(3-(3-methylpyridin-4-yl)phenyl)propan-2-yl)phenylsulfonamido)butanamido)propane-1-sulfonic acid;
188) 4-(3-chloro-2-methyl-N-(2-(3-(3-methylpyridin-4-yl)phenyl)propan-2-yl)phenylsulfonamido)-N-(2-sulfamoylethyl)butanamide;
189) 4-(3-chloro-2-methyl-N-(2-(3-(3-methylpyridin-4-yl)phenyl)propan-2-yl)phenyl sulfonamido)-N-((2R,3S,4S,5S)-2,3,4,5,6-pentahydroxyhexyl)butanamide;
190) 2-(4-(3-chloro-2-methyl-N-(2-(3-(3-methylpyridin-4-yl)phenyl)propan-2-yl)phenylsulfonamido)butanamido)ethanesulfonic acid;
191) (S)-2-(5-(3-chloro-2-methyl-N-(1-(3-(3-methylpyridin-4-yl)phenyl)ethyl)phenylsulfonamido)pentanamido)ethanesulfonic acid;
192) 5-(3-chloro-2-methyl-N—((S)-1-(3-(3-methylpyridin-4-yl)phenyl)ethyl)phenylsulfonamido)-N-((2R,3S,4S,5S)-2,3,4,5,6-pentahydroxyhexyl) pentanamide;
193) (S)-4-(3-chloro-2-methyl-N-(1-(3-(3-methylpyridin-4-yl)phenyl)ethyl)phenylsulfonamido)-N-(2-sulfamoylethyl)butanamide;
194) 4-(3-chloro-2-methyl-N—((S)-1-(3-(3-methylpyridin-4-yl)phenyl)ethyl)phenylsulfonamido)-N-((2R,3S,4S,5S)-2,3,4,5,6-pentahydroxyhexyl)butanamide;
195) (S)-3-(4-(3-chloro-2-methyl-N-(1-(3-(3-methylpyridin-4-yl)phenyl)ethyl)phenylsulfonamido)butanamido) propane-1-sulfonic acid;
196) (S)-3-(4-(3-chloro-N-(1-(3-(3-ethylpyridin-4-yl)phenyl)ethyl)-2-methyl phenylsulfonamido)butanamido)propane-1-sulfonic acid;
197) 4-(3-chloro-N—((S)-1-(3-(3-ethylpyridin-4-yl)phenyl)ethyl)-2-methylphenyl sulfonamido)-N-((2R,3S,4S,5S)-2,3,4,5,6-pentahydroxyhexyl)butanamide;
198) 2-(4-(3-chloro-N-(2-(3-(3-(hydroxymethyl)pyridin-4-yl)phenyl)propan-2-yl)-2-methylphenylsulfonamido)butanamido)ethanesulfonic acid;
199) (S)-2-(4-(3-chloro-N-(1-(3-(3-(hydroxymethyl)pyridin-4-yl)phenyl)ethyl)-2-methylphenylsulfonamido) butanamido)ethanesulfonic acid;
200) (S)-2-(4-(2-methyl-N-(1-(3-(3-methylpyridin-4-yl)phenyl)ethyl)phenylsulfonamido)butanamido)ethanesulfonic acid;
201) (S)-2-(4-(N-(1-(3-(3-ethylpyridin-4-yl)phenyl)ethyl)-2-methylphenyl sulfonamido)butanamido)ethanesulfonic acid;
202) (S)-2-(5-(3-chloro-N-(1-(3-(3-ethylpyridin-4-yl)phenyl)ethyl)-2-methylphenylsulfonamido)pentanamido)ethanesulfonic acid;
203) (S)—N-(2-(2-aminoethoxy)ethyl)-5-(3-chloro-2-methyl-N-(1-(3-(3-methylpyridin-4-yl)phenyl)ethyl)phenylsulfonamido)pentanamide;
204) (S)-3-((3-chloro-2-methylphenyl)sulfonyl)-2-(3-(3-methylpyridin-4-yl)phenyl)-7-oxo-11,14,17-trioxa-3,8-diazaicosan-20-oic acid;
205) tert-butyl (2-(4-(3-chloro-2-methyl-N-(2-(3-(3-methylpyridin-4-yl)phenyl)propan-2-yl)phenylsulfonamido)butanamido)ethyl)carbamate;

206) (4-(3-chloro-2-methyl-N-(2-(3-(3-methylpyridin-4-yl)phenyl)propan-2-yl)phenylsulfonamido)-N-butanamidoethylsulfonamido)acetic acid;
207) (S)-2-(4-(2-methyl-N-(1-(3-(3-methylpyridin-4-yl)phenyl)ethyl)phenylsulfonamido)butanamidoethylsulfonamido)acetate;
208) (S)-4-(3-Chloro-2-methyl-N-(1-(3-(3-methylpyridin-4-yl)phenyl)ethyl)phenylsulfonamido) butanamide;
209) (S) 2-(3-(4-(3-chloro-2-methyl-N-(1-(3-(3-ethylpyridin-4-yl)phenyl)ethyl)phenylsulfonamido)butanamido)ethylsulfonamido)propanoic acid;
210) N-(2-(hydroxythio)ethyl)-4-(N-(1-(3-(3-methylpyridin-4-yl)phenyl)ethyl)-2-(trifluoromethyl) phenylsulfonamido)butanamide;
211) N-(2-(hydroxythio)ethyl)-4-(N-(1-(3-(3-methylpyridin-4-yl)phenyl)ethyl)-3-(trifluoromethyl)phenylsulfonamido)butanamide;
212) (S)-(4-(N-(1-(3-(3-ethylpyridin-4-yl)phenyl)ethyl)-2-(trifluoromethyl)phenylsulfonamido)butanamido)methanesulfonic acid;
213) (S)-2-(4-(N-(1-(3-(3-ethylpyridin-4-yl)phenyl)ethyl)-2-(trifluoromethyl)phenylsulfonamido)butanamido)ethanesulfonic acid;
214) (S) 2-(4-(N-(1-(3-(3-ethylpyridin-4-yl)phenyl)ethyl)-2-(trifluoromethyl)phenylsulfonamido)butanamido)ethylsulfonamido)acetic acid;
215) (S)-2-(4-(N-(1-(3-(3-methylpyridin-4-yl)phenyl)ethyl)-2-(trifluoromethyl)phenylsulfonamido)butanamido)ethanesulfonic acid;
216) (S) 2-(4-(N-(1-(3-(3-methylpyridin-4-yl)phenyl)ethyl)-2-(trifluoromethyl)phenylsulfonamido)butanamido)ethylsulfonamido)propanoic acid;
217) (S) 2-(4-(N-(1-(3-(3-methylpyridin-4-yl)phenyl)ethyl)-2-(trifluoromethyl)phenylsulfonamido)butanamido)ethylsulfonamido)acetic acid;
218) (S) 2-(4-(N-(1-(3-(3-methylpyridin-4-yl)phenyl)ethyl)-2-(trifluoromethyl)phenylsulfonamido)butanamido)ethylsulfonamido)butanoic acid;
219) (S) 2-(4-(N-(1-(3-(3-methylpyridin-4-yl)phenyl)ethyl)-2-(trifluoromethyl)phenylsulfonamidopentanamidoethylsulfonamido)acetic acid;
220) (S) 2-(4-(N-(1-(3-(3-methylpyridin-4-yl)phenyl)ethyl)-2-(trifluoromethyl)phenylsulfonamidopentanamidoethylsulfonamido)propanoic acid;
221) 2-(4-(3-chloro-2-methyl-N-(3-(3-(3-methylpyridin-4-yl)phenyl)oxetan-3-yl)phenylsulfonamido)butanamido)ethanesulfonic acid;
222) (S)-2-(4-(3-chloro-2-methyl-N-(1-3-(pyridazin-4-yl)phenyl)ethyl)phenylsulfonamido)butanamido)ethanesulfonic acid;
223) (S)-2-(4-(3-chloro-2-methyl-N-(1-(3-(4-methylisothiazol-5-yl)phenyl)ethyl)phenylsulfonamido)butanamido)ethanesulfonic acid;
224) (S)-(5-(3-(3-methylpyridin-4-yl)phenyl)-5-(2-(trifluoromethyl)phenylsulfonamido)pentanamido)methanesulfonic acid;
225) (S)-2-(4-(3-chloro-N-(1-(3-(3-(hydroxymethyl)pyridin-4-yl)phenyl)ethyl)-2-methylphenylsulfonamido) butanamido)ethanesulfonamido acetic acid;
226) 2-(4-(3-chloro-2-methyl-N-(3-(3-methylpyridin-4-yl)phenethyl)phenylsulfonamido)butanamido)ethanesulfonic acid;
227) (S)-2-(4-(2-methyl-N-(1-(3-(3-ethylpyridin-4-yl)phenyl)ethyl)phenylsulfonamido)butanamidoethylsulfonamido)acetate;
228) (S)-2-(3-(3-chloro-2-methyl-N-(1-(3-(3-methylpyridin-4-yl)phenyl)ethyl)phenylsulfonamido)propanamido)ethanesulfonic acid;
229) (S)-3-(N-(4-(3-chloro-2-methyl-N-(1-(3-(3-methylpyridin-4-yl)phenyl)ethyl)phenylsulfonamido)butanoyl)sulfamoyl)propanoic acid;
230) ((S)—N-(2-aminoethyl)-4-(N-(1-(3-(3-methylpyridin-4-yl)phenyl)ethyl)-2-(trifluoromethyl)phenylsulfonamido)butanamide;
231) N-(2-Aminoethyl)-4-(3-chloro-2-methyl-N-(2-(3-(3-methylpyridin-4-yl)phenyl)propan-2-yl)-phenylsulfonamido)butanamide;
232) (R)-2-(4-(3-chloro-2-methyl-N-(2-(3-(3-methylpyridin-4-yl)phenyl)propan-2-yl)phenylsulfonamido)butanamido)-3-sulfopropanoic acid;
233) 2-(4-(3-chloro-2-methyl-N-(2-(3-(3-methylpyridin-4-yl)phenyl)propan-2-yl)phenylsulfonamido)butanamido)acetic acid;
234) N-(2-amino-2-oxoethyl)-4-(3-chloro-2-methyl-N-(2-(3-(3-methylpyridin-4-yl)phenyl)propan-2-yl)phenylsulfonamido)butanamide;
235) 4-(3-chloro-2-methyl-N-(2-(3-(3-methylpyridin-4-yl)phenyl)propan-2-yl)phenylsulfonamido)-N-(2-(dimethylamino)ethyl)butanamide;
236) (R)-2-(4-(3-chloro-2-methyl-N-(2-(3-(3-methylpyridin-4-yl)phenyl)propan-2-yl)phenylsulfonamido)butanamido)propanoic acid;
237) (S)-2-(4-(3-chloro-2-methyl-N-(2-(3-(3-methylpyridin-4-yl)phenyl)propan-2-yl)phenylsulfonamido)butanamido)propanoic acid;
238) (S)-2-(4-(3-chloro-2-methyl-N-(1-(3-(3-methylpyridin-4-yl)phenyl)ethyl)phenylsulfonamido)butanamido)ethanesulfonic acid;
239) (S)-3-(4-(3-chloro-2-methyl-N-(1-(3-(3-methylpyridin-4-yl)phenyl)ethyl)phenylsulfonamido)butanamido)propanoic acid;
240) (S)-2-(4-(3-chloro-2-methyl-N—((S)-1-(3-(3-methylpyridin-4-yl)phenyl)ethyl)phenylsulfonamido)butanamido)-3-hydroxypropanoic acid;
241) (S)-1-(4-(3-chloro-2-methyl-N—((S)-1-(3-(3-methylpyridin-4-yl)phenyl)ethyl)phenylsulfonamido)butanoyl)pyrrolidine-2-carboxylic acid;
242) (S)-2,2'-((4-(3-chloro-2-methyl-N-(1-(3-(3-methylpyridin-4-yl)phenyl)ethyl)phenylsulfonamido)butanoyl)azanediyl)diacetic acid;
243) (S) 2-(3-(4-(3-chloro-2-methyl-N-(1-(3-(3-methylpyridin-4-yl)phenyl)ethyl)phenylsulfonamido)butanamido)ethylsulfonamido)propanoic acid;
244) (S)-2-(3-(4-(3-chloro-2-methyl-N-(1-(3-(3-methylpyridin-4-yl)phenyl)ethyl)phenylsulfonamido)butanamido)propanamido)acetic acid;
245) (S) 2-(3-(4-(3-chloro-2-methyl-N-(1-(3-(3-methylpyridin-4-yl)phenyl)ethyl)phenylsulfonamido)butanamido)ethylsulfonamido)acetic acid;
246) (S)-2-(2-(2-(3-Chloro-2-methyl-N-(1-(3-(3-methylpyridin-4-yl)phenyl)ethyl)phenylsulfonamido) ethoxy)acetamido)ethanesulfonic acid;
247) (R)-2-(4-(3-Chloro-2-methyl-N-(1-(3-(3-methylpyridin-4-yl)phenyl)ethyl)phenyl sulfonamido)butanamido)ethanesulfonic acid;
248) (S)-2-(4-(3-chloro-N-(1-(3-(3-ethylpyridin-4-yl)phenyl)ethyl)-2-methylphenylsulfonamido)butanamido)ethanesulfonic acid;
249) (S)-(4-(3-chloro-N-(1-(3-(3-ethylpyridin-4-yl)phenyl)ethyl)-2-methylphenylsulfonamido)butanamido)methanesulfonic acid;

250) (S)—N-(2-aminoethyl)-4-(3-chloro-N-(1-(3-(3-ethylpyridin-4-yl)phenyl)ethyl)-2-methylphenylsulfonamido)butanamide;
251) (S) 2-(3-(4-(3-chloro-2-methyl-N-(1-(3-(3-ethylpyridin-4-yl)phenyl)ethyl)phenylsulfonamido)butanamidoethylsulfonamido)acetic acid;
252) N-(2-(3-(3-Ethylpyridin-4-yl)-5-hydroxyphenyl)propan-2-yl)-2-(trifluoromethylbenzenesulfonamide;
253) (S)-2-(4-(N-(1-(3-(3-hydroxypyridin-4-yl)phenyl)ethyl)-2-methylphenyl sulfonamido)butanamido)ethanesulfonic acid;
254) N-(3-aminopropyl)-3-chloro-2-methyl-N-(2-(3-(3-methylpyridin-4-yl)phenyl)propan-2-yl)benzenesulfonamide;
255) (S)—N-(4-aminobutyl)-N-(1-(3-(3-methylpyridin-4-yl)phenyl)ethyl)-2-(trifluoromethyl) benzenesulfonamide;
256) N-(5-amino-1-(3-(3-methylpyridin-4-yl)phenyl)pentyl)-2-(trifluoromethyl)benzenesulfonamide;
257) (S)—N-(4-aminobutyl)-3-chloro-N-(1-(3-(3-ethylpyridin-4-yl)phenyl)ethyl)-2-methylbenzenesulfonamide;
258) (E)-3-(3-(3-((3-chloro-2-methyl-N-(2-(3-(3-methylpyridin-4-yl)phenyl)propan-2-yl)phenyl)sulfonamido)propyl)-2-cyanoguanidino)propanoic acid;
259) Ethyl (E)-3-(3-(3-((3-chloro-2-methyl-N-(2-(3-(3-methylpyridin-4-yl)phenyl)propan-2-yl)phenyl)sulfonamido)propyl)-2-cyanoguanidino)propanoate;
260) N-(3-((2-aminoethyl)sulfonamido)propyl)-3-chloro-2-methyl-N-(2-(3-(3-methylpyridin-4-yl)phenyl)propan-2-yl)benzenesulfonamide;
261) 3-Chloro-N-(3-((2-(1,3-dioxoisoindolin-2-yl)ethyl)sulfonamido)propyl)-2-methyl-N-(2-(3-(3-methylpyridin-4-yl)phenyl)propan-2-yl)benzenesulfonamide;
262) (S)-4-(3-chloro-2-methyl-N-(1-(3-(3-methylpyridin-4-yl)phenyl)ethyl)phenylsulfonamido)butanamido-2-(N-ethylsulfamoyl)acetic acid;
263) (S)-4-(3-chloro-2-methyl-N-(1-(3-(3-methylpyridin-4-yl)phenyl)ethyl)phenylsulfonamido) butanamido-2-(N-ethylsulfamoyl)propanoic acid;
264) (S)-Methyl-4-(3-chloro-2-methyl-N-(1-(3-(3-methylpyridin-4-yl)phenyl)ethyl)phenylsulfonamido) butanamido-2-(N-(2-(2-aminoethoxy)ethylsulfamoyl) acetate;
265) (S)-4-(3-chloro-2-methyl-N-(1-(3-(3-methylpyridin-4-yl)phenyl)ethyl)phenylsulfonamido) butanamido-2-(N-(2-(2-aminoethoxy)ethylsulfamoyl)acetic acid;
266) (S)-3-(N-(4-(3-chloro-N-(1-(3-(3-ethylpyridin-4-yl)phenyl)ethyl)-2-methylphenylsulfonamido)butyl) sulfamoyl)propanoic acid;
267) 2-((3-((3-chloro-2-methyl-N-(2-(3-(3-methylpyridin-4-yl)phenyl)propan-2-yl)phenyl)sulfonamido)propyl)amino)pyrimidine-5-carboxylic acid;
268) 2-((2-(4-(3-chloro-2-methyl-N-(2-(3-(3-methylpyridin-4-yl)phenyl) propan-2-yl)phenylsulfonamido) butanamido)ethyl)amino)pyrimidine-5-carboxylic acid;
269) 4-(3-chloro-2-methyl-N-(2-(3-(3-methylpyridin-4-yl)phenyl)propan-2-yl)phenylsulfonamido)-N-(2-guanidinoethyl)butanamide;
270) 3-chloro-N-(3-((2-guanidinoethyl)sulfonamido)propyl)-2-methyl-N-(2-(3-(3-methylpyridin-4-yl)phenyl)propan-2-yl)benzenesulfonamide;
271) 2-(4-(3-chloro-2-methyl-N-(2-(3-(3-methylpyridin-4-yl)phenyl)propan-2-yl)phenylsulfonamido) butanamido)-N,N,N-trimethylethanaminium;
272) (S)-2-(4-(3-chloro-N-(1-(3-(3-ethylpyridin-4-yl)phenyl)ethyl)-2-methylphenylsulfonamido)butanamido)-N,N,N-trimethylethanaminium;
273) (S)-2-(3-(4-(N-(1-(3-(3-methylpyridin-4-yl)phenyl)ethyl)-2-(trifluoromethyl)phenylsulfonamido)butyl) ureido)ethanesulfonamidopropanoic acid;
274) (S)-2-(4-(N-(1-(3-(3-methylpyridin-4-yl)phenyl)ethyl)-2-(trifluoromethyl)phenylsulfonamido)butyl) ureido) ethanesulfonamido acetic acid;
275) (S)-2-(4-(N-(1-(3-(3-methylpyridin-4-yl)phenyl)ethyl)-2-(trifluoromethyl)phenylsulfonamido) butyl)ureido)ethanesulfonic acid;
276) (S)-(3-(4-(N-(1-(3-(3-methylpyridin-4-yl)phenyl)ethyl)-2-(trifluoromethyl)phenylsulfonamido)butyl) ureido)methanesulfonic acid;
277) 2-(3-(2-(N-(3-((3-chloro-2-methyl-N-(2-(3-(3-methylpyridin-4-yl) phenyl)propan-2-yl)phenyl) sulfonamido)propyl)sulfamoyl)ethyl) ureido)ethane-1-sulfonic acid;
278) 3-(3-(2-(N-(3-((3-chloro-2-methyl-N-(2-(3-(3-methylpyridin-4-yl)phenyl)-propan-2-yl)phenyl)sulfonamido)-propyl)sulfamoyl)ethyl)ureido) propane-1-sulfonic acid;
279) (S)-17-((3-chloro-2-methylphenyl)sulfonyl)-18-(3-(3-methylpyridin-4-yl)phenyl)-4,12-dioxo-8-oxa-3,5,11,17-tetraazanonadecane-1-sulfonic acid;
280) 2-(3-(5-(3-(3-methylpyridin-4-yl)phenyl)-5-(2-(trifluoromethyl)phenyl sulfonamido)pentyl)ureido) ethanesulfonic acid;
281) (S)-(3-(4-(N-(1-(3-(3-ethylpyridin-4-yl)phenyl)ethyl)-2-(trifluoromethyl)phenylsulfonamido)butyl) ureido)methanesulfonic acid;
282) (3-(3-(3-chloro-2-methyl-N-(3-(3-methylpyridin-4-yl)benzyl)phenylsulfonamido)propyl)ureido)methanesulfonic acid;
283) (3-(3-((3-Chloro-2-methyl-N-(2-(3-(3-methylpyridin-4-yl) phenyl) propan-2-yl) phenyl) sulfonamide) propyl) ureido) methanesulfonic acid;
284) 2-(3-(3-((3-Chloro-2-methyl-N-(2-(3-(3-methylpyridin-4-yl) phenyl) propan-2-yl) phenyl) sulfonamide) propyl) ureido)ethane-1-sulfonic acid;
285) 3-Chloro-2-methyl-N-(2-(3-(3-methylpyridin-4-yl) phenyl) propan-2-yl)-N-(3-(3-(2-sulfamoylethyl) ureido) propyl) benzenesulfonamide;
286) 34343-((3-Chloro-2-methyl-N-(2-(3-(3-methylpyridin-4-yl) phenyl) sulfonamide) propyl) ureido) propane-1-sulfonic acid;
287) (3-(3-(3-chloro-2-methyl-N-(3-(3-methylpyridin-4-yl)phenethyl)phenylsulfonamido)propyl)ureido)methanesulfonic acid;
288) (S)-3-((3-Chloro-2-methylphenyl)sulfonyl)-2-(3-(3-methylpyridin-4-yl)phenyl)-7,12-dioxo-3,8,11,13-tetraazahexadecane-16-oic acid;
289) (S)-15-((3-chloro-2-methylphenyl)sulfonyl)-16-(3-(3-methylpyridin-4-yl)phenyl)-2,10-dioxo-6-oxa-3,9,15-triazaheptadecane-1-sulfonic acid;
290) (S)-2-((4-(N-(1-(3-(3-methylpyridin-4-yl)phenyl)ethyl)-2-(trifluoromethyl)phenylsulfonamido)butyl) amino)-2-oxoethanesulfonic acid;
291) 2-((3-(3-chloro-2-methyl-N-(2-(3-(3-methylpyridin-4-yl)phenyl)propan-2-yl)phenylsulfonamido)propyl) amino)-2-oxoethanesulfonic acid;
292) (R)-2-amino-3-((4-(N—((S)-1-(3-(3-methylpyridin-4-yl)phenyl)ethyl)-2-(trifluoromethyl)phenylsulfonamido)butyl)amino)-3-oxopropane-1-sulfonic acid;

293) (R)-2-amino-3-((4-(3-chloro-N—((S)-1-(3-(3-ethylpyridin-4-yl)phenyl)ethyl)-2-methylphenylsulfonamido)butyl) amino)-3-oxopropane-1-sulfonic acid;
294) (S)-2-((2-(4-(N-(1-(3-(3-methylpyridin-4-yl)phenyl)ethyl)-2-(trifluoromethyl)phenylsulfonamido)butanamido)ethyl)amino)-2-oxoethanesulfonic acid;
295) (R)-2-amino-3-((2-(4-(N—((S)-1-(3-(3-methylpyridin-4-yl)phenyl)ethyl)-2-(trifluoromethyl)phenylsulfonamido)butanamido)ethyl)amino)-3-oxopropane-1-sulfonic acid;
296) 2-((2-((2-(3-chloro-2-methyl-N-(1-(3-(3-methylpyridin-4-yl)phenyl)ethyl)phenylsulfonamido)ethyl) amino)-3,4-dioxocyclobut-1-en-1-yl)amino)methanesulfonic acid;
297) ((2-((3-(3-chloro-2-methyl-N-(1-(3-(3-methylpyridin-4-yl)phenyl)ethyl)phenylsulfonamido)propyl) amino)-3,4-dioxocyclobut-1-en-1-yl)amino)methanesulfonic acid;
298) 3-((2-((2-(3-chloro-2-methyl-N-(1-(3-(3-methylpyridin-4-yl)phenyl)ethyl)phenylsulfonamido)ethyl) amino)-3,4-dioxocyclobut-1-en-1-yl)amino)propanoic acid;
299) ((2-((3-(3-chloro-2-methyl-N-(1-(3-(3-methylpyridin-4-yl)phenyl)ethyl)phenylsulfonamido)propyl) amino)-3,4-dioxocyclobut-1-en-1-yl)amino)methanesulfonic acid;
300) (S)-3-((4-(3-chloro-2-methyl-N-(1-(3-(3-methylpyridin-4-yl)phenyl)ethyl)phenylsulfonamido)butyl) amino)propanoic acid;
301) (S)-3-(N-(4-(3-chloro-2-methyl-N-(1-(3-(3-methylpyridin-4-yl)phenyl)ethyl)phenylsulfonamido)butyl) acetamido)propanoic acid 302);
302) 3-chloro-N-(5-cyano-1-(3-(3-methylpyridin-4-yl)phenyl)pentyl)-2-methylbenzenesulfonamide;
303) N-(5-cyano-1-(3-(3-methylpyridin-4-yl)phenyl)pentyl)-5-methylpyridine-2-sulfonamide;
304) (S)-2-(4-(4-fluoro-N-(1-(3-(3-methylpyridin-4-yl)phenyl)ethyl)-2-(trifluoromethyl) phenylsulfonamido) butanamido)ethanesulfonamido acetic acid;
305) (S)-2-(4-(3-chloro-N-(1-(3-(3-methylpyridin-4-yl)phenyl)ethyl)-2-chloro-phenylsulfonamido)butanamido)ethanesulfonamido acetic acid;
306) (S)-4-(3-chloro-2-methyl-N-(1-(3-(3-methylpyridin-4-yl)phenyl)ethyl)phenylsulfonamido)-N-(2-(sulfamoylamino)ethyl)butanamide;
307) (S)—N-(2-((N-(tert-butoxy)sulfamoyl)amino) ethyl)-4-(3-chloro-2-methyl-N-(1-(3-(3-methylpyridin-4-yl)phenyl)ethyl)phenyl sulfonamido)butanamide;
308) (S)-4-(3-chloro-N-(1-(3-(3-ethylpyridin-4-yl)phenyl)ethyl)-2-methylphenylsulfonamido)-N-(2-(sulfamoylamino)ethyl)butanamide;
309) (S)-2-((N-(2-(4-(3-chloro-2-methyl-N-(1-(3-(3-methylpyridin-4-yl)phenyl)ethyl)phenylsulfonamido) butanamido)ethyl)sulfamoyl)amino)acetic acid;
310) (S)-2-((N-(2-(4-(3-chloro-N-(1-(3-(3-ethylpyridin-4-yl)phenyl)ethyl)-2-methylphenylsulfonamido) butanamido)ethyl)sulfamoyl)amino)acetic acid;
311) (S)-3-chloro-N-(4-hydroxybutyl)-2-methyl-N-(1-(3-(3-methylpyridin-4-yl)phenyl)ethyl) benzenesulfonamide;
or a pharmaceutically acceptable salt thereof.

8. The compound of claim 7, which is selected from the group consisting of:
1) (S)-3-chloro-N-(4-cyano-1-(3-(3-methylpyridin-4-yl)phenyl)butyl)-2-methylbenzenesulfonamide;
2) (S)—N-(4-cyano-1-(3-(3-methylpyridin-4-yl)phenyl)butyl)-2-(trifluoromethyl)-benzenesulfonamide;
3) (S)—N-(4-cyano-1-(3-(3-ethylpyridin-4-yl)phenyl) butyl)-2-(trifluoromethyl)-benzenesulfonamide;
4) N-(3-cyano-1-(3-(3-methylpyridin-4-yl)phenyl)-propyl)-2-(trifluoromethyl)-benzenesulfonamide;
5) Methyl 2-(N-(2-(3-(3-methylpyridin-4-yl)phenyl)propan-2-yl)-2-(trifluoromethyl)phenylsulfonamido)acetate;
6) N-(2-methoxyethyl)-N-(2-(3-(3-methylpyridin-4-yl)phenyl)propan-2-yl)-2-(trifluoromethyl)benzenesulfonamide;
7) 4-(N-(2-(3-(3-methylpyridin-4-yl)phenyl)propan-2-yl)-2-(trifluoromethyl)phenylsulfonamido)butanoic acid;
8) Ethyl 4-(N-(2-(3-(3-methylpyridin-4-yl)phenyl)propan-2-yl)-2-(trifluoromethyl)phenylsulfonamido)butanoate;
9) (S)-4-(N-(1-(3-(3-methylpyridin-4-yl)phenyl)ethyl)-2-(trifluoromethyl)phenylsulfonamido)-butanoic acid;
10) (S)-4-(N-(1-(3-(3-ethylpyridin-4-yl)phenyl)ethyl)-2-(trifluoromethyl) phenylsulfonamido)butanoic acid;
11) (S)-5-(3-chloro-2-methyl-N-(1-(3-(3-methylpyridin-4-yl)phenyl)ethyl)phenylsulfonamido)pentanoic acid;
12) (S)-5-(3-chloro-N-(1-(3-(3-ethylpyridin-4-yl)phenyl)-ethyl)-2-methylphenyl-sulfonamido)pentanoic acid;
13) (S)-ethyl 3-(3-(3-methylpyridin-4-yl)phenyl)-3-(2-(trifluoromethyl)phenylsulfonamido)-propanoate;
14) 2-(4-(N-(2-(3-(3-ethylpyridin-4-yl)phenyl)propan-2-yl)-2-(trifluoromethyl)phenylsulfonamido)butanamido)ethanesulfonic acid;
15) 2-(4-(N-(2-(3-(3-methylpyridin-4-yl)phenyl)propan-2-yl)-2-(trifluoromethyl)phenylsulfonamido)butanamido)ethanesulfonic acid;
16) (4-(N-(2-(3-(3-methylpyridin-4-yl)phenyl)propan-2-yl)-2-(trifluoromethyl)phenylsulfonamido)butanamido)methanesulfonic acidtrifluoromethyl)benzenesulfonamide;
17) 2-(4-(3-chloro-N-(2-(3-(3-ethylpyridin-4-yl)phenyl) propan-2-yl)-2-methylphenylsulfonamido)butanamido)ethanesulfonic acid;
18) 3-(4-(3-chloro-2-methyl-N-(2-(3-(3-methylpyridin-4-yl)phenyl)propan-2-yl)phenylsulfonamido)butanamido)propane-1-sulfonic acid;
19) 4-(3-chloro-2-methyl-N-(2-(3-(3-methylpyridin-4-yl)phenyl)propan-2-yl)phenylsulfonamido)-N-(2-sulfamoylethyl)butanamide;
20) 4-(3-chloro-2-methyl-N-(2-(3-(3-methylpyridin-4-yl)phenyl)propan-2-yl)phenylsulfonamido)-N-((2R,3S,4S,5S)-2,3,4,5,6-pentahydroxyhexyl)butanamide;
21) 2-(4-(3-chloro-2-methyl-N-(2-(3-(3-methylpyridin-4-yl)phenyl)propan-2-yl)phenylsulfonamido)butanamido)ethanesulfonic acid;
22) (S)-2-(5-(3-chloro-2-methyl-N-(1-(3-(3-methylpyridin-4-yl)phenyl)ethyl)phenylsulfonamido)pentanamido)ethanesulfonic acid;
23) 5-(3-chloro-2-methyl-N—((S)-1-(3-(3-methylpyridin-4-yl)phenyl)ethyl)phenylsulfonamido)-N-((2R,3S,4S,5S)-2,3,4,5,6-pentahydroxyhexyl)pentanamide;
24) (S)-4-(3-chloro-2-methyl-N-(1-(3-(3-methylpyridin-4-yl)phenyl)ethyl)phenylsulfonamido)-N-(2-sulfamoylethyl)butanamide;
25) 4-(3-chloro-2-methyl-N—((S)-1-(3-(3-methylpyridin-4-yl)phenyl)ethyl)phenylsulfonamido)-N-((2R,3S,4S,5S)-2,3,4,5,6-pentahydroxyhexyl)butanamide;

26) (S)-3-(4-(3-chloro-2-methyl-N-(1-(3-(3-methylpyridin-4-yl)phenyl)ethyl)phenylsulfonamido)butanamido)propane-1-sulfonic acid;
27) (S)-3-(4-(3-chloro-N-(1-(3-(3-ethylpyridin-4-yl)phenyl)ethyl)-2-methylphenylsulfonamido)butanamido)propane-1-sulfonic acid;
28) 4-(3-chloro-N—((S)-1-(3-(3-ethylpyridin-4-yl)phenyl)ethyl)-2-methylphenylsulfonamido)-N-((2R,3S,4S,5S)-2,3,4,5,6-pentahydroxyhexyl)butanamide;
29) 2-(4-(3-chloro-N-(2-(3-(3-(hydroxymethyl)pyridin-4-yl)phenyl)propan-2-yl)-2-methylphenylsulfonamido)butanamido)ethanesulfonic acid;
30) (S)-2-(4-(2-methyl-N-(1-(3-(3-methylpyridin-4-yl)phenyl)ethyl)phenylsulfonamido)butanamido)ethanesulfonic acid;
31) (S)-2-(4-(N-(1-(3-(3-ethylpyridin-4-yl)phenyl)ethyl)-2-methylphenyl-sulfonamido)butanamido)ethane sulfonic acid;
32) (S)-2-(5-(3-chloro-N-(1-(3-(3-ethylpyridin-4-yl)phenyl)ethyl)-2-methylphenylsulfonamido)pentanamido)ethanesulfonic acid;
33) (S)—N-(2-(2-aminoethoxy)ethyl)-5-(3-chloro-2-methyl-N-(1-(3-(3-methylpyridin-4-yl)phenyl)ethyl)phenylsulfonamido)pentanamide;
34) tert-butyl (2-(4-(3-chloro-2-methyl-N-(2-(3-(3-methylpyridin-4-yl)phenyl)propan-2-yl)phenylsulfonamido)butanamido)ethyl)carbamate;
35) (4-(3-chloro-2-methyl-N-(2-(3-(3-methylpyridin-4-yl)phenyl)propan-2-yl)phenylsulfonamido)-N-butanamidoethylsulfonamido)acetic acid;
36) (S)-2-(4-(2-methyl-N-(1-(3-(3-methylpyridin-4-yl)phenyl)ethyl)phenylsulfonamido)butanamidoethylsulfonamido)acetate;
37) (S)-4-(3-Chloro-2-methyl-N-(1-(3-(3-methylpyridin-4-yl)phenyl)ethyl)phenylsulfonamido)butanamide;
38) (S) 2-(3-(4-(3-chloro-2-methyl-N-(1-(3-(3-ethylpyridin-4-yl)phenyl)ethyl)phenylsulfonamido)butanamido)ethylsulfonamido)propanoic acid;
39) N-(2-(hydroxythio)ethyl)-4-(N-(1-(3-(3-methylpyridin-4-yl)phenyl)ethyl)-2-(trifluoromethyl)phenylsulfonamido)butanamide;
40) (S)-(4-(N-(1-(3-(3-ethylpyridin-4-yl)phenyl)ethyl)-2-(trifluoromethyl)phenylsulfonamido)butanamido)methanesulfonic acid;
41) (S)-2-(4-(N-(1-(3-(3-ethylpyridin-4-yl)phenyl)ethyl)-2-(trifluoromethyl)phenylsulfonamido)butanamido)ethanesulfonic acid;
42) (S) 2-(4-(N-(1-(3-(3-ethylpyridin-4-yl)phenyl)ethyl)-2-(trifluoromethyl)phenylsulfonamido)butanamido)ethylsulfonamido)acetic acid;
43) (S)-2-(4-(N-(1-(3-(3-methylpyridin-4-yl)phenyl)ethyl)-2-(trifluoromethyl)phenylsulfonamido)butanamido)ethanesulfonic acid;
44) (S) 2-(4-(N-(1-(3-(3-methylpyridin-4-yl)phenyl)ethyl)-2-(trifluoromethyl)phenylsulfonamido)butanamido)ethylsulfonamido)propanoic acid;
45) (S) 2-(4-(N-(1-(3-(3-methylpyridin-4-yl)phenyl)ethyl)-2-(trifluoromethyl)phenylsulfonamido)butanamido)ethylsulfonamido)acetic acid;
46) (S) 2-(4-(N-(1-(3-(3-methylpyridin-4-yl)phenyl)ethyl)-2-(trifluoromethyl)phenylsulfonamido)butanamido)butanoic acid;
47) (S) 2-(4-(N-(1-(3-(3-methylpyridin-4-yl)phenyl)ethyl)-2-(trifluoromethyl)phenylsulfonamidopentanamido)ethylsulfonamido)acetic acid;
48) (S) 2-(4-(N-(1-(3-(3-methylpyridin-4-yl)phenyl)ethyl)-2-(trifluoromethyl)phenylsulfonamidopentanamido)ethylsulfonamido)propanoic acid;
49) 2-(4-(3-chloro-2-methyl-N-(3-(3-(3-methylpyridin-4-yl)phenyl)oxetan-3-yl)phenylsulfonamido)butanamido)ethanesulfonic acid;
50) (S)-2-(4-(2-methyl-N-(1-(3-(3-ethylpyridin-4-yl)phenyl)ethyl)phenylsulfonamido)butanamidoethylsulfonamido)acetate;
51) ((S)—N-(2-aminoethyl)-4-(N-(1-(3-(3-methylpyridin-4-yl)phenyl)ethyl)-2-(trifluoromethyl)phenylsulfonamido)butanamide;
52) N-(2-Aminoethyl)-4-(3-chloro-2-methyl-N-(2-(3-(3-methylpyridin-4-yl)phenyl)propan-2-yl)-phenylsulfonamido)butanamide;
53) 2-(4-(3-chloro-2-methyl-N-(2-(3-(3-methylpyridin-4-yl)phenyl)propan-2-yl)phenylsulfonamido)butanamido)acetic acid;
54) N-(2-amino-2-oxoethyl)-4-(3-chloro-2-methyl-N-(2-(3-(3-methylpyridin-4-yl)phenyl)propan-2-yl)phenylsulfonamido)butanamide;
55) 4-(3-chloro-2-methyl-N-(2-(3-(3-methylpyridin-4-yl)phenyl)propan-2-yl)phenylsulfonamido)-N-(2-(dimethylamino)ethyl)butanamide;
56) (R)-2-(4-(3-chloro-2-methyl-N-(2-(3-(3-methylpyridin-4-yl)phenyl)propan-2-yl)phenylsulfonamido)butanamido)propanoic acid;
57) (S)-2-(4-(3-chloro-2-methyl-N-(2-(3-(3-methylpyridin-4-yl)phenyl)propan-2-yl)phenylsulfonamido)butanamido)propanoic acid;
58) (S)-2-(4-(3-chloro-2-methyl-N-(1-(3-(3-methylpyridin-4-yl)phenyl)ethyl)phenylsulfonamido)butanamido)ethanesulfonic acid 59) (S)-3-(4-(3-chloro-2-methyl-N-(1-(3-(3-methylpyridin-4-yl)phenyl)ethyl)phenylsulfonamido)butanamido)propanoic acid;
60) (S)-2-(4-(3-chloro-2-methyl-N—((S)-1-(3-(3-methylpyridin-4-yl)phenyl)ethyl)phenylsulfonamido)butanamido)-3-hydroxypropanoic acid;
61) (S)-1-(4-(3-chloro-2-methyl-N—((S)-1-(3-(3-methylpyridin-4-yl)phenyl)ethyl)phenylsulfonamido)butanoyl)pyrrolidine-2-carboxylic acid;
62) (S) 2-(3-(4-(3-chloro-2-methyl-N-(1-(3-(3-methylpyridin-4-yl)phenyl)ethyl)phenylsulfonamido)butanamido)ethylsulfonamido)propanoic acid;
63) (S)-2-(3-(4-(3-chloro-2-methyl-N-(1-(3-(3-methylpyridin-4-yl)phenyl)ethyl)phenylsulfonamido)butanamido)propanamido)acetic acid;
64) (S) 2-(3-(4-(3-chloro-2-methyl-N-(1-(3-(3-methylpyridin-4-yl)phenyl)ethyl)phenylsulfonamido)butanamido)ethylsulfonamido)acetic acid;
65) (R)-2-(4-(3-chloro-2-methyl-N-(1-(3-(3-methylpyridin-4-yl)phenyl)ethyl)phenyl sulfonamido)butanamido)ethanesulfonic acid;
66) (S)-2-(4-(3-chloro-N-(1-(3-(3-ethylpyridin-4-yl)phenyl)ethyl)-2-methylphenylsulfonamido)butanamido)ethanesulfonic acid;
67) (S)-(4-(3-chloro-N-(1-(3-(3-ethylpyridin-4-yl)phenyl)ethyl)-2-methylphenyl sulfonamido)butanamido)methanesulfonic acid;
68) (S)—N-(2-aminoethyl)-4-(3-chloro-N-(1-(3-(3-ethylpyridin-4-yl)phenyl)ethyl)-2-methylphenylsulfonamido)butanamide;
69) (S) 2-(3-(4-(3-chloro-2-methyl-N-(1-(3-(3-ethylpyridin-4-yl)phenyl)ethyl)phenylsulfonamido)butanamido)ethylsulfonamido)acetic acid;
70) N-(2-(3-(3-Ethylpyridin-4-yl)-5-hydroxyphenyl)propan-2-yl)-2-(trifluoromethyl)benzenesulfonamide;

71) N-(3-aminopropyl)-3-chloro-2-methyl-N-(2-(3-(3-methylpyridin-4-yl)phenyl)propan-2-yl)benzenesulfonamide;
72) (S)—N-(4-aminobutyl)-N-(1-(3-(3-methylpyridin-4-yl)phenyl)ethyl)-2-(trifluoromethyl)Benzenesulfonamide;
73) (E)-3-(3-(3-((3-chloro-2-methyl-N-(2-(3-(3-methylpyridin-4-yl)phenyl)propan-2-yl)phenyl)sulfonamido)propyl)-2-cyanoguanidino)propanoic acid;
74) N-(3-((2-aminoethyl)sulfonamido)propyl)-3-chloro-2-methyl-N-(2-(3-(3-methylpyridin-4-yl)phenyl)propan-2-yl)benzenesulfonamide;
75) 3-chloro-N-(3-((2-(1,3-dioxoisoindolin-2-yl)ethyl)sulfonamido)propyl)-2-methyl-N-(2-(3-(3-methylpyridin-4-yl)phenyl)propan-2-yl)benzenesulfonamide;
76) (S)-4-(3-chloro-2-methyl-N-(1-(3-(3-methylpyridin-4-yl)phenyl)ethyl)phenylsulfonamido)butanamido-2-(N-ethylsulfamoyl)acetic acid;
77) (S)-4-(3-chloro-2-methyl-N-(1-(3-(3-methylpyridin-4-yl)phenyl)ethyl)phenylsulfonamido)butanamido-2-(N-ethylsulfamoyl)propanoic acid;
78) (S)-4-(3-chloro-2-methyl-N-(1-(3-(3-methylpyridin-4-yl)phenyl)ethyl)phenylsulfonamido)butanamido-2-(N-(2-(2-aminoethoxy)ethylsulfamoyl)acetic acid;
79) (S)-3-(N-(4-(3-chloro-N-(1-(3-(3-ethylpyridin-4-yl)phenyl)ethyl)-2-methylphenylsulfonamido)butyl)sulfamoyl)propanoic acid;
80) 2-((3-((3-chloro-2-methyl-N-(2-(3-(3-methylpyridin-4-yl)phenyl)propan-2-yl)phenyl)sulfonamido)propyl)amino)pyrimidine-5-carboxylic acid;
81) 2-((2-(4-(3-chloro-2-methyl-N-(2-(3-(3-methylpyridin-4-yl)Phenyl)propan-2-yl)phenylsulfonamido)butanamido)ethyl)amino)pyrimidine-5-carboxylic acid;
82) 4-(3-chloro-2-methyl-N-(2-(3-(3-methylpyridin-4-yl)phenyl)propan-2-yl)phenylsulfonamido)-N-(2-guanidinoethyl)butanamide;
83) 3-chloro-N-(3-((2-guanidinoethyl)sulfonamido)propyl)-2-methyl-N-(2-(3-(3-methylpyridin-4-yl)phenyl)propan-2-yl)benzenesulfonamide;
84) 2-(4-(3-chloro-2-methyl-N-(2-(3-(3-methylpyridin-4-yl)phenyl)propan-2-yl)phenylsulfonamido)butanamido)-N,N,N-trimethylethanaminium;
85) (S)-2-(4-(3-chloro-N-(1-(3-(3-ethylpyridin-4-yl)phenyl)ethyl)-2-methylphenylsulfonamido)butanamido)-N,N,N-trimethylethanaminium;
86) (S)-2-(3-(4-(N-(1-(3-(3-methylpyridin-4-yl)phenyl)ethyl)-2-(trifluoromethyl)phenylsulfonamido)butyl)ureido)ethanesulfonamidopropanoic acid;
87) (S)-2-(3-(4-(N-(1-(3-(3-methylpyridin-4-yl)phenyl)ethyl)-2-(trifluoromethyl)phenylsulfonamido)butyl)ureido)ethanesulfonamido acetic acid;
88) (S)-2-(3-(4-(N-(1-(3-(3-methylpyridin-4-yl)phenyl)ethyl)-2-(trifluoromethyl)phenylsulfonamido)butyl)ureido)ethanesulfonic acid;
89) (S)-(3-(4-(N-(1-(3-(3-methylpyridin-4-yl)phenyl)ethyl)-2-(trifluoromethyl)phenylsulfonamido)butyl)ureido)methanesulfonic acid;
90) 2-(3-(2-(N-(3-((3-chloro-2-methyl-N-(2-(3-(3-methylpyridin-4-yl)phenyl)propan-2-yl)phenyl)sulfonamido)propyl)sulfamoyl)ethyl)ureido)ethane-1-sulfonic acid;
91) 3-(3-(2-(N-(3-((3-chloro-2-methyl-N-(2-(3-(3-methylpyridin-4-yl)phenyl)-propan-2-yl)phenyl)sulfonamido)-propyl)sulfamoyl)ethyl)ureido)propane-1-sulfonic acid;
92) (S)-17-((3-chloro-2-methylphenyl)sulfonyl)-18-(3-(3-methylpyridin-4-yl)phenyl)-4,12-dioxo-8-oxa-3,5,11,17-tetraazanonadecane-1-sulfonic acid;
93) (S)-(3-(4-(N-(1-(3-(3-ethylpyridin-4-yl)phenyl)ethyl)-2-(trifluoromethyl)phenylsulfonamido)butyl)ureido)methanesulfonic acid;
94) (3-(3-((3-chloro-2-methyl-N-(2-(3-(3-methylpyridin-4-yl) phenyl) propan-2-yl) phenyl) sulfonamide) propyl) ureido) methanesulfonic acid;
95) 2-(3-(3-((3-chloro-2-methyl-N-(2-(3-(3-methylpyridin-4-yl) phenyl) propan-2-yl) phenyl) sulfonamide) propyl) ureido)ethane-1-sulfonic acid;
96) 3-chloro-2-methyl-N-(2-(3-(3-methylpyridin-4-yl) phenyl) propan-2-yl)-N-(3-(3-(2-sulfamoylethyl) ureido) propyl) benzenesulfonamide;
97) 34343-((3-chloro-2-methyl-N-(2-(3-(3-methylpyridin-4-yl) phenyl) sulfonamide)propyl) ureido) propane-1-sulfonic acid;
98) (S)-15-((3-chloro-2-methylphenyl)sulfonyl)-16-(3-(3-methylpyridin-4-yl)phenyl)-2,10-dioxo-6-oxa-3,9,15-triazaheptadecane-1-sulfonic acid;
99) (S)-2-((4-(N-(1-(3-(3-methylpyridin-4-yl)phenyl)ethyl)-2-(trifluoromethyl)phenylsulfonamido)butyl)amino)-2-oxoethanesulfonic acid;
100) 2-((3-(3-chloro-2-methyl-N-(2-(3-(3-methylpyridin-4-yl)phenyl)propan-2-yl)phenylsulfonamido)propyl)amino)-2-oxoethanesulfonic acid;
101) (R)-2-amino-3-((4-(N—((S)-1-(3-(3-methylpyridin-4-yl)phenyl)ethyl)-2-(trifluoromethyl)phenylsulfonamido)butyl)amino)-3-oxopropane-1-sulfonic acid;
102) (R)-2-amino-3-((4-(3-chloro-N—((S)-1-(3-(3-ethylpyridin-4-yl)phenyl)ethyl)-2-methylphenylsulfonamido)butyl)amino)-3-oxopropane-1-sulfonic acid;
103) (S)-2-((2-(4-(N-(1-(3-(3-methylpyridin-4-yl)phenyl)ethyl)-2-(trifluoromethyl)phenylsulfonamido)butanamido)ethyl)amino)-2-oxoethanesulfonic acid;
104) (R)-2-amino-3-((2-(4-(N—((S)-1-(3-(3-methylpyridin-4-yl)phenyl)ethyl)-2-(trifluoromethyl)phenylsulfonamido)butanamido)ethyl)amino)-3-oxopropane-1-sulfonic acid;
105) ((2-((3-(3-chloro-2-methyl-N-(1-(3-(3-methylpyridin-4-yl)phenyl)ethyl)phenylsulfonamido)propyl)amino)-3,4-dioxocyclobut-1-en-1-yl)amino)methanesulfonic acid;
106) (S)-2-(4-(4-fluoro-N-(1-(3-(3-methylpyridin-4-yl)phenyl)ethyl)-2-(trifluoromethyl)phenylsulfonamido)butanamido)ethanesulfonamido acetic acid;
107) (S)-2-(4-(3-chloro-N-(1-(3-(3-methylpyridin-4-yl)phenyl)ethyl)-2-chloro-phenylsulfonamido)butanamido)ethanesulfonamido acetic acid;
108) (S)-4-(3-chloro-2-methyl-N-(1-(3-(3-methylpyridin-4-yl)phenyl)ethyl)phenylsulfonamido)-N-(2-(sulfamoylamino)ethyl)butanamide;
109) (S)—N-(2-((N-(tert-butoxy)sulfamoyl)amino)ethyl)-4-(3-chloro-2-methyl-N-(1-(3-(3-methylpyridin-4-yl)phenyl)ethyl)phenylsulfonamido)butanamide;
110) (S)-4-(3-chloro-N-(1-(3-(3-ethylpyridin-4-yl)phenyl)ethyl)-2-methylphenylsulfonamido)-N-(2-(sulfamoylamino)ethyl)butanamide;
111) S)-2-((N-(2-(4-(3-chloro-2-methyl-N-(1-(3-(3-methylpyridin-4-yl)phenyl)ethyl)phenylsulfonamido)butanamido)ethyl)sulfamoyl)amino)acetic acid;
112) (S)-2-((N-(2-(4-(3-chloro-N-(1-(3-(3-ethylpyridin-4-yl)phenyl)ethyl)-2-methylphenylsulfonamido)butanamido)ethyl)sulfamoyl)amino)acetic acid; and 113) (S)-3-chloro-N-(4-hydroxybutyl)-2-methyl-N-(1-(3-(3-methylpyridin-4-yl)phenyl)ethyl)benzenesulfonamide;

or a pharmaceutically acceptable salt thereof.

9. The compound of claim 7, which is selected from the group consisting of:
1) 2-(4-(N-(2-(3-(3-ethylpyridin-4-yl)phenyl)propan-2-yl)-2-(trifluoromethyl)phenylsulfonamido)butanamido)ethanesulfonic acid;
2) (4-(N-(2-(3-(3-methylpyridin-4-yl)phenyl)propan-2-yl)-2-(trifluoromethyl)phenylsulfonamido)butanamido)methanesulfonic acidtrifluoromethyl)benzenesulfonamide;
3) 3-(4-(3-chloro-2-methyl-N-(2-(3-(3-methylpyridin-4-yl)phenyl)propan-2-yl)phenylsulfonamido)butanamido)propane-1-sulfonic acid;
4) 2-(4-(3-chloro-2-methyl-N-(2-(3-(3-methylpyridin-4-yl)phenyl)propan-2-yl)phenylsulfonamido)butanamido)ethanesulfonic acid;
5) (S)-2-(5-(3-chloro-2-methyl-N-(1-(3-(3-methylpyridin-4-yl)phenyl)ethyl)phenylsulfonamido)pentanamido)ethanesulfonic acid;
6) (S)-3-(4-(3-chloro-N-(1-(3-(3-ethylpyridin-4-yl)phenyl)ethyl)-2-methylphenylsulfonamido)butanamido)propane-1-sulfonic acid;
7) 4-(3-chloro-N—((S)-1-(3-(3-ethylpyridin-4-yl)phenyl)ethyl)-2-methyl phenyl sulfonamido)-N-((2R,3S,4S,5S)-2,3,4,5,6-pentahydroxyhexyl)butanamide;
8) (S)-2-(4-(N-(1-(3-(3-ethylpyridin-4-yl)phenyl)ethyl)-2-methylphenyl-sulfonamido)butanamido)ethane sulfonic acid;
9) (S)-2-(5-(3-chloro-N-(1-(3-(3-ethylpyridin-4-yl)phenyl)ethyl)-2-methyl phenylsulfonamido)pentanamido)ethanesulfonic acid;
10) (4-(3-chloro-2-methyl-N-(2-(3-(3-methylpyridin-4-yl)phenyl)propan-2-yl)phenylsulfonamido)-N-butanamidoethylsulfonamido)acetic acid;
11) (S) 2-(3-(4-(3-chloro-2-methyl-N-(1-(3-(3-ethylpyridin-4-yl)phenyl)ethyl)phenylsulfonamido)butanamido)ethylsulfonamido)propanoic acid;
12) (S)-2-(4-(N-(1-(3-(3-ethylpyridin-4-yl)phenyl)ethyl)-2-(trifluoromethyl)phenylsulfonamido)butanamido)ethanesulfonic acid;
13) (S) 2-(4-(N-(1-(3-(3-ethylpyridin-4-yl)phenyl)ethyl)-2-(trifluoromethyl)phenylsulfonamido)butanamido)ethylsulfonamido)acetic acid;
14) (S) 2-(4-(N-(1-(3-(3-methylpyridin-4-yl)phenyl)ethyl)-2-(trifluoromethyl)phenylsulfonamido)butanamido)ethylsulfonamido)butanoic acid;
15) (S) 2-(4-(N-(1-(3-(3-methylpyridin-4-yl)phenyl)ethyl)-2-(trifluoromethyl)phenylsulfonamidopentanamido)ethylsulfonamido)acetic acid;
16) (S) 2-(4-(N-(1-(3-(3-methylpyridin-4-yl)phenyl)ethyl)-2-(trifluoromethyl)phenylsulfonamidopentanamido)ethylsulfonamido)propanoic acid;
17) (S)-2-(4-(2-methyl-N-(1-(3-(3-ethylpyridin-4-yl)phenyl)ethyl)phenylsulfonamido) butanamidoethylsulfonamido)acetate;
18) (S) 2-(3-(4-(3-chloro-2-methyl-N-(1-(3-(3-methylpyridin-4-yl)phenyl)ethyl)phenylsulfonamido)butanamido)ethylsulfonamido)acetic acid;
19) (S)-2-(4-(3-chloro-N-(1-(3-(3-ethylpyridin-4-yl)phenyl)ethyl)-2-methyl phenylsulfonamido)butanamido) ethanesulfonic acid;
20) (S) 2-(3-(4-(3-chloro-2-methyl-N-(1-(3-(3-ethylpyridin-4-yl)phenyl)ethyl)phenylsulfonamido)butanamido)ethylsulfonamido)acetic acid;
21) (E)-3-(3-(3-((3-chloro-2-methyl-N-(2-(3-(3-methylpyridin-4-yl)phenyl)propan-2-yl)phenyl)sulfonamido)propyl)-2-cyanoguanidino)propanoic acid;
22) (S)-4-(3-chloro-2-methyl-N-(1-(3-(3-methylpyridin-4-yl)phenyl)ethyl)phenylsulfonamido)butanamido-2-(N-ethylsulfamoyl)acetic acid;
23) (S)-4-(3-chloro-2-methyl-N-(1-(3-(3-methylpyridin-4-yl)phenyl)ethyl)phenylsulfonamido)butanamido-2-(N-ethylsulfamoyl)propanoic acid;
24) (S)-2-(3-(4-(N-(1-(3-(3-methylpyridin-4-yl)phenyl)ethyl)-2-(trifluoromethyl)phenylsulfonamido)butyl)ureido)ethanesulfonamidopropanoic acid;
25) (S)-2-(3-(4-(N-(1-(3-(3-methylpyridin-4-yl)phenyl)ethyl)-2-(trifluoromethyl)phenylsulfonamido)butyl)ureido)ethanesulfonamido acetic acid;
26) (S)-(3-(4-(N-(1-(3-(3-methylpyridin-4-yl)phenyl)ethyl)-2-(trifluoromethyl)phenylsulfonamido)butyl)ureido)methanesulfonic acid;
27) (S)-(3-(4-(N-(1-(3-(3-ethylpyridin-4-yl)phenyl)ethyl)-2-(trifluoromethyl)phenylsulfonamido)butyl)ureido)methanesulfonic acid;
28) (3-(3-((3-Chloro-2-methyl-N-(2-(3-(3-methylpyridin-4-yl) phenyl) propan-2-yl) phenyl) sulfonamide)propyl) ureido) methanesulfonic acid;
29) 2-(3-(3-((3-Chloro-2-methyl-N-(2-(3-(3-methylpyridin-4-yl) phenyl) propan-2-yl) phenyl) sulfonamide) propyl) ureido)ethane-1-sulfonic acid;
30) (S)-2-((4-(N-(1-(3-(3-methylpyridin-4-yl)phenyl)ethyl)-2-(trifluoromethyl) phenylsulfonamido)butyl) amino)-2-oxoethanesulfonic acid;
31) (R)-2-amino-3-((4-(N—((S)-1-(3-(3-methylpyridin-4-yl)phenyl)ethyl)-2-(trifluoromethyl)phenylsulfonamido)butyl)amino)-3-oxopropane-1-sulfonic acid; and
32) (S)-2-((N-(2-(4-(3-chloro-2-methyl-N-(1-(3-(3-methylpyridin-4-yl)phenyl)ethyl)phenylsulfonamido)butanamido)ethyl)sulfamoyl)amino)acetic acid;

or a pharmaceutically acceptable salt thereof.

10. A pharmaceutical composition comprising the compound of claim 1, or a pharmaceutically acceptable salt thereof, and a pharmaceutically acceptable carrier.

11. A method of treating a human afflicted with a metabolic disorder selected from the group consisting of type-2 diabetes, pre-diabetes, and obesity, comprising the step of administering to said human a therapeutically effective amount of the compound of claim 1.

12. A method of treating a human afflicted with a metabolic disorder selected from the group consisting of type-2 diabetes, pre-diabetes, and obesity, comprising the step of administering to said human a therapeutically effective amount of the compound of claim 7.

13. A method of treating a human afflicted with a metabolic disorder selected from the group consisting of type-2 diabetes, pre-diabetes, and obesity, comprising the step of administering to said human a therapeutically effective amount of the compound of claim 8.

14. A method of treating a human afflicted with a metabolic disorder selected from the group consisting of type-2 diabetes, pre-diabetes, and obesity, comprising the step of administering to said human a therapeutically effective amount of the compound of claim 9.

15. A method of treating a human afflicted with a metabolic disorder selected from the group consisting of type-2 diabetes, pre-diabetes, and obesity, comprising the step of administering to said human a therapeutically effective amount of the compound of claim 1, and a therapeutically effective amount of at least one other compound useful for treating type-2 diabetes, pre-diabetes, and obesity.

16. A method of treating a human afflicted with a metabolic disorder selected from the group consisting of type-2 diabetes, pre-diabetes, and obesity, comprising the step of administering to said human a therapeutically effective amount of the compound of claim 7, and a therapeutically effective amount of at least one other compound useful for treating type-2 diabetes, pre-diabetes, and obesity.

17. A method of treating a human afflicted with metabolic disorder selected from the group consisting of type-2 diabetes, pre-diabetes, and obesity, comprising the step of administering to said human a therapeutically effective amount of the compound of claim 8, and a therapeutically effective amount of at least one other compound useful for treating type-2 diabetes, pre-diabetes, and obesity.

18. A method of treating a human afflicted with metabolic disorder selected from the group consisting of type-2 diabetes, pre-diabetes, and obesity, comprising the step of administering to said human a therapeutically effective amount of the compound of claim 9, and a therapeutically effective amount of at least one other compound useful for treating type-2 diabetes, pre-diabetes, and obesity.

19. A compound according to claim 1 of formula:

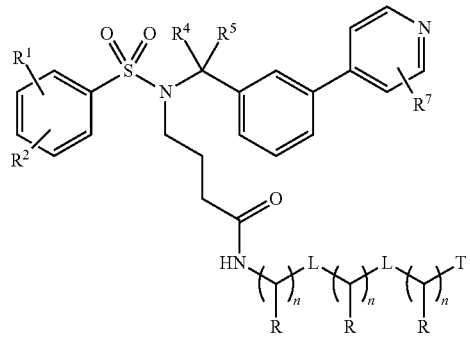

wherein $R^7$ is selected from halogen, $(C_1-C_3)$alkyl, $(C_1-C_3)$alkoxy, $(C_1-C_3)$alkylO$(C_1-C_3)$alkyl, $(C_1-C_3)$alkylOH, —OH, —NH$_2$, —N[$(C_1-C_3)$alkyl]$_2$, —C(O)N[$(C_1-C_3)$alkyl]$_2$, —NHC(O) $(C_1-C_3)$alkyl, —C(O)O$(C_1-C_3)$alkyl and —$(C_1-C_3)$alkylC(O)NH$(C_1-C_3)$alkylS(O)$_2$OH.

20. A compound according to claim 19 of formula:

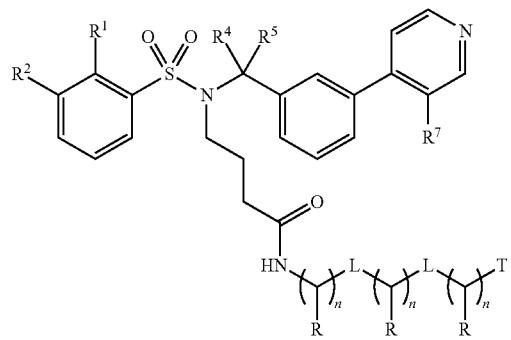

wherein $R^4$ and $R^5$ are independently chosen from H and CH$_3$.

21. A compound according to claim 20 wherein R is H, $R^1$ is CH$_3$ or CF$_3$, $R^2$ is H or Cl, and $R^7$ is $(C_1-C_3)$alkyl.

22. A compound according to claim 21 wherein L is chosen from —SO$_2$NH—, —NHSO$_2$— —NHSO$_2$NH— and absent; and T is chosen from COOH, SO$_3$H and

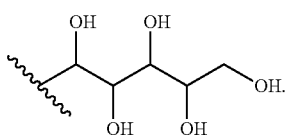 [SMILES: *C(O)C(O)C(O)C(O)CO]

23. A compound according to claim 22 of formula:

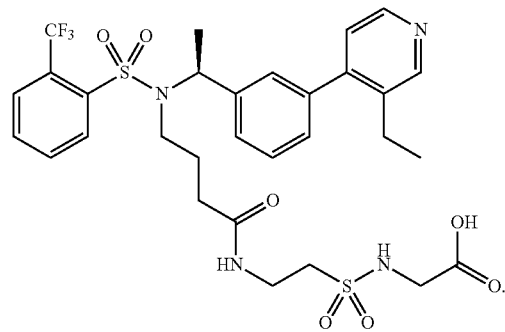 [SMILES: CCc1cnccc1-c1cccc([C@H](C)N(CCCC(=O)NCCS(=O)(=O)NCC(=O)O)S(=O)(=O)c2ccccc2C(F)(F)F)c1]

* * * * *

UNITED STATES PATENT AND TRADEMARK OFFICE
CERTIFICATE OF CORRECTION

PATENT NO. : 11,236,055 B2  
APPLICATION NO. : 16/311723  
DATED : February 1, 2022  
INVENTOR(S) : Huang et al.

Page 1 of 1

It is certified that error appears in the above-identified patent and that said Letters Patent is hereby corrected as shown below:

In the Claims

Column 378, Line 63: Claim 7, Delete "2,5-bi s(trifluoromethyl)" and insert -- 2,5-bis(trifluoromethyl) --

Column 380, Line 19: Claim 7, Delete "phenyl sulfonamido)propanamide;" and insert -- phenylsulfonamido)propanamide; --

Column 380, Line 22: Claim 7, Delete "phenyl sulfonamido)propanamide;" and insert -- phenylsulfonamido)propanamide; --

Column 380, Line 64: Claim 7, Delete "(21H)-yl)phenyl)ethyl)benzene" and insert -- (2H)-yl)phenyl)ethyl)benzene --

Column 382, Line 18: Claim 7, Delete "phenyl sulfonamido)-N-" and insert -- phenylsulfonamido)-N- --

Column 386, Line 28: Claim 7, Delete "phenyl sulfonamido)pentyl)ureido)" and insert -- phenylsulfonamido)pentyl)ureido) --

Column 386, Line 47: Claim 7, Delete "34343-((3-Chloro-2" and insert -- 3-(3-(3-((3-Chloro-2 --

Column 392, Line 17: Claim 8, Delete "34343-((3-Chloro-2" and insert -- 3-(3-(3-((3-Chloro-2 --

Column 393, Line 27: Claim 9, Delete "phenyl sulfonamido)butanoic acid;" and insert -- phenylsulfonamido)butanoic acid; --

Signed and Sealed this  
Twenty-ninth Day of March, 2022

Drew Hirshfeld  
*Performing the Functions and Duties of the*  
*Under Secretary of Commerce for Intellectual Property and*  
*Director of the United States Patent and Trademark Office*